(12) United States Patent
Leonard et al.

(10) Patent No.: US 9,284,308 B2
(45) Date of Patent: *Mar. 15, 2016

(54) METHYLENE LINKED QUINOLINYL MODULATORS OF RORγT

(71) Applicant: Janssen Pharmaceutica NV, Beerse (BE)

(72) Inventors: Kristi A. Leonard, Lansdale, PA (US); Kent Barbay, Flourtown, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Anne Fourie, San Diego, CA (US); Xiaohua Xue, San Diego, CA (US); Maxwell D. Cummings, Ambler, PA (US); William Moore Jones, San Diego, CA (US); Steven Goldberg, Encinitas, CA (US)

(73) Assignee: Janssen Pharmaceutica NV

( * ) Notice: Subject to any disclaimer, the term of this patent is extended or adjusted under 35 U.S.C. 154(b) by 0 days.

This patent is subject to a terminal disclaimer.

(21) Appl. No.: 14/053,797

(22) Filed: Oct. 15, 2013

(65) Prior Publication Data

US 2015/0105366 A1    Apr. 16, 2015

(51) Int. Cl.

| | |
|---|---|
| *A61K 31/4709* | (2006.01) |
| *C07D 413/14* | (2006.01) |
| *C07D 417/14* | (2006.01) |
| *C07D 405/14* | (2006.01) |
| *A61K 45/06* | (2006.01) |
| *C07D 401/14* | (2006.01) |
| *C07D 409/14* | (2006.01) |
| *C07D 401/06* | (2006.01) |
| *A61K 31/506* | (2006.01) |
| *A61K 31/5377* | (2006.01) |

(52) U.S. Cl.
CPC .......... *C07D 417/14* (2013.01); *A61K 31/4709* (2013.01); *A61K 31/506* (2013.01); *A61K 31/5377* (2013.01); *A61K 45/06* (2013.01); *C07D 401/06* (2013.01); *C07D 401/14* (2013.01); *C07D 405/14* (2013.01); *C07D 409/14* (2013.01); *C07D 413/14* (2013.01)

(58) Field of Classification Search
CPC ............ A61K 31/4709; A61K 31/506; A61K 31/5377; C07D 413/14; C07D 401/06; C07D 401/14; C07D 409/14
USPC ........................................... 546/159; 514/312
See application file for complete search history.

(56) References Cited

U.S. PATENT DOCUMENTS

| | | | |
|---|---|---|---|
| 3,472,859 | A | 10/1969 | Lesher |
| 4,656,283 | A | 4/1987 | Doehner, Jr. |
| 4,710,507 | A | 12/1987 | Campbell et al. |
| 4,910,327 | A | 3/1990 | Doehner, Jr. |
| 4,927,926 | A | 5/1990 | Corominas et al. |
| 5,409,930 | A | 4/1995 | Spada et al. |
| 5,780,634 | A | 7/1998 | Inoue et al. |
| 6,248,739 | B1 | 6/2001 | Turner et al. |
| 6,451,812 | B1 * | 9/2002 | End et al. ...................... 514/312 |
| 6,624,159 | B2 | 9/2003 | Anderson et al. |
| 6,686,356 | B2 | 2/2004 | Strohbach et al. |
| 6,743,805 | B2 * | 6/2004 | End et al. ...................... 514/312 |

(Continued)

FOREIGN PATENT DOCUMENTS

| | | |
|---|---|---|
| CN | 101143845 | 3/2008 |
| CN | 101899011 | 12/2010 |

(Continued)

OTHER PUBLICATIONS

Codarri, Nature Innumology, Jun. 2011, vol. 12(6), p. 560-568.*

(Continued)

*Primary Examiner* — D M Seaman
(74) *Attorney, Agent, or Firm* — Yuriy P. Stercho

(57) ABSTRACT

The present invention comprises compounds of Formula I.

Formula I wherein:
$R^1$, $R^2$, $R^3$, $R^4$, $R^5$, $R^6$, $R^7$, $R^8$, and $R^9$ are defined in the specification.
The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

21 Claims, No Drawings

(56) References Cited

U.S. PATENT DOCUMENTS

| | | |
|---|---|---|
| 7,053,105 B2 | 5/2006 | Angibaud et al. |
| 7,652,014 B2 | 1/2010 | Mabire et al. |
| 7,902,225 B2 | 3/2011 | Guillemont et al. |
| 8,017,606 B2 | 9/2011 | Andries et al. |
| 8,389,739 B1 | 3/2013 | Thacher et al. |
| 2003/0166675 A1 | 9/2003 | Yang |
| 2005/0131014 A1 | 6/2005 | Collini et al. |
| 2007/0072844 A1 | 3/2007 | Jones et al. |
| 2008/0188521 A1 | 8/2008 | Grimm et al. |
| 2009/0197859 A1 | 8/2009 | Collantes et al. |
| 2009/0286829 A1 | 11/2009 | Heidelbaugh et al. |
| 2010/0311760 A1 | 12/2010 | de Vicente Fidalgo et al. |
| 2011/0124870 A1 | 5/2011 | Guillemont et al. |
| 2012/0322837 A1 | 12/2012 | Maeba et al. |
| 2014/0107094 A1* | 4/2014 | Leonard et al. .......... 514/210.18 |

FOREIGN PATENT DOCUMENTS

| | | |
|---|---|---|
| EP | 371564 A2 | 6/1990 |
| EP | 709377 A1 | 5/1996 |
| EP | 1106612 A1 | 6/2001 |
| EP | 2368886 A1 | 9/2011 |
| GB | 2095668 A | 10/1982 |
| JP | 48026772 | 4/1973 |
| JP | 2000169451 A | 6/2000 |
| WO | WO 9718208 A1 | 5/1997 |
| WO | WO 9721701 A1 | 6/1997 |
| WO | WO 9744339 A1 | 11/1997 |
| WO | WO 9855124 A1 | 12/1998 |
| WO | WO 9932450 A1 | 7/1999 |
| WO | WO 9950660 A1 | 10/1999 |
| WO | WO 0001386 A1 | 1/2000 |
| WO | WO 0001411 A1 | 1/2000 |
| WO | WO 0001714 A1 | 1/2000 |
| WO | WO 0039082 A2 | 7/2000 |
| WO | WO 0040561 A1 | 7/2000 |
| WO | WO 0040563 A1 | 7/2000 |
| WO | WO 0047574 A1 | 8/2000 |
| WO | WO 0156552 A2 | 8/2001 |
| WO | WO 0162234 A2 | 8/2001 |
| WO | WO 0164194 A2 | 9/2001 |
| WO | WO 0164195 A2 | 9/2001 |
| WO | WO 0164196 A2 | 9/2001 |
| WO | WO 0164197 A2 | 9/2001 |
| WO | WO 0164198 A2 | 9/2001 |
| WO | WO 0164199 A2 | 9/2001 |
| WO | WO 0164217 A2 | 9/2001 |
| WO | WO 0164218 A2 | 9/2001 |
| WO | WO 0164226 A2 | 9/2001 |
| WO | WO 0164246 A2 | 9/2001 |
| WO | WO 0164252 A2 | 9/2001 |
| WO | WO 0202558 A1 | 1/2002 |
| WO | WO 0204445 A1 | 1/2002 |
| WO | WO 0204462 A1 | 1/2002 |
| WO | WO 0224682 A1 | 3/2002 |
| WO | WO 0224686 A2 | 3/2002 |
| WO | WO 0224687 A1 | 3/2002 |
| WO | WO 0228837 A1 | 4/2002 |
| WO | WO 0243733 A1 | 6/2002 |
| WO | WO 02051835 A1 | 7/2002 |
| WO | WO 02064142 A1 | 8/2002 |
| WO | WO 02070487 A1 | 9/2002 |
| WO | WO 02085364 A1 | 10/2002 |
| WO | WO 03/00705 | 1/2003 |
| WO | WO 03053971 A1 | 7/2003 |
| WO | WO 03053972 A1 | 7/2003 |
| WO | WO 03082350 A2 | 10/2003 |
| WO | WO 2004019932 A1 | 3/2004 |
| WO | WO 2004024693 A1 | 3/2004 |
| WO | WO 2004037792 A2 | 5/2004 |
| WO | WO 2005054201 A1 | 6/2005 |
| WO | WO 2005054210 A1 | 6/2005 |
| WO | WO 2005058843 A1 | 6/2005 |
| WO | WO 2005070430 A1 | 8/2005 |
| WO | WO 2005075428 A1 | 8/2005 |
| WO | WO 2006003146 A1 | 1/2006 |
| WO | WO 2006013896 A1 | 2/2006 |
| WO | 2006025683 | 3/2006 |
| WO | WO 2006052718 A2 | 5/2006 |
| WO | WO 2007014940 A2 | 2/2007 |
| WO | WO 2007014941 A2 | 2/2007 |
| WO | WO 2007088978 A1 | 8/2007 |
| WO | WO 2008051805 A2 | 5/2008 |
| WO | WO 2008068267 A1 | 6/2008 |
| WO | WO 2008098104 A8 | 8/2008 |
| WO | WO 2008112525 A2 | 9/2008 |
| WO | WO 2008144767 A1 | 11/2008 |
| WO | WO 2009091735 A1 | 7/2009 |
| WO | WO 2009140138 A1 | 11/2009 |
| WO | WO 2010068296 A1 | 6/2010 |
| WO | WO 2010127208 A1 | 11/2010 |
| WO | WO 2010151740 A4 | 12/2010 |
| WO | WO 2011020861 A1 | 2/2011 |
| WO | WO 2011112264 A1 | 9/2011 |
| WO | WO 2011130707 A2 | 10/2011 |
| WO | WO 2012064744 A2 | 5/2012 |
| WO | WO 2012116137 A2 | 8/2012 |
| WO | WO 2012158784 A2 | 11/2012 |
| WO | WO 2013061074 A1 | 5/2013 |
| WO | WO 2013064231 A1 | 5/2013 |
| WO | WO 2013079223 A1 | 6/2013 |

OTHER PUBLICATIONS

International Search Report—PCT/US2013/065007, Jan. 7, 2014.
International Search Report—PCT/US2013/065013, Dec. 16, 2013.
International Search Report—PCT/US2013/065031, Dec. 13, 2013.
International Search Report—PCT/US2013/065040, Dec. 16, 2013.
International Search Report—PCT/US2013/065048, Dec. 3, 2013.
International Search Report—PCT/US2013/065053, Jan. 7, 2014.
International Search Report—PCT/US2013/065026, Feb. 21, 2014.
U.S. Appl. No. 14/053,682.
U.S. Appl. No. 14/053,736.
U.S. Appl. No. 14/053,773.
U.S. Appl. No. 14/053,906.
U.S. Appl. No. 14/053,653.
U.S. Appl. No. 14/053,707.
Bink A, (A fungicidal piperazine-1-carboxamidine induces mitochondrial fission-dependent apoptosis in yeast), FEMS Yeast Research (2010), 10(7), 812-818.
Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.
Tanis S, (The design and development of 2-aryl-2-hydroxy ethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.
Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.
Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.
Aghera V, (Synthesis, spectral and microbial studies of some novel quinoline derivatives via Vilsmeier-Haack reagent) Journal; (online computer file) URL:http://www.arkat-usa.org/get-file/25177/, 2010.
Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.
Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.
Hirao I, (Studies on the synthesis of quinoline compounds. I. Syntheses of 3,3'-dicarboxy-1,1'-diethyl-4,4'-dioxo-1,1',4,4'-tetrahydrobiquinolines), Memoirs of the Kyushu Institute of Technology, Engineering (1984), 14, 13-16.

(56) References Cited

OTHER PUBLICATIONS

Abdul-Ahad P, (Trends in dehydrogenase inhibitory potencies of some quinolones, using quantum chemical indices), European Journal of Medicinal Chemistry (1982), 17(4), 301-6.
Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.
Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.
Dong C, (Diversification of T-helper-cell lineages: finding the family root of IL-17-producing cells), Nat Rev Immunol (2006), 6(4), 329-333.
McKenzie B, (Understanding the IL-23-IL-17 immune pathway), Trends Immunol (2006), 27(1), 17-23.
Ivanov II B, (The orphan nuclear receptor RORgammat directs the differentiation program of proinflammatory IL-17+ T helper cells), Cell (2006), 126(6), 1121-33.
Cua, D (Interleukin-23 rather than interleukin-12 is the critical cytokine for autoimmune inflammation of the brain), Nature (2003), 421(6924), 744-748.
Langrish C, (IL-23 drives a pathogenic T cell population that induces autoimmune inflammation), J Exp Med (2005), 201(2), 233-240.
Tonel G, (Cutting edge: A critical functional role for IL-23 in psoriasis), J Immunol (2010), 185(10), 5688-5691.
Barczyk A, (Interleukin-17 in sputum correlates with airway hyperresponsiveness to methacholine), Respir Med (2003), 97(6), 726-733.
Lock C, (Gene-microarray analysis of multiple sclerosis lesions yields new targets validated in autoimmune encephalomyelitis) Nat Med (2002), 8(5), 500-8.
Papp K, (Brodalumab, an anti-interleukin-17-receptor antibody for psoriasis), N Engl J Med (2012), 366(13), 1181-1189.
Leonardi C, (Anti-interleukin-17 monoclonal antibody ixekizumab in chronic plaque psoriasis), N Engl J Med (2012), 366(13), 1190-1199.
Hueber W, (Effects of AIN457, a fully human antibody to interleukin-17A, on psoriasis, rheumatoid arthritis, and uveitis), Sci Transl Med (2010), 2, 5272.
Gao W, (Clean and Convienient One-Pot Synthesis of 4-Hydroxycoumarin and 4-Hydroxy-2-Quinolone Derivatives), Synthetic Communications (2010) 40, 732-738.
Moriarty R, Organic Reactions (2001), 57, 327-415.
Pongratz E, et al., (Ylide von Heterocyclen, VIII Reaktionen von Iodonium-Yliden mit Säuren), Monatshefte fur Chemie (1984) 115(2), 231-242.
Osborne A, (Regioselective Al koxydehalogenation of 2,4- Di halogenoquinolines and a Reinvestigation of the Bromination of 2-Methoxyquinoline), J Chem Soc Perkin Trans 1 (1993), 181-184.
Osborne A, (Further studies of regioselective alkoxydehalogenation of 2,4- dichloroquinolines, 2,6-dichloropyridine and 2,4-dichloronitrobenzene), J Chem Research (S) (2002), 4.
Ramachary D, (Development of Pharmaceutical Drugs, Drug Intermediates and Ingredients by Using Direct Organo-Click Reactions), Eur. J. Org. Chem. (2008), 975-993.
Korn T, (IL-17 and Th17 Cells), Annual Reviews of Immunology (2009), 27, 485-517.
Kolls J, (Interleukin-17 family members and inflammation), Immunity (2004), 21(4), 467-476.
Stamp L, (Interleukin-17: the missing link between T-cell accumulation and effector cell actions in rheumatoid arthritis), Immunol Cell Biol (2004), 82(1), 1-9.
Kamenecka T, (Synthetic modulators of the retinoic acid receptor-related orphan receptors), Med Chem Commun (2013), 4, 764-776.
Yen D, (IL-23 is essential for T cell-mediated colitis and promotes inflammation via IL-17 and IL-6), J Clin Invest (2006), 116(5), 1310-1316.
Fujino S, (Increased expression of interleukin 17 in inflammatory bowel disease) Gut (2003), 52(1), 65-70.
Krueger J, (IL-17A is essential for cell activation and inflammatory gene circuits in subjects with psoriasis) J Allergy Clin Immunol (2012), 130(1), 145-154.
Nunez C, (IL23R: a susceptibility locus for celiac disease and multiple sclerosis?) Genes Immun (2008), 9(4), 289-93.
Bowes J, (The genetics of psoriatic arthritis: lessons from genome-wide association studies), Discov Med (2010), 10(52), 177-83.
Kochi Y, (A regulatory variant in CCR6 is associated with rheumatoid arthritis susceptibility), Nat Genet (2010), 42(6), 515-9.
Garber K, (Psoriasis: from bed to bench and back), Nat Biotech (2011), 29, 563-566.
Madrid P, et al. (Synthesis of ring-substituted 4-aminoquinolines and evaluation of their antimalarial activities), Bioorganic & Medicinal Chemistry Letters (2005), 15, 1015-1018.
Gore T, (Synthesis of substituted 6,6'-biquinolines from ethyl ethoxymethyleneacetoacetate), Indian Journal of Chemistry (1965), 3(2), 90-1.
Gazouli, M, (NOD2/CARD15, ATG16L1 and IL23R gene polymorphisms and childhood-onset of Crohn's disease) World J. Gastroenterol (2010) 16(14), 1753-8.
Knochel P, (Preparation of Polyfunctional Ketones by a Cobalt(II) Mediated Carbonylation of Organozinc Reagents), Tetrahedron Letters (1995), 36(46), 8411-8414.
U.S. Appl. No. 14/513,426.
U.S. Appl. No. 14/513,455.
International Search Report—PCT/US2014/60372, Mar. 27, 2015.
International Search Report—PCT/US2014/60375, Mar. 26, 2015.
U.S. Appl. No. 14/053,653, Office Action dated Sep. 15, 2014.
U.S. Appl. No. 14/053,653, Notice of Allowance dated Mar. 30, 2015.
U.S. Appl. No. 14/053,682, Office Action dated Sep. 12, 2014.
U.S. Appl. No. 14/053,682, Notice of Allowance dated Sep. 12, 2014.
U.S. Appl. No. 14/053,707, Office Action dated Sep. 11, 2014.
U.S. Appl. No. 14/053,707, Notice of Allowance dated Sep. 11, 2014.
U.S. Appl. No. 12/053,736, Office action dated Mar. 26, 2015.
U.S. Appl. No. 14/053,736, Office Action dated Oct. 3, 2014.
U.S. Appl. No. 14/053,773, Office Action dated Apr. 6, 2015.
U.S. Appl. No. 14/053,773, Office Action dated Jan. 9, 2015.
U.S. Appl. No. 14/053,797, Office Action dated Sep. 12, 2014.
U.S. Appl. No. 14/053,797, Notice of Allowance Apr. 7, 2015.
U.S. Appl. No. 14/513,426, Office Action dated Apr. 16, 2015.
U.S. Appl. No. 14/513,455, Office Action dated Apr. 28, 2015.
U.S. Appl. No. 14/053,906, Office Action dated Sep. 12, 204.
U.S. Appl. No. 14/053,906, Notice of Allowance dated Mar. 23, 2015.
Dorwald F. A. "SLIDE Reactions in Organic Synthesis", 2005, Wiley: VCH, Weinheim p. IX of Preface p. 1-15.
Venkatesh, et al. "Role of the Development Scientist in Compound Lead Selection and Optimization", J. Pharm. Sci. vol. 89, No. 2, pp. 145-154 2000.
STN Search Report Mar. 12, 2015, RN 1347913-41-0.

* cited by examiner

METHYLENE LINKED QUINOLINYL MODULATORS OF RORγT

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4$^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, I I, B. S. McKenzie, et al. (2006). "The orphan nuclear receptor ROR-gammat directs the differentiation program of proinflammatory IL-17+ T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet. 42(6): 515-9). Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

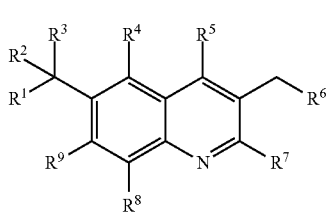

Formula I wherein:
R$^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with SO$_2$CH$_3$, C(O)CH$_3$, C(O)NH$_2$, CH$_3$, CH$_2$CH$_3$, CF$_3$, Cl, F, —CN, OCH$_3$, N(CH$_3$)$_2$, —(CH$_2$)$_3$OCH$_3$, SCH$_3$, OH, CO$_2$H, CO$_2$C(CH$_3$)$_3$, or OCH$_2$OCH$_3$; and optionally substituted with up to two additional substituents independently selected from the group consisting of Cl, OCH$_3$, and CH$_3$; and wherein said triazolyl, oxazolyl, isoxazolyl, and thiazolyl are optionally substituted with one or two CH$_3$ groups; and wherein said azetidinyl is optionally substituted with CO$_2$C(CH$_3$)$_3$, C(O)NH$_2$, CH$_3$, SO$_2$CH$_3$, or C(O)CH$_3$;

R$^2$ is 1-methyl-1,2,3-triazolyl, pyridyl, pyridyl-N-oxide, 1-methylpyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, 1-H-azetidin-3-yl, N-acetyl piperidinyl, 1-H-piperidinyl, N-Boc-piperidinyl, N—C$_{(1-2)}$alkyl-piperidinyl, thiazol-5-yl, 1-(3-methoxypropyl)-imidazol-5-yl, or 1-C$_{(1-2)}$alkyl imidazol-5-yl; wherein said 1-C$_{(1-2)}$alkyl imidazol-5-yl is optionally substituted with up to two additional CH$_3$ groups, or one substituent selected from the group consisting of SCH$_3$, and Cl; and said pyridyl, and pyridyl-N-oxide are optionally substituted with up to two substituents independently selected from the group consisting of C(O)NH$_2$, —CN, OCH$_3$, CF$_3$, Cl, and CH$_3$; and said thiazol-5-yl, oxazolyl, and isoxazolyl are optionally substituted with up to two CH$_3$ groups; and said 1-methylpyrazol-4-yl is optionally substituted with up to two additional CH$_3$ groups;

R$^3$ is H, OH, OCH$_3$, NHCH$_3$, N(CH$_3$)$_2$, or NH$_2$;

R$^4$ is H, or F;

R$^5$ is H, Cl, —CN, CF$_3$, SCH$_3$, OC$_{(1-3)}$alkyl, OH, C$_{(1-4)}$alkyl, N(CH$_3$)OCH$_3$, NH(C$_{(1-2)}$alkyl), N(C$_{(1-2)}$alkyl)$_2$, NH-cyclopropyl, OCHF$_2$, 4-hydroxy-piperidinyl, azetidin-1-yl, or fur-2-yl;

R$^6$ is pyridyl, pyrimidinyl, phenyl, benzothiophenyl, or thiophenyl; wherein said pyridyl or phenyl is optionally substituted with N(CH$_3$)$_2$, SCH$_3$, OCF$_3$, SO$_2$CH$_3$, CF$_3$, CHF$_2$, imidazol-1-yl, pyrazol-1-yl, 1,2,4-triazol-1-yl, CH$_3$, OCH$_3$, Cl, F, or —CN; and said thiophenyl is optionally substituted with CF$_3$;

R$^7$ is H, Cl, —CN, C$_{(1-4)}$alkyl, OCH$_2$CF$_3$, OCH$_2$CH$_2$OCH$_3$, CF$_3$, SCH$_3$, SO$_2$CH$_3$, OCHF$_2$, NA$^1$A$^2$, C(O)NHCH$_3$, N(CH$_3$)CH$_2$CH$_2$NA$^1$A$^2$, OCH$_2$CH$_2$NA$^1$A$^2$, OC$_{(1-3)}$alkyl, OCH$_2$-(1-methyl)-imidazol-2-yl, imidazol-2-yl, fur-2-yl, pyrazol-1-yl, pyrazol-4-yl, pyrid-3-yl, or pyrimidin-5-yl; thiophen-3-yl, 1-methyl-indazol-5-yl, 1-methyl-indazol-6-yl, phenyl, or

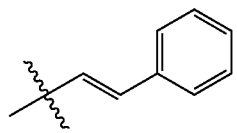 [SMILES: */C=C/c1ccccc1]

wherein said imidazolyl or pyrazolyl can be optionally substituted with a CH$_3$ group;

A$^1$ is H or C$_{(1-4)}$alkyl;

A$^2$ is H, C$_{(1-4)}$alkyl, cyclopropyl, C$_{(1-4)}$alkylOC$_{(1-4)}$alkyl, C$_{(1-4)}$alkylOH, C(O)C$_{(1-2)}$alkyl, or OCH$_3$; or A$^1$ and A$^2$ may be taken together with their attached nitrogen to form a ring selected from the group consisting of:

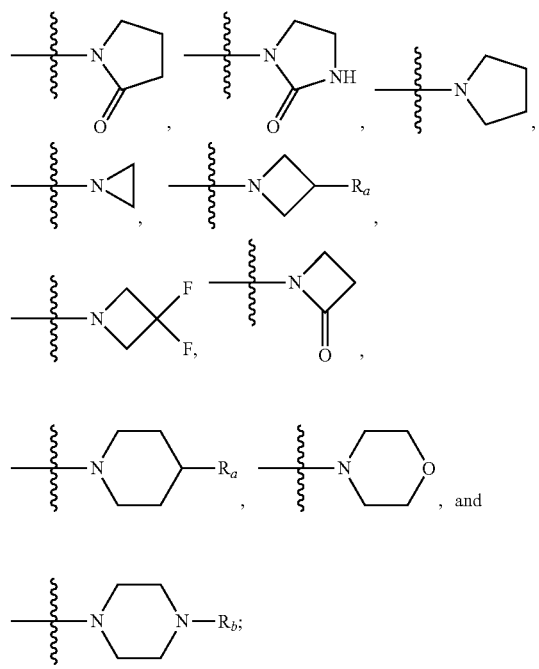

R$_a$ is H, F, OCH$_3$, or OH;

R$_b$ is CH$_3$, or phenyl;

R$^8$ is H, CH$_3$, OCH$_3$, or F;

R$^9$ is H, or F;

and pharmaceutically acceptable salts thereof;

provided that (4-chloro-2-methoxy-3-(4-(trifluoromethyl)benzyl)quinolin-6-yl)bis(1,2,5-trimethyl-1H-imidazol-4-yl)methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide, and (3-(4-(1H-pyrazol-1-yl)benzyl)-4-chloro-2-(4-methylpiperazin-1-yl)quinolin-6-yl)(1-methyl-1H-imidazol-5-yl)(6-(trifluoromethyl)pyridin-3-yl)methanol are excluded from the embodiment.

DETAILED DESCRIPTION OF THE INVENTION

The present invention comprises compounds of Formula I.

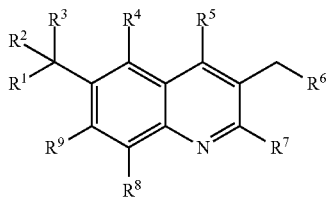

Formula I

R[1] is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;

R[2] is 1-methyl-1,2,3-triazolyl, pyridyl, pyridyl-N-oxide, 1-methylpyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, 1-H-azetidin-3-yl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methylpyrazol-4-yl is optionally substituted with up to two additional $CH_3$ groups;

R[3] is H, OH, $OCH_3$, $NHCH_3$, $N(CH_3)_2$, or $NH_2$;

R[4] is H, or F;

R[5] is H, Cl, —CN, $CF_3$, $SCH_3$, $OC_{(1-3)}$alkyl (including $OCH_3$), OH, $C_{(1-4)}$alkyl, $N(CH_3)OCH_3$, $NH(C_{(1-2)}$alkyl), $N(C_{(1-2)}$alkyl)$_2$, NH-cyclopropyl, $OCHF_2$, 4-hydroxy-piperidinyl, azetidin-1-yl, or fur-2-yl;

R[6] is pyridyl, pyrimidinyl, phenyl, benzothiophenyl, or thiophenyl; wherein said pyridyl or phenyl is optionally substituted with $N(CH_3)_2$, $SCH_3$, $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN; and said thiophenyl is optionally substituted with $CF_3$;

R[7] is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OC_{(1-3)}$alkyl (including $OCH_3$), $OCH_2$-(1-methyl)-imidazol-2-yl, imidazol-2-yl, fur-2-yl, pyrazol-1-yl, pyrazol-4-yl, pyrid-3-yl, or pyrimidin-5-yl; thiophen-3-yl, 1-methyl-indazol-5-yl, 1-methyl-indazol-6-yl, phenyl, or

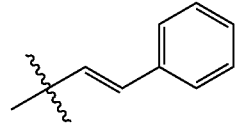 [SMILES: */C=C/c1ccccc1]

wherein said imidazolyl or pyrazolyl can be optionally substituted with a $CH_3$ group;

A[1] is H or $C_{(1-4)}$alkyl (including $C_{(1-2)}$alkyl);

A[2] is H, $C_{(1-4)}$alkyl (including $C_{(1-2)}$alkyl), cyclopropyl, $C_{(1-4)}$alkyl$OC_{(1-4)}$alkyl (including $CH_2CH_2OCH_3$), $C_{(1-4)}$alkylOH, $C(O)C_{(1-2)}$alkyl, or $OCH_3$; or A[1] and A[2] may be taken together with their attached nitrogen to form a ring selected from the group consisting of:

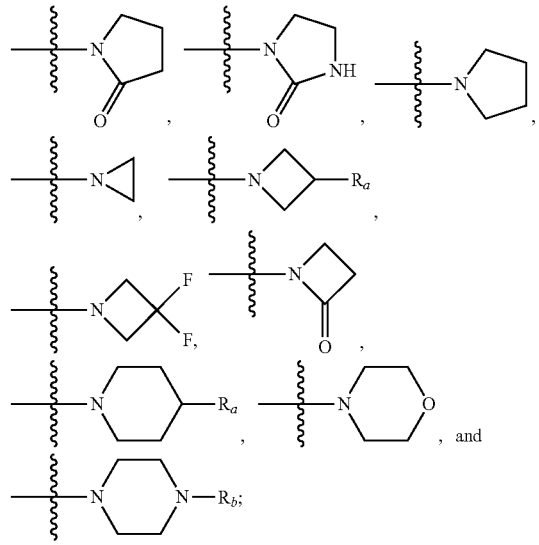

$R_a$ is H, F, $OCH_3$, or OH;

$R_b$ is $CH_3$, or phenyl;

R[8] is H, $CH_3$, $OCH_3$, or F;

R[9] is H, or F;

and pharmaceutically acceptable salts thereof;

provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide, and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

In another embodiment of the invention:

R[1] is oxazolyl, azetidinyl, imidazolyl, pyrimidinyl, triazolyl, tetrahydropyranyl, thiazolyl, pyridyl, phenyl, or isoxazolyl; wherein said pyridyl, imidazolyl, and phenyl are optionally substituted with $CH_3$, $CF_3$, Cl, F, —CN, or $OCH_3$; and optionally substituted with up to one additional group independently selected from the group consisting of Cl, $OCH_3$, and $CH_3$; and wherein said oxazolyl, triazolyl, isoxazolyl, and thiazolyl are optionally substituted with one or two $CH_3$ groups; and wherein said azetidinyl is optionally substituted with $CO_2C(CH_3)_3$, or $C(O)CH_3$;

$R^2$ is 1-methyl-1,2,3-triazol-5-yl, pyrid-3-yl, N-acetyl-piperidin-4-yl, N-Boc-azetidin-3-yl, N-acetyl-azetidin-3-yl, N-methyl-azetidin-3-yl, N-acetamidyl-azetidin-3-yl, 1-H-azetidin-3-yl, 1,2-dimethyl imidazol-5-yl, or 1-methyl imidazol-5-yl;

$R^3$ is OH, $NHCH_3$, $N(CH_3)_2$, or $NH_2$;

$R^4$ is H;

$R^5$ is H, Cl, OH, —CN, $N(CH_3)OCH_3$, NH-cyclopropyl, $OCHF_2$, or $OCH_3$;

$R^6$ is phenyl, pyrimidin-5-yl, 2-trifluoromethyl-pyrid-5-yl, 2-trifluoromethyl-thiophen-5-yl, or benzothiophenyl; wherein said phenyl is optionally substituted with pyrazol-1-yl, 1,2,4-triazol-1-yl, imidazol-1-yl, $SO_2CH_3$, $CH_3$, F, $CF_3$, $OCF_3$, $N(CH_3)_2$, —CN, or $SCH_3$;

$R^7$ is Cl, —CN, $CF_3$, $C_{(1-4)}$alkyl, $SO_2CH_3$, $OCHF_2$, $NA^1A^2$, $OCH_2CH_2OCH_3$, 1-methyl imidazol-2-yl, pyrazol-1-yl, 1-methylpyrazol-4-yl, or $OCH_3$;

$A^1$ is H, or $C_{(1-2)}$alkyl;

$A^2$ is $C_{(1-2)}$alkyl, cyclopropyl, $CH_2CH_2OCH_3$, or $OCH_3$; or $A^1$ and $A^2$ may be taken together with their attached nitrogen to form a ring which is:

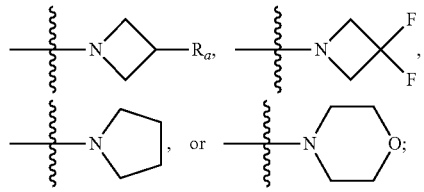

$R_a$ is H, OH, $OCH_3$, or F;

$R^8$ is H, or $CH_3$;

$R^9$ is H;

and pharmaceutically acceptable salts thereof.

Another embodiment of the invention is a compound selected from the group consisting of:

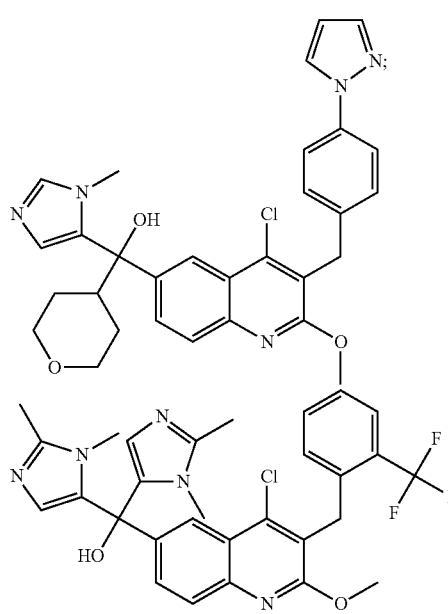

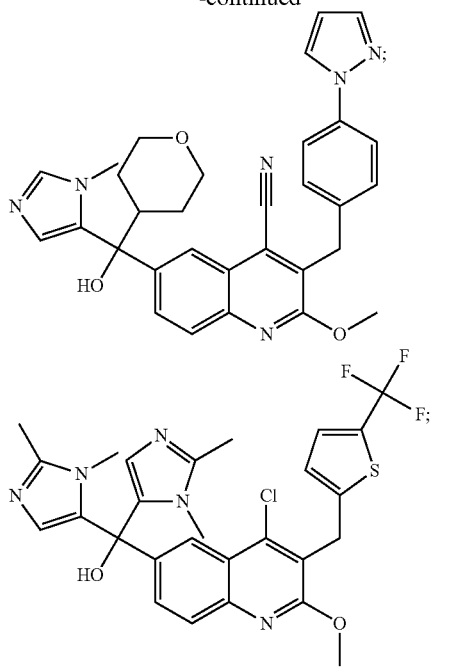

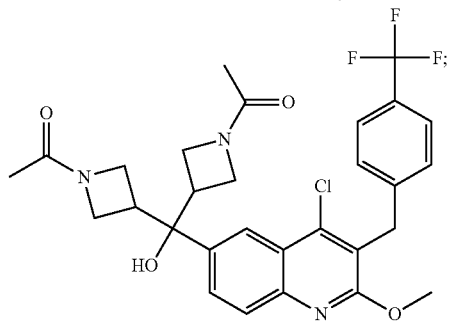

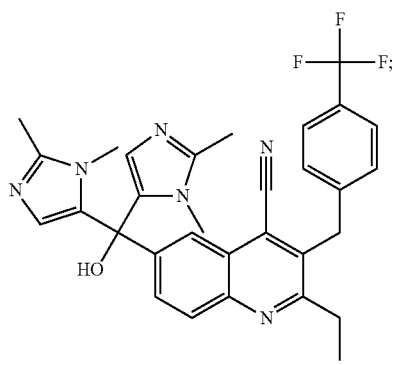

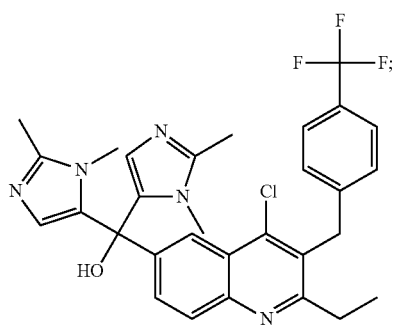

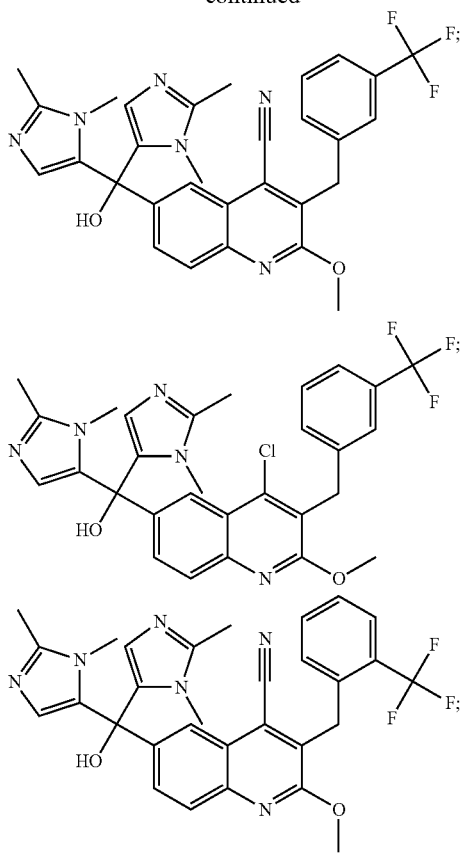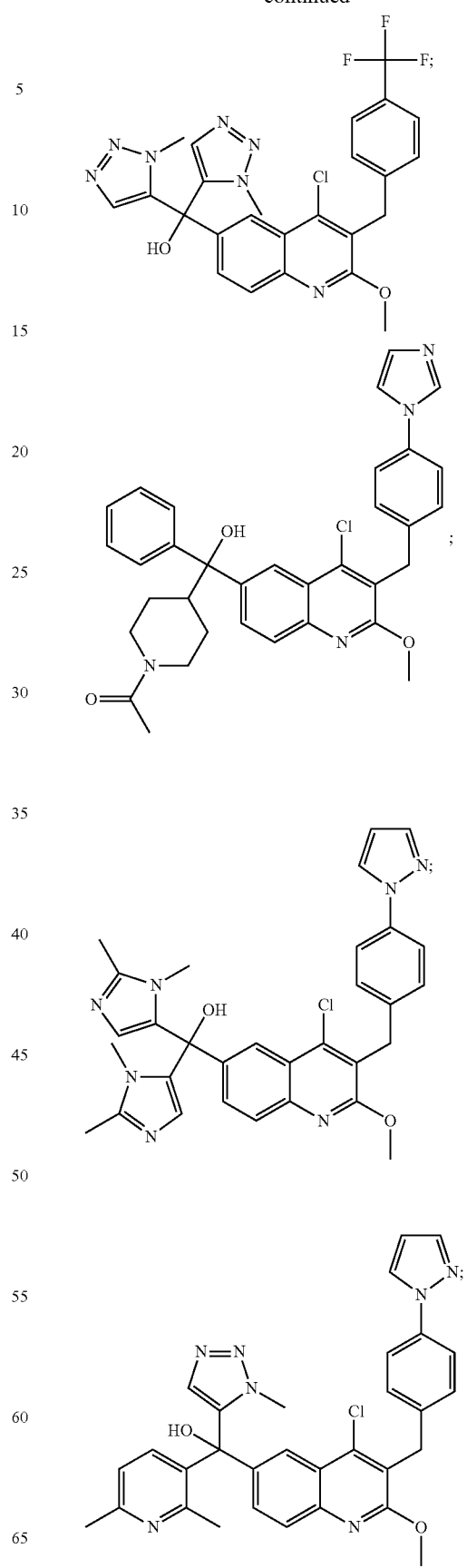

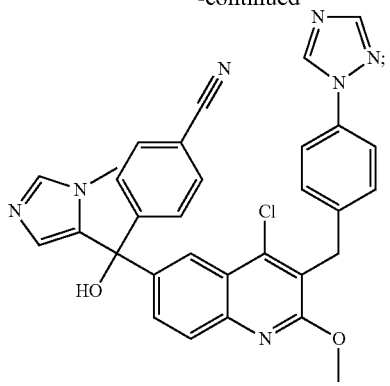
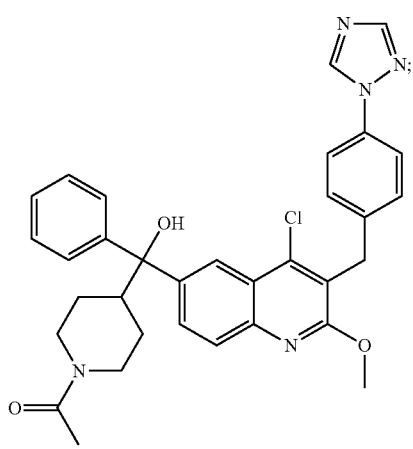
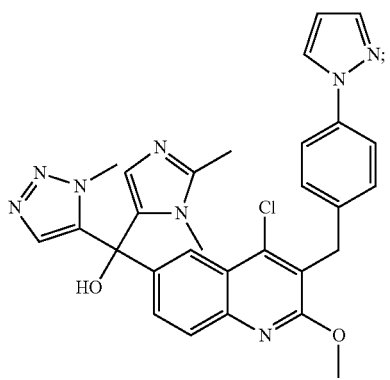
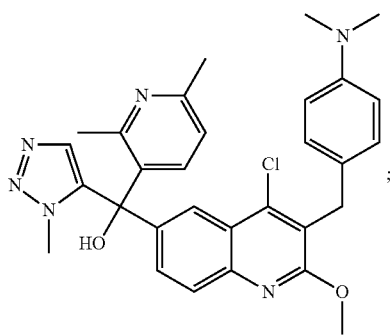
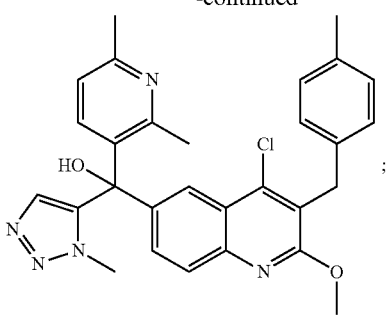
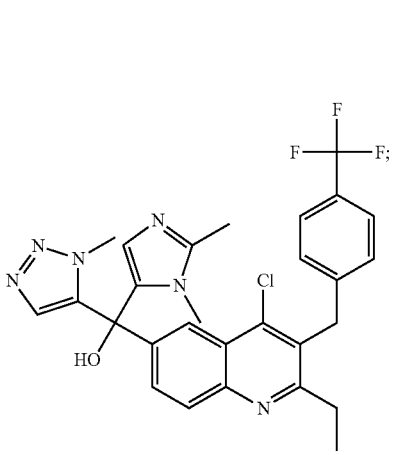
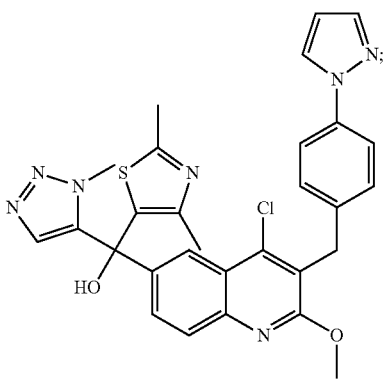
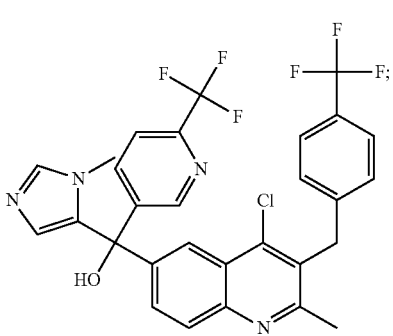

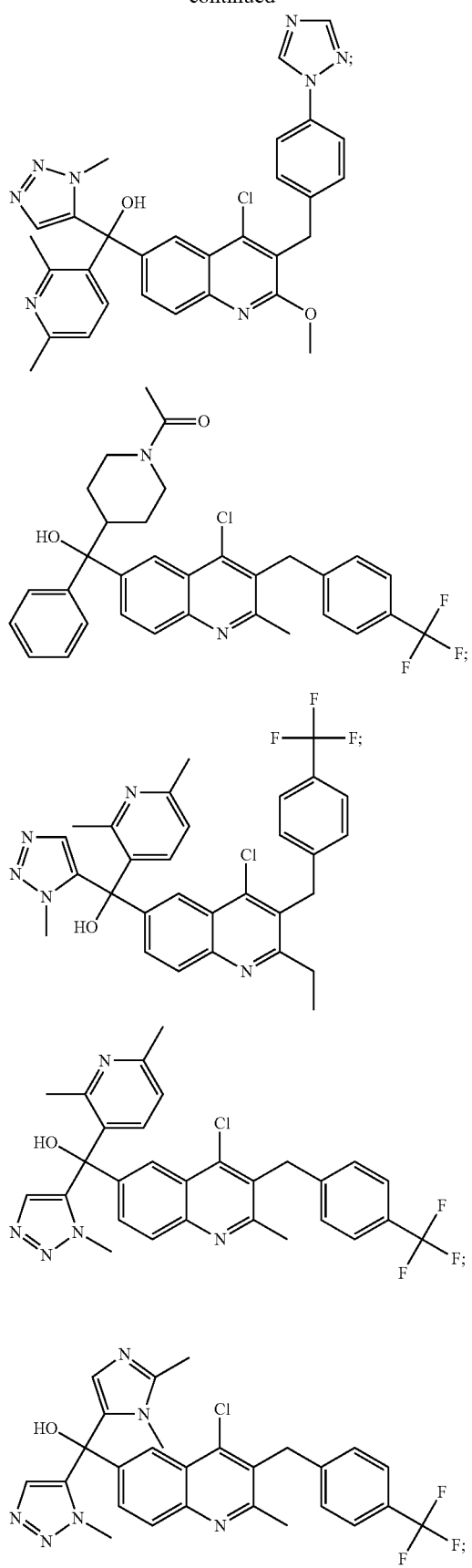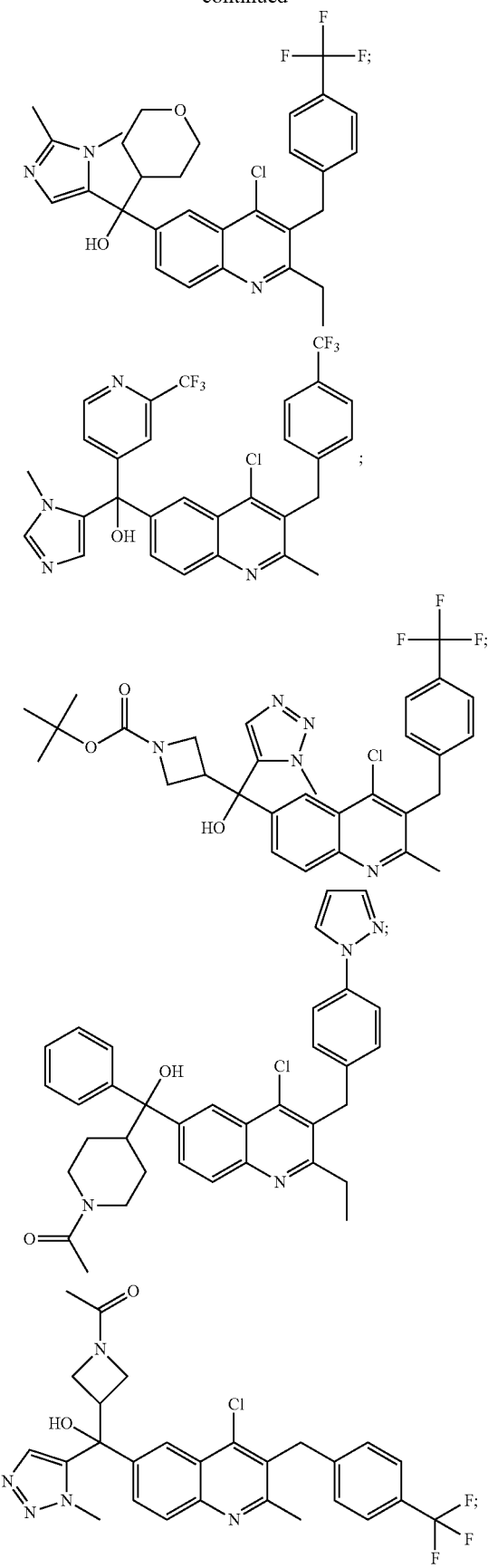

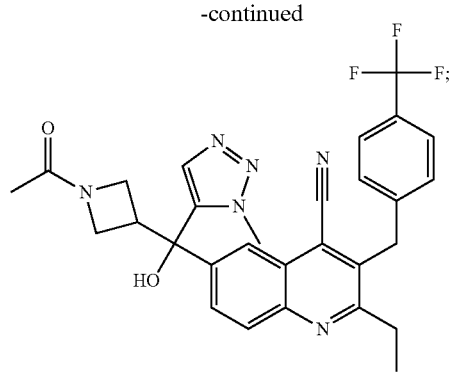
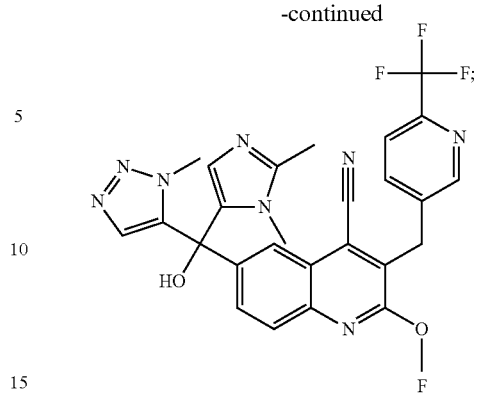
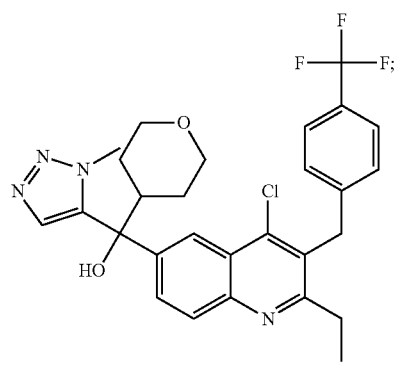
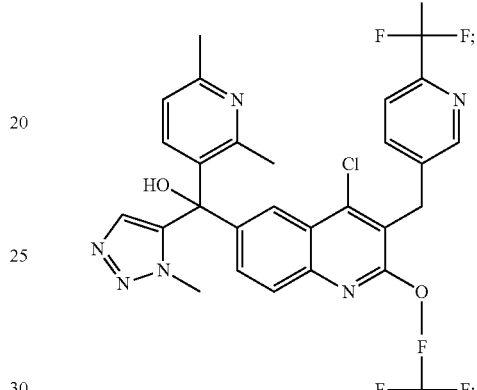
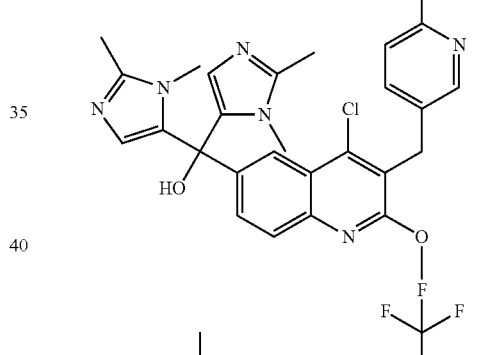
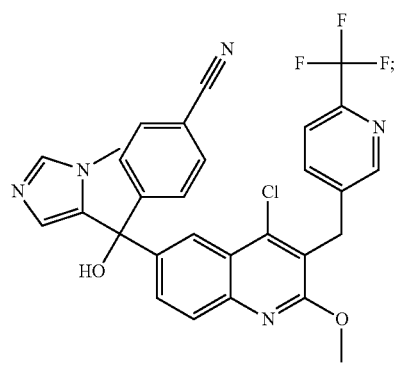
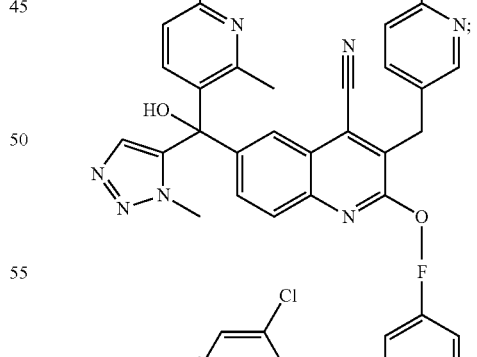
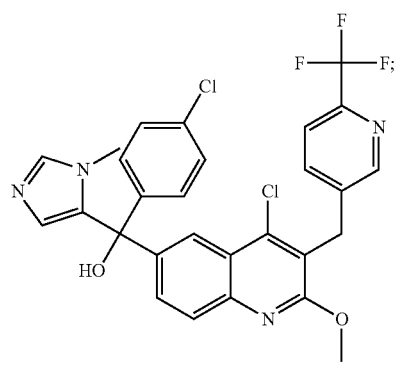
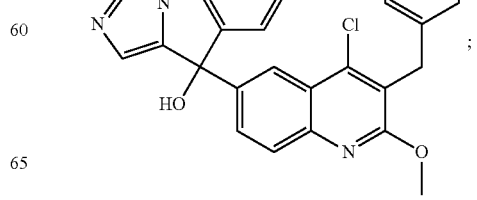

17
-continued
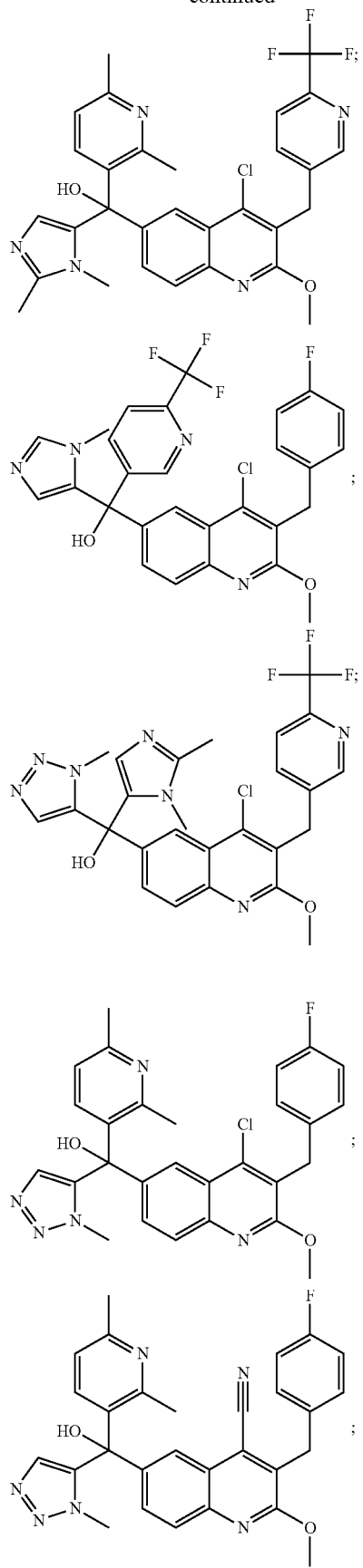
18
-continued
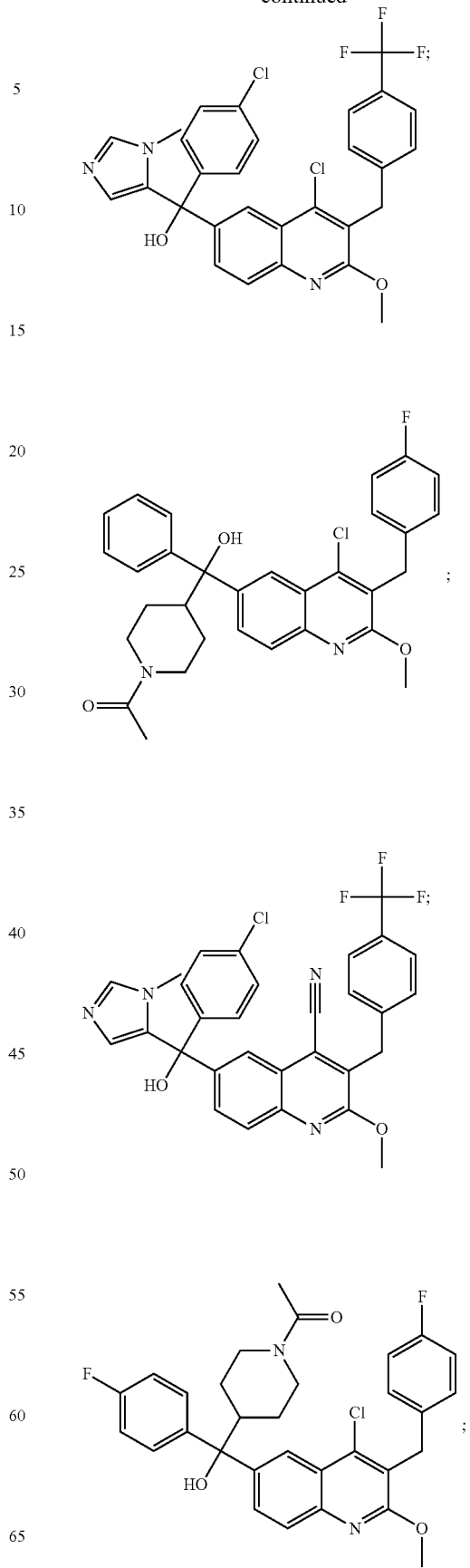

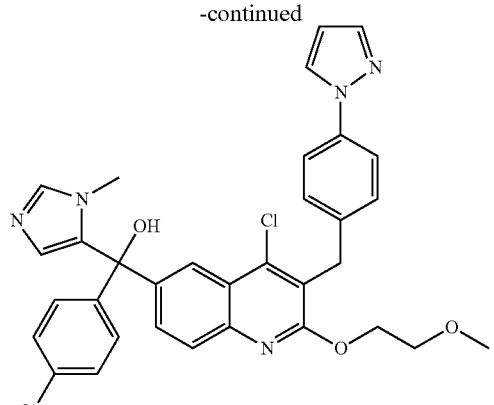
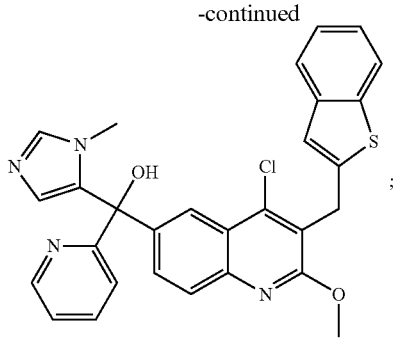
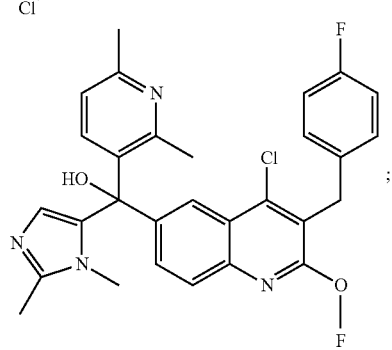
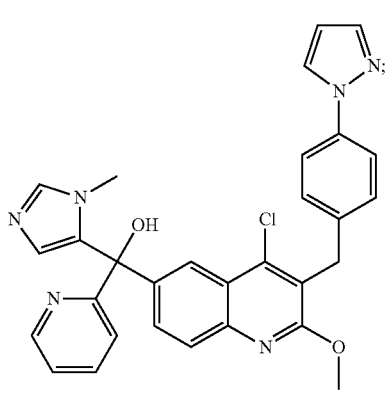
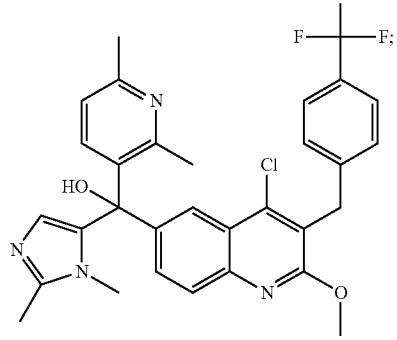
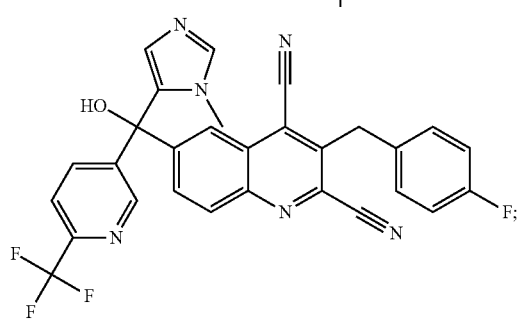
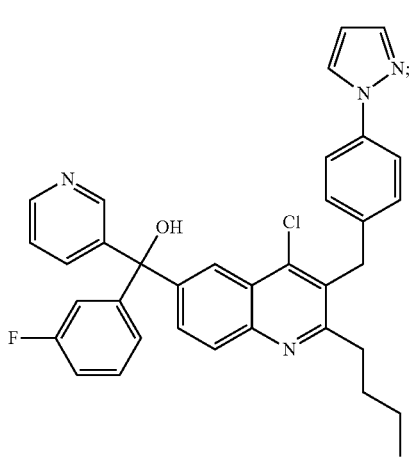
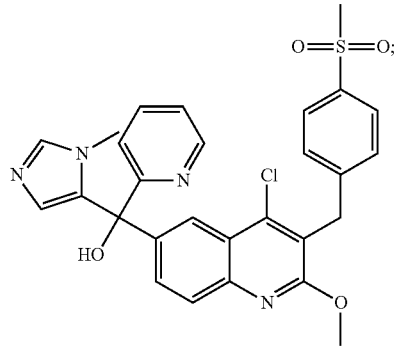
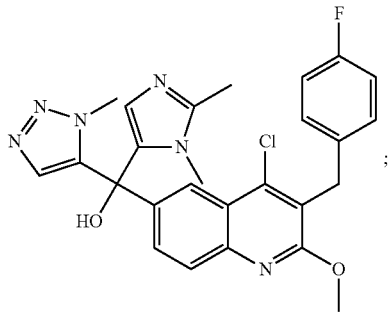

-continued
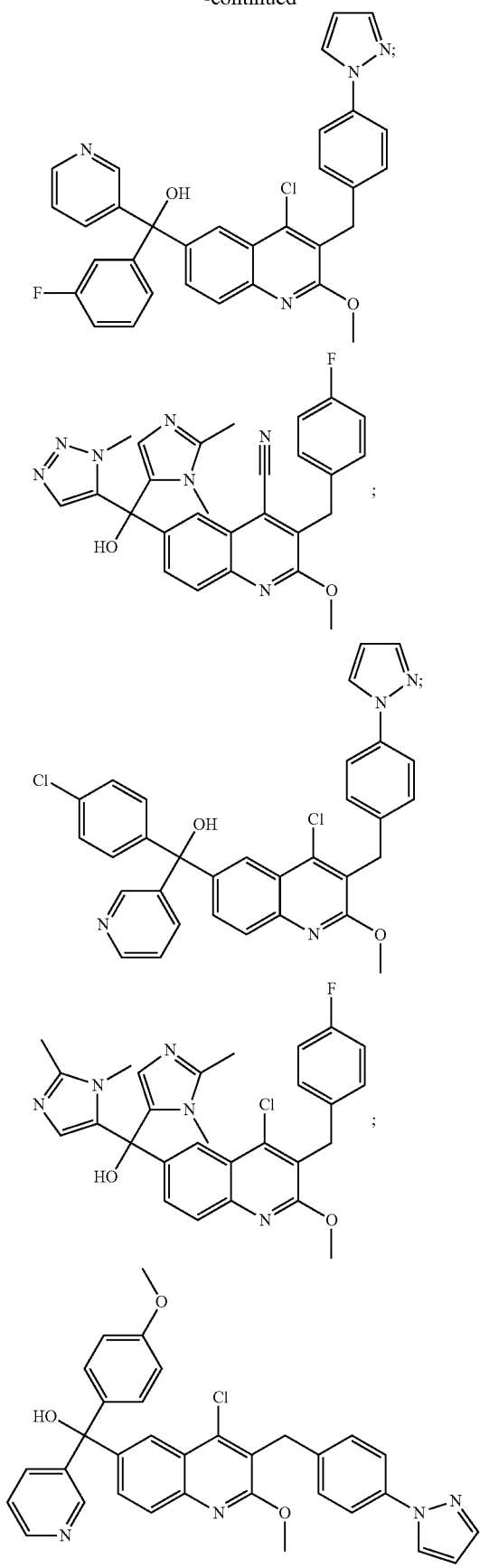
-continued
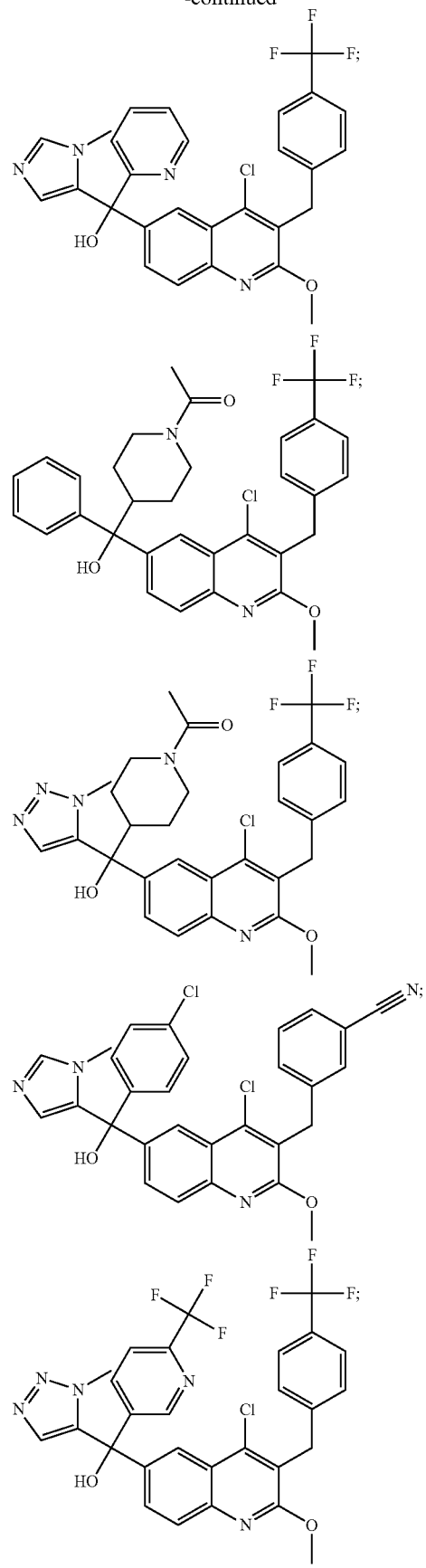

23
-continued
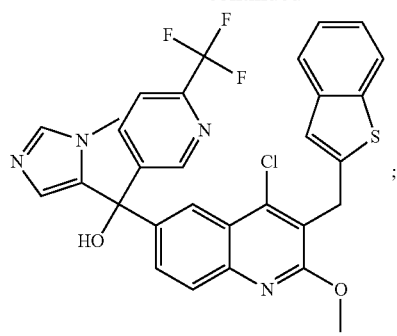
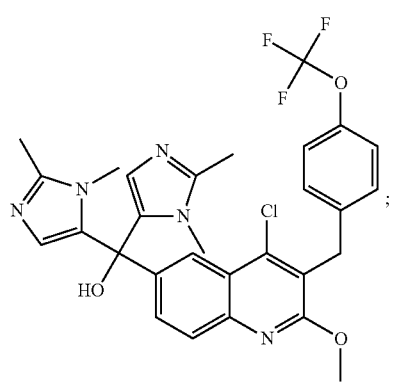
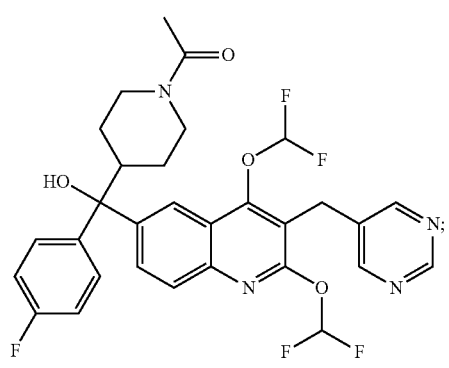
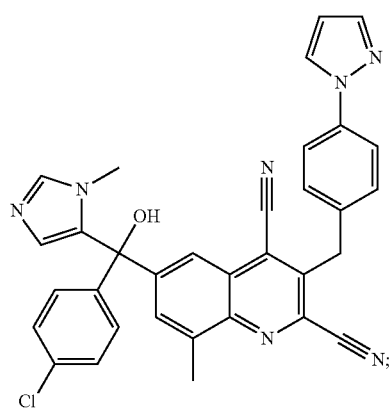
24
-continued
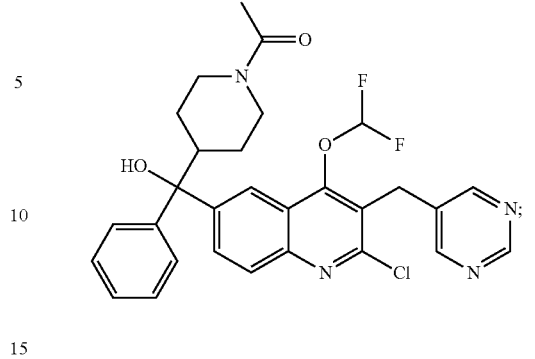
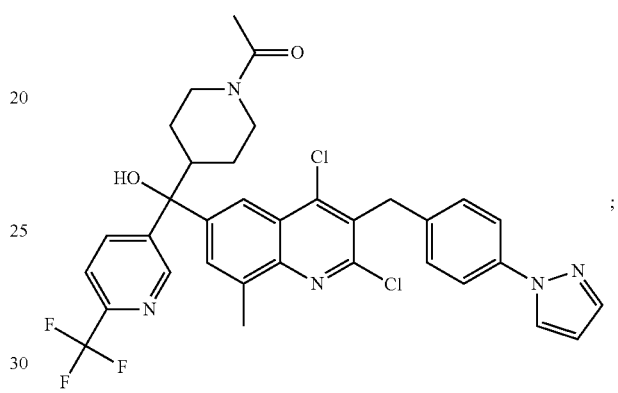
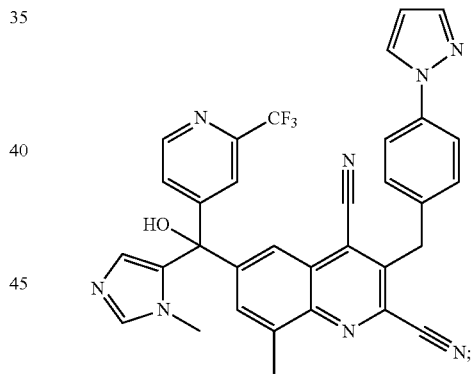
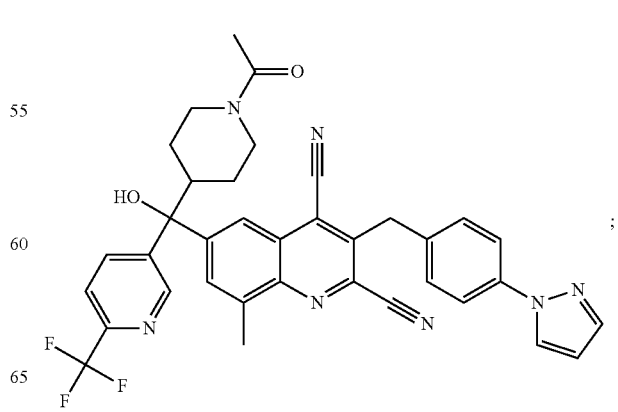

25
-continued
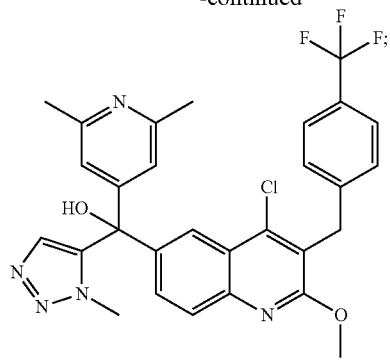
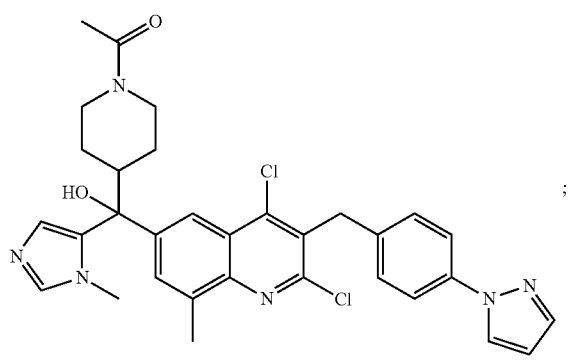
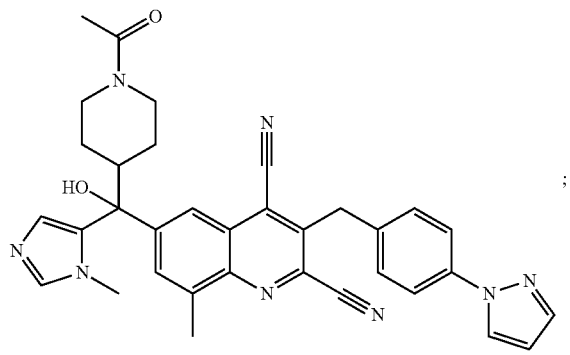
26
-continued
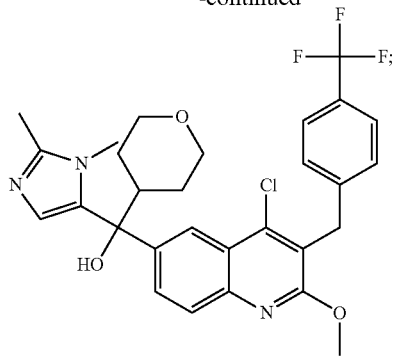
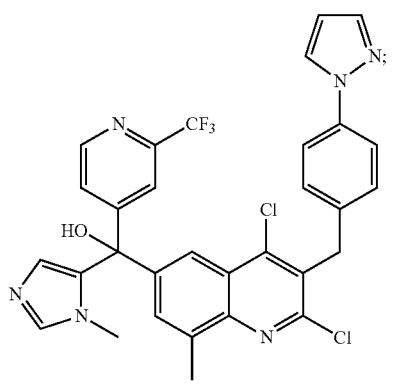
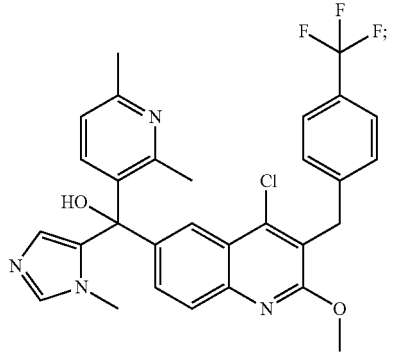

-continued
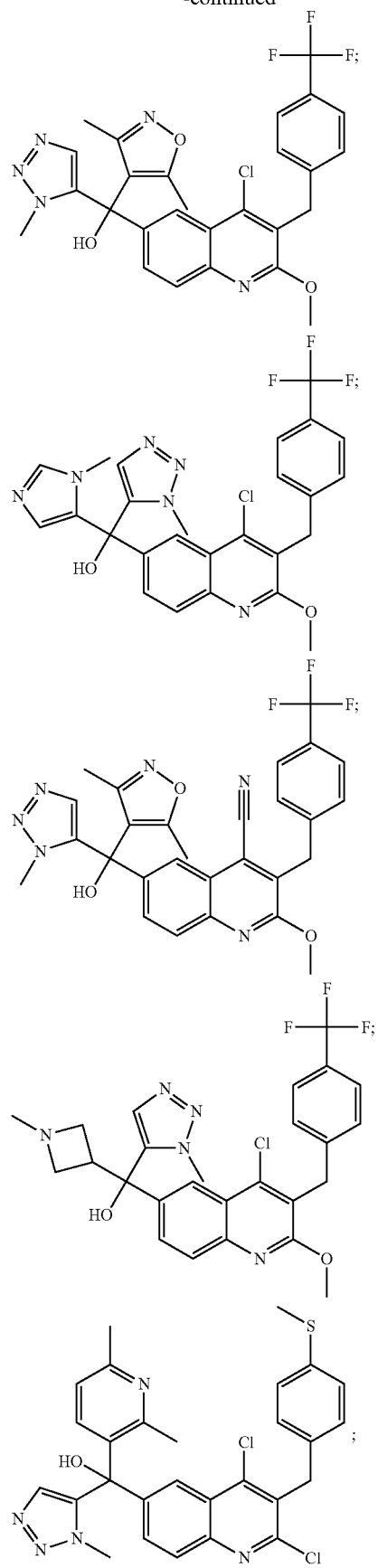
-continued
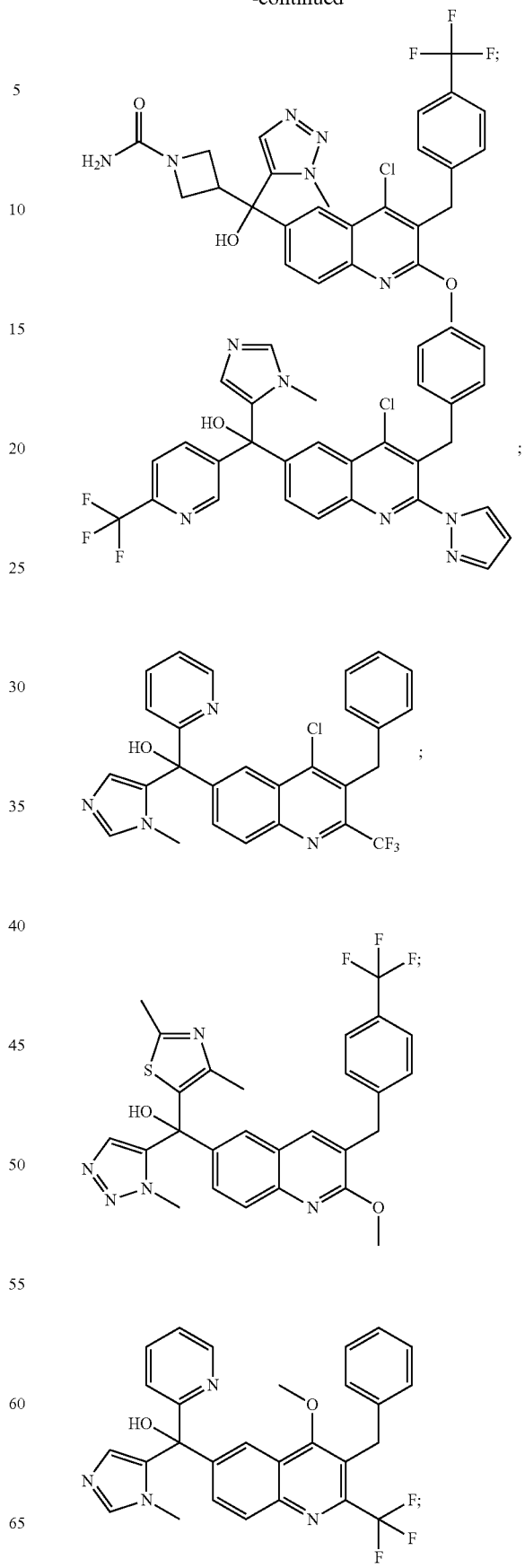

29
-continued
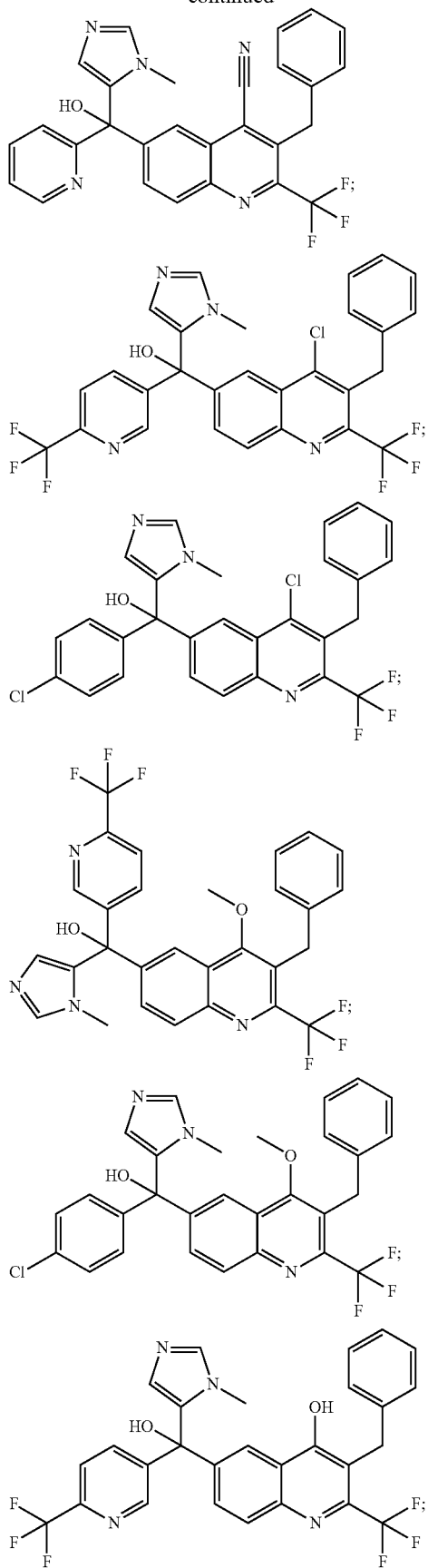
30
-continued
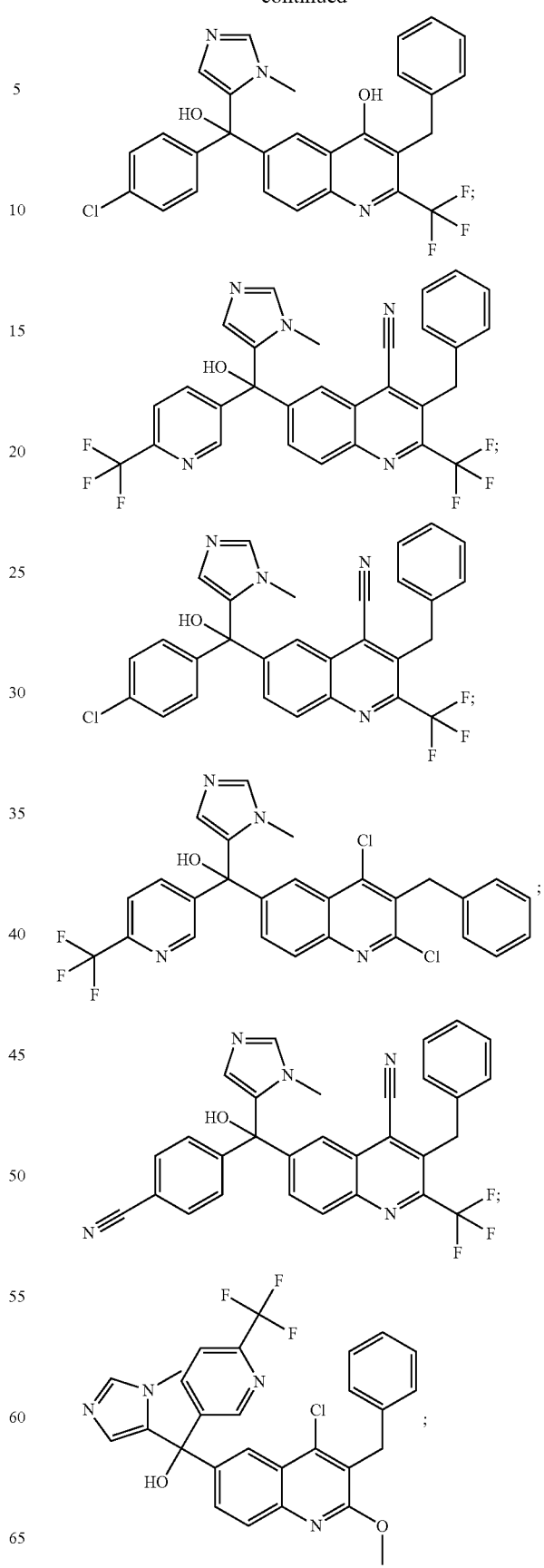

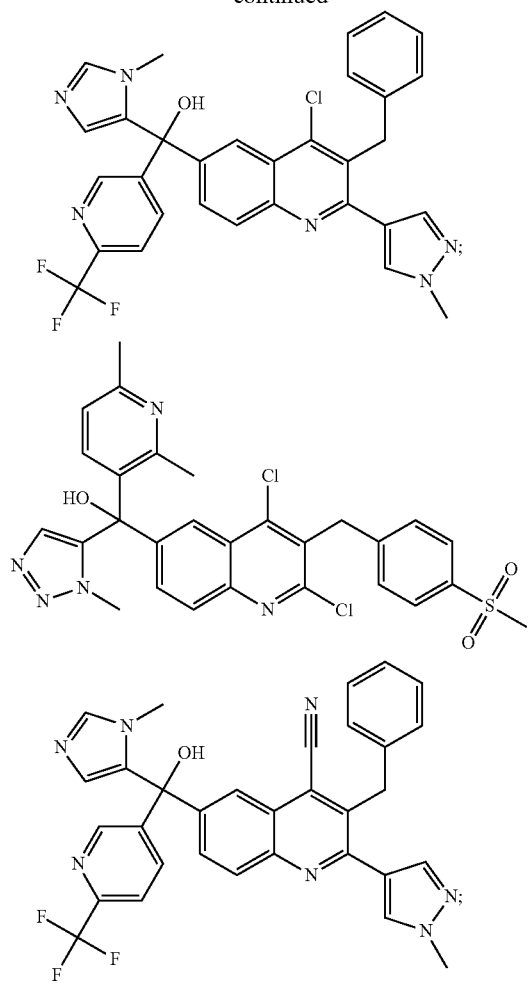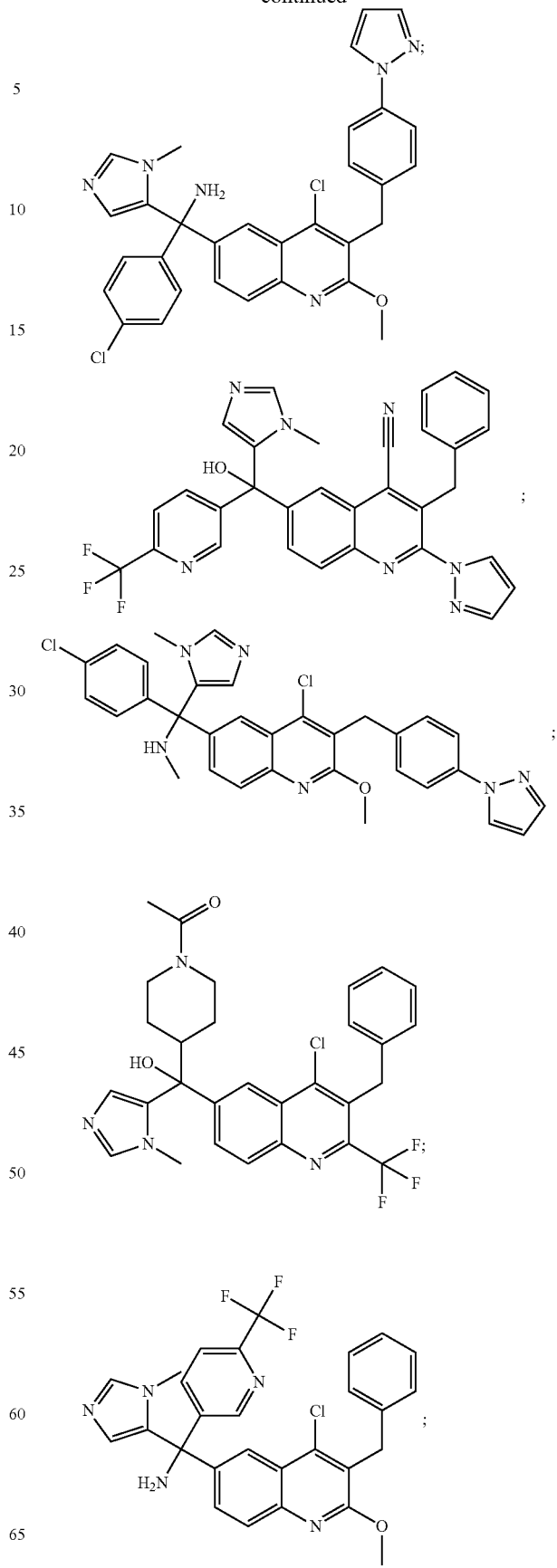

33
-continued
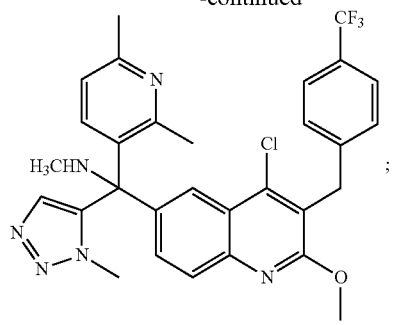
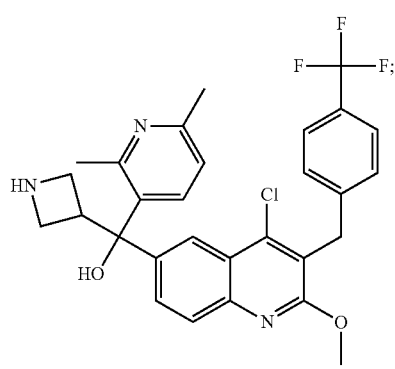
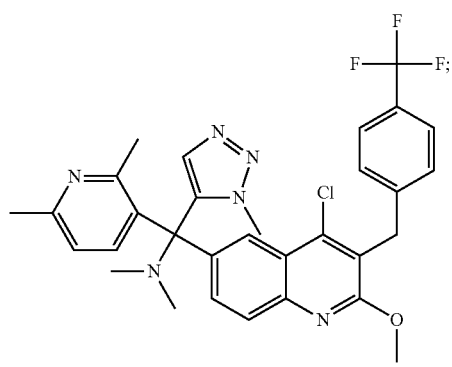
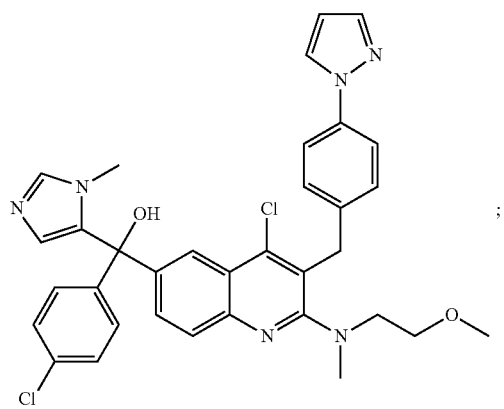
34
-continued
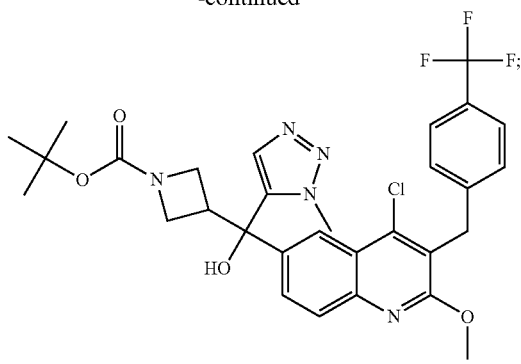
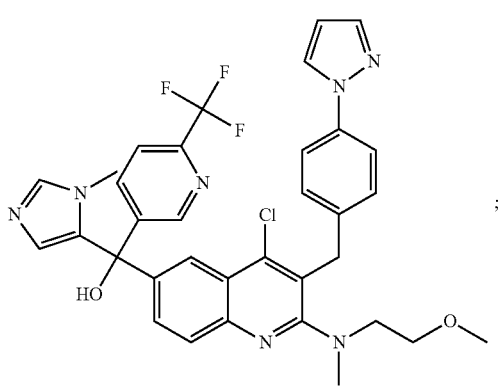
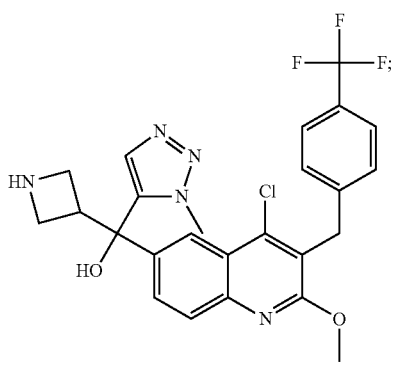
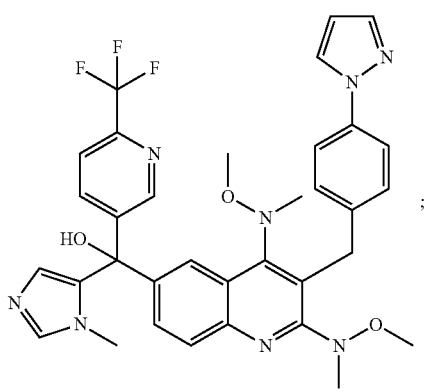

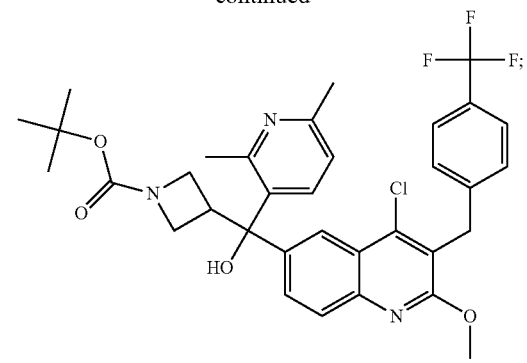
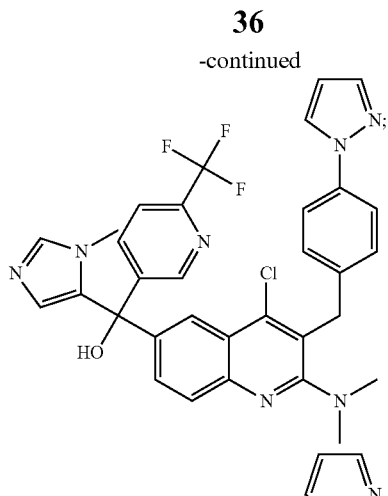
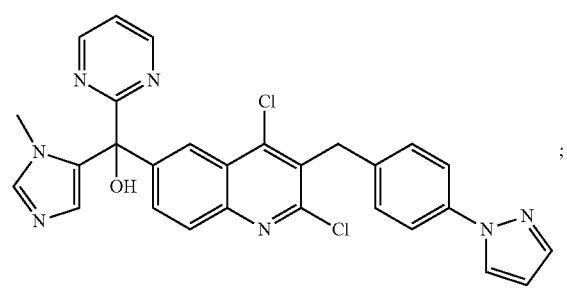
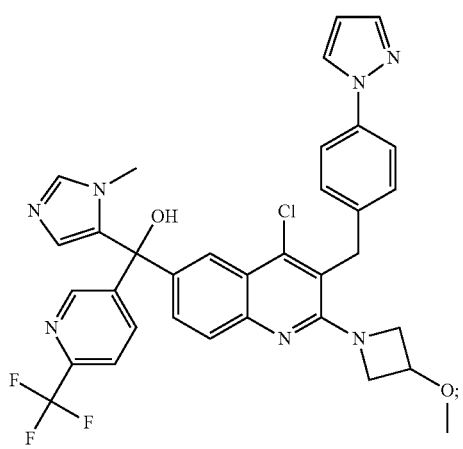
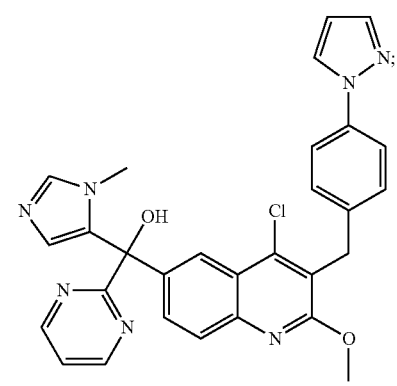
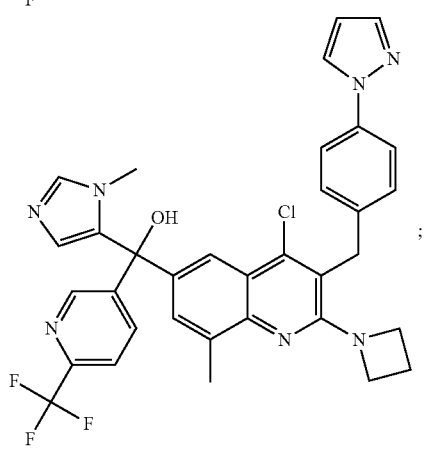
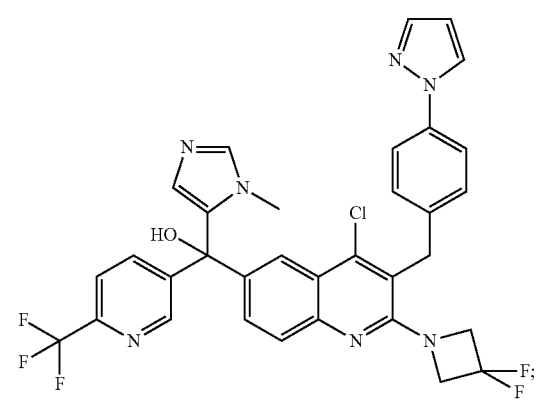

37
-continued
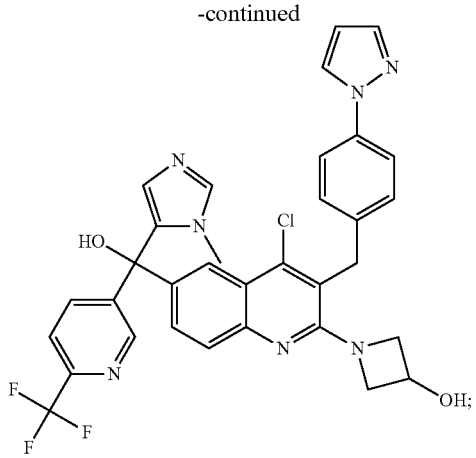
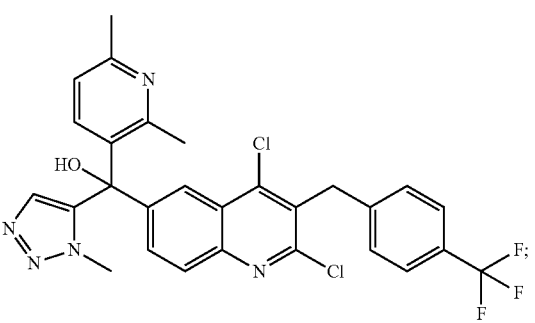
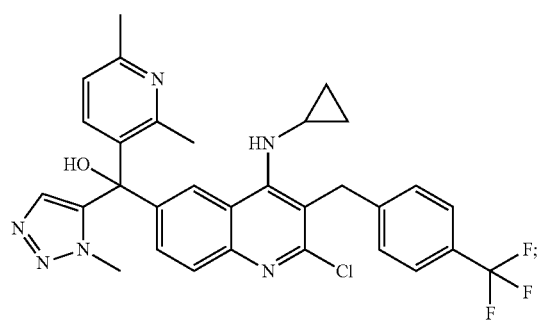
38
-continued
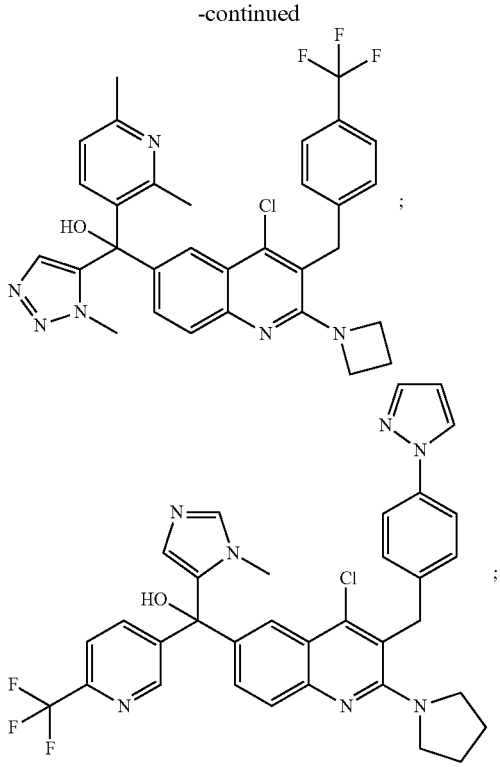
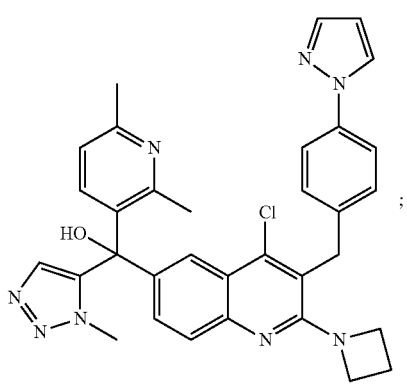
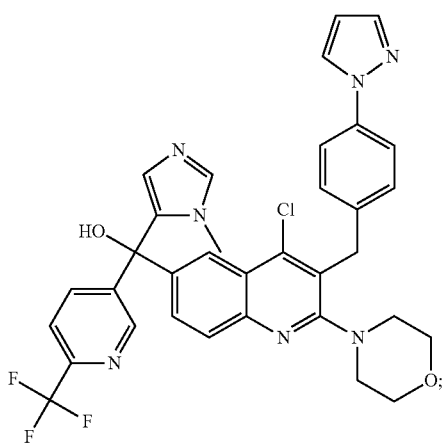

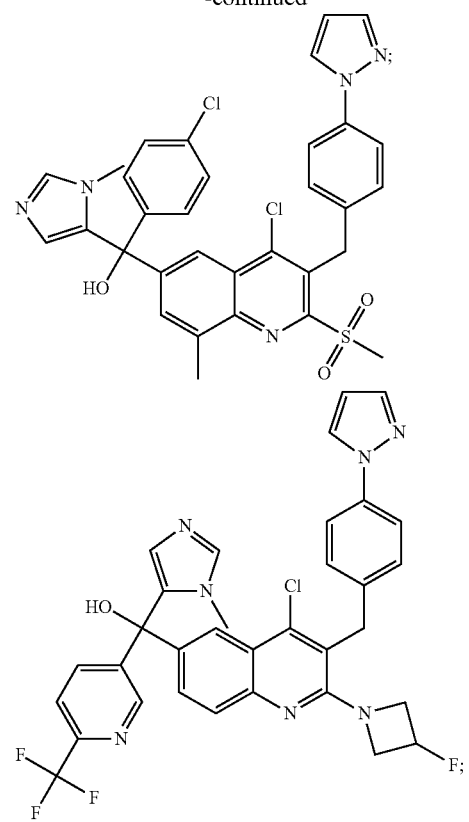
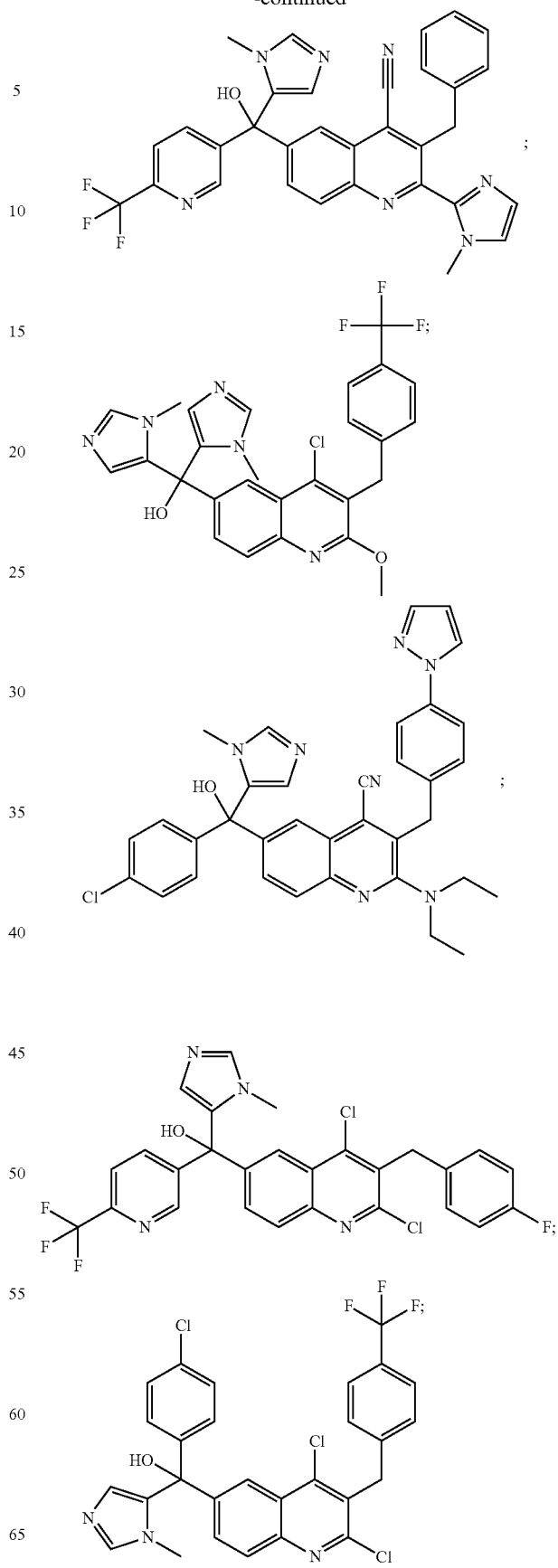

41
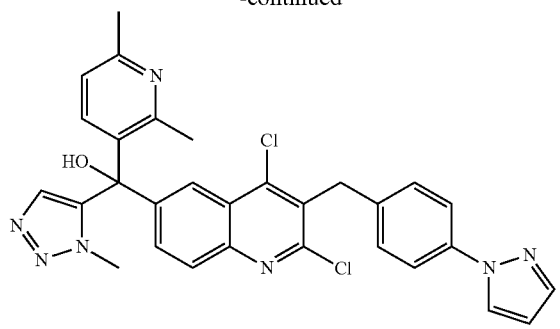
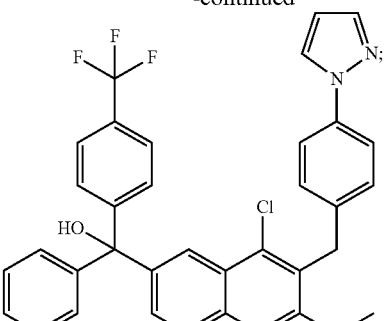
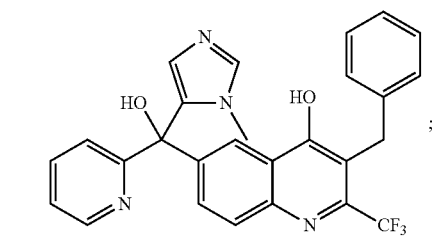
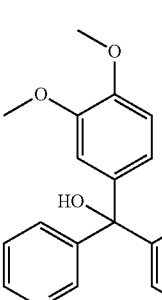
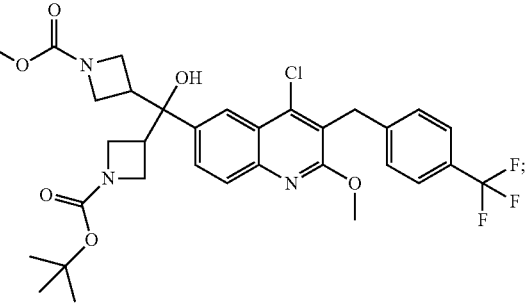
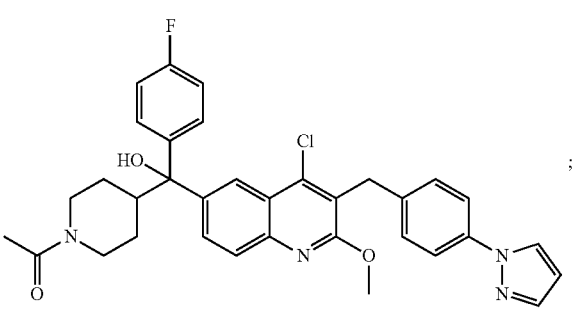
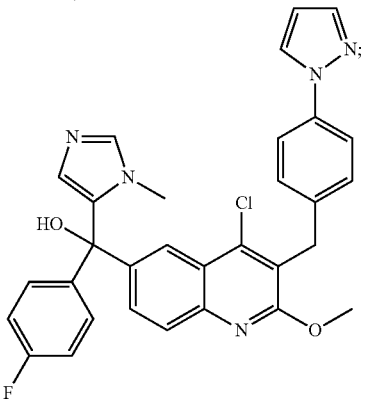
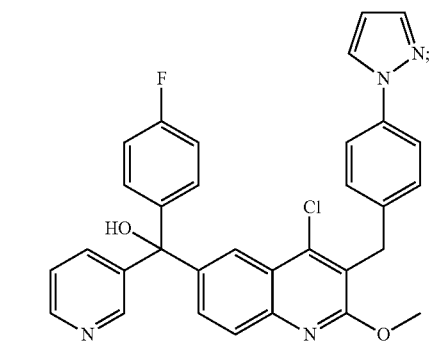
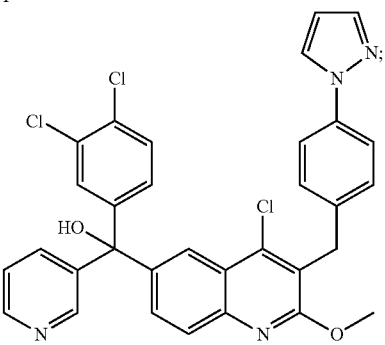

-continued

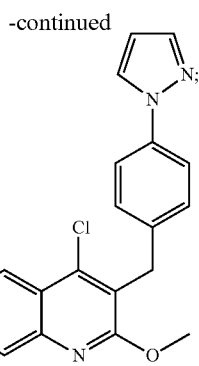

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

DEFINITIONS

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with aberrant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

The compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

Furthermore, it is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of Formula I may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereocenter, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.

Å angstrom
Ac acetyl
$Ac_2O$ acetic anhydride
Boc tert-butyloxy carbonyl
BHT butylated hydroxytoluene
br broad
Bu butyl
n-BuLi n-butyl lithium
CDI 1,1'-carbonyldiimidazole
d doublet
dba dibenzylideneacetone
DCM dichloromethane
Dess-Martin periodinane 1,1,1-tris(acetyloxy)-1,1-dihydro-1,2-benziodoxol-3-(1H)-one
DMA dimethylacetamide
DMF N,N-dimethylformamide
DMSO dimethyl sulfoxide
dppf (diphenylphosphino)ferrocene
Eaton's Reagent 7.7 wt % phosphorus pentoxide solution in methanesulfonic acid
EDCI N-(3-dimethylaminopropyl)-N'-ethylcarbodiimide hydrochloride
EDTA ethylenediaminetetraacetic acid
EtMgBr ethylmagnesium bromide
ESI electrospray ionization
Et ethyl
$Et_2O$ diethyl ether
EtOAc ethyl acetate
EtOH ethyl alcohol
$Et_3SiCl$ chlorotriethylsilane
FCC flash column chromatography
HATU O-(7-azabenzotriazol-1-yl)-N,N,N',N'-tetramethyluronium hexafluorophosphate
HPLC high pressure liquid chromatography
Hunig's base diisopropylethylamine
Hz hertz
i-PrOH isopropyl alcohol
KHMDS potassium bis(trimethylsilyl)amide
LCMS liquid chromatography-mass spectrometry
m multiplet
M molar (moles/liter)
Me methyl
Meldrum's acid 2,2-dimethyl-1,3-dioxane-4,6-dione
MeOH methanol
MHz megahertz
min minutes
mL milliliters
MTBE methyl tertiary butyl ether
m/z mass to charge ratio
nm nanometers
NaOiPr sodium isopropoxide
NMP N-methyl-2-pyrrolidone
NMR nuclear magnetic resonance
Ph phenyl
ppm parts per million
Pr propyl
q quartet
RP-HPLC reverse phase high pressure liquid chromatography
s singlet
t triplet
TEA triethylamine
TEMPO (2,2,6,6-tetramethylpiperidin-1-yl)oxidanyl
TFA trifluoroacetic acid
THF tetrahydrofuran
TLC thin layer chromatography
UV ultra-violet
X-Phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Scheme 1 describes the preparation of 6-bromo or 6-iodoquinolines of formula VI by various methods (path 1 to 8). As illustrated in path 1, the 2-substituted malonic acids IV (Q=H) can be prepared by addition of aromatic aldehydes to Meldrum's acid or dialkyl malonates as described by D. B. Ramachary et al. (*Tetrahedron Letters* 47 (2006) 651-656) followed by aqueous base hydrolysis under either microwave conditions or by heating at temperatures between 100 and 115° C., or treatment with an acid such as trifluoracetic acid in water at temperatures ranging from room temperature to 100° C. Haloanilines V (Z=Br or I) can be condensed with malonic acids IV (Q=H) in phosphorus oxychloride at temperatures between 80-120° C. affording 6-haloquinolines VI wherein $R^5$ and $R^7$ are Cl. Displacement of the 2-Cl of 2,4-dichloroquinoline VI with sodium alkoxides can be accomplished in an alcoholic solvent such as methanol, ethanol or isopropanol or at elevated temperatures in a non-polar solvent such as toluene (Alan Osborne et. al. *J. Chem. Soc. Perkin Trans.* 1 (1993) 181-184 and *J. Chem. Research* (S), 2002, 4) to provide substituted quinolines VI wherein $R^5$ is Cl and $R^7$ is Oalkyl. Alternatively, as shown in path 2, the haloanilines V can be treated in one pot directly with Meldrum's acid then subsequently heated in the presence of Eaton's reagent as described by W. T. Gao, et. al. (*Synthetic Communications* 40 (2010) 732) to form the 4-hydroxy-2(1H)-quinolinone XLI. Once treated with phosphorus oxychloride as previously described, the resulting 2,4-dichloroquinolines XLII can be deprotonated with a strong base such as lithium diisopropylamide and then added to substituted benzyl bromides to afford the intermediate quinolines VI (wherein $R^5$ and $R^7$ are chloro). In path 3, methyl 2-amino-5-halobenzoates VII can undergo acylation with acid chlorides VIII in the presence of a base such as triethylamine to form an amide intermediate, which can be further treated with a base, such as sodium ethoxide or potassium bis(trimethylsilyl)amide, affording 6-halo-4-hydroxyquinolin-2(1H)-ones IX. Conversion of hydroxyquinolin-2(1H)-ones IX to 2,4-dichloroquinolines VI can be carried out in phosphorus oxychloride at elevated temperatures. Displacement of the Cl of 2,4-dichloroquinolines VI with disubstituted amines, such as $NHMe_2$, $NHEt_2$, or NHMeEt, can be done in a hot polar solvent, such as MeOH, EtOH, or DMF to provide 2-N(alkyl)$_2$ quinolines VI wherein $R^7$ is N(alkyl)$_2$. In path 4, amides XI can be generated from anilines V and acids X in the presence of an appropriate coupling agent such as EDCI or HATU and a base such as Et$_3$N. In-situ formylation under Vilsmeier-Haack conditions (POCl$_3$/DMF) followed by heating to promote ring cyclization as described in WO2007014940 can provide 2-chloroquinolines VI wherein $R^5$ is H and $R^7$ is Cl.

Scheme 1

PATH 1

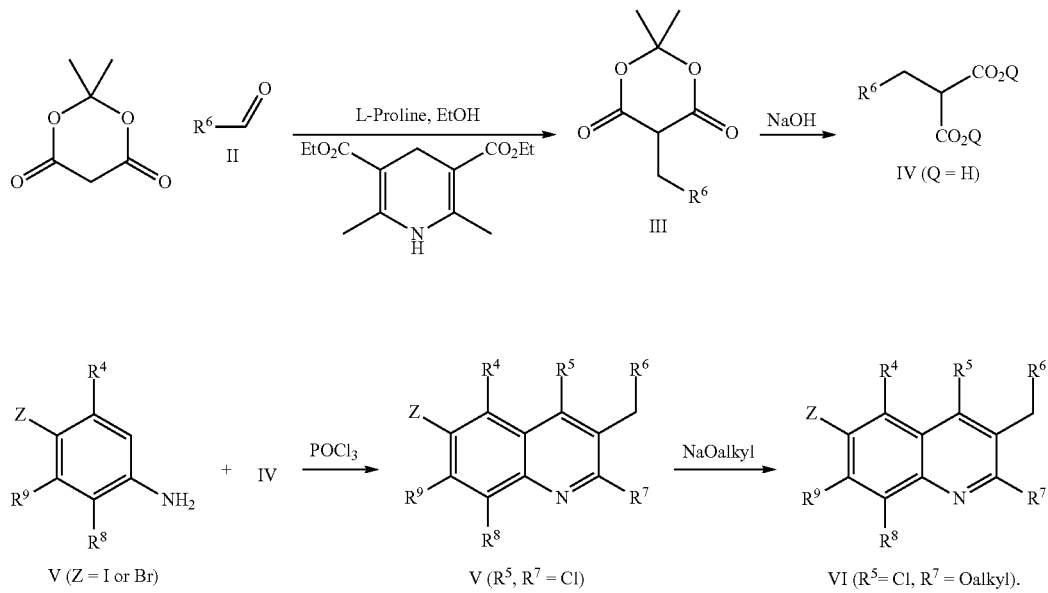

PATH 2

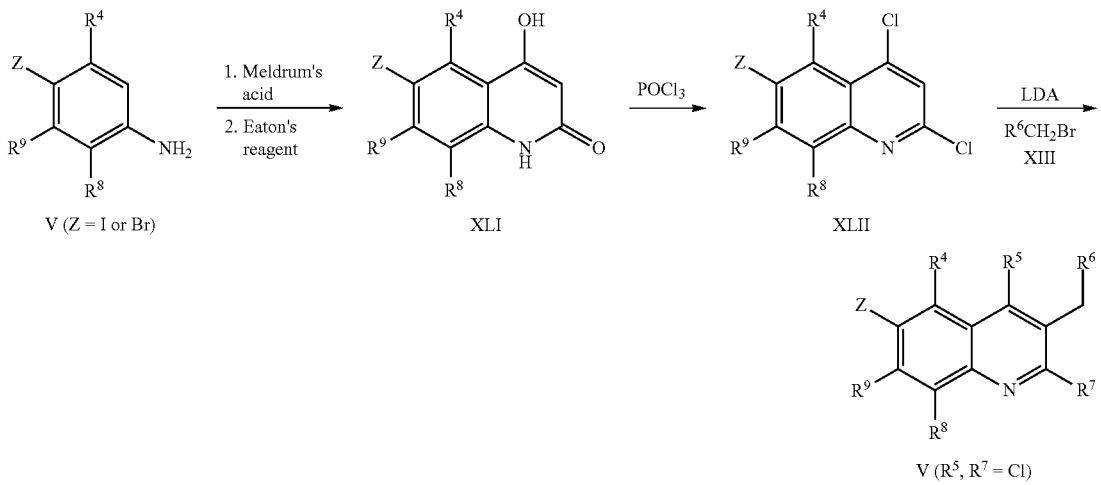

PATH 3

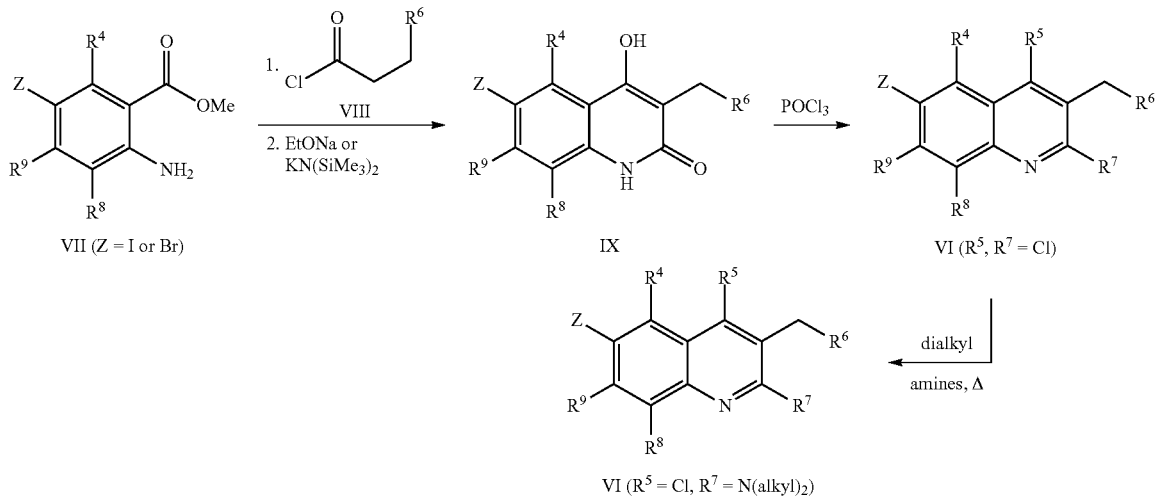

PATH 4

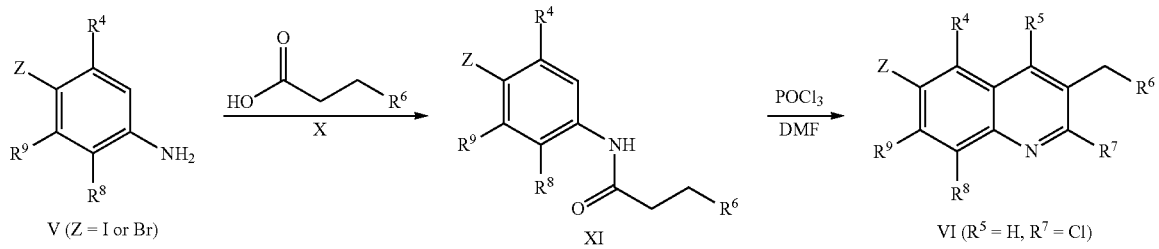

PATH 5

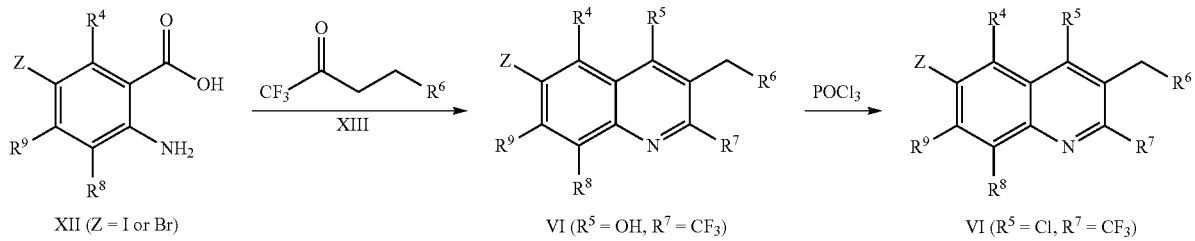

Compounds of Formula VI wherein $R^7$ is trifluoromethyl, can be prepared starting from the 2-carboxyaniline XII as described in path 5. One pot addition of 1,1,1-trifluoro-4-arylbutan-2-one XIII to 2-aminobenzoic acids XII and cyclization with Eaton's reagent at elevated temperatures yields 4-hydroxy-2-trifluoromethylquinolines VI, wherein $R^5$ is OH and $R^7$ is $CF_3$. The hydroxyl group could then be converted to chloro upon heating in phosphorus oxychloride to provide 6-bromo or 6-iodoquinolines VI wherein $R^5$ is Cl and $R^7$ is $CF_3$.

Scheme 1 cont'd

PATH 6

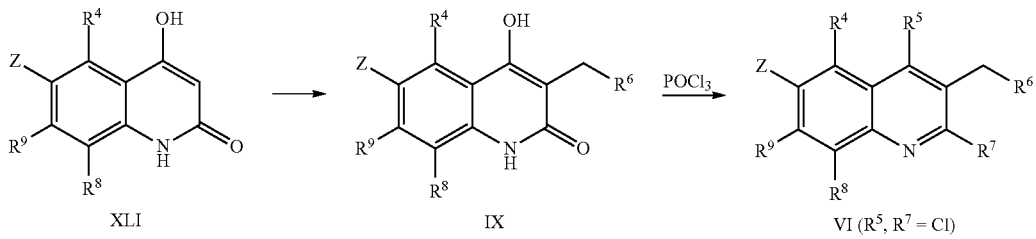

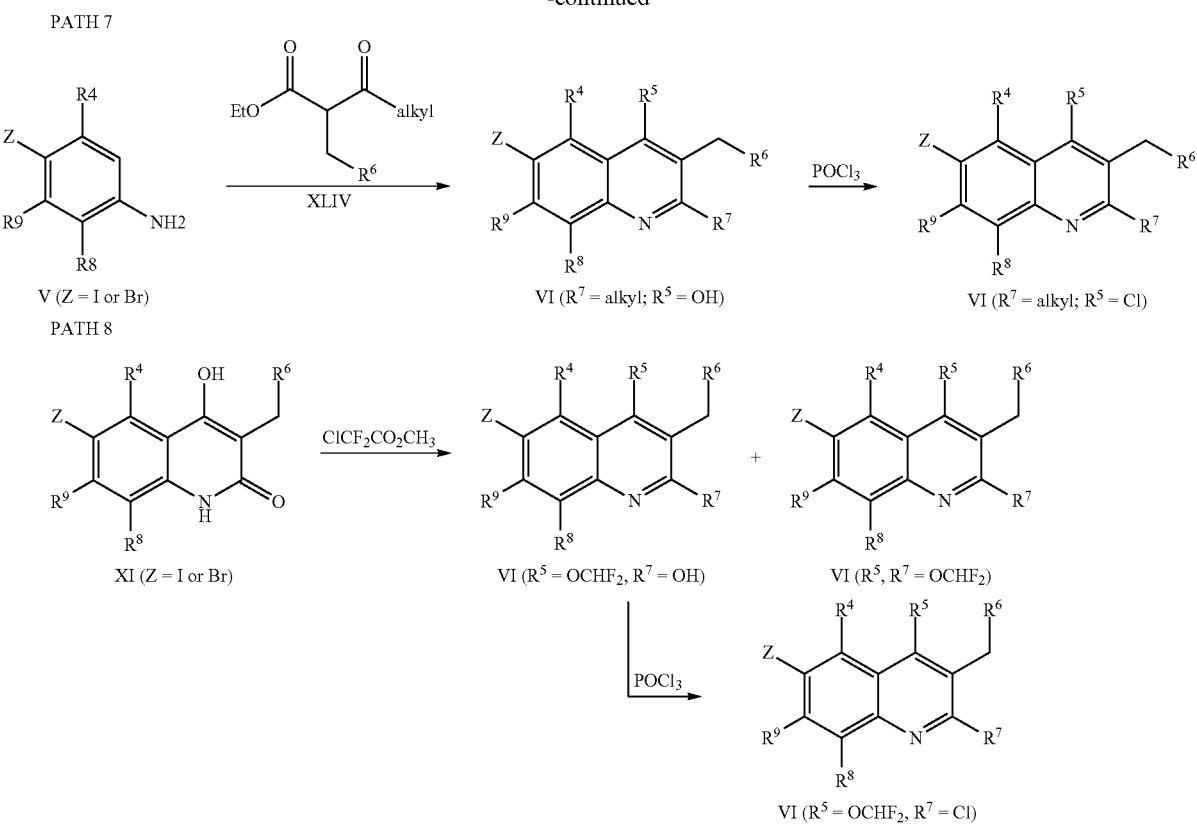

As shown in path 6, compounds of Formula VI can also be prepared from 4-hydroxy-2(1H)-quinolinones XLI by condensation with substituted aldehydes of the formula $R^6$CHO in the presence of a Hantzsch ester, such as diethyl 2,6-dimethyl-1,4-dihydropyridine-3,5-dicarboxylate, in solvents like ethanol and pyridine to afford 2,4-dihydroxyquinolines IX. Further treatment with phosphorus oxychloride as previously described, can provide quinolines of Formula VI (wherein $R^5$ and $R^7$ are chloro).

Compounds of Formula VI, wherein $R^7$ is alkyl, can be prepared as illustrated in path 7. Intermediates of Formula XLIV can be prepared by deprotonation of β-keto esters, such as ethyl 3-oxobutanoate or ethyl 3-oxopentanoate, with a base like sodium hydride followed by alkylation with substituted alkyl halides such as $R^6$CH$_2$Br or $R^6$CH$_2$I. Condensation with 4-haloanilines (V) in the presence of an acid, such as para-toluenesulfonic acid (PTSA), in toluene as solvent with concomitant removal of water followed by intramolecular cyclization at elevated temperature affords 4-hydroxy quinolines VI, wherein $R^5$ is OH and $R^7$ is alkyl. The hydroxyl group could then be converted to a chloro group upon heating in acetonitrile with phosphorus oxychloride to provide 6-bromo or 6-iodoquinolines VI wherein $R^5$ is Cl and $R^7$ is alkyl.

Path 8 describes how one skilled in the art could generate compounds of Formula VI wherein $R^5$ is difluoromethoxy and $R^7$ is hydroxyl or chloro and compounds of Formula VI wherein both $R^5$ and $R^7$ are difluoromethoxy by treating hydroxyquinolin-2(1H)-ones XI with 2-chloro-2,2-difluoroacetate and a base such as potassium carbonate in a polar aprotic solvent such as DMF. The 6-haloquinolin-2-one VI ($R^5$ is OCHF$_2$ and $R^7$ is OH) can be subsequently treated with phosphorus oxychloride as previously described to provide 6-haloquinolines VI wherein $R^5$ is difluoromethoxy and $R^7$ is Cl.

Scheme 2

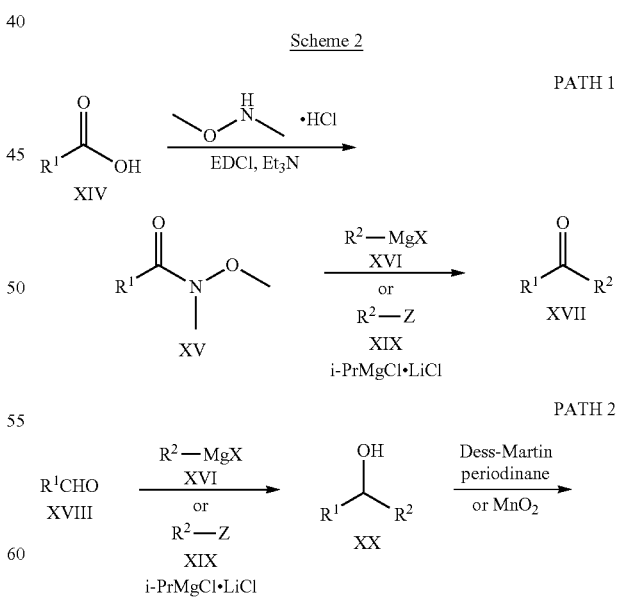

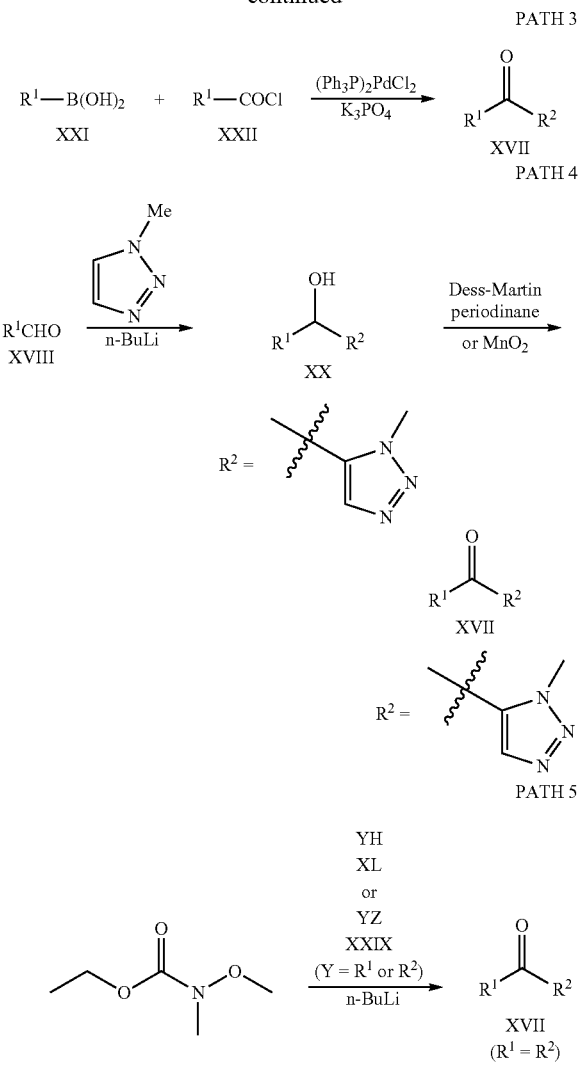

Scheme 2 outlines synthetic routes (path 1 to 5) to aryl ketones of Formula XVII. In path 1, Weinreb amides XV can be prepared from carboxylic acids XIV and N,O-dimethylhydroxylamine hydrochloride in the presence of a base such as triethylamine or Hunig's base and a coupling reagent such as EDCI. The amides XV can be further treated with Grignard reagents such as $R^2MgX$ (X is Br or Cl) XVI that can be obtained commercially or preformed by treatment of $R^2Z$ XIX (Z=Br or I) with organometallic reagents such as i-PrMgCl or EtMgCl in THF or dichloromethane to afford the ketones XVII, wherein $R^1$ and $R^2$ are as defined above. As shown in path 2, aldehydes XVIII can also be treated with Grignard reagents, as described in path 1, to afford the intermediate alcohols XX. Subsequent oxidation with Dess-Martin periodinane or $MnO_2$ in a suitable solvent such as 1,4-dioxane or tetrahydrofuran at elevated temperatures can provide ketones XVII. path 3, which employs palladium catalyzed cross-coupling of arylboronic acids XXI with acid chlorides XXII using $K_3PO_4$ as a base and $(Ph_3P)_2PdCl_2$ as a catalyst in a high boiling non-polar solvent such as toluene, can also be used to generate ketones XVII. In path 4, aryl ketones XVII, wherein $R^2$ is triazolyl, can be prepared by treatment of 1-methyl-1H-1,2,3-triazole, made according to PCT Int. Appl. 2008098104, with n-butyllithium followed by reaction with aldehydes XVIII to yield alcohols XX, which can undergo oxidation with Dess-Martin periodinane or $MnO_2$. Path 5 exemplifies the preparation of symmetrical ketones XVII, wherein $R^1$ and $R^2$ are the same. As illustrated, an aryl or heteroaryl group containing an acidic proton XL (Y=$R^1$ or $R^2$) can be deprotonated in the presence of a strong base such as n-butyllithium once solubilized in a preferred solvent such as tetrahydrofuran at temperatures between 0 and −78° C. then added in excess to ethyl methoxy(methyl) carbamate to provide aryl ketones XVII wherein $R^1$ and $R^2$ are the same. Aryl or heteroaryl bromide XXIX can also be lithiated through a lithium/halogen exchange with n-butyllithium before adding in excess to ethyl methoxy(methyl) carbamate as previously described to provide symmetrical ketones XVII.

Scheme 3

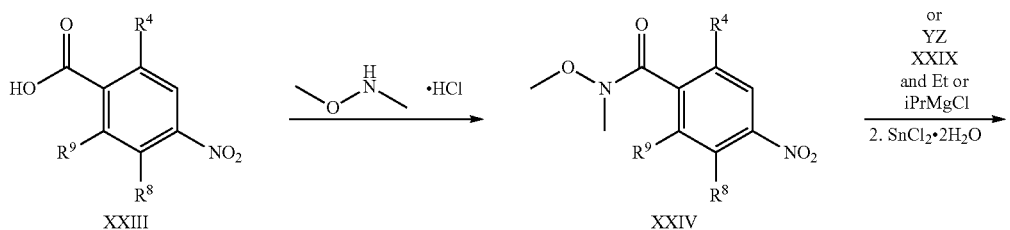

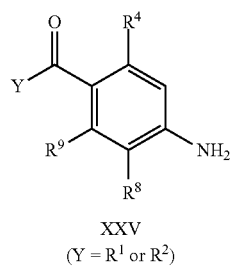 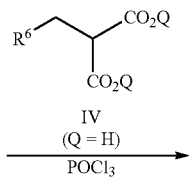 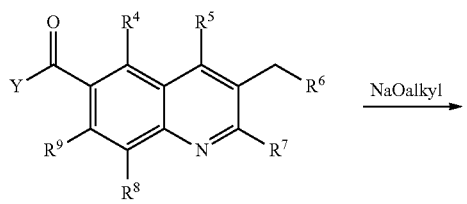
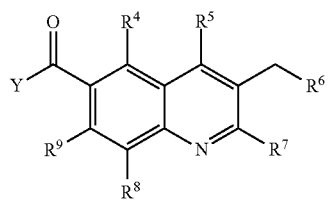
PATH 2
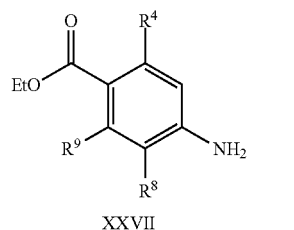  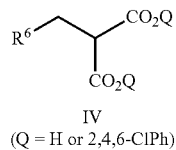
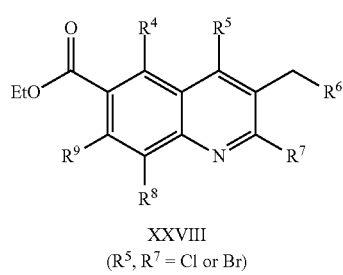 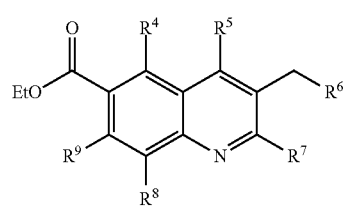
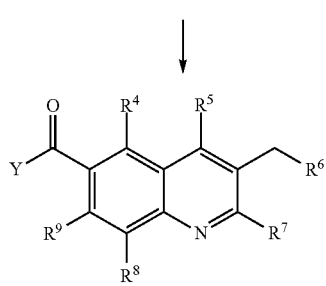
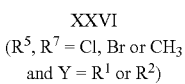

PATH 3

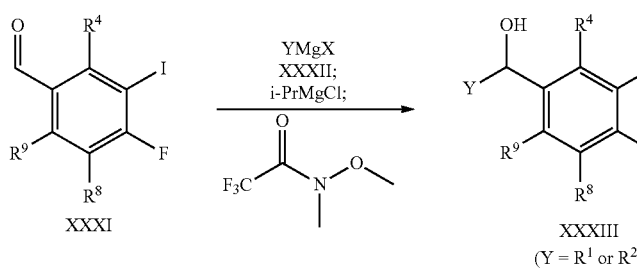

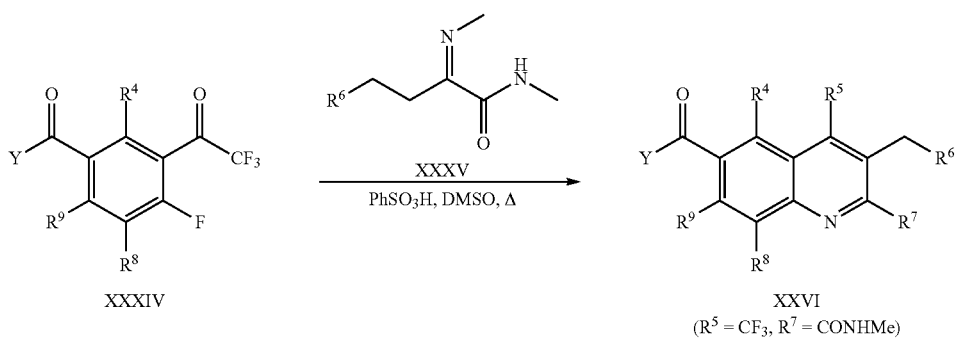

Scheme 3 shows examples of methods used to introduce either $R^1$ or $R^2$ to form ketoquinolines of Formula XXVI (path 1 to 3). As shown in path 1, Weinreb amides XXIV can be formed from 4-nitrobenzoic acids XXIII and N,O-dimethylhydroxylamine hydrochloride in the presence of a coupling reagent, for example, EDCI and a base such as triethylamine or Hunig's base in a chlorinated solvent at ambient temperature. Ketoanilines XXV can be prepared in two steps by reaction of the Weinreb amide XXIV with a Grignard reagent such as YMgX XXXII (X is bromide or chloride and Y is $R^1$ or $R^2$) or one that is pre-formed by combining YZ XXIX (Z=Br or I and Y is $R^1$ or $R^2$) with an organometallic reagent, such as EtMgCl or iPrMgCl, at 0° C. to ambient temperature to introduce ketone functionality followed by reduction of the nitro group by using an appropriate reducing agent such as $SnCl_2·2H_2O$ in a polar solvent such as ethanol or THF at refluxing temperatures. The ketoanilines XXV can then be treated with malonic acids IV in phosphorus oxychloride at elevated temperatures to provide ketoquinolines XXVI wherein $R^5$ and $R^7$ are Cl and Y is $R^1$ or $R^2$. The 2-Cl group can be displaced with NaOalkyl in an appropriate alcoholic solvent such as methanol, ethanol or isopropanol or in a nonpolar solvent such as toluene at elevated temperatures to afford quinolines XXVI, wherein $R^5$ is Cl and $R^7$ is Oalkyl. Alternatively, as illustrated in path 2, ethyl 4-aminobenzoates XXVII can be condensed with either malonic acid IV (Q=H) in phosphorus oxychloride at elevated temperatures or treated with activated malonic acid esters such as bis(2,4,6-trichlorophenyl)-2-benzyl malonates (Q=2,4,6-trichlorophenyl) at high temperatures in the microwave followed by heating in phosphoryl tribromide or phosphorus oxychloride to afford cyclized quinolines XXVIII wherein $R^5$ and $R^7$ are Cl or Br. The 2,4-dibromoquinolines XXVIII can be further treated with trimethylboroxine under Suzuki reaction conditions to provide 2,4-dimethylquinolines XXX. The ethyl ester of quinolines XXVIII and XXX can then be either converted to the Weinreb amide using N,O-dimethylhydroxylamine hydrochloride and isopropylmagnesium chloride before addition of aryl magnesium bromide or chloride YMgX XXXII ($Y=R^1$ or $R^2$) as previously described or treated directly with aryl halides XXIX (Z=Br or I and $Y=R^1$ or $R^2$) and n-butyllithium at −78 to 0° C. to provide ketoquinolines XXVI, wherein $R^5$ and $R^7$ are Cl, Br or $CH_3$ and $Y=R^1$ or $R^2$ and are as defined above.

In path 3, one-pot reaction of aldehydes XXXI and Grignard reagents such as YMgX XXXII (X is bromide or chloride and Y is $R^1$ or $R^2$) followed by treatment with i-PrMgCl and addition of 2,2,2-trifluoro-N-methoxy-N-methylacetamide yields hydroxyl compounds XXXIII. The hydroxyl group can be oxidized using, for example, bleach and TEMPO. Fluoro displacement can then be achieved with ammonia in hot DMSO to provide anilines XXXIV. In the presence of benzenesulfonic acid, condensation of anilines XXXIV and N-methyl-2-(methylimino)-4-arylbutanamide XXXV in hot DMSO furnishes ketoquinolines XXVI wherein $R^5$ is $CF_3$, $R^7$ is CONHMe and Y is $R^1$ or $R^2$ and are as defined above.

Scheme 4

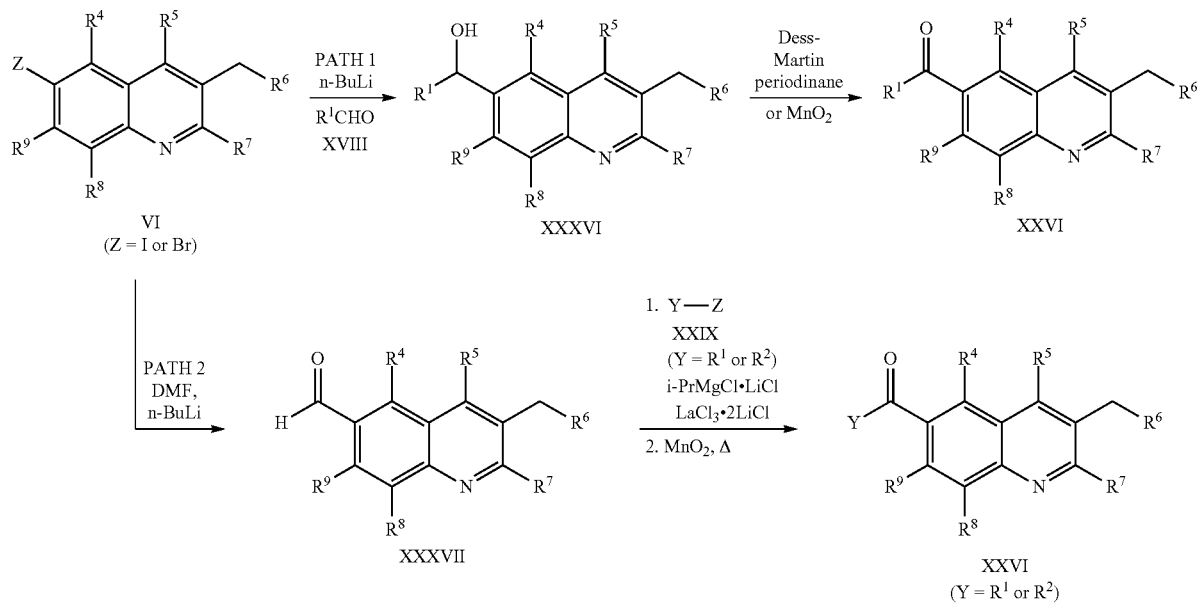

Synthesis of the intermediate ketoquinolines XXVI may also be achieved via chemical routes shown in Scheme 4. In path 1, treatment of 6-bromo or 6-iodoquinolines VI with n-BuLi followed by addition of aldehydes XVIII, at temperatures between 0 and −78° C., provides secondary alcohol quinolines XXXVI. Final oxidation to ketoquinoline XXVI can be achieved with Dess-Martin periodinane or $MnO_2$, as previously described. Alternatively, 6-bromo or 6-iodoquinolines VI can be treated with n-BuLi at −78° C. then quenched with DMF to afford quinoline carboxaldehydes XXXVII. Ketoquinolines XXVI, wherein Y is $R^1$ or $R^2$, can then be obtained in a two-step process by addition of the aldehydes XXXVII to a reaction mixture of aryl halide XXIX (Y=$R^1$ or $R^2$ and Z=Br or I) and i-PrMgCl.LiCl followed by oxidation with $MnO_2$ (path 2).

Scheme 5

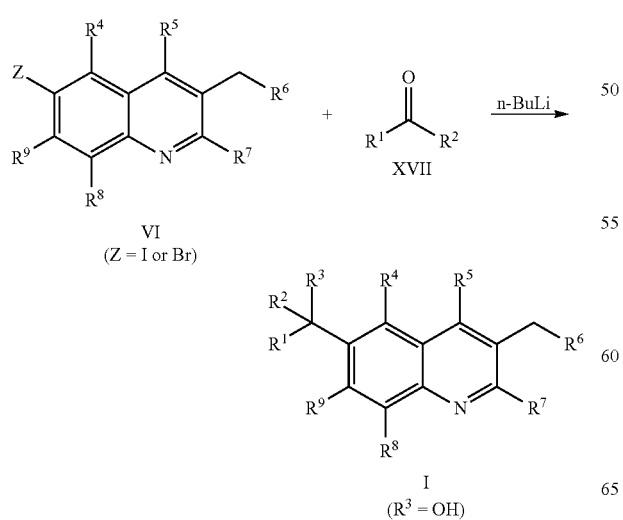

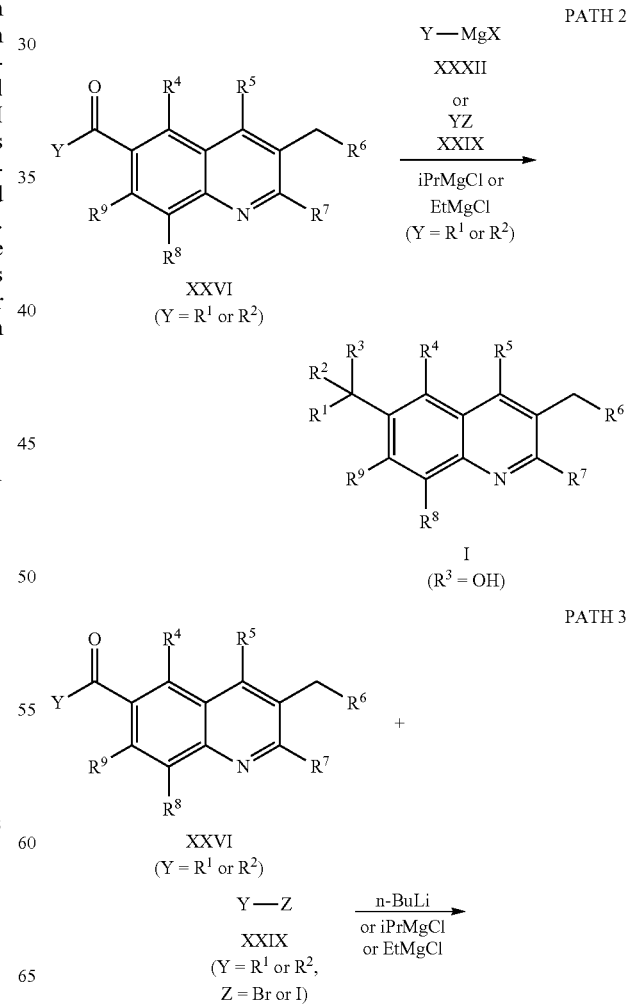

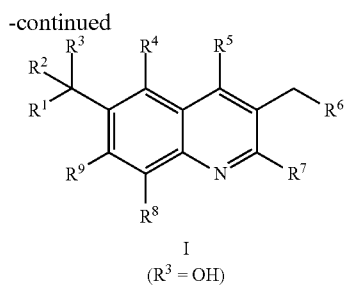

Scheme 5 exemplifies synthetic methods that could be used to prepare compounds of Formula I (paths 1-3). As illustrated in path 1, a mixture of the 6-bromo or 6-iodoquinolines VI in an appropriate solvent such as THF can be either premixed with the ketones XVII at −78° C. followed by addition of n-BuLi or can be pretreated with n-BuLi at −78° C. prior to the addition of the ketones XVII to afford the tertiary alcohols of Formula I, wherein $R^3$ is OH.

Path 2 illustrates the formation of tertiary alcohols of Formula I by treatment of the ketoquinolines XXVI (Y is $R^1$ or $R^2$) with Grignard reagents XXXII that are either commercially available or can be prepared by a metal-halogen exchange of aryl halides XXIX with ethyl or isopropyl magnesium chloride as previously described. Similarly, as shown in path 3, an organometallic reagent, such as n-BuLi can be added to an aryl halide XXIX at temperatures between −78° C. and ambient temperature in a preferred solvent such as tetrahydrofuran followed by the addition of the quinoline ketone XXVI to afford the tertiary alcohols of Formula I wherein $R^3$ is OH and $R^1$ and $R^2$ are as defined above.

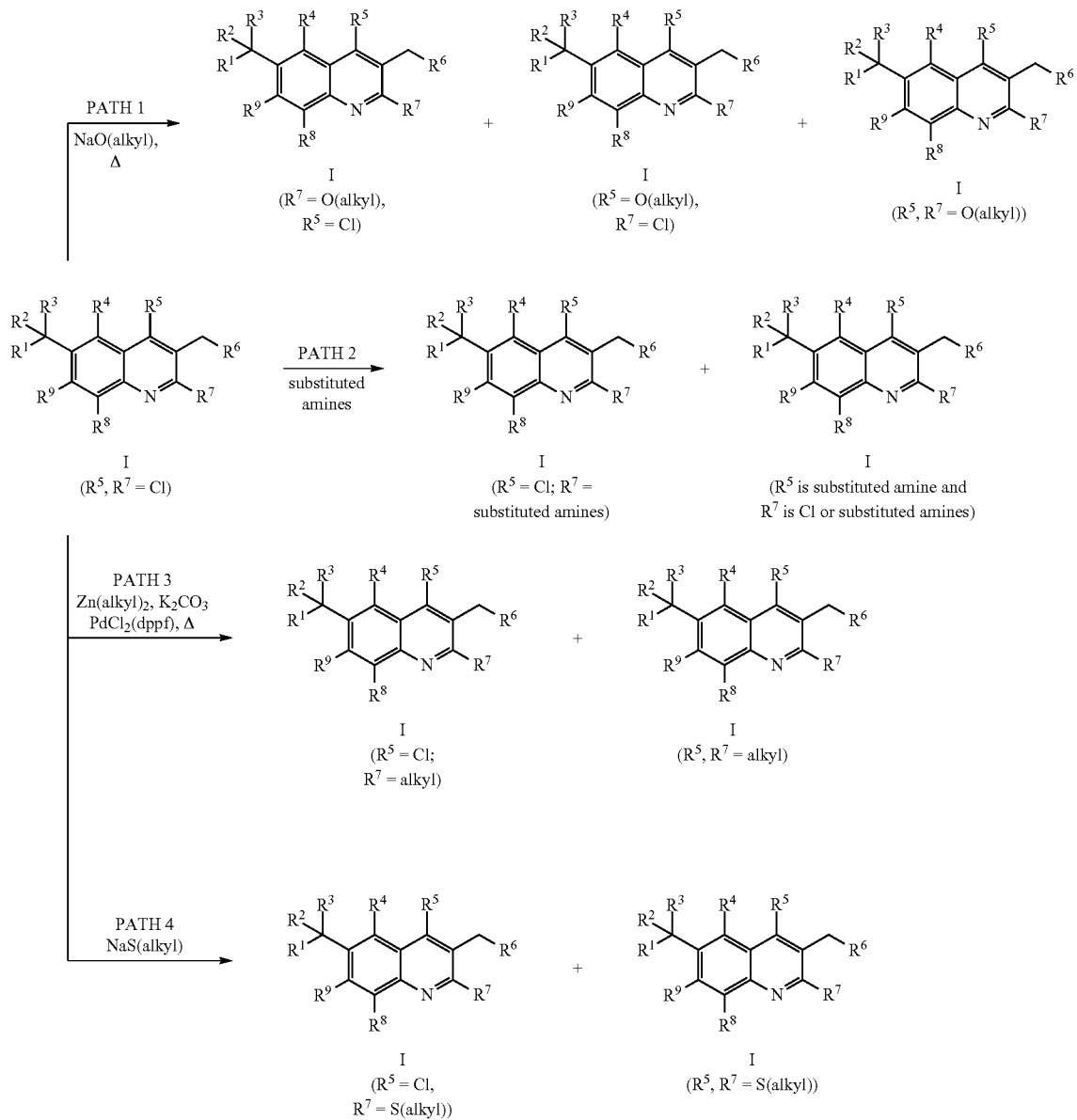

Scheme 6 illustrates methods used to synthesize compounds of Formula I wherein either the chlorine at $R^7$ or $R^5$ or at both $R^5$ and $R^7$ positions are replaced with nitrogen, oxygen, sulfur or alkyl groups. In path 1 and 4, nucleophilic displacement of 2,4-dichloroquinolines I ($R^5$ and $R^7$ are Cl) with NaO(alkyl), NaS(alkyl), such as NaOMe, NaSMe, NaOEt, or NaOiPr, in an appropriate solvent, such as MeOH, EtOH, i-PrOH or DMF at elevated temperatures or with substituted hydroxy reagents such as 2-methoxyethanol in the presence of a base like sodium hydride in a non-polar solvent such as toluene provides compounds of Formula I wherein $R^5$ is Cl and $R^7$ is O(alkyl), O(CH$_2$)$_2$OCH$_3$ or S(alkyl) and compounds of Formula I wherein $R^5$ and $R^7$ are O(alkyl) or S(alkyl). Likewise, nucleophilic displacement of 2,4-dichloroquinolines I ($R^5$ and $R^7$ are Cl) with primary or secondary alkyl amines, heterocyclic amines, or N,O-dimethylhydroxylamine in polar solvents such as MeOH, EtOH, Et$_2$NCHO, or DMF provides quinolines of Formula I (path 2) wherein $R^5$ is NH(alkyl), N(alkyl)$_2$, N(CH$_3$)OCH$_3$, or Cl, and $R^7$ is NH(alkyl), N(alkyl)$_2$, N(CH$_3$)OCH$_3$, NA$^1$A$^2$, NHC$_{(2-3)}$alkylNA$^1$A$^2$ or N(CH$_3$)C$_{(2-4)}$alkylNA$^1$A$^2$, wherein A$^1$ and A$^2$ are as defined above. Introduction of cyclic amides can be accomplished using Buchwald palladium catalyzed coupling conditions to provide compounds of Formula I, wherein $R^7$ are rings such as azetidin-2-ones or pyrrolidin-2-ones. Replacement of chlorine at positions 2 and 4 of quinolines I ($R^5$ and $R^7$ are Cl) with alkyl groups can be carried out using Zn(alkyl)$_2$ in the presence of K$_2$CO$_3$ and a palladium catalyst, such as PdCl$_2$(dppf), to afford 2-alkyl and 2,4-dialkylquinolines of Formula I (path 3).

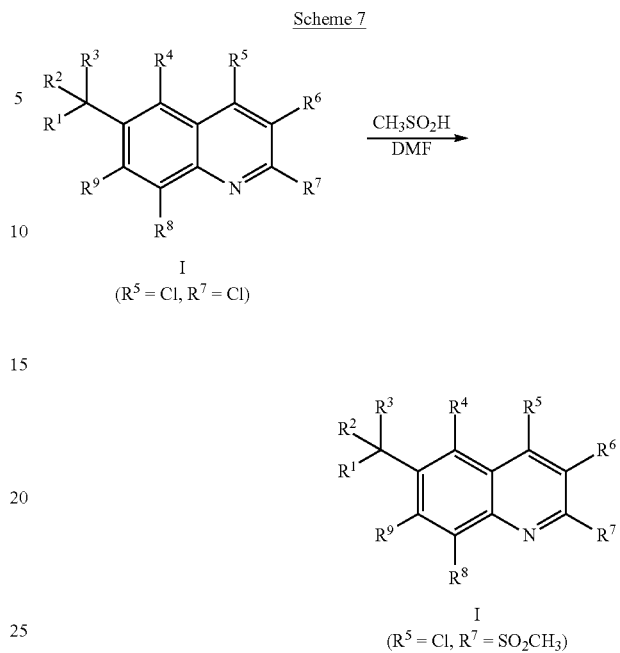

Scheme 7 illustrates methods used to prepare quinolines of Formula I wherein $R^7$ is SO$_2$CH$_3$. This can be accomplished by displacement of chlorine at the 2-position of 2,4-dichloroquinolines I by treatment with methanesulfinic acid in a solvent such as DMF under elevated temperature between 90 and 110° C.

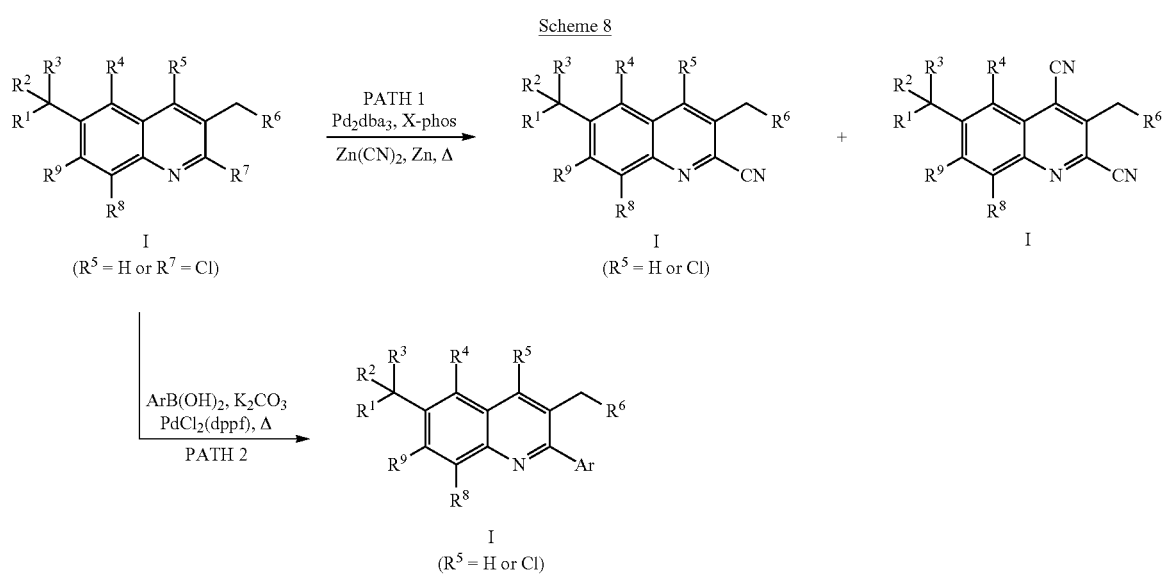

Synthetic routes to compounds of Formula I, wherein $R^5$ is H or Cl or CN, and $R^7$ is CN or aryl, are illustrated in Scheme 8. In path 1, cyanation of the 2,4-dichloroquinolines I with $Zn(CN)_2$ in the presence of Zn, a palladium catalyst, such as $Pd_2(dba)_3$, and a ligand, such as dppf or X-phos, at high temperatures can provide 2-CN and 2,4-diCN quinolines of Formula I. The 2,4-dichloroquinolines I can also undergo a Suzuki palladium catalyzed cross-coupling reaction with $ArB(OH)_2$ or $ArB(OR)_2$ with a palladium catalyst, such as $PdCl_2(dppf)$, yielding compounds of Formula I wherein $R^7$ is phenyl, substituted phenyl and five or six-membered heteroaryls such as furan, pyridine, pyridazine, pyrazine, pyrimidine, pyrrole, pyrazole, or imidazole (path 2).

As illustrated in Scheme 9, compounds of Formula I prepared in Schemes 6 and 7 wherein only $R^5$ is a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein $R^5$ is alkyl, O(alkyl) or CN and $R^7$ is as defined above. Palladium catalyzed hydrogenation, as shown in path 4, could also provide compounds of Formula I wherein $R^5$ is H.

Scheme 9

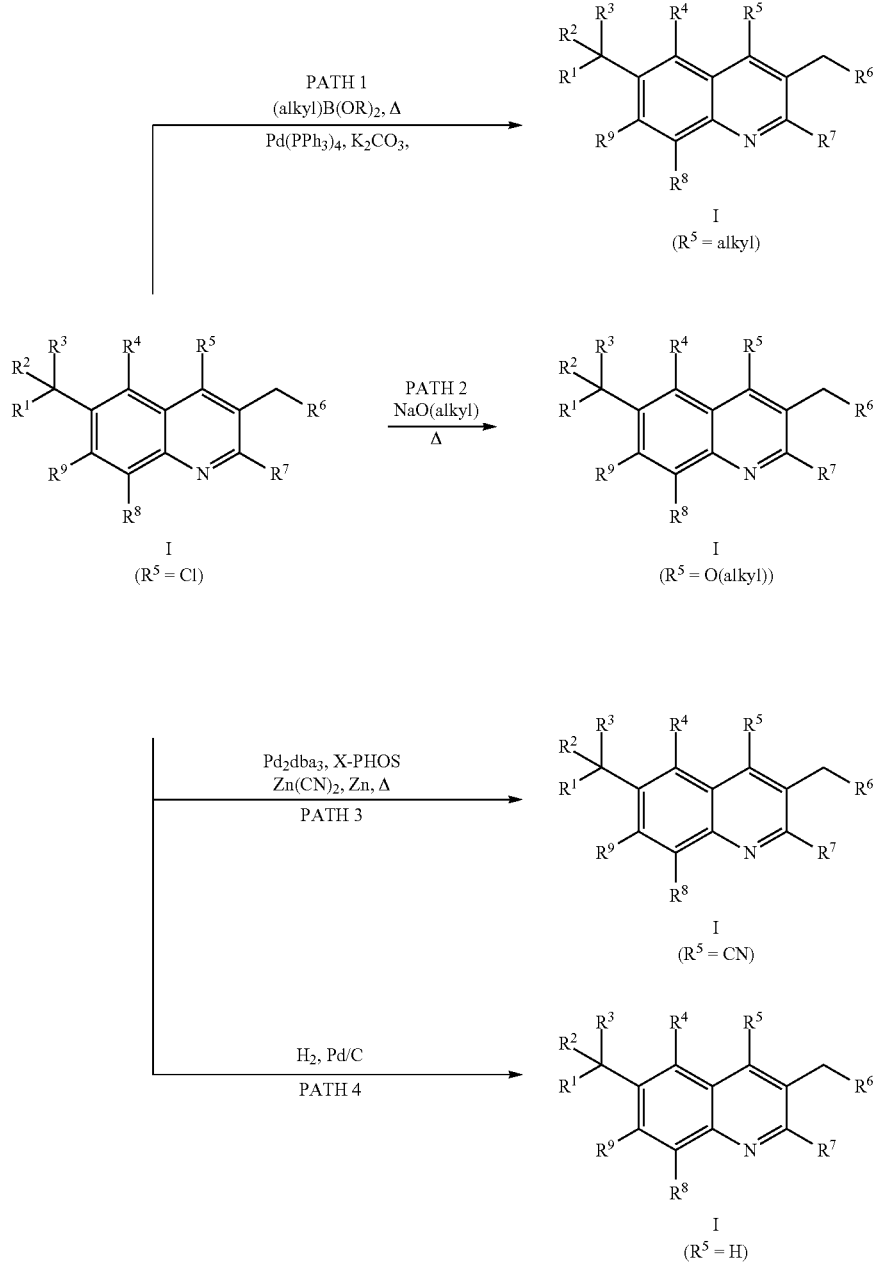

Scheme 10

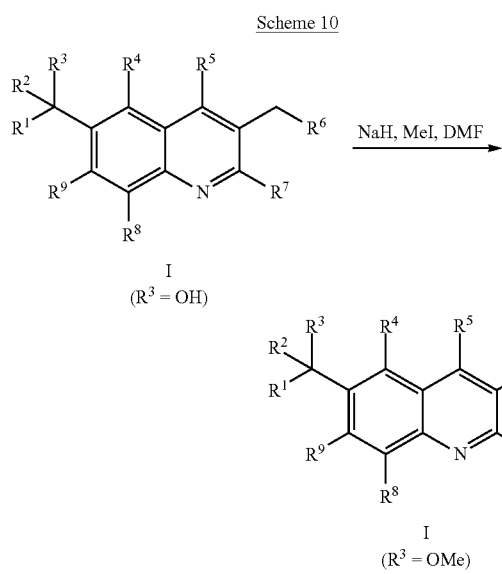

As shown in Scheme 10, tertiary alcohols of Formula I can be treated with base, such as NaH, and alkylated with MeI in DMF to provide compounds of Formula I wherein $R^3$ is OMe.

Synthetic routes to compounds of Formula I, wherein $R^3$ is $NH_2$, alkylamine or dialkylamine are illustrated in Scheme 11. Ketimines XXXVIII may be prepared by $Ti(OEt)_4$ mediated condensation of ketones XVII with 2-methylpropane-2-sulfinamide in refluxing THF. Addition of n-BuLi to the reaction mixture of ketimines XXXVIII and 6-bromo or 6-iodoquinolines VI at −78° C. followed by cleavage of the tert-butanesulfinyl group with HCl in MeOH liberates tertiary amines of Formula I.

Alternatively, compounds of Formula I, wherein $R^3$ is OH can be treated with sodium hydride followed by addition of acetic anhydride or acetyl chloride and stirred at room temperature over a 24 to 72 hour period to provide the intermediate acetate wherein $R^3$ is OAc. The acetate can then be combined with a methanolic solution of ammonia, alkylamines or diakylamines and heated at temperatures between 60 and 85° C. to provide compounds of Formula I, wherein $R^3$ is $NH_2$, $NHCH_3$ or $N(CH_3)_2$.

Scheme 11

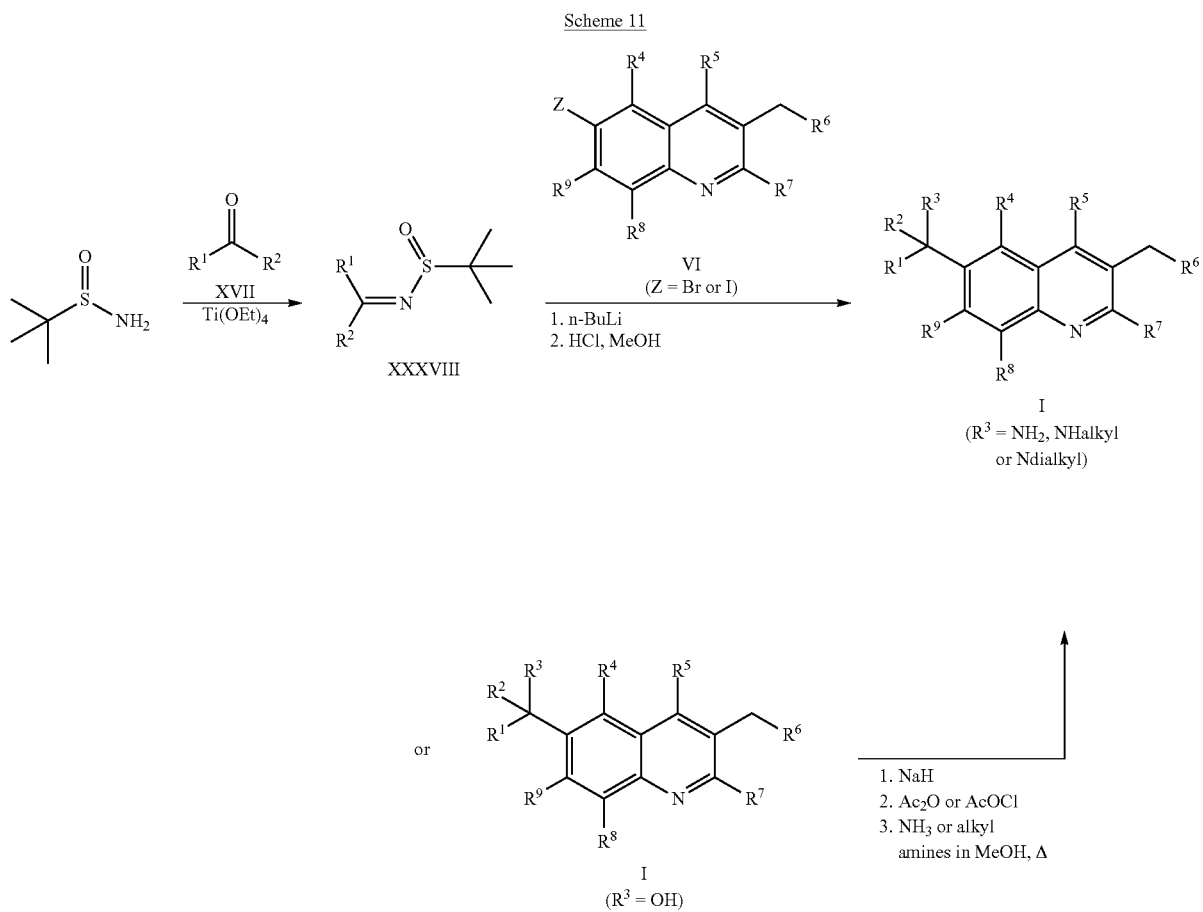

Scheme 12

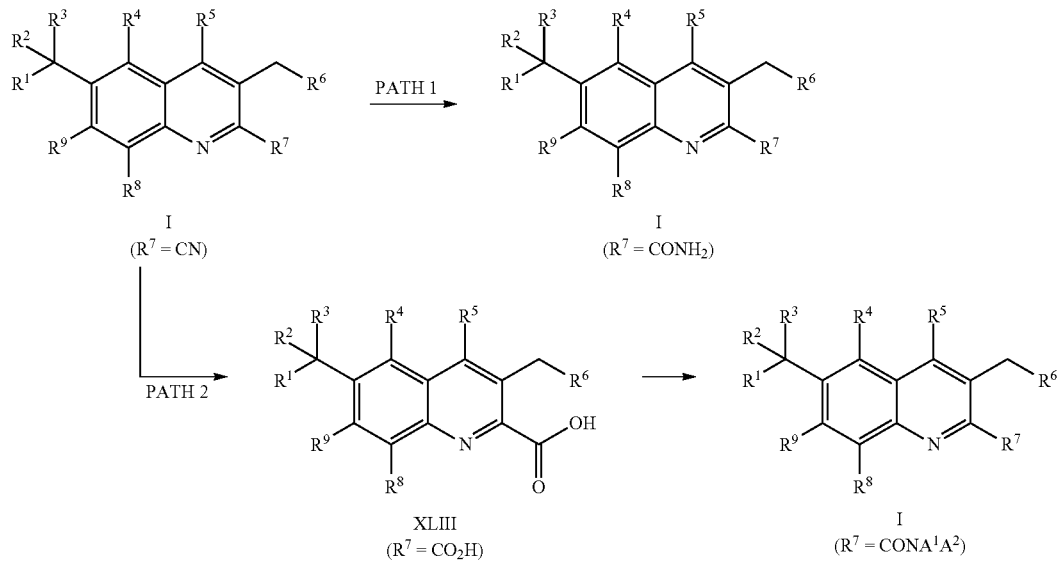

As shown in Scheme 12, the quinolines of Formula I wherein $R^7$ is CN can be hydrolyzed as described in US20080188521 by treatment with sodium carbonate and hydrogen peroxide to provide compounds of Formula I wherein $R^7$ is $CONH_2$ (path 1) or can be treated with a strong acid like HCl to convert CN to a carboxylic acid XLIII (path 2). Once formed the acid can be further coupled to substituted amines using appropriate coupling reagents such as EDCI or HATU in the presence of a base like triethylamine or Hunig's base to provide compounds of Formula I wherein $R^7$ is $CONA^1A^2$.

Synthesis of compounds of Formula I, wherein $R^7$ is an aminoalkylaminomethylene or an aminoalkoxymethylene can be prepared from 2-methylquinolines as shown in Scheme 13. Bromination of 2-methylquinolines of Formula I can accomplished with N-bromosuccinimide in acetic acid at elevated temperatures as described in WO2010151740, to provide the methylbromide intermediate XXXIX. Nucleophilic displacement of the bromide under basic conditions using procedures known in the art could afford compounds of Formula I wherein $R^7$ is $-CH_2NHC_{(2-3)}alkylNA^1A^2$ or Scheme 13

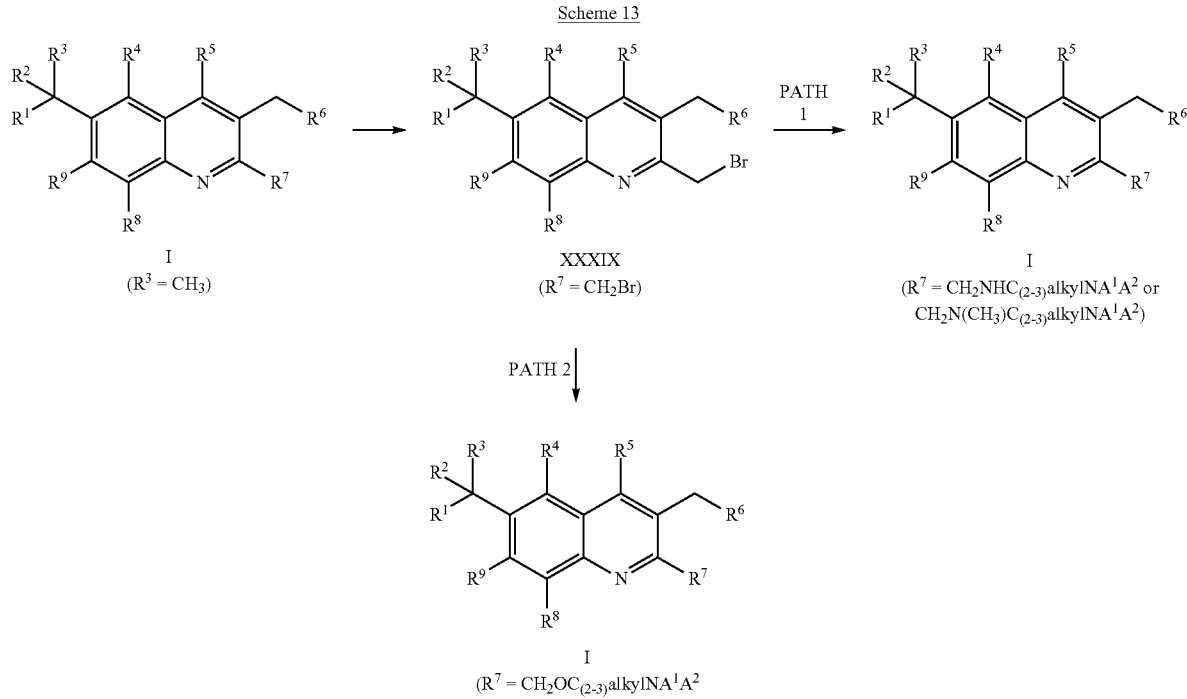

—CH$_2$N(CH$_3$)C$_{(2-3)}$alkylNA$^1$A$^2$ (path 1) or CH$_2$OC$_{(2-3)}$alkylNA$^1$A$^2$ (path 2) and A$^1$ and A$^2$ are defined above.

Scheme 14

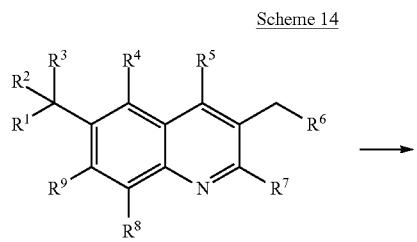

As shown in Scheme 14, compounds of the Formula I wherein R$^3$ is H can be prepared by treating compounds of Formula I wherein R$^3$ is OH with a hydride source such as triethylsilane and an acid such as trifluoroacetic acid in a solvent such as dichloromethane at room temperature or with heating (WO2009091735).

Scheme 15

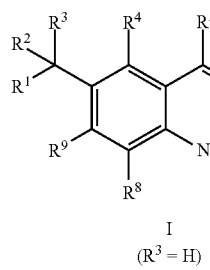

Compounds of Formula I, wherein R$^1$ and R$^2$ are the same, can also be prepared as described in Scheme 15. The starting 6-bromoquinolines VI can be treated with n-butyllithium, quenched with carbon dioxide then subsequently treated with methyl iodide as described in U.S. Pat. No. 4,710,507 A1, 1987 to provide the intermediate quinoline methylester XLV. Further treatment of the methyl ester with excess R$^1$Li, R$^2$Li, R$^1$MgBr or R$^2$MgBr, in the presence or absence of lanthanum chloride, can afford the symmetrical compounds (R$^1$ and R$^2$ are the same) of Formula I.

Scheme 16

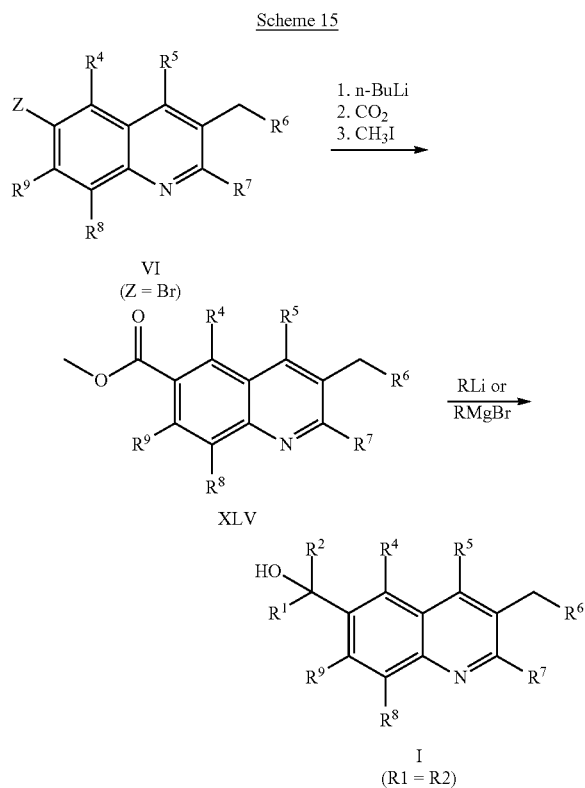

Scheme 16 describes methods used to prepare symmetrical tertiary alcohol of Formula I wherein R$^1$ and R$^2$ are the same. The symmetrical ketones XLVII can be prepared from organozinc reagents XLVI (prepared from readily available iodides as described in US2009/197859) by carbonylation mediated by cobalt(II)bromide as described by Knochel (*Tetrahedron Letters,* 1995, 36, pp. 8411-8414) to provide the symmetrical ketones XLVII wherein R$^1$ and R$^2$ are both Boc protected azetidinyl. Addition of the symmetrical ketones XLVII to haloquinolines VI as previously described, can provide the tertiary alcohols of Formula I wherein R$^3$ is OH. The BOC protecting group can be removed under acidic conditions using procedures well known in the art. The azetidine nitrogen can then be further functionalized by alkylating with an alkylhalide (bromide or iodide), acylating with an anhydride or substituted acid chloride or treated with trimethylsilylisocyanate in the presence of an appropriate base using methods well known in the art to provide compounds of Formula I wherein $R^1$ and $R^2$ are N-acetyl-azetidin-3-yl, N-methyl-azetidin-3-yl and N-acetamidylacetidin-3-yl.

Compounds of Formula I wherein $R^1$, $R^2$ or $R^6$ are pyridyl can be treated with m-chloroperbenzoic acid in a chlorinated solvent at ambient temperature to 40° C. to form the pyridyl-N-oxides of Formula I.

EXAMPLES

Compounds of the present invention can be prepared by methods known to those who are skilled in the art. The following examples are only meant to represent examples of the invention and are in no way meant to be a limit of the invention.

Intermediate 1: Step a

N-Methoxy-N-methyltetrahydro-2H-pyran-4-carboxamide

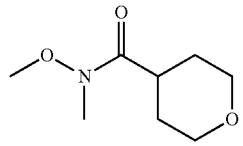

Procedure A

Triethylamine (10.6 mL, 76.4 mmol) was added slowly to a mixture of tetrahydro-2H-pyran-4-carboxylic acid (4.97 g, 38.2 mmol), N,O-dimethylhydroxylamine hydrochloride (4.18 g, 42.0 mmol), and EDCI (8.79 g, 45.8 mmol) in DCM (48 mL). The white suspension was stirred at room temperature overnight. The mixture was diluted with saturated aqueous $NaHCO_3$ and water and was stirred for 30 minutes. The phases were separated and the organic phase was washed with 1 N aqueous HCl followed by water. The organic phase was dried ($Na_2SO_4$), filtered, and concentrated to provide the title compound as a colorless oil.

Procedure B

To tetrahydro-2H-pyran-4-carboxylic acid (5.2 g, 39.9 mmol) in DCM (8.3 mL), CDI (7.12 g, 43.9 mmol) was added and the mixture was stirred for 45 minutes after which N,O-dimethylhydroxylamine hydrochloride (4.29 g, 43.9 mmol) was added and the mixture was stirred for 48 hours. The reaction mixture was quenched with 0.3 M aqueous solution of NaOH and partitioned between water and DCM. The aqueous layer was extracted with DCM, washed with aqueous saturated solution of NaCl, dried ($MgSO_4$) and concentrated. The crude product was used in the next step without any further purification.

Intermediate 1: Step b (1-Methyl-1H-imidazol-5-yl)(tetrahydro-2H-pyran-4-yl)methanone

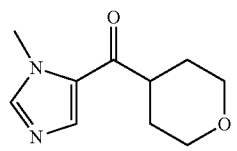

A clear colorless solution of 5-bromo-1-methyl-1H-imidazole (1.12 g, 6.93 mmol) in THF (10 mL) was placed in an ice bath and ethylmagnesium bromide (3.0 M in $Et_2O$, 2.31 mL, 6.93 mmol) was added via syringe. The reaction mixture was stirred for 20 minutes at room temperature. N-Methoxy-N-methyltetrahydro-2H-pyran-4-carboxamide (1.0 g, 5.8 mmol, Intermediate 1: step a, Procedure A) was added neat by syringe (using 1 mL THF rinse to quantitate transfer), and the resulting white suspension was stirred at room temperature for 2 days. The mixture was diluted with saturated aqueous $NH_4Cl$ followed by water, then was extracted with EtOAc (3×). The organic phase was dried ($Na_2SO_4$), filtered, and concentrated to dryness. The crude product was purified by flash column chromatography two times (1-4% MeOH-DCM first column; 40-60% $CH_3CN$-DCM second column) to provide the title compound as a white crystalline solid.

Intermediate 2: Step a 6-(Trifluoromethyl)nicotinoyl chloride

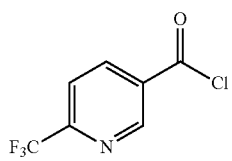

To a 1 L 3-neck flask equipped with an overhead stirrer, Claisen adaptor, nitrogen bubbler, 60 mL addition funnel, and thermocouple was added 6-(trifluoromethyl)nicotinic acid (45 g, 235.5 mmol), dichloromethane (540 mL) and DMF (0.910 mL, 11.77 mmol) via syringe. To this solution was added oxalyl chloride (24.51 mL, 282.56 mmol) and the reaction was allowed to stir at ambient temperature overnight. The reaction was then filtered and the clear filtrate was condensed in vacuo to afford the title compound as a brownish semisolid.

Intermediate 2: Step b

N-Methoxy-N-methyl-6-(trifluoromethyl)nicotinamide

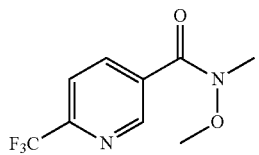 [SMILES: CON(C)C(=O)c1ccc(C(F)(F)F)nc1]

To a 1 L 3-neck flask equipped with an overhead stirrer, Claisen adaptor, nitrogen bubbler, 125 mL addition funnel, and thermocouple was added 6-(trifluoromethyl)nicotinoyl chloride (49.3 g, 235.2 mmol, Intermediate 2: step a), dichloromethane (493 mL), and N,O-dimethylhydroxylamine hydrochloride (25.63 g, 258.8 mmol). After the mixture was cooled to 7° C., diisopropylethylamine (90.263 mL, 517.6 mmol) was added such that the addition temperature did not exceed 16° C. After the addition, the reaction was allowed to warm to room temperature. The reaction was then transferred to a separatory funnel and the organic layer was washed with saturated aqueous $NaHCO_3$ (2×100 mL) followed by water (100 mL) and then dried over sodium sulfate and filtered. Solvent removal afforded the title compound as a brownish oil.

Intermediate 2: Step c (1-Methyl-1H-imidazol-5-yl)(6-(trifluoromethyl)pyridin-3-yl)methanone

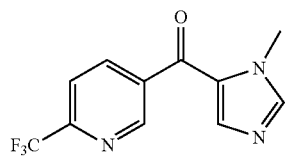

To a 3 L 4-neck flask equipped with an overhead stirrer, nitrogen bubbler, and thermocouple was added 5-bromo-1-methyl-1H-imidazole (47.96 g, 297.9 mmol), followed by THF (537 mL). To this room temperature solution was added isopropylmagnesium chloride/lithium chloride complex [1.3 M in THF] (246.8 mL, 320.8 mmol) (addition temperature maintained between 16.6 and 25° C.) to afford a milky suspension and the reaction was stirred for 60 minutes and then cooled to 5.3° C. in an ice bath. To this mixture was added a solution of N-methoxy-N-methyl-6-(trifluoromethyl)nicotinamide (53.66 g, 229.14 mmol, Intermediate 2: step b) in THF (268.3 mL) (addition temperature between 5.3 and 5.6° C.) to afford an orange mixture. After addition, the reaction was warmed to room temperature over 2 hours. After stirring at room temperature for 18 hours, THF (200 mL) was added and the reaction was stirred for 2 hours. The reaction was then cooled to 4° C. with an ice bath and carefully quenched with 2 N aqueous HCl to pH=7 (quenching temperature reached 12° C.). The mixture was diluted with ethyl acetate (500 mL), phase split and the organic layer was washed with brine (2×200 mL) and dried over sodium sulfate, filtered, and the solvent was removed. Hot ether was added and the mixture was filtered to give the title compound as a solid.

Intermediate 3: Step a 5-(4-(1H-Pyrazol-1-yl)benzyl)-2,2-dimethyl-1,3-dioxane-4,6-dione

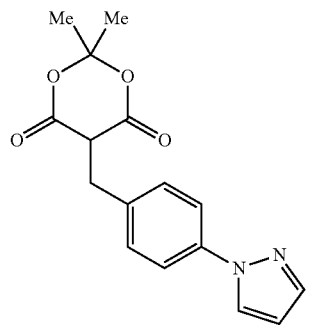 [SMILES: CC1(C)OC(=O)C(Cc2ccc(-n3cccn3)cc2)C(=O)O1]

L-Proline (4.07 g, 35.0 mmol) was added to a semi-heterogeneous mixture of 4-(1H-pyrazol-1-yl)benzaldehyde (30.0 g, 174 mmol) and 2,2-dimethyl-1,3-dioxane-4,6-dione (25.6 g, 174 mmol) in ethanol (996 mL) at room temperature. After 40 minutes, diethyl 1,4-dihydro-2,6-dimethyl-3,5-pyridinedicarboxylate (44.1 g, 174 mmol) was added in one portion followed by ethanol (125 mL). After overnight stirring, the mixture was concentrated under reduced pressure to afford a yellow solid. Isopropanol (300 mL) was added and the heterogeneous mixture was sonicated for 30 minutes. The mixture was filtered and the filter cake was washed with isopropanol. The solids were collected and dried under vacuum to provide the title compound as a white solid.

Intermediate 3: Step b 2-(4-(1H-Pyrazol-1-yl)benzyl)malonic acid

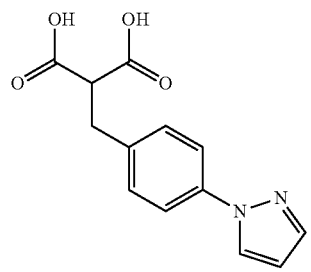 [SMILES: O=C(O)C(Cc1ccc(-n2cccn2)cc1)C(=O)O]

A mixture of 5-(4-(1H-pyrazol-1-yl)benzyl)-2,2-dimethyl-1,3-dioxane-4,6-dione (41.4 g, 137 mmol, Intermediate 3: step a) and 3 M aqueous NaOH solution (300 mL, 900 mmol) was heated for 48 hours at 110° C. The mixture was cooled to room temperature, diluted with water (200 mL) and extracted with EtOAc (1×100 mL) and then acidified to pH 1 with concentrated aqueous HCl at 0° C. The resulting mixture was stirred at 0° C. for 1.5 hours, filtered and the filter cake was washed with water. The solids were collected and dried under vacuum at 40° C. to provide the title compound as a white solid.

Intermediate 3: Step c 3-(4-(1H-Pyrazol-1-yl)benzyl)-6-bromo-2,4-dichloroquinoline

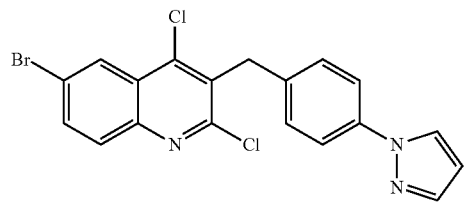 [SMILES: Clc1nc2ccc(Br)cc2c(Cl)c1Cc1ccc(-n2cccn2)cc1]

A mixture of 2-(4-(1H-pyrazol-1-yl)benzyl)malonic acid (3.37 g, 19.6 mmol, Intermediate 3: step b) and 4-bromoaniline (5.10 g, 19.6 mmol) in POCl$_3$ (18 mL) was heated at 105° C. for 3 hours, cooled to room temperature and evaporated in vacuo to remove excess POCl$_3$. The residue was poured into ice H$_2$O and treated with aqueous NH$_4$OH to pH 8-9 (temperature of the aqueous mixture was kept cold during addition). The precipitates were collected, rinsed with H$_2$O and dried under reduced pressure. After drying the resulting crude pale yellow solid was washed several times with Et$_2$O then acetonitrile and dried to provide the title compound as a pale yellow solid.

Intermediate 3: Step d (3-(4-(1H-Pyrazol-1-yl)benzyl)-2,4-dichloroquinolin-6-yl)(1-methyl-1H-imidazol-5-yl)(6-(trifluoromethyl)pyridin-3-yl)methanol

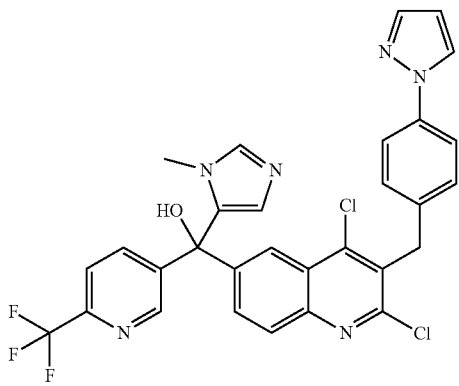 [SMILES: Cn1cncc1C(O)(c1ccc(C(F)(F)F)nc1)c1ccc2nc(Cl)c(Cc3ccc(-n4cccn4)cc3)c(Cl)c2c1]

A round bottom flask was charged with 3-(4-(1H-pyrazol-1-yl)benzyl)-6-bromo-2,4-dichloroquinoline (827 mg, 1.91 mmol, Intermediate 3: step c) and (1-methyl-1H-imidazol-5-yl)(6-(trifluoromethyl)pyridin-3-yl)methanone (536 mg, 2.10 mmol, Intermediate 2: step c). The flask was evacuated and back-filled with argon, then THF (27 mL) was added. The resulting yellow suspension was heated until nearly all solid dissolved, and the slightly cloudy yellow suspension was allowed to cool to room temperature, and then was cooled in a dry ice acetone bath for 7 minutes before addition of n-BuLi (1.6 M in hexane, 1.55 mL, 2.48 mmol) dropwise. The mixture was stirred for 5 minutes in dry ice/acetone bath, then was moved to an ice/water bath and stirred for 1 hour. The reaction was quenched by the addition of saturated aqueous NH$_4$Cl, and was diluted with water. The aqueous was then extracted with EtOAc (3×). The organic layers were combined and washed once with water. The organic phase was dried (Na$_2$SO$_4$), filtered, and concentrated to dryness. The residue was purified by flash column chromatography (silica gel, 0-2% MeOH-DCM) affording impure title compound which was used without further purification in the next step.

Intermediate 4: Step a 3-((4-Iodophenyl)amino)-3-oxopropanoic acid

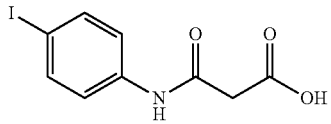 [SMILES: O=C(O)CC(=O)Nc1ccc(I)cc1]

A mixture containing 4-iodoaniline (400 g, 1.83 mol) and 2,2-dimethyl-1,3-dioxane-4,6-dione (263 g, 1.83 mol) was stirred at 80° C. After 2 hours, the mixture was cooled to 23° C. and then ethyl acetate (5 L) was added. The mixture was extracted with aqueous sodium hydroxide solution (110 g of sodium hydroxide dissolved in 5 L of water). The basic aqueous layer was washed with ethyl acetate (3 L). The washed layer was brought to pH 2 with 6 M aqueous hydrochloric acid solution. The acidic aqueous solution was extracted with ethyl acetate (3×3 L). The organic layers were combined and the combined solution was dried with magnesium sulfate. The dried solution was filtered and the filtrate was concentrated to afford the title compound as a yellow solid.

Intermediate 4: Step b

6-Iodoquinoline-2,4-diol

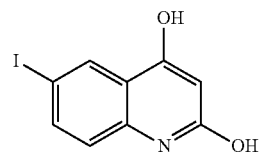 [SMILES: Oc1cc(O)c2cc(I)ccc2n1]

A mixture containing 3-((4-iodophenyl)amino)-3-oxopropanoic acid (260 g, 852 mmol, Intermediate 4: step a) and polyphosphoric acid (3 kg) was heated to 90° C. After 2 hours, the mixture was cooled to 23° C. and then poured into ice water (20 L) resulting in the formation of a solid. The mixture was stirred overnight and then filtered. The filter cake was collected and then recrystallized from dimethylformamide-water to provide the title compound as a solid.

Intermediate 4: Step c 3-(4-(1H-Pyrazol-1-yl)benzyl)-6-iodoquinoline-2,4-diol

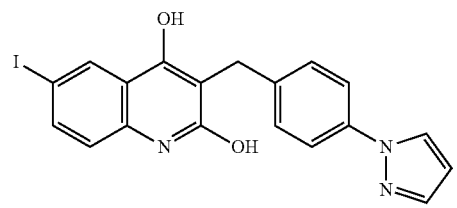 [SMILES: Oc1nc2ccc(I)cc2c(O)c1Cc1ccc(-n2cccn2)cc1]

A suspension of 6-iodoquinoline-2,4-diol (320 g, 1110 mmol, Intermediate 4: step b), 4-(1H-pyrazol-1-yl)benzaldehyde (211 g, 1230 mmol) and diethyl 1,4-dihydro-2,6-dimethyl-3,5-pyridinecarboxylate (282 g, 1110 mol) in pyridine (1.92 L) was stirred at 115° C. for 6 hours. The reaction was cooled to room temperature, diluted with EtOH (4.5 L) and stirred at room temperature for 3 hours. A solid precipitated out of solution and was collected by filtration. The solids were washed with EtOH (2×750 mL) and dried under vacuum at 60° C. for 2 days to provide the title compound as a white solid.

Intermediate 4: Step d 3-(4-(1H-Pyrazol-1-yl)benzyl)-2,4-dichloro-6-iodoquinoline

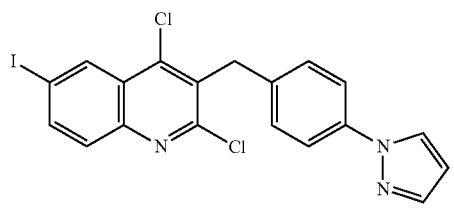 [SMILES: Clc1nc2ccc(I)cc2c(Cl)c1Cc1ccc(-n2cccn2)cc1]

A mixture of 3-(4-(1H-pyrazol-1-yl)benzyl)-6-iodoquinoline-2,4-diol (300 g, 677 mmol, Intermediate 4: step c) in POCl$_3$ (629 mL, 6770 mmol) was stirred at 85° C. for 1 hour. The reaction became homogeneous once the temperature reached 85° C., and after 30 minutes a precipitate formed. The mixture was cooled to room temperature and poured slowly into ice-water (9 L), during which a precipitate formed. The pH of the mixture was adjusted to ~pH 8 by the addition of saturated aqueous NH$_4$OH. The suspension was stirred for 30 minutes, filtered, and the filtrate washed with water (2×500 mL). The solids were dried under vacuum at 40° C. to provide the title compound as a light red solid.

Intermediate 4: Step e 3-(4-(1H-Pyrazol-1-yl)benzyl)-4-chloro-6-iodo-2-methoxyquinoline

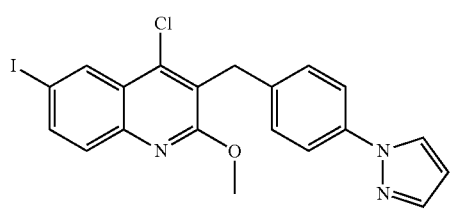 [SMILES: COc1nc2ccc(I)cc2c(Cl)c1Cc1ccc(-n2cccn2)cc1]

To a mixture of 3-(4-(1H-pyrazol-1-yl)benzyl)-2,4-dichloro-6-iodoquinoline (556.9 g, 1160 mmol, Intermediate 4: step d) in toluene (5.6 L) was added sodium methoxide (639.4 g, 11600 mmol) and the resulting suspension was stirred at 100° C. for 6 hours. The reaction was cooled to room temperature, diluted with CH$_2$Cl$_2$ (2 L) and stirred for 15 minutes. The mixture was filtered through a pad of Celite®, rinsing with CH$_2$Cl$_2$ (2×800 mL). The filtrate was concentrated to dryness. The crude solid was suspended in MeOH (250 mL) and stirred at room temperature for 15 minutes. Then the suspension was filtered, rinsing the solids with MeOH (2×125 mL). The solids were dried under vacuum at 40° C. for 18 hours to provide the title compound as a tan solid.

Intermediate 5: Step a

Ethyl 3-oxo-2-(4-(trifluoromethyl)benzyl)pentanoate

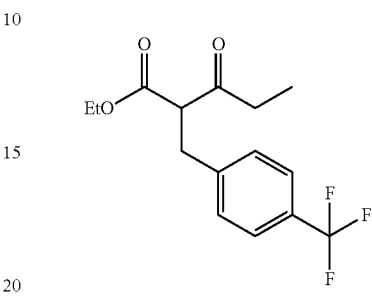

Sodium hydride (60% dispersion in mineral oil, 1.75 g, 43.7 mmol) was added in portions over 1 minute to an ice-cooled, stirring solution of ethyl 3-oxopentanoate (6.30 g, 43.7 mmol) in dry dimethoxyethane (87 mL). After 5 minutes, the flask was removed from the cooling bath and stirring continued at room temperature. After 30 minutes, a solution of 4-(trifluoromethyl)benzyl bromide (10.4 g, 43.7 mmol) in dry dimethoxyethane (10 mL) was added dropwise over 2 minutes. After 2.5 hours, ethyl acetate (300 mL) and water (100 mL) were added. The layers were separated. The organic layer was dried with sodium sulfate and the dried solution was filtered. The filtrate was concentrated and the residue was purified by flash-column chromatography on silica gel eluting with hexanes initially, grading to 50% dichloromethane-hexanes to provide the title compound as a colorless liquid.

Intermediate 5: Step b

6-Bromo-2-ethyl-3-(4-(trifluoromethyl)benzyl) quinolin-4-ol

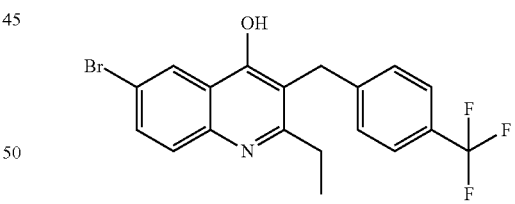

A round-bottomed flask equipped with a Dean-Stark apparatus was charged with ethyl 3-oxo-2-(4-(trifluoromethyl) benzyl)pentanoate (8.84 g, 29.2 mmol, Intermediate 5: step a), 4-bromoaniline (5.00 g, 29.2 mmol), para-toluenesulfonic acid (0.503 g, 2.9 mmol), and toluene (146 mL). The mixture was heated to 125° C. After 18 hours, the flask was cooled to room temperature. The toluene was removed by rotary evaporation to provide an amber colored solid. A mixture of the solid and diphenyl ether (29.1 mL) was heated to 220° C. After 70 minutes, the mixture was cooled to room temperature. Ether (100 mL) and hexanes (50 mL) were added. The mixture was allowed to stir for 30 minutes during which time a white solid crashed out of solution. The suspension was filtered through filter paper, rinsing with ether. The gummy solids were collected. Acetonitrile (20 mL) was added and the mixture was sonicated for 5 minutes. The slurry was filtered through filter paper and the solids were rinsed with acetonitrile. The off-white solids were collected, dried, and then used in the next step without further purification.

Intermediate 5: Step c

6-Bromo-4-chloro-2-ethyl-3-(4-(trifluoromethyl)benzyl)quinoline

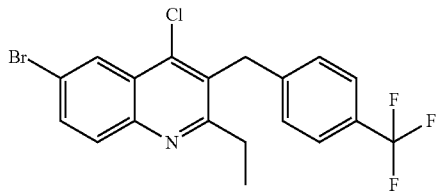 [SMILES: CCc1nc2ccc(Br)cc2c(O)c1Cc1ccc(C(F)(F)F)cc1]

A round-bottomed flask containing a mixture of 6-bromo-2-ethyl-3-(4-(trifluoromethyl)benzyl)quinolin-4-ol (4.00 g, 8.29 mmol, Intermediate 5: step b), phosphorous oxychloride (3.50 mL, 37.3 mmol) and acetonitrile (27 mL) was placed into a metal heating block at 90° C. After 65 minutes, the reaction mixture was cooled to room temperature. The acetonitrile and excess phosphorous oxychloride was removed by rotary evaporation. The residue was dissolved in dichloromethane (100 mL) and the solution was cooled in an ice-water bath. Ice (50 mL) was added. Concentrated aqueous ammonia solution was added dropwise until pH=8-9 by litmus paper test. The biphasic mixture was separated and the aqueous layer was extracted with dichloromethane (50 mL). The combined organics were dried with sodium sulfate and the dried solution was filtered. Silica gel (8 g) was added to the filtrate and the solvents were removed by rotary evaporation to provide a free-flowing powder. The powder was loaded onto a silica gel column. Elution with hexanes initially, grading to 20% ethyl acetate-hexanes provided the title compound as an off-white solid.

Intermediate 6

Methyl 4-chloro-2-ethyl-3-(4-(trifluoromethyl)benzyl)quinoline-6-carboxylate

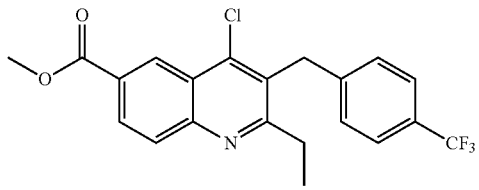 [SMILES: CCc1nc2ccc(C(=O)OC)cc2c(Cl)c1Cc1ccc(C(F)(F)F)cc1]

A solution of 6-bromo-4-chloro-2-ethyl-3-(4-(trifluoromethyl)benzyl)quinoline (0.5 g, 1.166 mmol, Intermediate 5: step c) in dry THF (10 mL) at −78° C. was treated dropwise with n-BuLi (2.5 M in hexanes, 0.5 mL, 1.25 mmol) under a nitrogen atmosphere. After 2 minutes of stirring at −78° C., the reaction was quenched with solid $CO_2$ (~6 g) and allowed to warm to room temperature. The reaction was then cooled to 0° C. and methyl iodide (0.223 mL, 3.58 mmol), sodium carbonate (0.185 g, 1.75 mmol), and DMSO (2 mL) were added sequentially. The reaction was heated at 40° C. for 16 hours and then cooled to room temperature. The reaction was diluted with EtOAc and washed with saturated aqueous NaCl (2×). The organic layer was dried ($MgSO_4$), filtered and concentrated in vacuo. The crude residue was purified (FCC, 40 g $SiO_2$, 0-10% EtOAc/hexanes over 30 minutes) to afford the title compound.

Intermediate 7: Step a

4-Hydroxy-6-iodo-3-(3-(trifluoromethyl)benzyl)quinolin-2(1H)-one

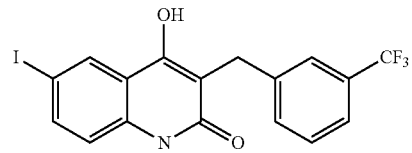 [SMILES: O=c1[nH]c2ccc(I)cc2c(O)c1Cc1cccc(C(F)(F)F)c1]

A suspension of 6-iodoquinoline-2,4-diol (1.998 g, 6.96 mmol, Intermediate 4: step b), 3-(trifluoromethyl)benzaldehyde (1.0 mL, 7.472 mmol), and diethyl 2,6-dimethyl-1,4-dihydropyridine-3,5-dicarboxylate (1.776 g, 7.012 mmol) in pyridine (40 mL) was heated at 105° C. for 16 hours. The reaction was then cooled, diluted with EtOAc, washed with 1 N aqueous HCl (2×), and saturated aqueous NaCl (1×). The organic layer was dried ($MgSO_4$), filtered and concentrated in vacuo to afford the title compound, which was used without further purification.

Intermediate 7: Step b 2,4-Dichloro-6-iodo-3-(3-(trifluoromethyl)benzyl)quinoline

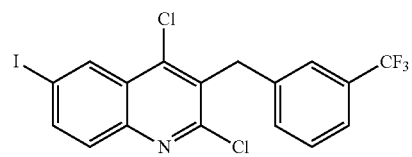 [SMILES: FC(F)(F)c1cccc(Cc2c(Cl)nc3ccc(I)cc3c2Cl)c1]

A suspension of 4-hydroxy-6-iodo-3-(3-(trifluoromethyl)benzyl)quinolin-2(1H)-one (3.099 g, 6.961 mmol, Intermediate 7: step a) in dry acetonitrile (25 mL) was treated with phosphorus oxychloride (3.0 mL, 32.283 mmol) and heated at 80° C. for 1 hour. The reaction was cooled to room temperature and concentrated in vacuo. The residue was suspended between EtOAc and deionized $H_2O$ before adjusting the pH to ~7-8 with 10% aqueous NaOH. The organic layer was then washed with saturated aqueous NaCl (2×), dried ($MgSO_4$), filtered and concentrated in vacuo. The crude residue was purified (FCC, 120 g SiO$_2$, 0-5% EtOAc/hexanes) to afford the title compound.

Intermediate 7: Step c

4-Chloro-6-iodo-2-methoxy-3-(3-(trifluoromethyl) benzyl)quinoline

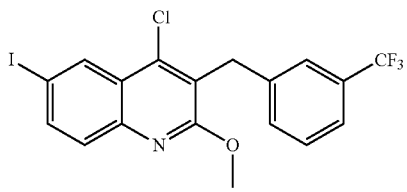 [SMILES: COc1nc2ccc(I)cc2c(Cl)c1Cc1cccc(C(F)(F)F)c1]

A suspension of 2,4-dichloro-6-iodo-3-(3-(trifluoromethyl)benzyl)quinoline (1.551 g, 3.217 mmol, Intermediate 7: step b) and sodium methoxide (1.738 g, 32.174 mmol) in dry toluene (16 mL) was heated at 90° C. for 16 hours. The reaction was cooled to room temperature and quenched by the addition of saturated aqueous NaHCO$_3$. The organic layer was dried (MgSO$_4$), filtered and concentrated in vacuo. The crude residue was purified (FCC, 80 g SiO$_2$, 0-20% CH$_2$Cl$_2$/hexanes over 20 minutes) to afford the title compound.

Intermediate 7: Step d

Methyl 4-chloro-2-methoxy-3-(3-(trifluoromethyl) benzyl)quinoline-6-carboxylate

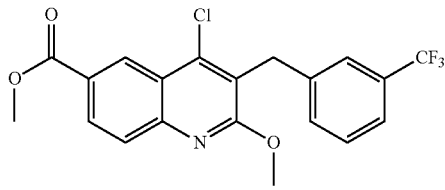 [SMILES: COC(=O)c1ccc2nc(OC)c(Cc3cccc(C(F)(F)F)c3)c(Cl)c2c1]

The title compound was prepared following the procedure described for the preparation of Intermediate 6, substituting 6-bromo-4-chloro-2-ethyl-3-(4-(trifluoromethyl)benzyl)quinoline (Intermediate 5: step c) with 4-chloro-6-iodo-2-methoxy-3-(3-(trifluoromethyl)benzyl)quinoline (Intermediate 7: step c).

Intermediate 8: Step a

4-Hydroxy-6-iodo-3-(2-(trifluoromethyl)benzyl) quinolin-2(1H)-one

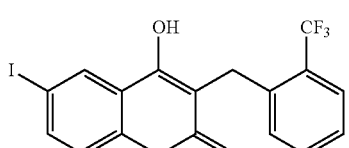

The title compound was prepared following the procedure described for the preparation of Intermediate 7: step a), substituting 3-(trifluoromethyl)benzaldehyde with 2-(trifluoromethyl)benzaldehyde.

Intermediate 8: Step b 2,4-Dichloro-6-iodo-3-(2-(trifluoromethyl)benzyl) quinoline

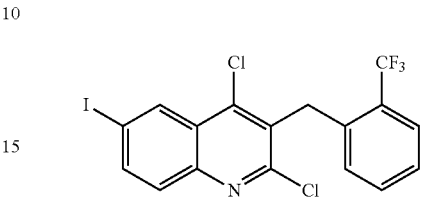

The title compound was prepared following the procedure described for the preparation of Intermediate 7: step b, substituting 4-hydroxy-6-iodo-3-(3-(trifluoromethyl)benzyl)quinolin-2(1H)-one (Intermediate 7: step a) with 4-hydroxy-6-iodo-3-(2-(trifluoromethyl)benzyl)quinolin-2(1H)-one (Intermediate 8: step a).

Intermediate 8: Step c

4-Chloro-6-iodo-2-methoxy-3-(2-(trifluoromethyl) benzyl)quinoline

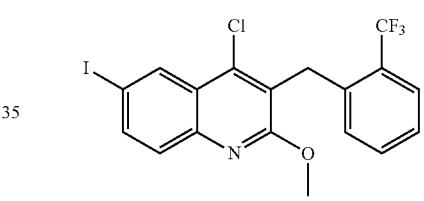

The title compound was prepared following the procedure described for the preparation of Intermediate 7: step c, substituting 2,4-dichloro-6-iodo-3-(3-(trifluoromethyl)benzyl)quinoline (Intermediate 7: step b) with 2,4-dichloro-6-iodo-3-(2-(trifluoromethyl)benzyl)quinoline (Intermediate 8: step b).

Intermediate 8: Step d

Methyl 4-chloro-2-methoxy-3-(2-(trifluoromethyl) benzyl)quinoline-6-carboxylate

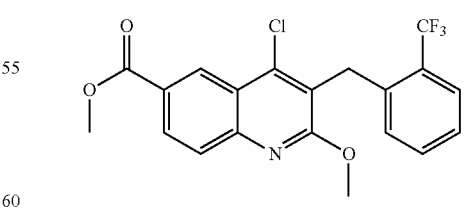

The title compound was prepared following the procedure described for the preparation of Intermediate 6, substituting 6-bromo-4-chloro-2-ethyl-3-(4-(trifluoromethyl)benzyl)quinoline (Intermediate 5: step c) with 4-chloro-6-iodo-2-methoxy-3-(2-(trifluoromethyl)benzyl)quinoline (Intermediate 8: step c).

Intermediate 9: Step a

4-Hydroxy-6-iodo-3-((5-(trifluoromethyl)thiophen-2-yl)methyl)quinolin-2(1H)-one

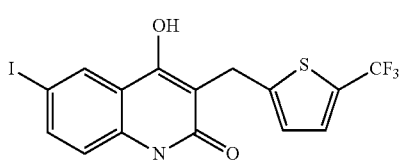 [SMILES: O=c1[nH]c2ccc(I)cc2c(O)c1Cc1ccc(C(F)(F)F)s1]

The title compound was prepared following the procedure described for the preparation of Intermediate 7: step a, substituting 3-(trifluoromethyl)benzaldehyde with 5-(trifluoromethyl)thiophene-2-carbaldehyde.

Intermediate 9: Step b 2,4-Dichloro-6-iodo-3-((5-(trifluoromethyl)thiophen-2-yl)methyl)quinoline

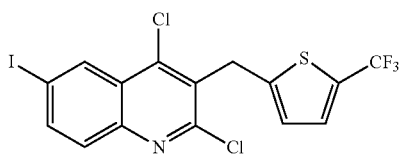 [SMILES: FC(F)(F)c1ccc(Cc2c(Cl)nc3ccc(I)cc3c2Cl)s1]

The title compound was prepared following the procedure described for the preparation of Intermediate 7: step b, substituting 4-hydroxy-6-iodo-3-(3-(trifluoromethyl)benzyl)quinolin-2(1H)-one (Intermediate 7: step a) with 4-hydroxy-6-iodo-3-((5-(trifluoromethyl)thiophen-2-yl)methyl)quinolin-2(1H)-one (Intermediate 9: step a).

Intermediate 9: Step c

4-Chloro-6-iodo-2-methoxy-3-((5-(trifluoromethyl)thiophen-2-yl)methyl)quinoline

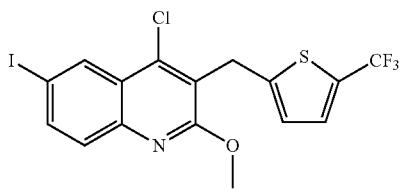 [SMILES: COc1nc2ccc(I)cc2c(Cl)c1Cc1ccc(C(F)(F)F)s1]

The title compound was prepared following the procedure described for the preparation of Intermediate 7: step c, substituting 2,4-dichloro-6-iodo-3-(3-(trifluoromethyl)benzyl)quinoline (Intermediate 7: step b) with 2,4-dichloro-6-iodo-3-((5-(trifluoromethyl)thiophen-2-yl)methyl)quinoline (Intermediate 9: step b).

Intermediate 9: Step d

Methyl 4-chloro-2-methoxy-3-((5-(trifluoromethyl)thiophen-2-yl)methyl)quinoline-6-carboxylate

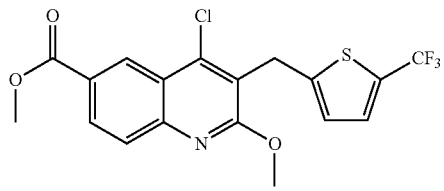 [SMILES: COC(=O)c1ccc2nc(OC)c(Cc3ccc(C(F)(F)F)s3)c(Cl)c2c1]

The title compound was prepared following the procedure described for the preparation of Intermediate 6, substituting 6-bromo-4-chloro-2-ethyl-3-(4-(trifluoromethyl)benzyl)quinoline (Intermediate 5: step c) with 4-chloro-6-iodo-2-methoxy-3-((5-(trifluoromethyl)thiophen-2-yl)methyl)quinoline (Intermediate 9: step c).

Intermediate 10

3-(4-(1H-Pyrazol-1-yl)benzyl)-6-bromo-4-chloro-2-methoxyquinoline

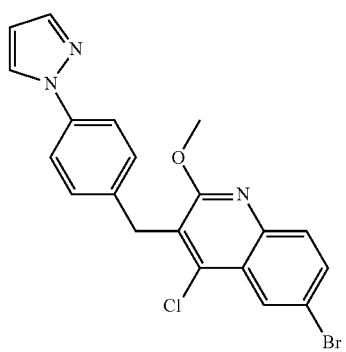 [SMILES: COc1nc2ccc(Br)cc2c(Cl)c1Cc1ccc(-n2cccn2)cc1]

A heterogeneous mixture of 3-(4-(1H-pyrazol-1-yl)benzyl)-6-bromo-2,4-dichloroquinoline (13.0 g, 30.0 mmol, Intermediate 3: step c), sodium methoxide (9.73 g, 180 mmol), and toluene (120 mL) was heated at 110° C. After 5.5 hours, the mixture was cooled to room temperature then filtered through Celite® rinsing with dichloromethane. The filtrate was concentrated to provide a crude yellow solid. The crude solid was purified by flash column chromatography (silica gel, 50% dichloromethane-hexanes initially, grading to 100% dichloromethane) to provide the title compound as a white solid.

Intermediate 11 bis(1,2-Dimethyl-1H-imidazol-5-yl)methanone

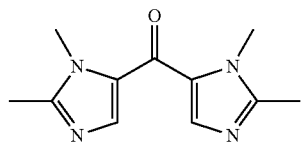

A solution of n-BuLi (2.66 M in hexane, 19.5 mL, 51.9 mmol) in THF (100 mL) was stirred under argon at ~-70° C. while a solution of 5-bromo-1,2-dimethyl-1H-imidazole (9.13 g, 52.2 mmol) in THF [60 mL; containing 3 Å molecular sieves (18 g)] was added dropwise over 8 minutes via cannula. After stirring for another 4 minutes at ~-70° C., neat ethyl methoxy(methyl)carbamate (2.96 mL, 22.7 mmol) was added dropwise over 3 minutes. This mixture was stirred at ~-70° C. for an additional 5 minutes, and the cold bath was then removed and the slurry was allowed to warm to room temperature with stirring for 1.5 hours. The reaction was then quenched with 5 M aqueous NH$_4$Cl (15 mL), dried (Na$_2$SO$_4$), filtered, and concentrated under high vacuum at 80° C. The resulting orange gummy residue was triturated with hot heptane (~40 mL) and the decanted supernatant was allowed to crystallize to provide impure title compound. This was recrystallized from toluene (~30 mL) to provide, after washing the off-white crystalline filter cake with toluene (2×~3 mL), the title compound as an off-white crystalline solid.

Intermediate 12: Step a 2,2-Dimethyl-5-(4-(trifluoromethyl)benzyl)-1,3-dioxane-4,6-dione

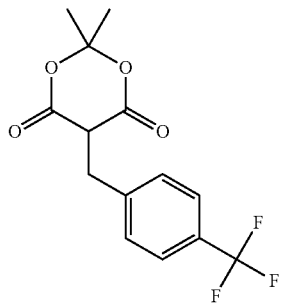 [SMILES: CC1(C)OC(=O)C(Cc2ccc(C(F)(F)F)cc2)C(=O)O1]

Similar procedures to those referenced in Tett. Lett. (2006), 651, D. Ramachary; Eur. J. Org. Chem. (2008), 975, D. Ramachary were employed. To a 5 L 3-necked flask fitted with an overhead mechanical stirrer was charged with 4-(trifluoromethyl)benzaldehyde (43.5 g, 250 mmol) followed by the addition of anhydrous EtOH (3,000 mL), Meldrum's acid (37.5 g, 260 mmol), diethyl 2,6-dimethyl-1,4-dihydropyridine-3,5-dicarboxylate (67.5 g, 266 mmol) and L-proline (6.0 g, 51 mmol) at room temperature. The yellowish reaction mixture was stirred at room temperature under N$_2$. An aliquot was removed after 4 hours and rinsed with EtOH and then Et$_2$O, and air dried. The $^1$H NMR of this aliquot showed the reaction to be complete. The full reaction was stopped and the white precipitate from the reaction was collected by filtration and rinsed with EtOH and then Et$_2$O and dried under vacuum to give the title compound in the first crop as a fine white solid. The yellowish mother liquors were concentrated and allowed to crystallize overnight from EtOH and the solid material was collected as before to provide the title compound.

Intermediate 12: Step b 2-(4-(Trifluoromethyl)benzyl)malonic acid

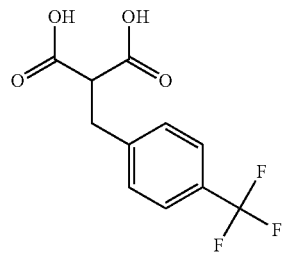 [SMILES: O=C(O)C(Cc1ccc(C(F)(F)F)cc1)C(=O)O]

To a 2 L flask containing 2,2-dimethyl-5-(4-(trifluoromethyl)benzyl)-1,3-dioxane-4,6-dione (65 g, 215 mmol, Intermediate 12: step a) was added a TFA/water solution (v/v, 560 mL/280 mL) at room temperature and the white suspension was heated between 70° C. and 78° C. in a large oil bath. The suspension did not dissolve until a temperature of 72° C. was reached. After approximately 40 minutes, the suspension became a clear homogeneous solution. After 3 hours, HPLC indicated that the reaction was complete. The mixture was concentrated on the rotary evaporator and azeotroped with toluene (4×100 mL) to give white solid which was used without further purification.

Intermediate 12: Step c

6-Bromo-2,4-dichloro-3-(4-(trifluoromethyl)benzyl)quinoline

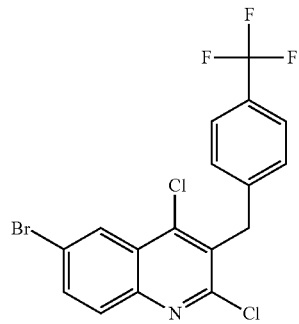 [SMILES: FC(F)(F)c1ccc(Cc2c(Cl)nc3ccc(Br)cc3c2Cl)cc1]

A 500 mL 3-necked flask fitted with a reflux condenser and Drierite® drying tube, was charged with POCl$_3$ (190 mL) and then 2-(4-(trifluoromethyl)benzyl)malonic acid (28.5 g, 109 mmol, Intermediate 12: step b) was added followed by 4-bromoaniline (19 g, 110 mmol) at room temperature. The heterogeneous mixture was heated in an aluminum mantle to 100° C. which resulted in a light amber homogenous solution after approximately 10 minutes. The reaction was stirred at 110° C. for 6.5 hours, after which removal of an aliquot and TLC (20% hexane-DCM) showed the reaction to be complete. The contents were transferred to a 1 L single-necked round bottom flask and the POCl$_3$ was removed by evaporation. The resulting dark brown material was then poured onto ice chips (~500 g) in a 2 L Erlenmeyer flask pre-cooled to 0° C. DCM (~500 mL) was added and the solution was stirred at 0° C. as a solution of 6 M aqueous KOH (~500 mL) was added carefully. 5 N Aqueous NH₄OH (~100 mL) was also added to bring the pH to ~8-9. The neutralization process was kept at 0° C. throughout. More DCM was added and the organic phase was separated. The aqueous portion was washed with DCM (3×250 mL) and the combined organics were washed with brine, dried over Na₂SO₄, filtered and concentrated to provide a brown solid. The crude solid was triturated with CH₃CN which provided the title compound as a white fluffy solid after filtration.

Intermediate 12: Step d

6-Bromo-4-chloro-2-methoxy-3-(4-(trifluoromethyl)benzyl)quinoline

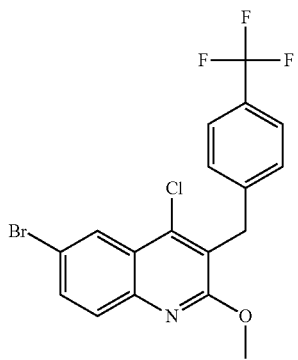 [SMILES: COc1nc2ccc(Br)cc2c(Cl)c1Cc1ccc(C(F)(F)F)cc1]

To a 1 L flask containing 6-bromo-2,4-dichloro-3-(4-(trifluoromethyl)benzyl)quinoline (32.5 g, 74.7 mmol, Intermediate 12: step c) was added toluene (550 mL) followed by solid sodium methoxide (40 g, 740 mmol, 97% purity) at room temperature. The suspension was stirred at reflux (~118° C.) in an aluminum mantle. TLC (50% hexane-DCM) and HPLC after 5.5 hours showed the reaction to be complete. The reaction mixture was filtered through Celite® while still warm (~80° C.) and rinsed with warm toluene (~70° C., 500 mL). The colorless filtrate was concentrated and the resulting residue solidified to provide the title compound as an off white solid.

Intermediate 12: Step e (4-Chloro-2-methoxy-3-(4-(trifluoromethyl)benzyl)quinolin-6-yl)(2,6-dimethylpyridin-3-yl)methanol

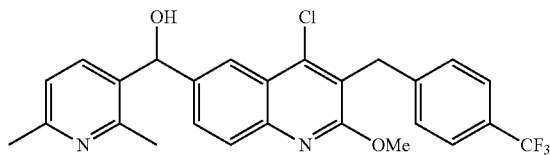 [SMILES: COc1nc2ccc(C(O)c3ccc(C)nc3C)cc2c(Cl)c1Cc1ccc(C(F)(F)F)cc1]

To a 100 mL flask containing 6-bromo-4-chloro-2-methoxy-3-(4-(trifluoromethyl)benzyl)quinoline (2.5 g, 5.8 mmol, Intermediate 12: step d) was added THF (55 mL) at room temperature which resulted in a colorless homogeneous mixture. The solution was cooled to −70° C. (the solution remained homogeneous) and then n-butyllithium (2.5 M in hexanes, 2.6 mL, 6.5 mmol) was added dropwise. The color of the solution became a reddish-brown color. After 1 minute, (2,6-dimethylpyridine-3-carboxaldehyde (1.01 g, 7.5 mmol in 2 mL THF) was introduced and the color of the mixture became a light greenish-yellow color. After 15 minutes, HPLC and TLC (50% acetone-hexane) indicated that the reaction was complete. The mixture was allowed to warm to −20° C. over 40 minutes at which time the reaction was quenched with aqueous NH₄Cl solution. The reaction was diluted further with water and extracted with EtOAc (3×50 mL). The combined organics were washed with brine, dried over Na₂SO₄, filtered and concentrated to provide an orange foam. The crude product was chromatographed on silica gel (10% acetone-hexane increasing to 30% acetone) to afford the title compound as a light yellow foam.

Intermediate 12: Step f (4-Chloro-2-methoxy-3-(4-(trifluoromethyl)benzyl)quinolin-6-yl)(2,6-dimethylpyridin-3-yl)methanone

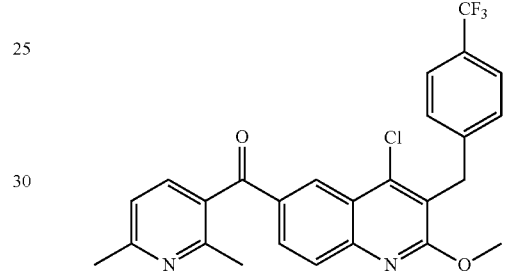

To a 100 mL flask containing (4-chloro-2-methoxy-3-(4-(trifluoromethyl)benzyl)quinolin-6-yl)(2,6-dimethylpyridin-3-yl)methanol (1.51 g, 3.1 mmol, Intermediate 12: step e) was added 1,4-dioxane (50 mL) followed by activated MnO₂ (1.3 g, 15 mmol) and the mixture was heated to reflux in an aluminum heating mantle under N₂. After 1 hour, TLC (25% acetone:hexane) indicated that the reaction was complete. The contents were filtered while still hot through Celite® and rinsed with THF. The resulting light yellow solution was concentrated and chromatographed by passing through a silica gel column (10% acetone-hexane increasing to 25% acetone) to give the title compound as a light yellowish amorphous solid.

Intermediate 13

Bis(1-Methyl-1H-1,2,3-triazol-5-yl)methanone

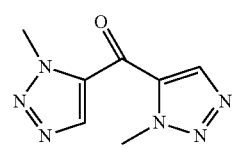

A solution of 1-methyl-1H-1,2,3-triazole (0.954 g, 11.4 mmol, prepared according to PCT Int. Appl., 2008098104) in THF (22 mL) was stirred at ~−70° C. under argon while n-BuLi (2.56 M in hexanes, 4.29 mL, 11.0 mmol) was added dropwise over 5 minutes. After stirring for another 5 minutes, a solution of ethyl methoxy(methyl)carbamate (0.665 g, 4.99 mmol) in THF (3 mL) was added dropwise over 5 minutes. After stirring at ~−70° C. for an additional 5 minutes, the cold bath was removed and the light slurry was allowed to warm to room temperature with stirring for 1 hour 20 minutes. The reaction was then quenched at room temperature with 5 M aqueous NH$_4$Cl (3 mL) and the aqueous layer was extracted with THF (1×6 mL). The combined organic layers were dried (Na$_2$SO$_4$), filtered, and concentrated. A portion of the residue was crystallized from ~30 mL toluene to provide, after washing the filter cake with ether (1×3 mL) and heptane (1×3 mL), to yield the title compound as blunt needles.

Intermediate 14: Step a

N-Methoxy-N,3-dimethyl-4-nitrobenzamide

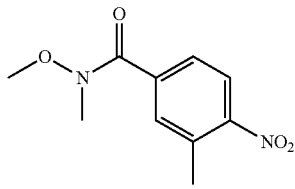 [SMILES: CON(C)C(=O)c1ccc([N+](=O)[O-])c(C)c1]

Triethylamine (37.9 mL, 273 mmol) was added slowly to a mixture of 3-methyl-4-nitrobenzoic acid (25.0 g, 136 mmol), N,O-dimethylhydroxylamine hydrochloride (14.95 g, 150.3 mmol), and EDCI (31.40 g, 163.9 mmol) in DCM (171 mL). The mixture was stirred at room temperature overnight, quenched with saturated aqueous NaHCO$_3$ and stirred at room temperature for 30 minutes. Water (50 mL) was added followed by additional DCM. The mixture was stirred for 10 minutes and layers were separated. The aqueous layer was again extracted with DCM. The combined organic layers were dried over MgSO$_4$, then filtered. The solvent was removed and the residual oil chromatographed (0 to 20% EtOAc/DCM) to provide the title compound as a yellow oil.

Intermediate 14: Step b (1-Methyl-1H-imidazol-5-yl)(3-methyl-4-nitrophenyl)methanone

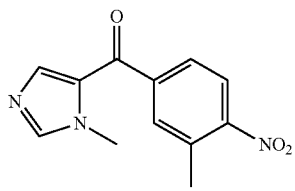 [SMILES: Cc1cc(C(=O)c2cncn2C)ccc1[N+](=O)[O-]]

A solution of EtMgBr (3.0 M in diethylether, 15.1 mL, 45.2 mmol) was added dropwise, to a solution of 5-bromo-1-methyl-1H-imidazole (7.28 g, 45.2 mmol) in dry DCM (40 mL) at 0° C. and stirred for 10 minutes. The mixture was then stirred at room temperature for 30 minutes, cooled in an ice-brine bath and N-methoxy-N,3-dimethyl-4-nitrobenzamide (8.45 g, 37.7 mmol, Intermediate 14: step a) dissolved in 22 mL of DCM was added dropwise. A dark brown solid mass formed. The ice bath was removed and mixture stirred at room temperature for 18 hours. Water was added to the suspension followed by 6 M aqueous HCl slowly to neutralize the mixture (pH=6-7). More DCM was added and layers separated. The organic layer was dried over MgSO$_4$, filtered and concentrated. Et$_2$O was added, the slurry sonicated, and precipitates were filtered and dried to provide the title compound.

Intermediate 14: Step c (4-Amino-3-methylphenyl)(1-methyl-1H-imidazol-5-yl)methanone

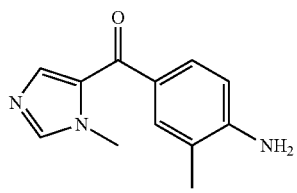

Zn (2.66 g, 40.7 mmol) was added in 2 portions over a period of 2 minutes to a mixture of (1-methyl-1H-imidazol-5-yl)(3-methyl-4-nitrophenyl)methanone (2.0 g, 8.1 mmol, Intermediate 14: step b) and NH$_4$Cl (2.18 g, 40.7 mmol) in acetone (18.5 mL) and water (8.2 mL) at 0° C. After stirring for 1 hour, the reaction mixture was filtered through Celite®, rinsing with EtOAc. Acetone and EtOAc were removed on a rotary evaporator and the aqueous layer was filtered and the solids dried under vacuum to provide the title compound.

Intermediate 14: Step d (3-(4-(1H-Pyrazol-1-yl)benzyl)-2,4-dichloro-8-methylquinolin-6-yl)(1-methyl-1H-imidazol-5-yl)methanone

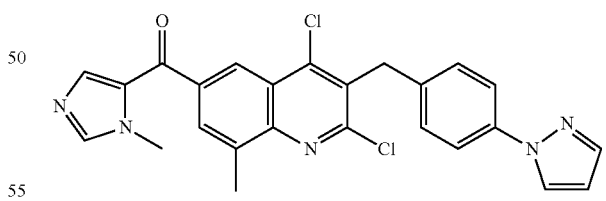

A heterogeneous mixture of (4-amino-3-methylphenyl)(1-methyl-1H-imidazol-5-yl)methanone (1.0 g, 4.6 mmol, Intermediate 14: step c), 2-(4-(1H-pyrazol-1-yl)benzyl)malonic acid (1.3 g, 4.6 mmol, Intermediate 3: step b) and POCl$_3$ (4.3 mL) was heated at 105° C. for 18 hours then cooled to room temperature. The mixture was poured into ice water and treated with aqueous NH$_4$OH solution (kept adding ice during addition) to a basic pH 8-9. The aqueous layer was extracted with DCM, washed with a saturated aqueous solution of NaCl, dried (MgSO$_4$) and concentrated. The crude product was purified by flash column chromatography (silica gel, 0-100% EtOAc/DCM) to provide the title compound.

Intermediate 14: Step e 3-(4-(1H-Pyrazol-1-yl)benzyl)-8-methyl-6-(1-methyl-1H-imidazole-5-carbonyl)quinoline-2,4-dicarbonitrile.TFA

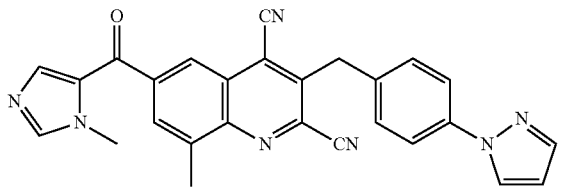 [SMILES: Cc1cc(C(=O)c2cncn2C)cc2c(C#N)c(Cc3ccc(-n4cccn4)cc3)c(C#N)nc12]

A microwave vial was charged with 3-(4-(1H-pyrazol-1-yl)benzyl)-2,4-dichloro-8-methylquinolin-6-yl)(1-methyl-1H-imidazol-5-yl)methanone (100 mg, 0.21 mmol, Intermediate 14: step d), Zn(CN)₂ (40.1 mg, 0.341 mmol), chloro(2-dicyclohexylphosphino-2',4',6'-triisopropyl-1,1'-biphenyl)[2-(2-aminoethyl)phenyl]palladium(II) (15.5 mg, 0.021 mmol) and zinc dust (3.43 mg, 0.053 mmol). Dimethylacetamide (3.5 mL) was then added and the mixture was purged with nitrogen for 10 minutes and placed in a pre-heated aluminum block at 120° C. for 4 hours. The mixture was cooled to room temperature and filtered through Celite®, rinsing with EtOAc and DCM. The filtrate was concentrated and the residue was purified by flash column chromatography (silica gel, 50 to 100% EtOAc-DCM). The product was further purified by reverse-phase HPLC (5-85% CH₃CN—H₂O, 0.05% TFA) to provide the title compound.

Intermediate 15: Step a

N-Methoxy-N-methyl-4-nitrobenzamide

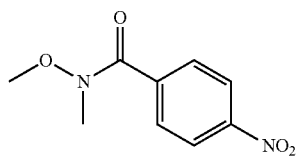

Triethylamine (4.89 mL, 35.184 mmol) was added slowly to a mixture of commercially available 4-nitrobenzoic acid (3.0 g, 17.592 mmol), N,O-dimethylhydroxylamine hydrochloride (1.92 g, 19.351 mmol), and EDCI (4.05 g, 21.11 mmol) in CH₂Cl₂ (30 mL). The mixture was stirred at room temperature overnight then quenched with saturated aqueous NaHCO₃. Water (50 mL) was added followed by additional CH₂Cl₂. The mixture as stirred for 10 minutes and layers were separated. The CH₂Cl₂ layer was dried over Na₂SO₄, then filtered. The solvent was removed under reduced pressure and the residual oil chromatographed (CH₂Cl₂/EtOAc) to provide the title compound as a white solid.

Intermediate 15: Step b (1-Methyl-1H-imidazol-5-yl)(4-nitrophenyl)methanone

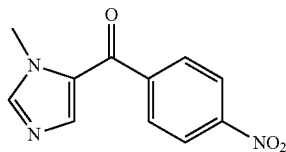

To a solution of 5-bromo-1-methyl-1H-imidazole (3.22 g, 19.982 mmol) in DCM (15 mL) was added ethyl magnesium bromide (6.66 mL, 19.982 mmol; 3.0 M in diethyl ether) dropwise over a 10 minute period. The resulting orange-red solution was stirred at room temperature for 15 minutes, cooled in an ice bath to 0° C. and N-methoxy-N-methyl-4-nitrobenzamide (3.5 g, 16.652 mmol, Intermediate 15: step a) dissolved in DCM (10 mL) was added dropwise. The cold bath was removed and the solid suspension stirred at room temperature for 48 hours. Water was added followed by 6 M aqueous HCl to a neutral pH (pH=6-7). The aqueous mixture was extracted with DCM, dried over Na₂SO₄, filtered and concentrated. Et₂O was added and the mixture sonicated. The precipitate was collected by filtration and dried to provide the title compound as a tan solid.

Intermediate 15: Step c (4-Aminophenyl)(1-methyl-1H-imidazol-5-yl)methanone

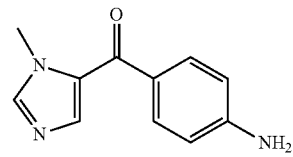

A mixture of (1-methyl-1H-imidazol-5-yl)(4-nitrophenyl)methanone (1.30 g, 5.62 mmol, Intermediate 15: step b and tin(II)chloride dihydrate (6.54 g, 28.1 mmol) in EtOH (35 mL) was stirred at reflux for 1 hour, cooled to room temperature and evaporated in vacuo to remove most of the EtOH. The residue was poured into a 3 M aqueous NaOH/ice solution rinsing with EtOAc. The mixture was stirred at room temperature for 15 minutes then layers were separated. The aqueous layer was again extracted with EtOAc. The combined EtOAc extracts were washed with brine, dried (Na₂SO₄), filtered and evaporated in vacuo to provide the title compound as a yellow solid.

Intermediate 16: Step a (4-Chlorophenyl)(4-nitrophenyl)methanone

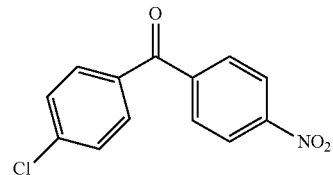

A mixture of (4-chlorophenyl)boronic acid (1.50 g, 9.59 mmol), 4-nitrobenzoyl chloride (1.78 g 9.59 mmol), bis(triphenylphosphine)palladium(II) chloride (0.137 g, 0.192 mmol) and K$_3$PO$_4$ (3.34 g, 19.2 mmol) in toluene (30 mL) was treated as described in WO 2010/015355 to provide the title compound.

Intermediate 16: Step b (4-Aminophenyl)(4-chlorophenyl)methanone

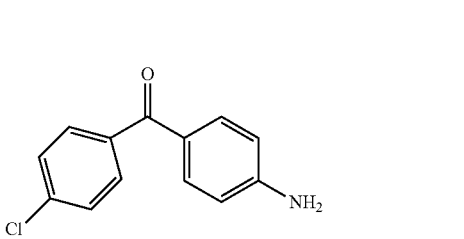 [SMILES: O=C(c1ccc(Cl)cc1)c1ccc([N+](=O)[O-])cc1]

The title compound was prepared by using (4-chlorophenyl)(4-nitrophenyl)methanone (Intermediate 16: step a) in place of (1-methyl-1H-imidazol-5-yl)(4-nitrophenyl)methanone (Intermediate 15: step b) then following the procedure described for the preparation of (4-aminophenyl)(1-methyl-1H-imidazol-5-yl)methanone (Intermediate 15: step c).

Intermediate 16: Step c 4-(4-Aminobenzoyl)benzonitrile

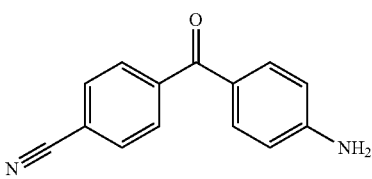 [SMILES: N#Cc1ccc(C(=O)c2ccc(N)cc2)cc1]

A mixture containing (4-aminophenyl)(4-chlorophenyl)methanone (2.5 g, 11 mmol, Intermediate 16: step b), zinc cyanide (1.65 g, 14.0 mmol), tris(dibenzylideneacetone)dipalladium (692 mg, 0.755 mmol), zinc powder (141 mg, 2.16 mmol), 2-dicyclohexylphosphino-2',4',6'-triisopropylbiphenyl (XPhos, 371 mg, 0.755 mmol), and dimethylacetamide (54 mL, sparged with nitrogen for 45 minutes) was heated to 120° C. After 2 hours, the flask was allowed to cool to 23° C. The mixture was diluted with ethyl acetate (150 mL) and then filtered through Celite®. The filtrate was washed with saturated aqueous sodium chloride solution (2×100 mL). The organic phase was dried over sodium sulfate and then filtered. Silica gel (8 g) was added to the filtrate and the solvent was removed by rotary evaporation to afford a free-flowing powder. The powder was loaded onto a column of silica gel for purification. Elution with dichloromethane initially, grading to 5% methanol-dichloromethane provided the title compound as a solid.

Intermediate 16: Step d 4-(3-(4-(1H-1,2,4-Triazol-1-yl)benzyl)-2,4-dichloroquinoline-6-carbonyl)benzonitrile

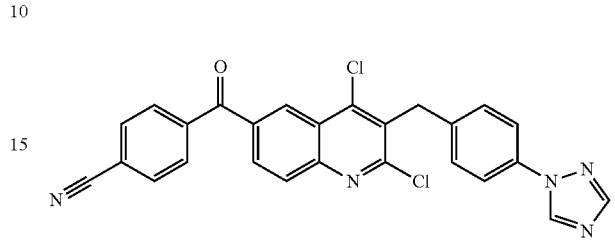

A mixture containing 4-(4-aminobenzoyl)benzonitrile (1.30 g, 5.85 mmol, Intermediate 16: step c), 2-(4-(1H-1,2,4-triazol-1-yl)benzyl)malonic acid (1.53 g, 5.85 mmol, Intermediate 82: step c), and phosphorus oxychloride (6.5 mL) was heated to 120° C. After 105 minutes, the flask was allowed to cool to 23° C. Dichloromethane (50 mL) and ice (50 mL) were added and the resulting mixture cooled in an ice-water bath. 6 M aqueous potassium hydroxide solution was added dropwise with stirring until the pH was between 8-9 by litmus paper test. The biphasic mixture was allowed to warm to 23° C. and then the layers were separated. The aqueous layer was extracted with dichloromethane (50 mL). The organic layers were combined and the combined solution was dried over sodium sulfate. The dried solution was filtered. Silica gel (7 g) was added to the filtrate and then the solvents were removed by rotary evaporation to afford a free-flowing powder. The powder was loaded onto a column of silica gel for purification. Elution with hexanes initially, grading to 75% ethyl acetate-hexanes provided the title compound as an impure yellow solid. The yellow solid was suspended in acetonitrile (30 mL). The suspension was sonicated at 23° C. After 10 minutes, the solids were collected by filtration and rinsed with acetonitrile. The collected solids were dried to provide pure title compound as a pale-yellow solid.

Intermediate 16: Step e 4-(3-(4-(1H-1,2,4-Triazol-1-yl)benzyl)-4-chloro-2-methoxyquinoline-6-carbonyl)benzonitrile

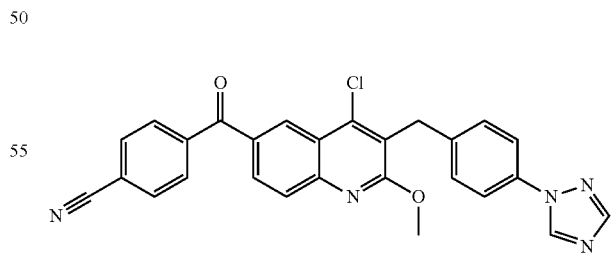

A heterogeneous mixture containing 4-(3-(4-(1H-1,2,4-triazol-1-yl)benzyl)-2,4-dichloroquinoline-6-carbonyl)benzonitrile (583 mg, 1.20 mmol, Intermediate 16: step d), sodium methoxide (780 mg, 14.4 mmol), and toluene (17 mL) was heated to 110° C. After 45 minutes, the flask was allowed to cool to 23° C. Dichloromethane (100 mL) was added to the flask and then the mixture was filtered through Celite®, rinsing with dichloromethane. Silica gel (5 g) was added to the filtrate and the solvent was removed by rotary evaporation to provide a free-flowing powder. The powder was loaded onto a column of silica gel for flash chromatography purification. Elution with hexanes initially, grading to 80% ethyl acetate-hexanes afforded the title compound as a white solid.

Intermediate 17: Step a 3-(4-(1H-Imidazol-1-yl)benzyl)-6-iodoquinoline-2,4-diol

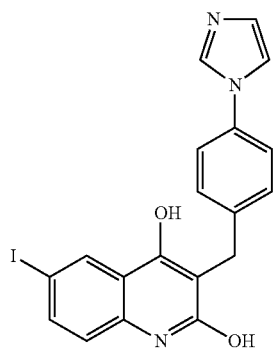 [SMILES: Oc1nc2ccc(I)cc2c(O)c1Cc1ccc(-n2ccnc2)cc1]

A mixture containing 6-iodoquinoline-2,4-diol (7.77 g, 27.1 mmol, Intermediate 4: step b), 4-(1H-imidazol-1-yl)benzaldehyde (4.66 g, 27.1 mmol) and diethyl 1,4-dihydro-2,6-dimethyl-3,5-pyridinedicarboxylate (6.86 g, 27.1 mmol) in pyridine (54 mL) was heated to 110° C. After 16 hours, the flask was allowed to cool to 23° C. and then the solvent was removed by rotary evaporation at 40° C. Ethanol (150 mL) was added with stirring to the residue resulting in the formation of a fine suspension. After 1 hour, the mixture was filtered through filter paper and the solids were rinsed with ethanol. The rinsed solids were collected and dried to provide the title compound as an off-white solid.

Intermediate 17: Step b 3-(4-(1H-Imidazol-1-yl)benzyl)-2,4-dichloro-6-iodoquinoline

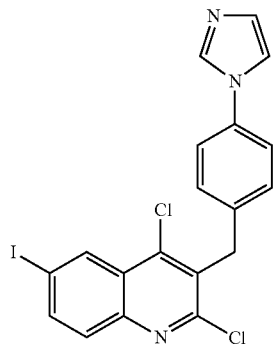 [SMILES: Clc1nc2ccc(I)cc2c(Cl)c1Cc1ccc(-n2ccnc2)cc1]

A mixture containing 3-(4-(1H-imidazol-1-yl)benzyl)-6-iodoquinoline-2,4-diol (3.0 g, 6.8 mmol, Intermediate 17: step a) and phosphorus oxychloride (1.9 mL, 20 mmol) in acetonitrile (34 mL) was heated to 100° C. After 16 hours, the flask was allowed to cool to 23° C. Dichloromethane (200 mL) and saturated aqueous sodium bicarbonate solution were added in sequence and the resulting biphasic mixture was stirred for 30 minutes. The biphasic mixture was filtered through Celite® and the layers of the biphasic filtrate were separated. The organic layer was dried with magnesium sulfate and the dried solution was filtered. Silica gel (7 g) was added to the filtrate and the solvent was removed by rotary evaporation to afford a free-flowing powder. The powder was loaded onto a column of silica gel for purification. Elution with dichloromethane initially, grading to 5% methanol-dichloromethane provided the title compound as a solid.

Intermediate 17: Step c 3-(4-(1H-Imidazol-1-yl)benzyl)-4-chloro-6-iodo-2-methoxyquinoline

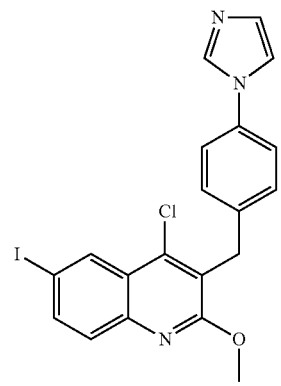 [SMILES: COc1nc2ccc(I)cc2c(Cl)c1Cc1ccc(-n2ccnc2)cc1]

A heterogeneous mixture containing 3-(4-(1H-imidazol-1-yl)benzyl)-2,4-dichloro-6-iodoquinoline (1.2 g, 2.5 mmol, Intermediate 17: step b) and sodium methoxide (1.6 g, 30 mmol) in toluene (25 mL) was heated to 110° C. After 2 hours, the flask was allowed to cool to 23° C. Dichloromethane (100 mL) was added and the mixture was filtered through Celite®, rinsing the filter cake with dichloromethane. The filtrate was concentrated to provide the title compound as an off-white solid. This material was used without further purification.

Intermediate 18

1-(4-Benzoylpiperidin-1-yl)ethanone

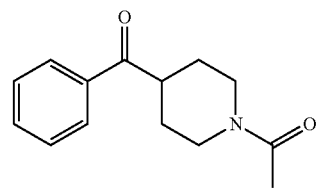 [SMILES: CC(=O)N1CCC(C(=O)c2ccccc2)CC1]

A mixture of phenyl(piperidin-4-yl)methanone hydrochloride (743 mg, 3.29 mmol) in dichloromethane (13.2 mL) and triethylamine (1.10 mL, 7.90 mmol) was treated with Ac₂O (0.373 mL, 3.95 mmol) dropwise over 1 minute in an ice bath under argon, and the resulting translucent mixture was immediately removed from the ice bath and stirred at room temperature overnight. The reaction was then extracted with 1 M aqueous HCl (1×8 mL) and 1 M aqueous NaOH (1×8 mL), and the organic layer was dried (Na$_2$SO$_4$), filtered, and concentrated to provide the title compound as a translucent beige oil that crystallized upon standing.

Intermediate 19: Step a (2,6-Dimethylpyridin-3-yl)(1-methyl-1H-1,2,3-triazol-5-yl)methanol

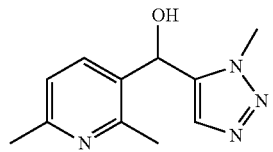 [SMILES: Cc1ccc(C(O)c2cnnn2C)c(C)n1]

A solution of n-butyllithium in hexanes (2.5 M, 22.5 mL, 56.3 mmol) was added dropwise by syringe to a stirring solution of 1-methyl-1H-1,2,3-triazole (5.00 g, 60.2 mmol, prepared according to PCT Int. Appl., 2008098104) in dry tetrahydrofuran (400 mL) at −55° C. The resulting off-white slurry was stirred at −45° C. for 20 minutes, whereupon a solution of 2,6-dimethyl-pyridine-3-carbaldehyde (8.33 g, 61.7 mmol) in dry tetrahydrofuran (10 mL) was added dropwise by syringe. After 5 minutes, the cooling bath was removed and the reaction mixture was allowed to slowly warm. After 45 minutes, saturated aqueous ammonium chloride solution (10 mL) and ethyl acetate (100 mL) were added. The mixture was concentrated by rotary evaporation. The residue was dissolved in ethyl acetate (300 mL). The organic solution was washed with saturated aqueous sodium chloride solution (100 mL, containing excess solid sodium chloride). The aqueous layer was extracted with ethyl acetate (2×100 mL). The organic layers were combined and the combined solution was concentrated. Ether (100 mL) was added to the residue and the mixture was sonicated for 20 minutes during which time a white solid crashed out. The solids were collected by filtration. Ether (100 mL) was added to the collected solids and the mixture sonicated a second time. After 20 minutes, the mixture was filtered and the solids were collected to provide the title compound as a fine powder.

Intermediate 19: Step b (2,6-Dimethylpyridin-3-yl)(1-methyl-1H-1,2,3-triazol-5-yl)methanone

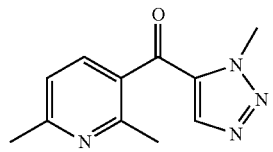 [SMILES: Cc1ccc(C(=O)c2cnnn2C)c(C)n1]

A mixture containing (2,6-dimethylpyridin-3-yl)(1-methyl-1H-1,2,3-triazol-5-yl)methanol (9.8 g, 44.9 mmol, Intermediate 19: step a) and manganese dioxide (18.8 g, 184 mmol) in dry dioxane (225 mL) was heated to 100° C. with stirring. After 1 hour, the mixture was cooled to 40° C. The cooled mixture was filtered through a 2 cm pad of Celite® and rinsed with tetrahydrofuran (100 mL). The filtrate was concentrated to provide the title compound as an off-white solid.

Intermediate 20: Step a 3-(4-(1H-1,2,4-Triazol-1-yl)benzyl)-6-iodoquinoline-2,4-diol

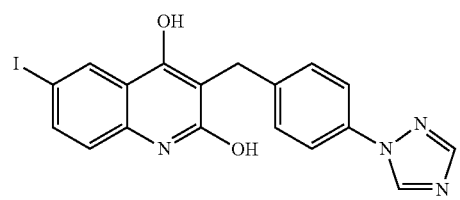 [SMILES: Oc1nc2ccc(I)cc2c(O)c1Cc1ccc(-n2cncn2)cc1]

A mixture containing 6-iodoquinoline-2,4-diol (1.0 g, 3.5 mmol, Intermediate 4: step b), 4-(1H-1,2,4-triazol-1-yl)benzaldehyde (0.60 g, 3.5 mmol, Intermediate 82: step c), and diethyl 1,4-dihydro-2,6-dimethyl-3,5-pyridinedicarboxylate (0.93 g, 3.5 mmol) in pyridine (17 mL) was heated to 80° C. After 2 hours, the flask was allowed to cool to 23° C. resulting in the formation of a solid. Diethyl ether (20 mL) was added. The solids were collected, washed with diethyl ether, and then dried to provide the title compound as an off-white solid.

Intermediate 20: Step b 3-(4-(1H-1,2,4-Triazol-1-yl)benzyl)-2,4-dichloro-6-iodoquinoline

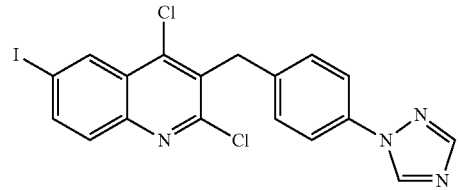 [SMILES: Clc1nc2ccc(I)cc2c(Cl)c1Cc1ccc(-n2cncn2)cc1]

A mixture containing 3-(4-(1H-1,2,4-triazol-1-yl)benzyl)-6-iodoquinoline-2,4-diol (1.0 g, 2.3 mmol, Intermediate 20: step a) and phosphorus oxychloride (0.84 mL, 9.0 mmol) in acetonitrile (11 mL) was heated to 100° C. After 2 hours, additional phosphorus oxychloride (0.84 mL) was added. After 4 hours, the flask was allowed to cool to 23° C. After 12 hours, water (15 mL) was slowly added with stirring resulting in the formation of a solid. After 30 minutes, the mixture was filtered through filter paper and the filter cake was rinsed with a 2:1 mixture of acetonitrile-water (100 mL). The solids were collected, air dried for 30 minutes, and then dried under high vacuum to provide the title compound as an off-white solid which was used in the next step without further purification.

Intermediate 20: Step c 3-(4-(1H-1,2,4-Triazol-1-yl)benzyl)-4-chloro-6-iodo-2-methoxyquinoline

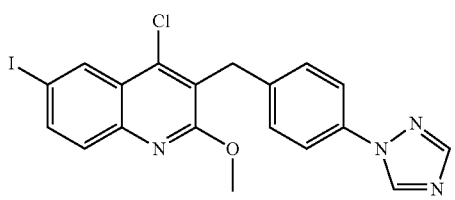 [SMILES: COc1nc2ccc(I)cc2c(Cl)c1Cc1ccc(-n2cncn2)cc1]

Sodium methoxide (741 mg, 13.7 mmol) was added to a solution of 3-(4-(1H-1,2,4-triazol-1-yl)benzyl)-2,4-dichloro-6-iodoquinoline (1.1 g, 2.3 mmol, Intermediate 20: step b) in toluene (11 mL) with stirring. The mixture was heated to 105° C. After 2 hours, additional sodium methoxide (250 mg, 4.6 mmol) was added. After 3 hours, the flask was allowed to cool to 23° C. Dichloromethane (50 mL) was added and then the mixture was filtered through Celite®. The filter cake was washed with dichloromethane. The filtrate was concentrated to provide the title compound as a white solid.

Intermediate 21: Step a (3-(4-(1H-Pyrazol-1-yl)benzyl)-4-chloro-2-methoxyquinolin-6-yl)(1,2-dimethyl-1H-imidazol-5-yl)methanol

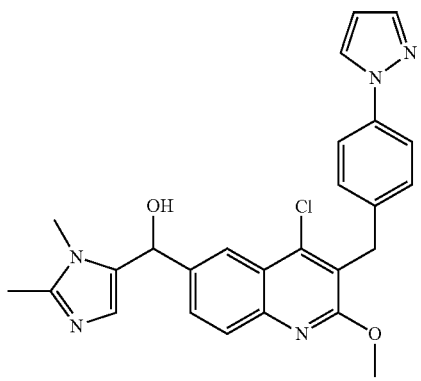 [SMILES: COc1nc2ccc(C(O)c3cnc(C)n3C)cc2c(Cl)c1Cc1ccc(-n2cccn2)cc1]

A solution of n-butyllithium in hexanes (1.6 M, 1.5 mL, 2.3 mmol) was added dropwise to a stirring solution of 3-(4-(1H-pyrazol-1-yl)benzyl)-6-bromo-4-chloro-2-methoxyquinoline (1 g, 2.3 mmol, Intermediate 10) in tetrahydrofuran (18 mL) at −78° C. After 3 minutes, a solution of 1,2-dimethyl-1H-imidazole-5-carbaldehyde (347 mg, 2.8 mmol) in tetrahydrofuran (5 mL) was added dropwise. After 5 minutes, the flask was placed into an ice-water bath. After 30 minutes, water (10 mL) was added and the biphasic mixture was allowed to warm to 23° C. The mixture was partitioned between half-saturated sodium chloride solution (50 mL) and ethyl acetate (100 mL). The layers were separated. The organic layer was dried with sodium sulfate and the dried solution was filtered. Silica gel (3 g) was added to the filtrate and the solvent was removed by rotary evaporation to afford a free-flowing powder. The powder was loaded onto a column of silica gel for purification. Elution with ethyl acetate initially, grading to 7% methanol-ethyl acetate provided the title compound as an off-white solid.

Intermediate 21: Step b (3-(4-(1H-Pyrazol-1-yl)benzyl)-4-chloro-2-methoxyquinolin-6-yl)(1,2-dimethyl-1H-imidazol-5-yl)methanone

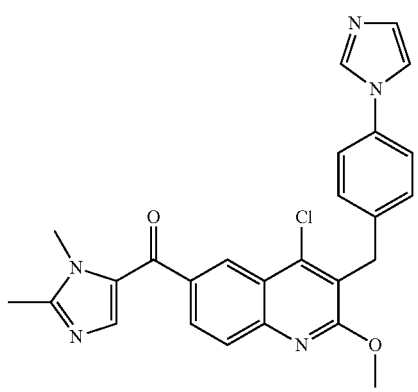 [SMILES: COc1nc2ccc(C(=O)c3cnc(C)n3C)cc2c(Cl)c1Cc1ccc(-n2ccnc2)cc1]

A heterogeneous mixture of (3-(4-(1H-pyrazol-1-yl)benzyl)-4-chloro-2-methoxyquinolin-6-yl)(1,2-dimethyl-1H-imidazol-5-yl)methanol (625 mg, 1.32 mmol, Intermediate 21: step a) and manganese dioxide (809 mg, 7.91 mmol) in dioxane (13 mL) was heated to 100° C. After 135 minutes, the flask was allowed to cool to 23° C. Dichloromethane (40 mL) was added and the mixture was filtered through Celite®, rinsing with dichloromethane. Silica gel (3 g) was added to the filtrate and the solvent was removed by rotary evaporation to afford a free-flowing powder. The powder was loaded onto a column of silica gel for purification. Elution with 30% ethyl acetate-hexanes initially, grading to 100% ethyl acetate provided the title compound as an off-white solid.

Intermediate 22: Step a

6-Iodo-3-(4-methylbenzyl)quinoline-2,4-diol

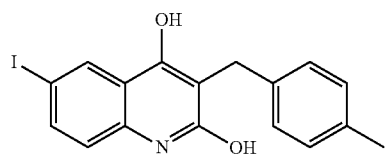

A mixture containing 6-iodoquinoline-2,4-diol (6.5 g, 22 mmol, Intermediate 4: step b), 4-methylbenzaldehyde (2.5 g, 21 mmol), and diethyl 1,4-dihydro-2,6-dimethyl-3,5-pyridinedicarboxylate (6.0 g, 24 mmol) in pyridine (112 mL) was heated to 80° C. After 4 hours, the flask was allowed to cool to 23° C., resulting in the formation of a solid. The mixture was filtered through filter paper and the filter cake was washed with diethyl ether. The solids were collected and then dried to provide the title compound as a white solid.

Intermediate 22: Step b 2,4-Dichloro-6-iodo-3-(4-methylbenzyl)quinoline

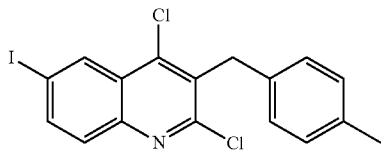 [SMILES: Cc1ccc(Cc2c(Cl)nc3ccc(I)cc3c2Cl)cc1]

A mixture containing 6-iodo-3-(4-methylbenzyl)quinoline-2,4-diol (5.0 g, 11 mmol, Intermediate 22: step a) and phosphorus oxychloride (4.0 mL, 43 mmol) in acetonitrile (53 mL) was heated to 90° C. During heating a white solid formed. After 6 hours, the flask was allowed to cool to 23° C. After 12 hours, water (30 mL) was slowly added with stirring. After 30 minutes, the mixture was filtered through filter paper and the filter cake was rinsed sequentially with water (50 mL) and diethyl ether (50 mL). The solids were collected, air dried for 60 minutes, and then dried under high vacuum at 40° C. to provide the title compound as an impure off-white solid which was used in the next step without further purification.

Intermediate 22: Step c

4-Chloro-6-iodo-2-methoxy-3-(4-methylbenzyl)quinoline

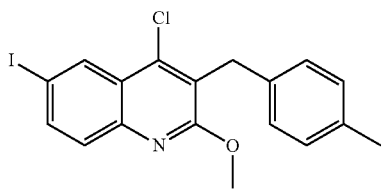 [SMILES: COc1nc2ccc(I)cc2c(Cl)c1Cc1ccc(C)cc1]

Sodium methoxide (3.2 g, 60 mmol) was added to a solution of 2,4-dichloro-6-iodo-3-(4-methylbenzyl)quinoline (4.3 g, 10 mmol, Intermediate 22: step b) in toluene (50 mL) with stirring. The mixture was heated to 105° C. After 18 hours, the flask was allowed to cool to 23° C. Dichloromethane (100 mL) was added and then the mixture was filtered through Celite®. The filter cake was washed with dichloromethane. The filtrate was concentrated and the residue was purified by flash column chromatography on silica gel eluting with hexanes initially, grading to 20% ethyl acetate-hexanes to provide the title compound as a white solid.

Intermediate 23: Step a (2,4-Dimethylthiazol-5-yl)(1-methyl-1H-1,2,3-triazol-5-yl)methanol

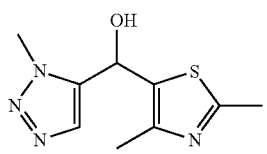

1-Methyl-1H-1,2,3-triazole was prepared according to the literature reference WO2008/98104. To a 2 L flask containing 1-methyl-1H-1,2,3-triazole (9 g, 108.3 mmol) was added THF (1500 mL) and the solution was cooled to −40° C. To this colorless homogeneous solution was added n-butyllithium (2.5 M in hexanes, 45 mL, 112.5 mmol) dropwise which immediately afforded a dark brown viscous mixture. The mixture was kept between −10 to −20° C. for 60 minutes, then a THF solution of 2,4-dimethylthiazole-5-carbaldehyde (17.2 g, 121.8 mmol in 200 mL THF) was introduced via cannula. Once the aldehyde was added the reaction was allowed to warm to room temperature. After 3 hours, the reaction was quenched by pouring into a saturated solution of aqueous NH₄Cl. The aqueous portion was extracted with EtOAc in portions, 7×400 mL. The combined organics were washed with brine, dried over MgSO₄, filtered and concentrated to give a brown oil. Chromatography on silica gel (10% acetone-DCM increasing to 50% acetone and increasing to 10% MeOH-DCM) provided the title compound as an amber solid.

Intermediate 23: Step b (2,4-Dimethylthiazol-5-yl)(1-methyl-1H-1,2,3-triazol-5-yl)methanone

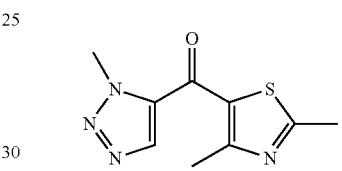

To a 500 mL flask containing (2,4-dimethylthiazol-5-yl)(1-methyl-1H-1,2,3-triazol-5-yl)methanol (10.5 g, 46.8 mmol, Intermediate 23: step a) was added 1,4-dioxane (400 mL) and the contents were warmed to form a homogeneous solution. Activated MnO₂ (18 g, 207 mmol) was added and the dark brownish mixture was heated to reflux in an aluminum heating mantle under an atmosphere of N₂. After 1.5 hours, the contents were filtered while still hot through Celite® and rinsed with warm THF. The resulting light orange solution was concentrated and passed through a silica gel column (25% acetone-DCM) to provide the title compound as a light orange solid.

Intermediate 24: Step a 3-(4-(Dimethylamino)benzyl)-6-iodoquinoline-2,4-diol

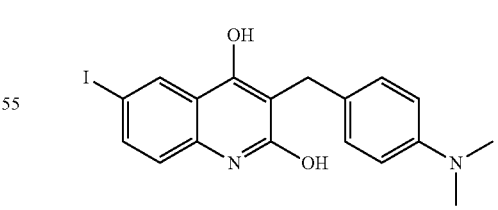

A mixture containing 6-iodoquinoline-2,4-diol (9.62 g, 33.5 mmol, Intermediate 4: step b), 4-dimethylaminobenzaldehyde (5.00 g, 33.5 mmol), and diethyl 1,4-dihydro-2,6-dimethyl-3,5-pyridinedicarboxylate (8.91 g, 35.2 mmol) in pyridine (112 mL) was heated to 80° C. After 18 hours, the flask was allowed to cool to 23° C. The mixture was concentrated to half-volume resulting in the formation of a solid.

Diethyl ether (100 mL) was added and the resulting suspension was sonicated for 5 minutes. The solids were collected by filtration through filter paper, rinsing with diethyl ether. The washed solids were dried under high vacuum at 50° C. to afford the title compound as a tan solid.

Intermediate 24: Step b 4-((2,4-Dichloro-6-iodoquinolin-3-yl)methyl)-N,N-dimethylaniline

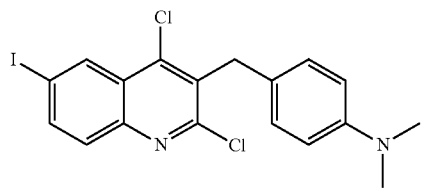 [SMILES: CN(C)c1ccc(Cc2c(Cl)nc3ccc(I)cc3c2Cl)cc1]

A mixture containing 3-(4-(dimethylamino)benzyl)-6-iodoquinoline-2,4-diol (6.0 g, 12 mmol, Intermediate 24: step a) and phosphorus oxychloride (8.9 mL, 96 mmol) in acetonitrile (60 mL) was heated to 100° C. After 5 hours, the flask was allowed to cool to 23° C. Water (100 mL) was slowly added with stirring resulting in the formation of a solid. After 30 minutes, the mixture was concentrated. Dichloromethane (500 mL) and water (100 mL) were added with stirring. Saturated aqueous sodium bicarbonate solution was added dropwise until the pH was 10 by litmus paper test. The biphasic mixture was separated. The aqueous layer was extracted with dichloromethane (100 mL). The organic layers were combined and the combined solution was dried with sodium sulfate. The dried solution was filtered. Silica gel (5 g) was added to the filtrate and the solvent was removed by rotary evaporation to afford a free-flowing powder. The powder was loaded onto a column of silica gel for purification. Elution with dichloromethane provided the title compound as a yellow solid.

Intermediate 24: Step c 4-((4-Chloro-6-iodo-2-methoxyquinolin-3-yl)methyl)-N,N-dimethylaniline

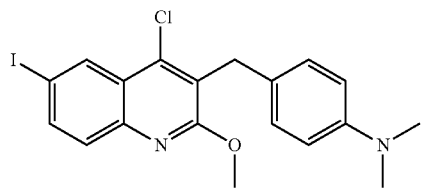 [SMILES: COc1nc2ccc(I)cc2c(Cl)c1Cc1ccc(N(C)C)cc1]

Sodium methoxide (2.9 g, 54 mmol) was added to a solution of 4-((2,4-dichloro-6-iodoquinolin-3-yl)methyl)-N,N-dimethylaniline (3.5 g, 7.7 mmol, Intermediate 24: step b) in toluene (38 mL) with stirring. The mixture was heated to 110° C. After 3 hours, additional sodium methoxide (2 g, 37.2 mmol) was added. After 18 hours, the flask was allowed to cool to 50° C. The warm mixture was filtered through Celite®, rinsing with tetrahydrofuran. Silica gel (5 g) was added to the filtrate and the solvent was removed by rotary evaporation to afford a free-flowing powder. The powder was loaded onto a column of silica gel for purification. Elution with dichloromethane initially, grading to 1% methanol-dichloromethane provided the title compound as a solid.

Intermediate 25: Step a (4-Chloro-2-ethyl-3-(4-(trifluoromethyl)benzyl)quinolin-6-yl)(1,2-dimethyl-1H-imidazol-5-yl)methanol

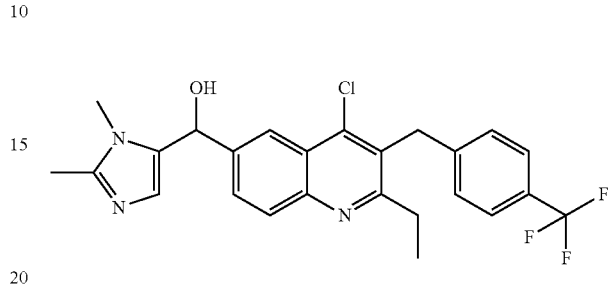

A solution of n-butyllithium in hexanes (2.5 M, 0.37 mL, 0.92 mmol) was added dropwise to a stirring solution of 6-bromo-4-chloro-2-ethyl-3-(4-(trifluoromethyl)benzyl)quinoline (393 mg, 0.917 mmol, Intermediate 5: step c) in tetrahydrofuran (7 mL) at −78° C. After 2 minutes, a solution of 1,2-dimethyl-1H-imidazole-5-carbaldehyde (125 mg, 1.01 mmol) in tetrahydrofuran (2 mL) was added dropwise. After 5 minutes, the flask was placed into an ice-water bath. After 30 minutes, water (5 mL) was added and the biphasic mixture was allowed to warm to 23° C. The mixture was partitioned between half-saturated sodium chloride solution (25 mL) and ethyl acetate (50 mL). The layers were separated. The organic layer was dried with sodium sulfate and the dried solution was filtered. Silica gel (5 g) was added to the filtrate and the solvent was removed by rotary evaporation to afford a free-flowing powder. The powder was loaded onto a column of silica gel for purification. Elution with dichloromethane initially, grading to 7% methanol-dichloromethane provided the title compound as an off-white solid.

Intermediate 25: Step b (4-Chloro-2-ethyl-3-(4-(trifluoromethyl)benzyl)quinolin-6-yl)(1,2-dimethyl-1H-imidazol-5-yl)methanone

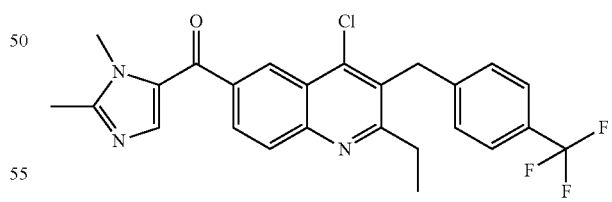

A mixture containing (4-chloro-2-ethyl-3-(4-(trifluoromethyl)benzyl)quinolin-6-yl)(1,2-dimethyl-1H-imidazol-5-yl)methanol (325 mg, 0.601 mmol, Intermediate 25: step a) and manganese dioxide (308 mg, 3.01 mmol) in dioxane (3 mL) was heated to 100° C. After 2 hours, the mixture was cooled to 23° C. Dichloromethane (20 mL) was added and the mixture was filtered through Celite®, rinsing with dichloromethane. Silica gel (5 g) was added to the filtrate and the solvent was removed by rotary evaporation to afford a free-flowing powder. The powder was loaded onto a column of silica gel for purification. Elution with hexanes-ethyl acetate provided the title compound as an off-white solid.

Intermediate 26: Step a

Ethyl 3-oxo-2-(4-(trifluoromethyl)benzyl)butanoate

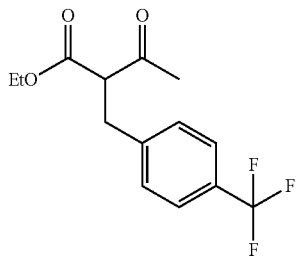 [SMILES: CCOC(=O)C(Cc1ccc(C(F)(F)F)cc1)C(C)=O]

Sodium hydride (60% dispersion in mineral oil, 1.5 g, 38.4 mmol) was added in portions over 2 minutes to an ice-cooled, stirring solution of ethyl 3-oxobutanoate (5 g, 38.4 mmol) in dry dimethoxyethane (65 mL). After 30 minutes, a solution of 4-(trifluoromethyl)benzyl bromide (9.2 g, 38.4 mmol) in dry dimethoxyethane (10 mL) was added dropwise over 2 minutes. The flask was removed from the cooling bath. After 2 hours, water (10 mL) was added. The mixture was partitioned between half-saturated aqueous sodium chloride solution (50 mL) and ethyl acetate (150 mL). The layers were separated. The organic layer was dried with magnesium sulfate and the dried solution was filtered. The filtrate was concentrated and the residue was purified by flash-column chromatography on silica gel eluting with hexanes-ethyl acetate to provide the title compound as a colorless liquid.

Intermediate 26: Step b

6-Bromo-2-methyl-3-(4-(trifluoromethyl)benzyl)quinolin-4-ol

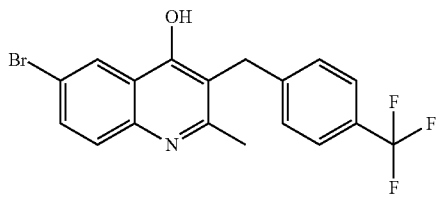 [SMILES: Cc1nc2ccc(Br)cc2c(O)c1Cc1ccc(C(F)(F)F)cc1]

A round-bottomed flask equipped with a Dean-Stark apparatus was charged with ethyl 3-oxo-2-(4-(trifluoromethyl)benzyl)butanoate (7.00 g, 24.3 mmol, Intermediate 26: step a), 4-bromoaniline (4.20 g, 24.2 mmol), para-toluenesulfonic acid (0.418 g, 2.4 mmol), and toluene (121 mL). The mixture was heated to 125° C. After 16 hours, the flask was cooled to room temperature. The toluene was removed by rotary evaporation to provide an orange colored solid. A mixture of the solid and diphenyl ether (48.4 mL) was heated to 220° C. After 60 minutes, the mixture was cooled to room temperature at which point a yellow solid crashed out of solution. Hexanes (150 mL) were added. The mixture was filtered through filter paper, rinsing with hexanes. The yellow solids were collected, dried, and then used in the next step without further purification.

Intermediate 26: Step c

6-Bromo-4-chloro-2-methyl-3-(4-(trifluoromethyl)benzyl)quinoline

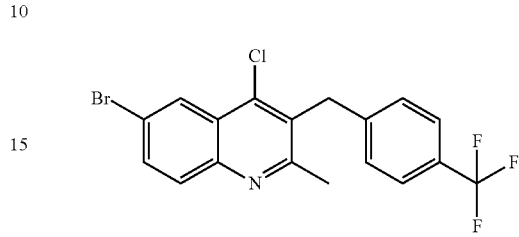

A round-bottomed flask containing a mixture of 6-bromo-2-methyl-3-(4-(trifluoromethyl)benzyl)quinolin-4-ol (5.00 g, 12.6 mmol, Intermediate 26: step b), phosphorous oxychloride (5.90 mL, 63.1 mmol) and acetonitrile (42 mL) was warmed to 90° C. After 3 hours, the reaction mixture was cooled to room temperature. The acetonitrile and excess phosphorous oxychloride was removed by rotary evaporation. The residue was dissolved in dichloromethane (100 mL) and the solution was cooled in an ice-water bath. Ice (100 mL) was added. Concentrated aqueous ammonia solution was added dropwise until the pH=~9 by litmus paper test. The biphasic mixture was separated and the aqueous layer was extracted with dichloromethane (50 mL). The combined organics were dried with magnesium sulfate and the dried solution was filtered. Celite® (5 g) was added to the filtrate and the solvents were removed by rotary evaporation to provide a free-flowing powder. The powder was loaded onto a silica gel column. Elution with hexanes initially, grading to 20% ethyl acetate-hexanes provided the title compound as an off-white solid.

Intermediate 27: Step a (1-Methyl-1H-imidazol-5-yl)(2-(trifluoromethyl)pyridin-4-yl)methanol

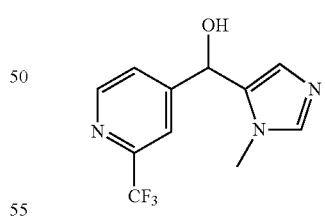

A solution of isopropylmagnesium chloride/lithium chloride complex (1.3 M in THF, 10.6 mL, 13.8 mmol) was added dropwise by syringe to a solution of 4-bromo-2-(trifluoromethyl)pyridine (3.12 g, 13.8 mmol) in dry THF (50 mL) at 0° C. After 30 minutes, a solution of 1-methyl-1H-imidazole-5-carbaldehyde (1.38 g, 12.5 mmol) in THF (28.5 mL) was added to the Grignard solution by syringe at 0° C. The reaction mixture was warmed to room temperature over 2 hours after which it was quenched with saturated aqueous ammonium chloride solution. The mixture was partitioned between water and ethyl acetate. The separated aqueous phase was further extracted with ethyl acetate and washed with saturated aqueous NaCl solution. The organic phase was dried (MgSO$_4$), filtered, and concentrated. The crude product was purified by flash column chromatography (silica gel, 0-10% MeOH-DCM) to provide the title compound.

Intermediate 27: Step b (1-Methyl-1H-imidazol-5-yl)(2-(trifluoromethyl)pyridin-4-yl)methanone

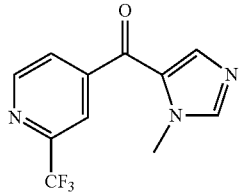 [SMILES: Cn1cncc1C(=O)c1ccnc(C(F)(F)F)c1]

A heterogeneous mixture of (1-methyl-1H-imidazol-5-yl)(2-(trifluoromethyl)pyridin-4-yl)methanol (0.300 g, 1.16 mmol, Intermediate 27: step a) and manganese dioxide (0.506 g, 5.83 mmol) in 1,4-dioxane (12 mL) was stirred at 100° C. for 1 hour. The reaction mixture was then cooled to room temperature, filtered through Celite®, washed with EtOAc, and concentrated. The organic phase was dried (MgSO$_4$), filtered, and concentrated. The crude product was purified by flash column chromatography (silica gel, 0-100% EtOAc-DCM) to provide the title compound as a white solid.

Intermediate 28: Step a tert-Butyl 3-(hydroxy(1-methyl-1H-1,2,3-triazol-5-yl)methyl)azetidine-1-carboxylate

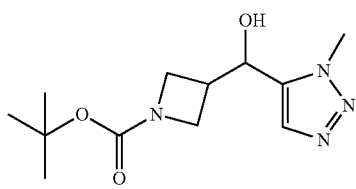 [SMILES: Cn1nncc1C(O)C1CN(C(=O)OC(C)(C)C)C1]

A 2.5 M solution of n-butyllithium in hexanes (9.60 mL, 24.0 mmol) was added dropwise to a stirring solution of 1-methyl-1H-1,2,3-triazole (2.00 g, 24.0 mmol, prepared according to PCT Int. Appl., 2008098104) in dry THF (100 mL) at −50° C. The reaction became heterogeneous and yellow during addition. After 15 minutes, a solution of tert-butyl 3-formylazetidine-1-carboxylate (4.45 g, 24.0 mmol) in dry THF (10 mL) was added dropwise by syringe. The reaction mixture became homogeneous and was allowed to slowly warm to 0° C. Water (10 mL) and ethyl acetate (100) mL were added. The biphasic mixture was warmed to 23° C. The mixture was partitioned between half-saturated aqueous sodium chloride solution (100 mL) and ethyl acetate (300 mL). The layers were separated. The organic layer was dried with sodium sulfate and the dried solution was filtered. Celite® (14 g) was added to the filtrate and the solvents were removed by rotary evaporation to provide a free-flowing powder. The powder was loaded onto a silica gel column. Elution with ethyl acetate initially, grading to 5% methanol-ethyl acetate provided the title compound as a white foam.

Intermediate 28: Step b tert-Butyl 3-(1-methyl-1H-1,2,3-triazole-5-carbonyl)azetidine-1-carboxylate

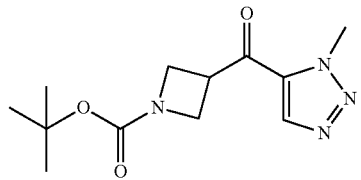 [SMILES: Cn1nncc1C(=O)C1CN(C(=O)OC(C)(C)C)C1]

Dess-Martin periodinane (10.9 g, 25.7 mmol) was added in one portion to a stirring solution of tert-butyl 3-(hydroxy(1-methyl-1H-1,2,3-triazol-5-yl)methyl)azetidine-1-carboxylate (4.60 g, 17.1 mmol, Intermediate 28: step a) in dry dichloromethane (86 mL). The resulting mixture was stirred at 23° C. After 18 hours, a mixture containing equal parts water, saturated aqueous sodium thiosulfate solution, and saturated aqueous sodium bicarbonate solution was added (200 mL). Dichloromethane (100 mL) was added. The resulting biphasic mixture was stirred for 15 minutes. The layers were separated. The organic layer was dried with sodium sulfate and the dried solution was concentrated. The residue was purified by flash-column chromatography on silica gel eluting with dichloromethane initially, grading to 5% methanol-dichloromethane to provide the title compound as a clear, colorless oil.

Intermediate 29: Step a

N-Methoxy-N,2,6-trimethylisonicotinamide

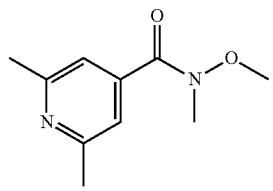

To 2,6-dimethylisonicotinic acid (1.00 g, 6.61 mmol) in DCM (8.3 mL), CDI (1.18 g, 7.27 mmol) was added and the mixture was stirred for 45 minutes after which N,O-dimethylhydroxylamine hydrochloride (0.71 g, 7.3 mmol) was added and the mixture was stirred for 20 hours. The reaction mixture was quenched with 0.3 M aqueous solution of NaOH and partitioned between water and DCM. The aqueous layer was extracted with DCM, washed with aqueous saturated solution of NaCl, dried (MgSO$_4$) and concentrated. The crude product was purified by flash column chromatography (silica gel, 0-100% EtOAc-DCM) to provide the title compound.

Intermediate 29: Step b (2,6-Dimethylpyridin-4-yl)(1-methyl-1H-1,2,3-triazol-5-yl)methanone

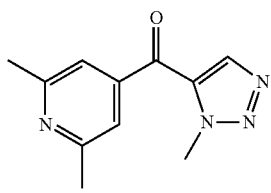 [SMILES: Cc1cc(C(=O)c2cnnn2C)cc(C)n1]

A solution of n-BuLi (3.8 mL, 9.5 mmol, 2.5 M solution in hexane) was added slowly to a solution of 1-methyl-1H-1,2,3-triazole (0.83 g, 10 mmol) in THF (48 mL) at −50° C. After addition, stirring was continued for an additional 30 minutes and N-methoxy-N,2,6-trimethylisonicotinamide (0.97 g, 5.0 mmol, Intermediate 29: step a) dissolved in THF (12 mL) was slowly added. An additional 2 mL of THF was used to complete the quantitative addition. The mixture was stirred at −50° C. for 5 minutes then warmed to room temperature and stirred overnight. The solution was quenched with saturated aqueous NH₄Cl. H₂O was added and layers were separated. The aqueous layer was extracted with EtOAc and the combined organic extracts washed with brine, dried over MgSO₄, filtered and evaporated in vacuo. The crude product was purified using flash column chromatography (0 to 100% EtOAc/DCM) to provide the title compound.

Intermediate 30

(1-Methyl-1H-1,2,3-triazol-5-yl)(tetrahydro-2H-pyran-4-yl)methanone

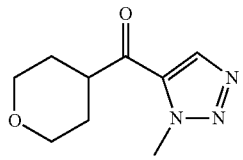

The title compound was prepared analogously to the method in Intermediate 29: step b using N-methoxy-N-methyltetrahydro-2H-pyran-4-carboxamide (Intermediate 1: step a, Procedure B) in place of N-methoxy-N,2,6-trimethylisonicotinamide (Intermediate 29: step a).

Intermediate 31

(1,2-Dimethyl-1H-imidazol-5-yl)(tetrahydro-2H-pyran-4-yl)methanone

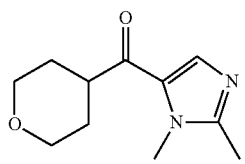

A solution of n-BuLi (4.0 mL, 10 mmol, 2.5 M solution in hexane) was slowly added to a solution of 5-bromo-1,2-dimethyl-1H-imidazole (1.77 g, 10.2 mmol) in THF (70 mL) at −78° C. After addition, stirring was continued for an additional 30 minutes and N-methoxy-N-methyltetrahydro-2H-pyran-4-carboxamide (1.76 g, 10.1 mmol, Intermediate 1: step a, Procedure A) dissolved in THF (25 mL) was slowly added. An additional 6 mL of THF was used to complete the quantitative addition. The mixture was stirred at −78° C. for 5 minutes then warmed to room temperature and stirred for 1 hour. The solution was quenched with water and layers were separated. The aqueous layer was extracted with DCM and the combined organic extracts washed with brine, dried over MgSO₄, filtered and evaporated in vacuo. The crude product was purified using flash column chromatography (0 to 6% MeOH/DCM) to provide the title compound.

Intermediate 32: Step a

Methyl 2-(4-(1H-pyrazol-1-yl)benzylidene)-3-oxopentanoate

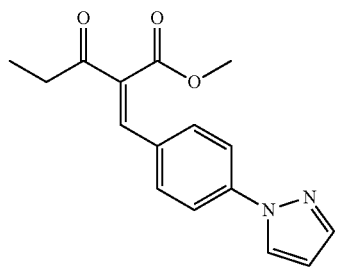 [SMILES: CCC(=O)/C(=C/c1ccc(-n2cccn2)cc1)C(=O)OC]

A mixture containing methyl 3-oxopentanoate (2.2 g, 17 mmol), 4-(1H-pyrazol-1-yl)benzaldehyde (2.5 g, 14 mmol), piperidine (0.3 mL, 3.0 mmol), and acetic acid (0.16 mL, 2.8 mmol) in benzene (70 mL) was heated to 90° C. with removal of water (Dean-Stark trap). After 4 hours, the mixture was cooled to 23° C. and then concentrated to provide the title compound. The residue (mixture of alkene isomers) was taken onto the next step without further purification.

Intermediate 32: Step b

Methyl 2-(4-(1H-pyrazol-1-yl)benzyl)-3-oxopentanoate

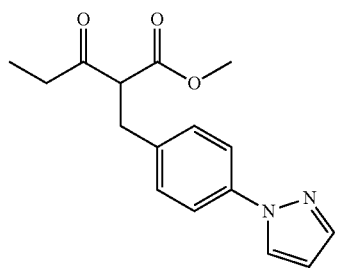 [SMILES: CCC(=O)C(Cc1ccc(-n2cccn2)cc1)C(=O)OC]

A mixture containing methyl 2-(4-(1H-pyrazol-1-yl)benzylidene)-3-oxopentanoate (mixture of alkene isomers, 3.5 g, 12 mmol, Intermediate 32: step a) and wet 10% palladium on carbon (2.6 g) in ethanol (123 mL) was stirred at 23° C. under an atmosphere of hydrogen gas (balloon pressure). After 2 hours, the reaction mixture was degassed by bubbling nitrogen gas through the solution. The degassed mixture was filtered through Celite®, rinsing with ethanol. The filtrate was concentrated to afford a colorless oil. Ethyl acetate (100 mL) was added. Celite® (8 g) was added to the solution and the solvent was removed by rotary evaporation to afford a free-flowing powder. The powder was loaded onto a column of silica gel for purification. Elution with hexanes initially, grading to 40% ethyl acetate-hexanes provided the title compound as a clear, colorless oil.

Intermediate 32: Step c 3-(4-(1H-Pyrazol-1-yl)benzyl)-6-bromo-2-ethylquinolin-4-ol

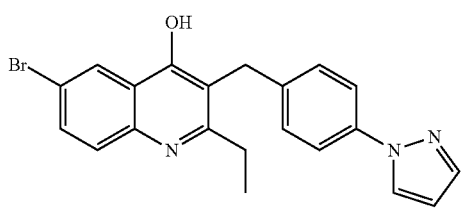 [SMILES: CCc1nc2ccc(Br)cc2c(O)c1Cc1ccc(-n2cccn2)cc1]

A mixture containing methyl 2-(4-(1H-pyrazol-1-yl)benzyl)-3-oxopentanoate (2.7 g, 9.4 mmol, Intermediate 32: step b), 4-bromoaniline (1.6 g, 9.4 mmol), and para-toluenesulfonic acid monohydrate (162 mg, 0.943 mmol) in diphenyl ether (31 mL) was heated to 220° C. After 2 hours, the flask was cooled to 23° C. Diethyl ether (50 mL) was added resulting in the formation of a solid. The heterogeneous mixture was stirred at 23° C. After 30 minutes, the mixture was filtered through filter paper and the filter cake was rinsed with diethyl ether. The solids were collected and dried to afford the title compound which was taken onto the next step without further purification.

Intermediate 32: Step d 3-(4-(1H-Pyrazol-1-yl)benzyl)-6-bromo-4-chloro-2-ethylquinoline

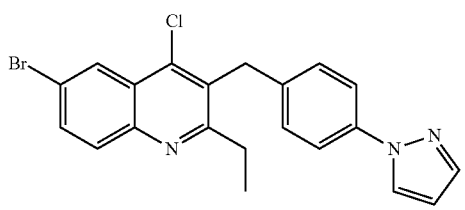 [SMILES: CCc1nc2ccc(Br)cc2c(Cl)c1Cc1ccc(-n2cccn2)cc1]

A mixture containing 3-(4-(1H-pyrazol-1-yl)benzyl)-6-bromo-2-ethylquinolin-4-ol (1.78 g, 4.36 mmol, Intermediate 32: step c) and phosphorus oxychloride (1.8 mL, 20 mmol) in acetonitrile (15 mL) was heated to 90° C. After 3 hours, the flask was allowed to cool to 23° C. The mixture was concentrated. Dichloromethane (100 mL) and ice (50 mL) were added to the residue. Concentrated aqueous ammonia solution was added dropwise with stirring until the pH was 9 by litmus paper test. The biphasic mixture was stirred at 23° C. for 30 minutes. The layers were separated. The aqueous layer was extracted with dichloromethane (25 mL). The organic layers were combined and the combined solution was dried with sodium sulfate. The dried solution was filtered. Celite® (8 g) was added to the filtrate and the solvent was removed by rotary evaporation to afford a free-flowing powder. The powder was loaded onto a column of silica gel for purification. Elution with hexanes initially, grading to 25% ethyl acetate-hexanes provided the title compound as an off-white solid.

Intermediate 33: Step a (1-Methyl-1H-imidazol-5-yl)(pyridin-2-yl)methanol

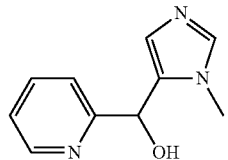

A solution of isopropylmagnesium chloride/lithium chloride complex (1.3 M in THF, 19.5 mL, 25.35 mmol) was added dropwise by syringe to a solution of 5-bromo-1-methyl-1H-imidazole (4.12 g, 25.58 mmol) in dry THF (130 mL) at 0° C. After 15 minutes, the Grignard solution was added via cannulation to a solution of picolinaldehyde (2.0 mL, 20.93 mmol) in dry THF (55 mL) at 0° C. The reaction mixture was stirred for 5 minutes at 0° C., then warmed to room temperature for 1 hour. The reaction mixture was then cooled in an ice bath and quenched with saturated aqueous ammonium chloride. The mixture was partitioned between brine and ethyl acetate. The separated aqueous phase was further extracted with ethyl acetate. The organic phase was dried ($Na_2SO_4$), filtered, and concentrated. The crude product was purified by flash column chromatography (silica gel, 0-5% MeOH-DCM) to provide the title compound as a white solid.

Intermediate 33: Step b (1-Methyl-1H-imidazol-5-yl)(pyridin-2-yl)methanone

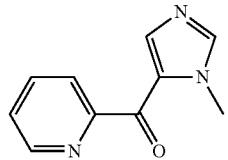

A heterogenous mixture of (1-methyl-1H-imidazol-5-yl)(pyridin-2-yl)methanol (1.41 g, 7.45 mmol, Intermediate 33: step a) and manganese dioxide (3.24 g, 37.27 mmol) in 1,4-dioxane (52 mL) was stirred at 100° C. for 2 hours. The reaction mixture was then cooled to room temperature, filtered through Celite®, washed with DCM, and concentrated to provide the title compound as an off-white solid.

Intermediate 34: Step a (3-Fluorophenyl)(pyridin-3-yl)methanol

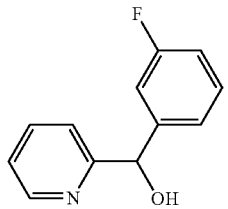 [SMILES: OC(c1cccc(F)c1)c1ccccn1]

(3-Fluorophenyl)magnesium bromide (1 M in THF, 9.3 mL, 9.3 mmol) was added dropwise by syringe to a solution of nicotinaldehyde (0.88 mL, 9.3 mmol) in dry THF (20 mL) at 0° C. The reaction mixture was stirred while warming to room temperature for 30 minutes, then quenched with saturated aqueous ammonium chloride solution. The mixture was partitioned between water and ethyl acetate. The aqueous phase was extracted with ethyl acetate once and the organic layer was washed with water three times. The combined organic layers were dried ($Na_2SO_4$), filtered, and concentrated to dryness. The crude product was purified by flash column chromatography (silica gel, 0-60% EtOAc-hexanes) to provide the title compound.

Intermediate 34: Step b (3-Fluorophenyl)(pyridin-3-yl)methanone

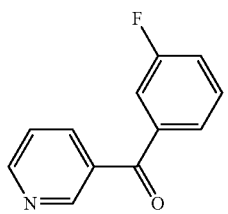 [SMILES: O=C(c1cccnc1)c1cccc(F)c1]

The title compound was prepared analogously to the method in Intermediate 33: step b using (3-fluorophenyl)(pyridin-3-yl)methanol (Intermediate 34: step a) in place of (1-methyl-1H-imidazol-5-yl)(pyridin-2-yl)methanol.

Intermediate 35: Step a (4-Methoxyphenyl)(pyridin-3-yl)methanol

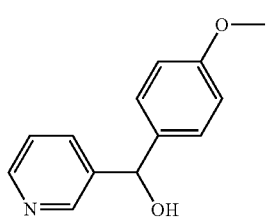 [SMILES: COc1ccc(C(O)c2cccnc2)cc1]

The title compound was prepared analogously to the method in Intermediate 34: step a using (4-methoxyphenyl)magnesium bromide in place of (3-fluorophenyl)magnesium bromide.

Intermediate 35: Step b (4-Methoxyphenyl)(pyridin-3-yl)methanone

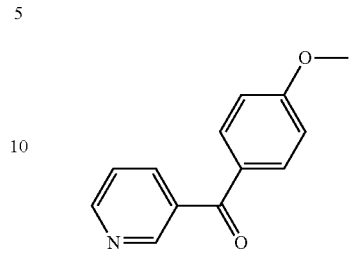

The title compound was prepared analogously to the method in Intermediate 33: step b using (4-methoxyphenyl)(pyridin-3-yl)methanol (Intermediate 35: step a) in place of (1-methyl-1H-imidazol-5-yl)(pyridin-2-yl)methanol.

Intermediate 36

(3-(4-(1H-Pyrazol-1-yl)benzyl)-2,4-dichloroquinolin-6-yl)(3-fluorophenyl)(pyridin-3-yl)methanol

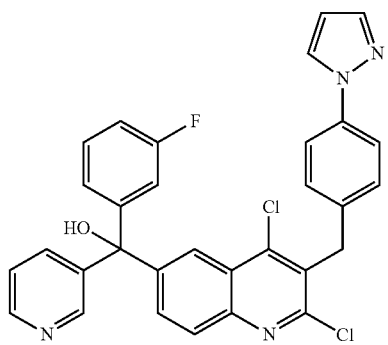 [SMILES: OC(c1cccnc1)(c1cccc(F)c1)c1ccc2nc(Cl)c(Cc3ccc(-n4cccn4)cc3)c(Cl)c2c1]

The title compound was prepared analogously to the method in Intermediate 37 using (3-fluorophenyl)(pyridin-3-yl)methanone (Intermediate 34: step b) in place of (4-chlorophenyl)(pyridin-3-yl)methanone, except that 1.2 equivalents of Intermediate 34: step b and 1.1 equivalents of n-BuLi were used relative to 3-(4-(1H-pyrazol-1-yl)benzyl)-6-bromo-2,4-dichloroquinoline (Intermediate 3: step c).

Intermediate 37

(3-(4-(1H-Pyrazol-1-yl)benzyl)-2,4-dichloroquinolin-6-yl)(4-chlorophenyl)(pyridin-3-yl)methanol

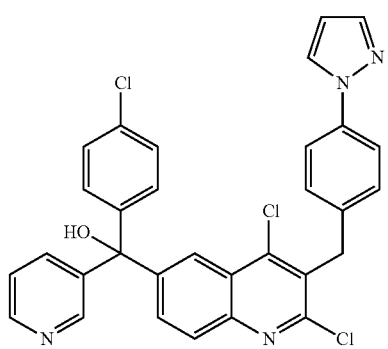 [SMILES: OC(c1ccc(Cl)cc1)(c1cccnc1)c1ccc2nc(Cl)c(Cc3ccc(-n4cccn4)cc3)c(Cl)c2c1]

A suspension of 3-(4-(1H-pyrazol-1-yl)benzyl)-6-bromo-2,4-dichloroquinoline (214.5 mg, 0.495 mmol, Intermediate 3: step c) in dry THF (5 mL) was heated with a heat gun to form a solution. The solution was cooled in a dry ice-acetone bath for 2 minutes, then a solution of n-BuLi (2.5 M in hexanes, 0.18 mL, 0.45 mmol) was added dropwise by syringe. After 1 minute, a solution of (4-chlorophenyl)(pyridin-3-yl)methanone (0.117 mg, 0.541 mmol) in dry THF (0.2 mL) was added dropwise. The reaction mixture was stirred for 5 minutes in a dry ice-acetone bath, then the reaction flask was placed into an ice-water bath that was allowed to warm to room temperature. The reaction was quenched with saturated ammonium chloride. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 50-100% EtOAc-hexanes) followed by reverse-phase chromatography (acetonitrile with 0.05% TFA in water). Product fractions were mixed with saturated aqueous sodium bicarbonate and DCM, the layers were separated, and the aqueous layer was extracted with DCM. The combined organic layers were dried (Na$_2$SO$_4$), filtered, and concentrated to provide the title compound as a clear oil.

Intermediate 38

(3-(4-(1H-Pyrazol-1-yl)benzyl)-2,4-dichloroquinolin-6-yl)(4-methoxyphenyl)(pyridin-3-yl)methanol

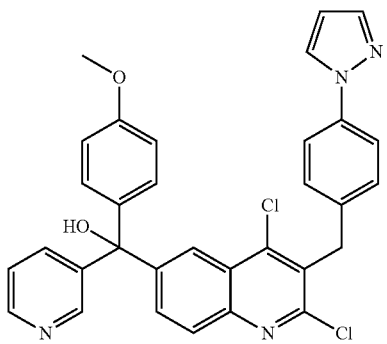 [SMILES: COc1ccc(C(O)(c2cccnc2)c2ccc3nc(Cl)c(Cc4ccc(-n5cccn5)cc4)c(Cl)c3c2)cc1]

The title compound was prepared analogously to the method in Intermediate 37 using (4-methoxyphenyl)(pyridin-3-yl)methanone (Intermediate 35: step b) in place of (4-chlorophenyl)(pyridin-3-yl)methanone.

Intermediate 39: Step a 5-(Benzo[b]thiophen-2-ylmethyl)-2,2-dimethyl-1,3-dioxane-4,6-dione

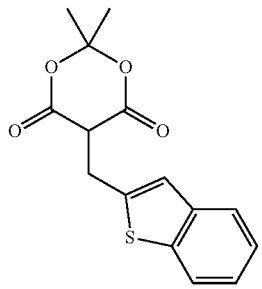 [SMILES: CC1(C)OC(=O)C(Cc2cc3ccccc3s2)C(=O)O1]

Proline (0.695 g, 5.98 mmol) was added to a solution of benzo[b]thiophene-2-carbaldehyde (5.00 g, 29.9 mmol) and Meldrum's acid (4.31 g, 29.9 mmol) in EtOH (50 mL). The mixture was stirred at room temperature for 1 hour and diethyl 1,4-dihydro-2,6-dimethyl-3,5-pyridinedicarboxylate (7.57 g, 29.9 mmol) was added. Stirring was continued for 5 hours at room temperature and the precipitated product isolated by filtration rinsing further with iPrOH and dried under reduced pressure to provide the title compound as a white solid.

Intermediate 39: Step b 2-(Benzo[b]thiophen-2-ylmethyl)malonic acid

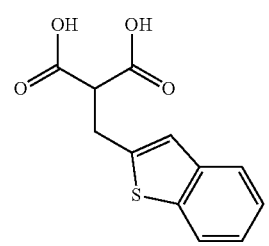 [SMILES: O=C(O)C(Cc1cc2ccccc2s1)C(=O)O]

A solution of 5-(benzo[b]thiophen-2-ylmethyl)-2,2-dimethyl-1,3-dioxane-4,6-dione (2.0 g, 6.88 mmol, Intermediate 39: step a) and 3 M aqueous NaOH (14 mL) was heated in a 102° C. oil bath for 28 hours. The reaction mixture was poured over ice and acidified to pH 1 with concentrated aqueous HCl. The suspension was stirred at room temperature for 2 hours then filtered rinsing further with water and dried to provide the title compound as a tan solid.

Intermediate 40: Step a (3-(Benzo[b]thiophen-2-ylmethyl)-2,4-dichloroquinolin-6-yl)(1-methyl-1H-imidazol-5-yl)methanone

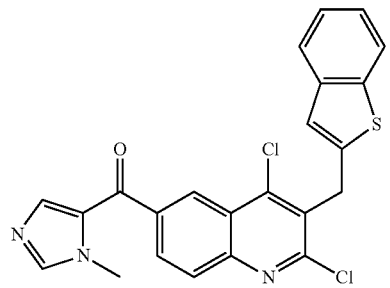 [SMILES: Cn1cncc1C(=O)c1ccc2nc(Cl)c(Cc3cc4ccccc4s3)c(Cl)c2c1]

A solution of 2-(benzo[b]thiophen-2-ylmethyl)malonic acid (0.311 g, 1.24 mmol, Intermediate 39: step b), (4-aminophenyl)(1-methyl-1H-imidazol-5-yl)methanone (0.25 g, 1.24 mmol, Intermediate 15: step c) and POCl$_3$ (2 mL) was refluxed at 100° C. overnight. The solution was cooled to room temperature, then slowly poured portion-wise into an ice water bath, adding additional ice as needed to regulate the exotherm. Aqueous ammonium hydroxide (5 M) was added to basify the mixture to pH 9-10. The solids that precipitated were filtered, collected, then dissolved in chloroform and filtered. The filtrate was concentrated and product was precipitated from methanol and filtered to provide the title compound.

Intermediate 40: Step b (3-(Benzo[b]thiophen-2-ylmethyl)-4-chloro-2-methoxyquinolin-6-yl)(1-methyl-1H-imidazol-5-yl)methanone

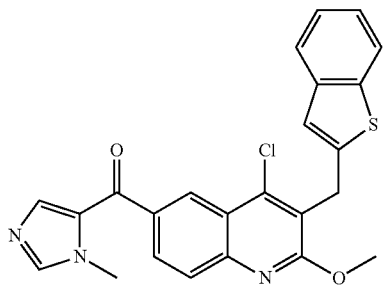 [SMILES: COc1nc2ccc(C(=O)c3cncn3C)cc2c(Cl)c1Cc1cc2ccccc2s1]

(3-(Benzo[1]thiophen-2-ylmethyl)-2,4-dichloroquinolin-6-yl)(1-methyl-1H-imidazol-5-yl)methanone (190 mg, 0.42 mmol, Intermediate 40: step a) and sodium methoxide (113.8 mg, 2.106 mmol) were charged to a microwave vial with dry toluene (2 mL) and heated to 105° C. overnight. The mixture was allowed to cool to room temperature, then filtered through Celite® and rinsed with dichloromethane. The filtrate was concentrated to dryness to provide the title compound which was used without further purification.

Intermediate 41: Step a 5-(4-Methylsulfonylbenzyl)-2,2-dimethyl-1,3-dioxane-4,6-dione

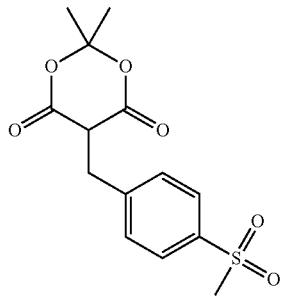 [SMILES: CC1(C)OC(=O)C(Cc2ccc(S(C)(=O)=O)cc2)C(=O)O1]

The title compound was prepared using 4-(methylsulfonyl)benzaldehyde in place of benzo[b]thiophene-2-carbaldehyde using the procedure described for the preparation of 5-(benzo[b]thiophen-2-ylmethyl)-2,2-dimethyl-1,3-dioxane-4,6-dione (Intermediate 39: step a).

Intermediate 41: Step b 2-(4-Methylsulfonylbenzyl)malonic acid

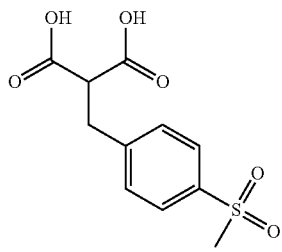 [SMILES: CS(=O)(=O)c1ccc(CC(C(=O)O)C(=O)O)cc1]

The title compound was prepared by substituting 5-(benzo[b]thiophen-2-ylmethyl)-2,2-dimethyl-1,3-dioxane-4,6-dione (Intermediate 39: step a) with 5-(4-methylsulfonylbenzyl)-2,2-dimethyl-1,3-dioxane-4,6-dione (Intermediate 41: step a) then following the procedure described for the preparation of 2-(benzo[b]thiophen-2-ylmethyl)malonic acid (Intermediate 39: step b).

Intermediate 41: Step c (2,4-Dichloro-3-(4-(methylsulfonyl)benzyl)quinolin-6-yl)(1-methyl-1H-imidazol-5-yl)methanone

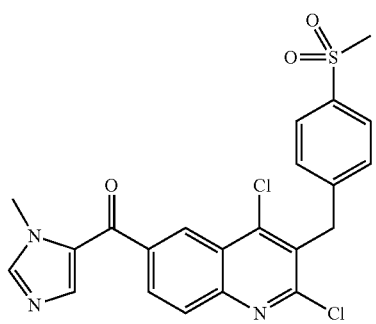 [SMILES: Cn1cncc1C(=O)c1ccc2nc(Cl)c(Cc3ccc(S(C)(=O)=O)cc3)c(Cl)c2c1]

A mixture of (4-aminophenyl)(1-methyl-1H-imidazol-5-yl)methanone (0.80 g, 3.976 mmol, Intermediate 15: step c) and 2-(4-methylsulfonylbenzyl)malonic acid (1.08 g, 3.976 mmol, Intermediate 41: step b), in $POCl_3$ (10 mL) was heated at 105° C. for 4 hours, cooled to room temperature and concentrated to remove excess $POCl_3$. The residue was poured into ice $H_2O$ and treated with aqueous $NH_4OH$ to pH 8-9 (temperature of the aqueous mixture was kept cold during addition). The mixture was stirred for 2 hours and filtered to provide a crude brown solid.

The crude solids were dried under reduced pressure overnight, rinsed with $Et_2O$ and dried. The solids were diluted with DCM and filtered, rinsing several times. The filtrate containing the product was evaporated to dryness to provide the title compound which was used without further purification.

Intermediate 41: Step d (4-Chloro-2-methoxy-3-(4-(methylsulfonyl)benzyl)quinolin-6-yl)(1-methyl-1H-imidazol-5-yl)methanone

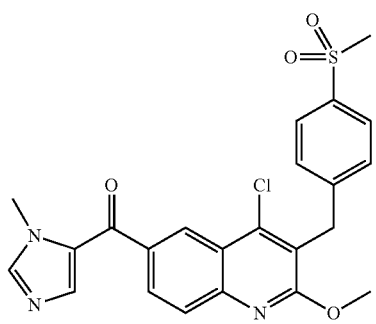 [SMILES: COc1nc2ccc(C(=O)c3cncn3C)cc2c(Cl)c1Cc1ccc(S(C)(=O)=O)cc1]

A mixture of (2,4-dichloro-3-(4-(methylsulfonyl)benzyl)quinolin-6-yl)(1-methyl-1H-imidazol-5-yl)methanone (1 g, 2.085 mmol, Intermediate 41: step c) and solid sodium methoxide (0.56 g, 10.42 mmol) in toluene (10 mL) was heated in a sealed tube at 105° C. for 12 hours, cooled to room temperature, diluted with DCM and the resulting suspension filtered through Celite®, rinsing several times with DCM. The solvents were removed under reduced pressure and the residue chromatographed (heptane/EtOAc) to provide the title compound as a white solid.

Intermediate 42: Step a 5-(4-Fluorobenzyl)-2,2-dimethyl-1,3-dioxane-4,6-dione

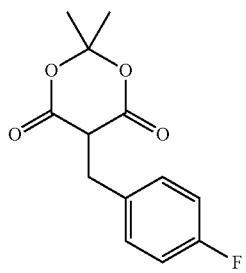 [SMILES: CC1(C)OC(=O)C(Cc2ccc(F)cc2)C(=O)O1]

The title compound was prepared using 4-fluorobenzaldehyde in place of benzo[b]thiophene-2-carbaldehyde using the procedure described for the preparation of 5-(benzo[b]thiophen-2-ylmethyl)-2,2-dimethyl-1,3-dioxane-4,6-dione (Intermediate 39: step a).

Intermediate 42: Step b 2-(4-Fluorobenzyl)malonic acid

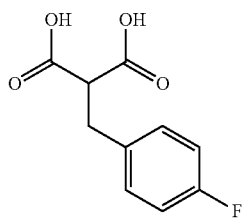 [SMILES: O=C(O)C(Cc1ccc(F)cc1)C(=O)O]

The title compound was prepared by substituting 5-(benzo[b]thiophen-2-ylmethyl)-2,2-dimethyl-1,3-dioxane-4,6-dione (Intermediate 39: step a) with 5-(4-fluorobenzyl)-2,2-dimethyl-1,3-dioxane-4,6-dione (Intermediate 42: step a) then following the procedure described for the preparation of 2-(benzo[b]thiophen-2-ylmethyl)malonic acid (Intermediate 39: step b).

Intermediate 42: Step c

6-Bromo-2,4-dichloro-3-(4-fluorobenzyl)quinoline

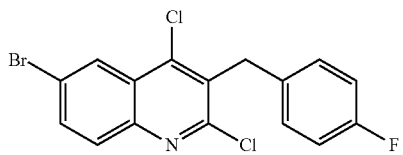 [SMILES: Fc1ccc(Cc2c(Cl)nc3ccc(Br)cc3c2Cl)cc1]

A mixture of 2-(4-fluorobenzyl)malonic acid (25.75 g, 112.9 mmol, Intermediate 42: step b) and 4-bromoaniline (19.43 g, 112.9 mmol) in POCl$_3$ (106 mL) was heated with a condenser at 105° C. for three hours, followed by 80° C. overnight. The solution was allowed to cool to room temperature, then slowly poured portion-wise into room temperature water in a water bath, using ice as needed to regulate the exotherm. Concentrated aqueous ammonium hydroxide was added to basify the mixture to pH 10. Dichloromethane was added, the layers were separated, and the aqueous layer was extracted with additional dichloromethane. The combined organic layers were dried (Na$_2$SO$_4$), filtered and concentrated to dryness. The crude product was triturated with minimal acetonitrile and filtered to provide the title compound.

Intermediate 42: Step d

6-Bromo-4-chloro-3-(4-fluorobenzyl)-2-methoxyquinoline

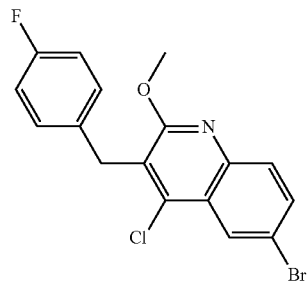 [SMILES: COc1nc2ccc(Br)cc2c(Cl)c1Cc1ccc(F)cc1]

A mixture of 6-bromo-2,4-dichloro-3-(4-fluorobenzyl)quinoline (0.350 g, 0.909 mmol, Intermediate 42: step c) and a 0.5 M sodium methoxide in methanol solution (9.09 mL, 4.55 mmol) was stirred at reflux for 16 hours. The mixture was poured into ice water and extracted with EtOAc (2×). The combined EtOAc extract was dried (Na$_2$SO$_4$), filtered, evaporated in vacuo and purified by column chromatography with silica gel (heptane/CH$_2$Cl$_2$) to provide the title compound as a white solid.

Intermediate 43: Step a

4-Chloro-N-methoxy-N-methylbenzamide

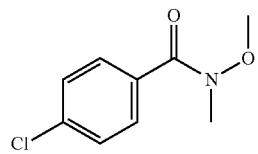

Pyridine (27.6 mL, 343 mmol) was added to N,O-dimethylhydroxylamine hydrochloride (16.7 g, 172 mmol) in DCM (400 mL). 4-Chlorobenzoyl chloride (20 mL, 156 mmol) was then added and the mixture was stirred at room temperature for 3 days. Solids were removed by vacuum filtration, washing with DCM. The filtrate was washed with 1 N aqueous HCl followed by water. The organic phase was dried (Na$_2$SO$_4$), filtered, and concentrated, affording the crude title compound as a colorless liquid which was used without purification in the next step.

Intermediate 43: Step b (4-Chlorophenyl)(1-methyl-1H-imidazol-5-yl)methanone

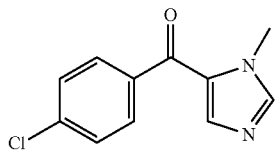

Ethyl magnesium bromide (3.0 M in diethyl ether, 21.5 mL, 64.4 mmol) was added via syringe over a few minutes to a clear colorless solution of 5-bromo-1-methyl-1H-imidazole (10.4 g, 64.4 mmol) in THF (100 mL) under a nitrogen atmosphere in an ice bath. A white precipitate formed during the addition. The mixture was removed from the ice bath and was stirred for 20 minutes, then was again cooled in an ice bath before addition of 4-chloro-N-methoxy-N-methylbenzamide (10.7 g, 53.6 mmol, Intermediate 43: step a). The resulting white suspension was stirred overnight at room temperature. The reaction was quenched by addition of saturated aqueous NH$_4$Cl and diluted with water. The mixture was partially concentrated to remove THF and was diluted with DCM. The mixture was acidified to pH 1 with 1 N aqueous HCl, then neutralized with saturated aqueous NaHCO$_3$. The phases were separated and the aqueous phase was further extracted with DCM. The organic extracts were washed with water, then were dried (Na$_2$SO$_4$), filtered, and concentrated, affording a white solid. The crude product was triturated with a mixture of EtOAc:heptanes (1:1, 150 mL). The precipitated solid was collected by vacuum filtration, washing with heptanes, to afford the title compound.

Intermediate 43: Step c 4-(1-Methyl-1H-imidazole-5-carbonyl)benzonitrile

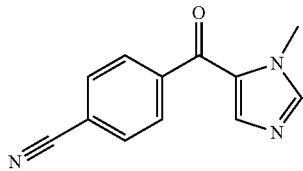 [SMILES: Cn1cncc1C(=O)c1ccc(C#N)cc1]

(4-Chlorophenyl)(1-methyl-1H-imidazol-5-yl)methanone (500.0 mg, 2.266 mmol, Intermediate 43: step b), zinc cyanide (531.2 mg, 4.524 mmol), zinc dust (58.7 mg, 0.898 mmol), X-Phos (216.9 mg, 0.455 mmol) and Pd$_2$(dba)$_3$ (312.2 mg, 0.341 mmol) were charged to a round-bottom flask. The flask was evacuated and back-filled with nitrogen. Dimethylacetamide (11 mL) was sparged with argon and added to the mixture via syringe. Argon was bubbled through the reaction mixture for 1 minute and the mixture was stirred and heated at 120° C. overnight under a positive pressure of nitrogen. The mixture was allowed to cool to ambient temperature, filtered through Celite®, and rinsed with dichloromethane. The filtrate was washed with saturated aqueous sodium bicarbonate, the layers were separated and the aqueous layer was extracted with excess dichloromethane. The combined organic layers were dried (Na$_2$SO$_4$), filtered, and concentrated to dryness. The crude product was purified by flash column chromatography (silica gel, 20-100% EtOAc-hexanes) to provide the title compound.

Intermediate 44

1-(4-(4-Fluorobenzoyl)piperidin-1-yl)ethanone

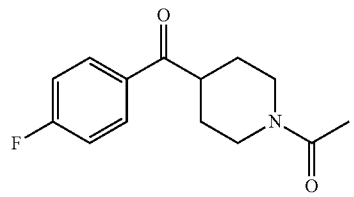 [SMILES: CC(=O)N1CCC(C(=O)c2ccc(F)cc2)CC1]

Acetic anhydride (2.32 g, 24.6 mmol) was added dropwise to a cold (0° C.) solution of (4-fluorophenyl)(piperidin-4-yl)methanone (5.00 g, 20.5 mmol) in DCM (33 mL) and triethylamine (10.0 mL, 71.8 mmol). The resulting mixture was removed from the ice bath after 5 minutes and stirred at room temperature for 2 hours. The reaction was then added to a mixture of 1 M aqueous K$_3$PO$_4$ (100 mL), H$_2$O, and DCM. The layers were separated and the aqueous layer again extracted with DCM. The combined organic layers were dried (Na$_2$SO$_4$), filtered, concentrated under reduced pressure and chromatographed (DCM/EtOAc) to provide the title compound as a clear oil.

Intermediate 45: Step a

6-Bromo-4-hydroxyquinolin-2(1H)-one

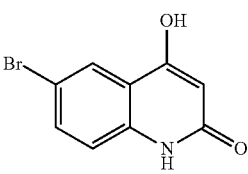

According to the general method described in Synthetic Communications 2010, 40, 732, a mixture of 4-bromoaniline (30.0 g, 174 mmol) and 2,2-dimethyl-1,3-dioxan-4,6-dione (25.1 g, 174 mmol) was heated to 80° C. for 1.5 hours and cooled to ambient temperature to receive 3-((4-bromophenyl)amino)-3-oxopropanoic acid. The acetone byproduct was removed under vacuum to provide the intermediate product as a dry solid. Eaton's reagent (100 mL) was added to the solid, and the resulting mixture heated to 70° C. overnight then cooled to room temperature. The mixture was poured into water and the brown precipitate was filtered and rinsed with water. The brown precipitate was triturated with ethanol, then filtered to provide the title compound as a light brown solid.

Intermediate 45: Step b

6-Bromo-3-((6-(trifluoromethyl)pyridin-3-yl)methyl)quinoline-2,4-diol

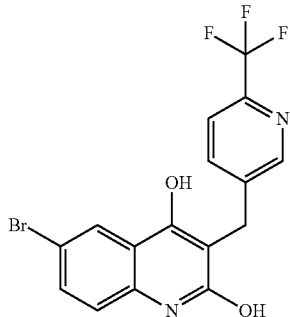 [SMILES: Oc1nc2ccc(Br)cc2c(O)c1Cc1ccc(C(F)(F)F)nc1]

A mixture of 6-bromo-4-hydroxyquinolin-2(1H)-one (3.2 g, 18.3 mmol, Intermediate 45: step a), 6-(trifluoromethyl)nicotinaldehyde (4.0 g, 16.7 mmol) and diethyl 2,6-dimethyl-1,4-dihydropyridine-3,5-dicarboxylate (4.2 g, 16.7 mmol) in pyridine (34 mL) was heated to 105° C. for 3 hours. The solution was allowed to cool to ambient temperature, resulting in the formation of solid. Minimal isopropanol was added to the mixture and the slurry was stirred for 1 hour, sonicated, and filtered. The filtered solids were rinsed with isopropanol and dried under continuous air flow to provide the title compound as an off-white solid. Additional product was recrystallized from the filtrate, filtered, and rinsed with isopropanol.

Intermediate 45: Step c

6-Bromo-2,4-dichloro-3-((6-(trifluoromethyl)pyridin-3-yl)methyl)quinoline

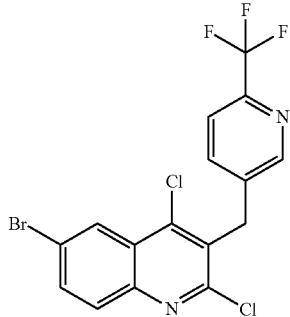 [SMILES: FC(F)(F)c1ccc(Cc2c(Cl)nc3ccc(Br)cc3c2Cl)cn1]

POCl$_3$ (1.5 mL) was added to a mixture of 6-bromo-3-((6-(trifluoromethyl)pyridin-3-yl)methyl)quinoline-2,4-diol (1.8 g, 4.6 mmol, Intermediate 45: step b) in acetonitrile (23 mL). The mixture was heated to 80° C. and refluxed overnight, forming an amber-colored solution. The solution was allowed to cool to ambient temperature and was quenched with water, resulting in the formation of precipitate. Concentrated ammonium hydroxide was added to the suspension to attain pH 9-10, and the slurry was stirred for 1 hour. The solids were filtered then washed with 50:50 acetonitrile/water, followed by additional water, and dried in a high vacuum oven to provide the title compound.

Intermediate 45: Step d

6-Bromo-4-chloro-2-methoxy-3-((6-(trifluoromethyl)pyridin-3-yl)methyl)quinoline

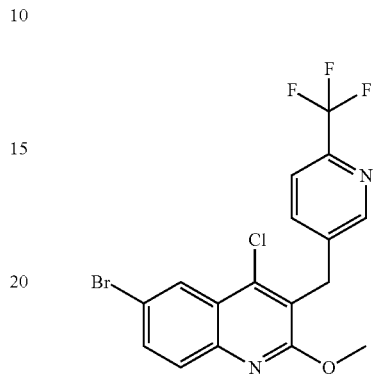

A mixture of 6-bromo-2,4-dichloro-3-((6-(trifluoromethyl)pyridin-3-yl)methyl)quinoline (1.0 g, 2.3 mmol, Intermediate 45: step c) and sodium methoxide (1.2 g, 22 mmol) in dry toluene (12 mL) was heated to 80° C. under a positive pressure of nitrogen overnight. The mixture was allowed to cool to ambient temperature. Aqueous saturated sodium bicarbonate solution was added to the mixture and the layers were separated. The aqueous layer was extracted with ethyl acetate. The combined organic layers were dried over sodium sulfate, filtered, and concentrated to dryness. The crude material was purified by flash column chromatography (silica gel, 0-20% EtOAc-hexane) to provide the title compound as a white solid.

Intermediate 45: Step e (4-Chloro-2-methoxy-3-((6-(trifluoromethyl)pyridin-3-yl)methyl)quinolin-6-yl)(1,2-dimethyl-1H-imidazol-5-yl)methanol

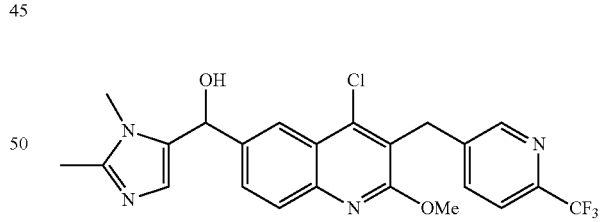

A solution of n-BuLi (2.5 M in hexanes, 0.9 mL, 2.25 mmol) was added dropwise by syringe to a solution of 6-bromo-4-chloro-2-methoxy-3-((6-(trifluoromethyl)pyridin-3-yl)methyl)quinoline (1.009 g, 2.338 mmol, Intermediate 45: step d) in dry THF (12.5 mL) in a dry ice-acetone bath. After 1-2 minutes, a solution of 1,2-dimethyl-1H-imidazole-5-carbaldehyde (359.6 mg, 2.897 mmol) in dry THF (5 mL) was added dropwise. The reaction was stirred for 10 minutes, then was moved into an ice bath and allowed to warm to room temperature. The reaction was quenched with saturated aqueous ammonium chloride. Water was added and the separated aqueous layer was extracted with EtOAc/THF 10:1. The organic phase was dried (Na$_2$SO$_4$), filtered, and concentrated.

The crude was triturated with EtOAc/ether 1:1 and filtered, rinsing with additional ether. The collected solids were purified by flash column chromatography (silica gel, 0-5% MeOH-DCM) to afford the title compound.

Intermediate 45: Step f (4-Chloro-2-methoxy-3-((6-(trifluoromethyl)pyridin-3-yl)methyl)quinolin-6-yl)(1,2-dimethyl-1H-imidazol-5-yl)methanone

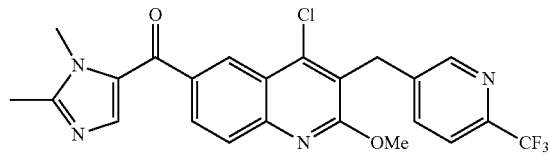 [SMILES: COc1nc2ccc(C(=O)c3cnc(C)n3C)cc2c(Cl)c1Cc1ccc(C(F)(F)F)nc1]

(4-Chloro-2-methoxy-3-((6-(trifluoromethyl)pyridin-3-yl)methyl)quinolin-6-yl)(1,2-dimethyl-1H-imidazol-5-yl)methanol (0.552 g, 1.158 mmol, Intermediate 45: step e), 1,4-dioxane (25 mL), dry THF (3 mL) and activated MnO$_2$ (0.503 g, 5.788 mmol) were combined in a round-bottom flask and the mixture was heated at 80° C. under a condenser and a positive pressure of N$_2$ overnight. The reaction was allowed to cool to ambient temperature and was filtered through Celite®, rinsing with THF. The filtrate was concentrated to provide the title compound which was used without further purification.

Intermediate 46: Step a (4-Chloro-3-(4-fluorobenzyl)-2-methoxyquinolin-6-yl)(1,2-dimethyl-1H-imidazol-5-yl)methanol

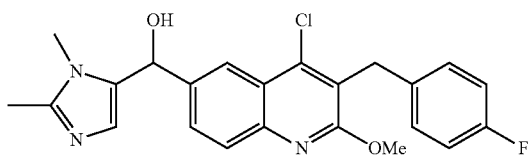 [SMILES: COc1nc2ccc(C(O)c3cnc(C)n3C)cc2c(Cl)c1Cc1ccc(F)cc1]

A solution of n-BuLi (2.5 M in hexanes, 0.52 mL, 1.3 mmol) was added dropwise by syringe to a solution of 6-bromo-4-chloro-3-(4-fluorobenzyl)-2-methoxyquinoline (0.5 g, 1.3 mmol, Intermediate 42: step d) in dry THF (13 mL) in a dry ice-acetone bath. After 1-2 minutes, a solution of 1,2-dimethyl-1H-imidazole-5-carbaldehyde (147.1 mg, 1.185 mmol) in dry THF (3 mL) was added dropwise. The reaction was stirred for 5 minutes, then was moved to ice bath and allowed to warm to room temperature. The reaction was quenched with saturated aqueous ammonium chloride. The mixture was partitioned between water and dichloromethane. The separated aqueous phase was further extracted with dichloromethane. The organic phase was dried (Na$_2$SO$_4$), filtered, and concentrated. The crude product was purified by flash column chromatography (silica gel, 0-3% MeOH-DCM) to provide the title compound.

Intermediate 46: Step b (4-Chloro-3-(4-fluorobenzyl)-2-methoxyquinolin-6-yl)(1,2-dimethyl-1H-imidazol-5-yl)methanone

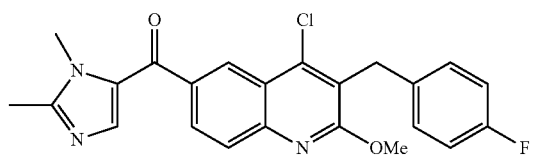 [SMILES: COc1nc2ccc(C(=O)c3cnc(C)n3C)cc2c(Cl)c1Cc1ccc(F)cc1]

(4-Chloro-3-(4-fluorobenzyl)-2-methoxyquinolin-6-yl)(1,2-dimethyl-1H-imidazol-5-yl)methanol (224.2 mg, 0.526 mmol, Intermediate 46: step a), 1,4-dioxane (2.6 mL) and activated MnO$_2$ (232 mg, 2.67 mmol) were combined in a round-bottom flask and the mixture was refluxed under a positive pressure of N$_2$ overnight. The reaction was allowed to cool to ambient temperature, then filtered through Celite® and rinsed with dichloromethane. The filtrate was washed with water, and the aqueous layer was extracted with additional dichloromethane. The combined organic layers were dried (Na$_2$SO$_4$), filtered, and concentrated to provide the title compound which was used without further purification.

Intermediate 47: Step a (4-Chloro-2-methoxy-3-((6-(trifluoromethyl)pyridin-3-yl)methyl)quinolin-6-yl)(2,6-dimethylpyridin-3-yl)methanol

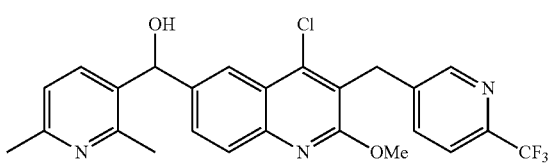

A solution of n-BuLi (2.5 M in hexanes, 1.6 mL, 4.0 mmol) was added dropwise by syringe to a solution of 6-bromo-4-chloro-2-methoxy-3-((6-(trifluoromethyl)pyridin-3-yl)methyl)quinoline (1.711 g, 3.964 mmol, Intermediate 45: step d) in dry THF (20 mL) in a dry ice-acetone bath. After 1-2 minutes, a solution of 2,6-dimethylnicotinaldehyde (0.8 mL, 6.3 mmol) in dry THF (6 mL) was added dropwise. The reaction was stirred for 5 minutes, then was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried (Na$_2$SO$_4$), filtered, and concentrated. The crude product was purified by flash column chromatography (silica gel, 0-3% MeOH-DCM) to provide the title compound.

Intermediate 47: Step b (4-Chloro-2-methoxy-3-((6-(trifluoromethyl)pyridin-3-yl)methyl)quinolin-6-yl)(2,6-dimethylpyridin-3-yl)methanone

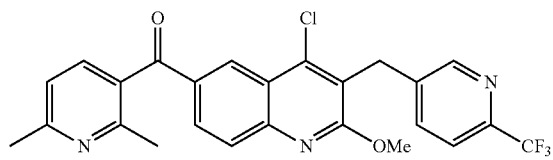 [SMILES: COc1nc2ccc(C(=O)c3ccc(C)nc3C)cc2c(Cl)c1Cc1ccc(C(F)(F)F)nc1]

(4-Chloro-2-methoxy-3-((6-(trifluoromethyl)pyridin-3-yl)methyl)quinolin-6-yl)(2,6-dimethylpyridin-3-yl)methanol (810 mg, 1.66 mmol, Intermediate 47: step a), 1,4-dioxane (8.5 mL) and activated MnO₂ (724.4 mg, 8.332 mmol) were combined in a round-bottom flask and the mixture was heated to reflux under a positive pressure of N₂. After 4 hours, the reaction was cooled to room temperature and filtered through Celite®, rinsing with dichloromethane. The filtrate was washed with water, and the aqueous layer was extracted with additional dichloromethane. The combined organic layers were dried (Na₂SO₄), filtered, and concentrated to dryness to provide the title compound which was used without further purification.

Intermediate 48: Step a (4-Chloro-3-(4-fluorobenzyl)-2-methoxyquinolin-6-yl)(2,6-dimethylpyridin-3-yl)methanol

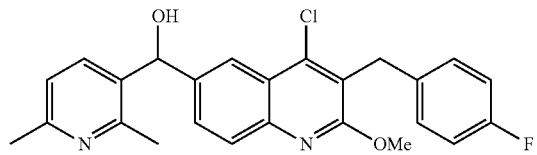 [SMILES: COc1nc2ccc(C(O)c3ccc(C)nc3C)cc2c(Cl)c1Cc1ccc(F)cc1]

A solution of n-BuLi (2.5 M in hexanes, 0.84 mL, 2.1 mmol) was added dropwise by syringe to a solution of 6-bromo-4-chloro-3-(4-fluorobenzyl)-2-methoxyquinoline (0.826 g, 2.17 mmol, Intermediate 42: step d) in dry THF (11 mL) in a dry ice-acetone bath. After 1-2 minutes, a solution of 2,6-dimethylnicotinaldehyde (0.23 mL, 1.8 mmol) in dry THF (3 mL) was added dropwise. The reaction was stirred for 5 minutes, then was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried (Na₂SO₄), filtered, and concentrated to dryness. The crude product was purified by flash column chromatography (silica gel, 0-3% MeOH-DCM) to provide the title compound.

Intermediate 48: Step b (4-Chloro-3-(4-fluorobenzyl)-2-methoxyquinolin-6-yl)(2,6-dimethylpyridin-3-yl)methanone

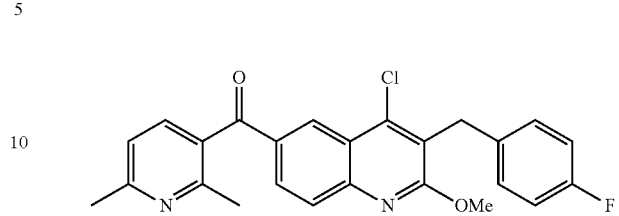

(4-Chloro-3-(4-fluorobenzyl)-2-methoxyquinolin-6-yl)(2,6-dimethylpyridin-3-yl)methanol (550 mg, 1.26 mmol, Intermediate 48: step a), 1,4-dioxane (6.2 mL) and activated MnO₂ (551 mg, 6.34 mmol) were combined in a round-bottom flask and the mixture was refluxed under a positive pressure of N₂. After 4 hours, the reaction was allowed to cool to ambient temperature, then filtered through Celite® and rinsed with dichloromethane. The filtrate was washed with water, and the aqueous layer was extracted with additional dichloromethane. The combined organic layers were dried (Na₂SO₄), filtered, and concentrated to afford the title compound which was used without further purification.

Intermediate 49: Step a

6-Bromo-4-hydroxy-3-(pyrimidin-5-ylmethyl)quinolin-2(1H)-one

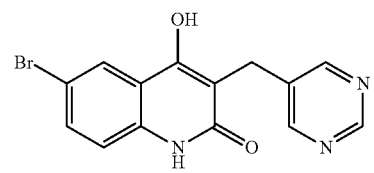 [SMILES: O=c1[nH]c2ccc(Br)cc2c(O)c1Cc1cncnc1]

To a dark solution of 6-bromo-4-hydroxyquinolin-2(1H)-one (3.92 g, 16.31 mmol, Intermediate 45: step a) and pyrimidine-5-carbaldehyde (1.94 g, 17.95 mmol) in pyridine (29 mL) was added diethyl 2,6-dimethyl-1,4-dihydropyridine-3,5-dicarboxylate (4.13 g, 16.31 mol). The resulting mixture was warmed with stirring in a 100° C. oil bath for a period of 5 hours. After cooling to room temperature, the mixture was diluted with ethanol. The tan precipitate was isolated by filtration, rinsing further with EtOH then acetonitrile and dried to provide the title compound that was carried to the next step without further purification.

Intermediate 49: Step b

6-Bromo-4-(difluoromethoxy)-3-(pyrimidin-5-ylmethyl)quinolin-2-ol

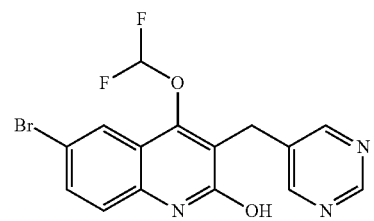 [SMILES: Oc1nc2ccc(Br)cc2c(OC(F)F)c1Cc1cncnc1]

A mixture of 6-bromo-4-hydroxy-3-(pyrimidin-5-ylmethyl)quinolin-2(1H)-one (0.5 g, 1.51 mmol, Intermediate 49: step a) methyl 2-chloro-2,2-difluoroacetate (0.24 mL, 2.26 mmol) and $K_2CO_3$ (0.52 mg, 3.76 mmol) in DMF (0.6 mL) was stirred at 80° C. for 2 hours, cooled to room temperature, diluted with $H_2O$ and extracted with EtOAc (2×). The combined organic extracts were washed with brine, dried, filtered, evaporated in-vacuo and purified by chromatography (0-10% MeOH in DCM, gradient) to provide the title compound.

Intermediate 49: Step c

6-Bromo-2-chloro-4-(difluoromethoxy)-3-(pyrimidin-5-ylmethyl)quinoline

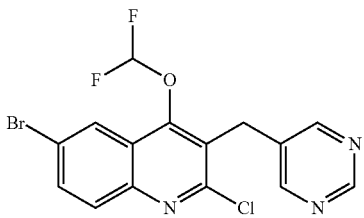 [SMILES: FC(F)Oc1c(Cc2cncnc2)c(Cl)nc2ccc(Br)cc12]

A mixture of 6-bromo-4-(difluoromethoxy)-3-(pyrimidin-5-ylmethyl)quinolin-2-ol (0.38 g, 1.02 mmol, Intermediate 49: step b) and $POCl_3$ was heated at 105° C. for 3 hours, then cooled to room temperature, concentrated, poured into ice water and treated with $NH_4OH$ to a basic pH 8-9. The solid precipitates were collected by filtration and dried to provide crude product. The solids were dissolved in DCM and chromatographed (0-100% EtOAc/DCM, gradient) to provide the title compound.

Intermediate 50

6-Bromo-2,4-bis(difluoromethoxy)-3-(pyrimidin-5-ylmethyl)quinoline

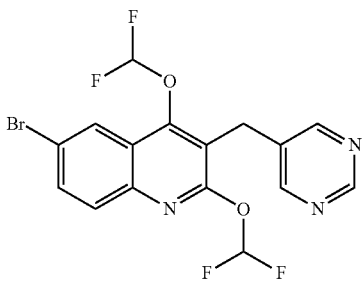 [SMILES: FC(F)Oc1nc2ccc(Br)cc2c(OC(F)F)c1Cc1cncnc1]

The title compound was obtained as an additional product following the procedure used to prepare Intermediate 49: step b.

Intermediate 51: Step a 3-(Benzo[b]thiophen-2-ylmethyl)-6-bromo-2,4-dichloroquinoline

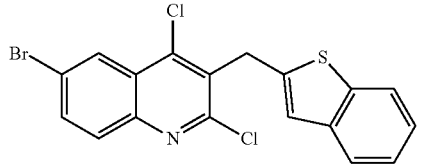 [SMILES: Clc1nc2ccc(Br)cc2c(Cl)c1Cc1cc2ccccc2s1]

A mixture of 2-(benzo[b]thiophen-2-ylmethyl)malonic acid (4.49 g, 17.94 mmol, Intermediate 39: step b) and 4-bromoaniline (3.08 g, 17.94 mmol) in $POCl_3$ (40 mL) was heated at 80° C. for 5 hours, cooled to room temperature and concentrated under reduced pressure to remove excess $POCl_3$. The residue was poured into ice $H_2O$, and treated with aqueous $NH_4OH$ to pH 8-9. The solid precipitates were collected by filtration, rinsed with water, air dried and rinsed with $Et_2O$ to provide the title compound as a dark solid.

Intermediate 51: Step b 3-(Benzo[b]thiophen-2-ylmethyl)-6-bromo-4-chloro-2-methoxyquinoline

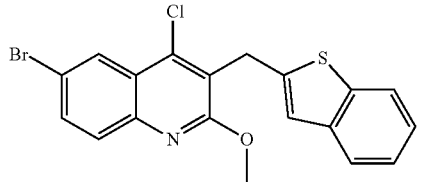 [SMILES: COc1nc2ccc(Br)cc2c(Cl)c1Cc1cc2ccccc2s1]

A heterogeneous mixture of 3-(benzo[b]thiophen-2-ylmethyl)-6-bromo-2,4-dichloroquinoline (7.5 g, 17.73 mmol, Intermediate 51: step a), sodium methoxide (4.79 g, 88.62 mmol), and toluene (25 mL) was heated at 110° C. in a sealed tube for 6 hours. The resulting black tar was diluted with DCM, then filtered through Celite®, rinsing with dichloromethane. The filtrate was concentrated and the crude product purified by chromatography (heptanes/DCM, gradient) to provide the title compound as a tan solid.

Intermediate 51: Step c (3-(Benzo[b]thiophen-2-ylmethyl)-4-chloro-2-methoxyquinolin-6-yl)(1-methyl-1H-imidazol-5-yl)(6-(trifluoromethyl)pyridin-3-yl)methanol

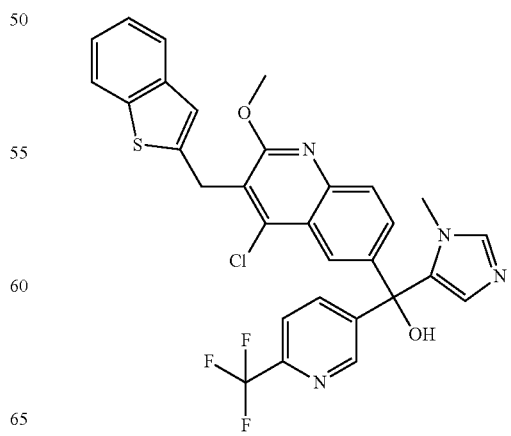

n-Butyllithium (1.6 M in hexane, 1.9 mL, 3.17 mmol) was added dropwise to a mixture of 3-(benzo[b]thiophen-2-ylmethyl)-6-bromo-4-chloro-2-methoxyquinoline (1.02 g, 2.44 mmol, Intermediate 51: step b) and (1-methyl-1H-imidazol-5-yl)(2-(trifluoromethyl)pyridin-4-yl)methanone (0.684 g, 2.68 mmol, Intermediate 2: step c) in dry THF (25 mL) at −78° C. over a 2 minute period. After complete addition stirring was continued at −78° C. for 10 minutes then warmed in an ice bath to 0° C. The mixture was stirred for 30 minutes then quenched with saturated aqueous NH₄Cl and warmed to room temperature. After stirring for 10 minutes, water was added, layers were separated and the aqueous layer extracted with EtOAc (2×). The combined organic extracts were washed with brine, dried over Na₂SO₄, filtered, evaporated in vacuo and chromatographed (0-10% MeOH in DCM) to provide the title compound.

Intermediate 51: Step d (3-(Benzo[b]thiophen-2-ylmethyl)-4-chloro-2-methoxyquinolin-6-yl)(1-methyl-1H-imidazol-5-yl)(6-(trifluoromethyl)pyridin-3-yl)methyl acetate

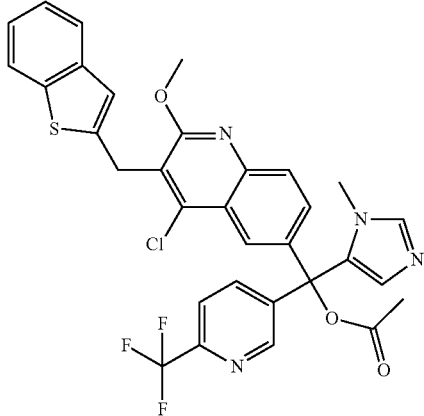 [SMILES: COc1nc2ccc(C(OC(C)=O)(c3ccc(C(F)(F)F)nc3)c3cncn3C)cc2c(Cl)c1Cc1cc2ccccc2s1]

Sodium hydride (0.12 g, 2.98 mmol) was added to a yellow solution of (3-(benzo[b]thiophen-2-ylmethyl)-4-chloro-2-methoxyquinolin-6-yl)(1-methyl-1H-imidazol-5-yl)(6-(trifluoromethyl)pyridin-3-yl)methanol (0.88 g, 1.49 mmol, Intermediate 51: step c) in dry DMF (25 mL) at room temperature. The mixture was stirred at room temperature for 45 minutes and then acetic anhydride (0.28 mL, 2.98 mmol) was added. The resulting dark mixture was stirred at room temperature overnight. Ice was added followed by NaHCO₃ (saturated aqueous solution). The aqueous mixture was extracted with EtOAc (2×). The combined organic extracts were washed with brine, dried over Na₂SO₄, filtered and evaporated in vacuo to provide the title compound which was carried on to the next step without further purification.

Intermediate 52: Step a

1-Acetyl-N-methoxy-N-methylpiperidine-4-carboxamide

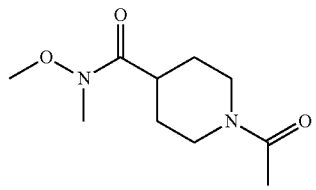

1,1'-Carbonyldiimidazole (6.43 g, 39.64 mmol) was added slowly to a mixture of 1-acetylpiperidine-4-carboxylic acid (5 g, 29.21 mmol) in dry THF (40 mL). The mixture was stirred at room temperature for one hour. In a separate flask, triethylamine was added to a mixture of N,O-dimethylhydroxylamine hydrochloride (3.92 g, 40.18 mmol) in acetonitrile (32 mL). The two mixtures were combined and stirred at room temperature for 12 hours. The solvents were removed under reduced pressure and the residue dissolved in DCM. The organic mixture was washed with water, HCl (0.1 N aqueous solution) and finally a concentrated aqueous Na₂CO₃ solution. The organic layer was dried over MgSO₄, filtered and evaporated to give a crude oil. The oil was purified by chromatography to provide the title compound visible by HPLC at 214 wavelength.

Intermediate 52: Step b 1-(4-(1-Methyl-1H-1,2,3-triazole-5-carbonyl)piperidin-1-yl)ethanone

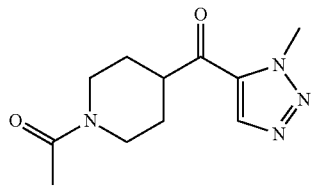 [SMILES: CC(=O)N1CCC(C(=O)c2cnnn2C)CC1]

A solution of 1-methyl-1H-1,2,3-triazole (0.28 g, 3.37 mmol) in dry THF (3 mL) was cooled in a −78° C. bath and n-butyllithium (2.5 M in hexanes, 1.26 mL, 3.15 mmol) was added dropwise over a 20 minute period. The suspension was stirred in the cold bath for 30 minutes and then 1-acetyl-N-methoxy-N-methylpiperidine-4-carboxamide (0.74 g, 3.45 mmol, Intermediate 52: step a) dissolved in THF (3 mL) was added dropwise. The resulting suspension was stirred at −78° C. for 5 minutes then warmed to 0° C. and stirred for an additional 30 minutes. The mixture was warmed to room temperature and stirred for 2.5 hours then quenched with saturated aqueous NH₄Cl. The aqueous mixture was extracted with EtOAc (2×). The combined EtOAc extracts were dried over Na$_2$SO$_4$, filtered, concentrated to dryness and chromatographed (EtOAc/DCM) to provide the title compound.

Intermediate 53: Step a (1-Methyl-1H-1,2,3-triazol-5-yl)(6-(trifluoromethyl)pyridin-3-yl)methanol

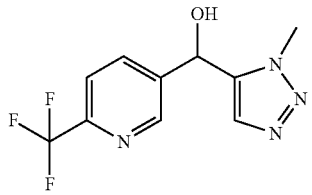 [SMILES: Cn1nncc1C(O)c1ccc(C(F)(F)F)nc1]

A 50 mL flask containing 1-methyl-1H-1,2,3-triazole (0.47 g, 5.71 mmol) in dry THF (3 mL) was cooled to −43° C. (CH$_3$CN—CO$_2$ bath). n-Butyllithium (2.5 M in THF, 2.43 mL, 6.08 mmol) was then added dropwise resulting in a light blue suspension. The suspension was stirred at −40° C. for 40 minutes, and then a homogeneous solution of 6-(trifluoromethyl)nicotinaldehyde (1 g, 5.71 mmol) in THF (7 mL) was introduced at −40° C. The resulting homogeneous colorless solution was allowed to warm gradually to room temperature, and after 30 minutes, LC/MS showed that the reaction was complete. The mixture was quenched with water and aqueous NH$_4$Cl and extracted with EtOAc (2×). The combined organic extracts were washed with brine, dried over Na$_2$SO$_4$, filtered and concentrated to provide the title compound as a semi-solid which was carried on to the next step without further purification.

Intermediate 53: Step b (1-Methyl-1H-1,2,3-triazol-5-yl)(6-(trifluoromethyl)pyridin-3-yl)methanone

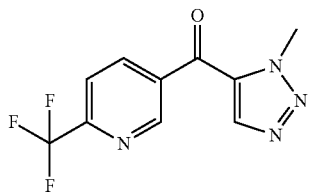 [SMILES: Cn1nncc1C(=O)c1ccc(C(F)(F)F)nc1]

To a 25 mL flask containing (1-methyl-1H-1,2,3-triazol-5-yl)(6-(trifluoromethyl)pyridin-3-yl)methanol (1 g, 3.87 mmol, Intermediate 53: step a) in 1,4-dioxane (10 mL) was added manganese dioxide (2.67 g, 30.65 mmol). The mixture was stirred in an 80° C. oil bath for 2 hours, then cooled to room temperature, diluted with EtOAc and filtered through Celite®. The solvents were removed under reduced pressure and the residue chromatographed (0-100% EtOAc/heptane gradient) to provide the title compound.

Intermediate 54: Step a

6-Bromo-4-hydroxy-3-(4-(trifluoromethoxy)benzyl)quinolin-2(1H)-one

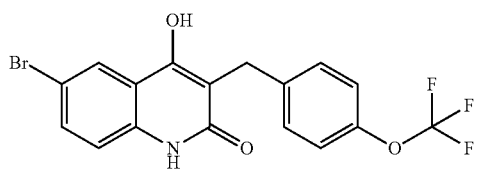 [SMILES: O=c1[nH]c2ccc(Br)cc2c(O)c1Cc1ccc(OC(F)(F)F)cc1]

To a dark solution of 6-bromo-4-hydroxyquinolin-2(1H)-one (1.0 g, 4.25 mmol, Intermediate 45: step a) and 4-(trifluoromethoxy)benzaldehyde (0.67 mL, 4.67 mmol) in pyridine (7.5 mL) was added diethyl 2,6-dimethyl-1,4-dihydropyridine-3,5-dicarboxylate (1.08 g, 4.25 mmol). The resulting mixture was warmed with stirring in a 100° C. oil bath for a period of 5 hours. After cooling to room temperature, the solvent was removed under reduced pressure and the residue diluted with acetonitrile. The semi-solid mixture was sonicated and filtered, rinsing further with acetonitrile, to provide the title compound as a white solid.

Intermediate 54: Step b

6-Bromo-2,4-dichloro-3-(4-(trifluoromethoxy)benzyl)quinoline

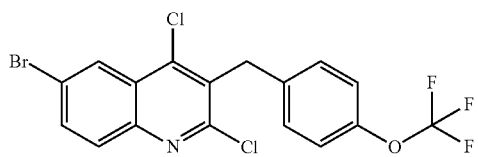 [SMILES: FC(F)(F)Oc1ccc(Cc2c(Cl)nc3ccc(Br)cc3c2Cl)cc1]

A mixture of 6-bromo-4-hydroxy-3-(4-(trifluoromethoxy)benzyl)quinolin-2(1H)-one (1.1 g, 2.66 mmol, Intermediate 54: step a) and POCl$_3$ (3.7 mL, 39.83 mmol) was stirred at 105° C. for 3 hours, cooled to room temperature and evaporated to remove excess POCl$_3$. Then, ice was added and an aqueous NH$_4$OH solution was slowly added to the suspension, while stirring, to a basic pH 8-9 (ice was added during addition to maintain a cold suspension). The white solid precipitates were collected by filtration and dried to provide the title compound.

Intermediate 54: Step c

6-Bromo-4-chloro-2-methoxy-3-(4-(trifluoromethoxy)benzyl)quinoline

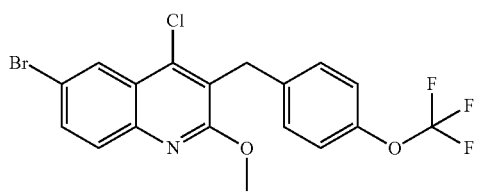 [SMILES: COc1nc2ccc(Br)cc2c(Cl)c1Cc1ccc(OC(F)(F)F)cc1]

A mixture of 6-bromo-2,4-dichloro-3-(4-(trifluoromethoxy)benzyl)quinoline (1.1 g, 2.44 mmol, Intermediate 54: step b) and sodium methoxide (1.32 g, 24.39 mmol) in toluene (14 mL) was heated in a sealed tube at 110° C. for 12 hours. The mixture was diluted with DCM and stirred for 30 minutes then filtered through Celite®. The filtrate was evaporated in vacuo and chromatographed (0-100% EtOAc/heptane, gradient) to provide the title compound as a white solid.

Intermediate 54: Step d

Methyl 4-chloro-2-methoxy-3-(4-(trifluoromethoxy)benzyl)quinoline-6-carboxylate

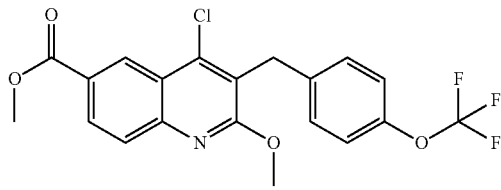 [SMILES: COC(=O)c1ccc2nc(OC)c(Cc3ccc(OC(F)(F)F)cc3)c(Cl)c2c1]

To a −78° C. solution of 6-bromo-4-chloro-2-methoxy-3-(4-(trifluoromethoxy)benzyl)quinoline (0.26 g, 0.57 mmol, Intermediate 54: step c) in dry THF (3 mL) was added n-BuLi (2.5 M in hexanes, 0.23 mL, 0.57 mmol) dropwise over a one minute period (solution turned brown). Stirring was continued for 1 minute at −78° C. and then carbon dioxide was bubbled into the reaction mixture ($CO_2$ was passed through drierite before introduction through a double pointed needle). After 5 minutes, the flask was removed from the dry-ice/acetone bath and warmed slowly, while maintaining $CO_2$ stream, to room temperature. The mixture was stirred at room temperature for 20 minutes. LC/MS of a quenched aliquot shows the mass of the carboxylic acid. DMSO (0.05 mL), methyl iodide (0.12 mL, 1.71 mmol) and $Na_2CO_3$ (0.06 g, 0.57 mmol) were added at 0° C. The mixture was warmed to room temperature, then heated for 30 minutes in a 40° C. oil bath. LC/MS still showed a significant amount of carboxylic acid product. Most of the THF was removed under reduced pressure and additional DMSO (0.05 mL) MeI (0.12 mL, 1.71 mmol) and $Na_2CO_3$ (0.06 g, 0.57 mmol) were introduced into the oily residue. The mixture was heated in a 40° C. oil bath for 30 minutes, cooled to room temperature and ice-$H_2O$ added. The mixture was stirred at room temperature and then extracted with EtOAc (2×). The combined EtOAc extracts were dried over $Na_2SO_4$, filtered, evaporated in vacuo and the residue chromatographed (0-100% EtOAc/heptane, gradient) to provide the title compound as a white solid.

Intermediate 55: Step a

N-Methoxy-N,1-dimethyl-1H-imidazole-5-carboxamide

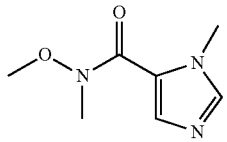

Triethylamine (5.51 mL, 39.646 mmol) was added slowly to a mixture of 1-methyl-1H-imidazole-5-carboxylic acid (2 g, 15.86 mmol), N,O-dimethylhydroxylamine hydrochloride (1.55 g, 15.86 mmol), and EDCI (3.65 g, 19.03 mmol) in $CH_2Cl_2$ (10 mL). The mixture was stirred at room temperature for 72 hours then quenched with saturated aqueous $NaHCO_3$. Water (50 mL) was added followed by additional $CH_2Cl_2$. The mixture was stirred for 10 minutes and layers were separated. The $CH_2Cl_2$ layer was dried over $Na_2SO_4$, then filtered. The solvent was removed under reduced pressure and the residual oil chromatographed ($CH_2Cl_2$/EtOAc) to provide the title compound as a solid.

Intermediate 55: Step b

Bis(1-methyl-1H-imidazol-5-yl)methanone

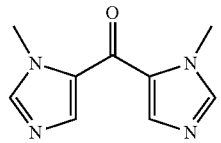

To a solution of 5-bromo-1-methyl-1H-imidazole (1.2 g, 7.45 mmol) in DCM (10 mL) was added ethyl magnesium bromide (2.5 mL, 7.45 mmol, 3.0 M in diethyl ether) dropwise over a 10 minute period. The resulting pale yellow solution was stirred at room temperature for 15 minutes, cooled in an ice bath to 0° C. and then N-methoxy-N,1-dimethyl-1H-imidazole-5-carboxamide (1.0 g, 6.21 mmol, Intermediate 55: step a) dissolved in DCM (3 mL) was added dropwise. The cold bath was removed and the reaction mixture stirred at room temperature for 48 hours. To the resulting yellow suspension was added water followed by 6 M aqueous HCl to a neutral pH (pH=6-7). The aqueous mixture was extracted with DCM (2×). The combined DCM extracts were dried over $MgSO_4$, filtered and concentrated under reduced pressure. The product was precipitated with $Et_2O$, filtered and dried to provide the title compound as a tan solid.

Intermediate 56: Step a tert-Butyl 4-(hydroxy(6-(trifluoromethyl)pyridin-3-yl)methyl)piperidine-1-carboxylate

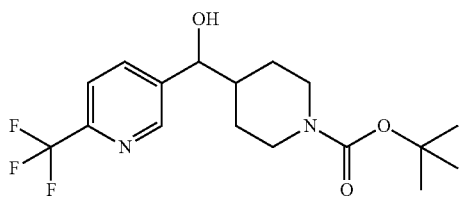 [SMILES: CC(C)(C)OC(=O)N1CCC(C(O)c2ccc(C(F)(F)F)nc2)CC1]

A solution of isopropylmagnesium chloride (2.0 M in THF, 40.3 mL, 80.6 mmol) was added dropwise by syringe to a solution of 5-bromo-2-(trifluoromethyl)pyridine (19.5 g, 86.3 mmol) in dry THF (12 mL) at 2° C. After 30 minutes, tert-butyl 4-formylpiperidine-1-carboxylate (12.3 g, 57.3 mmol) was added to the Grignard solution at 2° C. as a solid. The reaction mixture was warmed to 10° C. over 1.5 hours after which it was quenched with saturated aqueous ammonium chloride solution. The mixture was partitioned between water and ethyl acetate. The separated aqueous phase was further extracted with ethyl acetate and washed with saturated aqueous NaCl solution. The organic phase was dried ($MgSO_4$), filtered, and concentrated to afford the title compound which was used without further purification in the next step.

Intermediate 56: Step b tert-Butyl 4-(6-(trifluoromethyl)nicotinoyl)piperidine-1-carboxylate

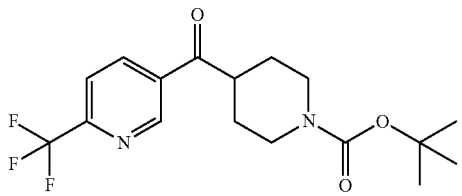 [SMILES: CC(C)(C)OC(=O)N1CCC(C(=O)c2ccc(C(F)(F)F)nc2)CC1]

Dess-Martin periodinane reagent (30.0 g, 70.8 mmol) was added to a solution of tert-butyl 4-(hydroxy(6-(trifluoromethyl)pyridin-3-yl)methyl)piperidine-1-carboxylate (Intermediate 56: step a, 17.8 g, 49.5 mmol) in DCM (354 mL) at room temperature and the mixture was stirred for 2 hours. The reaction mixture was diluted with DCM and washed with saturated aqueous solution of NaHCO$_3$. The organic phase was dried (MgSO$_4$), filtered, and concentrated to dryness. The crude product was purified by flash column chromatography (silica gel, 0-60% EtOAc-hexanes) to provide the title compound that was 90% pure by NMR and was carried on to the next step.

Intermediate 56: Step c

Piperidin-4-yl(6-(trifluoromethyl)pyridin-3-yl)methanone

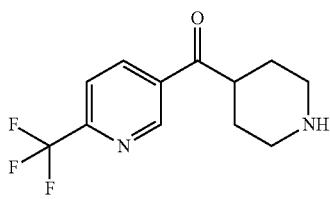 [SMILES: O=C(c1ccc(C(F)(F)F)nc1)C1CCNCC1]

TFA (34.4 mL, 449.3 mmol) was added to a solution of tert-butyl 4-(6-(trifluoromethyl)nicotinoyl)piperidine-1-carboxylate (Intermediate 56: step b, 16.1 g, 44.9 mmol) in DCM (450 mL) and the resulting solution was stirred at room temperature for 3 hours. The mixture was concentrated to remove most of the TFA on the rotary evaporator and a mixture of EtOAc/hexanes was added. The white solid that precipitated was filtered and dried to provide the title compound which was used in the next step without purification.

Intermediate 56: Step d 1-(4-(6-(Trifluoromethyl)nicotinoyl)piperidin-1-yl)ethanone

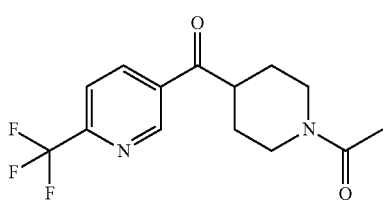 [SMILES: CC(=O)N1CCC(C(=O)c2ccc(C(F)(F)F)nc2)CC1]

TEA (32.1 mL, 230.9 mmol) was added to a solution of piperidin-4-yl(6-(trifluoromethyl)pyridin-3-yl)methanone (Intermediate 56: step c, 14.3 g, 38.5 mmol) in DCM (427 mL) followed by acetic anhydride (5.28 mL, 55.8 mmol). The mixture was stirred for 2 hours and then transferred to a separatory funnel and washed with 100 mL of aqueous 2 M NaH$_2$PO$_4$ solution. The organic layer was dried (MgSO$_4$), filtered and concentrated. The crude product was purified by flash column chromatography (silica gel, 0-3% MeOH-DCM) to provide the title compound.

Intermediate 57

3-(4-(1H-Pyrazol-1-yl)benzyl)-6-bromo-2,4-dichloro-8-methylquinoline

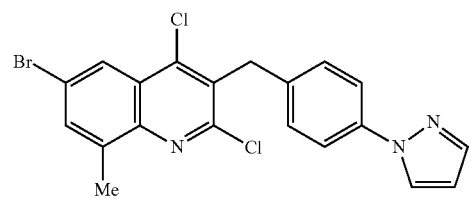 [SMILES: Cc1cc(Br)cc2c(Cl)c(Cc3ccc(-n4cccn4)cc3)c(Cl)nc12]

A mixture of 2-(4-(1H-pyrazol-1-yl)benzyl)malonic acid (20.0 g, 71.5 mmol, Intermediate 3: step b) and 4-bromo-2-methylaniline (13.3 g, 71.5 mmol) in phosphorus oxychloride (66.8 mL, 712 mmol) was heated at 105° C. After 5 hours, the mixture was cooled to 23° C. and added to water (600 mL) with cooling so that the internal temperature did not exceed 35° C. The pH of the mixture was adjusted to 8-9 by the slow addition of saturated aqueous ammonia solution such that the internal temperature did not exceed 35° C. After 30 minutes of stirring at room temperature, the mixture was filtered and the solid material was suspended in acetonitrile (200 mL), sonicated and filtered. The solid material was collected and suspended in DCM (80 mL), sonicated, filtered and washed with ether (40 mL). The filtrate was concentrated, suspended in DCM (40 mL), sonicated and filtered to provide more of the title compound. To 5 g of the isolated solid, DCM (300 mL) and saturated aqueous NaHCO$_3$ (100 mL) were added and the mixture was transferred to a separatory funnel, and the layers were separated. The DCM layer was further washed with brine (100 mL), dried (MgSO$_4$), filtered and the solvents were removed under reduced pressure. The crude material was purified using flash-column chromatography on silica gel eluting with DCM to provide the title compound as an off-white solid.

Intermediate 58: Step a tert-Butyl 4-(hydroxy(1-methyl-1H-imidazol-5-yl)methyl)piperidine-1-carboxylate

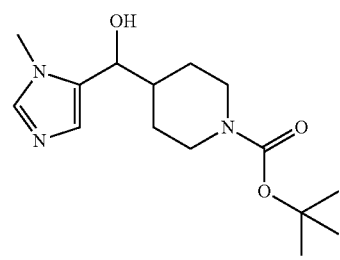 [SMILES: Cn1cncc1C(O)C1CCN(C(=O)OC(C)(C)C)CC1]

A solution of 5-bromo-1-methyl-1H-imidazole (25.0 g, 155 mmol; dried over 3 Å molecular sieves, then filtered) in DCM (310 mL) was stirred in an ice bath while iPrMgCl (72 mL, 2.01 M solution in THF, 145 mmol) was added rapidly dropwise under argon via pressure-equalizing addition funnel. Residual iPrMgCl was rinsed down with 50 mL THF, and the ice bath was removed and the reaction stirred for 25 minutes. A solution of tert-butyl 4-formylpiperidine-1-carboxylate (27.6 g, 130 mmol) in THF (65 mL) was added dropwise over ~5 minutes via pressure-equalizing addition funnel at room temperature. After stirring 1 hour at room temperature, the yellow mixture was quenched with 5 M aqueous NH₄Cl (250 mL) in one portion. The organic layer was dried (Na₂SO₄), filtered, and concentrated to provide the crude title compound as a clear light amber oil.

Intermediate 58: Step b tert-Butyl 4-(1-methyl-1H-imidazole-5-carbonyl)piperidine-1-carboxylate

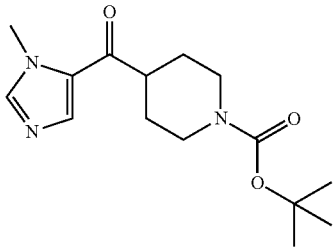 [SMILES: Cn1cncc1C(=O)C1CCN(C(=O)OC(C)(C)C)CC1]

A homogeneous solution of tert-butyl 4-(hydroxy(1-methyl-1H-imidazol-5-yl)methyl)piperidine-1-carboxylate (32.2 g, 109 mmol; Intermediate 58: step a) in dioxane (436 mL) was treated with MnO₂ (47.6 g, 547 mmol) and stirred at 100° C. under air overnight (17 hours). Since the reaction was only ~50% complete by NMR, the reaction was cooled to room temperature, additional MnO₂ (48.0 g, 552 mmol) was added and the reaction stirred under air at 100° C. for 6.5 hours, then at room temperature for 18 days. The mixture was then filtered through a pad of Celite® and the black filter cake washed with EtOAc. The crude filtrate was treated with a third portion of MnO₂ (28.5 g, 327 mmol) and stirred at room temperature overnight. The reaction was then filtered as above and concentrated to provide the crude title compound as a clear dark yellow oil. The crude material was flash chromatographed with an EtOAc to 50% acetone/EtOAc gradient to provide the title compound as a clear dark yellow oil.

Intermediate 58: Step c 1-(4-(1-Methyl-1H-imidazole-5-carbonyl)piperidin-1-yl)ethanone

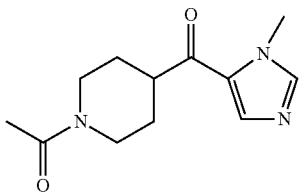 [SMILES: CC(=O)N1CCC(C(=O)c2cncn2C)CC1]

A homogeneous yellow solution of tert-butyl 4-(1-methyl-1H-imidazole-5-carbonyl)piperidine-1-carboxylate (10.1 g, 34.4 mmol; Intermediate 58: step b) in DCM (172 mL) was treated with TFA (26.4 mL, 344 mmol) and stirred at room temperature for 2.5 hours. The reaction was concentrated from toluene (2×100 mL), and the resulting clear light amber residue was taken up in DCM (344 mL) and TEA (23.9 mL, 172 mmol). Acetic anhydride (3.91 mL, 41.3 mmol) was added dropwise and the reaction stirred at room temperature for 1 hour. The reaction was concentrated under high vacuum and the residue was purified by FCC using 95:5 DCM/MeOH with 2% TEA as eluent. The combined fractions were concentrated, dissolved in DCM (200 mL), and washed with water (2×200 mL) to remove TEA. The organic layer was dried (Na₂SO₄), filtered, and concentrated, and the residue was triturated with MTBE (75 mL) at reflux for 15 minutes and then allowed to cool to room temperature. The mixture was filtered and the off-white filter cake was washed with MTBE (2×3 mL) to provide the title compound as an off-white fine powder.

Intermediate 59

(4-Chloro-2-methoxy-3-(4-(trifluoromethyl)benzyl)quinolin-6-yl)(2,4-dimethylthiazol-5-yl)(1-methyl-1H-1,2,3-triazol-5-yl)methanol

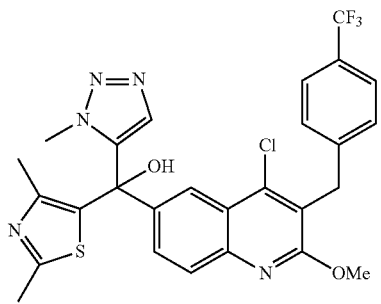 [SMILES: COc1nc2ccc(C(O)(c3sc(C)nc3C)c3cnnn3C)cc2c(Cl)c1Cc1ccc(C(F)(F)F)cc1]

To a flask containing 6-bromo-4-chloro-2-methoxy-3-(4-(trifluoromethyl)benzyl)quinoline (500 mg, 116 mmol, Intermediate 12: step d) was added THF (15 mL) at room temperature which resulted in a colorless homogeneous mixture. The solution was cooled to −70° C. (the solution remained homogeneous) and then n-butyllithium (2.5 M in hexanes, 0.45 mL, 1.13 mmol) was added dropwise. The color of the solution became a dark brown. After 1 minute, (2,4-dimethylthiazol-5-yl)(1-methyl-1H-1,2,3-triazol-5-yl)methanone (275 mg, 1.24 mmol in 2 mL THF, Intermediate 23: step b) was introduced and the color of the mixture went from dark brown to greenish to light orange color all within 1 minute. The mixture was allowed to warm to 0° C. over 45 minutes at which time the reaction was quenched with aqueous NH₄Cl solution. The mixture was diluted further with water and extracted with EtOAc (3×45 mL). The combined organics were washed with brine, dried over MgSO₄, filtered and concentrated to afford a light orange foam. The crude was chromatographed on silica gel (initially using 10% CH₃CN-toluene then changing to 80% CH₃CN-DCM) to provide the title compound as an off white solid.

Intermediate 60: Step a (4-Chloro-2-methoxy-3-(4-(trifluoromethyl)benzyl)quinolin-6-yl)(1,2-dimethyl-1H-imidazol-5-yl)methanol

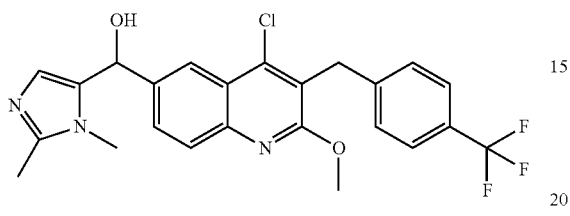

To a flask containing 6-bromo-4-chloro-2-methoxy-3-(4-(trifluoromethyl)benzyl)quinoline (2.0 g, 4.64 mmol, Intermediate 12: step d) was added THF (25 mL). The solution was cooled to −70° C. and then n-BuLi (2.5 M in hexanes, 1.8 mL, 4.5 mmol) was added dropwise. After 2 minutes, 1,2-dimethyl-1H-imidazole-5-carbaldehyde (720 mg, 5.8 mmol in 5 mL THF) was introduced. The reaction mixture was allowed to warm to 0° C. over 60 minutes at which time it was quenched with aqueous NH₄Cl solution. The aqueous portion was extracted with EtOAc:THF (10:1, 5×50 mL). The combined organics were washed with brine, dried over MgSO₄, filtered and concentrated to dryness. The solid was triturated with EtOAc:Et₂O (1:1), collected by filtration and rinsed with additional Et₂O and dried to afford the title compound. The mother liquors were concentrated and chromatographed on silica gel (3% MeOH-DCM increasing to 10% MeOH) to provide additional title compound.

Intermediate 60: Step b (4-Chloro-2-methoxy-3-(4-(trifluoromethyl)benzyl)quinolin-6-yl)(1,2-dimethyl-1H-imidazol-5-yl)methanone

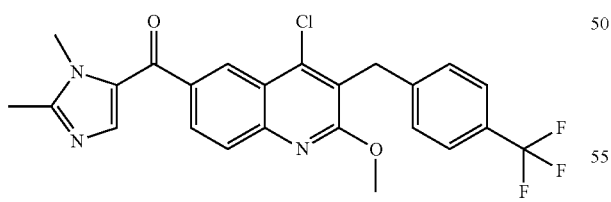

To a flask containing (4-chloro-2-methoxy-3-(4-(trifluoromethyl)benzyl)quinolin-6-yl)(1,2-dimethyl-1H-imidazol-5-yl)methanol (1.68 g, 3.53. mmol, Intermediate 60: step a) was added 1,4-dioxane (75 mL) and THF (10 mL) which produced a suspension at room temperature. Warming the suspension to 45° C. formed a homogeneous solution. Manganese dioxide (1.5 g, 17.25 mmol) was introduced and the mixture was heated to 80° C. After 60 minutes, the mixture was filtered through a Celite® pad, rinsing with THF. The filtrate was then concentrated to dryness. Titutration with Et₂O provided the title compound as a white powder.

Intermediate 61: Step a tert-Butyl-3-((4-chloro-2-methoxy-3-(4-(trifluoromethyl)benzyl)quinolin-6-yl)(hydroxy)methyl)azetidine-1-carboxylate

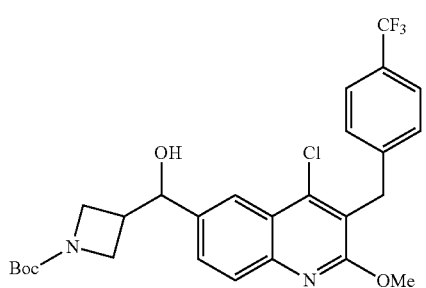 [SMILES: COc1nc2ccc(C(O)C3CN(C(=O)OC(C)(C)C)C3)cc2c(Cl)c1Cc1ccc(C(F)(F)F)cc1]

To a flask containing 6-bromo-4-chloro-2-methoxy-3-(4-(trifluoromethyl)benzyl)quinoline (1.0 g, 2.32 mmol, Intermediate 12: step d) was added THF (30 mL) resulting in a colorless homogeneous mixture. The solution was cooled to −70° C. and then n-BuLi (2.5 M in hexanes, 1.08 mL, 2.69 mmol) was added dropwise. The color of the solution became a dark opaque reddish-brown color. After 2 minutes, a THF solution of tert-butyl 3-formylazetidine-1-carboxylate (545 mg, 2.94 mmol, in 3 mL THF) was introduced. After 5 minutes, the reaction mixture was placed in an ice-water bath and allowed to stir for 30 minutes at which time the mixture was quenched with aqueous NH₄Cl solution. The contents were diluted further with water and extracted with EtOAc (5×40 mL). The combined organics were washed with brine, dried over MgSO₄, filtered and concentrated to provide a yellow foam. The crude material was chromatographed on silica gel (20% EtOAc-hexanes increasing to 50% EtOAc) to afford the title compound as a white solid.

Intermediate 61: Step b tert-Butyl-3-(4-chloro-2-methoxy-3-(4-(trifluoromethyl)benzyl)quinoline-6-carbonyl)azetidine-1-carboxylate

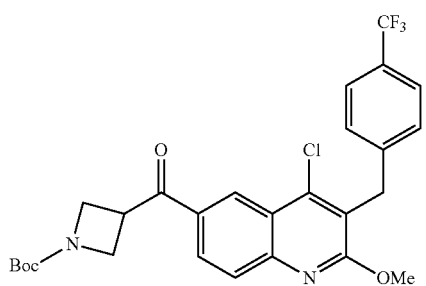 [SMILES: COc1nc2ccc(C(=O)C3CN(C(=O)OC(C)(C)C)C3)cc2c(Cl)c1Cc1ccc(C(F)(F)F)cc1]

To a flask containing tert-butyl-3-((4-chloro-2-methoxy-3-(4-(trifluoromethyl)benzyl)quinolin-6-yl)(hydroxy)methyl)azetidine-1-carboxylate (525 mg, 0.98 mmol, Intermediate 61: step a) was added 1,4-dioxane (40 mL) to give a homogeneous solution at room temperature. Manganese dioxide (715 mg, 8.23 mmol) was then added and the mixture was heated to 85° C. in an aluminum heating mantle under nitrogen. After 60 minutes, the contents were filtered through a Celite® pad while the solution was still warm, rinsing with THF. The effluent was concentrated and purified by passing through a short column of silica gel (10% acetone-hexane increasing to 25% acetone) to provide the title compound as a white amorphous solid.

Intermediate 62

4-Chloro-2-methoxy-3-(4-(trifluoromethyl)benzyl) quinolin-6-yl)(2,6-dimethylpyridin-3-yl)(1-methyl-1H-1,2,3-triazol-5-yl)methyl acetate

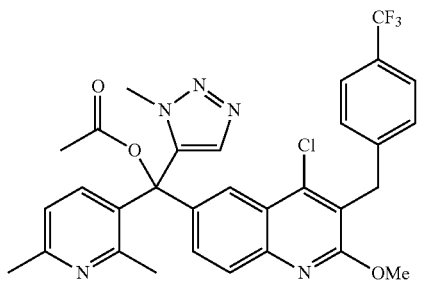 [SMILES: COc1nc2ccc(C(OC(C)=O)(c3ccc(C)nc3C)c3cnnn3C)cc2c(Cl)c1Cc1ccc(C(F)(F)F)cc1]

To a solution of the first eluting enantiomer of 4-chloro-2-methoxy-3-(4-(trifluoromethyl)benzyl)quinolin-6-yl)(2,6-dimethylpyridin-3-yl)(1-methyl-1H-1,2,3-triazol-5-yl) methanol (544 mg, 0.960 mmol, Intermediate 84b) in 20 mL of dry DMF at room temperature was added NaH (60% in mineral oil, 75 mg, 1.9 mmol). After stirring for 20 minutes, acetic anhydride (0.18 mL, 1.9 mmol) was added. The mixture was stirred for one hour and a suspension formed. After the mixture was quenched with a few drops of water, the suspension was filtered and the filtrate was concentrated in vacuo. The residue was partitioned between dichloromethane and saturated NaHCO₃ (aq). The organic extracts were dried (Na₂SO₄), filtered, and concentrated to provide the title compound as a semi-solid.

Intermediate 63: Step a (4-Chloro-2-methoxy-3-(4-(trifluoromethyl)benzyl) quinolin-6-yl)(3,5-dimethylisoxazol-4-yl)methanol

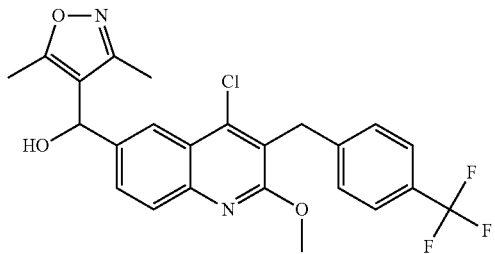 [SMILES: COc1nc2ccc(C(O)c3c(C)noc3C)cc2c(Cl)c1Cc1ccc(C(F)(F)F)cc1]

To a flask containing 6-bromo-4-chloro-2-methoxy-3-(4-(trifluoromethyl)benzyl)quinoline (2.0 g, 4.64 mmol, Intermediate 12: step d) was added THF (65 mL) and the solution was cooled to −78° C. n-BuLi (2.5 M in hexanes, 2.1 mL, 5.25 mmol) was added dropwise producing a dark reddish-brown mixture. After 2 minutes, a THF solution of 3,5-dimethyl-isoxazole-4-carbaldehyde (700 mg, 5.63 mmol in 2 mL THF) was introduced. The reaction mixture immediately became a homogeneous yellow solution. After 25 minutes the mixture was quenched with aqueous NH₄Cl solution and the aqueous portion was extracted with EtOAc (3×50 mL). The combined organics were washed with brine, dried over MgSO₄, filtered and concentrated to dryness. Chromatography on silica gel (100% DCM increasing to 20% CH₃CN/DCM) provided the titled compound an off white amorphous solid.

Intermediate 63: Step b (4-Chloro-2-methoxy-3-(4-(trifluoromethyl)benzyl) quinolin-6-yl)(3,5-dimethylisoxazol-4-yl)methanone

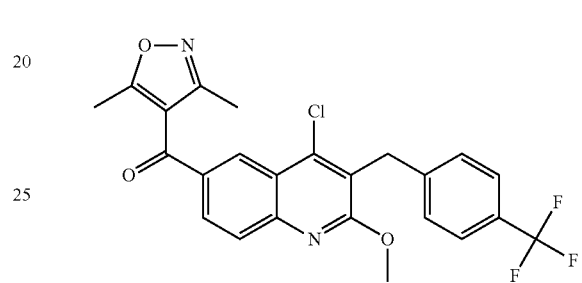

To a flask containing (4-chloro-2-methoxy-3-(4-(trifluoromethyl)benzyl)quinolin-6-yl)(3,5-dimethylisoxazol-4-yl) methanol (1.4 g, 2.94 mmol, Intermediate 63: step a) was added THF (75 mL) followed by manganese dioxide (1.1 g, 12.6 mmol). The reaction mixture was heated to reflux for 2 hours, and then the contents were filtered through Celite® and rinsed with additional THF. The effluent was concentrated to provide the title compound as a white amorphous solid which was used without further purification.

Intermediate 64

(3-(4-(1H-Pyrazol-1-yl)benzyl)-2,4-dichloroquinolin-6-yl)(4-chlorophenyl)(1-methyl-1H-imidazol-5-yl)methanol•TFA

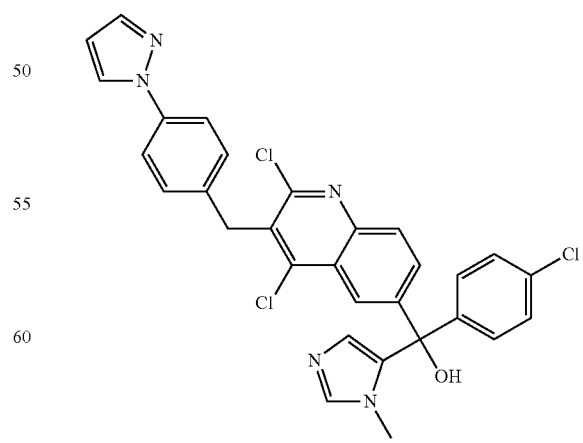

A mixture of 3-(4-(1H-pyrazol-1-yl)benzyl)-6-bromo-2,4-dichloroquinoline (0.2 g, 0.462 mmol, Intermediate 3: step c)

and (4-chlorophenyl)(1-methyl-1H-imidazol-5-yl)methanone (0.113 g, 0.462 mmol, Intermediate 43: step b) in dry THF (5 mL) was cooled to −78° C. and then n-BuLi (0.375 mL, 0.6 mmol, 1.6 M in hexane) was added dropwise over a 30 minute period. Stirring was continued at −78° C. for 30 minutes, then the mixture was warmed up to 0° C. and stirred for 1 hour. Saturated aqueous NH$_4$Cl was added and the layers were separated. The aqueous mixture was extracted further with EtOAc. The combined organic extracts were dried over Na$_2$SO$_4$, filtered, evaporated in vacuo, and chromatographed (EtOAc/CH$_2$Cl$_2$) to provide the product. Further purification by reverse phase HPLC (H$_2$O/acetonitrile/0.1% TFA) provided the title compound as a white solid.

Intermediate 65

(3-(4-(1H-Pyrazol-1-yl)benzyl)-2,4-dichloroquinolin-6-yl)(1-methyl-1H-imidazol-5-yl)(6-(trifluoromethyl)pyridin-3-yl)methanol•TFA

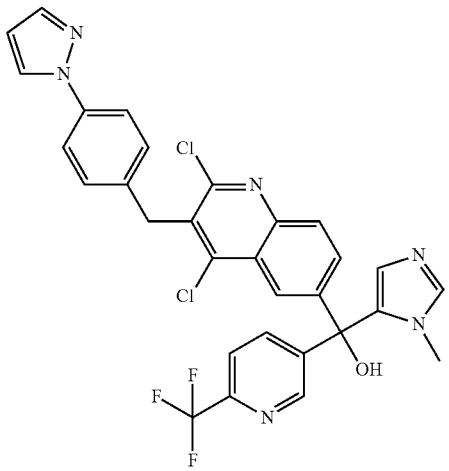 [SMILES: Cn1cncc1C(O)(c1ccc(C(F)(F)F)nc1)c1ccc2nc(Cl)c(Cc3ccc(-n4cccn4)cc3)c(Cl)c2c1]

The title compound was prepared by substituting (4-chlorophenyl)(1-methyl-1H-imidazol-5-yl)methanone (Intermediate 43: step b) with (1-methyl-1H-imidazol-5-yl)(6-(trifluoromethyl)pyridin-3-yl)methanone (Intermediate 2: step c) following the procedure described for Intermediate 64.

Intermediate 66: Step a

N-Methoxy-N-methylpyrimidine-2-carboxamide

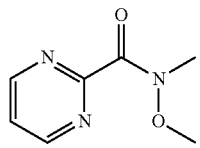

Sodium pyrimidine-2-carboxylate (4.00 g, 27.4 mmol), imidazole hydrochloride (3.15 g, 30.1 mmol), and 1-carbonyldiimidazole (5.26 g, 31.5 mmol) was slurried in acetonitrile (30 mL) at room temperature under an N$_2$ atmosphere. The mixture was then warmed to 52° C. over 30 minutes. Evolution of carbon dioxide was seen when the reaction mixture reached approximately 50° C. The mixture was then stirred at 52° C. for approximately 2 hours. The reaction was cooled to room temperature, then N,O-dimethylhydroxylamine hydrochloride (3.54 g, 35.6 mmol) was added slowly, portion wise over approximately 15 minutes and a mild exotherm was seen after each addition. The contents were stirred at room temperature overnight. To the reaction mixture was then added deionized water (25 mL) and dichloromethane (25 mL). 6 M aqueous hydrochloric acid was added dropwise to acidify the aqueous layer to approximately pH 1. The organic phase was then separated and the aqueous phase was extracted twice with dichloromethane. The combined organics were washed with 2 M aqueous hydrochloric acid and the layers separated. The acidic layer was extracted twice with dichloromethane and the organics combined. The organics were washed with a saturated, aqueous NaHCO$_3$ solution, then dried over MgSO$_4$, filtered and the solvent was removed by distillation under reduced pressure to provide the title compound.

Intermediate 66: step b (1-Methyl-1H-imidazol-5-yl)(pyrimidin-2-yl)methanone

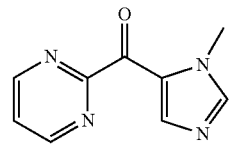

5-Bromo-1-methyl-1H-imidazole (6.66 g, 41.4 mmol) was added to a round bottom flask followed by tetrahydrofuran (150 mL) under an N$_2$ atmosphere. The contents were cooled to 0° C. in an ice water bath. EtMgBr (3.0 M solution in THF, 13.3 mL, 39.8 mmol) was added slowly via syringe over approximately 5 minutes, then the ice bath was removed and the contents allowed to warm and stirred at room temperature for approximately 30 minutes. The vessel was then re-cooled to 0° C. and a solution of N-methoxy-N-methylpyrimidine-2-carboxamide (3.09 g, 15.9 mmol, Intermediate 66: step a) in THF (20 mL) was cannulated into the reaction vessel. The contents were allowed to stir at 0° C., then slowly warmed to room temperature, then heated to 40° C. in an oil bath for approximately 36 hours. The contents were then cooled to 0° C., quenched with a saturated aqueous NH$_4$Cl solution, diluted with ethyl acetate and transferred to a separatory funnel. The aqueous layer was separated, extracted twice with EtOAc, then the combined organic phases were dried over MgSO$_4$, filtered, then distilled under reduced pressure to yield an amber oil. The crude product was purified by flash column chromatography (silica gel, 0-10% DCM/(10% of a 2 M NH$_3$ MeOH in DCM)) to provide the title compound.

Intermediate 67

(3-(4-(1H-Pyrazol-1-yl)benzyl)-2,4-dichloro-8-methylquinolin-6-yl)(4-chlorophenyl)(1-methyl-1H-imidazol-5-yl)methanol

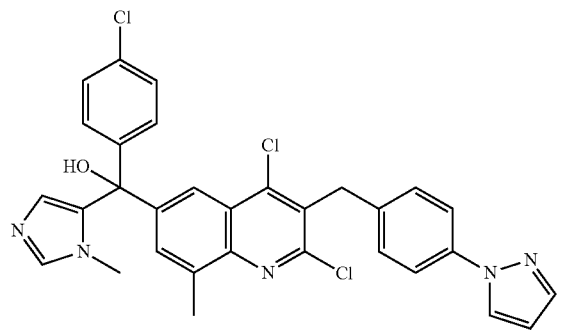 [SMILES: Cc1cc(C(O)(c2ccc(Cl)cc2)c2cncn2C)cc2c(Cl)c(Cc3ccc(-n4cccn4)cc3)c(Cl)nc12]

A mixture of 3-(4-(1H-pyrazol-1-yl)benzyl)-6-bromo-2,4-dichloro-8-methylquinoline (393 mg, 0.880 mmol, Intermediate 57) and (4-chlorophenyl)(1-methyl-1H-imidazol-5-yl)methanone (194 mg, 0.880 mmol, Intermediate 43: step b) in dry THF (16 mL, sparged with nitrogen) sparged with nitrogen was cooled to −78° C. n-BuLi (1.6 M in hexane, 0.5 mL, 0.8 mmol) was added over 1.5 minutes. Stirring was continued at −78° C. for 10 minutes and then the dry ice acetone bath was replaced with an ice water bath. Stirring was continued for 1 hour and the reaction mixture was quenched with saturated aqueous NH$_4$Cl solution. EtOAc was added, the layers were separated and the aqueous mixture further extracted with EtOAc. The combined organic extracts were dried over MgSO$_4$, filtered, and the solvents were removed under reduced pressure. Purification using flash column chromatography (5% MeOH in dichloromethane) provided the title compound.

Intermediate 68

(3-(4-(1H-Pyrazol-1-yl)benzyl)-2,4-dichloro-8-methylquinolin-6-yl)(1-methyl-1H-imidazol-5-yl)(6-(trifluoromethyl)pyridin-3-yl)methanol

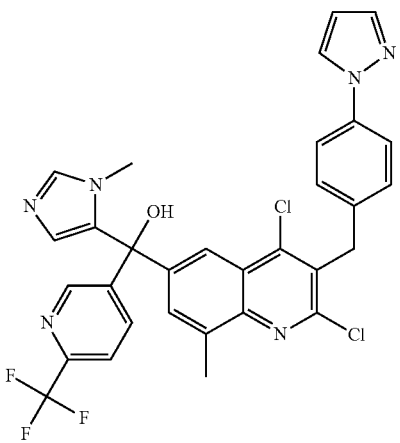 [SMILES: Cc1cc(C(O)(c2ccc(C(F)(F)F)nc2)c2cncn2C)cc2c(Cl)c(Cc3ccc(-n4cccn4)cc3)c(Cl)nc12]

6-Bromo-2,4-dichloro-8-methyl-3-[4-(1H-pyrazol-1-yl)benzyl]quinoline (3.00 g, 6.71 mmol, Intermediate 57) and (1-methyl-1H-imidazol-5-yl)(6-(trifluoromethyl)pyridin-3-yl)methanone (1.88 g, 7.38 mmol, Intermediate 2: step c) were dissolved in THF (300 mL) in a dry round bottom flask under an N$_2$ atmosphere, then cooled to −40° C. in a dry ice acetonitrile bath. n-BuLi (1.6 M in hexanes, 5.45 mL, 8.72 mmol) was then added dropwise via syringe over approximately 2 minutes. The reaction solution was stirred at −40° C. for approximately 5 minutes, then the dry ice bath was removed and replaced with an ice water bath and stirred at that temperature for approximately 90 minutes. The reaction was then quenched with a saturated, aqueous NH$_4$Cl solution, then transferred to a reparatory funnel with EtOAc. The organic phase was separated and the aqueous layer was back extracted with EtOAc. The organic phases were combined, dried over MgSO$_4$, filtered and concentrated under reduced pressure. The crude product was purified by flash column chromatography (silica gel, 0-100% hexane/ethyl acetate) to afford the title compound.

Intermediate 69: Step a 2-(Azetidin-1-yl)-6-bromo-4-chloro-3-(4-(trifluoromethyl)benzyl)quinoline

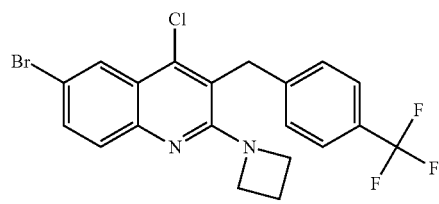 [SMILES: FC(F)(F)c1ccc(Cc2c(N3CCC3)nc3ccc(Br)cc3c2Cl)cc1]

6-Bromo-2,4-dichloro-3-[4-(trifluoromethyl)benzyl]quinoline (2.50 g, 5.75 mmol, Intermediate 12: step c), azetidine (0.984 g, 17.2 mmol) and DMF (29 mL) were combined in a reaction tube, then sealed and heated to 100° C. overnight. The reaction vessel was then cooled and the contents were transferred to a separatory funnel with EtOAc dilution. The organics were extracted once with a saturated, aqueous NH$_4$Cl solution and three times with deionized water. The organic phase was separated, dried over MgSO$_4$, filtered and concentrated under reduced pressure. The crude product was purified by flash column chromatography (silica gel, 0-20% hexane/ethyl acetate) to afford the title compound.

Intermediate 69: Step b

{2-Azetidin-1-yl-4-chloro-3-[4-(trifluoromethyl)benzyl]quinolin-6-yl}(1,2-dimethyl-1H-imidazol-5-yl)methanol

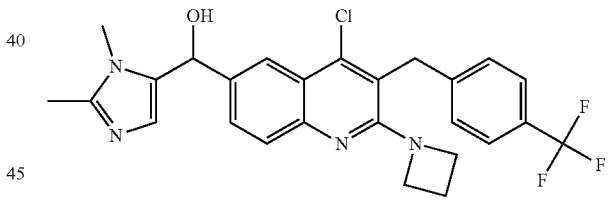

2-(Azetidin-1-yl)-6-bromo-4-chloro-3-(4-(trifluoromethyl)benzyl)quinoline (1.00 g, 2.19 mmol, Intermediate 69: step a) was dissolved in THF (20 mL) in a dry round bottom flask under an N$_2$ atmosphere, then cooled to −78° C. in dry ice acetone bath. n-BuLi (1.6 M in hexanes, 1.74 mL, 2.79 mmol) was then added dropwise via syringe over approximately 5 minutes. The contents were stirred at −78° C. for approximately 10 minutes, then a solution of 1,2-dimethyl-1H-imidazole-5-carbaldehyde (0.30 g, 2.4 mmol) in THF (20 mL) was added via cannula and the resulting mixture stirred for 10 minutes at −78° C. The dry ice bath was then removed and replaced with an ice water bath and the mixture stirred at 0° C. for approximately one hour. The reaction was then quenched with a saturated, aqueous NH$_4$Cl solution, then transferred to a separatory funnel with EtOAc. The organic phase was extracted with a saturated, aqueous NH$_4$Cl solution and deionized water, then separated and dried over MgSO$_4$, filtered and concentrated under reduced pressure. The crude product was purified by flash column chromatography (silica gel, 0-10% DCM/(10% of a 2 M NH$_3$ MeOH in DCM) to provide the title compound.

Intermediate 70: Step a 3-((2,2-Dimethyl-4,6-dioxo-1,3-dioxan-5-yl)methyl)benzonitrile

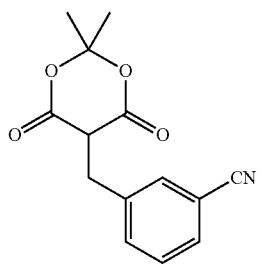 [SMILES: CC1(C)OC(=O)C(Cc2cccc(C#N)c2)C(=O)O1]

Proline (0.459 g, 3.95 mmol) was added to a mixture of 3-cyanobenzaldehyde (2.59 g, 19.7 mmol) and Meldrum's acid (2.84 g, 19.7 mmol) in ethanol (200 mL). The mixture was stirred at room temperature for 45 minutes and then diethyl 1,4-dihydro-2,6-dimethyl-3,5-pyridinedicarboxylate (5 g, 20 mmol) was added. The mixture was stirred for an additional hour at room temperature before being concentrated to dryness. The residue was triturated with isopropanol and filtered to provide the title compound as a white solid.

Intermediate 70: Step b 2-(3-Cyanobenzyl)malonic acid

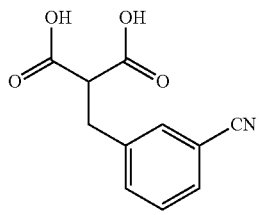 [SMILES: N#Cc1cccc(CC(C(=O)O)C(=O)O)c1]

A flask containing a mixture of 3-((2,2-dimethyl-4,6-dioxo-1,3-dioxan-5-yl)methyl)benzonitrile (4.53 g, 17.5 mmol, Intermediate 70: step a) TFA (30 mL) and water (14 mL) was equipped with a reflux condenser and Drierite® at the outlet, then heated in a 65° C. oil bath for 4 hours. The mixture was concentrated and the title compound was precipitated from water and filtered.

Intermediate 70: Step c 3-((6-Bromo-2,4-dichloroquinolin-3-yl)methyl)benzonitrile

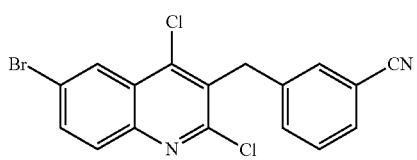 [SMILES: N#Cc1cccc(Cc2c(Cl)nc3ccc(Br)cc3c2Cl)c1]

A mixture of 2-(3-cyanobenzyl)malonic acid (2.16 g, 9.85 mmol, Intermediate 70: step b) and 4-bromoaniline (1.7 g, 9.9 mmol) in POCl$_3$ (9.2 mL, 99 mmol) was heated at 92° C. overnight in a sealed tube. The mixture was allowed to cool to room temperature and concentrated to remove excess POCl$_3$. The residue was mixed with dichloromethane before ice and saturated aqueous sodium bicarbonate were added. The mixture was stirred for 2 hours in an ice bath, then the layers were separated and the aqueous layer was extracted with dichloromethane. The combined organic layers were dried over MgSO$_4$, filtered and concentrated to dryness with silica gel. The dry-loaded crude material was purified by flash column chromatography (silica gel, 0-10% EtOAc-hexanes) to provide the title compound.

Intermediate 70: Step d 3-((6-Bromo-4-chloro-2-methoxyquinolin-3-yl)methyl)benzonitrile

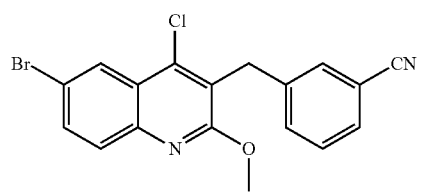 [SMILES: COc1nc2ccc(Br)cc2c(Cl)c1Cc1cccc(C#N)c1]

Sodium methoxide (449 mg, 8.31 mmol) was added to a mixture of 3-((6-bromo-2,4-dichloroquinolin-3-yl)methyl)benzonitrile (0.326 g, 0.831 mmol, Intermediate 70: step c) in toluene (5 mL). The mixture was heated in an oil bath at 105° C. overnight, then allowed to cool to room temperature, filtered through Celite® and rinsed with dichloromethane. The filtrate was concentrated and purified by flash column chromatography (silica gel, 0-25% EtOAc-hexanes) to provide the title compound without further purification.

Intermediate 71: Step a

3-Benzyl-6-iodo-2-(trifluoromethyl)quinolin-4-ol

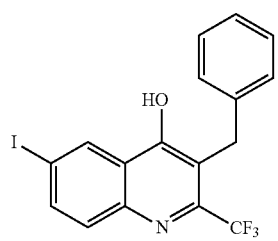 [SMILES: Oc1c(Cc2ccccc2)c(C(F)(F)F)nc2ccc(I)cc12]

A mixture of 2-amino-5-iodobenzoic acid (5.73 g, 21.8 mmol), 1,1,1-trifluoro-4-phenylbutan-2-one (5.30 g, 26.2 mmol, see reference Yang, D; Wong, M; Yan, Z. *J. Org. Chem.* 2000, 65, 4179-4184), and Eaton's reagent (16 mL) in a sealed pressure tube was heated at 100° C. for 1.5 hours. The reaction was then cooled to room temperature and ice-water and DCM were added. Then the pH was adjusted to pH 9 by the slow addition of 50% aqueous NaOH and concentrated NH$_4$OH solutions (the mixture was periodically cooled in an ice-water bath to maintain the temperature below 40° C.). The

Intermediate 71: Step b

3-Benzyl-4-chloro-6-iodo-2-(trifluoromethyl)quinoline

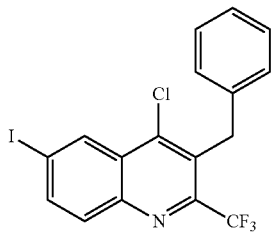 [SMILES: FC(F)(F)c1nc2ccc(I)cc2c(Cl)c1Cc1ccccc1]

A solution of 3-benzyl-6-iodo-2-(trifluoromethyl)quinolin-4-ol (6.10 g, 14.2 mmol, Intermediate 71: step a) in phosphoryl trichloride (18 mL, 194 mmol) was heated at 110° C. for 3 hours, then concentrated in vacuo. After cooling down to room temperature, ice-water and DCM were added to the residue, and the mixture was basified at 4° C. by the addition of 50% aqueous NaOH and concentrated $NH_4OH$ to pH 9. The organic layer was separated and the aqueous layer was extracted with DCM. The combined organic phases were dried ($Na_2SO_4$), filtered, concentrated, and purified by flash column chromatography (silica gel, 2-6% EtOAc in heptanes), affording a mixture of the title compound and 3-benzyl-4-chloro-2-(trifluoromethyl)quinoline in ~2:1 ratio.

Intermediate 72: Step a

3-Benzyl-6-bromo-2-(trifluoromethyl)quinolin-4-ol

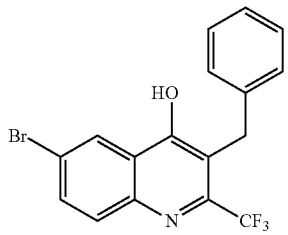 [SMILES: Oc1c(Cc2ccccc2)c(C(F)(F)F)nc2ccc(Br)cc12]

A mixture of 2-amino-5-bromobenzoic acid (2.53 g, 11.7 mmol), 1,1,1-trifluoro-4-phenylbutan-2-one (2.83 g, 14.0 mmol, see reference Yang, D; Wong, M; Yan, Z. *J. Org. Chem.* 2000, 65, 4179-4184), and Eaton's reagent (8.8 mL) in a sealed pressure tube was heated at 100° C. for 4 hours. The mixture was then cooled down to room temperature, ice-water was added slowly, and the mixture was stirred vigorously for about 15 minutes. The precipitated solid was filtered, washed with water, and air dried over night to afford the title compound as a light brown solid.

Intermediate 72: Step b

3-Benzyl-6-bromo-4-chloro-2-(trifluoromethyl)quinoline

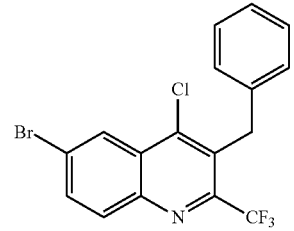 [SMILES: FC(F)(F)c1nc2ccc(Br)cc2c(Cl)c1Cc1ccccc1]

The title compound was prepared using 3-benzyl-6-bromo-2-(trifluoromethyl)quinolin-4-ol (Intermediate 72: step a) in place of 3-benzyl-6-iodo-2-(trifluoromethyl)quinolin-4-ol (Intermediate 71: step a) using the procedure described for Intermediate 71: step b.

Intermediate 73: Step a

Methyl 5-bromo-2-(3-phenylpropanamido)benzoate

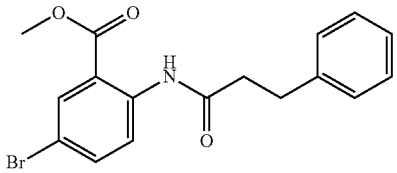 [SMILES: COC(=O)c1cc(Br)ccc1NC(=O)CCc1ccccc1]

Into a 100-mL round-bottom flask was placed a solution of methyl 2-amino-5-bromobenzoate (5.0 g, 21.73 mmol), triethylamine (4.39 g, 43.38 mmol), 3-phenylpropanoyl chloride (3.67 g, 21.76 mmol) in dichloromethane (50 mL). The resulting mixture was stirred for 12 hours at room temperature. The reaction was then quenched by the addition of 50 mL of water. The resulting mixture was extracted with dichloromethane (3×50 mL). The combined organic layers were dried over anhydrous sodium sulfate, filtered and concentrated under vacuum. The residue was purified by chromatography over a silica gel column with ethyl acetate/petroleum ether (2:1) to give the title compound as a white solid.

Intermediate 73: Step b

3-Benzyl-6-bromo-4-hydroxy-1,2-dihydroquinolin-2-one

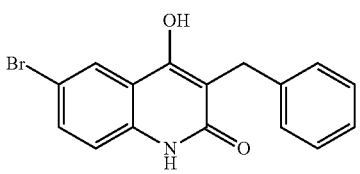 [SMILES: O=c1[nH]c2ccc(Br)cc2c(O)c1Cc1ccccc1]

Into a 50-mL round-bottom flask, purged and maintained with an inert atmosphere of nitrogen, was placed a solution of methyl 5-bromo-2-(3-phenylpropanamido)benzoate (2.8 g, 7.8 mmol, Intermediate 73: step a) and KHMDS (47 mL, 15% in toluene) in tetrahydrofuran (50 mL). The resulting solution was stirred for 12 hours at room temperature. The reaction was then quenched by the addition of 2 mL of methanol and 10 mL of aqueous HCl (1 M). The resulting solution was extracted with ethyl acetate (2×100 mL). The combined organic layers were dried over anhydrous sodium sulfate, filtered and concentrated under vacuum. The crude product was purified by re-crystallization from ethyl acetate to afford the title compound as a white solid.

Intermediate 73: Step c

3-Benzyl-6-bromo-2,4-dichloroquinoline

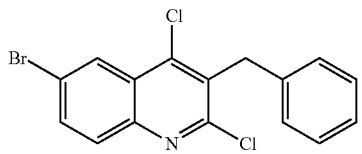 [SMILES: Clc1nc2ccc(Br)cc2c(Cl)c1Cc1ccccc1]

Into a 100-mL round-bottom flask, was placed a solution of 3-benzyl-6-bromo-4-hydroxy-1,2-dihydroquinolin-2-one (2.9 g, 8.78 mmol, Intermediate 73: step b) in POCl₃ (20 mL). The resulting solution was stirred for 1 hour at 110° C. The reaction was then quenched by the addition of 50 mL of water/ice. The pH value of the solution was adjusted to 7-8 with aqueous ammonia and the resulting solution was extracted with ethyl acetate (3×50 mL). The combined organic layers were dried over anhydrous sodium sulfate, filtered and concentrated under vacuum. The residue was purified by chromatography over a silica gel column with ethyl acetate/petroleum ether (2:1) to provide the title compound as a white solid.

Intermediate 73: Step d

3-Benzyl-6-bromo-4-chloro-2-(1H-pyrazol-1-yl)quinoline

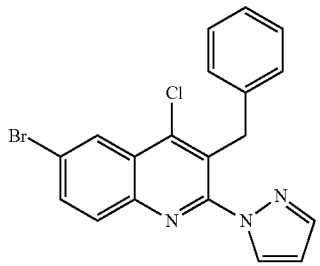 [SMILES: Clc1c(Cc2ccccc2)c(-n2cccn2)nc2ccc(Br)cc12]

To a mixture of 3-benzyl-6-bromo-2,4-dichloroquinoline (1.66 g, 4.52 mmol, Intermediate 73: step c), 1H-pyrazole (370 mg, 5.43 mmol), DMF (13 mL), and THF (27 mL) at 4° C. was added NaH (60% in mineral oil, 270 mg, 6.78 mmol). The mixture was stirred at 4° C. to room temperature for 6 hours, and then quenched with MeOH. After concentration in vacuo, water and DCM were added to the residue. The organic layer was separated, and the aqueous layer was extracted with DCM. The combined organic phases were dried over Na₂SO₄, filtered, and concentrated to dryness. The crude mixture was purified by flash column chromatography (silica gel, 10-40% EtOAc in heptanes) to give the title compound as a white solid.

Intermediate 74: Step a

6-Bromo-3-(4-(methylthio)benzyl)quinoline-2,4-diol

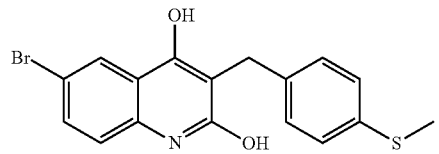 [SMILES: CSc1ccc(Cc2c(O)nc3ccc(Br)cc3c2O)cc1]

A mixture of 4-(methylthio)benzaldehyde (3.00 g, 19.7 mmol), 6-bromo-4-hydroxyquinolin-2(1H)-one (4.72 g, 19.7 mmol, Intermediate 45: step a), diethyl 2,6-dimethyl-1,4-dihydropyridine-3,5-dicarboxylate (5.23 g, 20.7 mmol), and pyridine (100 mL) was stirred at 80° C. for 4 hours and then at room temperature overnight. The reaction was cooled and the formed precipitate was filtered, washed with Et₂O (100 mL), and dried to afford the title compound as a white solid.

Intermediate 74: Step b

6-Bromo-2,4-dichloro-3-(4-(methylthio)benzyl)quinoline

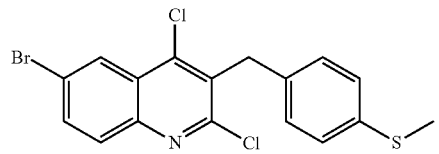 [SMILES: CSc1ccc(Cc2c(Cl)nc3ccc(Br)cc3c2Cl)cc1]

The heterogeneous mixture of 6-bromo-3-(4-(methylthio)benzyl)quinoline-2,4-diol (5.34 g, 14.2 mmol, Intermediate 74: step a), phosphoryl trichloride (7.0 mL, 75 mmol), and CH₃CN (40 mL) was stirred at 100° C. for 2 hours. After two hours, the mixture became a clear solution with a very small amount of white solid still present. After standing at room temperature overnight, additional white solid precipitated out of solution. The mixture was cooled down to 4° C., water was added slowly, and the mixture was stirred at room temperature for ~30 minutes. The white solid was filtered, washed with water, and dried under air. The solid was dissolved in DCM and passed through a layer of silica gel. The DCM solution was then concentrated to dryness to afford the title compound as a white solid.

Intermediate 75

Methyl 4-chloro-2-methoxy-3-(4-(trifluoromethyl)benzyl)quinoline-6-carboxylate

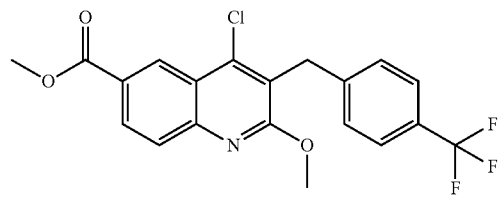 [SMILES: COC(=O)c1ccc2nc(OC)c(Cc3ccc(C(F)(F)F)cc3)c(Cl)c2c1]

n-BuLi (2.66 M in hexanes, 0.883 mL, 2.35 mmol) was added dropwise over 4 minutes to a stirred solution of 6-bromo-4-chloro-2-methoxy-3-(4-(trifluoromethyl)benzyl)quinoline (1.01 g, 2.35 mmol, Intermediate 12: step d) in THF (11.5 mL) under argon at ~−70° C. After an additional minute, a pellet of dry ice (~4 g, ~90 mmol) was added to the dark solution, and the flask was quickly resealed, evacuated and flushed with argon. After another minute, the resulting homogeneous yellow reaction was removed from the cold bath and stirred under ambient conditions for 5 minutes, and was then transferred to an ice bath and quenched with iodomethane (0.146 mL, 2.35 mmol) and DMSO (4.6 mL). The clear yellow reaction was stirred at 0° C. for 5 minutes, and was then concentrated to remove the THF at room temperature to provide a thick light yellow slurry. This was treated with $Li_2CO_3$ (173 mg, 2.35 mmol) and iodomethane (0.438 mL, 7.03 mmol) and stirred at 40° C. for 30 minutes. The resulting opaque thin slurry was then diluted with DCM (15 mL), washed with water (2×25 mL), dried ($Na_2SO_4$), filtered, and concentrated to dryness to provide a white solid. This solid was recrystallized from hot heptane (10 mL), and the globular crystals were filtered and washed with heptane (2×6 mL) to provide the title compound as an off-white powder.

Intermediate 76

(4-Chloro-2-methoxy-3-(4-(trifluoromethyl)benzyl)quinolin-6-yl)bis(1,2-dimethyl-1H-imidazol-5-yl)methanol

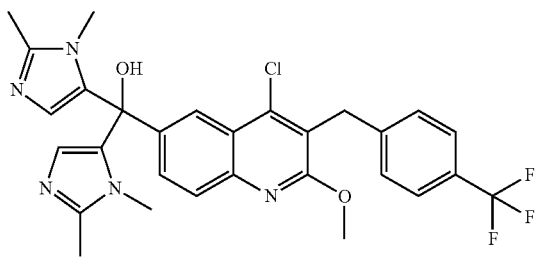 [SMILES: COc1nc2ccc(C(O)(c3cnc(C)n3C)c3cnc(C)n3C)cc2c(Cl)c1Cc1ccc(C(F)(F)F)cc1]

n-BuLi (2.66 M in hexanes, 0.963 mL, 2.56 mmol) was added dropwise to a stirred slurry of 5-bromo-1,2-dimethyl-1H-imidazole (470 mg, 2.68 mmol) in THF (7 mL) at ~−70° C. under argon. After stirring for another 7 minutes, the slurry was treated dropwise over 5 minutes with a solution of methyl 4-chloro-2-methoxy-3-(4-(trifluoromethyl)benzyl)quinoline-6-carboxylate (500 mg, 1.22 mmol, Intermediate 75) in THF (6 mL). The reaction was stirred in the dry ice/acetone bath for another 10 minutes, then removed from the cold bath and stirred for 6 minutes, then stirred in an ice bath for 2 minutes, then quenched with 5 M aqueous $NH_4Cl$ (0.77 mL, 3.85 mmol) to give an orange solution. The reaction mixture was dried ($Na_2SO_4$), filtered, and concentrated to dryness. The residue was purified by silica flash column chromatography (0-10% MeOH/DCM) to provide the title compound.

Intermediate 77: Step a

N-Methoxy-N,1-dimethyl-1H-1,2,3-triazole-5-carboxamide

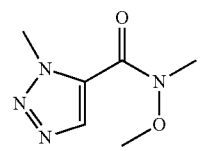

A solution of 1-methyl-1H-1,2,3-triazole (12.9 g, 155 mmol) in THF (260 mL) was cooled to −45° C. Maintaining a temperature of <−35° C., n-BuLi (62.1 mL, 2.5 M in hexanes, 155 mmol) was added over 10 minutes. The reaction mixture was stirred for 30 minutes with cooling to −45° C. and then treated with a sub-surface stream of $CO_{2(g)}$ for a period of 2 hours. After flushing the −35° C. slurry with $N_{2(g)}$ for 5 minutes, thionyl chloride (11.8 mL, 163 mmol) was added. The mixture was allowed to warm to room temperature with stirring over 1.25 hours. Then, N,O-dimethylhydroxylamine hydrochloride (18.14 g, 186 mmol) and N,N-diisopropylethylamine (68.3 mL, 396 mmol) were added and the resulting mixture stirred for 15 hours. Aqueous sodium carbonate (500 mL, 10 wt %) was then added, and the layers were mixed and separated. The aqueous layer was washed with dichloromethane (250 mL and then 125 mL), and the combined organic layers were dried over $MgSO_4$, filtered, and concentrated. The residue was taken up in ethyl acetate (225 mL), treated with $MgSO_4$, and filtered through a pad of silica gel (115 g). The silica gel pad was washed with additional ethyl acetate (800 mL). The eluent was concentrated to provide the title compound as a yellow solid.

Intermediate 77: Step b (1,2-Dimethyl-1H-imidazol-5-yl)(1-methyl-1H-1,2,3-triazol-5-yl)methanone

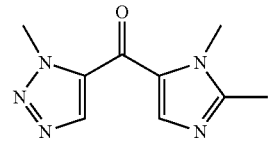

A solution of 5-bromo-1,2-dimethyl-1H-imidazole (1.5 g, 7.54 mmol) in tetrahydrofuran (25 mL) was cooled to −66° C. Maintaining a temperature of <−50° C., n-butyllithium (3.2 mL, 2.5 M in hexanes, 8.3 mmol) was added over 5 minutes. The reaction mixture was stirred for 15 minutes and then a solution of N-methoxy-N,1-dimethyl-1H-1,2,3-triazole-5-carboxamide (1.3 g, 7.54 mmol, Intermediate 77: step a) in tetrahydrofuran (3 mL) was added over 3 minutes. The mixture was allowed to warm to room temperature while stirring over 30 minutes. Half-saturated aqueous ammonium chloride solution (40 mL) was added and the layers were mixed and separated. The aqueous layer was extracted twice with tetrahydrofuran (50 mL) and then with dichloromethane (50 mL). The combined organic layers were dried over magnesium sulfate, filtered, and concentrated to dryness. The material was triturated with isopropyl alcohol (29 mL), filtered, and rinsed twice with hexanes (25 mL) providing the title compound as a white solid.

Intermediate 78 tert-Butyl 3-((4-chloro-2-ethyl-3-(4-(trifluoromethyl)benzyl)quinolin-6-yl)(hydroxy)(1-methyl-1H-1,2,3-triazol-5-yl)methyl)azetidine-1-carboxylate

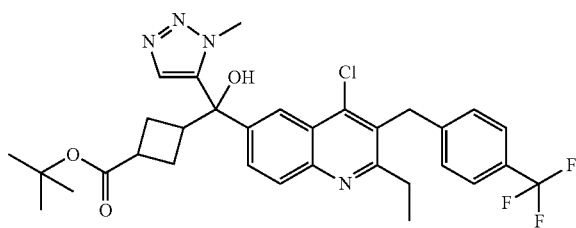 [SMILES: CCc1nc2ccc(C(O)(c3cnnn3C)C3CC(C(=O)OC(C)(C)C)C3)cc2c(Cl)c1Cc1ccc(C(F)(F)F)cc1]

A solution of n-BuLi (2.5 M in hexanes, 0.746 mL, 1.87 mmol) was added dropwise by syringe to a stirring solution of 6-bromo-4-chloro-2-ethyl-3-(4-(trifluoromethyl)benzyl)quinoline (0.800 g, 1.87 mmol, Intermediate 5: step c) in dry THF (18 mL) at −78° C. After 5 minutes, a solution of tert-butyl 3-(1-methyl-1H-1,2,3-triazole-5-carbonyl)azetidine-1-carboxylate (0.604 g, 2.27 mmol, Intermediate 28: step b) in dry THF (5 mL) was added dropwise by syringe. After 5 minutes, the flask was removed from the cooling bath and allowed to warm at room temperature briefly. After 5 minutes, the flask was placed into an ice-water bath. After 20 minutes, water (20 mL) and ethyl acetate (100 mL) were added. The layers were separated. The organic layer was dried with sodium sulfate and the dried solution was filtered. Celite® (5 g) was added to the filtrate and the solvents were removed by rotary evaporation to provide a free-flowing powder. The powder was loaded onto a silica gel column. Elution with 30% ethyl acetate-hexanes initially, grading to 80% ethyl acetate-hexanes provided the title compound as a yellow solid.

Intermediate 79

1-(3-((4-Chloro-2-ethyl-3-(4-(trifluoromethyl)benzyl)quinolin-6-yl)(hydroxy)(1-methyl-1H-1,2,3-triazol-5-yl)methyl)azetidin-1-yl)ethanone

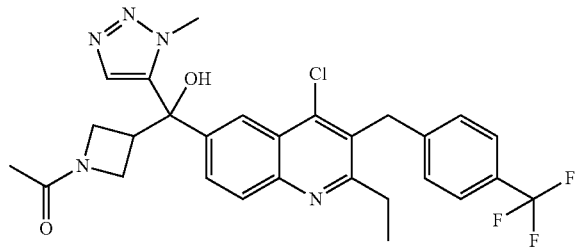 [SMILES: CCc1nc2ccc(C(O)(c3cnnn3C)C3CN(C(C)=O)C3)cc2c(Cl)c1Cc1ccc(C(F)(F)F)cc1]

Trifluoroacetic acid (0.442 mL, 5.78 mmol) was added dropwise by syringe to an ice-cooled, stirring solution of tert-butyl 3-((4-chloro-2-ethyl-3-(4-(trifluoromethyl)benzyl)quinolin-6-yl)(hydroxy)(1-methyl-1H-1,2,3-triazol-5-yl)methyl)azetidine-1-carboxylate (0.356 g, 0.578 mmol, Intermediate 78) in dichloromethane (2.9 mL). After 20 minutes, the flask was removed from the cooling bath and allowed to warm to room temperature. After 18 hours, dichloromethane (15 mL) and saturated aqueous sodium bicarbonate solution (10 mL) were added in sequence. The biphasic mixture was stirred for 10 minutes. The mixture was partitioned between water (10 mL) and dichloromethane (10 mL). The layers were separated. The organic layer was dried with sodium sulfate. The dried solution was filtered and the filtrate was concentrated to afford an oily residue. The residue was dissolved in dichloromethane (5.8 mL). Triethylamine (0.401 mL, 2.89 mmol) and acetic anhydride (0.218 mL, 2.31 mmol) were added in sequence and the solution was heated to 46° C. After 2 hours, the reaction was cooled to room temperature. Dichloromethane (50 mL) and saturated aqueous sodium bicarbonate solution were added in sequence. The biphasic mixture was stirred for 10 minutes. The layers were separated. The organic layer was dried over sodium sulfate and the dried solution was filtered. Celite® (4 g) was added to the filtrate and the solvents were removed by rotary evaporation to provide a free-flowing powder. The powder was loaded onto a silica gel column. Elution with dichloromethane initially, grading to 10% methanol-dichloromethane provided the title compound as a white solid. 1-(3-((4-Chloro-2-ethyl-3-(4-(trifluoromethyl)benzyl)quinolin-6-yl)(hydroxy)(1-methyl-1H-1,2,3-triazol-5-yl)methyl)azetidin-1-yl)ethanone was purified by chiral SFC [Chiracel OD-H column, 5 μm, 250 mm×20 mm, mobile phase: 60% carbon dioxide, 40% ethanol (containing 0.3% diisopropylamine)] to give two enantiomers. The first eluting enantiomer was Intermediate 79b and the second eluting enantiomer was Intermediate 79c.

Intermediate 80: Step a (4-Chloro-2-methoxy-3-(4-(trifluoromethyl)benzyl)quinolin-6-yl)(1-methyl-1H-imidazol-5-yl)methanol

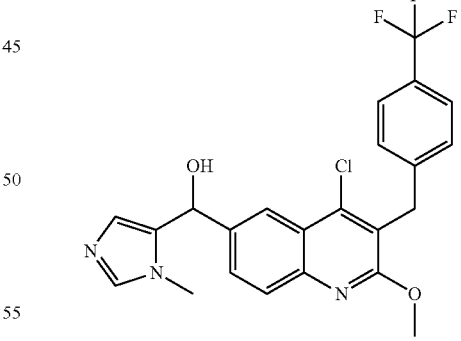

To a flask containing 6-bromo-4-chloro-2-methoxy-3-(4-(trifluoromethyl)benzyl)quinoline (Intermediate 12: step d, 3.0 g, 6.97 mmol) was added THF (40 ml) and the solution was cooled to −70° C. n-BuLi (2.5 M in hexanes, 2.8 mL, 7 mmol) was added dropwise. After 2 minutes, 1-methyl-1H-imidazole-5-carbaldehyde (1.2 g, 9 mmol, in 10 mL THF) was introduced. After 15 minutes, the dry-ice bath was replaced with a 0° C. bath. After 35 minutes the reaction mixture was quenched with aqueous NH$_4$Cl solution and the aqueous portion was extracted with EtOAc:THF (10:2) 5×50 mL. The combined organics were washed with brine, dried over Na$_2$SO$_4$, filtered and concentrated to dryness to give the title compound.

Intermediate 80: Step b (4-Chloro-2-methoxy-3-(4-(trifluoromethyl)benzyl)quinolin-6-yl)(1-methyl-1H-imidazol-5-yl)methanone

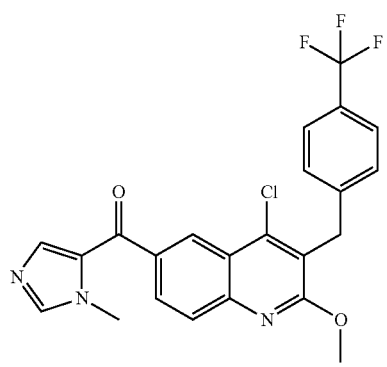 [SMILES: COc1nc2ccc(C(=O)c3cncn3C)cc2c(Cl)c1Cc1ccc(C(F)(F)F)cc1]

To a flask containing (4-chloro-2-methoxy-3-(4-(trifluoromethyl)benzyl)quinolin-6-yl)(1-methyl-1H-imidazol-5-yl)methanol (2.3 g, 4.98 mmol, Intermediate 80: step a) was added 1,4-dioxane (80 mL) to give a suspension at room temperature. The flask was fitted with a reflux condenser and heated briefly to 50° C. which resulted in a homogeneous solution. Then, activated manganese dioxide (1.73 g, 19.9 mmol) was introduced and the temperature was raised to 80° C. After 65 minutes, the reaction mixture was filtered through Celite® and rinsed with warm THF. The effluent was concentrated to give the title compound as a white solid.

Intermediate 81: Step a (4-Chloro-2-methoxy-3-(4-(trifluoromethyl)benzyl)quinolin-6-yl)(2,6-dimethylpyridin-3-yl)methanol

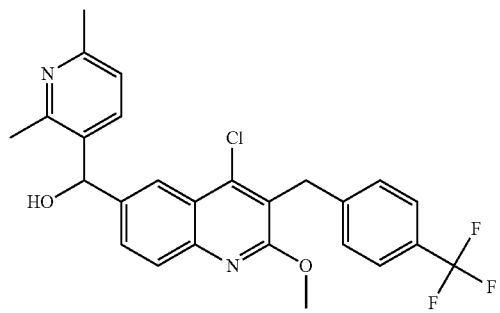 [SMILES: COc1nc2ccc(C(O)c3ccc(C)nc3C)cc2c(Cl)c1Cc1ccc(C(F)(F)F)cc1]

To a flask containing 6-bromo-4-chloro-2-methoxy-3-(4-(trifluoromethyl)benzyl)quinoline (1.85 g, 4.3 mmol, Intermediate 12: step d) was added THF (45 mL) at room temperature which resulted in a colorless homogeneous solution. The solution was cooled to −70° C. and then n-BuLi (2.5 M in hexanes, 1.75 mL, 4.38 mmol) was added dropwise. After 2 minutes, 2,6-dimethylnicotinaldehyde (755 mg, 5.50 mmol, in 2 mL THF) was introduced and the color of the mixture went from a reddish-brown to green. The reaction mixture was allowed to warm to −20° C. over 40 minutes at which time the reaction was quenched with aqueous NH$_4$Cl solution. The aqueous portion was extracted with EtOAc (3×50 mL) and the combined organics were washed with brine, dried over MgSO$_4$, filtered and concentrated to dryness. The residue was purified by FCC (10% acetone-hexane increasing to 30% acetone) to afford the title compound.

Intermediate 81: Step b (4-Chloro-2-methoxy-3-(4-(trifluoromethyl)benzyl)quinolin-6-yl)(2,6-dimethylpyridin-3-yl)methanone

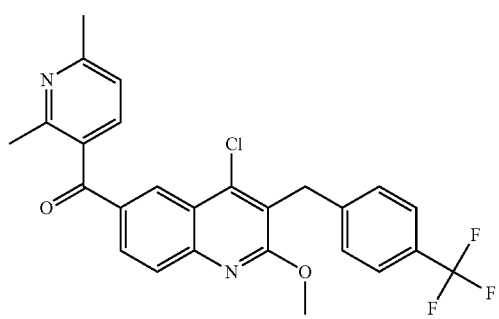 [SMILES: COc1nc2ccc(C(=O)c3ccc(C)nc3C)cc2c(Cl)c1Cc1ccc(C(F)(F)F)cc1]

To a flask containing (4-chloro-2-methoxy-3-(4-(trifluoromethyl)benzyl)quinolin-6-yl)(2,6-dimethylpyridin-3-yl)methanol (1.51 g, 3.1 mmol, Intermediate 81: step a) was added 1,4-dioxane (50 mL) followed by activated manganese dioxide (1.31 g, 15.1 mmol) and the reaction mixture was heated to reflux. After 1 hour, the contents were filtered while still hot through a pad of Celite® and rinsed with THF. The resulting light yellow solution was concentrated and chromatographed on silica gel (10% acetone-hexane increasing to 25% acetone) to provide the title compound as a light yellowish amorphous solid.

Intermediate 82: Step a 4-(1H-1,2,4-Triazol-1-yl)benzaldehyde

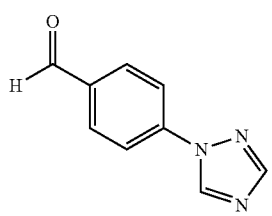 [SMILES: O=Cc1ccc(-n2cncn2)cc1]

4-Fluorobenzaldehyde (12.0 mL, 112 mmol) was added dropwise by syringe to a stirring, heterogeneous mixture of 1,2,4-triazole (11.6 g, 168 mmol) and potassium carbonate (24.7 g, 179 mmol) in dimethyl formamide (220 mL) at 23° C. The mixture was heated to 105° C. After 3.5 hours, the mixture was allowed to cool to 23° C. The cooled solution was transferred to a 2 L Erlenmeyer flask and diluted with water (500 mL) and ethyl acetate (1200 mL). The biphasic mixture was stirred until the layers cleanly separated. The layers were separated. The organic layer was washed with half-saturated aqueous sodium chloride solution (3×100 mL). The washed solution was dried with sodium sulfate, and the dried solution was filtered. The filtrate was concentrated to provide an off-white solid. The solid was suspended in a mixture of heptanes and isopropyl acetate (5:1, 600 mL). The mixture was filtered and the filter cake was washed with heptanes-isopropyl acetate (5:1). The solids were collected and dried under vacuum to afford the title compound as a white solid.

Intermediate 82: Step b 5-(4-(1H-1,2,4-Triazol-1-yl)benzyl)-2,2-dimethyl-1,3-dioxane-4,6-dione

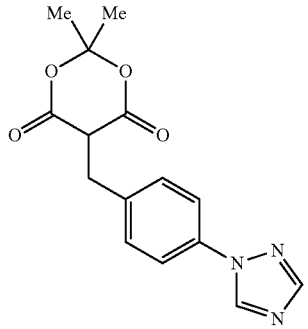 [SMILES: CC1(C)OC(=O)C(Cc2ccc(-n3cncn3)cc2)C(=O)O1]

L-Proline (1.81 g, 15.6 mmol) was added to a stirring, heterogeneous mixture of 4-(1H-1,2,4-triazol-1-yl)benzaldehyde (13.5 g, 78.0 mmol, Intermediate 82: step a) and 2,2-dimethyl-1,3-dioxane-4,6-dione (11.2 g, 78.0 mmol) in ethanol (520 mL) at 23° C. After 1.5 hours, diethyl 1,4-dihydro-2,6-dimethyl-3,5-pyridinedicarboxylate (19.7 g, 78.0 mmol) was added in one portion. After 16 hours, the ethanol was removed by rotary evaporation at 35° C. to afford a yellow solid. Isopropanol (300 mL) was added and the heterogeneous mixture was stirred for 10 minutes at 23° C. The mixture was filtered and the filter cake was washed with isopropanol (150 mL). The solids were collected and dried under vacuum to provide the titled compound as a white solid.

Intermediate 82: Step c 2-(4-(1H-1,2,4-Triazol-1-yl)benzyl)malonic acid

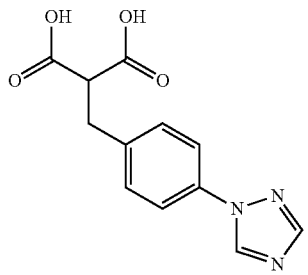 [SMILES: O=C(O)C(Cc1ccc(-n2cncn2)cc1)C(=O)O]

5-(4-(1H-1,2,4-Triazol-1-yl)benzyl)-2,2-dimethyl-1,3-dioxane-4,6-dione (10.0 g, 33.2 mmol, Intermediate 82: step b) was dissolved in a mixture of water (30 mL) and trifluoroacetic acid (50 mL). The mixture was heated to 65° C. After 2.5 hours, the mixture was allowed to cool to 23° C. Water and trifluoroacetic acid were removed by rotary evaporation at 45° C. Toluene (100 mL) was added to the residue then the mixture was concentrated by rotary evaporation at 45° C. Tetrahydrofuran (100 mL) and 6 M aqueous hydrochloric acid solution (28 mL) was added to the residue in sequence. The resulting heterogeneous mixture was stirred at 23° C. After 10 minutes, the mixture was concentrated by rotary evaporation at 45° C. Tetrahydrofuran (100 mL) was added to the residue and the residue and the mixture concentrated by rotary evaporation at 45° C. Toluene (100 mL) was added to the residue and the mixture concentrated by rotary evaporation at 45° C. The resulting white solid was dried under vacuum at 40° C. The solid product was used directly in the next step without further purification.

Intermediate 83a (3-(4-(1H-Pyrazol-1-yl)benzyl)-4-chloro-2-methoxyquinolin-6-yl)(4-chlorophenyl)(1-methyl-1H-imidazol-5-yl)methanol

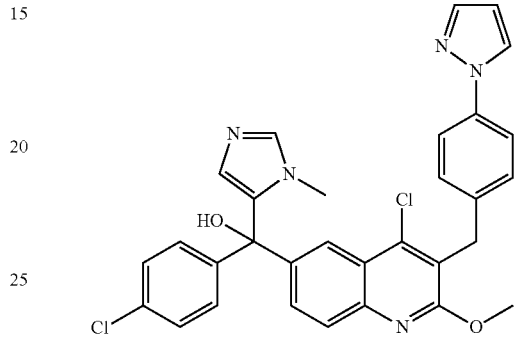

A solution of n-BuLi (2.5 M in hexanes, 2.67 mL, 6.66 mmol) was added dropwise by syringe to a solution of 3-(4-(1H-pyrazol-1-yl)benzyl)-6-bromo-4-chloro-2-methoxyquinoline (3.00 g, 7.00 mmol, Intermediate 10) in dry THF (80 mL) at −78° C. After 3 minutes, a solution of (4-chlorophenyl)(1-methyl-1H-imidazol-5-yl)methanone (1.65 g, 7.48 mmol, Intermediate 43: step b) in dry THF (80 mL) was added dropwise over the course of 3 minutes. The reaction mixture was stirred for 10 minutes at −78° C., then the reaction flask was removed from the cooling bath. After 10 minutes, the reaction flask was placed into an ice-water bath. After 30 minutes, saturated aqueous ammonium chloride solution (10 mL) was added. The biphasic mixture was warmed to room temperature then partitioned between half-saturated aqueous ammonium chloride solution (300 mL) and ethyl acetate (300 mL). The layers were separated. The aqueous layer was extracted with ethyl acetate (150 mL). The organic layers were combined. The combined solution was dried with sodium sulfate. The dried solution was filtered and the filtrate was concentrated.

Intermediate 84

(4-Chloro-2-methoxy-3-(4-(trifluoromethyl)benzyl)quinolin-6-yl)(2,6-dimethylpyridin-3-yl)(1-methyl-1H-1,2,3-triazol-5-yl)methanol

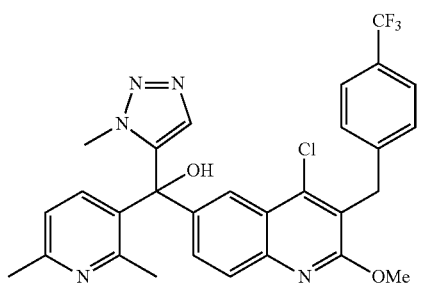 [SMILES: COc1nc2ccc(C(O)(c3ccc(C)nc3C)c3cnnn3C)cc2c(Cl)c1Cc1ccc(C(F)(F)F)cc1]

To a flask containing 1-methyl-1H-1,2,3-triazole (275 mg, 3.31 mmol, prepared according to PCT Int. Appl., 2008098104) was added THF (35 mL) and the colorless solution was cooled to −50° C. Then, n-butyllithium (2.5 M in hexanes, 1.2 mL, 3.0 mmol) was added dropwise which afforded a dark reddish-brown viscous solution. The mixture was stirred between −20 to −10° C. for 30 minutes, then a homogeneous THF solution of (4-chloro-2-methoxy-3-(4-(trifluoromethyl)benzyl)quinolin-6-yl)(2,6-dimethylpyridin-3-yl)methanone (700 mg, 1.44 mmol in 4 mL THF, Intermediate 12: step f) was introduced at 0° C. The reaction mixture became a dark brown color and was allowed to warm gradually to room temperature. The mixture was stirred for 60 minutes at room temperature then quenched with aqueous NH₄Cl solution. The aqueous portion was extracted with EtOAc, 3×50 mL. The combined organics were washed with brine, dried over MgSO₄, filtered and concentrated to provide a brown oil. Chromatography on silica gel (1% MeOH-DCM increasing to 5% MeOH-DCM) provided the title compound as a light brown solid. Racemic (4-chloro-2-methoxy-3-(4-(trifluoromethyl)benzyl)quinolin-6-yl)(2,6-dimethylpyridin-3-yl)(1-methyl-1H-1,2,3-triazol-5-yl)methanol was separated into its individual enantiomers using the following conditions: Chiralcel OD, 20 uM (Diacel) using ethanol with 242 nM detection to give the first eluting enantiomer as Intermediate 84b and the second eluting enantiomer as Intermediate 84c.

Intermediate 85: Step a tert-Butyl 3-(chlorocarbonyl)azetidine-1-carboxylate

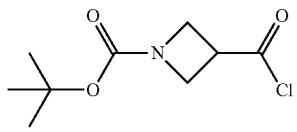

A solution of tert-butyl 3-(chlorocarbonyl)azetidine-1-carboxylate (2.01 g, 9.99 mmol) in toluene (20 mL) and DMF (0.0387 mL, 0.499 mmol) was stirred at 0° C. under air (Drierite® drying tube) while neat oxalyl chloride (0.845 mL, 9.99 mmol) was added dropwise over 2 minutes. The reaction was stirred at 0° C. for 1 hour and was then stirred at room temperature overnight. NMR of an aliquot after 1 hour at 0° C. showed (after simple high vacuum at room temperature) a ~60% conversion of carboxylic acid starting material to title compound. NMR of an aliquot after ~5 days at room temperature showed complete, clean conversion to the title compound, so the reaction was decanted from the sticky solids and concentrated by rotary evaporation at room temperature, followed by high vacuum at room temperature to provide the title compound as a clear, colorless oil that was used immediately in the next step.

Intermediate 85: Step b

Di-tert-butyl 3,3'-carbonylbis(azetidine-1-carboxylate)

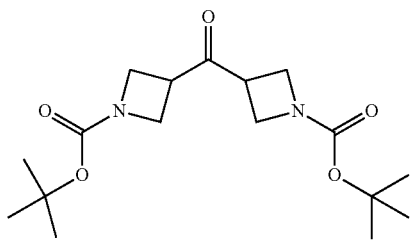 [SMILES: CC(C)(C)OC(=O)N1CC(C(=O)C2CN(C(=O)OC(C)(C)C)C2)C1]

A solution of chlorotrimethylsilane (0.086 mL, 0.679 mmol) and 1,2-dibromoethane (0.058 mL, 0.679 mmol) was added dropwise over ~1 minute to a mixture of zinc dust (0.524 g, 8.01 mmol) in DMA (1 mL) with stirring in a room temperature water bath under argon. After 20 minutes stirring, a solution of tert-butyl 3-iodoazetidine-1-carboxylate (1.92 g, 6.79 mmol) in DMA (2.4 mL) was added dropwise over 2 minutes. The reaction was then stirred at 40° C. for 30 minutes and then stirred at room temperature while Pd(PPh₃)₄ (0.392 g, 0.339 mmol) was added in one portion under air (quickly evacuated/flushed with argon 6×). The slurry was stirred at room temperature for 10 minutes and a solution of tert-butyl 3-(chlorocarbonyl)azetidine-1-carboxylate (1.64 g, 0.339 mmol, Intermediate 85: step a) in toluene (13.6 mL) was then transferred rapidly dropwise by cannula under argon over 2 minutes. After 2 hours stirring at room temperature, the reaction was filtered through Celite® and the filter cake washed with EtOAc (2×25 mL). The combined filtrates were concentrated and the residue was flash chromatographed (0-100% EtOAc in heptane) to provide the title compound as a thick amber oil.

Intermediate 86: Step a 3-(4-(1H-pyrazol-1-yl)benzyl)-6-bromo-4-chloro-N,N-diethylquinolin-2-amine

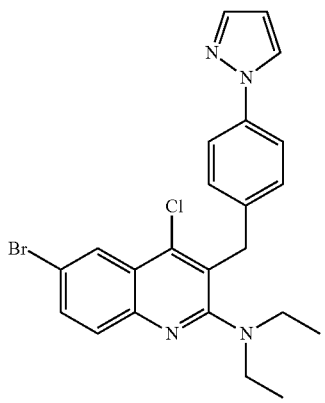 [SMILES: CCN(CC)c1nc2ccc(Br)cc2c(Cl)c1Cc1ccc(-n2cccn2)cc1]

A mixture of 3-(4-(1H-pyrazol-1-yl)benzyl)-6-bromo-2,4-dichloroquinoline (1.44 g, 3.33 mmol, Intermediate 3: step c) and diethylamine (6.91 mL, 66.5 mmol) in DMF (10 mL) in a sealed tube was heated in a 115° C. oil bath for 23 h. The mixture was diluted with EtOAc and extracted with water (5×, sat. aq. NaCl added as needed to achieve phase separation). The organic phase was dried (Na₂SO₄), filtered, and concentrated. The residue was purified by flash column chromatography (silica gel, dry loading, 2-10% EtOAc-heptanes first column, 0-4% EtOAc-heptanes second column) to afford the title compound as a white solid.

Intermediate 86: Step b (3-(4-(1H-pyrazol-1-yl)benzyl)-4-chloro-2-(diethylamino)quinolin-6-yl)(4-chlorophenyl)(1-methyl-1H-imidazol-5-yl)methanol

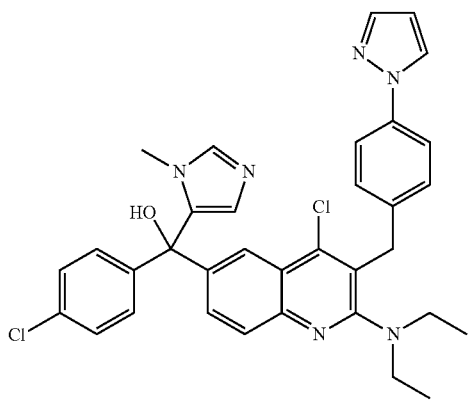 [SMILES: CCN(CC)c1nc2ccc(C(O)(c3ccc(Cl)cc3)c3cncn3C)cc2c(Cl)c1Cc1ccc(-n2cccn2)cc1]

A mixture of 3-(4-(1H-pyrazol-1-yl)benzyl)-6-bromo-4-chloro-N,N-diethylquinolin-2-amine (376 mg, 0.800 mmol, Intermediate 86: step a) and (4-chlorophenyl)(1-methyl-1H-imidazol-5-yl)methanone (176.6 mg, 0.800 mmol, Intermediate 43: step b) in THF (17.5 mL) under argon was briefly (2 min) cooled in a dry-ice acetone bath. n-Butyllithium (1.6 M in hexane, 0.50 mL, 0.80 mmol) was added dropwise by syringe. The mixture was stirred at −78° C. for 30 minutes, then was transferred to an ice bath and stirred for 1 hour. The reaction was quenched by the addition of saturated aqueous $NH_4Cl$, diluted with water and extracted with EtOAc (3×). The organic phase was dried ($Na_2SO_4$), filtered, and concentrated. The residue was purified by flash column chromatography (50-100% EtOAc-heptanes) to afford the title compound.

Intermediate 87: Step a (4-Chloro-2-methoxy-3-(4-(trifluoromethyl)benzyl)quinolin-6-yl)(2,4-dimethyloxazol-5-yl)methanol

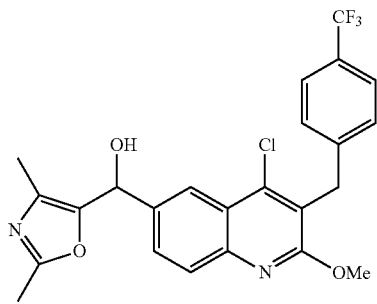 [SMILES: COc1nc2ccc(C(O)c3oc(C)nc3C)cc2c(Cl)c1Cc1ccc(C(F)(F)F)cc1]

To a 50 mL flask containing 6-bromo-4-chloro-2-methoxy-3-(4-(trifluoromethyl)benzyl)quinoline (1.5 g, 3.48 mmol, Intermediate 12: step d) was added THF (65 mL) at room temperature which resulted in a colorless homogeneous mixture. The solution was cooled to −70° C. which remained homogeneous and then n-butyllithium (2.5 M in hexanes, 1.62 mL, 4.04 mmol) was added drop wise. The color of the solution became a dark opaque reddish-brown color. After 2 minutes, 2,4-dimethyloxazole-5-carbaldehyde (520 mg, 4.16 mmol, in 3 mL THF) was introduced and the color of the mixture went from an opaque dark brown to a light yellow homogeneous color within about 1 minute. After 25 minutes the mixture was quenched with aqueous $NH_4Cl$. The reaction was diluted further with water and extracted with EtOAc (5×40 mL). The combined organics were washed with brine, dried over $MgSO_4$, filtered and concentrated to give a light yellowish foam. The crude material was chromatographed on silica gel (10% $CH_3CN$-DCM grading to 30% $CH_3CN$ containing 1% MeOH) to provide the title compound as a white amorphous solid.

Intermediate 87: Step b (4-Chloro-2-methoxy-3-(4-(trifluoromethyl)benzyl)quinolin-6-yl)(2,4-dimethyloxazol-5-yl)methanone

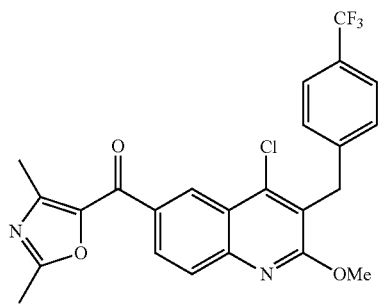 [SMILES: COc1nc2ccc(C(=O)c3oc(C)nc3C)cc2c(Cl)c1Cc1ccc(C(F)(F)F)cc1]

To a 100 mL flask containing (4-chloro-2-methoxy-3-(4-(trifluoromethyl)benzyl)quinolin-6-yl)(2,4-dimethyloxazol-5-yl)methanol (960 mg, 2.01 mmol, Intermediate 87: step a) was added 1,4-dioxane (50 mL) and activated $MnO_2$ (900 mg, 10.3 mmol) at room temperature. The mixture was heated to 85° C. in an aluminum heating mantle under a nitrogen atmosphere. After 60 minutes, the contents were filtered through Celite® while the solution is still warm and rinsed with THF, and concentrated to give an off white solid. The crude material was triturated with $Et_2O$ to give a white solid.

Intermediate 88: Step a (3,4-Dimethoxyphenyl)(pyridin-3-yl)methanol

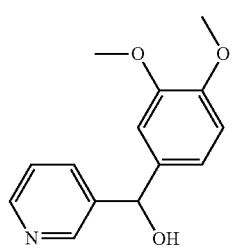 [SMILES: COc1ccc(C(O)c2cccnc2)cc1OC]

(3,4-Dimethoxyphenyl)magnesium bromide (0.5 M in THF, 9.5 mL, 4.75 mmol) was added dropwise by syringe to a solution of nicotinaldehyde (0.88 mL, 9.37 mmol) in dry THF (20 mL) at 0° C. The reaction mixture was stirred for 30 minutes at 0° C., then quenched with saturated aqueous ammonium chloride solution. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 0-60% EtOAc-hexanes) to provide the title compound as a brown oil.

Intermediate 88: Step b (3,4-Dimethoxyphenyl)(pyridin-3-yl)methanone

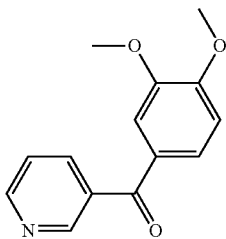 [SMILES: COc1ccc(C(=O)c2cccnc2)cc1OC]

The title compound was prepared analogously to the method in Intermediate 33: step b using (3,4-dimethoxyphenyl)(pyridin-3-yl)methanol (Intermediate 88: step a) in place of (1-methyl-1H-imidazol-5-yl)(pyridin-2-yl)methanol.

Intermediate 89: Step a (4-Fluorophenyl)(1-methyl-1H-imidazol-5-yl)methanol

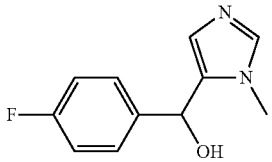

The title compound was prepared analogously to the method in Intermediate 88: step a using (4-fluorophenyl)magnesium bromide and 1-methyl-1H-imidazole-5-carbaldehyde in place of (3,4-dimethoxyphenyl)magnesium bromide and nicotinaldehyde, respectively.

Intermediate 89: Step b (4-Fluorophenyl)(1-methyl-1H-imidazol-5-yl)methanone

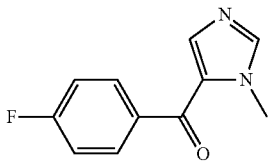

The title compound was prepared analogously to the method in Intermediate 33: step b using (4-fluorophenyl)(1-methyl-1H-imidazol-5-yl)methanol (Intermediate 89: step a) in place of (1-methyl-1H-imidazol-5-yl)(pyridin-2-yl)methanol.

Intermediate 90: Step a (3,4-Dichlorophenyl)(pyridin-3-yl)methanol

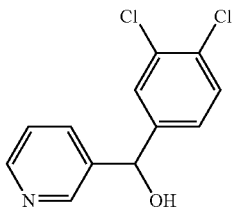 [SMILES: OC(c1cccnc1)c1ccc(Cl)c(Cl)c1]

The title compound was prepared analogously to the method in Intermediate 88: step a using (3,4-dichlorophenyl)magnesium bromide in place of (3,4-dimethoxyphenyl)magnesium bromide.

Intermediate 90: Step b (3,4-Dichlorophenyl)(pyridin-3-yl)methanone

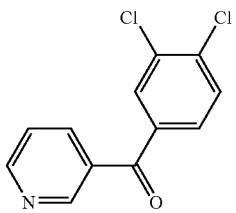 [SMILES: O=C(c1cccnc1)c1ccc(Cl)c(Cl)c1]

The title compound was prepared analogously to the method in Intermediate 33: step b using 3,4-dichlorophenyl)(pyridin-3-yl)methanol (Intermediate 90: step a) in place of (1-methyl-1H-imidazol-5-yl)(pyridin-2-yl)methanol.

Intermediate 91: Step a

Pyridin-3-yl(4-(trifluoromethyl)phenyl)methanol

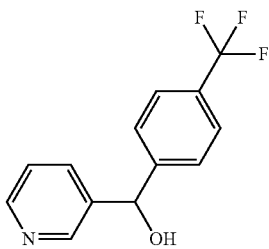 [SMILES: OC(c1ccc(C(F)(F)F)cc1)c1cccnc1]

The title compound was prepared analogously to the method in Intermediate 33: step a using 3-bromopyridine and 4-(trifluoromethyl)benzaldehyde in place of 5-bromo-1-methyl-1H-imidazole and picolinaldehyde, respectively.

Intermediate 91: Step b

Pyridin-3-yl(4-(trifluoromethyl)phenyl)methanone

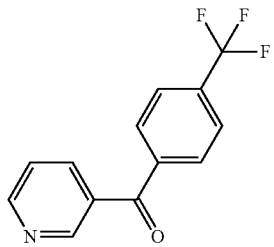 [SMILES: O=C(c1ccc(C(F)(F)F)cc1)c1cccnc1]

The title compound was prepared analogously to the method in Intermediate 33: step b using pyridin-3-yl(4-(trifluoromethyl)phenyl)methanol (Intermediate 91: step a) in place of (1-methyl-1H-imidazol-5-yl)(pyridin-2-yl)methanol.

Example 1a (3-(4-(1H-Pyrazol-1-yl)benzyl)-4-chloro-2-methoxyquinolin-6-yl)(1-methyl-1H-imidazol-5-yl)(tetrahydro-2H-pyran-4-yl)methanol

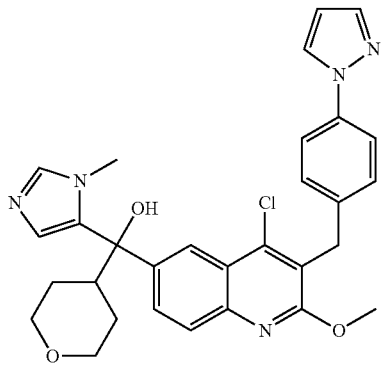 [SMILES: COc1nc2ccc(C(O)(c3cncn3C)C3CCOCC3)cc2c(Cl)c1Cc1ccc(-n2cccn2)cc1]

To a solution of 3-(4-(1H-pyrazol-1-yl)benzyl)-4-chloro-6-iodo-2-methoxyquinoline (579 mg, 1.22 mmol, Intermediate 4: step e) in THF (5 mL) at −78° C. under argon was added n-butyllithium (1.6 M in hexane, 0.725 mL, 1.16 mmol) over 1 minute. The resulting dark brown solution was stirred for 1 minute before addition of a solution of (1-methyl-1H-imidazol-5-yl)(tetrahydro-2H-pyran-4-yl)methanone (237 mg, 1.22 mmol, Intermediate 1: step b) in THF (4 mL). The resulting orange solution was stirred at −78° C. for 5 minutes, then was transferred to an ice bath and stirred 30 minutes. The reaction was quenched by the addition of saturated aqueous NH$_4$Cl, diluted with water and extracted with EtOAc (3×). The organic phase was dried (Na$_2$SO$_4$), filtered, and concentrated to dryness. The residue was purified by flash column chromatography (0-6% MeOH-DCM) to afford the title compound. MS m/e 544.2 [M+H]$^+$. Example 1a was purified by chiral HPLC (Chiralcel OD-H, 20% EtOH-heptane) to give 2 enantiomers. The second enantiomer to elute was then further purified on a silica gel column (0-5% MeOH-DCM). Example 1b: (first enantiomer to elute off chiral column) $^1$H NMR (400 MHz, CD$_3$OD) δ 8.21 (s, 1H), 8.09 (d, J=2.53 Hz, 1H), 7.75 (d, J=8.59 Hz, 1H), 7.66 (d, J=2.02 Hz, 1H), 7.56 (d, J=8.59 Hz, 2H), 7.43-7.52 (m, 2H), 7.34 (d, J=8.59 Hz, 2H), 7.24 (s, 1H), 6.38-6.54 (m, 1H), 4.28 (s, 2H), 4.05 (s, 3H), 4.00 (dd, J=3.28, 11.37 Hz, 1H), 3.79 (dd, J=3.54, 11.12 Hz, 1H), 3.54 (t, J=11.12 Hz, 1H), 3.32-3.37 (m, 1H), 3.30 (s, 3H), 2.46-2.61 (m, 1H), 2.07 (d, J=13.64 Hz, 1H), 1.57-1.75 (m, 1H), 1.39 (qd, J=4.55, 12.63 Hz, 1H), 0.95 (d, J=13.14 Hz, 1H); MS m/e 544.1 [M+H]$^+$ and Example 1c: (second enantiomer to elute off chiral column) $^1$H NMR (400 MHz, CDCl$_3$) δ 8.12 (s, 1H), 7.86 (d, J=2.02 Hz, 1H), 7.76 (d, J=8.59 Hz, 1H), 7.69 (s, 1H), 7.57 (d, J=8.59 Hz, 2H), 7.36-7.46 (m, 3H), 7.32 (s, 1H), 7.21 (s, 1H), 6.43 (s, 1H), 4.32 (s, 2H), 4.03-4.14 (m, 4H), 3.90 (dd, J=3.28, 11.37 Hz, 1H), 3.52 (t, J=11.12 Hz, 1H), 3.33 (t, J=11.37 Hz, 1H), 3.25 (s, 3H), 2.42-2.54 (m, 1H), 2.36 (s, 1H), 2.12 (d, J=13.64 Hz, 1H), 1.42 (qd, J=4.29, 12.72 Hz, 1H), 1.21-1.35 (m, 1H), 1.03 (d, J=13.14 Hz, 1H); MS m/e 544.2 [M+H]$^+$.

Example 2a 3-(4-(1H-Pyrazol-1-yl)benzyl)-6-(hydroxy(1-methyl-1H-imidazol-5-yl)(tetrahydro-2H-pyran-4-yl)methyl)-2-methoxyquinoline-4-carbonitrile

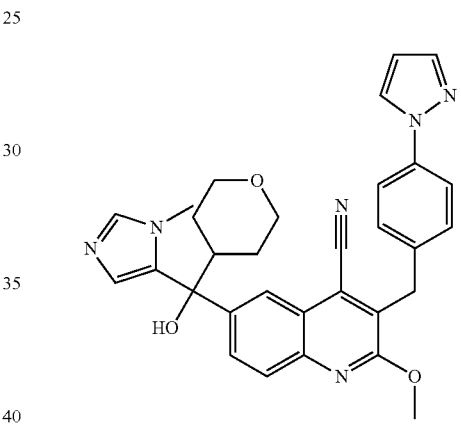

A round bottom flask was charged with (3-(4-(1H-pyrazol-1-yl)benzyl)-4-chloro-2-methoxyquinolin-6-yl)(1-methyl-1H-imidazol-5-yl)(tetrahydro-2H-pyran-4-yl)methanol (111 mg, 0.203 mmol, Example 1a), Zn(CN)$_2$ (42.9 mg, 0.366 mmol), Pd$_2$(dba)$_3$ (27.9 mg, 0.031 mmol), zinc nanopowder (4.0 mg, 0.061 mmol) and dicyclohexyl(2',4',6'-triisopropyl-[1,1'-biphenyl]-2-yl)phosphine (X-Phos, 20.0 mg, 0.041 mmol). The flask was evacuated and re-filled with argon (three cycles). Dimethylacetamide (2 mL, sparged with argon for 30 minutes) was then added and the mixture was heated at 120° C. for 6 hours. The mixture was cooled to room temperature and was filtered through Celite®, washing with EtOAc. The filtrate was washed sequentially with 2 M aqueous NH$_4$OH, water, and saturated aqueous NaCl. The organic phase was dried (Na$_2$SO$_4$), filtered, and concentrated. The residue was purified by flash column chromatography (silica gel, 2-6% MeOH-DCM) to afford the title compound. MS m/e 535.2 [M+H]$^+$.

Example 2a was purified by chiral HPLC (Chiralcel OD-H, 20% EtOH-heptane) to give two enantiomers. Example 2b: (first enantiomer to elute off chiral column) $^1$H NMR (400 MHz, CDCl$_3$) δ 8.19 (s, 1H), 7.87 (d, J=2.53 Hz, 1H), 7.78 (d, J=8.59 Hz, 1H), 7.70 (s, 1H), 7.61 (d, J=8.08 Hz, 2H), 7.47 (d, J=8.59 Hz, 2H), 7.39 (d, J=9.09 Hz, 1H), 7.31 (s, 1H), 7.21 (s, 1H), 6.44 (s, 1H), 4.37 (s, 2H), 4.10 (s, 3H), 4.05-4.09 (m, 1H), 3.89 (dd, J=3.54, 11.62 Hz, 1H), 3.53 (t, J=11.37 Hz, 1H), 3.33 (t, J=11.12 Hz, 1H), 3.26 (s, 3H), 2.57 (s, 1H), 2.50

(t, J=12.13 Hz, 1H), 2.13 (d, J=13.14 Hz, 1H), 1.51-1.60 (m, 1H), 1.43 (qd, J=4.55, 12.46 Hz, 1H), 0.98 (d, J=13.1, 1H); MS m/e 535.2 [M+H]+; and Example 2C (second enantiomer to elute off chiral column).

Example 3

1,1'-(3,3'-((4-Chloro-2-methoxy-3-(4-(trifluoromethyl)benzyl)quinolin-6-yl)(hydroxy)methylene)bis(azetidine-3,1-diyl))diethanone

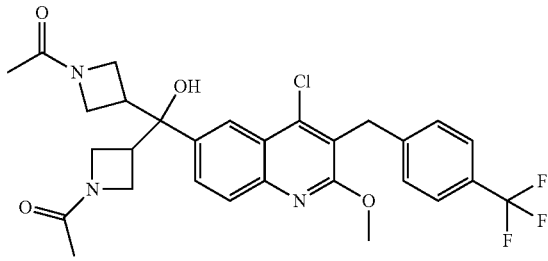 [SMILES: COc1nc2ccc(C(O)(C3CN(C(C)=O)C3)C3CN(C(C)=O)C3)cc2c(Cl)c1Cc1ccc(C(F)(F)F)cc1]

A solution of di-tert-butyl 3,3'-((4-chloro-2-methoxy-3-(4-(trifluoromethyl)benzyl)quinolin-6-yl)(hydroxy)methylene)bis(azetidine-1-carboxylate) (49.4 mg, 0.0714 mmol, Intermediate 85: step c) in DCM (0.5 mL) was treated with TFA (0.187 mL, 2.44 mmol) and stirred at room temperature for 30 minutes. The reaction was concentrated by rotary evaporation at room temperature, taken up with toluene (3×2 mL) and concentrated at 40° C. under rotary evaporation. The residue was dissolved in DCM (1 mL), TEA (0.15 mL, 1.08 mmol) and DMF (0.5 mL). Acetic anhydride (0.0202 mL, 0.213 mmol) was added dropwise with stirring at room temperature, and the reaction was stirred for 1 hour. The reaction was partitioned between DCM (3 mL) and water (5 mL), and the aqueous layer was back-extracted with DCM (1×2 mL). The combined organic layers were dried (Na$_2$SO$_4$), filtered, and concentrated, and the residue was flash chromatographed (0-10% MeOH in DCM over 4 column volumes, then isocratic for 65 column volumes) to provide the title compound as a colorless film. $^1$H NMR (400 MHz, CDCl$_3$) δ 8.12-8.26 (m, 1H), 7.77-7.85 (m, 1H), 7.63 (d, J=8.59 Hz, 1H), 7.50 (d, J=8.08 Hz, 2H), 7.35-7.43 (m, 2H), 4.30-4.40 (m, 3H), 4.21 (dd, J=6.57, 9.60 Hz, 1H), 4.01-4.12 (m, 4H), 3.83-3.99 (m, 2H), 3.59-3.78 (m, 3H), 3.11-3.26 (m, 2H), 1.80 (s, ~1.5H), 1.77 (s, ~1.5H), 1.73 (s, ~1.5H), 1.71 (s, ~1.5H); MS m/e 576.3 [M+H]+.

Example 4

(4-Chloro-2-ethyl-3-(4-(trifluoromethyl)benzyl)quinolin-6-yl)bis(1,2-dimethyl-1H-imidazol-5-yl)methanol•TFA

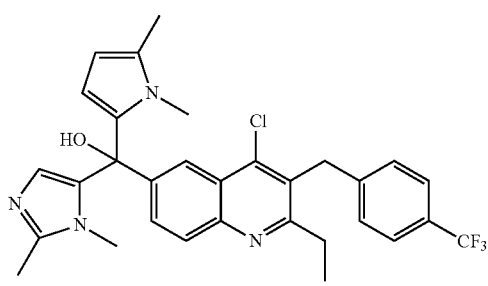 [SMILES: CCc1nc2ccc(C(O)(c3ccc(C)n3C)c3cnc(C)n3C)cc2c(Cl)c1Cc1ccc(C(F)(F)F)cc1]

A solution of 5-bromo-1,2-dimethyl-1H-imidazole (0.712 g, 1.15 mmol) in dry THF (20 mL), cooled to −78° C., was treated dropwise with n-BuLi (2.5 M in hexanes, 1.6 mL, 4 mmol). After minutes of stirring, a solution of methyl 4-chloro-2-ethyl-3-(4-(trifluoromethyl)benzyl)quinoline-6-carboxylate (0.469 g, 1.15 mmol, Intermediate 6) in dry THF (5 mL) was added dropwise. The reaction was then allowed to warm to room temperature over the course of 30 minutes. Once at room temperature, the reaction was quenched via the addition of saturated aqueous NH$_4$Cl, diluted with EtOAc, and washed with saturated aqueous NaCl. The organic layer was dried (MgSO$_4$), filtered, and concentrated in vacuo. The crude residue was purified (FCC, 40 g SiO$_2$, 0-25% MeOH/CH$_2$Cl$_2$ over 60 minutes) and then further purified via prep HPLC (H$_2$O/acetonitrile/0.05% TFA) to afford the title compound. $^1$H NMR (500 MHz, CD$_3$OD) δ 8.54 (d, J=2.3 Hz, 1H), 8.17 (d, J=8.8 Hz, 1H), 7.74-7.70 (m, 1H), 7.59 (d, J=8.1 Hz, 2H), 7.31 (d, J=8.0 Hz, 2H), 7.12 (s, 2H), 4.63 (s, 2H), 3.72 (s, 6H), 3.03 (q, J=7.5 Hz, 2H), 2.66 (s, 6H), 1.28 (t, J=7.5 Hz, 3H). MS m/e 568.3 [M+H]+.

Example 5

(4-Chloro-2-methoxy-3-(3-(trifluoromethyl)benzyl)quinolin-6-yl)bis(1,2-dimethyl-1H-imidazol-5-yl)methanol•TFA

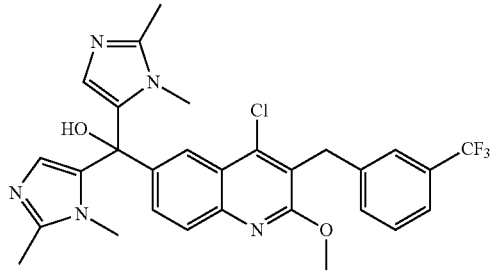 [SMILES: COc1nc2ccc(C(O)(c3cnc(C)n3C)c3cnc(C)n3C)cc2c(Cl)c1Cc1cccc(C(F)(F)F)c1]

The title compound was prepared following the procedure described for the preparation of Example 4 substituting methyl 4-chloro-2-ethyl-3-(4-(trifluoromethyl)benzyl)quinoline-6-carboxylate (Intermediate 6) with methyl 4-chloro-2-methoxy-3-(3-(trifluoromethyl)benzyl)quinoline-6-carboxylate (Intermediate 7: step d). $^1$H NMR (400 MHz, CD$_3$OD) δ 8.39 (d, J=2.2 Hz, 1H), 7.96 (d, J=8.7 Hz, 1H), 7.62-7.42 (m, 5H), 7.08 (s, 2H), 4.42 (s, 2H), 4.11 (s, 3H), 3.71 (s, 6H), 2.65 (s, 6H). MS m/e 570.1 [M+H]+.

Example 6

(4-Chloro-2-methoxy-3-(2-(trifluoromethyl)benzyl)quinolin-6-yl)bis(1,2-dimethyl-1H-imidazol-5-yl)methanol•TFA

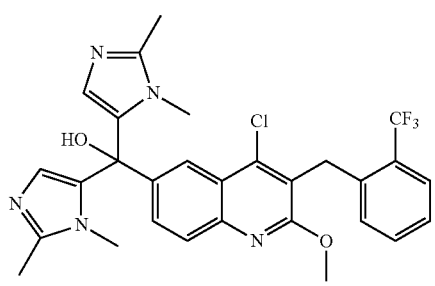 [SMILES: COc1nc2ccc(C(O)(c3cnc(C)n3C)c3cnc(C)n3C)cc2c(Cl)c1Cc1ccccc1C(F)(F)F]

The title compound was prepared following the procedure described for the preparation of Example 4, substituting methyl 4-chloro-2-ethyl-3-(4-(trifluoromethyl)benzyl)quinoline-6-carboxylate (Intermediate 6) with methyl 4-chloro-2-methoxy-3-(2-(trifluoromethyl)benzyl)quinoline-6-carboxylate (Intermediate 8: step d). $^1$H NMR (500 MHz, CD$_3$OD) δ 8.40 (d, J=2.3 Hz, 1H), 8.00 (d, J=8.8 Hz, 1H), 7.75-7.72 (m, 1H), 7.65-7.61 (m, 1H), 7.40-7.35 (m, 2H), 7.10 (s, 2H), 6.78-6.74 (m, 1H), 4.53 (s, 2H), 4.03 (s, 3H), 3.73 (s, 6H), 2.66 (s, 6H). MS m/e 570.2 [M+H]$^+$.

Example 7

(4-Chloro-2-methoxy-3-((5-(trifluoromethyl)thiophen-2-yl)methyl)quinolin-6-yl)bis(1,2-dimethyl-1H-imidazol-5-yl)methanol•TFA

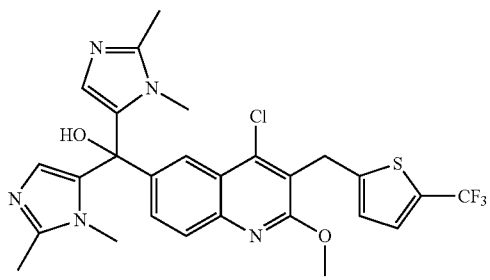 [SMILES: COc1nc2ccc(C(O)(c3cnc(C)n3C)c3cnc(C)n3C)cc2c(Cl)c1Cc1ccc(C(F)(F)F)s1]

The title compound was prepared following the procedure described for the preparation of Example 4, substituting methyl 4-chloro-2-ethyl-3-(4-(trifluoromethyl)benzyl)quinoline-6-carboxylate (Intermediate 6) with methyl 4-chloro-2-methoxy-3-((5-(trifluoromethyl)thiophen-2-yl)methyl)quinoline-6-carboxylate (Intermediate 9: step d). $^1$H NMR (500 MHz, CD$_3$OD) δ 8.38 (d, J=2.4 Hz, 1H), 7.99-7.94 (m, 1H), 7.62-7.58 (m, 1H), 7.35-7.32 (m, 1H), 7.08 (s, 2H), 7.04-7.01 (m, 1H), 4.55 (s, 2H), 4.17 (s, 3H), 3.71 (s, 6H), 2.65 (d, J=2.5 Hz, 6H). MS m/e 576.2 [M+H]$^+$.

Example 8

6-(bis(1,2-Dimethyl-1H-imidazol-5-yl)(hydroxy)methyl)-2-ethyl-3-(4-(trifluoromethyl)benzyl)quinoline-4-carbonitrile.TFA

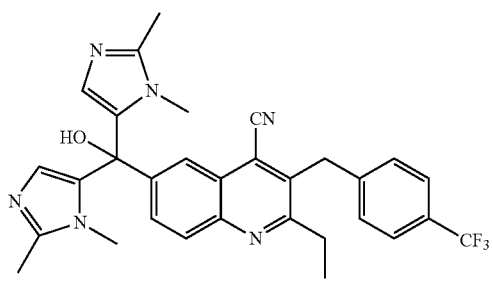 [SMILES: CCc1nc2ccc(C(O)(c3cnc(C)n3C)c3cnc(C)n3C)cc2c(C#N)c1Cc1ccc(C(F)(F)F)cc1]

A 20 mL scintillation vial with piercing septum cap containing (4-chloro-2-ethyl-3-(4-(trifluoromethyl)benzyl)quinolin-6-yl)bis(1,2-dimethyl-1H-imidazol-5-yl)methanol•TFA (0.256 g, 0.045 mmol, Example 4), Zn(CN)$_2$ (0.114 g, 0.971 mmol), X-Phos (0.076 g, 0.159 mmol), Zn powder (0.06 g, 0.917 mmol) and Pd$_2$(dba)$_3$ (0.041 g, 0.045 mmol), under a nitrogen atmosphere, was charged with DMA (5 mL, sparged with nitrogen). The reaction was heated at 120° C. for 16 hours, cooled to room temperature, filtered, and purified directly via reverse phase prep HPLC (H$_2$O/acetonitrile/0.05% TFA) to afford the title compound. $^1$H NMR (500 MHz, CDCl$_3$) δ 8.34 (d, J=2.2 Hz, 1H), 8.00 (d, J=8.8 Hz, 1H), 7.56 (d, J=8.1 Hz, 2H), 7.53-7.50 (m, 1H), 7.23 (s, 2H), 6.12 (s, 2H), 4.53 (s, 2H), 3.42 (s, 6H), 2.92 (q, J=7.4 Hz, 2H), 2.24 (s, 6H), 1.29 (t, J=7.4 Hz, 3H). MS m/e 559.3 [M+H]$^+$.

Example 9

6-(bis(1,2-Dimethyl-1H-imidazol-5-yl)(hydroxy)methyl)-2-methoxy-3-(3-(trifluoromethyl)benzyl)quinoline-4-carbonitrile•TFA

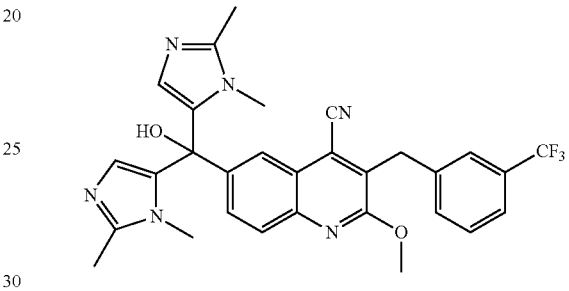

The title compound was prepared following the procedure described for the preparation of Example 8, substituting (4-chloro-2-ethyl-3-(4-(trifluoromethyl)benzyl)quinolin-6-yl)bis(1,2-dimethyl-1H-imidazol-5-yl)methanol•TFA (Example 4) with (4-chloro-2-methoxy-3-(3-(trifluoromethyl)benzyl)quinolin-6-yl)bis(1,2-dimethyl-1H-imidazol-5-yl)methanol•TFA (Example 5). $^1$H NMR (500 MHz, CD$_3$OD) δ 8.25 (d, J=2.3 Hz, 1H), 8.06 (d, J=8.8 Hz, 1H), 7.80-7.75 (m, 1H), 7.73-7.69 (m, 1H), 7.46-7.40 (m, 2H), 7.13 (s, 2H), 6.86-6.82 (m, 1H), 4.57 (s, 2H), 4.02 (s, 3H), 3.73 (s, 6H), 2.66 (s, 6H). MS m/e 561.3 [M+H]$^+$.

Example 10

6-(bis(1,2-Dimethyl-1H-imidazol-5-yl)(hydroxy)methyl)-2-methoxy-3-(2-(trifluoromethyl)benzyl)quinoline-4-carbonitrile•TFA

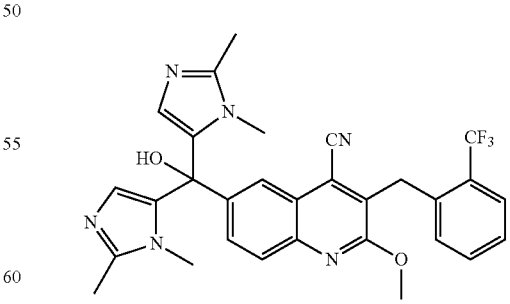

The title compound was prepared following the procedure described for the preparation of Example 8, substituting (4-chloro-2-ethyl-3-(4-(trifluoromethyl)benzyl)quinolin-6-yl)bis(1,2-dimethyl-1H-imidazol-5-yl)methanol•TFA (Example 4) with (4-chloro-2-methoxy-3-(2-(trifluoromethyl)

benzyl)quinolin-6-yl)bis(1,2-dimethyl-1H-imidazol-5-yl)methanol•TFA (Example 6). $^1$H NMR (500 MHz, CD$_3$OD) δ 8.25 (d, J=2.3 Hz, 1H), 8.06 (d, J=8.8 Hz, 1H), 7.80-7.75 (m, 1H), 7.73-7.69 (m, 1H), 7.46-7.40 (m, 2H), 7.13 (s, 2H), 6.86-6.82 (m, 1H), 4.57 (s, 2H), 4.02 (s, 3H), 3.73 (s, 6H), 2.66 (s, 6H). MS m/e 561.3 [M+H]$^+$.

Example 11

6-(bis(1,2-Dimethyl-1H-imidazol-5-yl)(hydroxy)methyl)-2-methoxy-3-(4-(trifluoromethyl)benzyl)quinoline-4-carbonitrile

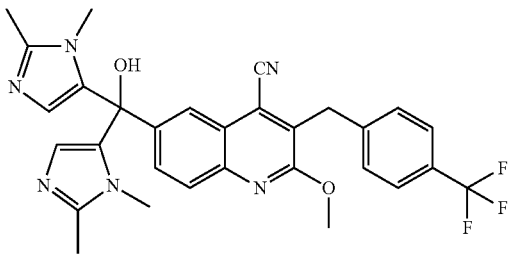 [SMILES: COc1nc2ccc(C(O)(c3cnc(C)n3C)c3cnc(C)n3C)cc2c(C#N)c1Cc1ccc(C(F)(F)F)cc1]

DMA (1.22 mL) was added to a mixture of (4-chloro-2-methoxy-3-(4-(trifluoromethyl)benzyl)quinolin-6-yl)bis(1,2-dimethyl-1H-imidazol-5-yl)methanol (70.6 mg, 0.124 mmol, Intermediate 76), zinc cyanide (27.5 mg, 0.234 mmol), Pd$_2$(dba)$_3$ (18.5 mg, 0.0202 mmol), zinc nanopowder (2.5 mg, 0.0382 mmol) and X-Phos (12.9 mg, 0.0262 mmol). The mixture was stirred at 120° C. under argon for 4 hours. After cooling to room temperature, the reaction was diluted with EtOAc (2 mL), filtered through Celite®, and the filter cake washed with EtOAc (2×1 mL). The combined filtrates were washed with 0.75 M aqueous EDTA tetrasodium salt (2×1 mL), water (1×2 mL), and 5 M aqueous NaCl (1×2 mL). The organic layer was diluted with DCM/MeOH, dried (Na$_2$SO$_4$), filtered, and concentrated, and the residue was dry load flash chromatographed with a DCM to 10% MeOH/DCM gradient to provide the title compound as an off-white solid. $^1$H NMR (400 MHz, CDCl$_3$) δ 8.23 (d, J=1.81 Hz, 1H), 7.76 (d, J=9.09 Hz, 1H), 7.55 (d, J=8.59 Hz, 2H), 7.49 (d, J=8.08 Hz, 2H), 7.41 (dd, J=2.06 Hz, 9.04 Hz, 1H), 6.16 (s, 2H), 4.39 (s, 2H), 4.10 (s, 3H), 3.42 (s, 6H), 2.27 (s, 6H); MS m/e 561.3 [M+H]$^+$.

Example 12

(4-Chloro-2-methoxy-3-(4-(trifluoromethyl)benzyl)quinolin-6-yl)bis(1-methyl-1H-1,2,3-triazol-5-yl)methanol

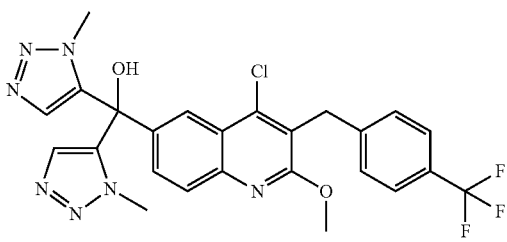 [SMILES: COc1nc2ccc(C(O)(c3cnnn3C)c3cnnn3C)cc2c(Cl)c1Cc1ccc(C(F)(F)F)cc1]

n-BuLi (1.63 M in hexane, 0.139 mL, 0.226 mmol) was added dropwise over 1 minute to a solution of 6-bromo-4-chloro-2-methoxy-3-(4-(trifluoromethyl)benzyl)quinoline (90.1 mg, 0.209 mmol, Intermediate 12: step d in THF (2.1 mL) at ~−70° C. under argon. After 2 additional minutes, a homogeneous solution of bis(1-methyl-1H-1,2,3-triazol-5-yl)methanone (41.4 mg, 0.215 mmol, Intermediate 13) in THF (2.1 mL) was added dropwise over 1 minute, and the resulting solution was allowed to warm to room temperature overnight as the dry ice/acetone bath expired. The resulting homogeneous yellow reaction was then quenched with 5 M aqueous NH$_4$Cl (0.06 mL), dried (Na$_2$SO$_4$), filtered, and concentrated to dryness. The residue was purified by C18 HPLC (20% to 100% CH$_3$CN, with 0.1% TFA throughout) and the lyophilisate neutralized with 9:1 DCM/MeOH and 2 M aqueous K$_2$CO$_3$. The organic layer was dried (Na$_2$SO$_4$), filtered, and concentrated to dryness to provide the title compound as a white solid. $^1$H NMR (400 MHz, DMSO-d$_6$) δ 8.16 (d, J=2.02 Hz, 1H), 7.99 (br. s., 1H), 7.91 (d, J=8.59 Hz, 1H), 7.65 (d, J=8.08 Hz, 2H), 7.41-7.51 (m, 3H), 7.19 (s, 2H), 4.36 (s, 2H), 4.04 (s, 3H), 3.84 (s, 6H); MS m/e 544.1 [M+H]$^+$.

Example 13

(3-(4-(1H-Pyrazol-1-yl)benzyl)-4-chloro-2-methoxyquinolin-6-yl)bis(1,2-dimethyl-1H-imidazol-5-yl)methanol

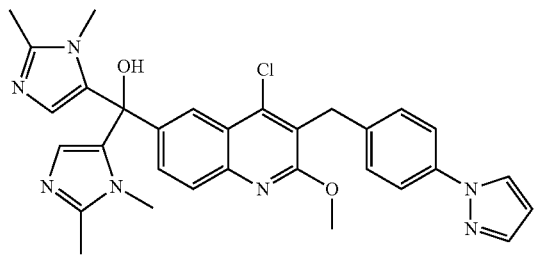 [SMILES: COc1nc2ccc(C(O)(c3cnc(C)n3C)c3cnc(C)n3C)cc2c(Cl)c1Cc1ccc(-n2cccn2)cc1]

n-BuLi (1.63 M in hexane, 0.124 mL, 0.203 mmol) was added dropwise under argon at ~−70° C. to a solution of 3-(4-(1H-pyrazol-1-yl)benzyl)-6-bromo-4-chloro-2-methoxyquinoline (81.6 mg, 0.19 mmol, Intermediate 10) in THF (1.9 mL). After 2 additional minutes, an opaque milky suspension of bis(1,2-dimethyl-1H-imidazol-5-yl)methanone (42.4 mg, 0.194 mmol, Intermediate 11) in LaCl$_3$·2LiCl (0.5 M in THF, 0.381 mL, 0.19 mmol) and THF (2.5 mL) was added rapidly dropwise over 1.5 minutes. The resulting yellow slurry was stirred in the dry ice/acetone bath for 10 minutes, and was then transferred to an ice bath and stirred overnight as the bath warmed to room temperature. The reaction was then quenched with 5 M aqueous NH$_4$Cl (0.06 mL) and diluted with DCM (~5 mL) and MeOH (~2 mL), and the suspension was partitioned with 0.75 M aqueous tetrasodium EDTA (4 mL) and 9:1 DCM/MeOH (10 mL). The organic layer was dried (Na$_2$SO$_4$), filtered, and concentrated. The residue was purified by C18 HPLC (20% to 100% CH$_3$CN gradient with 0.1% TFA throughout) and the lyophilisate neutralized with 9:1 DCM/MeOH and 2 M aqueous K$_2$CO$_3$. The organic layer was dried (Na$_2$SO$_4$), filtered, and concentrated to dryness to provide the title compound as a colorless film. $^1$H NMR (400 MHz, CDCl$_3$) δ 8.23 (s, 1H), 7.86 (d, J=2.53 Hz, 1H), 7.63-7.70 (m, 2H), 7.58 (d, J=8.59 Hz, 2H), 7.38 (d, J=8.59 Hz, 2H), 7.37 (m, 1H), 6.42 (t, J=1.99 Hz, 1H), 6.14 (s, 2H), 5.82 (br. s., 1H), 4.29 (s, 2H), 4.08 (s, 3H), 3.38 (s, 6H), 2.26 (s, 6H); MS m/e 568.3 [M+H]+.

Example 14a 4-((3-(4-(1H-1,2,4-Triazol-1-yl)benzyl)-4-chloro-2-methoxyquinolin-6-yl)(hydroxy)(1-methyl-1H-imidazol-5-yl)methyl)benzonitrile

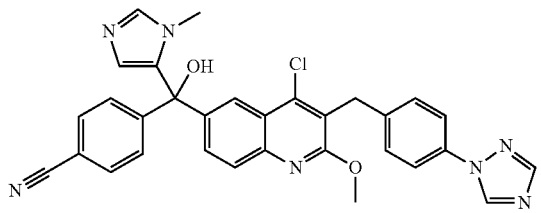 [SMILES: COc1nc2ccc(C(O)(c3ccc(C#N)cc3)c3cncn3C)cc2c(Cl)c1Cc1ccc(-n2cncn2)cc1]

A solution of isopropylmagnesium chloride-lithium chloride complex in tetrahydrofuran (1.3 M, 0.986 mL, 1.28 mmol) was added dropwise to an ice-water cooled, stirring suspension of 5-bromo-1-methyl-1H-imidazole (241 mg, 1.50 mmol) in dry tetrahydrofuran (6 mL). After 5 minutes, the flask was removed from the cooling bath and the white suspension was stirred at 23° C. After 10 minutes, the Grignard suspension was added to an ice-water cooled, stirring mixture containing 4-(3-(4-(1H-1,2,4-triazol-1-yl)benzyl)-4-chloro-2-methoxyquinoline-6-carbonyl)benzonitrile (205 mg, 0.427 mmol, Intermediate 16: step e) and lanthanum(III) chloride bis(lithium chloride) complex (0.6 M solution in tetrahydrofuran, 1.42 mL, 0.854 mmol) in dry tetrahydrofuran (8 mL). After 20 minutes, 1 M aqueous citric acid solution (1 mL) was added. The flask was removed from the cooling bath and then ethyl acetate (100 mL) was added. Additional 1 M aqueous citric acid solution (~15 mL) was added until the mixture was comprised of two homogeneous layers, at which point saturated aqueous sodium bicarbonate solution was added until the pH of the aqueous layer was ~8 by litmus paper test. The layers were separated. The aqueous layer was extracted with ethyl acetate (20 mL). The organic layers were combined and the combined solution was dried over sodium sulfate. The dried solution was filtered. Silica gel (5 g) was added to the filtrate and the mixture was concentrated by rotary evaporation to afford a free-flowing powder. The powder was loaded onto a silica gel column for flash-column chromatography purification. Elution with dichloromethane initially, grading to 10% methanol-dichloromethane provided the title compound as a white solid. $^1$H NMR (500 MHz, CDCl$_3$) δ ppm 8.45 (s, 1H), 8.10 (d, J=2.2 Hz, 1H), 8.06 (s, 1H), 7.81 (d, J=8.8 Hz, 1H), 7.65 (d, J=8.5 Hz, 2H), 7.58-7.51 (m, 5H), 7.44-7.38 (m, 3H), 6.41 (d, J=1.1 Hz, 1H), 4.33 (s, 2H), 4.09 (s, 3H), 3.94 (s, 1H), 3.38 (s, 3H); MS (ESI): mass calcd. C$_{31}$H$_{24}$ClN$_7$O$_2$, 561.2. m/z found, 562.1 [M+H]+.

4-((3-(4-(1H-1,2,4-Triazol-1-yl)benzyl)-4-chloro-2-methoxyquinolin-6-yl)(hydroxy)(1-methyl-1H-imidazol-5-yl)methyl)benzonitrile was purified by chiral SFC (Chiralpak AD-H column, 5 µm, 250 mm×20 mm, mobile phase: 60% CO$_2$, 40% methanol) to give two enantiomers. The first eluting enantiomer was Example 14b: $^1$H NMR (500 MHz, CDCl$_3$) δ ppm 8.44 (d, J=1.0 Hz, 1H), 8.10 (d, J=2.1 Hz, 1H), 8.06 (s, 1H), 7.81 (d, J=8.7 Hz, 1H), 7.66 (d, J=8.2 Hz, 2H), 7.58-7.50 (m, 5H), 7.44-7.38 (m, 3H), 6.42 (d, J=1.1 Hz, 1H), 4.33 (s, 2H), 4.09 (s, 3H), 4.02-3.81 (br s, 1H), 3.38 (s, 3H); MS (ESI): mass calcd. C$_{31}$H$_{24}$ClN$_7$O$_2$, 561.2. m/z found, 562.3 [M+H]+ and the second eluting enantiomer was Example 14c: $^1$H NMR (500 MHz, CDCl$_3$) δ ppm 8.45 (s, 1H), 8.09 (d, J=2.2 Hz, 1H), 8.06 (s, 1H), 7.81 (d, J=8.9 Hz, 1H), 7.66 (d, J=8.1 Hz, 2H), 7.58-7.51 (m, 5H), 7.45-7.38 (m, 3H), 6.43 (s, 1H), 4.33 (s, 2H), 4.09 (s, 3H), 3.38 (s, 3H); MS (ESI): mass calcd. C$_{31}$H$_{24}$ClN$_7$O$_2$, 561.2. m/z found, 562.3 [M+H]+.

Example 15a 3-(4-(1H-1,2,4-Triazol-1-yl)benzyl)-6-((4-cyanophenyl)(hydroxy)(1-methyl-1H-imidazol-5-yl)methyl)-2-methoxyquinoline-4-carbonitrile

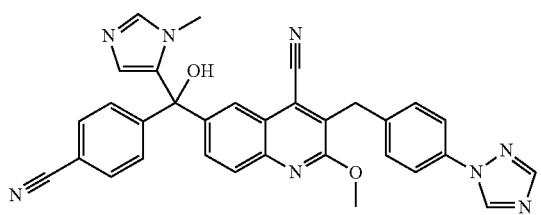 [SMILES: COc1nc2ccc(C(O)(c3ccc(C#N)cc3)c3cncn3C)cc2c(C#N)c1Cc1ccc(-n2cncn2)cc1]

A mixture containing 4-((3-(4-(1H-1,2,4-triazol-1-yl)benzyl)-4-chloro-2-methoxyquinolin-6-yl)(hydroxy)(1-methyl-1H-imidazol-5-yl)methyl)benzonitrile (150 mg, 0.267 mmol, Example 14a), zinc cyanide (56 mg, 0.48 mmol), tris(dibenzylideneacetone)dipalladium (37 mg, 0.04 mmol), zinc powder (5 mg, 0.08 mmol), 2-dicyclohexylphosphino-2',4',6'-triisopropylbiphenyl (XPhos, 26 mg, 0.05 mmol) and dimethylacetamide (1.4 mL, sparged with argon for 20 minutes) was heated to 120° C. After 2 hours, the flask was allowed to cool to 23° C. Ethyl acetate (20 mL) was added. The mixture was filtered through Celite®, rinsing with ethyl acetate. The filtrate was washed sequentially with saturated aqueous sodium bicarbonate solution (25 mL), water (25 mL), and saturated aqueous sodium chloride solution (25 mL). The organic layer was dried with sodium sulfate and the dried solution was filtered. Silica gel (4 g) was added to the filtrate and the mixture was concentrated by rotary evaporation to afford a free-flowing powder. The powder was loaded onto a silica gel column for flash column chromatography purification. Elution with dichloromethane initially, grading to 5% methanol-dichloromethane provided the title compound as an impure off-white solid. The impure solid was further purified by RP-HPLC eluting initially with 5% acetonitrile-water (containing 0.05% trifluoroacetic acid), grading to 95% acetonitrile-water (containing 0.05% trifluoroacetic acid) to provide the title compound as a white solid after partitioning the twice purified material between dichloromethane-saturated aqueous sodium bicarbonate solution, separating the layers, drying the organic layer with sodium sulfate, filtering the dried solution, and concentrating the filtrate to dryness. $^1$H NMR (500 MHz, CDCl$_3$) δ ppm 8.47 (s, 1H), 8.16 (d, J=2.1 Hz, 1H), 8.05 (s, 1H), 7.82 (d, J=8.8 Hz, 1H), 7.68-7.63 (m, 2H), 7.61-7.45 (m, 7H), 7.35 (s, 1H), 6.38 (s, 1H), 4.93 (s, 1H), 4.38 (s, 2H), 4.11 (s, 3H), 3.37 (s, 3H); MS (ESI): mass calcd. for C$_{32}$H$_{24}$N$_8$O$_2$, 552.2. m/z found, 553.0 [M+H]+.

3-(4-(1H-1,2,4-Triazol-1-yl)benzyl)-6-((4-cyanophenyl)(hydroxy)(1-methyl-1H-imidazol-5-yl)methyl)-2-methoxyquinoline-4-carbonitrile was purified by chiral SFC (Chiralcel OJ-H column, 5 µm, 250 mm×20 mm, mobile phase: 65% CO$_2$, 35% methanol containing 0.3% isopropylamine) to give two enantiomers. The first eluting enantiomer was Example 15b: $^1$H NMR (500 MHz, CDCl$_3$) δ ppm 8.47 (s, 1H), 8.17 (d, J=2.1 Hz, 1H), 8.04 (s, 1H), 7.82 (d, J=8.8 Hz, 1H), 7.66 (d, J=8.5 Hz, 2H), 7.61-7.46 (m, 7H), 7.35 (s, 1H), 6.38 (d, J=1.1 Hz, 1H), 4.92 (br s, 1H), 4.38 (s, 2H), 4.11 (s, 3H), 3.38 (s, 3H); MS (ESI): mass calcd. for C$_{32}$H$_{24}$N$_8$O$_2$, 552.2. m/z found, 553.0 [M+H]+ and the second eluting enantiomer was Example 15c: $^1$H NMR (500 MHz, CDCl$_3$) δ ppm 8.47 (s, 1H), 8.17 (d, J=2.0 Hz, 1H), 8.05 (s, 1H), 7.82 (d, J=8.8 Hz, 1H), 7.66 (d, J=8.4 Hz, 2H), 7.61-7.46 (m, 7H), 7.36 (s, 1H), 6.38 (s, 1H), 4.93 (br s, 1H), 4.38 (s, 2H), 4.11 (s, 3H), 3.38 (s, 3H); MS (ESI): mass calcd. for C$_{32}$H$_{24}$N$_8$O$_2$, 552.2. m/z found, 553.0 [M+H]+.

Example 16a 1-(4-((3-(4-(1H-Imidazol-1-yl)benzyl)-4-chloro-2-methoxyquinolin-6-yl)(hydroxy)(phenyl)methyl)piperidin-1-yl)ethanone

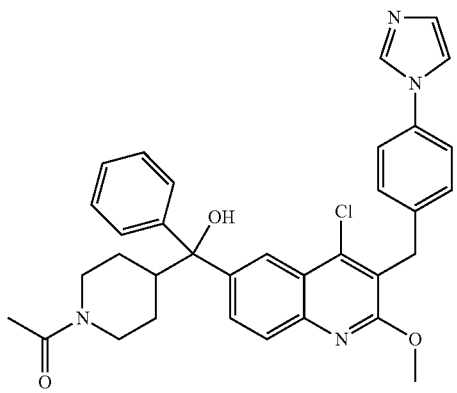 [SMILES: COc1nc2ccc(C(O)(c3ccccc3)C3CCN(C(C)=O)CC3)cc2c(Cl)c1Cc1ccc(-n2ccnc2)cc1]

A solution of isopropylmagnesium chloride-lithium chloride complex in tetrahydrofuran (1.3 M, 0.70 mL, 0.92 mmol) was added dropwise to a stirring mixture containing 3-(4-(1H-imidazol-1-yl)benzyl)-4-chloro-6-iodo-2-methoxyquinoline (350 mg, 0.736 mmol, Intermediate 17: step c) and 1-(4-benzoylpiperidin-1-yl)ethanone (170 mg, 0.736 mmol, Intermediate 18) in tetrahydrofuran (7.4 mL) at −35° C. (dry ice-acetone cooling bath). The cooling bath was allowed to slowly warm to 23° C. After 16 hours, water (30 mL) and ethyl acetate (30 mL) were added. The layers were separated. The aqueous layer was extracted with ethyl acetate (30 mL) and the organic layers were combined. The combined solution was dried with sodium sulfate and the dried solution was filtered. Silica gel (2 g) was added to the filtrate and the mixture was concentrated by rotary evaporation to afford a free-flowing powder. The powder was loaded onto a silica gel column for flash column chromatography purification. Elution with ethyl acetate initially, grading to 10% methanol-ethyl acetate provided the title compound as an impure off-white solid. The impure solid was further purified by RP-HPLC eluting initially with 5% acetonitrile-water (containing 0.05% trifluoroacetic acid), grading to 95% acetonitrile-water (containing 0.05% trifluoroacetic acid) to provide the title compound as a white solid after partitioning the twice purified material between dichloromethane-saturated aqueous sodium bicarbonate solution, separating the layers, drying the organic layer with sodium sulfate, filtering the dried solution, and concentrating the filtrate to dryness. MS (ESI): 581.1 [M+H]$^+$.

Example 16a was purified by chiral SFC (Chiralpak AD-H, 5 μm, 250×20 mm, mobile phase: 60% CO$_2$, 40% isopropanol containing 0.3% isopropylamine) to provide two enantiomers. The first eluting enantiomer was Example 16b: $^1$H NMR (500 MHz, CDCl$_3$) δ ppm 8.29 (dd, J=10.1, 2.1 Hz, 1H), 7.78 (s, 1H), 7.75 (d, J=8.4 Hz, 1H), 7.72-7.62 (m, 1H), 7.56-7.48 (m, 2H), 7.42-7.36 (m, 2H), 7.37-7.29 (m, 2H), 7.29-7.19 (m, 4H), 7.17 (s, 1H), 4.76-4.61 (m, 1H), 4.33 (s, 2H), 4.06 (s, 3H), 3.88-3.76 (m, 1H), 3.17-3.01 (m, 1H), 2.82-2.69 (m, 1H), 2.65-2.50 (m, 1H), 2.36 (s, 1H), 2.05 (s, 3H), 2.04 (s, 3H, amide rotamer), 1.74-1.28 (m, 4H); MS (ESI): mass calcd. for C$_{34}$H$_{33}$ClN$_4$O$_3$, 580.2. m/z found, 581.1 [M+H]$^+$ and the second eluting enantiomer was Example 16c: $^1$H NMR (500 MHz, CDCl$_3$) δ ppm 8.29 (dd, J=10.1, 2.1 Hz, 1H), 7.78 (s, 1H), 7.77-7.73 (m, 1H), 7.72-7.63 (m, 1H), 7.56-7.48 (m, 2H), 7.39 (d, J=8.3 Hz, 2H), 7.37-7.29 (m, 2H), 7.28-7.19 (m, 4H), 7.17 (s, 1H), 4.75-4.63 (m, 1H), 4.33 (s, 2H), 4.06 (s, 3H), 3.89-3.77 (m, 1H), 3.15-3.02 (m, 1H), 2.81-2.70 (m, 1H), 2.64-2.50 (m, 1H), 2.31 (s, 1H), 2.05 (s, 3H), 2.04 (s, 3H, amide rotamer) 1.75-1.28 (m, 4H); MS (ESI): mass calcd. for C$_{34}$H$_{33}$ClN$_4$O$_3$, 580.2. m/z found, 581.1 [M+H]$^+$.

Example 17a (3-(4-(1H-Pyrazol-1-yl)benzyl)-4-chloro-2-methoxyquinolin-6-yl)(2,6-dimethylpyridin-3-yl)(1-methyl-1H-1,2,3-triazol-5-yl)methanol

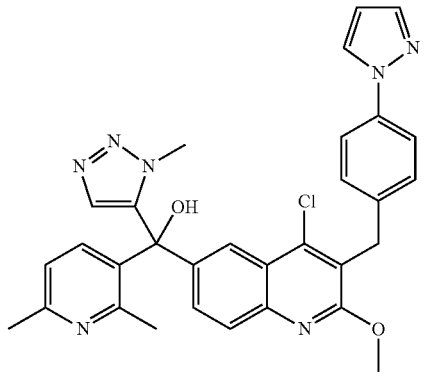 [SMILES: COc1nc2ccc(C(O)(c3ccc(C)nc3C)c3cnnn3C)cc2c(Cl)c1Cc1ccc(-n2cccn2)cc1]

A solution of n-butyllithium in hexanes (1.6 M, 0.73 mL, 1.2 mmol) was added dropwise to a stirring solution of 3-(4-(1H-pyrazol-1-yl)benzyl)-6-bromo-4-chloro-2-methoxyquinoline (500 mg, 1.2 mmol, Intermediate 10) in tetrahydrofuran (10 mL) at −78° C. After 5 minutes, a solution of (2,6-dimethylpyridin-3-yl)(1-methyl-1H-1,2,3-triazol-5-yl)methanone (250 mg, 1.2 mmol, Intermediate 19: step b) in tetrahydrofuran (1.6 mL) was added dropwise. After 5 minutes, the flask was placed into an ice-water bath. After 30 minutes, water (5 mL) was added and the mixture was allowed to warm to 23° C. The biphasic mixture was partitioned between half-saturated aqueous sodium chloride solution (100 mL) and ethyl acetate (100 mL). The layers were separated. The organic layer was dried with sodium sulfate and the dried solution was filtered. The filtrate was concentrated and the residue was purified by RP-HPLC eluting initially with 5% acetonitrile-water (containing 0.05% trifluoroacetic acid), grading to 95% acetonitrile-water (containing 0.05% trifluoroacetic acid) to provide the title compound as a white solid after partitioning the purified material between dichloromethane-saturated aqueous sodium bicarbonate solution, separating the layers, drying the organic layer with sodium sulfate, filtering the dried solution, and concentrating the filtrate to dryness. $^1$H NMR (600 MHz, CDCl$_3$) δ ppm 8.08 (d, J=2.2 Hz, 1H), 7.85 (d, J=2.5 Hz, 1H), 7.83 (d, J=8.7

Hz, 1H), 7.67 (d, J=1.7 Hz, 1H), 7.59-7.54 (m, 2H), 7.40-7.34 (m, 3H), 6.98-6.91 (m, 3H), 6.45-6.41 (m, 1H), 4.32 (s, 2H), 4.10 (s, 3H), 3.93 (s, 3H), 3.61 (s, 1H), 2.55 (s, 3H), 2.38 (s, 3H); MS (ESI): mass calcd. for $C_{31}H_{28}ClN_7O_2$, 565.2. m/z found, 566.1 [M+H]$^+$.

(3-(4-(1H-Pyrazol-1-yl)benzyl)-4-chloro-2-methoxyquinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 60% $CO_2$, 40% methanol) to provide two enantiomers. The first eluting enantiomer was Example 17b: $^1$H NMR (400 MHz, CDCl$_3$) δ ppm 8.11-8.05 (m, 1H), 7.85 (d, J=2.4 Hz, 1H), 7.85-7.77 (m, 1H), 7.67 (d, J=2.0 Hz, 1H), 7.60-7.53 (m, 2H), 7.40-7.32 (m, 3H), 6.99-6.89 (m, 3H), 6.46-6.39 (m, 1H), 4.31 (s, 2H), 4.10 (s, 3H), 3.93 (s, 3H), 2.55 (s, 3H), 2.38 (s, 3H); MS (ESI): mass calcd. for $C_{31}H_{28}ClN_7O_2$, 565.2. m/z found, 566.1 [M+H]$^+$ and the second eluting enantiomer was Example 17c: $^1$H NMR (400 MHz, CDCl$_3$) δ ppm 8.08 (d, J=2.1 Hz, 1H), 7.85 (d, J=2.4 Hz, 1H), 7.82 (d, J=8.5 Hz, 1H), 7.67 (s, 1H), 7.57 (d, J=8.2 Hz, 2H), 7.40-7.32 (m, 3H), 6.99-6.89 (m, 3H), 6.46-6.40 (m, 1H), 4.31 (s, 2H), 4.10 (s, 3H), 3.93 (s, 3H), 3.69 (br s, 1H), 2.55 (s, 3H), 2.38 (s, 3H); MS (ESI): mass calcd. for $C_{31}H_{28}ClN_7O_2$, 565.2. m/z found, 566.0 [M+H]$^+$.

Example 18a 1-(4-((3-(4-(1H-1,2,4-Triazol-1-yl)benzyl)-4-chloro-2-methoxyquinolin-6-yl)(hydroxy)(phenyl)methyl) piperidin-1-yl)ethanone

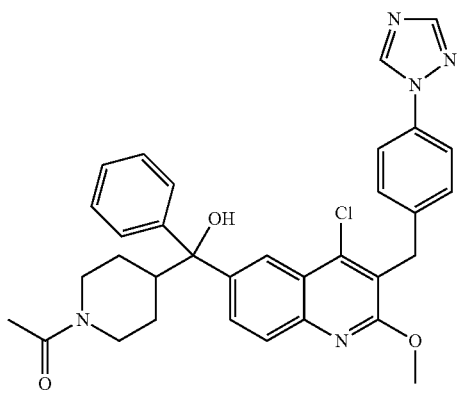 [SMILES: COc1nc2ccc(C(O)(c3ccccc3)C3CCN(C(C)=O)CC3)cc2c(Cl)c1Cc1ccc(-n2cncn2)cc1]

A solution of isopropylmagnesium chloride-lithium chloride complex in tetrahydrofuran (1.3 M, 0.73 mL, 0.94 mmol) was added dropwise to an ice-water cooled, stirring solution of 3-(4-(1H-1,2,4-triazol-1-yl)benzyl)-4-chloro-6-iodo-2-methoxyquinoline (300 mg, 0.63 mmol, Intermediate 20: step c) in dry tetrahydrofuran (6 mL). After 10 minutes, a solution of 1-(4-benzoylpiperidin-1-yl)ethanone (218 mg, 0.94 mmol, Intermediate 18) in tetrahydrofuran (5 mL) was added dropwise. After 30 minutes, the flask was warmed to 23° C. After 1 hour, the flask was warmed to 55° C. After 30 minutes, the flask was allowed to cool to 23° C. Water (20 mL), saturated aqueous sodium chloride solution (20 mL), and ethyl acetate (100 mL) were added. The layers were separated. The organic layer was dried with sodium sulfate and the dried solution was filtered. Silica gel (5 g) was added to the filtrate and the mixture was concentrated by rotary evaporation to afford a free-flowing powder. The powder was loaded onto a silica gel column for flash column chromatography purification. Elution with dichloromethane initially, grading to 5% methanol-dichloromethane provided the title compound which was further purified by RP-HPLC eluting initially with 5% acetonitrile-water (containing 0.05% trifluoroacetic acid), grading to 95% acetonitrile-water (containing 0.05% trifluoroacetic acid) to provide the title compound as a white solid after partitioning the purified material between dichloromethane-saturated aqueous sodium bicarbonate solution, separating the layers, drying the organic layer with sodium sulfate, filtering the dried solution, and concentrating the filtrate to dryness. $^1$H NMR (500 MHz, CDCl$_3$) δ ppm 8.47 (s, 1H), 8.32-8.25 (m, 1H), 8.06 (s, 1H), 7.80-7.72 (m, 1H), 7.72-7.62 (m, 1H), 7.57-7.48 (m, 4H), 7.44-7.38 (m, 2H), 7.37-7.29 (m, 2H), 7.26-7.18 (m, 1H), 4.75-4.63 (m, 1H), 4.34 (s, 2H), 4.05 (s, 3H), 3.90-3.75 (m, 1H), 3.17-2.99 (m, 1H), 2.76 (t, J=11.8 Hz, 1H), 2.66-2.49 (m, 1H), 2.28 (s, 1H, rotamer), 2.27 (s, 1H, rotamer), 2.05 (s, 3H, rotamer), 2.04 (s, 3H, rotamer), 1.75-1.62 (m, 1H), 1.55-1.28 (m, 3H); MS (ESI): mass calcd. for $C_{33}H_{32}ClN_5O_3$, 581.2. m/z found, 582.0 [M+H]$^+$.

1-(4-((3-(4-(1H-1,2,4-Triazol-1-yl)benzyl)-4-chloro-2-methoxyquinolin-6-yl)(hydroxy)(phenyl)methyl)piperidin-1-yl)ethanone was purified by chiral SFC (Chiralpak AD-H, 5 μm, 250×20 mm, mobile phase: 55% $CO_2$, 45% mixture of methanol-isopropanol 50/50 v/v containing 0.03% isopropylamine) to provide two enantiomers. The first eluting enantiomer was Example 18b: $^1$H NMR (500 MHz, CDCl$_3$, * denotes rotameric peaks) δ ppm 8.48 (s, 1H), 8.32-8.26 (m, 1H), 8.07 (s, 1H), 7.80-7.73 (m, 1H), 7.72-7.62 (m, 1H), 7.57-7.49 (m, 4H), 7.44-7.38 (m, 2H), 7.38-7.30 (m, 2H), 7.26-7.19 (m, 1H), 4.76-4.63 (m, 1H), 4.34 (s, 2H), 4.06 (s, 3H), 3.91-3.77 (m, 1H), 3.17-3.01 (m, 1H), 2.82-2.71 (m, 1H), 2.66-2.50 (m, 1H), 2.24 (br s, 1H), 2.06* (s, 3H), 2.05* (s, 3H), 1.75-1.28 (m, 4H); MS (ESI): mass calcd. for $C_{33}H_{32}ClN_5O_3$, 581.2. m/z found, 582.5 [M+H]$^+$ and the second eluting enantiomer was Example 18c: $^1$H NMR (500 MHz, CDCl$_3$, * denotes rotameric peaks) δ ppm 8.48 (s, 1H), 8.32-8.26 (m, 1H), 8.07 (s, 1H), 7.80-7.73 (m, 1H), 7.71-7.63 (m, 1H), 7.57-7.49 (m, 4H), 7.45-7.38 (m, 2H), 7.38-7.30 (m, 2H), 7.26-7.19 (m, 1H), 4.77-4.62 (m, 1H), 4.34 (s, 2H), 4.06 (s, 3H), 3.89-3.75 (m, 1H), 3.17-3.00 (m, 1H), 2.76 (t, J=12.0 Hz, 1H), 2.66-2.52 (m, 1H), 2.25 (br s, 1H), 2.05* (s, 3H), 2.04* (s, 3H), 1.76-1.28 (m, 4H); MS (ESI): mass calcd. for $C_{33}H_{32}ClN_5O_3$, 581.2. m/z found, 582.5 [M+H]$^+$.

Example 19a (3-(4-(1H-Pyrazol-1-yl)benzyl)-4-chloro-2-methoxyquinolin-6-yl)(1,2-dimethyl-1H-imidazol-5-yl)(1-methyl-1H-1,2,3-triazol-5-yl)methanol

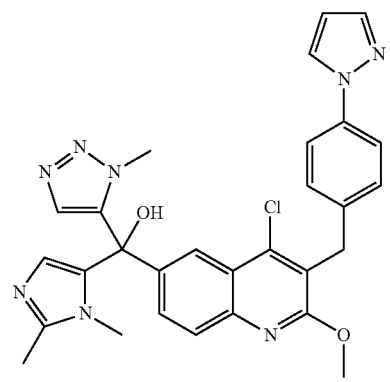 [SMILES: COc1nc2ccc(C(O)(c3cnnn3C)c3cnc(C)n3C)cc2c(Cl)c1Cc1ccc(-n2cccn2)cc1]

A solution of n-butyllithium in hexanes (2.5 M, 0.32 mL, 0.81 mmol) was added dropwise to a stirring solution of 1-methyl-1H-1,2,3-triazole (70.4 mg, 0.848 mmol, prepared according to PCT Int. Appl., 2008098104) in tetrahydrofuran (1 mL) at −50° C. After 20 minutes, a solution (gently warmed with a heat gun to dissolve the ketone starting material) of (3-(4-(1H-pyrazol-1-yl)benzyl)-4-chloro-2-methoxyquinolin-6-yl)(1,2-dimethyl-1H-imidazol-5-yl)methanone (200 mg, 0.42 mmol, Intermediate 21: step b) in tetrahydrofuran (1 mL) was added dropwise. After 5 minutes, the flask was allowed to warm to 23° C. After 20 minutes, water (1 mL) was added. The biphasic mixture was partitioned between saturated aqueous sodium chloride solution (25 mL) and ethyl acetate (50 mL). The layers were separated and the organic layer was dried with sodium sulfate. The dried solution was filtered. Silica gel (2 g) was added to the filtrate and the mixture was concentrated by rotary evaporation to afford a free-flowing powder. The powder was loaded onto a silica gel column for flash column chromatography purification. Elution with dichloromethane initially, grading to 10% methanol-dichloromethane provided the title compound which was further purified by RP-HPLC eluting initially with 5% acetonitrile-water (containing 0.05% trifluoroacetic acid), grading to 95% acetonitrile-water (containing 0.05% trifluoroacetic acid) to provide the title compound as a white solid after partitioning the purified material between dichloromethane-saturated aqueous sodium bicarbonate solution, separating the layers, drying the organic layer with sodium sulfate, filtering the dried solution, and concentrating the filtrate to dryness. $^1$H NMR (400 MHz, CDCl$_3$) δ ppm 8.21 (s, 1H), 7.85 (d, J=2.4 Hz, 1H), 7.74 (d, J=8.8 Hz, 1H), 7.67 (d, J=1.7 Hz, 1H), 7.60-7.53 (m, 2H), 7.41-7.33 (m, 3H), 7.11 (d, J=1.4 Hz, 1H), 6.46-6.39 (m, 1H), 6.08-6.02 (m, 1H), 4.27 (s, 2H), 4.08 (s, 3H), 3.89 (s, 3H), 3.35 (s, 3H), 2.20 (s, 3H); MS (ESI): mass calcd. for C$_{29}$H$_{27}$ClN$_8$O$_2$, 554.2. m/z found, 555.2 [M+H]$^+$.

(3-(4-(1H-Pyrazol-1-yl)benzyl)-4-chloro-2-methoxyquinolin-6-yl)(1,2-dimethyl-1H-imidazol-5-yl)(1-methyl-1H-1,2,3-triazol-5-yl)methanol was purified by chiral SFC (Chiralpak AD-H, 5 μm, 250×20 mm, mobile phase: 55% CO$_2$, 45% methanol containing 0.03% isopropylamine) to provide two enantiomers. The first eluting enantiomer was Example 19b: $^1$H NMR (500 MHz, CDCl$_3$) δ ppm 8.17 (d, J=2.2 Hz, 1H), 7.88-7.84 (m, 1H), 7.78 (d, J=8.7 Hz, 1H), 7.70-7.66 (m, 1H), 7.61-7.55 (m, 2H), 7.41-7.34 (m, 3H), 7.18 (s, 1H), 6.47-6.39 (m, 1H), 6.16 (s, 1H), 4.32 (s, 2H), 4.10 (s, 3H), 3.92 (s, 3H), 3.40 (s, 3H), 2.33 (s, 3H); MS (ESI): mass calcd. for C$_{29}$H$_{27}$ClN$_8$O$_2$, 554.2. m/z found, 555.5 [M+H]$^+$ and the second eluting enantiomer was Example 19c: $^1$H NMR (500 MHz, CDCl$_3$) δ ppm 8.18 (d, J=2.2 Hz, 1H), 7.85 (d, J=2.5 Hz, 1H), 7.76 (d, J=8.8 Hz, 1H), 7.68 (d, J=1.7 Hz, 1H), 7.61-7.55 (m, 2H), 7.42-7.34 (m, 3H), 7.17 (s, 1H), 6.43 (t, J=2.1 Hz, 1H), 6.13 (s, 1H), 4.31 (s, 2H), 4.10 (s, 3H), 3.91 (s, 3H), 3.39 (s, 3H), 2.31 (s, 3H); MS (ESI): mass calcd. for C$_{29}$H$_{27}$ClN$_8$O$_2$, 554.2. m/z found, 555.5 [M+H]$^+$.

Example 20a (4-Chloro-2-methoxy-3-(4-methylbenzyl)quinolin-6-yl)(2,6-dimethylpyridin-3-yl)(1-methyl-1H-1,2,3-triazol-5-yl)methanol

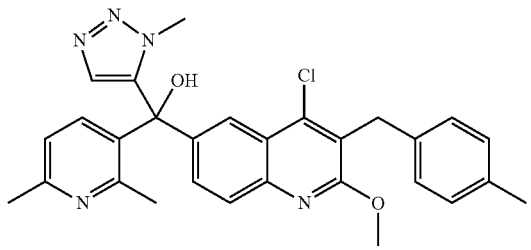

A solution of n-butyllithium in hexanes (2.5 M, 0.47 mL, 1.2 mmol) was added dropwise to a stirring solution of 4-chloro-6-iodo-2-methoxy-3-(4-methylbenzyl)quinoline (500 mg, 1.2 mmol, Intermediate 22: step c) in tetrahydrofuran (9 mL) at −78° C. After 2 minutes, a solution of (2,6-dimethylpyridin-3-yl)(1-methyl-1H-1,2,3-triazol-5-yl)methanone (255 mg, 1.2 mmol, Intermediate 19: step b) in tetrahydrofuran (2 mL) was added dropwise. After 5 minutes, the flask was placed into an ice-water bath. After 15 minutes, water (5 mL) and ethyl acetate (50 mL) were added and the biphasic mixture was poured into saturated aqueous sodium chloride solution (15 mL). The layers were separated. The organic layer was dried with sodium sulfate and the dried solution was filtered. Silica gel (6 g) was added to the filtrate and the mixture was concentrated by rotary evaporation to afford a free-flowing powder. The powder was loaded onto a silica gel column for flash column chromatography purification. Elution with 100% hexanes initially, grading to 100% ethyl acetate provided the title compound as a white foam. MS (ESI): mass calcd. for C$_{29}$H$_{28}$ClN$_5$O$_2$, 513.2. m/z found, 514.1 [M+H]$^+$.

(4-Chloro-2-methoxy-3-(4-methylbenzyl)quinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 70% CO$_2$, 30% mixture containing methanol-isopropanol 50/50 v/v containing 0.03% isopropylamine) to provide two enantiomers. The first eluting enantiomer was Example 20b: $^1$H NMR (400 MHz, CDCl$_3$) δ ppm 8.04 (d, J=2.3 Hz, 1H), 7.82 (d, J=8.7 Hz, 1H), 7.38-7.33 (m, 1H), 7.22-7.16 (m, 2H), 7.06 (d, J=7.7 Hz, 2H), 6.98 (s, 1H), 6.97-6.91 (m, 2H), 4.26 (s, 2H), 4.10 (s, 3H), 3.93 (s, 3H), 3.28 (s, 1H), 2.55 (s, 3H), 2.39 (s, 3H), 2.29 (s, 3H); MS (ESI): mass calcd. for C$_{29}$H$_{28}$ClN$_5$O$_2$, 513.2. m/z found, 514.1 [M+H]$^+$ and the second eluting enantiomer was Example 20c: $^1$H NMR (500 MHz, CDCl$_3$) δ ppm 8.04 (d, J=2.2 Hz, 1H), 7.82 (d, J=8.8 Hz, 1H), 7.38-7.32 (m, 1H), 7.19 (d, J=7.9 Hz, 2H), 7.06 (d, J=7.8 Hz, 2H), 6.98 (s, 1H), 6.97-6.92 (m, 2H), 4.26 (s, 2H), 4.10 (s, 3H), 3.94 (s, 3H), 3.28 (s, 1H), 2.56 (s, 3H), 2.39 (s, 3H), 2.29 (s, 3H); MS (ESI): mass calcd. for C$_{29}$H$_{28}$ClN$_5$O$_2$, 513.2. m/z found, 514.1 [M+H]$^+$.

Example 21a (3-(4-(1H-Pyrazol-1-yl)benzyl)-4-chloro-2-methoxyquinolin-6-yl)(2,4-dimethylthiazol-5-yl)(1-methyl-1H-1,2,3-triazol-5-yl)methanol

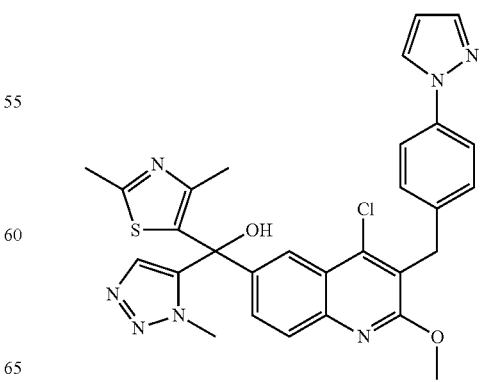

A solution of n-butyllithium in hexanes (2.5 M, 0.47 mL, 1.2 mmol) was added dropwise to a stirring solution of 3-(4-(1H-pyrazol-1-yl)benzyl)-6-bromo-4-chloro-2-methoxyquinoline (500 mg, 1.2 mmol, Intermediate 10) in tetrahydrofuran (9 mL) at −78° C. After 5 minutes, a solution of (2,4-dimethylthiazol-5-yl)(1-methyl-1H-1,2,3-triazol-5-yl)methanone (259 mg, 1.2 mmol, Intermediate 23: step b) in tetrahydrofuran (2 mL) was added dropwise. After 2 minutes, the flask was placed into an ice-water bath. After 90 minutes, water (4 mL) was added and the mixture was allowed to warm to 23° C. The biphasic mixture was partitioned between saturated aqueous sodium chloride solution (20 mL) and ethyl acetate (50 mL). The layers were separated. The organic layer was dried with sodium sulfate and the dried solution was filtered. Silica gel (5 g) was added to the filtrate and the mixture was concentrated by rotary evaporation to afford a free-flowing powder. The powder was loaded onto a silica gel column for flash column chromatography purification. Elution with 40% ethyl acetate-hexanes initially, grading to 90% ethyl acetate-hexanes provided the title compound as an off-white foam. $^1$H NMR (400 MHz, CDCl$_3$) δ ppm 8.15 (d, J=2.2 Hz, 1H), 7.89-7.81 (m, 2H), 7.67 (d, J=1.7 Hz, 1H), 7.59-7.54 (m, 2H), 7.54-7.48 (m, 1H), 7.41-7.34 (m, 2H), 7.23 (s, 1H), 6.45-6.41 (m, 1H), 4.32 (s, 2H), 4.11 (s, 3H), 3.91 (s, 3H), 3.71 (s, 1H), 2.58 (s, 3H), 2.15 (s, 3H); MS (ESI): mass calcd. for $C_{29}H_{26}ClN_7O_2S$, 571.2. m/z found, 572.1 [M+H]$^+$.

(3-(4-(1H-Pyrazol-1-yl)benzyl)-4-chloro-2-methoxyquinolin-6-yl)(2,4-dimethylthiazol-5-yl)(1-methyl-1H-1,2,3-triazol-5-yl)methanol was purified by chiral SFC (Chiralpak AD-H, 5 μm, 250×20 mm, mobile phase: 60% CO$_2$, 40% mixture containing methanol-isopropanol 50/50 v/v containing 0.03% isopropylamine) to provide two enantiomers. The first eluting enantiomer was Example 21b: $^1$H NMR (600 MHz, CDCl$_3$) δ ppm 8.17-8.13 (m, 1H), 7.86-7.84 (m, 2H), 7.70-7.66 (m, 1H), 7.59-7.54 (m, 2H), 7.53-7.49 (m, 1H), 7.40-7.35 (m, 2H), 7.24 (s, 1H), 6.46-6.41 (m, 1H), 4.32 (s, 2H), 4.11 (s, 3H), 3.92 (s, 3H), 3.59 (s, 1H), 2.59 (s, 3H), 2.16 (s, 3H); MS (ESI): mass calcd. for $C_{29}H_{26}ClN_7O_2S$, 571.2. m/z found, 572.1 [M+H]$^+$ and the second eluting enantiomer was Example 21c: $^1$H NMR (600 MHz, CDCl$_3$) δ ppm 8.15 (d, J=2.3 Hz, 1H), 7.88-7.82 (m, 2H), 7.68 (d, J=1.7 Hz, 1H), 7.60-7.55 (m, 2H), 7.51 (dd, J=8.7, 2.2 Hz, 1H), 7.40-7.36 (m, 2H), 7.25 (s, 1H), 6.46-6.42 (m, 1H), 4.32 (s, 2H), 4.11 (s, 3H), 3.92 (s, 3H), 3.48 (s, 1H), 2.59 (s, 3H), 2.16 (s, 3H); MS (ESI): mass calcd. for $C_{29}H_{26}ClN_7O_2S$, 571.2. m/z found, 572.1 [M+H]$^+$.

Example 22a (3-(4-(1H-1,2,4-Triazol-1-yl)benzyl)-4-chloro-2-methoxyquinolin-6-yl)(2,6-dimethylpyridin-3-yl)(1-methyl-1H-1,2,3-triazol-5-yl)methanol

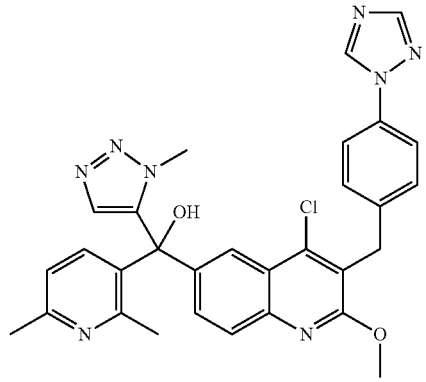 [SMILES: COc1nc2ccc(C(O)(c3ccc(C)nc3C)c3cnnn3C)cc2c(Cl)c1Cc1ccc(-n2cncn2)cc1]

A solution of isopropylmagnesium chloride-lithium chloride complex in tetrahydrofuran (1.3 M, 0.79 mL, 1.0 mmol) was added dropwise to an ice-water cooled, stirring solution of 3-(4-(1H-1,2,4-triazol-1-yl)benzyl)-4-chloro-6-iodo-2-methoxyquinoline (325 mg, 0.682 mmol, Intermediate 20: step c) in dry tetrahydrofuran (5 mL). After 15 minutes, a solution of (2,6-dimethylpyridin-3-yl)(1-methyl-1H-1,2,3-triazol-5-yl)methanone (177 mg, 0.818 mmol, Intermediate 19: step b) in tetrahydrofuran (1.5 mL) was added dropwise. After 10 minutes, the flask was removed from the cooling bath and allowed to warm to 23° C. After 4 hours, water (5 mL) was added. The mixture was partitioned between saturated aqueous sodium chloride solution (25 mL) and ethyl acetate (50 mL). The layers were separated. The organic layer was dried with sodium sulfate and the dried solution was filtered. Silica gel (5 g) was added to the filtrate and the mixture was concentrated by rotary evaporation to afford a free-flowing powder. The powder was loaded onto a silica gel column for flash column chromatography purification. Elution with dichloromethane initially, grading to 10% methanol-dichloromethane provided the title compound as a white solid. MS (ESI): mass calcd. for $C_{30}H_{27}ClN_8O_2$, 566.2. m/z found, 567.0 [M+H]$^+$.

(3-(4-(1H-1,2,4-Triazol-1-yl)benzyl)-4-chloro-2-methoxyquinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 60% CO$_2$, 40% methanol containing 0.03% isopropylamine) to provide two enantiomers. The first eluting enantiomer was Example 22b: $^1$H NMR (500 MHz, CDCl$_3$) δ ppm 8.46 (s, 1H), 8.10-8.05 (m, 2H), 7.85 (d, J=8.7 Hz, 1H), 7.58-7.53 (m, 2H), 7.46-7.42 (m, 2H), 7.42-7.37 (m, 1H), 6.99 (s, 1H), 6.98-6.93 (m, 2H), 4.35 (s, 2H), 4.11 (s, 3H), 3.95 (s, 3H), 3.37 (s, 1H), 2.56 (s, 3H), 2.40 (s, 3H); MS (ESI): mass calcd. for $C_{30}H_{27}ClN_8O_2$, 566.2. m/z found, 567.5 [M+H]$^+$ and the second eluting enantiomer was Example 22c: $^1$H NMR (500 MHz, CDCl$_3$) δ ppm 8.46 (s, 1H), 8.10-8.05 (m, 2H), 7.84 (d, J=8.8 Hz, 1H), 7.58-7.53 (m, 2H), 7.45-7.41 (m, 2H), 7.41-7.37 (m, 1H), 6.98 (s, 1H), 6.97-6.93 (m, 2H), 4.35 (s, 2H), 4.11 (s, 3H), 3.95 (s, 3H), 3.43 (br s, 1H), 2.56 (s, 3H), 2.40 (s, 3H); MS (ESI): mass calcd. for $C_{30}H_{27}ClN_8O_2$, 566.2. m/z found, 567.5 [M+H]$^+$.

Example 23a (4-Chloro-2-ethyl-3-(4-(trifluoromethyl)benzyl) quinolin-6-yl)(2,6-dimethylpyridin-3-yl)(1-methyl-1H-1,2,3-triazol-5-yl)methanol

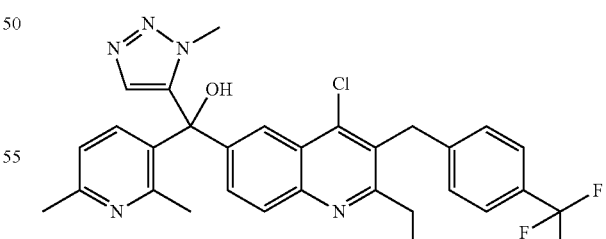

A solution of n-butyllithium (2.5 M in hexanes, 0.36 mL, 0.91 mmol) was added dropwise by syringe to a stirring solution of 6-bromo-4-chloro-2-ethyl-3-(4-(trifluoromethyl) benzyl)quinoline (390 mg, 0.91 mmol, Intermediate 5: step c) in dry THF (8 mL) at −78° C. After 1 minute, a solution of (2,6-dimethylpyridin-3-yl)(1-methyl-1H-1,2,3-triazol-5-yl) methanone (197 mg, 0.91 mmol, Intermediate 19: step b) in dry THF (2 mL) was added dropwise by syringe. After 2 minutes, the flask was removed from the cooling bath and allowed to warm. After 5 minutes, the flask was placed into an ice-water bath. After 60 minutes, water (4 mL) was added and the biphasic mixture was partitioned between saturated aqueous sodium chloride solution (20 mL) and ethyl acetate (50 mL). The layers were separated. The organic layer was dried with sodium sulfate and the dried solution was filtered. Silica gel (5 g) was added to the filtrate and the solvents were removed by rotary evaporation to provide a free-flowing powder. The powder was loaded onto a silica gel column. Elution with 40% ethyl acetate-hexanes initially, grading to 90% ethyl acetate-hexanes provided the title compound as an off-white foam. $^1$H NMR (400 MHz, CDCl$_3$) δ ppm 8.19 (d, J=2.2 Hz, 1H), 8.06 (d, J=8.8 Hz, 1H), 7.53 (d, J=8.0 Hz, 2H), 7.51-7.47 (m, 1H), 7.20 (d, J=8.0 Hz, 2H), 6.99-6.93 (m, 3H), 4.49 (s, 2H), 3.95 (s, 3H), 3.82 (s, 1H), 3.00-2.90 (m, 2H), 2.55 (s, 3H), 2.40 (s, 3H), 1.36-1.27 (m, 3H); MS (ESI): mass calcd. for C$_{30}$H$_{27}$ClF$_3$N$_5$O, 565.2. m/z found, 566.1 [M+H]$^+$.

(4-Chloro-2-ethyl-3-(4-(trifluoromethyl)benzyl)quinolin-6-yl)(2,6-dimethylpyridin-3-yl)(1-methyl-1H-1,2,3-triazol-5-yl)methanol was purified by chiral SFC (Chiralpak AD, 5 μm, 250×30 mm, mobile phase: 80% CO$_2$, 20% mixture containing methanol-isopropanol 50/50 v/v containing 0.03% isopropylamine) to provide two enantiomers. The first eluting enantiomer was Example 23b: $^1$H NMR (600 MHz, CDCl$_3$) δ ppm 8.19 (d, J=2.2 Hz, 1H), 8.08-8.05 (m, 1H), 7.53 (d, J=8.0 Hz, 2H), 7.51-7.47 (m, 1H), 7.21 (d, J=7.9 Hz, 2H), 6.99 (s, 1H), 6.96 (s, 2H), 4.49 (s, 2H), 3.96 (s, 3H), 3.48 (s, 1H), 2.99-2.92 (m, 2H), 2.56 (s, 3H), 2.42 (s, 3H), 1.35-1.29 (m, 3H); MS (ESI): mass calcd. for C$_{30}$H$_{27}$ClF$_3$N$_5$O, 565.2. m/z found, 566.1 [M+H]$^+$ and the second eluting enantiomer was Example 23c: $^1$H NMR (600 MHz, CDCl$_3$) δ ppm 8.19 (d, J=2.1 Hz, 1H), 8.07 (d, J=8.8 Hz, 1H), 7.53 (d, J=8.0 Hz, 2H), 7.52-7.47 (m, 1H), 7.21 (d, J=8.0 Hz, 2H), 7.00 (s, 1H), 6.96 (s, 2H), 4.50 (s, 2H), 3.97 (s, 3H), 3.37 (s, 1H), 2.98-2.91 (m, 2H), 2.56 (s, 3H), 2.42 (s, 3H), 1.36-1.27 (m, 3H); MS (ESI): mass calcd. for C$_{30}$H$_{27}$ClF$_3$N$_5$O, 565.2. m/z found, 566.1 [M+H]$^+$.

Example 24a (4-Chloro-3-(4-(dimethylamino)benzyl)-2-methoxyquinolin-6-yl)(2,6-dimethylpyridin-3-yl)(1-methyl-1H-1,2,3-triazol-5-yl)methanol wise by syringe. After 3 minutes, the flask was removed from the cooling bath and allowed to warm. After 5 minutes, the flask was placed into an ice-water bath. After 15 minutes, water (5 mL) and ethyl acetate (25 mL) were added. The biphasic mixture was partitioned between half-saturated aqueous sodium chloride solution (20 mL) and ethyl acetate (25 mL). The layers were separated. The organic layer was dried with sodium sulfate and the dried solution was filtered. Silica gel (4 g) was added to the filtrate and the solvents were removed by rotary evaporation to provide a free-flowing powder. The powder was loaded onto a silica gel column. Elution with 30% ethyl acetate-hexanes initially, grading to 90% ethyl acetate-hexanes provided the title compound as an off-white solid. $^1$H NMR (500 MHz, CDCl$_3$) δ ppm 8.03 (s, 1H), 7.83-7.78 (m, 1H), 7.34 (d, J=8.8 Hz, 1H), 7.23-7.17 (m, 2H), 7.00-6.90 (m, 3H), 6.68-6.61 (m, 2H), 4.19 (s, 2H), 4.11 (s, 3H), 3.92 (s, 3H), 3.45 (s, 1H), 2.88 (s, 6H), 2.55 (s, 3H), 2.39 (s, 3H); MS (ESI): mass calcd. for C$_{30}$H$_{31}$ClN$_6$O$_2$, 542.2. m/z found, 543.1 [M+H]$^+$.

(4-Chloro-3-(4-(dimethylamino)benzyl)-2-methoxyquinolin-6-yl)(2,6-dimethylpyridin-3-yl)(1-methyl-1H-1,2,3-triazol-5-yl)methanol was purified by chiral SFC (Chiralpak AD, 5 μm, 250×20 mm, mobile phase: 65% CO$_2$, 35% mixture containing methanol-isopropanol 50/50 v/v containing 0.03% isopropylamine) to provide two enantiomers. The first eluting enantiomer was Example 24b: $^1$H NMR (600 MHz, CDCl$_3$) δ ppm 8.04 (d, J=2.2 Hz, 1H), 7.80 (d, J=8.7 Hz, 1H), 7.33 (dd, J=8.7, 2.3 Hz, 1H), 7.23-7.18 (m, 2H), 6.98 (s, 1H), 6.97-6.92 (m, 2H), 6.66-6.63 (m, 2H), 4.19 (s, 2H), 4.10 (s, 3H), 3.93 (s, 3H), 3.33 (s, 1H), 2.88 (s, 6H), 2.55 (s, 3H), 2.39 (s, 3H); MS (ESI): mass calcd. for C$_{30}$H$_{31}$ClN$_6$O$_2$, 542.2. m/z found, 543.2 [M+H]$^+$ and the second eluting enantiomer was Example 24c: $^1$H NMR (600 MHz, CDCl$_3$) δ ppm 8.03 (d, J=2.3 Hz, 1H), 7.81 (d, J=8.7 Hz, 1H), 7.33 (dd, J=8.7, 2.2 Hz, 1H), 7.23-7.18 (m, 2H), 6.99 (s, 1H), 6.96-6.92 (m, 2H), 6.67-6.62 (m, 2H), 4.20 (s, 2H), 4.11 (s, 3H), 3.93 (s, 3H), 3.23 (s, 1H), 2.89 (s, 6H), 2.56 (s, 3H), 2.40 (s, 3H); MS (ESI): mass calcd. for C$_{30}$H$_{31}$ClN$_6$O$_2$, 542.2. m/z found, 543.2 [M+H]$^+$.

Example 25a (4-Chloro-2-ethyl-3-(4-(trifluoromethyl)benzyl)quinolin-6-yl)(1,2-dimethyl-1H-imidazol-5-yl)(1-methyl-1H-1,2,3-triazol-5-yl)methanol

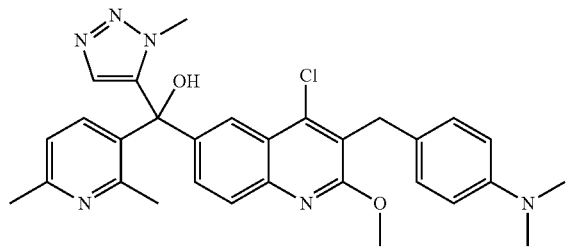

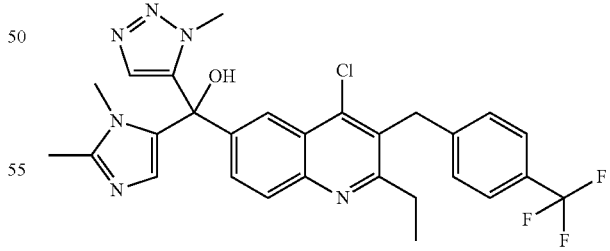

A solution of n-butyllithium (2.5 M in hexanes, 0.27 mL, 0.66 mmol) was added dropwise by syringe to a stirring solution of 4-((4-chloro-6-iodo-2-methoxyquinolin-3-yl)methyl)-N,N-dimethylaniline (300 mg, 0.663 mmol, Intermediate 24: step c) in dry THF (5 mL) at −78° C. After 2 minutes, a solution of (2,6-dimethylpyridin-3-yl)(1-methyl-1H-1,2,3-triazol-5-yl)methanone (143 mg, 0.663 mmol, Intermediate 19: step b) in dry THF (1 mL) was added drop- A solution of n-butyllithium in hexanes (2.5 M, 0.17 mL, 0.43 mmol) was added dropwise to a stirring solution of 1-methyl-1H-1,2,3-triazole (38.3 mg, 0.461 mmol, prepared according to PCT Int. Appl., 2008098104) in tetrahydrofuran (1.5 mL) at −50° C. After 20 minutes at −50° C., a solution of (4-chloro-2-ethyl-3-(4-(trifluoromethyl)benzyl)quinolin-6-yl)(1,2-dimethyl-1H-imidazol-5-yl)methanone (0.145 g, 0.307 mmol, Intermediate 25: step b) in tetrahydrofuran (1.5 mL) was added dropwise. After 5 minutes at −50° C., the flask was allowed to warm to 0° C. After 30 minutes, the mixture was partitioned between half-saturated aqueous sodium chloride solution (25 mL) and ethyl acetate (50 mL). The layers were separated and the organic layer was dried with sodium sulfate. The dried solution was filtered. Silica gel (3 g) was added to the filtrate and the mixture was concentrated by rotary evaporation to afford a free-flowing powder. The powder was loaded onto a silica gel column for flash column chromatography purification. Elution with dichloromethane initially, grading to 10% methanol-dichloromethane provided the title compound as an off-white solid. The solid was further purified by chiral SFC (Chiralpak AD-H, 5 μm, 250× 20 mm, mobile phase: 75% $CO_2$, 25% ethanol containing 0.03% isopropylamine) to provide two enantiomers. The first eluting enantiomer was Example 25b: $^1$H NMR (600 MHz, $CDCl_3$) δ ppm 8.30 (d, J=2.1 Hz, 1H), 8.02 (d, J=8.8 Hz, 1H), 7.57-7.49 (m, 3H), 7.21 (d, J=7.9 Hz, 2H), 7.17 (s, 1H), 6.18 (s, 1H), 4.91 (s, 1H), 4.49 (s, 2H), 3.95 (s, 3H), 3.40 (s, 3H), 3.00-2.90 (m, 2H), 2.30 (s, 3H), 1.35-1.28 (m, 3H); MS (ESI): mass calcd. for $C_{28}H_{26}ClF_3N_6O$, 554.2. m/z found, 555.2 $[M+H]^+$. and the second eluting enantiomer was Example 25c: $^1$H NMR (600 MHz, $CDCl_3$) δ ppm 8.32 (d, J=2.1 Hz, 1H), 7.99 (d, J=8.8 Hz, 1H), 7.56-7.51 (m, 3H), 7.21 (d, J=7.9 Hz, 2H), 7.12 (s, 1H), 6.14 (s, 1H), 5.83 (s, 1H), 4.48 (s, 2H), 3.93 (s, 3H), 3.38 (s, 3H), 2.98-2.90 (m, 2H), 2.24 (s, 3H), 1.34-1.27 (m, 3H); MS (ESI): mass calcd. for $C_{28}H_{26}ClF_3N_6O$, 554.2. m/z found, 555.0 $[M+H]^+$.

Example 26a (4-Chloro-2-methyl-3-(4-(trifluoromethyl)benzyl)quinolin-6-yl)(1-methyl-1H-imidazol-5-yl)(6-(trifluoromethyl)pyridin-3-yl)methanol

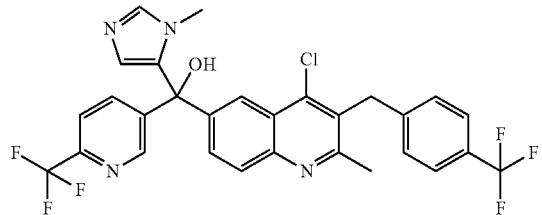 [SMILES: Cc1nc2ccc(C(O)(c3ccc(C(F)(F)F)nc3)c3cncn3C)cc2c(Cl)c1Cc1ccc(C(F)(F)F)cc1]

A 2.5 M solution of n-butyllithium in hexanes (0.24 mL, 0.603 mmol) was added dropwise by syringe to a stirring solution of 6-bromo-4-chloro-2-methyl-3-(4-(trifluoromethyl)benzyl)quinoline (250 mg, 0.603 mmol, Intermediate 26: step c) in dry tetrahydrofuran (5 mL) at −78° C. The resulting dark brown solution was stirred for 1 minute, whereupon a solution of (1-methyl-1H-imidazol-5-yl)(6-(trifluoromethyl)pyridin-3-yl)methanone (155 mg, 0.603 mmol, Intermediate 2: step c) in dry tetrahydrofuran (1 mL) was added dropwise by syringe. After 5 minutes, the flask was placed in an ice-water bath. After 30 minutes, water (2 mL) and ethyl acetate (15 mL) were added and the flask was removed from the cooling bath. After warming to 23° C., the biphasic mixture was partitioned between half-saturated aqueous sodium chloride solution (20 mL) and ethyl acetate (25 mL). The layers were separated. The organic layer was dried with sodium sulfate. The dried solution was filtered. Celite® (7 g) was added to the filtrate and the mixture was concentrated in vacuo. The dry solid was loaded onto a silica gel column for flash-column chromatography. Elution with 100% dichloromethane initially, grading to 7% methanol-dichloromethane provided the title compound as a white solid. $^1$H NMR (400 MHz, DMSO-$d_6$) δ ppm 8.79 (d, J=2.1 Hz, 1H), 8.21 (d, J=2.0 Hz, 1H), 8.04-7.90 (m, 3H), 7.75 (d, J=1.2 Hz, 1H), 7.72-7.62 (m, 3H), 7.50 (s, 1H), 7.34 (d, J=8.0 Hz, 2H), 6.25 (d, J=1.1 Hz, 1H), 4.51 (s, 2H), 3.35 (s, 3H), 2.60 (s, 3H); MS (ESI): mass calcd. for $C_{29}H_{21}ClF_6N_4O$, 590.1. m/z found, 591.2 $[M+H]^+$.

(4-Chloro-2-methyl-3-(4-(trifluoromethyl)benzyl)quinolin-6-yl)(1-methyl-1H-imidazol-5-yl)(6-(trifluoromethyl)pyridin-3-yl)methanol was purified by chiral SFC (Chiralpak AD-H, 5 μm, 250 mm×20 mm, mobile phase: 70% $CO_2$, 30% of a 1:1 mixture of methanol-isopropanol containing 0.3% v/v isopropylamine) to provide two enantiomers. The first eluting enantiomer was Example 26b: $^1$H NMR (600 MHz, $CDCl_3$) δ ppm 8.84 (d, J=2.2 Hz, 1H), 8.26 (d, J=2.1 Hz, 1H), 8.02 (d, J=8.8 Hz, 1H), 7.98-7.93 (m, 1H), 7.69 (dd, J=8.3, 0.8 Hz, 1H), 7.68-7.64 (m, 1H), 7.53 (d, J=8.1 Hz, 2H), 7.45 (s, 1H), 7.21 (d, J=8.0 Hz, 2H), 6.48 (s, 1H), 4.47 (s, 2H), 4.06 (s, 1H), 3.41 (s, 3H), 2.66 (s, 3H); MS (ESI): mass calcd. for $C_{29}H_{21}ClF_6N_4O$, 590.1. m/z found, 591.1 $[M+H]^+$ and the second eluting enantiomer was Example 26c: $^1$H NMR (600 MHz, $CDCl_3$) δ ppm 8.84 (d, J=2.3 Hz, 1H), 8.26 (d, J=2.1 Hz, 1H), 8.01 (d, J=8.8 Hz, 1H), 7.98-7.92 (m, 1H), 7.71-7.67 (m, 1H), 7.66 (dd, J=8.9, 2.2 Hz, 1H), 7.53 (d, J=8.0 Hz, 2H), 7.43 (s, 1H), 7.21 (d, J=7.9 Hz, 2H), 6.46 (s, 1H), 4.47 (s, 2H), 4.27 (s, 1H), 3.40 (s, 3H), 2.66 (s, 3H); MS (ESI): mass calcd. for $C_{29}H_{21}ClF_6N_4O$, 590.1. m/z found, 591.1 $[M+H]^+$.

Example 27a 1-(4-((4-Chloro-2-methyl-3-(4-(trifluoromethyl)benzyl)quinolin-6-yl)(hydroxy)(phenyl)methyl)piperidin-1-yl)ethanone

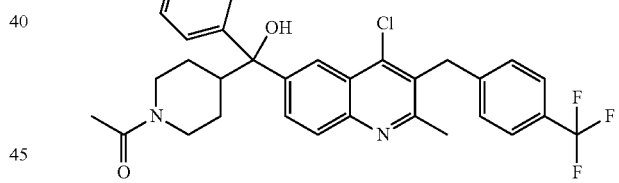

A 2.5 M solution of n-butyllithium in hexanes (0.34 mL, 0.844 mmol) was added dropwise by syringe to a stirring solution of 6-bromo-4-chloro-2-methyl-3-(4-(trifluoromethyl)benzyl)quinoline (350 mg, 0.844 mmol, Intermediate 26: step c) in dry tetrahydrofuran (6 mL) at −78° C. The resulting dark brown solution was stirred for 1 minute, whereupon a solution of 1-(4-benzoylpiperidin-1-yl)ethanone (195 mg, 0.844 mmol, Intermediate 18) in dry tetrahydrofuran (2 mL) was added dropwise by syringe. After 1 minute, the flask was removed from the cooling bath. After 3 minutes, the flask was placed in an ice-water bath. After 15 minutes, water (2 mL) and ethyl acetate (10 mL) were added and the flask was removed from the cooling bath. The biphasic mixture was partitioned between half-saturated aqueous sodium chloride solution (20 mL) and ethyl acetate (25 mL). The layers were separated. The organic layer was dried with sodium sulfate. The dry solution was filtered. Celite® (7 g) was added to the filtrate and the mixture was concentrated in vacuo. The dry solid was loaded onto a silica gel column for flash-column chromatography. Elution with 100% dichloromethane initially, grading to 5% methanol-dichloromethane provided the title compound as an off-white solid. $^1$H NMR (500 MHz, CDCl$_3$) δ ppm 8.44-8.38 (m, 1H), 7.97-7.92 (m, 1H), 7.79-7.72 (m, 1H), 7.58-7.50 (m, 4H), 7.39-7.32 (m, 2H), 7.25-7.19 (m, 3H), 4.77-4.65 (m, 1H), 4.47 (s, 2H), 3.90-3.78 (m, 1H), 3.17-3.04 (m, 1H), 2.85-2.76 (m, 1H), 2.65-2.53 (m, 4H), 2.43-2.37 (m, 1H), 2.10-2.01 (m, 3H), 1.77-1.64 (m, 1H), 1.57-1.30 (m, 3H); MS (ESI): mass calcd. for C$_{32}$H$_{30}$ClF$_3$N$_2$O$_2$, 566.2. m/z found, 567.1 [M+H]$^+$.

1-(4-((4-Chloro-2-methyl-3-(4-(trifluoromethyl)benzyl) quinolin-6-yl)(hydroxy)(phenyl)methyl)piperidin-1-yl)ethanone was purified by chiral SFC (Chiralpak AD-H, 5 μm, 250 mm×20 mm, mobile phase: 70% CO$_2$, 30% of a 1:1 mixture of methanol-isopropanol containing 0.3% v/v isopropylamine) to provide two enantiomers. The first eluting enantiomer was Example 27b: $^1$H NMR (600 MHz, CDCl$_3$) δ ppm 8.41 (dd, J=15.1, 2.0 Hz, 1H), 7.97-7.91 (m, 1H), 7.79-7.71 (m, 1H), 7.58-7.50 (m, 4H), 7.39-7.33 (m, 2H), 7.26-7.17 (m, 3H), 4.76-4.66 (m, 1H), 4.47 (s, 2H), 3.92-3.78 (m, 1H), 3.17-3.04 (m, 1H), 2.84-2.77 (m, 1H), 2.65-2.54 (m, 4H), 2.29-2.24 (m, 1H), 2.10-2.03 (m, 3H), 1.78-1.66 (m, 1H), 1.53-1.33 (m, 3H); MS (ESI): mass calcd. for C$_{32}$H$_{30}$ClF$_3$N$_2$O$_2$, 566.2. m/z found, 567.1 [M+H]$^+$ and the second eluting enantiomer was Example 27c: $^1$H NMR (600 MHz, CDCl$_3$) δ ppm 8.41 (dd, J=15.0, 2.0 Hz, 1H), 7.98-7.91 (m, 1H), 7.75 (ddd, J=23.2, 8.9, 2.1 Hz, 1H), 7.58-7.54 (m, 2H), 7.52 (d, J=8.0 Hz, 2H), 7.39-7.33 (m, 2H), 7.26-7.23 (m, 1H), 7.21 (d, J=8.0 Hz, 2H), 4.71 (dd, J=25.4, 13.4 Hz, 1H), 4.47 (s, 2H), 3.90-3.79 (m, 1H), 3.17-3.03 (m, 1H), 2.86-2.75 (m, 1H), 2.62 (s, 3H), 2.61-2.52 (m, 1H), 2.27 (s, 1H), 2.09-2.03 (m, 3H), 1.77-1.65 (m, 1H), 1.51-1.28 (m, 3H); MS (ESI): mass calcd. for C$_{32}$H$_{30}$ClF$_3$N$_2$O$_2$, 566.2. m/z found, 567.1 [M+H]$^+$.

between half-saturated aqueous sodium chloride solution (20 mL) and ethyl acetate (25 mL). The layers were separated. The organic layer was dried with sodium sulfate. The dry solution was filtered. Celite® (7 g) was added to the filtrate and the mixture was concentrated in vacuo. The dry solid was loaded onto a silica gel column for flash-column chromatography. Elution with 100% dichloromethane initially, grading to 5% methanol-dichloromethane provided the title compound as an off-white solid. $^1$H NMR (400 MHz, CDCl$_3$) δ ppm 8.21 (d, J=2.2 Hz, 1H), 8.00 (d, J=8.8 Hz, 1H), 7.54 (d, J=8.0 Hz, 2H), 7.51-7.46 (m, 1H), 7.22 (d, J=7.9 Hz, 2H), 6.98-6.91 (m, 3H), 4.47 (s, 2H), 4.08 (s, 1H), 3.95 (s, 3H), 2.66 (s, 3H), 2.55 (s, 3H), 2.39 (s, 3H); MS (ESI): mass calcd. for C$_{29}$H$_{25}$ClF$_3$N$_5$O, 551.2. m/z found, 552.2 [M+H]$^+$.

(4-Chloro-2-methyl-3-(4-(trifluoromethyl)benzyl)quinolin-6-yl)(2,6-dimethylpyridin-3-yl)(1-methyl-1H-1,2,3-triazol-5-yl)methanol was purified by chiral SFC (Chiracel OD-H, 5 μm, 250 mm×20 mm, mobile phase: 80% CO$_2$, 20% of a 1:1 v/v mixture of methanol-isopropanol containing 0.3% isopropylamine) to provide two enantiomers. The first eluting enantiomer was Example 28b: $^1$H NMR (500 MHz, CDCl$_3$) δ ppm 8.20 (d, J=2.1 Hz, 1H), 8.02 (d, J=8.9 Hz, 1H), 7.54 (d, J=8.0 Hz, 2H), 7.52-7.46 (m, 1H), 7.22 (d, J=7.8 Hz, 2H), 7.00-6.94 (m, 3H), 4.47 (s, 2H), 3.96 (s, 3H), 3.59 (s, 1H), 2.67 (s, 3H), 2.56 (s, 3H), 2.41 (s, 3H); MS (ESI): mass calcd. for C$_{29}$H$_{25}$ClF$_3$N$_5$O, 551.2. m/z found, 552.1 [M+H]$^+$ and the second eluting enantiomer was Example 28c: $^1$H NMR (500 MHz, CDCl$_3$) δ ppm 8.20 (d, J=2.1 Hz, 1H), 8.03 (d, J=8.8 Hz, 1H), 7.54 (d, J=8.0 Hz, 2H), 7.49 (dd, J=8.8, 2.2 Hz, 1H), 7.25-7.20 (m, 2H), 7.00-6.94 (m, 3H), 4.48 (s, 2H), 3.96 (s, 3H), 3.45 (s, 1H), 2.67 (s, 3H), 2.56 (s, 3H), 2.41 (s, 3H); MS (ESI): mass calcd. for C$_{29}$H$_{25}$ClF$_3$N$_5$O, 551.2. m/z found, 552.1 [M+H]$^+$.

Example 28a (4-Chloro-2-methyl-3-(4-(trifluoromethyl)benzyl) quinolin-6-yl)(2,6-dimethylpyridin-3-yl)(1-methyl-1H-1,2,3-triazol-5-yl)methanol

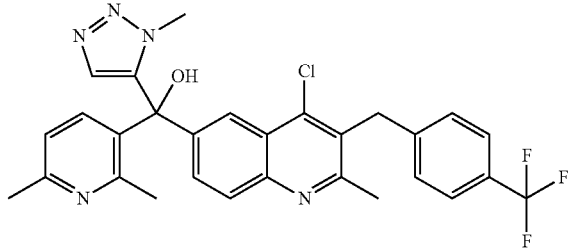 [SMILES: Cc1ccc(C(O)(c2ccc3nc(C)c(Cc4ccc(C(F)(F)F)cc4)c(Cl)c3c2)c2cnnn2C)c(C)n1]

Example 29a (4-Chloro-2-methyl-3-(4-(trifluoromethyl)benzyl) quinolin-6-yl)(1,2-dimethyl-1H-imidazol-5-yl)(1-methyl-1H-1,2,3-triazol-5-yl)methanol

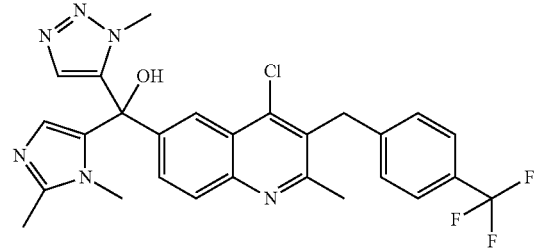 [SMILES: Cc1nc2ccc(C(O)(c3cnnn3C)c3cnc(C)n3C)cc2c(Cl)c1Cc1ccc(C(F)(F)F)cc1]

A 2.5 M solution of n-butyllithium in hexanes (0.34 mL, 0.844 mmol) was added dropwise by syringe to a stirring solution of 6-bromo-4-chloro-2-methyl-3-(4-(trifluoromethyl)benzyl)quinoline (350 mg, 0.844 mmol, Intermediate 26: step c) in dry tetrahydrofuran (6 mL) at −78° C. The resulting dark brown solution was stirred for 1 minute, whereupon a solution of (2,6-dimethylpyridin-3-yl)(1-methyl-1H-1,2,3-triazol-5-yl)methanone (180 mg, 0.844 mmol, Intermediate 19: step b) in dry tetrahydrofuran (2 mL) was added dropwise by syringe. After 1 minute, the flask was removed from the cooling bath. After 3 minutes, the flask was placed in an ice-water bath. After 15 minutes, water (2 mL) and ethyl acetate (10 mL) were added and the flask was removed from the cooling bath. The biphasic mixture was partitioned A 2.5 M solution of n-butyllithium in hexanes (0.290 mL, 0.725 mmol) was added dropwise by syringe to a stirring solution of 6-bromo-4-chloro-2-methyl-3-(4-(trifluoromethyl)benzyl)quinoline (300 mg, 0.723 mmol, Intermediate 26: step c) in dry tetrahydrofuran (6 mL) at −78° C. The resulting dark brown solution was stirred for 1 minute, whereupon a solution of (1,2-dimethyl-1H-imidazol-5-yl)(1-methyl-1H-1,2,3-triazol-5-yl)methanone (147 mg, 0.716 mmol, Intermediate 77: step b) in warm dry tetrahydrofuran (5 mL, warming was required to solubilize) was added dropwise by syringe. After 1 minute, the flask was removed from the cooling bath. After 3 minutes, the flask was placed in an ice-water bath. After 15 minutes, water (2 mL) and ethyl acetate (10 mL) were added and the flask was removed from the cooling bath. The biphasic mixture was partitioned between half-saturated aqueous sodium chloride solution (20 mL) and ethyl acetate (25 mL). The layers were separated. The organic layer was dried with sodium sulfate. The dry solution was filtered. Celite® (7 g) was added to the filtrate and the mixture was concentrated in vacuo. The dry solid was loaded onto a silica gel column for flash column chromatography. The column was eluted with 100% dichloromethane initially, grading to 10% methanol-dichloromethane provided the title compound as an off-white solid. $^1$H NMR (600 MHz, CDCl$_3$) δ ppm 8.31 (d, J=2.1 Hz, 1H), 7.91 (d, J=8.8 Hz, 1H), 7.54 (d, J=8.0 Hz, 2H), 7.52-7.49 (m, 1H), 7.22 (d, J=8.1 Hz, 2H), 7.11 (s, 1H), 6.47 (s, 1H), 6.06 (s, 1H), 4.44 (s, 2H), 3.92 (s, 3H), 3.37 (s, 3H), 2.65 (s, 3H), 2.21 (s, 3H); MS (ESI): mass calcd. for C$_{27}$H$_{24}$ClF$_3$N$_6$O, 540.2. m/z found, 541.0 [M+H]$^+$.

(4-Chloro-2-methyl-3-(4-(trifluoromethyl)benzyl)quinolin-6-yl)(1,2-dimethyl-1H-imidazol-5-yl)(1-methyl-1H-1,2,3-triazol-5-yl)methanol was purified by chiral SFC (Chiralpak AD-H, 5 μm, 250 mm×20 mm, mobile phase: 75% CO$_2$, 25% ethanol containing 0.3% isopropylamine) to provide two enantiomers. The first eluting enantiomer was Example 29b: $^1$H NMR (500 MHz, CDCl$_3$) δ ppm 8.31 (d, J=2.1 Hz, 1H), 7.92 (d, J=8.8 Hz, 1H), 7.55 (d, J=8.0 Hz, 2H), 7.49 (dd, J=8.8, 2.2 Hz, 1H), 7.25-7.20 (m, 2H), 7.16 (s, 1H), 6.11 (s, 1H), 5.44 (s, 1H), 4.47 (s, 2H), 3.94 (s, 3H), 3.40 (s, 3H), 2.67 (s, 3H), 2.28 (s, 3H); MS (ESI): mass calcd. for C$_{27}$H$_{24}$ClF$_3$N$_6$O, 540.2. m/z found, 541.0 [M+H]$^+$ and the second eluting enantiomer was Example 29c: $^1$H NMR (500 MHz, CDCl$_3$) δ ppm 8.30 (d, J=2.1 Hz, 1H), 7.93 (d, J=8.8 Hz, 1H), 7.55 (d, J=8.0 Hz, 2H), 7.52-7.47 (m, 1H), 7.23 (d, J=8.0 Hz, 2H), 7.17 (s, 1H), 6.12 (s, 1H), 5.14 (s, 1H), 4.47 (s, 2H), 3.94 (s, 3H), 3.41 (s, 3H), 2.67 (s, 3H), 2.30 (s, 3H); MS (ESI): mass calcd. for C$_{27}$H$_{24}$ClF$_3$N$_6$O, 540.2. m/z found, 541.1 [M+H]$^+$.

Example 30a (4-Chloro-2-methyl-3-(4-(trifluoromethyl)benzyl)quinolin-6-yl)(1-methyl-1H-imidazol-5-yl)(2-(trifluoromethyl)pyridin-4-yl)methanol

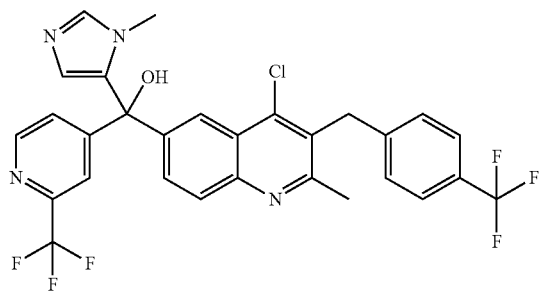 [SMILES: Cc1nc2ccc(C(O)(c3ccnc(C(F)(F)F)c3)c3cncn3C)cc2c(Cl)c1Cc1ccc(C(F)(F)F)cc1]

A 2.5 M solution of n-butyllithium in hexanes (0.290 mL, 0.723 mmol) was added dropwise by syringe to a stirring solution of 6-bromo-4-chloro-2-methyl-3-(4-(trifluoromethyl)benzyl)quinoline (300 mg, 0.723 mmol, Intermediate 26: step c) in dry tetrahydrofuran (5 mL) at −78° C. The resulting dark brown solution was stirred for 1 minute, whereupon a solution of (1-methyl-1H-imidazol-5-yl)(2-(trifluoromethyl)pyridin-4-yl)methanone (255 mg, 0.999 mmol, Intermediate 27: step b) in dry tetrahydrofuran (3 mL) was added dropwise by syringe. After 5 minutes, the flask was placed in an ice-water bath. After 30 minutes, water (2 mL) and ethyl acetate (15 mL) were added and the flask was removed from the cooling bath. The biphasic mixture was partitioned between half-saturated aqueous sodium chloride solution (20 mL) and ethyl acetate (25 mL). The layers were separated. The organic layer was dried with sodium sulfate. The dried solution was filtered. Celite® (7 g) was added to the filtrate and the mixture was concentrated in vacuo. The dry solid was loaded onto a silica gel column for flash column chromatography. Elution with 100% dichloromethane initially, grading to 7% methanol-dichloromethane provided the title compound as an off-white solid. $^1$H NMR (600 MHz, CDCl$_3$) δ ppm 8.68 (d, J=5.1 Hz, 1H), 8.27 (d, J=2.1 Hz, 1H), 7.99 (d, J=8.9 Hz, 1H), 7.94-7.92 (m, 1H), 7.68-7.64 (m, 1H), 7.52 (d, J=8.0 Hz, 2H), 7.51-7.49 (m, 1H), 7.25 (s, 1H), 7.21 (d, J=7.9 Hz, 2H), 6.31 (s, 1H), 5.88 (s, 1H), 4.52-4.41 (m, 2H), 3.34 (s, 3H), 2.65 (s, 3H); MS (ESI): mass calcd. for C$_{29}$H$_{21}$ClF$_6$N$_4$O, 590.1. m/z found, 591.0 [M+H]$^+$.

(4-Chloro-2-methyl-3-(4-(trifluoromethyl)benzyl)quinolin-6-yl)(1-methyl-1H-imidazol-5-yl)(2-(trifluoromethyl)pyridin-4-yl)methanol was purified by chiral SFC (Chiracel OJ-H, 5 μm, 250 mm×20 mm, mobile phase: 80% CO$_2$, 20% methanol containing 0.3% isopropylamine) to provide two enantiomers. The first eluting enantiomer was Example 30b: $^1$H NMR (500 MHz, CDCl$_3$) δ ppm 8.73 (d, J=5.1 Hz, 1H), 8.25 (d, J=2.1 Hz, 1H), 8.02 (d, J=8.9 Hz, 1H), 7.92-7.88 (m, 1H), 7.69-7.64 (m, 1H), 7.56-7.50 (m, 3H), 7.43 (s, 1H), 7.21 (d, J=8.0 Hz, 2H), 6.46 (d, J=1.1 Hz, 1H), 4.47 (s, 2H), 4.16 (s, 1H), 3.38 (s, 3H), 2.66 (s, 3H); MS (ESI): mass calcd. for C$_{29}$H$_{21}$ClF$_6$N$_4$O, 590.1. m/z found, 591.1 [M+H]$^+$ and the second eluting enantiomer was Example 30c: $^1$H NMR (500 MHz, CDCl$_3$) δ ppm 8.73 (d, J=5.1 Hz, 1H), 8.26 (d, J=2.1 Hz, 1H), 8.01 (d, J=8.8 Hz, 1H), 7.93-7.88 (m, 1H), 7.70-7.64 (m, 1H), 7.56-7.50 (m, 3H), 7.43-7.37 (m, 1H), 7.21 (d, J=8.0 Hz, 2H), 6.43 (d, J=1.1 Hz, 1H), 4.50 (s, 1H), 4.47 (s, 2H), 3.37 (s, 3H), 2.66 (s, 3H); MS (ESI): mass calcd. for C$_{29}$H$_{21}$ClF$_6$N$_4$O, 590.1. m/z found, 591.1 [M+H]$^+$.

Example 31 tert-Butyl 3-((4-chloro-2-methyl-3-(4-(trifluoromethyl)benzyl)quinolin-6-yl)(hydroxy)(1-methyl-1H-1,2,3-triazol-5-yl)methyl)azetidine-1-carboxylate

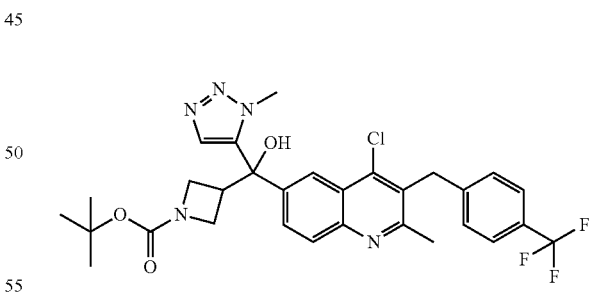

A solution of n-butyllithium in hexanes (2.5 M, 0.8 mL, 2.0 mmol) was added dropwise by syringe to a stirring solution of 6-bromo-4-chloro-2-methyl-3-(4-(trifluoromethyl)benzyl)quinoline (830 mg, 2.0 mmol, Intermediate 26: step c) in dry tetrahydrofuran (14 mL) at −78° C. After 2 minutes, a solution of tert-butyl 3-(1-methyl-1H-1,2,3-triazole-5-carbonyl)azetidine-1-carboxylate (567 mg, 2.13 mmol, Intermediate 28: step b) in dry tetrahydrofuran (6 mL) was added by syringe over 1 minute. After 5 minutes, the flask was removed from the cooling bath. After 5 minutes, the flask was placed into an ice-water bath. After 15 minutes, water (10 mL) and ethyl acetate (20 mL) were added. The biphasic mixture was warmed to 23° C. and then partitioned between half-saturated aqueous sodium chloride solution (20 mL) and ethyl acetate (30 mL). The layers were separated. The organic layer was dried over sodium sulfate. The dried solution was filtered. Celite® (7 g) was added to the filtrate and the mixture was concentrated in vacuo. The dry solid was loaded onto a silica gel column for flash column chromatography. Elution with 30% ethyl acetate-hexanes initially, grading to 100% ethyl acetate provided the title compound as a light yellow solid. $^1$H NMR (500 MHz, CDCl$_3$) δ 8.38 (d, J=2.0 Hz, 1H), 7.97 (d, J=8.8 Hz, 1H), 7.56 (s, 1H), 7.54 (d, J=8.1 Hz, 2H), 7.45-7.41 (m, 1H), 7.23 (d, J=8.0 Hz, 2H), 4.48 (s, 2H), 4.26-4.20 (m, 1H), 4.04-3.99 (m, 1H), 3.96-3.91 (m, 1H), 3.70 (s, 3H), 3.64 (t, J=8.8 Hz, 1H), 3.54-3.47 (m, 1H), 2.65 (s, 3H), 1.39 (s, 9H); MS (ESI): mass calcd. for $C_{30}H_{31}ClF_3N_5O_3$, 601.2. m/z found, 602.1 [M+H]$^+$.

Example 32a 1-(3-((4-Chloro-2-methyl-3-(4-(trifluoromethyl)benzyl)quinolin-6-yl)(hydroxy)(1-methyl-1H-1,2,3-triazol-5-yl)methyl)azetidin-1-yl)ethanone

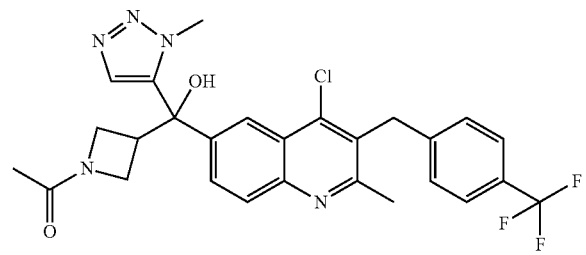

A mixture containing tert-butyl 3-((4-chloro-2-methyl-3-(4-(trifluoromethyl)benzyl)quinolin-6-yl)(hydroxy)(1-methyl-1H-1,2,3-triazol-5-yl)methyl)azetidine-1-carboxylate (250 mg, 0.42 mmol, Example 31) and trifluoroacetic acid (0.32 mL, 0.32 mmol) in dichloromethane (2 mL) was stirred at 23° C. After 18 hours, dichloromethane (50 mL) and saturated aqueous sodium bicarbonate solution (25 mL) were added. The biphasic mixture was stirred for 5 minutes. The layers were separated. The organic layer was dried with sodium sulfate and the dried solution was filtered. The filtrate was concentrated to provide a residue. This residue was used in the next step without further purification. A mixture of the residue (174 mg), triethylamine (0.25 mL), and acetic anhydride (0.14 mL) in dichloromethane (3.5 mL) was stirred at 46° C. After 2 hours, the flask was cooled to 23° C. Dichloromethane (40 mL) and saturated aqueous sodium bicarbonate solution (25 mL) were added. The biphasic mixture was stirred for 10 minutes at 23° C. The layers were separated. The organic layer was dried with sodium sulfate and the dried solution was filtered. Celite® (3 g) was added to the filtrate and the mixture was concentrated in vacuo. The dry solid was loaded onto a silica gel column for flash-column chromatography. Elution with 100% dichloromethane initially, grading to 5% methanol-dichloromethane provided the title compound as an off-white solid. $^1$H NMR (500 MHz, CDCl$_3$, 3:1 mixture of amide rotamers, asterisk denotes minor rotamer) δ ppm 8.44 (d, J=2.0 Hz, 1H), 8.38* (d, J=2.1 Hz, 1H), 8.00-7.94 (m, 1H), 7.60-7.51 (m, 3H), 7.48-7.42 (m, 1H), 7.25-7.20 (m, 2H), 6.23 (s, 1H), 5.09* (s, 1H), 4.54-4.45 (m, 2H), 4.43-4.36* (m, 1H), 4.34-4.28* (m, 1H), 4.27-4.19 (m, 1H), 4.19-4.13 (m, 1H), 4.08-3.96 (m, 1H), 3.80-3.65 (m, 4H), 3.63-3.54* (m, 1H), 3.54-3.46 (m, 1H), 2.69-2.63 (m, 3H), 1.82* (s, 3H), 1.65-1.54 (m, overlap with water, 3H); MS (ESI): mass calcd. for $C_{27}H_{25}ClF_3N_5O_2$, 543.2. m/z found, 544.1 [M+H]$^+$.

1-(3-((4-Chloro-2-methyl-3-(4-(trifluoromethyl)benzyl)quinolin-6-yl)(hydroxy)(1-methyl-1H-1,2,3-triazol-5-yl)methyl)azetidin-1-yl)ethanone was purified by chiral SFC (Chiralpak AD-H, 5 µm, 250 mm×20 mm, mobile phase: 70% CO$_2$, 30% isopropanol containing 0.3% isopropylamine) to provide two enantiomers. The first eluting enantiomer was Example 32b: $^1$H NMR (500 MHz, CDCl$_3$, 1.5:1 mixture of amide rotamers, asterisk denotes minor amide rotamer) δ ppm 8.41 (d, J=2.0 Hz, 1H), 8.37* (d, J=2.0 Hz, 1H), 8.00-7.95 (m, 1H), 7.63-7.57 (m, 1H), 7.56-7.50 (m, 2H), 7.48-7.43 (m, 1H), 7.25-7.18 (m, 2H), 5.28 (s, 1H), 4.81* (s, 1H), 4.52-4.45 (m, 2H), 4.42-4.37* (m, 1H), 4.32-4.26* (m, 1H), 4.25-4.14 (m, 2H), 4.14-4.07 (m, 1H), 4.05-3.99* (m, 1H), 3.83-3.69 (m, 4H), 3.63-3.50 (m, 1H), 2.66 (s, 3H), 2.65* (s, 3H), 1.84 (s, 3H), 1.79* (s, 3H); MS (ESI): mass calcd. for $C_{27}H_{25}ClF_3N_5O_2$, 543.2. m/z found, 544.1 [M+H]$^+$ and the second eluting enantiomer was Example 32c: $^1$H NMR (500 MHz, CDCl$_3$, 1.4:1 mixture of amide rotamers, asterisk denotes minor amide rotamer) δ ppm 8.41 (d, J=2.0 Hz, 1H), 8.38-8.35* (m, 1H), 8.01-7.95 (m, 1H), 7.63-7.58 (m, 1H), 7.57-7.50 (m, 2H), 7.48-7.42 (m, 1H), 7.24-7.18 (m, 2H), 5.21 (s, 1H), 4.73* (s, 1H), 4.53-4.44 (m, 2H), 4.43-4.37* (m, 1H), 4.31-4.26* (m, 1H), 4.25-4.19 (m, 1H), 4.19-4.14 (m, 1H), 4.14-4.08 (m, 1H), 4.05-3.99* (m, 1H), 3.83-3.69 (m, 4H), 3.64-3.50 (m, 1H), 2.66 (s, 3H), 2.65* (s, 3H), 1.84 (s, 3H), 1.79* (s, 3H); MS (ESI): mass calcd. for $C_{27}H_{25}ClF_3N_5O_2$, 543.2. m/z found, 544.1 [M+H]$^+$.

Example 33a (4-Chloro-2-ethyl-3-(4-(trifluoromethyl)benzyl)quinolin-6-yl)(1-methyl-1H-1,2,3-triazol-5-yl)(tetrahydro-2H-pyran-4-yl)methanol

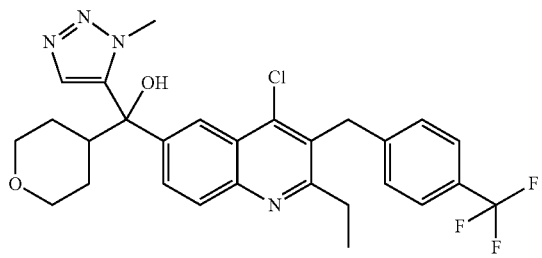 [SMILES: CCc1nc2ccc(C(O)(c3cnnn3C)C3CCOCC3)cc2c(Cl)c1Cc1ccc(C(F)(F)F)cc1]

A 2.5 M solution of n-butyllithium in hexanes (0.220 mL, 0.550 mmol) was added dropwise by syringe to a stirring solution of 6-bromo-4-chloro-2-ethyl-3-(4-(trifluoromethyl)benzyl)quinoline (245 mg, 0.572 mmol, Intermediate 5: step c) in dry tetrahydrofuran (4 mL) at −78° C. The resulting dark brown solution was stirred for 1 minute, whereupon a solution of (1-methyl-1H-1,2,3-triazol-5-yl)(tetrahydro-2H-pyran-4-yl)methanone (100 mg, 0.512 mmol, Intermediate 30) in dry tetrahydrofuran (1 mL) was added dropwise by syringe. After 1 minute, the flask was removed from the cooling bath and allowed to slowly warm. After 3 minutes, the flask was placed into an ice-water bath. After 20 minutes, water (2 mL) and ethyl acetate (15 mL) were added and the flask was removed from the cooling bath. After warming to 23° C., the biphasic mixture was partitioned between water (20 mL) and ethyl acetate (75 mL). The layers were separated. The organic layer was dried with sodium sulfate. The dried solution was filtered. Celite® (5 g) was added to the filtrate and the mixture was concentrated in vacuo to afford a free-flowing powder. The powder was loaded onto a silica gel column for flash column chromatography. Elution with 100% dichloromethane initially, grading to 5% methanol-dichloromethane provided the title compound as a light yellow powder. $^1$H NMR (500 MHz, CDCl$_3$) δ ppm 8.23 (d, J=2.1 Hz, 1H), 8.01 (d, J=8.8 Hz, 1H), 7.79 (s, 1H), 7.53 (d, J=8.0 Hz, 2H), 7.50-7.44 (m, 1H), 7.21 (d, J=8.0 Hz, 2H), 4.50 (s, 2H), 4.16-4.08 (m, 1H), 3.98-3.89 (m, 1H), 3.77 (s, 3H), 3.59-3.50 (m, 1H), 3.41-3.31 (m, 1H), 2.98-2.89 (m, 2H), 2.75 (s, 1H), 2.61-2.51 (m, 1H), 2.04-1.96 (m, 1H), 1.69-1.60 (m, 1H), 1.53-1.41 (m, 1H), 1.35-1.28 (m, 3H), 1.05 (d, J=13.4 Hz, 1H); MS (ESI): mass calcd. for C$_{28}$H$_{28}$ClF$_3$N$_4$O$_2$, 544.2. m/z found, 545.1 [M+H]$^+$.

(4-Chloro-2-ethyl-3-(4-(trifluoromethyl)benzyl)quinolin-6-yl)(1-methyl-1H-1,2,3-triazol-5-yl)(tetrahydro-2H-pyran-4-yl)methanol was purified by chiral SFC (Chiralpak AD-H, 5 μm, 250 mm×20 mm, mobile phase: 85% CO$_2$, 15% ethanol containing 0.3% isopropylamine) to provide two enantiomers. The first eluting enantiomer was Example 33b: $^1$H NMR (500 MHz, CDCl$_3$) δ ppm 8.23 (d, J=2.1 Hz, 1H), 8.01 (d, J=8.8 Hz, 1H), 7.82 (s, 1H), 7.53 (d, J=8.0 Hz, 2H), 7.47 (dd, J=8.8, 2.1 Hz, 1H), 7.21 (d, J=8.0 Hz, 2H), 4.50 (s, 2H), 4.17-4.06 (m, 1H), 3.98-3.89 (m, 1H), 3.77 (s, 3H), 3.60-3.50 (m, 1H), 3.43-3.29 (m, 1H), 3.00-2.86 (m, 2H), 2.61-2.51 (m, 1H), 2.50 (s, 1H), 2.01 (d, J=13.0 Hz, 1H), 1.73-1.58 (m, 1H), 1.53-1.40 (m, 1H), 1.35-1.26 (m, 3H), 1.05 (d, J=13.3 Hz, 1H); MS (ESI): mass calcd. for C$_{28}$H$_{28}$ClF$_3$N$_4$O$_2$, 544.2. m/z found, 545.1 [M+H]$^+$ and the second eluting enantiomer was Example 33c: $^1$H NMR (500 MHz, CDCl$_3$) δ ppm 8.23 (d, J=2.1 Hz, 1H), 8.01 (d, J=8.8 Hz, 1H), 7.81 (s, 1H), 7.53 (d, J=8.0 Hz, 2H), 7.47 (dd, J=8.8, 2.1 Hz, 1H), 7.21 (d, J=8.0 Hz, 2H), 4.50 (s, 2H), 4.17-4.07 (m, 1H), 3.97-3.90 (m, 1H), 3.77 (s, 3H), 3.60-3.50 (m, 1H), 3.40-3.31 (m, 1H), 2.98-2.89 (m, 2H), 2.62-2.50 (m, 2H), 2.01 (d, J=12.9 Hz, 1H), 1.69-1.59 (m, 1H), 1.53-1.42 (m, 1H), 1.34-1.27 (m, 3H), 1.10-1.01 (m, 1H); MS (ESI): mass calcd. for C$_{28}$H$_{28}$ClF$_3$N$_4$O$_2$, 544.2. m/z found, 545.2 [M+H]$^+$.

Example 34a (4-Chloro-2-ethyl-3-(4-(trifluoromethyl)benzyl)quinolin-6-yl)(1,2-dimethyl-1H-imidazol-5-yl)(tetrahydro-2H-pyran-4-yl)methanol

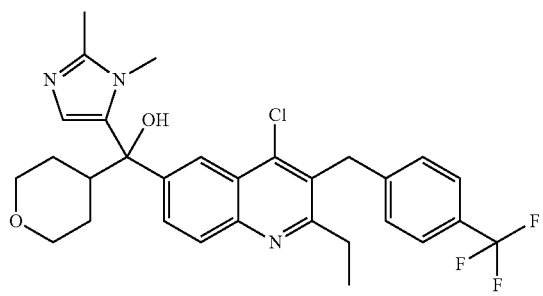 [SMILES: CCc1nc2ccc(C(O)(c3cnc(C)n3C)C3CCOCC3)cc2c(Cl)c1Cc1ccc(C(F)(F)F)cc1]

A 2.5 M solution of n-butyllithium in hexanes (0.200 mL, 0.500 mmol) was added dropwise by syringe to a stirring solution of 6-bromo-4-chloro-2-ethyl-3-(4-(trifluoromethyl)benzyl)quinoline (232 mg, 0.541 mmol, Intermediate 5: step c) in dry tetrahydrofuran (4 mL) at −78° C. The resulting dark brown solution was stirred for 1 minute, whereupon a solution of (1,2-dimethyl-1H-imidazol-5-yl)(tetrahydro-2H-pyran-4-yl)methanone (100 mg, 0.480 mmol, Intermediate 31) in dry tetrahydrofuran (0.8 mL) was added dropwise by syringe. After 1 minute, the flask was removed from the cooling bath and allowed to slowly warm. After 3 minutes, the flask was placed into an ice-water bath. After 20 minutes, water (2 mL) and ethyl acetate (50 mL) were added and the flask was removed from the cooling bath. After warming to 23° C., the biphasic mixture was partitioned between water (20 mL) and ethyl acetate (50 mL). The layers were separated. The organic layer was dried with sodium sulfate. The dried solution was filtered. Celite® (5 g) was added to the filtrate and the mixture was concentrated in vacuo to afford a free-flowing powder. The powder was loaded onto a silica gel column for flash-column chromatography. Elution with 100% dichloromethane initially, grading to 5% methanol-dichloromethane provided the title compound as an off-white solid. $^1$H NMR (500 MHz, CDCl$_3$) δ ppm 8.26 (s, 1H), 7.98 (d, J=8.6 Hz, 1H), 7.56-7.48 (m, 3H), 7.22 (d, J=7.9 Hz, 2H), 7.08 (s, 1H), 4.50 (s, 2H), 4.12-4.05 (m, 1H), 3.94-3.86 (m, 1H), 3.58-3.48 (m, 1H), 3.39-3.29 (m, 1H), 3.16 (s, 3H), 2.97-2.89 (m, 2H), 2.55-2.45 (m, 1H), 2.41 (s, 1H), 2.28 (s, 3H), 2.19-2.11 (m, 1H), 1.62-1.53 (m, 1H), 1.48-1.36 (m, 1H), 1.30 (t, J=7.5 Hz, 3H), 1.08-1.02 (m, 1H); MS (ESI): mass calcd. for C$_{30}$H$_{31}$ClF$_3$N$_3$O$_2$, 557.2. m/z found, 558.2 [M+H]$^+$.

(4-Chloro-2-ethyl-3-(4-(trifluoromethyl)benzyl)quinolin-6-yl)(1,2-dimethyl-1H-imidazol-5-yl)(tetrahydro-2H-pyran-4-yl)methanol was purified by chiral SFC (Chiralpak AD-H, 5 μm, 250 mm×20 mm, mobile phase: 75% CO$_2$, 25% methanol containing 0.3% isopropylamine) to provide two enantiomers. The first eluting enantiomer was Example 34b: $^1$H NMR (500 MHz, CDCl$_3$) δ ppm 8.26 (s, 1H), 7.98 (d, J=8.8 Hz, 1H), 7.57-7.48 (m, 3H), 7.22 (d, J=8.0 Hz, 2H), 7.11 (s, 1H), 4.50 (s, 2H), 4.13-4.05 (m, 1H), 3.94-3.86 (m, 1H), 3.60-3.48 (m, 1H), 3.39-3.29 (m, 1H), 3.17 (s, 3H), 2.98-2.89 (m, 2H), 2.55-2.45 (m, 1H), 2.30 (s, 3H), 2.20 (s, 1H), 2.18-2.11 (m, 1H), 1.66-1.54 (m, under water peak, 1H), 1.47-1.37 (m, 1H), 1.34-1.26 (m, 3H), 1.09-1.01 (m, 1H); MS (ESI): mass calcd. for C$_{30}$H$_{31}$ClF$_3$N$_3$O$_2$, 557.2. m/z found, 558.2 [M+H]$^+$ and the second eluting enantiomer was Example 34c: $^1$H NMR (500 MHz, CDCl$_3$) δ ppm 8.26 (s, 1H), 7.98 (d, J=8.8 Hz, 1H), 7.56-7.47 (m, 3H), 7.22 (d, J=8.0 Hz, 2H), 7.11 (s, 1H), 4.50 (s, 2H), 4.12-4.04 (m, 1H), 3.93-3.87 (m, 1H), 3.56-3.49 (m, 1H), 3.38-3.30 (m, 1H), 3.17 (s, 3H), 2.97-2.89 (m, 2H), 2.54-2.45 (m, 1H), 2.29 (s, 3H), 2.21 (s, 1H), 2.18-2.12 (m, 1H), 1.65-1.54 (m, peak under water, 1H), 1.48-1.37 (m, 1H), 1.33-1.27 (m, 3H), 1.10-1.00 (m, 1H); MS (ESI): mass calcd. for C$_{30}$H$_{31}$ClF$_3$N$_3$O$_2$, 557.2. m/z found, 558.2 [M+H]$^+$.

Example 35

1-(4-((3-(4-(1H-Pyrazol-1-yl)benzyl)-4-chloro-2-ethylquinolin-6-yl)(hydroxy)(phenyl)methyl)piperidin-1-yl)ethanone

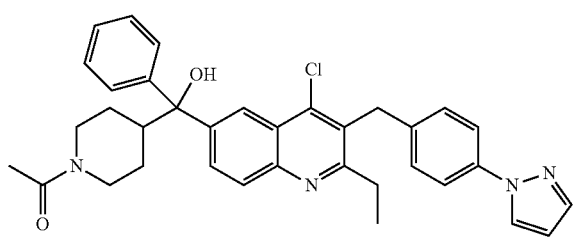 [SMILES: CCc1nc2ccc(C(O)(c3ccccc3)C3CCN(C(C)=O)CC3)cc2c(Cl)c1Cc1ccc(-n2cccn2)cc1]

A 2.5 M solution of n-butyllithium in hexanes (0.265 mL, 0.662 mmol) was added dropwise by syringe to a stirring solution of 3-(4-(1H-pyrazol-1-yl)benzyl)-6-bromo-4-chloro-2-ethylquinoline (300 mg, 0.703 mmol, Intermediate 32: step d) in dry tetrahydrofuran (4 mL) at −78° C. The resulting solution was stirred for 1 minute, whereupon a solution of 1-(4-benzoylpiperidin-1-yl)ethanone (165 mg, 0.713 mmol, Intermediate 18) in dry tetrahydrofuran (3 mL) was added dropwise by syringe. After 1 minute, the flask was removed from the cooling bath and allowed to slowly warm. After 3 minutes, the flask was placed into an ice-water bath. After 20 minutes, water (2 mL) and ethyl acetate (50 mL) were added and the flask was removed from the cooling bath. After warming to 23° C., the biphasic mixture was partitioned between water (20 mL) and ethyl acetate (50 mL). The layers were separated. The organic layer was dried with sodium sulfate. The dried solution was filtered. Celite® (6 g) was added to the filtrate and the mixture was concentrated in vacuo to afford a free-flowing powder. The powder was loaded onto a silica gel column for flash-column chromatography. Elution with 100% dichloromethane initially, grading to 5% methanol-dichloromethane provided the title compound as a white solid. $^1$H NMR (500 MHz, CDCl$_3$) δ 8.41 (d, J=11.2 Hz, 1H), 8.03-7.94 (m, 1H), 7.86 (d, J=2.5 Hz, 1H), 7.78-7.71 (m, 1H), 7.70 (d, J=1.7 Hz, 1H), 7.61-7.52 (m, 4H), 7.39-7.32 (m, 2H), 7.26-7.21 (m, 1H), 7.16 (d, J=8.2 Hz, 2H), 6.47-6.41 (m, 1H), 4.78-4.66 (m, 1H), 4.47 (s, 2H), 3.90-3.79 (m, 1H), 3.18-3.03 (m, 1H), 3.00-2.89 (m, 2H), 2.87-2.76 (m, 1H), 2.67-2.52 (m, 1H), 2.27 (d, J=2.4 Hz, 1H), 2.11-2.01 (m, 3H), 1.79-1.65 (m, 1H), 1.53-1.31 (m, 3H), 1.31-1.21 (m, 3H); MS (ESI): mass calcd. for C$_{35}$H$_{35}$ClN$_4$O$_2$, 578.2. m/z found, 579.1 [M+H]$^+$.

Example 36

6-((1-Acetylazetidin-3-yl)(hydroxy)(1-methyl-1H-1,2,3-triazol-5-yl)methyl)-2-ethyl-3-(4-(trifluoromethyl)benzyl)quinoline-4-carbonitrile

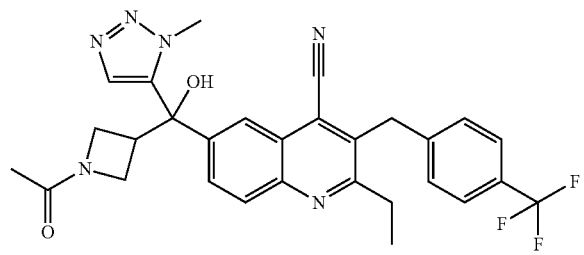 [SMILES: CCc1nc2ccc(C(O)(c3cnnn3C)C3CN(C(C)=O)C3)cc2c(C#N)c1Cc1ccc(C(F)(F)F)cc1]

Dimethylacetamide (5 mL, sparged with nitrogen gas) was added to a mixture containing 1-(3-((4-chloro-2-ethyl-3-(4-(trifluoromethyl)benzyl)quinolin-6-yl)(hydroxy)(1-methyl-1H-1,2,3-triazol-5-yl)methyl)azetidin-1-yl)ethanone (200 mg, 0.358 mmol, Intermediate 79b), zinc cyanide (85 mg, 0.724 mmol), zinc powder (10 mg, 0.153 mmol), 2-dicyclohexylphosphino-2',4',6'-triisopropylbiphenyl (XPhos, 36 mg, 0.0755 mmol) and tris(dibenzylideneacetone)dipalladium (33 mg, 0.0360 mmol). The resulting heterogeneous mixture was heated to 120° C. After 6 hours, the mixture was cooled to 23° C. and diluted with ethyl acetate (50 mL). The mixture was filtered through Celite®, rinsing with ethyl acetate. Hexanes (25 mL) were added to the filtrate and the resulting solution was washed with water (2×30 mL) and saturated aqueous sodium chloride solution (25 mL). The washed solution was dried with sodium sulfate and the dried solution was filtered. Celite® (6 g) was added to the filtrate and the mixture was concentrated to provide a free-flowing powder. The powder was loaded onto a column for flash-chromatography purification. Elution with dichloromethane initially, grading to 10% methanol-dichloromethane provided an off white solid. The purified solid was dissolved in a minimal amount of acetonitrile-water and the resulting solution was lyophilized to provide the title compound as a white solid. $^1$H NMR (400 MHz, CDCl$_3$, 3:1 mixture of rotamers, * denotes minor rotamer peaks) δ ppm 8.51 (d, J=2.1 Hz, 1H), 8.43* (d, J=2.0 Hz, 1H), 8.10-8.01 (m, 1H), 7.61 (s, 1H), 7.59-7.54 (m, 2H), 7.48* (dd, J=8.8, 2.0 Hz, 1H), 7.44-7.39 (m, 1H), 7.26-7.20 (m, 1H), 6.29 (s, 1H), 5.95* (s, 1H), 4.60-4.51 (m, 2H), 4.45-4.31 (m, 1H), 4.26-4.11 (m, 2H), 4.07-3.99* (m, 1H), 3.82-3.48 (m, 5H), 3.01-2.87 (m, 2H), 1.86 (s, 3H), 1.75* (s, 3H), 1.34-1.23 (m, 3H); MS (ESI): mass calcd. for C$_{29}$H$_{27}$F$_3$N$_6$O$_2$, 548.2. m/z found, 549.1 [M+H]$^+$. The enantiomeric purity of Example 36 was determined to be 99.5% by chiral SFC (Chiralpak AD-H, 4.6×20 mm, 85% CO$_2$, 15% ethanol containing 0.2% triethylamine).

Example 37

6-((1-Acetylazetidin-3-yl)(hydroxy)(1-methyl-1H-1,2,3-triazol-5-yl)methyl)-2-ethyl-3-(4-(trifluoromethyl)benzyl)quinoline-4-carbonitrile

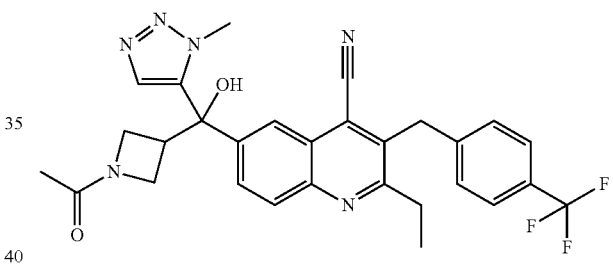

Dimethylacetamide (5 mL, sparged with nitrogen gas) was added to a mixture containing 1-(3-((4-chloro-2-ethyl-3-(4-(trifluoromethyl)benzyl)quinolin-6-yl)(hydroxy)(1-methyl-1H-1,2,3-triazol-5-yl)methyl)azetidin-1-yl)ethanone (200 mg, 0.358 mmol, Intermediate 79c), zinc cyanide (85 mg, 0.724 mmol), zinc powder (10 mg, 0.153 mmol), 2-dicyclohexylphosphino-2',4',6'-triisopropylbiphenyl (XPhos, 36 mg, 0.0755 mmol) and tris(dibenzylideneacetone)dipalladium (33 mg, 0.0360 mmol). The resulting heterogeneous mixture was heated to 120° C. After 6 hours, the mixture was cooled to 23° C. and diluted with 50 mL ethyl acetate. The mixture was filtered through Celite®, rinsing with ethyl acetate. Hexanes (25 mL) were added to the filtrate and the resulting solution was washed with water (2×30 mL) and saturated aqueous sodium chloride solution (25 mL). The washed solution was dried with sodium sulfate and the dried solution was filtered. Celite® (6 g) was added to the filtrate and the mixture was concentrated to provide a free-flowing powder. The powder was loaded onto a column for flash-chromatography purification. Elution with dichloromethane initially, grading to 10% methanol-dichloromethane provided an off white solid. The purified solid was dissolved in a minimal amount of acetonitrile-water and the resulting solution was lyophilized to provide the title compound as a white solid. $^1$H NMR (500 MHz, CDCl$_3$, 3:1 ratio of rotamers, * denotes minor rotamer) δ ppm 8.51 (d, J=2.0 Hz, 1H), 8.42* (d, J=2.0 Hz, 1H), 8.09-8.03 (m, 1H), 7.61 (s, 1H), 7.59-7.54 (m, 2H), 7.50-7.46* (m, 1H), 7.41 (dd, J=8.8, 2.0 Hz, 1H), 7.25-7.21 (m, 1H), 6.18 (s, 1H), 5.82* (s, 1H), 4.60-4.50 (m, 2H), 4.44-4.38* (m, 1H), 4.38-4.32* (m, 1H), 4.24-4.14 (m, 2H), 4.02* (dd, J=10.0, 5.8 Hz, 1H), 3.82-3.48 (m, 5H), 2.98-2.88 (m, 2H), 1.86 (s, 3H), 1.76* (s, 3H), 1.33-1.24 (m, 3H); MS (ESI): mass calcd. for $C_{29}H_{27}F_3N_6O_2$, 548.2. m/z found, 549.2 $[M+H]^+$. The enantiomeric purity of Example 37 was determined to be 100% and opposite that of Example 36 by chiral SFC (Chiralpak AD-H, 4.6×20 mm, 85% $CO_2$, 15% ethanol containing 0.2% triethylamine).

Example 38a 4-((4-Chloro-2-methoxy-3-((6-(trifluoromethyl)pyridin-3-yl)methyl)quinolin-6-yl)(hydroxy)(1-methyl-1H-imidazol-5-yl)methyl)benzonitrile

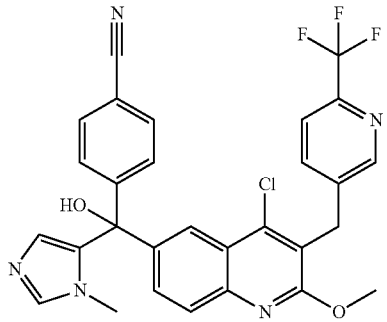 [SMILES: COc1nc2ccc(C(O)(c3ccc(C#N)cc3)c3cncn3C)cc2c(Cl)c1Cc1ccc(C(F)(F)F)nc1]

A solution of n-BuLi (2.5 M in hexanes, 0.7 mL, 1.75 mmol) was added dropwise by syringe to a solution of 6-bromo-4-chloro-2-methoxy-3-((6-(trifluoromethyl)pyridin-3-yl)methyl)quinoline (0.755 g, 0.175 mmol, Intermediate 45: step d) in dry THF (9 mL) in a dry ice-acetone bath. After 1-2 minutes, a solution of 4-(1-methyl-1H-imidazole-5-carbonyl)benzonitrile (0.370 g, 1.75 mmol, Intermediate 43: step c) in dry THF (17 mL) was added dropwise. The reaction was stirred for 5 minutes, then was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The crude product was purified by flash column chromatography (silica gel, 0-5% MeOH-DCM) to provide the title compound. $^1$H NMR (400 MHz, DMSO-$d_6$) δ 8.74 (d, J=2.1 Hz, 1H), 8.08 (d, J=2.1 Hz, 1H), 7.88-7.82 (m, 4H), 7.81-7.77 (m, 1H), 7.73-7.71 (m, 1H), 7.60 (dd, J=8.7, 2.1 Hz, 1H), 7.52 (dt, J=8.5, 2.0 Hz, 2H), 7.27 (s, 1H), 6.17 (d, J=1.2 Hz, 1H), 4.37 (s, 2H), 4.03 (s, 3H), 3.32 (s, 3H); MS m/e 564.5 $[M+H]^+$.

Example 38a was purified by chiral SFC (ChiralPak AD, 70:30 $CO_2$:mixture of MeOH/iPrOH (50:50+0.3% iPrNH$_2$)) to provide two pure enantiomers. The first eluting enantiomer was Example 38b: $^1$H NMR (500 MHz, CDCl$_3$) δ 8.72-8.70 (m, 1H), 8.11 (d, J=2.1 Hz, 1H), 7.79 (d, J=8.8 Hz, 1H), 7.77-7.74 (m, 1H), 7.66-7.62 (m, 2H), 7.57-7.53 (m, 4H), 7.29-7.27 (m, 1H), 6.30 (s, 1H), 4.98 (s, 1H), 4.34 (s, 2H), 4.08 (s, 3H), 3.33 (s, 3H); MS m/e 564.0 $[M+H]^+$. The second eluting enantiomer was Example 38c: $^1$H NMR (500 MHz, CDCl$_3$) δ 8.71 (d, J=2.1 Hz, 1H), 8.11 (d, J=2.1 Hz, 1H), 7.78 (d, J=8.8 Hz, 1H), 7.75 (dd, J=8.1, 2.2 Hz, 1H), 7.66-7.62 (m, 2H), 7.57-7.53 (m, 4H), 7.27 (s, 1H), 6.30 (s, 1H), 5.07 (s, 1H), 4.34 (s, 2H), 4.08 (s, 3H), 3.33 (s, 3H); MS m/e 564.0 $[M+H]^+$.

Example 39a

4-Chloro-2-methoxy-3-((6-(trifluoromethyl)pyridin-3-yl)methyl)quinolin-6-yl)(4-chlorophenyl)(1-methyl-1H-imidazol-5-yl)methanol

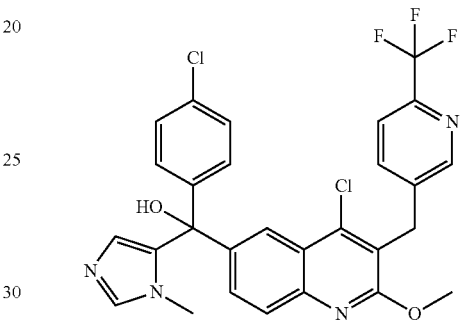

A solution of n-BuLi (2.5 M in hexanes, 0.36 mL, 0.90 mmol) was added dropwise by syringe to a solution of 6-bromo-4-chloro-2-methoxy-3-((6-(trifluoromethyl)pyridin-3-yl)methyl)quinoline (0.404 g, 0.936 mmol, Intermediate 45: step d) in dry THF (18 mL) in a dry ice-acetone bath. After 1-2 minutes, a solution of (4-chlorophenyl)(1-methyl-1H-imidazol-5-yl)methanone (0.200 g, 0.904 mmol, Intermediate 43: step b) in dry THF (4 mL) was added dropwise. The reaction was stirred for 5 minutes, then was moved into an ice bath and allowed to warm to ambient temperature overnight. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The crude product was purified by flash column chromatography (silica gel, 0-3% MeOH-DCM) to provide the title compound. $^1$H NMR (400 MHz, CDCl$_3$) δ 8.71 (d, J=1.6 Hz, 1H), 8.13 (d, J=2.0 Hz, 1H), 7.79-7.73 (m, 2H), 7.57-7.52 (m, 2H), 7.33-7.25 (m, 4H), 7.16 (s, 1H), 6.24 (d, J=1.0 Hz, 1H), 5.71 (s, 1H), 4.33 (s, 2H), 4.08 (s, 3H), 3.32 (s, 3H); MS m/e 573.0 $[M+H]^+$.

Example 39a was purified by chiral SFC (ChiralPak AD, 70:30 $CO_2$:mixture of MeOH/iPrOH (50:50+0.3% iPrNH$_2$)) to provide two pure enantiomers. The first eluting enantiomer was Example 39b: $^1$H NMR (400 MHz, CDCl$_3$) δ 8.71 (s, 1H), 8.12 (d, J=2.0 Hz, 1H), 7.79-7.72 (m, 2H), 7.57-7.52 (m, 2H), 7.31 (s, 4H), 7.20 (s, 1H), 6.27 (s, 1H), 4.33 (s, 2H), 4.07 (s, 3H), 3.33 (s, 3H); MS m/e 572.1 [M] The second eluting enantiomer was Example 39c: $^1$H NMR (400 MHz, CDCl$_3$) δ 8.72 (s, 1H), 8.12 (d, J=2.0 Hz, 1H), 7.79-7.72 (m, 2H), 7.57-7.52 (m, 2H), 7.30 (s, 4H), 7.22 (s, 1H), 6.28 (s, 1H), 4.33 (s, 2H), 4.07 (s, 3H), 3.33 (s, 3H); MS m/e 572.1 [M]+.

Example 40a (4-Chloro-2-methoxy-3-((6-(trifluoromethyl)pyridin-3-yl)methyl)quinolin-6-yl)(2,6-dimethylpyridin-3-yl)(1-methyl-1H-1,2,3-triazol-5-yl)methanol

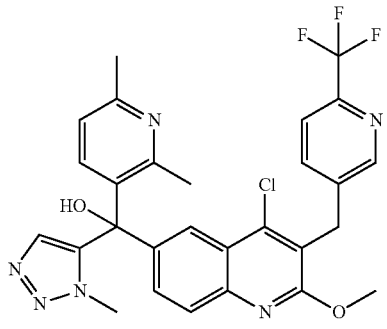 [SMILES: COc1nc2ccc(C(O)(c3ccc(C)nc3C)c3cnnn3C)cc2c(Cl)c1Cc1ccc(C(F)(F)F)nc1]

A solution of n-BuLi (2.5 M in hexanes, 0.68 mL, 1.7 mmol) was added dropwise by syringe to a solution of 6-bromo-4-chloro-2-methoxy-3-((6-(trifluoromethyl)pyridin-3-yl)methyl)quinoline (0.404 g, 0.936 mmol, Intermediate 45: step d) in dry THF (17 mL) in a dry ice-acetone bath. After 1-2 minutes, a solution of (2,6-dimethylpyridin-3-yl)(1-methyl-1H-1,2,3-triazol-5-yl)methanone (0.346 g, 1.601 mmol, Intermediate 19: step b) in dry THF (8 mL) was added dropwise. The reaction was stirred for 10 minutes, then was moved into an ice bath and allowed to warm to ambient temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The crude product was purified by flash column chromatography (silica gel, 0-4% MeOH-DCM) to provide the title compound. $^1$H NMR (400 MHz, $CDCl_3$) δ 8.71 (d, J=1.7 Hz, 1H), 8.11 (d, J=2.1 Hz, 1H), 7.80 (d, J=8.7 Hz, 1H), 7.76 (dd, J=8.1, 1.6 Hz, 1H), 7.56 (d, J=8.0 Hz, 1H), 7.40 (dd, J=8.8, 2.2 Hz, 1H), 6.96-6.90 (m, 2H), 6.83 (s, 1H), 5.01 (s, 1H), 4.33 (s, 2H), 4.09 (s, 3H), 3.91 (s, 3H), 2.51 (s, 3H), 2.32 (s, 3H); MS m/e 569.0 [M+H]+.

Example 40a was purified by chiral SFC (ChiralPak AD-H, 75:25 $CO_2$:mixture of MeOH/iPrOH (50:50)) to provide two pure enantiomers. The first eluting enantiomer was Example 40b: $^1$H NMR (400 MHz, $CDCl_3$) δ 8.72 (s, 1H), 8.10 (d, J=2.0 Hz, 1H), 7.81 (d, J=8.7 Hz, 1H), 7.76 (dd, J=8.1, 1.6 Hz, 1H), 7.57 (d, J=8.1 Hz, 1H), 7.38 (dd, J=8.8, 2.2 Hz, 1H), 6.94 (s, 2H), 6.87 (s, 1H), 4.34 (s, 2H), 4.32 (s, 1H), 4.09 (s, 3H), 3.93 (s, 3H), 2.54 (s, 3H), 2.35 (s, 3H); MS m/e 568.2 [M]+. The second eluting enantiomer was Example 40c: $^1$H NMR (400 MHz, $CDCl_3$) δ 8.70 (d, J=1.6 Hz, 1H), 8.12 (d, J=2.1 Hz, 1H), 7.78 (d, J=8.8 Hz, 1H), 7.77-7.73 (m, 1H), 7.56 (d, J=8.1 Hz, 1H), 7.37 (dd, J=8.8, 2.2 Hz, 1H), 6.94 (s, 1H), 6.94 (s, 1H), 6.81 (s, 1H), 5.15 (s, 1H), 4.31 (s, 2H), 4.08 (s, 3H), 3.92 (s, 3H), 2.52 (s, 3H), 2.32 (s, 3H); MS m/e 568.2 [M]+.

Example 41a 6-((2,6-Dimethylpyridin-3-yl)(hydroxy)(1-methyl-1H-1,2,3-triazol-5-yl)methyl)-2-methoxy-3-((6-(trifluoromethyl)pyridin-3-yl)methyl)quinoline-4-carbonitrile

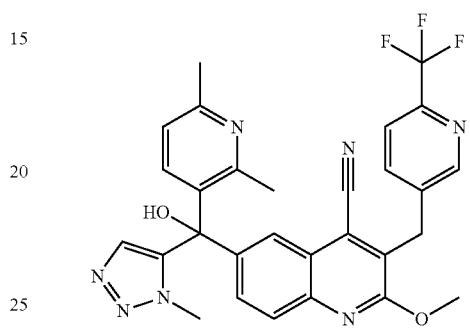

(4-Chloro-2-methoxy-3-((6-(trifluoromethyl)pyridin-3-yl)methyl)quinolin-6-yl)(2,6-dimethylpyridin-3-yl)(1-methyl-1H-1,2,3-triazol-5-yl)methanol (140 mg, 0.246 mmol, Example 40a), zinc cyanide (58.3 mg, 0.496 mmol), zinc dust (14.8 mg, 0.226 mmol), X-Phos (27.7 mg, 0.0581 mmol) and $Pd_2(dba)_3$ (32.8 mg, 0.0358 mmol) were charged to an oven-dried microwave vial. The vial was evacuated and back-filled with nitrogen. Dimethylacetamide (1.5 mL) was sparged with argon and added to the mixture via syringe. Argon was bubbled through the reaction mixture for 1 minute and the mixture was stirred and heated at 120° C. overnight under a positive pressure of nitrogen. The mixture was allowed to cool to ambient temperature, filtered through Celite®, and rinsed with dichloromethane. The filtrate was washed with saturated aqueous sodium bicarbonate, the layers were separated and the aqueous layer was extracted with excess dichloromethane. The combined organic layers were dried ($Na_2SO_4$), filtered, and concentrated to dryness. The crude product was purified by flash column chromatography (silica gel, 0-5% MeOH-DCM) to provide the title compound as a white solid. $^1$H NMR (400 MHz, $CDCl_3$) δ 8.80 (s, 1H), 8.14 (d, J=2.1 Hz, 1H), 7.88 (s, 1H), 7.87-7.84 (m, 1H), 7.61 (d, J=8.1 Hz, 1H), 7.38 (dd, J=8.7, 2.2 Hz, 1H), 6.97-6.86 (m, 3H), 4.41 (s, 2H), 4.13 (s, 3H), 3.96 (s, 3H), 2.53 (s, 3H), 2.39 (s, 3H); MS m/e 559.9 [M+H]+.

Example 41a was purified by chiral SFC (ChiralPak AD-H, 80:20 $CO_2$:mixture of MeOH/iPrOH (50:50+0.3% $iPrNH_2$)) to provide two pure enantiomers. The first eluting enantiomer was Example 41b: $^1$H NMR (400 MHz, $CDCl_3$) δ 8.81 (s, 1H), 8.14-8.11 (m, 1H), 7.89 (s, 1H), 7.87 (s, 1H), 7.61 (d, J=8.2 Hz, 1H), 7.41 (dd, J=8.8, 2.2 Hz, 1H), 6.96-6.93 (m, 1H), 6.93 (s, 1H), 6.89-6.86 (m, 1H), 4.41 (s, 2H), 4.14 (s, 3H), 3.96 (s, 3H), 2.55 (s, 3H), 2.41 (s, 3H); MS m/e [M]+. The second eluting enantiomer was Example 41c: $^1$H NMR (400 MHz, $CDCl_3$) δ 8.81 (s, 1H), 8.12 (d, J=2.2 Hz, 1H), 7.89 (s, 1H), 7.87 (s, 1H), 7.61 (d, J=8.1 Hz, 1H), 7.41

(dd, J=8.8, 2.2 Hz, 1H), 6.96-6.86 (m, 3H), 4.42 (s, 2H), 4.14 (s, 3H), 3.97 (s, 3H), 2.55 (s, 3H), 2.41 (s, 3H); MS m/e 559.2 [M]+.

Example 42a (4-Chloro-2-methoxy-3-((6-(trifluoromethyl)pyridin-3-yl)methyl)quinolin-6-yl)(1,2-dimethyl-1H-imidazol-5-yl)(2,6-dimethylpyridin-3-yl)methanol

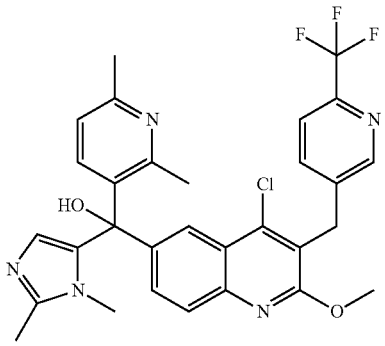 [SMILES: COc1nc2ccc(C(O)(c3ccc(C)nc3C)c3cnc(C)n3C)cc2c(Cl)c1Cc1ccc(C(F)(F)F)nc1]

A solution of n-BuLi (2.5 M in hexanes, 1.2 mL, 3.0 mmol) was added dropwise by syringe to a solution of 5-bromo-1,2-dimethyl-1H-imidazole (570.8 mg, 3.261 mmol) in dry THF (6 mL) in a dry ice-acetone bath. After 1-2 minutes, a solution of (4-chloro-2-methoxy-3-((6-(trifluoromethyl)pyridin-3-yl)methyl)quinolin-6-yl)(2,6-dimethylpyridin-3-yl)methanone (0.790 g, 1.626 mmol, Intermediate 47: step b) in dry THF (2 mL) was added dropwise. The reaction was stirred for 5 minutes, then was moved into an ice bath and allowed to warm to ambient temperature. The reaction was quenched with saturated aqueous ammonium chloride. The mixture was partitioned between water and dichloromethane. The separated aqueous phase was further extracted with dichloromethane. The organic phase was dried (Na2SO4), filtered, and concentrated. The crude product was purified by flash column chromatography (silica gel, 0-5% MeOH-DCM) followed by reverse-phase HPLC (acetonitrile/H2O+0.05% TFA). The product fractions were basified with saturated aqueous sodium bicarbonate and extracted with DCM, before being dried (Na2SO4), filtered, and concentrated to dryness to provide the title compound. $^1$H NMR (400 MHz, CDCl3) δ 8.76 (d, J=2.0 Hz, 1H), 8.13 (d, J=2.2 Hz, 1H), 7.79-7.73 (m, 2H), 7.57 (dd, J=8.1, 0.9 Hz, 1H), 7.41 (dd, J=8.7, 2.2 Hz, 1H), 7.11 (d, J=8.0 Hz, 1H), 6.94 (d, J=8.0 Hz, 1H), 6.04 (s, 1H), 4.35 (s, 2H), 4.08 (s, 3H), 3.39 (s, 3H), 2.53 (s, 3H), 2.41 (s, 3H), 2.37 (s, 3H); MS m/e 582.2 [M+H]+.

Example 42a was purified by chiral SFC (ChiralPak AD-H, 70:30 CO2:mixture of MeOH/iPrOH (50:50+0.3% iPrNH2)) to provide two pure enantiomers. The first eluting enantiomer was Example 42b: $^1$H NMR (400 MHz, CDCl3) δ ppm 8.77 (s, 1H), 8.15-8.12 (m, 1H), 7.77 (d, J=8.3 Hz, 2H), 7.57 (d, J=8.2 Hz, 1H), 7.45-7.40 (m, 1H), 7.11 (d, J=8.0 Hz, 1H), 6.94 (d, J=8.1 Hz, 1H), 6.06 (s, 1H), 4.36 (s, 2H), 4.09 (s, 3H), 3.40 (s, 3H), 3.30 (s, 1H), 2.54 (s, 3H), 2.42 (s, 3H), 2.39 (s, 3H); MS m/e 582.2 [M+H]+. The second eluting enantiomer was Example 42c: $^1$H NMR (400 MHz, CDCl3) δ ppm 8.76 (d, J=2.1 Hz, 1H), 8.16 (d, J=2.1 Hz, 1H), 7.79-7.74 (m, 1H), 7.70 (d, J=8.7 Hz, 1H), 7.60-7.55 (m, 1H), 7.37 (dd, J=8.7, 2.1 Hz, 1H), 7.11 (d, J=8.0 Hz, 1H), 6.93 (d, J=8.0 Hz, 1H), 5.98 (s, 1H), 4.35 (s, 2H), 4.28-4.18 (m, 1H), 4.07 (s, 3H), 3.37 (s, 3H), 2.53 (s, 3H), 2.40 (s, 3H), 2.33 (s, 3H); MS m/e 582.0 [M+H]+.

Example 43a (4-Chloro-2-methoxy-3-((6-(trifluoromethyl)pyridin-3-yl)methyl)quinolin-6-yl)(1,2-dimethyl-1H-imidazol-5-yl)(1-methyl-1H-1,2,3-triazol-5-yl)methanol

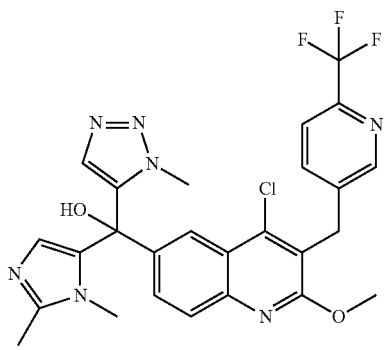 [SMILES: COc1nc2ccc(C(O)(c3cnnn3C)c3cnc(C)n3C)cc2c(Cl)c1Cc1ccc(C(F)(F)F)nc1]

A solution of n-BuLi (2.5 M in hexanes, 1.25 mL, 3.12 mmol) was added dropwise by syringe to a solution of 1-methyl-1H-1,2,3-triazole (268 mg, 3.22 mmol) in dry THF (32 mL) in a dry ice-methanol bath. The suspension was stirred for 30 minutes, slowly allowing the reaction mixture to warm to −10° C. (4-Chloro-2-methoxy-3-((6-(trifluoromethyl)pyridin-3-yl)methyl)quinolin-6-yl)(1,2-dimethyl-1H-imidazol-5-yl)methanone (0.500 g, 1.05 mmol, Intermediate 45: step f) in dry THF (5 mL) was added to the mixture via syringe and the resulting mixture was allowed to warm to ambient temperature overnight. The reaction was quenched with water. Brine was added and the aqueous mixture was extracted with ethyl acetate. The combined organic layers were dried (Na2SO4), filtered, and concentrated. The crude product was purified by flash column chromatography (silica gel, 0-8% MeOH-DCM) to provide the title compound. $^1$H NMR (500 MHz, CDCl3) δ 8.69 (d, J=1.7 Hz, 1H), 8.24 (d, J=1.9 Hz, 1H), 8.22 (s, 1H), 7.79-7.76 (m, 1H), 7.75 (d, J=8.7 Hz, 1H), 7.57 (d, J=8.1 Hz, 1H), 7.42 (dd, J=8.7, 2.0 Hz, 1H), 6.97 (s, 1H), 5.95 (s, 1H), 4.30 (s, 2H), 4.08 (s, 3H), 3.88 (s, 3H), 3.33 (s, 3H), 2.12 (s, 3H); MS m/e 557.8 [M+H]+.

Example 43a was purified by chiral SFC (ChiralPak AD-H, 70:30 CO2:mixture of MeOH/iPrOH (50:50 with 0.3% iPrNH2)) to provide two pure enantiomers. The first eluting enantiomer was Example 43b: $^1$H NMR (400 MHz, CDCl3) δ 8.72 (d, J=1.7 Hz, 1H), 8.21 (d, J=2.1 Hz, 1H), 7.78 (dd, J=8.1, 1.7 Hz, 1H), 7.74 (d, J=8.7 Hz, 1H), 7.58 (d, J=7.9 Hz, 1H), 7.40 (dd, J=8.7, 2.2 Hz, 1H), 7.10 (s, 1H), 6.04 (s, 1H), 4.34 (s, 2H), 4.08 (s, 3H), 3.89 (s, 3H), 3.36 (s, 3H), 2.24 (s, 3H); MS m/e 557.2 [M]+. The second eluting enantiomer was Example 43c: $^1$H NMR (400 MHz, CDCl3) δ 8.73 (d, J=1.8 Hz, 1H), 8.20 (d, J=2.0 Hz, 1H), 7.80-7.73 (m, 2H), 7.58 (d, J=8.0 Hz, 1H), 7.40 (dd, J=8.7, 2.1 Hz, 1H), 7.12 (s, 1H), 6.06

(s, 1H), 4.35 (s, 2H), 4.08 (s, 3H), 3.90 (s, 3H), 3.37 (s, 3H), 2.26 (s, 3H); MS m/e 557.2 [M]+.

Example 44a 6-((1,2-Dimethyl-1H-imidazol-5-yl)(hydroxy)(1-methyl-1H-1,2,3-triazol-5-yl)methyl)-2-methoxy-3-((6-(trifluoromethyl)pyridin-3-yl)methyl)quinoline-4-carbonitrile

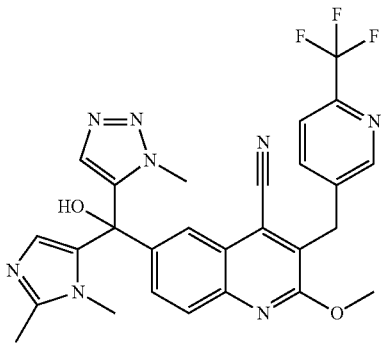 [SMILES: COc1nc2ccc(C(O)(c3cnnn3C)c3cnc(C)n3C)cc2c(C#N)c1Cc1ccc(C(F)(F)F)nc1]

(4-Chloro-2-methoxy-3-((6-(trifluoromethyl)pyridin-3-yl)methyl)quinolin-6-yl)(1,2-dimethyl-1H-imidazol-5-yl)(1-methyl-1H-1,2,3-triazol-5-yl)methanol (111.4 mg, 0.2 mmol, Example 43a) zinc cyanide (48.0 mg, 0.409 mmol), zinc dust (10.8 mg, 0.165 mmol), X-Phos (20.8 mg, 0.0436 mmol) and Pd$_2$(dba)$_3$ (27.7 mg, 0.0302 mmol) were charged to an oven-dried microwave vial. The vial was evacuated and back-filled with nitrogen. Dimethylacetamide (1.3 mL) was sparged with argon and added to the mixture via syringe. Argon was bubbled through the reaction mixture for 1 minute and the mixture was stirred and heated at 120° C. overnight under a positive pressure of nitrogen. The mixture was allowed to cool to ambient temperature, filtered through Celite®, and rinsed with dichloromethane. The filtrate was washed with saturated aqueous sodium bicarbonate, the layers were separated and the aqueous layer was extracted with excess dichloromethane. The combined organic layers were dried (Na$_2$SO$_4$), filtered, and concentrated to dryness. The crude product was purified by flash column chromatography (silica gel, 0-5% MeOH-DCM) to provide the title compound as a white solid. $^1$H NMR (400 MHz, CDCl$_3$) δ 8.78 (d, J=2.3 Hz, 1H), 8.28 (d, J=2.1 Hz, 1H), 7.87 (dd, J=8.1, 2.2 Hz, 1H), 7.81 (d, J=8.8 Hz, 1H), 7.62 (d, J=8.1 Hz, 1H), 7.36 (dd, J=8.7, 2.1 Hz, 1H), 7.05 (s, 1H), 5.94 (s, 1H), 4.40 (s, 2H), 4.12 (s, 3H), 3.92 (s, 3H), 3.37 (s, 3H), 2.15 (s, 3H); MS m/e 549.5 [M+H]+.

Example 44a was purified by chiral SFC (ChiralPak AD-H, 75:25 CO$_2$:mixture of MeOH/iPrOH (50:50+0.3% iPrNH$_2$)) to provide two pure enantiomers. The first eluting enantiomer was Example 44b: $^1$H NMR (400 MHz, CDCl$_3$) δ 8.78 (d, J=2.1 Hz, 1H), 8.29 (d, J=2.2 Hz, 1H), 7.87 (dd, J=8.0, 2.1 Hz, 1H), 7.82 (d, J=8.8 Hz, 1H), 7.62 (d, J=8.1 Hz, 1H), 7.37 (dd, J=8.7, 2.1 Hz, 1H), 7.01 (s, 1H), 5.93 (s, 1H), 4.40 (s, 2H), 4.12 (s, 3H), 3.91 (s, 3H), 3.37 (s, 3H), 2.21-2.12 (m, 3H); MS m/e 548.2 [M]+. The second eluting enantiomer was Example 44c: $^1$H NMR (400 MHz, CDCl$_3$) δ 8.78 (d, J=2.4 Hz, 1H), 8.31-8.28 (m, 1H), 7.91-7.85 (m, 1H), 7.82 (d, J=8.7 Hz, 1H), 7.62 (d, J=8.1 Hz, 1H), 7.37 (dd, J=8.0, 2.0 Hz, 1H), 7.01 (s, 1H), 5.93 (s, 1H), 4.40 (s, 2H), 4.12 (s, 3H), 3.91 (s, 3H), 3.37 (s, 3H), 2.16 (s, 3H); MS m/e 548.2 [M]+.

Example 45

(4-Chloro-2-methoxy-3-((6-(trifluoromethyl)pyridin-3-yl)methyl)quinolin-6-yl)bis(1,2-dimethyl-1H-imidazol-5-yl)methanol

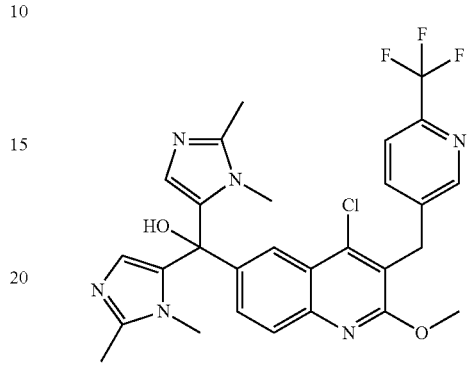

A solution of n-BuLi (2.5 M in hexanes, 1.3 mL, 3.25 mmol) was added dropwise by syringe to a solution of 5-bromo-1,2-dimethyl-1H-imidazole (614.1 mg, 3.509 mmol) in dry THF (12 mL) in a dry ice-acetone bath. After 1-2 minutes, a solution of (4-chloro-2-methoxy-3-((6-(trifluoromethyl)pyridin-3-yl)methyl)quinolin-6-yl)(1,2-dimethyl-1H-imidazol-5-yl)methanone (0.830 g, 1.75 mmol, Intermediate 45: step f) in dry THF (5 mL) was added dropwise. The reaction was stirred for 5 minutes, then was removed from the cold bath and allowed to warm to ambient temperature. The reaction was quenched with saturated aqueous ammonium chloride. The mixture was partitioned between water and dichloromethane. The separated aqueous phase was further extracted with dichloromethane. The organic phase was dried (Na$_2$SO$_4$), filtered, and concentrated to dryness. The crude product was purified by flash column chromatography (silica gel, 0-5% MeOH-DCM) followed by trituration with dichloromethane to provide the title compound. $^1$H NMR (400 MHz, CDCl$_3$) δ 8.74 (d, J=2.1 Hz, 1H), 8.22 (d, J=2.2 Hz, 1H), 7.79 (dd, J=8.0, 2.1 Hz, 1H), 7.67 (d, J=8.7 Hz, 1H), 7.59 (d, J=8.1 Hz, 1H), 7.41 (dd, J=8.8, 2.1 Hz, 1H), 6.15 (s, 2H), 5.47 (s, 1H), 4.34 (s, 2H), 4.06 (s, 3H), 3.40 (s, 6H), 2.29 (s, 6H); MS m/e 571.0 [M+H]+.

Example 46a (4-Chloro-3-(4-fluorobenzyl)-2-methoxyquinolin-6-yl)(4-chlorophenyl)(1-methyl-1H-imidazol-5-yl)methanol

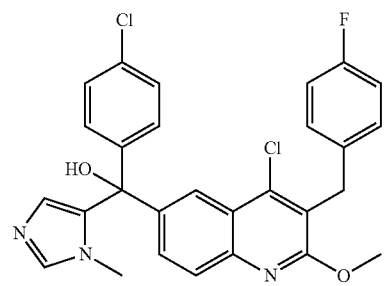 [SMILES: COc1nc2ccc(C(O)(c3ccc(Cl)cc3)c3cncn3C)cc2c(Cl)c1Cc1ccc(F)cc1]

A solution of n-BuLi (2.5 M in hexanes, 0.74 mL, 1.85 mmol) was added dropwise by syringe to a solution of 6-bromo-4-chloro-3-(4-fluorobenzyl)-2-methoxyquinoline (0.717 g, 1.88 mmol, Intermediate 42: step d) in dry THF (10 mL) in a dry ice-acetone bath. After 1-2 minutes, a solution of (4-chlorophenyl)(1-methyl-1H-imidazol-5-yl)methanone (0.429 g, 1.94 mmol, Intermediate 43: step b) in dry THF (5 mL) was added dropwise. The reaction was stirred for 3 minutes, then was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The crude product was purified by flash column chromatography (silica gel, 0-2.5% MeOH-DCM) to provide the title compound. $^1$H NMR (400 MHz, $CDCl_3$) δ 8.11 (d, J=1.9 Hz, 1H), 7.77 (d, J=8.7 Hz, 1H), 7.52 (dd, J=8.8, 2.2 Hz, 1H), 7.30 (s, 4H), 7.28 (d, J=0.6 Hz, 1H), 7.26-7.22 (m, 2H), 6.95-6.89 (m, 2H), 6.33 (d, J=1.1 Hz, 1H), 4.49 (s, 1H), 4.24 (d, J=6.7 Hz, 2H), 4.07 (s, 3H), 3.35 (s, 3H); MS m/e 522.1 $[M+H]^+$.

Example 46a was purified by chiral SFC (ChiralPak AD, 85:15 $CO_2$/MeOH+0.2% $iPrNH_2$) to provide two pure enantiomers. The first eluting enantiomer was Example 46b: $^1$H NMR (400 MHz, $CDCl_3$) δ 8.11 (d, J=2.0 Hz, 1H), 7.75 (d, J=8.7 Hz, 1H), 7.51 (dd, J=8.7, 2.1 Hz, 1H), 7.30 (s, 4H), 7.23 (m, 3H), 6.95-6.88 (m, 2H), 6.31 (s, 1H), 4.24 (s, 2H), 4.07 (s, 3H), 3.34 (s, 3H); MS m/e 522.2 $[M+H]^+$. The second eluting enantiomer was Example 46c: $^1$H NMR (400 MHz, $CDCl_3$) δ 8.11 (d, J=1.9 Hz, 1H), 7.75 (d, J=8.7 Hz, 1H), 7.50 (dd, J=8.7, 2.0 Hz, 1H), 7.30 (s, 4H), 7.26-7.19 (m, 3H), 6.95-6.87 (m, 2H), 6.29 (s, 1H), 4.23 (s, 2H), 4.07 (s, 3H), 3.33 (s, 3H); MS m/e 522.2 $[M+H]^+$.

Example 47a (4-Chloro-3-(4-fluorobenzyl)-2-methoxyquinolin-6-yl)(1-methyl-1H-imidazol-5-yl)(6-(trifluoromethyl)pyridin-3-yl)methanol

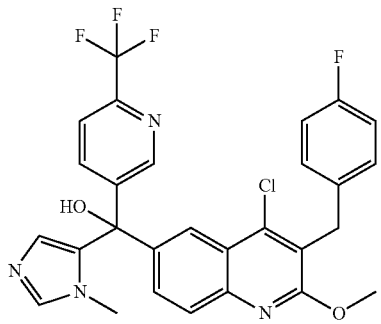 [SMILES: COc1nc2ccc(C(O)(c3ccc(C(F)(F)F)nc3)c3cncn3C)cc2c(Cl)c1Cc1ccc(F)cc1]

A solution of n-BuLi (2.5 M in hexanes, 0.9 mL, 2.25 mmol) was added dropwise by syringe to a solution of 6-bromo-4-chloro-3-(4-fluorobenzyl)-2-methoxyquinoline (0.712 g, 1.87 mmol, Intermediate 42: step d) in dry THF (9 mL) in a dry ice-acetone bath. After 1-2 minutes, a solution of (1-methyl-1H-imidazol-5-yl)(6-(trifluoromethyl)pyridin-3-yl)methanone (0.477 g, 1.87 mmol, Intermediate 2: step c) in dry THF (5 mL) was added dropwise. The reaction was stirred for 3 minutes, then was switched to an ice bath. After 10 minutes, the reaction was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The crude product was purified by flash column chromatography (silica gel, 0-5% MeOH-DCM) to provide the title compound. $^1$H NMR (400 MHz, $CDCl_3$) δ 8.81 (s, 1H), 8.15 (d, J=2.0 Hz, 1H), 7.88 (d, J=8.2 Hz, 1H), 7.79 (d, J=8.7 Hz, 1H), 7.62 (t, J=7.6 Hz, 1H), 7.52 (dd, J=8.7, 2.1 Hz, 1H), 7.26-7.21 (m, 2H), 7.19 (s, 1H), 6.91 (t, J=8.7 Hz, 2H), 6.24 (s, 1H), 4.23 (s, 2H), 4.15-4.05 (m, 3H), 3.32 (s, 3H); MS m/e 557.2 $[M+H]^+$.

Example 47a was purified by chiral SFC (ChiralPak IA, 100% EtOH) to provide two pure enantiomers. The first eluting enantiomer was Example 47b: $^1$H NMR (400 MHz, $CDCl_3$) δ 8.80 (s, 1H), 8.16 (d, J=1.7 Hz, 1H), 7.88 (d, J=8.1 Hz, 1H), 7.78 (d, J=8.7 Hz, 1H), 7.62 (d, J=8.2 Hz, 1H), 7.51 (dd, J=8.7, 1.9 Hz, 1H), 7.23 (m, 2H), 7.16 (s, 1H), 6.91 (t, J=8.7 Hz, 2H), 6.54 (s, 1H), 6.22 (s, 1H), 4.22 (s, 2H), 4.07 (s, 3H), 3.31 (s, 3H); MS m/e 557.2 $[M+H]^+$. The second eluting enantiomer was Example 47c: $^1$H NMR (400 MHz, $CDCl_3$) δ 8.80 (d, J=1.9 Hz, 1H), 8.16 (d, J=2.0 Hz, 1H), 7.88 (dd, J=8.2, 1.9 Hz, 1H), 7.78 (d, J=8.7 Hz, 1H), 7.63 (d, J=8.2 Hz, 1H), 7.51 (dd, J=8.7, 2.1 Hz, 1H), 7.23 (m, 2H), 7.16 (s, 1H), 6.95-6.88 (m, 2H), 6.55 (s, 1H), 6.22 (s, 1H), 4.22 (s, 2H), 4.07 (s, 3H), 3.31 (s, 3H); MS m/e 557.2 $[M+H]^+$.

Example 48a (4-Chloro-3-(4-fluorobenzyl)-2-methoxyquinolin-6-yl)(2,6-dimethylpyridin-3-yl)(1-methyl-1H-1,2,3-triazol-5-yl)methanol

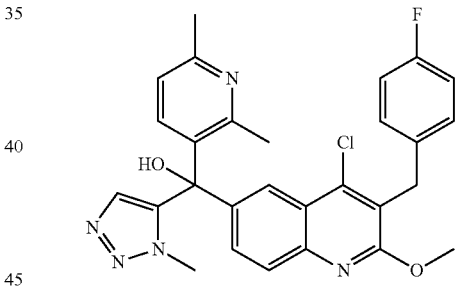

A solution of n-BuLi (2.5 M in hexanes, 0.79 mL, 1.98 mmol) was added dropwise by syringe to a solution of 6-bromo-4-chloro-3-(4-fluorobenzyl)-2-methoxyquinoline (0.750 g, 1.97 mmol, Intermediate 42: step d) in dry THF (17 mL) in a dry ice-acetone bath. After 1-2 minutes, a solution of (2,6-dimethylpyridin-3-yl)(1-methyl-1H-1,2,3-triazol-5-yl)methanone (0.405 g, 1.87 mmol, Intermediate 19: step b) in dry THF (8 mL) was added dropwise. The reaction was stirred for 10 minutes, then was moved to an ice bath. After 2 hours, the reaction was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated to dryness. The crude product was purified by flash column chromatography (silica gel, 0-5% MeOH-DCM) to provide the title compound. $^1$H NMR (400 MHz, $CDCl_3$) δ 8.08 (d, J=2.1 Hz, 1H), 7.79 (d, J=8.7 Hz, 1H), 7.36 (dd, J=8.7, 2.2 Hz, 1H), 7.26-7.23 (m, 2H), 6.96-6.90 (m, 4H), 6.89 (s, 1H), 4.29 (s, 1H), 4.23 (s, 2H), 4.09 (s, 3H), 3.92 (s, 3H), 2.53 (s, 3H), 2.36 (s, 3H); MS m/e 518.5 $[M+H]^+$.

Example 48a was purified by chiral SFC (ChiralPak AD, 75:25 CO$_2$/EtOH) to provide two pure enantiomers. The first eluting enantiomer was Example 48b: $^1$H NMR (400 MHz, CDCl$_3$) δ 8.09 (d, J=2.1 Hz, 1H), 7.78 (d, J=8.7 Hz, 1H), 7.34 (dd, J=8.7, 2.2 Hz, 1H), 7.26-7.21 (m, 2H), 6.97-6.90 (m, 4H), 6.88 (s, 1H), 4.26 (s, 1H), 4.22 (s, 2H), 4.08 (s, 3H), 3.93 (s, 3H), 2.53 (s, 3H), 2.36 (s, 3H); MS m/e 517.20 [M]$^+$. The second eluting enantiomer was Example 48c: $^1$H NMR (400 MHz, CDCl$_3$) δ 8.09 (d, J=2.1 Hz, 1H), 7.77 (d, J=8.7 Hz, 1H), 7.33 (dd, J=8.7, 2.2 Hz, 1H), 7.26-7.21 (m, 2H), 6.96-6.90 (m, 4H), 6.87 (s, 1H), 4.46 (s, 1H), 4.21 (s, 2H), 4.08 (s, 3H), 3.93 (s, 3H), 2.53 (s, 3H), 2.35 (s, 3H); MS m/e 517.20 [M]$^+$.

Example 49a 6-((2,6-Dimethylpyridin-3-yl)(hydroxy)(1-methyl-1H-1,2,3-triazol-5-yl)methyl)-3-(4-fluorobenzyl)-2-methoxyquinoline-4-carbonitrile

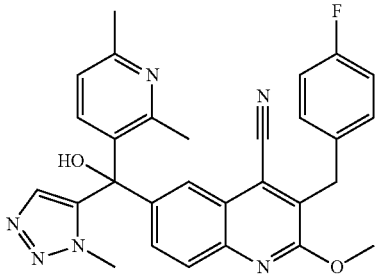 [SMILES: COc1nc2ccc(C(O)(c3ccc(C)nc3C)c3cnnn3C)cc2c(C#N)c1Cc1ccc(F)cc1]

(4-Chloro-3-(4-fluorobenzyl)-2-methoxyquinolin-6-yl)(2,6-dimethylpyridin-3-yl)(1-methyl-1H-1,2,3-triazol-5-yl) methanol (617.9 mg, 1.193 mmol, Example 48a), zinc cyanide (284.9 mg, 2.426 mmol), zinc dust (30.1 mg, 0.460 mmol), X-Phos (115 mg, 0.241 mmol) and Pd$_2$(dba)$_3$ (163 mg, 0.178 mmol) were charged to an oven-dried microwave vial. The vial was evacuated and back-filled with nitrogen. Dimethylacetamide (6 mL) was sparged with argon and added to the mixture via syringe. Argon was bubbled through the reaction mixture for 1 minute and the mixture was stirred and heated at 120° C. overnight under a positive pressure of nitrogen. The mixture was allowed to cool to ambient temperature, filtered through Celite®, and rinsed with dichloromethane. The filtrate was washed with saturated aqueous sodium bicarbonate, the layers were separated and the aqueous layer was extracted with excess dichloromethane. The combined organic layers were dried (Na$_2$SO$_4$), filtered, and concentrated to dryness. The crude product was purified by flash column chromatography (silica gel, 0-5% MeOH-DCM) to provide the title compound as a white solid. $^1$H NMR (400 MHz, CDCl$_3$) δ 8.12 (d, J=2.2 Hz, 1H), 7.84 (d, J=8.8 Hz, 1H), 7.38-7.31 (m, 3H), 7.00-6.87 (m, 5H), 4.30 (s, 2H), 4.12 (s, 3H), 3.95 (s, 3H), 2.53 (s, 3H), 2.40 (s, 3H); MS m/e 509.5 [M+H]$^+$.

Example 49a was purified by chiral SFC (ChiralPak OJ-H, 74:26 CO$_2$:MeOH (+0.3% iPrNH$_2$) to provide two pure enantiomers. The first eluting enantiomer was Example 49b: $^1$H NMR (400 MHz, CDCl$_3$) δ 8.11 (d, J=2.2 Hz, 1H), 7.84 (d, J=8.7 Hz, 1H), 7.36-7.32 (m, 3H), 7.00-6.87 (m, 5H), 4.30 (s, 2H), 4.12 (s, 3H), 3.95 (s, 3H), 2.53 (s, 3H), 2.40 (s, 3H); MS m/e 508.20 [M]$^+$. The second eluting enantiomer was Example 49c: $^1$H NMR (400 MHz, CDCl$_3$) δ 8.14 (d, J=2.1 Hz, 1H), 7.81 (d, J=8.8 Hz, 1H), 7.35-7.29 (m, 3H), 6.99-6.93 (m, 2H), 6.93-6.86 (m, 2H), 6.85 (s, 1H), 4.94 (s, 1H), 4.28 (s, 2H), 4.11 (s, 3H), 3.95 (s, 3H), 2.50 (s, 3H), 2.38 (s, 3H); MS m/e 508.20 [M]$^+$.

Example 50

1-(4-((4-Chloro-3-(4-fluorobenzyl)-2-methoxyquinolin-6-yl)(hydroxy)(phenyl)methyl)piperidin-1-yl)ethanone

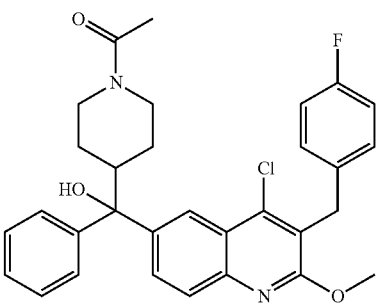 [SMILES: COc1nc2ccc(C(O)(c3ccccc3)C3CCN(C(C)=O)CC3)cc2c(Cl)c1Cc1ccc(F)cc1]

A solution of n-BuLi (2.5 M in hexanes, 0.75 mL, 1.9 mmol) was added dropwise by syringe to a solution of 6-bromo-4-chloro-3-(4-fluorobenzyl)-2-methoxyquinoline (0.728 g, 1.91 mmol, Intermediate 42: step d) in dry THF (10 mL) in a dry ice-acetone bath. After 1-2 minutes, a solution of 1-(4-benzoylpiperidin-1-yl)ethanone (0.478 g, 2.06 mmol, Intermediate 18) in dry THF (5 mL) was added dropwise. The reaction was stirred for 3 minutes, then was moved to an ice bath before allowing the reaction to warm to room temperature. The reaction was quenched with saturated aqueous ammonium chloride. The mixture was partitioned between water and dichloromethane. The separated aqueous phase was further extracted with dichloromethane. The organic phase was dried (Na$_2$SO$_4$), filtered, and concentrated. The crude product was purified by flash column chromatography (silica gel, 0-2.5% MeOH-DCM) to provide the title compound. $^1$H NMR (400 MHz, CDCl$_3$) δ ppm 8.28 (dd, J=7.9, 2.0 Hz, 1H), 7.77-7.71 (m, 1H), 7.66 (ddd, J=15.4, 8.8, 2.1 Hz, 1H), 7.55-7.49 (m, 2H), 7.35-7.28 (m, 2H), 7.25-7.16 (m, 3H), 6.94-6.88 (m, 2H), 4.72-4.60 (m, 1H), 4.23 (s, 2H), 4.04 (s, 3H), 3.84-3.73 (m, 1H), 3.12-2.98 (m, 1H), 2.79-2.69 (m, 1H), 2.61-2.49 (m, 1H), 2.01-1.98 (m, 3H), 1.70-1.24 (m, 4H); MS m/e 533.3 [M+H]$^+$.

Example 51a 1-(4-((4-Chloro-3-(4-fluorobenzyl)-2-methoxyquinolin-6-yl)(4-fluorophenyl)(hydroxy)methyl)piperidin-1-yl)ethanone

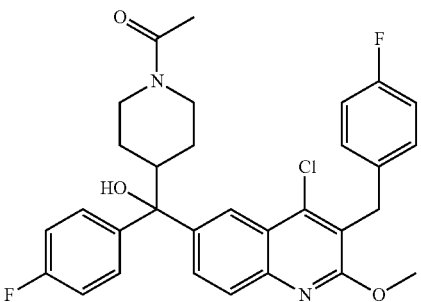 [SMILES: COc1nc2ccc(C(O)(c3ccc(F)cc3)C3CCN(C(C)=O)CC3)cc2c(Cl)c1Cc1ccc(F)cc1]

A solution of n-BuLi (2.5 M in hexanes, 0.77 mL, 1.9 mmol) was added dropwise by syringe to a solution of 6-bromo-4-chloro-3-(4-fluorobenzyl)-2-methoxyquinoline (0.752 g, 1.97 mmol, Intermediate 42: step d) in dry THF (10 mL) in a dry ice-acetone bath. After 1-2 minutes, a solution of 1-(4-(4-fluorobenzoyl)piperidin-1-yl)ethanone (0.519 g, 2.08 mmol, Intermediate 44) in dry THF (5 mL) was added dropwise. The reaction was stirred for 5 minutes, then was moved to an ice bath before allowing the reaction to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The crude product was purified by flash column chromatography (silica gel, 0-5% MeOH-DCM), followed by reverse-phase chromatography (acetonitrile/$H_2O$+0.05% TFA). The product remained impure and was taken forward to the chiral separation step.

Example 51a was purified by chiral SFC (ChiralPak OD-H, 100% MeOH, to provide two pure enantiomers. The first eluting enantiomer was Example 51b: $^1$H NMR (400 MHz, $CDCl_3$) δ ppm 8.27-8.23 (m, 1H), 7.78-7.72 (m, 1H), 7.64 (ddd, J=18.3, 8.8, 2.1 Hz, 1H), 7.53-7.44 (m, 2H), 7.27-7.21 (m, 2H), 7.03-6.96 (m, 2H), 6.95-6.88 (m, 2H), 4.71-4.61 (m, 1H), 4.24 (s, 2H), 4.04 (s, 3H), 3.86-3.74 (m, 1H), 3.12-3.00 (m, 1H), 2.91 (d, J=4.4 Hz, 1H), 2.75-2.66 (m, 1H), 2.61-2.50 (m, 1H), 2.02-1.98 (m, 3H), 1.66-1.29 (m, 4H); MS m/e 551.5 [M+H]$^+$. The second eluting enantiomer was Example 51c: $^1$H NMR (400 MHz, $CDCl_3$) δ ppm 8.27-8.23 (m, 1H), 7.80-7.73 (m, 1H), 7.63 (ddd, J=16.1, 8.8, 2.2 Hz, 1H), 7.53-7.45 (m, 2H), 7.25-7.22 (m, 2H), 7.04-6.97 (m, 2H), 6.96-6.88 (m, 2H), 4.74-4.63 (m, 1H), 4.25 (s, 2H), 4.05 (s, 3H), 3.88-3.76 (m, 1H), 3.14-3.01 (m, 1H), 2.76-2.66 (m, 1H), 2.62-2.51 (m, 1H), 2.48-2.44 (m, 1H), 2.07-2.01 (m, 3H), 1.60-1.25 (m, 4H); MS m/e 551.5 [M+H]$^+$.

Example 52a (4-Chloro-3-(4-fluorobenzyl)-2-methoxyquinolin-6-yl)(1,2-dimethyl-1H-imidazol-5-yl)(2,6-dimethylpyridin-3-yl)methanol

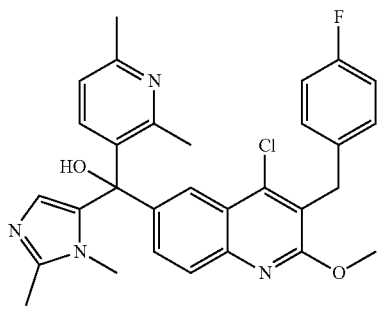 [SMILES: COc1nc2ccc(C(O)(c3ccc(C)nc3C)c3cnc(C)n3C)cc2c(Cl)c1Cc1ccc(F)cc1]

A solution of n-BuLi (2.5 M in hexanes, 0.90 mL, 2.2 mmol) was added dropwise by syringe to a solution of 5-bromo-1,2-dimethyl-1H-imidazole (408.9 mg, 2.336 mmol) in dry THF (12 mL) in a dry ice-acetone bath. After 1-2 minutes, (4-chloro-3-(4-fluorobenzyl)-2-methoxyquinolin-6-yl)(2,6-dimethylpyridin-3-yl)methanone (0.505 g, 1.16 mmol, Intermediate 48: step b) in dry THF (12 mL) was added to the mixture via syringe. After 5 minutes, the reaction was removed from the cold bath and was allowed to warm to ambient temperature overnight. The reaction was quenched with saturated aqueous ammonium chloride. Water was added and the aqueous mixture was extracted with dichloromethane. The combined organic layers were dried ($Na_2SO_4$), filtered, and concentrated. The crude product was purified by flash column chromatography (silica gel, 0-5% MeOH-DCM). Due to remaining impurities, the material was dissolved in ethyl acetate and washed several times with minimal water. The organic layer was dried ($Na_2SO_4$), filtered, and concentrated to dryness. The material was purified by reverse phase chromatography (acetonitrile/$H_2O$+0.05% TFA), basified with saturated aqueous sodium bicarbonate, and extracted with DCM, before being dried ($Na_2SO_4$), filtered, and concentrated to dryness to provide the title compound. $^1$H NMR (500 MHz, $CDCl_3$) δ 8.13 (d, J=2.2 Hz, 1H), 7.71 (d, J=8.7 Hz, 1H), 7.37 (dd, J=8.6, 2.2 Hz, 1H), 7.28-7.24 (m, 2H), 7.11 (d, J=8.0 Hz, 1H), 6.96-6.89 (m, 3H), 6.00 (s, 1H), 4.23 (s, 2H), 4.07 (s, 3H), 3.36 (s, 3H), 2.51 (s, 3H), 2.40 (s, 3H), 2.30 (s, 3H); MS m/e 531.2 [M+H]$^+$.

Example 52a was purified by chiral SFC (ChiralPak AD-H, 70:30 $CO_2$:EtOH (+0.3% iPrNH$_2$) to provide two pure enantiomers. The first eluting enantiomer was Example 52b: $^1$H NMR (400 MHz, $CDCl_3$) δ 8.17 (d, J=2.2 Hz, 1H), 7.64 (d, J=8.7 Hz, 1H), 7.33-7.29 (m, 1H), 7.29-7.24 (m, 2H), 7.10 (d, J=8.0 Hz, 1H), 6.97-6.88 (m, 3H), 5.94 (s, 1H), 4.90 (s, 1H), 4.23 (s, 2H), 4.06 (s, 3H), 3.34 (s, 3H), 2.51 (s, 3H), 2.38 (s, 3H), 2.27 (s, 3H); MS m/e 531.3 [M+H]$^+$. The second eluting enantiomer was Example 52c: $^1$H NMR (400 MHz, $CDCl_3$) δ ppm 8.14-8.10 (m, 1H), 7.75 (d, J=9.0 Hz, 1H), 7.41-7.37 (m, 1H), 7.32-7.23 (m, 2H), 7.11 (d, J=7.9 Hz, 1H), 6.98-6.90 (m, 3H), 6.07 (s, 1H), 4.25 (s, 2H), 4.08 (s, 3H), 3.39 (s, 3H), 3.24 (s, 1H), 2.54 (s, 3H), 2.43 (s, 3H), 2.39 (s, 3H); MS m/e 531.3 [M+H]$^+$.

Example 53a 3-(4-Fluorobenzyl)-6-(hydroxy(1-methyl-1H-imidazol-5-yl)(6-(trifluoromethyl)pyridin-3-yl)methyl)quinoline-2,4-dicarbonitrile

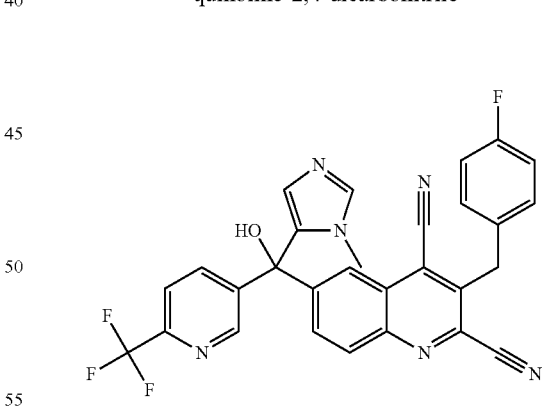

(2,4-Dichloro-3-(4-fluorobenzyl)quinolin-6-yl)(1-methyl-1H-imidazol-5-yl)(6-(trifluoromethyl)pyridin-3-yl)methanol (300 mg, 0.534 mmol, Example 150), zinc cyanide (125.5 mg, 1.069 mmol), zinc dust (13.98 mg, 0.214 mmol), X-Phos (50.95 mg, 0.107 mmol) and $Pd_2(dba)_3$ (73.4 mg, 0.080 mmol) were charged to an oven-dried microwave vial. The vial was evacuated and back-filled with nitrogen. Dimethylacetamide (8.4 mL) was sparged with argon and added to the mixture via syringe. Argon was bubbled through the reaction mixture for 1 minute and the mixture was stirred and heated at 120° C. overnight under a positive pressure of nitrogen. The mixture was allowed to cool to ambient temperature, filtered through Celite®, and rinsed with ethyl acetate. The filtrate was washed with saturated aqueous sodium bicarbonate, the layers were separated and the aqueous layer was extracted with excess ethyl acetate. The combined organic layers were dried (Na$_2$SO$_4$), filtered, and concentrated to dryness. The crude product was purified by flash column chromatography (silica gel, 0-5% MeOH-DCM) followed by reverse-phase HPLC (acetonitrile/H$_2$O+0.05% TFA). Impurities remained therefore the racemic product was taken forward to the chiral separation step.

Example 53a was purified by chiral SFC (ChiralPak OJ, 100% MeOH) to provide two pure enantiomers. The first eluting enantiomer was Example 53b: $^1$H NMR (400 MHz, CDCl$_3$) δ 8.77 (s, 1H), 8.44 (d, J=1.8 Hz, 1H), 8.17 (d, J=8.9 Hz, 1H), 7.92 (dd, J=8.2, 2.0 Hz, 1H), 7.76 (dd, J=9.0, 1.9 Hz, 1H), 7.67 (d, J=8.3 Hz, 1H), 7.41-7.34 (m, 2H), 7.23 (s, 1H), 7.06-6.98 (m, 2H), 6.22 (s, 1H), 4.58 (s, 2H), 3.36 (s, 3H); MS m/e 542.8 [M+H]$^+$. The second eluting enantiomer was Example 53c: $^1$H NMR (400 MHz, CDCl$_3$) δ 8.77 (s, 1H), 8.44 (d, J=1.7 Hz, 1H), 8.17 (d, J=8.9 Hz, 1H), 7.93 (d, J=8.1 Hz, 1H), 7.76 (dd, J=9.0, 1.9 Hz, 1H), 7.67 (d, J=8.3 Hz, 1H), 7.43-7.35 (m, 2H), 7.23 (s, 1H), 7.07-6.98 (m, 2H), 6.22 (s, 1H), 4.58 (s, 2H), 3.36 (s, 3H); MS m/e 542.8 [M+H]$^+$.

Example 54a

4-Chloro-2-methoxy-3-(4-(trifluoromethyl)benzyl)quinolin-6-yl)(4-chlorophenyl)(1-methyl-1H-imidazol-5-yl)methanol•TFA

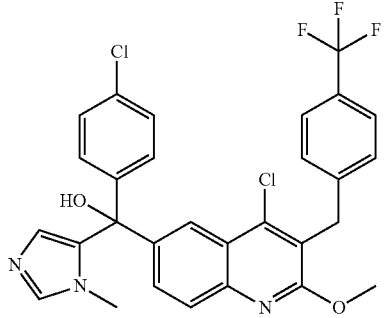 [SMILES: COc1nc2ccc(C(O)(c3ccc(Cl)cc3)c3cncn3C)cc2c(Cl)c1Cc1ccc(C(F)(F)F)cc1]

A solution of n-BuLi (2.5 M in hexanes, 0.38 mL, 0.61 mmol) was added dropwise by syringe over a 10 minute period to a mixture of 6-bromo-4-chloro-2-methoxy-3-(4-(trifluoromethyl)benzyl)quinoline (0.220 g, 0.511 mmol, Intermediate 12: step d) and (4-chlorophenyl)(1-methyl-1H-imidazol-5-yl)methanone (0.125 g, 0.511 mmol, Intermediate 43: step b) in dry THF (5 mL) and a dry ice-acetone bath. The reaction was stirred for 30 minutes, then removed from the cold bath and allowed to warm to room temperature. The reaction was quenched with saturated aqueous ammonium chloride. The mixture was partitioned between water and ethyl acetate. The separated aqueous phase was further extracted with dichloromethane. The organic phase was dried (Na$_2$SO$_4$), filtered, and concentrated. The crude product was purified by flash column chromatography (silica gel, 0-100% EtOAc-hexanes, 1% MeOH in DCM) followed by reverse-phase HPLC to provide the title compound as a white solid. $^1$H NMR (500 MHz, CDCl$_3$) δ 8.43 (s, 1H), 8.02 (d, J=2.0 Hz, 1H), 7.85 (d, J=8.8 Hz, 1H), 7.51 (dd, J=11.5, 5.1 Hz, 3H), 7.41-7.34 (m, 4H), 7.28 (d, J=8.6 Hz, 2H), 6.62 (s, 1H), 4.34 (s, 2H), 4.09 (s, 3H), 3.62 (s, 3H); MS m/e 572.2 [M+H]+.

Example 54a was purified by HPLC (Chiralpak AD column, ethanol eluent) to provide two pure enantiomers. The first eluting enantiomer was Example 54b: $^1$H NMR (500 MHz, CDCl$_3$) δ 8.05 (d, J=2.0 Hz, 1H), 7.90 (s, 1H), 7.83 (d, J=8.7 Hz, 1H), 7.51 (dd, J=12.2, 5.5 Hz, 3H), 7.37 (dd, J=11.9, 8.5 Hz, 4H), 7.28 (d, J=8.8 Hz, 2H), 6.54 (s, 1H), 4.34 (s, 2H), 4.08 (s, 3H), 3.51 (s, 3H); MS m/e 572.2 [M+H]$^+$. The second eluting enantiomer was Example 54c: $^1$H NMR (500 MHz, CDCl$_3$) δ 8.17 (s, 1H), 8.03 (d, J=2.1 Hz, 1H), 7.84 (d, J=8.7 Hz, 1H), 7.53-7.48 (m, 3H), 7.41-7.35 (m, 4H), 7.28 (d, J=8.7 Hz, 2H), 6.59 (s, 1H), 4.34 (s, 2H), 4.09 (s, 3H), 3.57 (s, 3H); MS m/e 572.2 [M+H]+.

Example 55a 6-((4-Chlorophenyl)(hydroxy)(1-methyl-1H-imidazol-5-yl)methyl)-2-methoxy-3-(4-(trifluoromethyl)benzyl)quinoline-4-carbonitrile

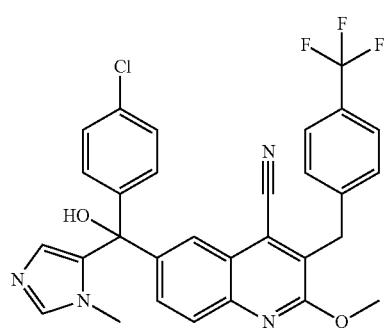 [SMILES: COc1nc2ccc(C(O)(c3ccc(Cl)cc3)c3cncn3C)cc2c(C#N)c1Cc1ccc(C(F)(F)F)cc1]

(4-Chloro-2-methoxy-3-(4-(trifluoromethyl)benzyl)quinolin-6-yl)(4-chlorophenyl)(1-methyl-1H-imidazol-5-yl)methanol (300.1 mg, 0.524 mmol, Example 54a), zinc cyanide (61.7 mg, 0.525 mmol), zinc dust (13.7 mg, 0.209 mmol), X-Phos (51.1 mg, 0.107 mmol) and Pd$_2$(dba)$_3$ (65.3 mg, 0.0713 mmol) were charged to an oven-dried microwave vial. The vial was evacuated and back-filled with nitrogen. Dimethylacetamide (8 mL) was sparged with argon and added to the mixture via syringe. Argon was bubbled through the reaction mixture for 2 minutes and the mixture was stirred at room temperature for 1.5 hours. The reaction vial was then placed in a heating block pre-heated to 80° C. for 30 minutes, then heated to 120° C. over 15 minutes and kept at this temperature for an additional 40 minutes. After allowing the reaction to cool to room temperature, the mixture was filtered through Celite®, and rinsed with ethyl acetate. The filtrate was washed with saturated aqueous sodium bicarbonate, the layers were separated and the aqueous layer was extracted with excess ethyl acetate. The combined organic layers were dried (Na$_2$SO$_4$), filtered, and concentrated to dryness. The crude product was purified by reverse-phase chromatography (acetonitrile/H$_2$O+0.05% TFA), basified with saturated aqueous sodium bicarbonate and extracted with DCM. The organics were dried (Na$_2$SO$_4$), filtered, and concentrated to dryness to provide the title compound. $^1$H NMR (400 MHz, CDCl$_3$) δ 8.18 (d, J=1.9 Hz, 1H), 7.78 (d, J=8.8 Hz, 1H), 7.49 (ddd, J=15.2, 12.1, 8.3 Hz, 5H), 7.34-7.25 (m, 4H), 7.11 (s, 1H), 6.22 (t, J=6.7 Hz, 1H), 4.36 (s, 2H), 4.09 (s, 3H), 3.32 (d, J=7.0 Hz, 3H); MS m/e 563.3 [M+H]$^+$.

Example 55a was purified by chiral SFC (ChiralPak OD-H, 80:20 heptane:EtOH) to provide two pure enantiomers. The first eluting enantiomer was Example 55b: ¹H NMR (400 MHz, CDCl₃) δ 8.16 (d, J=1.9 Hz, 1H), 7.78 (d, J=8.8 Hz, 1H), 7.55-7.49 (m, 3H), 7.46 (d, J=8.2 Hz, 2H), 7.31 (s, 4H), 7.24 (s, 1H), 6.30 (s, 1H), 4.37 (s, 2H), 4.09 (s, 3H), 3.36 (s, 3H); MS m/e 563.5 [M+H]⁺. The second eluting enantiomer was Example 55c: ¹H NMR (400 MHz, CDCl₃) δ 8.16 (d, J=1.9 Hz, 1H), 7.79 (d, J=8.8 Hz, 1H), 7.55-7.49 (m, 3H), 7.46 (d, J=8.2 Hz, 2H), 7.31 (s, 4H), 7.26 (s, 1H), 6.31 (s, 1H), 4.37 (s, 2H), 4.09 (s, 3H), 3.37 (s, 3H); MS m/e 563.5 [M+H]⁺.

Example 56

{4-Chloro-2-(2-methoxyethoxy)-3-[4-(1H-pyrazol-1-yl)benzyl]quinolin-6-yl}(4-chlorophenyl)(1-methyl-1H-imidazol-5-yl)methanol

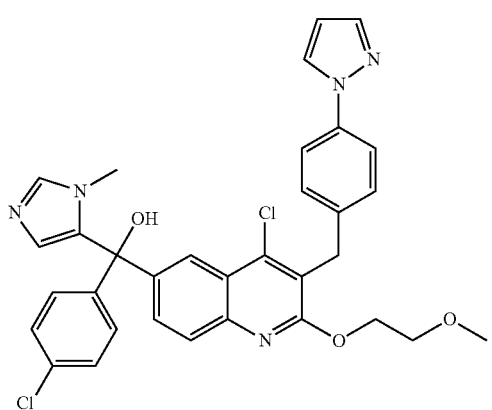 [SMILES: COCCOc1nc2ccc(C(O)(c3ccc(Cl)cc3)c3cncn3C)cc2c(Cl)c1Cc1ccc(-n2cccn2)cc1]

(3-(4-(1H-Pyrazol-1-yl)benzyl)-2,4-dichloroquinolin-6-yl)(4-chlorophenyl)(1-methyl-1H-imidazol-5-yl)methanol (100 mg, 0.174 mmol, Intermediate 64), 2-methoxyethanol (13.7 µL, 0.174 mmol), toluene (2 mL) and sodium hydride (60% dispersion in mineral oil, 17.4 mg, 0.435 mmol) were combined in a round bottom flask under an N₂ atmosphere. The contents were heated to reflux and refluxed overnight. The reaction solution turned from a heterogeneous white mixture to slightly yellowish with a moderate amount of precipitate. The contents were cooled to 0° C. in an ice water bath then transferred to a separatory funnel with EtOAc dilution and extracted with saturated, aqueous NH₄Cl and saturated, aqueous NaHCO₃ solutions. The organic phase was separated then dried over MgSO₄, filtered and concentrated under reduced pressure. The crude product was purified by flash column chromatography (silica gel, 0-10% DCM/(10% of a 2 M NH₃ MeOH in DCM)) then further purified via reverse phase chromatography using acetonitrile with ammonium hydroxide in water as eluent to afford the title compound. MS (ESI): mass calcd. for C₃₃H₂₉Cl₂N₅O₃, 613.2. m/z found, 614.3 [M+H]⁺. ¹H NMR (400 MHz, CD₃OD) δ ppm 8.14 (d, J=2.5 Hz, 1H), 8.11 (d, J=2.1 Hz, 1H), 7.88 (s, 1H), 7.80 (d, J=8.8 Hz, 1H), 7.68 (d, J=1.7 Hz, 1H), 7.64 (dd, J=8.8, 2.1 Hz, 1H), 7.60 (d, J=8.6 Hz, 2H), 7.45 (d, J=8.6 Hz, 2H), 7.41-7.32 (m, 4H), 6.50-6.46 (m, 1H), 6.36 (s, 1H), 4.66-4.59 (m, 2H), 4.35 (s, 2H), 3.81-3.74 (m, 2H), 3.49 (s, 3H), 3.40 (s, 3H).

Example 57a (4-Chloro-2-methoxy-3-(4-(trifluoromethyl)benzyl) quinolin-6-yl)(1,2-dimethyl-1H-imidazol-5-yl)(2,6-dimethylpyridin-3-yl)methanol

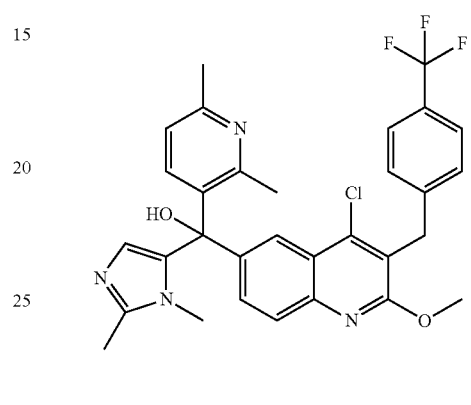

A solution of n-BuLi (2.5 M in hexanes, 0.82 mL, 2.05 mmol) was added dropwise by syringe to a solution of 5-bromo-1,2-dimethyl-1H-imidazole (361.1 mg, 2.063 mmol) in dry THF (20 mL) in a dry ice-acetone bath. After 1-2 minutes, a solution of (4-chloro-2-methoxy-3-(4-(trifluoromethyl)benzyl)quinolin-6-yl)(2,6-dimethylpyridin-3-yl)methanone (0.500 g, 1.03 mmol, Intermediate 12: step f) in dry THF (5 mL) was added dropwise. The reaction was stirred for 1.5 hours, then was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried (Na₂SO₄), filtered, and concentrated. The crude product was purified by flash column chromatography (silica gel, 0-3% MeOH-DCM) to provide the title compound. ¹H NMR (400 MHz, CDCl₃) δ 8.15 (d, J=2.2 Hz, 1H), 7.72 (d, J=8.7 Hz, 1H), 7.53-7.48 (m, 2H), 7.42-7.36 (m, 3H), 7.11 (d, J=8.0 Hz, 1H), 6.91 (d, J=8.0 Hz, 1H), 5.99 (s, 1H), 4.33 (s, 2H), 4.06 (s, 3H), 3.36 (s, 3H), 2.52 (s, 3H), 2.40 (s, 3H), 2.31 (s, 3H); MS m/e 581.1 [M+H]⁺.

Example 57a was purified by chiral SFC (ChiralPak AD-H, 70:30 CO₂:iPrOH+0.3% iPrNH₂) to provide two pure enantiomers. The first eluting enantiomer was Example 57b: ¹H NMR (400 MHz, CDCl₃) δ 8.13 (d, J=2.3 Hz, 1H), 7.75 (d, J=8.8 Hz, 1H), 7.51 (d, J=8.1 Hz, 2H), 7.43-7.38 (m, 3H), 7.11 (d, J=8.0 Hz, 1H), 6.94 (d, J=8.0 Hz, 1H), 6.06 (s, 1H), 4.34 (s, 2H), 4.07 (s, 3H), 3.39 (s, 3H), 2.54 (s, 3H), 2.42 (s, 3H), 2.38 (s, 3H); MS m/e 581.3 [M+H]⁺. The second eluting enantiomer was Example 57c: ¹H NMR (400 MHz, CDCl₃) δ 8.12 (d, J=2.1 Hz, 1H), 7.77 (d, J=8.7 Hz, 1H), 7.51 (d, J=8.1 Hz, 2H), 7.43-7.38 (m, 3H), 7.11 (d, J=8.0 Hz, 1H), 6.94 (d, J=8.1 Hz, 1H), 6.08 (s, 1H), 4.34 (s, 2H), 4.08 (s, 3H), 3.40 (s, 3H), 2.54 (s, 3H), 2.43 (s, 3H), 2.39 (s, 3H); MS m/e 581.3 [M+H]⁺.

Example 58a (4-Chloro-2-methoxy-3-(4-(methylsulfonyl)benzyl)quinolin-6-yl)(1-methyl-1H-imidazol-5-yl)(pyridin-2-yl)methanol

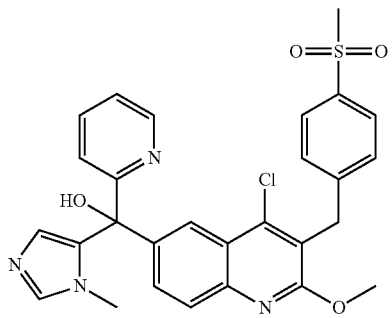 [SMILES: COc1nc2ccc(C(O)(c3ccccn3)c3cncn3C)cc2c(Cl)c1Cc1ccc(S(C)(=O)=O)cc1]

LaCl₃-2LiCl (0.6 M in THF, 0.78 mL, 0.47 mmol) was added dropwise by syringe to a solution of (4-chloro-2-methoxy-3-(4-(methylsulfonyl)benzyl)quinolin-6-yl)(1-methyl-1H-imidazol-5-yl)methanone (101.4 mg, 0.226 mmol, Intermediate 41: step d) in dry THF (2 mL). After 2 minutes, the solution was cooled in an ice bath and pyridin-2-ylmagnesium bromide (2.8 mL, 0.7 mmol) was added dropwise via syringe. The reaction was stirred for 3 hours, then quenched with saturated aqueous ammonium chloride and removed from the cold bath. The mixture was partitioned between water and ethyl acetate. The separated aqueous phase was further extracted with ethyl acetate. The organic phase was dried (Na₂SO₄), filtered, and concentrated. The crude product was purified by flash column chromatography (silica gel, 0-5% MeOH-DCM) followed by reverse-phase chromatography (acetonitrile/H₂O+0.05% TFA). The isolated product fractions were basified with saturated aqueous sodium bicarbonate, extracted with DCM, dried (Na₂SO₄), filtered, and concentrated to dryness to provide the title compound. ¹H NMR (400 MHz, CDCl₃) δ ppm 8.65-8.61 (m, 1H), 8.15 (d, J=2.0 Hz, 1H), 7.84-7.79 (m, 3H), 7.73-7.67 (m, 2H), 7.51 (s, 1H), 7.49-7.44 (m, 2H), 7.34-7.29 (m, 1H), 7.24-7.19 (m, 1H), 6.34 (s, 1H), 4.36 (s, 2H), 4.07 (s, 3H), 3.43 (s, 3H), 3.01 (s, 3H); MS m/e 549.2 [M+H]⁺.

Example 58a was purified by chiral SFC (ChiralPak AD, 50:50 EtOH:MeOH) to provide two pure enantiomers. The first eluting enantiomer was Example 58b: ¹H NMR (500 MHz, CDCl₃) δ 8.65 (d, J=4.4 Hz, 1H), 8.13 (d, J=1.9 Hz, 1H), 7.84 (d, J=8.7 Hz, 1H), 7.81 (d, J=8.4 Hz, 2H), 7.72 (td, J=7.7, 1.7 Hz, 1H), 7.67 (dd, J=8.7, 2.1 Hz, 1H), 7.46 (d, J=8.4 Hz, 2H), 7.34 (dd, J=7.1, 5.3 Hz, 1H), 7.20 (d, J=7.9 Hz, 1H), 6.71 (s, 1H), 6.43 (s, 1H), 4.37 (s, 2H), 4.07 (s, 3H), 3.49 (s, 3H), 3.01 (s, 3H); MS m/e 549.2 [M+H]⁺. The second eluting enantiomer was Example 58c: ¹H NMR (500 MHz, CDCl₃) δ 8.65 (d, J=4.3 Hz, 1H), 8.12 (d, J=2.0 Hz, 1H), 7.89 (s, 1H), 7.85 (d, J=8.7 Hz, 1H), 7.82 (d, J=8.4 Hz, 2H), 7.73 (td, J=7.7, 1.7 Hz, 1H), 7.66 (dd, J=8.7, 2.1 Hz, 1H), 7.47 (d, J=8.4 Hz, 2H), 7.35 (dd, J=6.7, 4.9 Hz, 1H), 7.20 (d, J=7.9 Hz, 1H), 6.73 (s, 1H), 6.46 (s, 1H), 4.37 (s, 2H), 4.07 (s, 3H), 3.51 (s, 3H), 3.01 (s, 3H); MS m/e 549.2 [M+H]⁺.

Example 59a (3-(Benzo[b]thiophen-2-ylmethyl)-4-chloro-2-methoxyquinolin-6-yl)(1-methyl-1H-imidazol-5-yl)(pyridin-2-yl)methanol

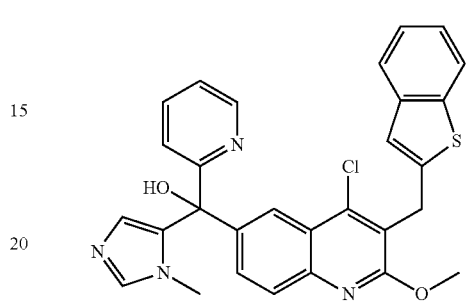

LaCl₃-2LiCl (0.6 M in THF, 0.78 mL, 0.47 mmol) was added dropwise by syringe to a solution of (3-(benzo[b]thiophen-2-ylmethyl)-4-chloro-2-methoxyquinolin-6-yl)(1-methyl-1H-imidazol-5-yl)methanone (101.4 mg, 0.226 mmol, Intermediate 40: step b) in dry THF (2 mL). After 5 minutes, the solution was cooled in an ice bath and pyridin-2-ylmagnesium bromide (2.8 mL, 0.7 mmol) was added dropwise via syringe. The reaction was stirred for 3 hours, then quenched with saturated aqueous ammonium chloride and removed from the cold bath. The mixture was partitioned between water and ethyl acetate. The separated aqueous phase was further extracted with ethyl acetate. The organic phase was dried (Na₂SO₄), filtered, and concentrated to dryness. The crude product was purified by flash column chromatography (silica gel, 0-5% MeOH-DCM) followed by reverse-phase chromatography (acetonitrile/H₂O+0.05% TFA). The isolated product fractions were basified with saturated aqueous sodium bicarbonate, extracted with DCM, dried (Na₂SO₄), filtered, and concentrated to dryness to provide the title compound. ¹H NMR (400 MHz, CDCl₃) δ ppm 8.63-8.59 (m, 1H), 8.13 (d, J=2.0 Hz, 1H), 7.82 (d, J=8.7 Hz, 1H), 7.71-7.60 (m, 4H), 7.49 (d, J=1.1 Hz, 1H), 7.30-7.18 (m, 4H), 7.08 (d, J=1.0 Hz, 1H), 6.32 (d, J=1.1 Hz, 1H), 4.50 (d, J=1.1 Hz, 2H), 4.13 (s, 3H), 3.41 (s, 3H); MS m/e 527.2 [M+H]⁺.

Example 59a was purified by chiral SFC (ChiralPak OD, 100% EtOH) to provide two pure enantiomers. The first eluting enantiomer was Example 59b: ¹H NMR (500 MHz, CDCl₃) δ 8.63 (d, J=4.8 Hz, 1H), 8.11 (d, J=2.0 Hz, 1H), 7.81 (d, J=8.7 Hz, 1H), 7.70 (d, J=8.9 Hz, 1H), 7.69-7.66 (m, 2H), 7.63 (d, J=7.9 Hz, 1H), 7.47 (s, 1H), 7.32-7.28 (m, 2H), 7.24-7.20 (m, 1H), 7.19 (d, J=8.0 Hz, 1H), 7.08 (s, 1H), 6.65 (s, 1H), 6.31 (s, 1H), 4.52 (s, 2H), 4.13 (s, 3H), 3.42 (s, 3H); MS m/e 526.9 [M+H]⁺. The second eluting enantiomer was Example 59c: ¹H NMR (500 MHz, CDCl₃) δ 8.63 (d, J=4.3 Hz, 1H), 8.11 (d, J=2.0 Hz, 1H), 7.81 (d, J=8.7 Hz, 1H), 7.70 (d, J=8.0 Hz, 1H), 7.67 (dt, J=7.7, 1.9 Hz, 2H), 7.62 (d, J=7.6 Hz, 1H), 7.47 (s, 1H), 7.29 (m, 2H), 7.24-7.20 (m, 1H), 7.19 (d, J=8.0 Hz, 1H), 7.08 (s, 1H), 6.65 (s, 1H), 6.32 (s, 1H), 4.52 (s, 2H), 4.13 (s, 3H), 3.42 (s, 3H); MS m/e 526.9 [M+H]⁺.

Example 60

(3-(4-(1H-Pyrazol-1-yl)benzyl)-2-butyl-4-chloro-quinolin-6-yl)(3-fluorophenyl)(pyridin-3-yl) methanol•TFA

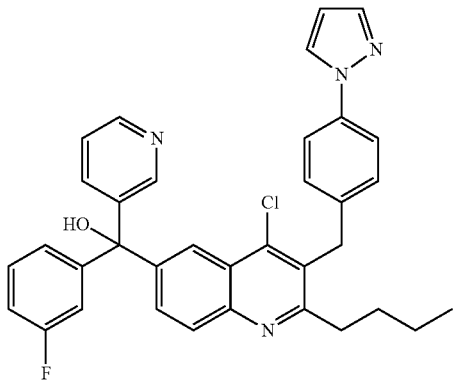 [SMILES: CCCCc1nc2ccc(C(O)(c3cccnc3)c3cccc(F)c3)cc2c(Cl)c1Cc1ccc(-n2cccn2)cc1]

A solution of n-BuLi (2.5 M in hexanes, 0.2 mL, 0.5 mmol) was added dropwise by syringe to a solution of 3-(4-(1H-pyrazol-1-yl)benzyl)-6-bromo-2,4-dichloroquinoline (0.200 g, 0.462 mmol, Intermediate 3: step c) in dry THF (4 mL) in a dry ice-acetone bath. After 30 seconds, a solution of (3-fluorophenyl)(pyridin-3-yl)methanone (111.6 mg, 0.555 mmol, Intermediate 34: step b) in dry THF (0.2 mL) was added dropwise. The reaction was stirred for 5 minutes, then was moved into an ice bath and allowed to warm to ambient temperature overnight. The reaction was quenched with saturated aqueous ammonium chloride. The mixture was partitioned between water and ethyl acetate. The separated aqueous phase was further extracted with ethyl acetate. The organic phase was dried ($Na_2SO_4$), filtered, and concentrated. The crude product was purified by flash column chromatography (silica gel, 0-5% MeOH-DCM) followed by reverse-phase chromatography (acetonitrile/$H_2O$+0.05% TFA) to provide the title compound. $^1$H NMR (400 MHz, $CD_3OD$) δ 8.73 (d, J=2.2 Hz, 1H), 8.59-8.54 (m, 1H), 8.40 (dt, J=8.3, 1.7 Hz, 1H), 8.19-8.13 (m, 1H), 7.96-7.93 (m, 1H), 7.81-7.66 (m, 3H), 7.65 (d, J=2.0 Hz, 1H), 7.32-7.25 (m, 1H), 7.24-7.18 (m, 4H), 6.99-6.96 (m, 1H), 6.94-6.90 (m, 2H), 6.14 (d, J=2.0 Hz, 1H), 4.36 (s, 2H), 3.11 (t, J=7.9 Hz, 2H), 1.64-1.47 (m, 4H), 0.98 (t, J=7.0 Hz, 3H); MS m/e 577.2 $[M+H]^+$.

Example 61

(3-(4-(1H-Pyrazol-1-yl)benzyl)-4-chloro-2-methoxyquinolin-6-yl)(3-fluorophenyl)(pyridin-3-yl)methanol

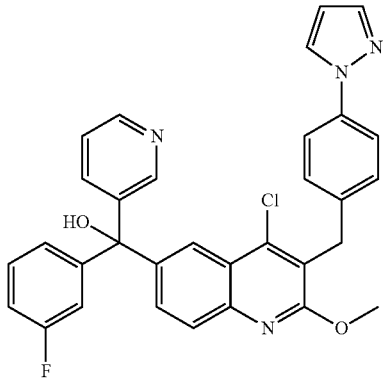 [SMILES: COc1nc2ccc(C(O)(c3cccnc3)c3cccc(F)c3)cc2c(Cl)c1Cc1ccc(-n2cccn2)cc1]

(3-(4-(1H-Pyrazol-1-yl)benzyl)-2,4-dichloroquinolin-6-yl)(3-fluorophenyl)(pyridin-3-yl)methanol (16.2 mg, 0.0292 mmol, Intermediate 36) and sodium methoxide (8.0 mg, 0.15 mmol) were charged to a microwave vial with dry toluene (0.14 mL) and heated to 105° C. for 4 hours. The mixture was allowed to cool to room temperature, then filtered through Celite® and rinsed with dichloromethane. The filtrate was concentrated to dryness and purified by reverse-phase chromatography (acetonitrile/$H_2O$+0.05% TFA). The isolated product fractions were basified with saturated aqueous sodium bicarbonate, extracted with DCM, dried ($Na_2SO_4$), filtered, and concentrated to dryness to provide the title compound. $^1$H NMR (400 MHz, $CDCl_3$) δ 8.58 (s, 2H), 8.03 (d, J=2.0 Hz, 1H), 7.85 (d, J=2.4 Hz, 1H), 7.81 (d, J=8.8 Hz, 1H), 7.70-7.66 (m, 2H), 7.58-7.51 (m, 3H), 7.35 (d, J=8.7 Hz, 2H), 7.33-7.28 (m, 2H), 7.09-7.04 (m, 2H), 7.04-6.99 (m, 1H), 6.45-6.41 (m, 1H), 4.31 (s, 2H), 4.08 (s, 3H); MS m/e 551.2 $[M+H]^+$.

Example 62

(3-(4-(1H-pyrazol-1-yl)benzyl)-4-chloro-2-methoxyquinolin-6-yl)(4-chlorophenyl)(pyridin-3-yl)methanol

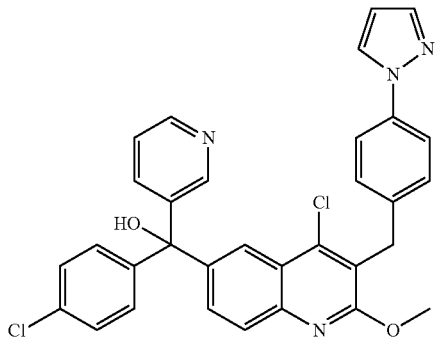 [SMILES: COc1nc2ccc(C(O)(c3ccc(Cl)cc3)c3cccnc3)cc2c(Cl)c1Cc1ccc(-n2cccn2)cc1]

(3-(4-(1H-Pyrazol-1-yl)benzyl)-2,4-dichloroquinolin-6-yl)(4-chlorophenyl)(pyridin-3-yl)methanol (61.9 mg, 0.108 mmol, Intermediate 37) and sodium methoxide (0.0313 g, 0.579 mmol) were charged to a microwave vial with dry toluene (0.57 mL) and heated to 105° C. for 4 hours. The mixture was allowed to cool to room temperature, then filtered through Celite® and rinsed with dichloromethane. The filtrate was concentrated to dryness and purified by reverse-phase chromatography (acetonitrile/$H_2O$+0.05% TFA). The isolated product fractions were basified with saturated aqueous sodium bicarbonate, extracted with DCM, dried ($Na_2SO_4$), filtered, and concentrated to dryness to provide the title compound. $^1$H NMR (400 MHz, $CDCl_3$) δ 8.50 (s, 1H), 8.46 (d, J=4.0 Hz, 1H), 8.02 (d, J=1.9 Hz, 1H), 7.84 (dd, J=2.5, 0.5 Hz, 1H), 7.78 (d, J=8.7 Hz, 1H), 7.68-7.63 (m, 2H), 7.56-7.52 (m, 2H), 7.49 (dd, J=8.8, 2.2 Hz, 1H), 7.33 (dd, J=6.5, 4.6 Hz, 2H), 7.31-7.27 (m, 2H), 7.25-7.20 (m, 3H), 6.42 (dd, J=2.4, 1.8 Hz, 1H), 4.29 (s, 2H), 4.08 (s, 3H); MS m/e 567.2 $[M+H]^+$.

Example 63

3-(4-(1H-Pyrazol-1-yl)benzyl)-4-chloro-2-methoxyquinolin-6-yl)(4-methoxyphenyl)(pyridin-3-yl)methanol

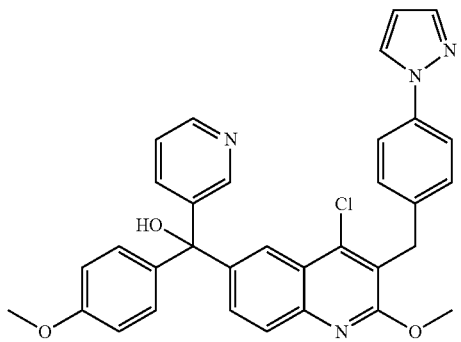 [SMILES: COc1ccc(C(O)(c2cccnc2)c2ccc3nc(OC)c(Cc4ccc(-n5cccn5)cc4)c(Cl)c3c2)cc1]

(3-(4-(1H-Pyrazol-1-yl)benzyl)-2,4-dichloroquinolin-6-yl)(4-methoxyphenyl)(pyridin-3-yl)methanol (46.3 mg, 0.0816 mmol, Intermediate 38) and sodium methoxide (0.0225 g, 0.416 mmol) were charged to a microwave vial with dry toluene (0.37 mL) and heated to 105° C. for 4 hours. The mixture was allowed to cool to room temperature, then filtered through Celite® and rinsed with dichloromethane. The filtrate was concentrated to dryness and purified by reverse-phase chromatography (acetonitrile/H$_2$O+0.05% TFA). The isolated product fractions were basified with saturated aqueous sodium bicarbonate, extracted with DCM, dried (Na$_2$SO$_4$), filtered, and concentrated to dryness to provide the title compound. $^1$H NMR (500 MHz, CDCl$_3$) δ 8.49 (s, 1H), 8.41 (d, J=4.5 Hz, 1H), 8.00 (d, J=2.0 Hz, 1H), 7.79 (t, J=4.4 Hz, 1H), 7.70 (d, J=8.8 Hz, 1H), 7.63-7.58 (m, 2H), 7.49-7.45 (m, 3H), 7.27 (d, J=8.5 Hz, 2H), 7.18 (dd, J=8.0, 4.8 Hz, 1H), 7.10 (d, J=8.8 Hz, 2H), 6.78 (d, J=8.6 Hz, 2H), 6.35 (t, J=2.0 Hz, 1H), 4.22 (s, 2H), 4.00 (s, 3H), 3.73 (s, 3H); MS m/e 563.3 [M+H]$^+$.

Example 64a (3-(4-(1H-Pyrazol-1-yl)benzyl)-4-chloro-2-methoxyquinolin-6-yl)(1-methyl-1H-imidazol-5-yl)(pyridin-2-yl)methanol

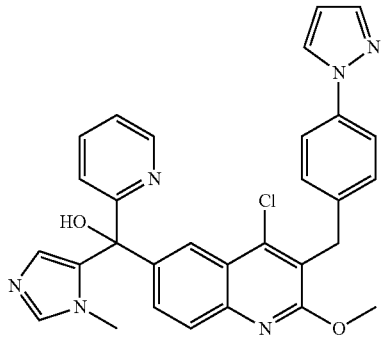 [SMILES: COc1nc2ccc(C(O)(c3ccccn3)c3cncn3C)cc2c(Cl)c1Cc1ccc(-n2cccn2)cc1]

A solution of n-BuLi (2.5 M in hexanes, 0.28 mL, 0.7 mmol) was added dropwise by syringe to a solution of 3-(4-(1H-pyrazol-1-yl)benzyl)-6-bromo-4-chloro-2-methoxyquinoline (0.303 g, 0.707 mmol, Intermediate 10) in dry THF (7 mL) in a dry ice-acetone bath. After 1-2 minutes, a solution of (1-methyl-1H-imidazol-5-yl)(pyridin-2-yl)methanone (0.144 g, 0.769 mmol, Intermediate 33: step b) in dry THF (0.5 mL) was added dropwise. The reaction was stirred for 5 minutes, switched to an ice bath for 10 minutes, then removed from the cold bath and allowed to warm to ambient temperature. The reaction was quenched with methanol. The mixture was partitioned between water and ethyl acetate. The separated aqueous phase was further extracted with ethyl acetate. The organic phase was dried (Na$_2$SO$_4$), filtered, and concentrated to dryness. The crude product was purified by flash column chromatography (silica gel, 100% EtOAc) followed by reverse-phase chromatography (acetonitrile/H$_2$O+0.05% TFA). The isolated product fractions were basified with saturated aqueous sodium bicarbonate, extracted with DCM, dried (Na$_2$SO$_4$), filtered, and concentrated to dryness. Impurities remained in the sample, therefore the product was taken forward to the chiral separation step.

Example 64a was purified by chiral SFC (ChiralPak IA, 100% ethanol) to provide two pure enantiomers. The first eluting enantiomer was Example 64b: $^1$H NMR (500 MHz, CDCl$_3$) δ 8.64-8.61 (m, 1H), 8.13 (d, J=2.0 Hz, 1H), 7.85 (d, J=2.4 Hz, 1H), 7.81 (d, J=8.7 Hz, 1H), 7.71-7.66 (m, 3H), 7.57-7.53 (m, 2H), 7.47 (s, 1H), 7.36 (d, J=8.2 Hz, 2H), 7.31-7.28 (m, 1H), 7.20 (d, J=7.9 Hz, 1H), 6.67 (s, 1H), 6.42 (t, J=2.1 Hz, 1H), 6.32 (d, J=1.2 Hz, 1H), 4.30 (s, 2H), 4.07 (s, 3H), 3.42 (s, 3H); MS m/e 537.3 [M+H]$^+$. The second eluting enantiomer was Example 64c: $^1$H NMR (500 MHz, CDCl$_3$) δ 8.63 (ddd, J=4.9, 1.8, 1.0 Hz, 1H), 8.13 (d, J=2.0 Hz, 1H), 7.85 (dd, J=2.5, 0.7 Hz, 1H), 7.81 (d, J=8.7 Hz, 1H), 7.71-7.66 (m, 3H), 7.57-7.54 (m, 2H), 7.47 (d, J=1.1 Hz, 1H), 7.38-7.33 (m, 2H), 7.30 (ddd, J=7.5, 4.9, 1.1 Hz, 1H), 7.20 (dt, J=7.9, 1.1 Hz, 1H), 6.42 (dd, J=2.4, 1.8 Hz, 1H), 6.32 (d, J=1.1 Hz, 1H), 4.30 (s, 2H), 4.08 (s, 3H), 3.42 (s, 3H); MS m/e 537.3 [M+H]$^+$.

Example 65a

4-Chloro-3-(4-fluorobenzyl)-2-methoxyquinolin-6-yl)(1,2-dimethyl-1H-imidazol-5-yl)(1-methyl-1H-1,2,3-triazol-5-yl)methanol

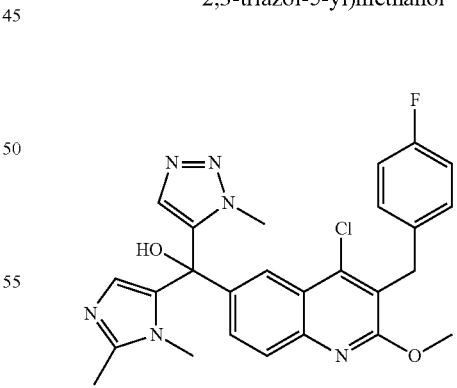

A solution of n-BuLi (2.5 M in hexanes, 1.5 mL, 3.75 mmol) was added dropwise by syringe to a solution of 1-methyl-1H-1,2,3-triazole (324 mg, 3.90 mmol) in dry THF (20 mL) in a dry ice-methanol bath. The suspension was stirred for 30 minutes, slowly allowing the reaction mixture to warm to −20° C. (4-Chloro-3-(4-fluorobenzyl)-2-methoxyquinolin-6-yl)(1,2-dimethyl-1H-imidazol-5-yl)methanone (0.800 g, 1.89 mmol, Intermediate 46: step b) in dry THF (10 mL) was added to the mixture via syringe and the resulting mixture was allowed to warm to ambient temperature overnight. The reaction was quenched with saturated aqueous ammonium chloride. Water was added and the aqueous mixture was extracted with dichloromethane. The combined organic layers were dried (Na$_2$SO$_4$), filtered, and concentrated to dryness. The crude product was purified by flash column chromatography (silica gel, 0-5% MeOH-DCM) to provide the title compound. $^1$H NMR (400 MHz, CDCl$_3$) δ 8.24 (d, J=1.9 Hz, 1H), 8.05 (s, 1H), 7.71 (d, J=8.7 Hz, 1H), 7.37 (dd, J=8.7, 2.0 Hz, 1H), 7.26-7.21 (m, 2H), 7.02 (s, 1H), 6.97-6.90 (m, 2H), 5.95 (s, 1H), 4.16 (s, 2H), 4.07 (s, 3H), 3.87 (s, 3H), 3.31 (s, 3H), 2.09 (s, 3H); MS m/e 506.9 [M+H]$^+$.

Example 65a was purified by chiral SFC (ChiralPak AD-H, 75:25 CO$_2$:MeOH+0.3% iPrNH$_2$) to provide two pure enantiomers. The first eluting enantiomer was Example 65b: $^1$H NMR (400 MHz, CDCl$_3$) δ 8.23-8.19 (d, J=2.1 Hz, 1H), 7.73-7.68 (d, J=8.7 Hz, 1H), 7.39-7.33 (dd, J=8.8, 2.2 Hz, 1H), 7.29-7.23 (m, 2H), 7.07 (s, 1H), 6.98-6.91 (m, 2H), 6.47 (br s, 1H), 6.03 (s, 1H), 4.21 (s, 2H), 4.07 (s, 3H), 3.89 (s, 3H), 3.34 (s, 3H), 2.20 (s, 3H); MS m/e 506.2 [M]$^+$. The second eluting enantiomer was Example 65c: $^1$H NMR (400 MHz, CDCl$_3$) δ 8.19 (d, J=2.1 Hz, 1H), 7.72 (d, J=8.7 Hz, 1H), 7.36 (dd, J=8.7, 2.2 Hz, 1H), 7.29-7.24 (m, 2H), 7.11 (s, 1H), 6.97-6.91 (m, 2H), 6.06 (s, 1H), 4.23 (s, 2H), 4.08 (s, 3H), 3.90 (s, 3H), 3.36 (s, 3H), 2.24 (s, 3H); MS m/e 506.2 [M]$^+$.

Example 66a 6-((1,2-Dimethyl-1H-imidazol-5-yl)(hydroxy)(1-methyl-1H-1,2,3-triazol-5-yl)methyl)-3-(4-fluorobenzyl)-2-methoxyquinoline-4-carbonitrile

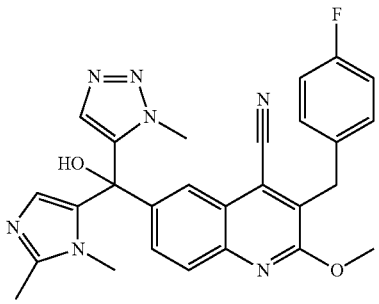 [SMILES: COc1nc2ccc(C(O)(c3cnnn3C)c3cnc(C)n3C)cc2c(C#N)c1Cc1ccc(F)cc1]

(4-Chloro-3-(4-fluorobenzyl)-2-methoxyquinolin-6-yl)(1,2-dimethyl-1H-imidazol-5-yl)(1-methyl-1H-1,2,3-triazol-5-yl)methanol (406.7 mg, 0.802 mmol, Example 65a), zinc cyanide (190.9 mg, 1.626 mmol), zinc dust (20.8 mg, 0.318 mmol), X-Phos (76.5 mg, 0.16 mmol) and Pd$_2$(dba)$_3$ (113.1 mg, 0.124 mmol) were charged to an oven-dried microwave vial. The vial was evacuated and back-filled with nitrogen. Dimethylacetamide (4.5 mL) was sparged with argon and added to the mixture via syringe. Argon was bubbled through the reaction mixture for 1 minute and the mixture was stirred and heated at 120° C. overnight under a positive pressure of nitrogen. The mixture was allowed to cool to ambient temperature, filtered through Celite®, and rinsed with dichloromethane. The filtrate was washed with saturated aqueous sodium bicarbonate, the layers were separated and the aqueous layer was extracted with excess dichloromethane. The combined organic layers were dried (Na$_2$SO$_4$), filtered, and concentrated to dryness. The crude product was purified by flash column chromatography (silica gel, 0-5% MeOH-DCM) to provide the title compound. $^1$H NMR (400 MHz, CDCl$_3$) δ 8.24 (d, J=2.0 Hz, 1H), 7.78 (d, J=8.8 Hz, 1H), 7.36-7.30 (m, 3H), 7.11 (s, 1H), 7.00-6.95 (m, 2H), 6.01 (s, 1H), 4.28 (s, 2H), 4.11 (s, 3H), 3.92 (s, 3H), 3.37 (s, 3H), 2.16 (s, 3H); MS m/e 498.5 [M+H]$^+$. Example 66a was purified by chiral SFC (ChiralPak AD-H, 70:30 CO$_2$: EtOH (+0.3% iPrNH$_2$)) to provide two pure enantiomers. The first eluting enantiomer was Example 66b: $^1$H NMR (400 MHz, CDCl$_3$) δ 8.23 (d, J=2.1 Hz, 1H), 7.78 (d, J=8.8 Hz, 1H), 7.37-7.29 (m, 3H), 7.11 (s, 1H), 7.01-6.94 (m, 2H), 6.83 (s, 1H), 6.02 (s, 1H), 4.29 (s, 2H), 4.11 (s, 3H), 3.91 (s, 3H), 3.40 (s, 3H), 2.18 (s, 3H); MS m/e 497.2 [M]$^+$. The second eluting enantiomer was Example 66c: $^1$H NMR (400 MHz, CDCl$_3$) δ 8.22 (d, J=2.1 Hz, 1H), 7.78 (d, J=8.8 Hz, 1H), 7.38-7.29 (m, 3H), 7.14 (s, 1H), 7.02-6.94 (m, 2H), 6.36 (s, 1H), 6.04 (s, 1H), 4.30 (s, 2H), 4.11 (s, 3H), 3.92 (s, 3H), 3.41 (s, 3H), 2.20 (s, 3H); MS m/e 497.2 [M]$^+$.

Example 67

(4-Chloro-3-(4-fluorobenzyl)-2-methoxyquinolin-6-yl)bis(1,2-dimethyl-1H-imidazol-5-yl)methanol

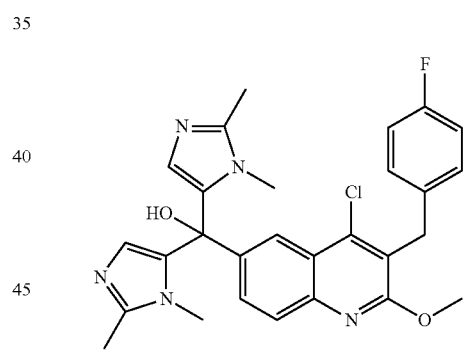

A solution of n-BuLi (2.5 M in hexanes, 0.24 mL, 0.6 mmol) was added dropwise by syringe to a solution of 5-bromo-1,2-dimethyl-1H-imidazole (107.8 mg, 0.616 mmol) in dry THF (6 mL) in a dry ice-acetone bath. After 1-2 minutes, (4-chloro-3-(4-fluorobenzyl)-2-methoxyquinolin-6-yl)(1,2-dimethyl-1H-imidazol-5-yl)methanone (0.217 g, 0.512 mmol, Intermediate 46: step b) in dry THF (2 mL) was added to the mixture via syringe. After 5 minutes, the reaction was removed from the cold bath and was allowed to warm to ambient temperature overnight. The reaction was quenched with saturated aqueous ammonium chloride. Water was added and the aqueous mixture was extracted with dichloromethane. The combined organic layers were dried (Na$_2$SO$_4$), filtered, and concentrated to dryness. The crude product was purified by flash column chromatography (silica gel, 0-10% MeOH-DCM) to provide the title compound. $^1$H NMR (400 MHz, CDCl$_3$) δ 8.23 (d, J=2.2 Hz, 1H), 7.63 (d, J=8.7 Hz, 1H), 7.37 (dd, J=8.8, 2.1 Hz, 1H), 7.30-7.25 (m, 2H), 6.97-6.92 (m, 2H), 6.19 (s, 1H), 6.12 (s, 2H), 4.22 (s, 2H), 4.07 (s, 3H), 3.37 (s, 6H), 2.24 (s, 6H); MS m/e 520.2 [M+H]⁺.

Example 68

(4-Chloro-2-methoxy-3-(4-(trifluoromethyl)benzyl) quinolin-6-yl)(1-methyl-1H-imidazol-5-yl)(pyridin-2-yl)methanol•TFA

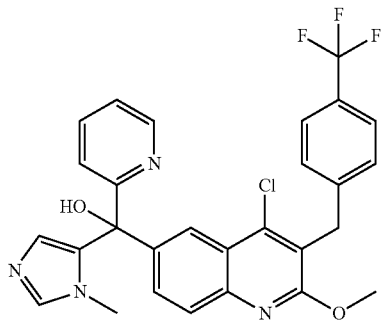 [SMILES: COc1nc2ccc(C(O)(c3ccccn3)c3cncn3C)cc2c(Cl)c1Cc1ccc(C(F)(F)F)cc1]

The title compound was prepared using 6-bromo-4-chloro-2-methoxy-3-(4-(trifluoromethyl)benzyl)quinoline (Intermediate 12: step d) and (1-methyl-1H-imidazol-5-yl)(pyridin-2-yl)methanone (Intermediate 33: step b) using the procedure described for Example 54a. ¹H NMR (500 MHz, CDCl₃) δ 8.68 (d, J=4.4 Hz, 1H), 8.57 (s, 1H), 8.10 (d, J=2.0 Hz, 1H), 7.89 (d, J=8.8 Hz, 1H), 7.78 (td, J=7.8, 1.7 Hz, 1H), 7.62 (dd, J=8.7, 2.1 Hz, 1H), 7.50 (d, J=8.2 Hz, 2H), 7.43-7.37 (m, 3H), 7.20 (d, J=7.9 Hz, 1H), 6.66 (s, 1H), 4.35 (s, 2H), 4.09 (s, 3H), 3.65 (s, 3H); MS m/e 538.1 [M+H]⁺.

Example 69a 1-(4-((4-Chloro-2-methoxy-3-(4-(trifluoromethyl) benzyl)quinolin-6-yl)(hydroxy)(phenyl)methyl)piperidin-1-yl)ethanone•TFA

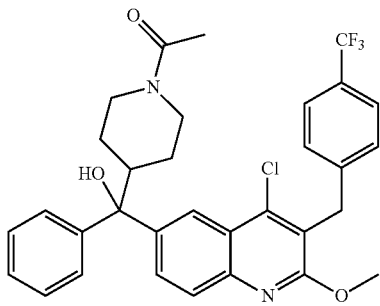 [SMILES: COc1nc2ccc(C(O)(c3ccccc3)C3CCN(C(C)=O)CC3)cc2c(Cl)c1Cc1ccc(C(F)(F)F)cc1]

The title compound was prepared using 6-bromo-4-chloro-2-methoxy-3-(4-(trifluoromethyl)benzyl)quinoline (Intermediate 12: step d) and 1-(4-benzoylpiperidin-1-yl)ethanone (Intermediate 18) using the procedure described for Example 54a. ¹H NMR (500 MHz, CDCl₃) δ 8.28 (s, 1H), 7.77 (d, J=8.0 Hz, 1H), 7.66 (s, 1H), 7.50 (t, J=8.0 Hz, 4H), 7.36 (dd, J=18.8, 7.7 Hz, 4H), 7.23 (d, J=7.0 Hz, 1H), 4.69 (t, J=13.0 Hz, 1H), 4.34 (s, 2H), 4.05 (s, 3H), 3.94-3.77 (m, 1H), 3.28-3.03 (m, 1H), 2.85-2.74 (m, 1H), 2.72-2.59 (m, 1H), 2.14 (s, 3H), 1.83-1.69 (m, 1H), 1.66-1.32 (m, 3H); MS m/e 583.3 [M+H]⁺.

Example 69a was purified by chiral HPLC (Diacel Chiralcel OD, 100% acetonitrile) to provide two pure enantiomers. The first eluting enantiomer was Example 69b: ¹H NMR (500 MHz, CDCl₃) δ 8.27 (d, J=5.9 Hz, 1H), 7.83-7.72 (m, 1H), 7.66 (t, J=7.7 Hz, 1H), 7.50 (t, J=8.9 Hz, 4H), 7.36 (dd, J=18.8, 7.6 Hz, 4H), 7.23 (d, J=7.1 Hz, 1H), 4.77-4.59 (m, 1H), 4.34 (s, 2H), 4.05 (s, 3H), 3.97-3.78 (m, 1H), 3.26-3.05 (m, 1H), 2.78 (t, J=11.8 Hz, 1H), 2.72-2.56 (m, 1H), 2.12 (s, 3H), 1.73 (s, 1H), 1.66-1.22 (m, 3H); MS m/e 583.3 [M+H]⁺. The second eluting enantiomer was Example 69c: ¹H NMR (500 MHz, CDCl₃) δ 8.27 (d, J=4.8 Hz, 1H), 7.80-7.70 (m, 1H), 7.66 (t, J=8.4 Hz, 1H), 7.54-7.46 (m, 4H), 7.41-7.32 (m, 4H), 7.26-7.20 (m, 1H), 4.80-4.57 (m, 1H), 4.34 (s, 2H), 4.05 (s, 3H), 3.85 (t, J=12.5 Hz, 1H), 3.23-3.05 (m, 1H), 2.78 (t, J=9.7 Hz, 1H), 2.73-2.58 (m, 1H), 2.12 (s, 3H), 1.81-1.66 (m, 1H), 1.65-1.32 (m, 3H); MS m/e 583.3 [M+H]⁺.

Example 70

3-((4-Chloro-6-((4-chlorophenyl)(hydroxy)(1-methyl-1H-imidazol-5-yl)methyl)-2-methoxyquinolin-3-yl)methyl)benzonitrile•TFA

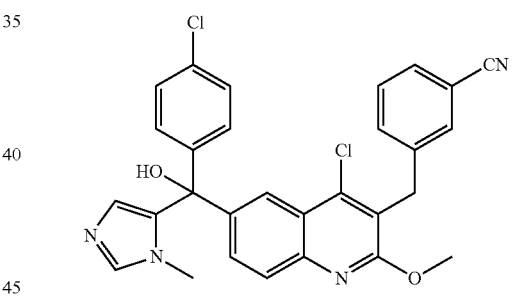

A solution of n-BuLi (2.5 M in hexanes, 0.18 mL, 0.45 mmol) was added dropwise by syringe over a 2 minute period to a mixture of 3-((6-bromo-4-chloro-2-methoxyquinolin-3-yl)methyl)benzonitrile (0.173 g, 0.446 mmol, Intermediate 70: step d) and (4-chlorophenyl)(1-methyl-1H-imidazol-5-yl)methanone (0.109 g, 0.446 mmol, Intermediate 43: step b) in dry THF (4.5 mL) and a dry ice-acetone bath. The reaction was stirred for 30 minutes, then removed from the cold bath and allowed to warm to room temperature overnight. The reaction was quenched with saturated aqueous ammonium chloride. The layers were separated and the aqueous phase was extracted with ethyl acetate. The combined organic phase was dried (MgSO₄), filtered, and concentrated to dryness. The crude product was purified by reverse-phase HPLC (CH₃CN—H₂O, 0.05% TFA) and lyophilized to provide the title compound as a white solid. ¹H NMR (500 MHz, CDCl₃) δ ppm 8.45 (s, 1H), 8.05 (d, J=2.1 Hz, 1H), 7.85 (d, J=8.8 Hz, 1H), 7.58-7.50 (m, 3H), 7.48 (d, J=7.7 Hz, 1H), 7.41-7.33 (m, 3H), 7.30 (d, J=8.7 Hz, 2H), 6.59 (s, 1H), 4.31 (s, 2H), 4.09 (s, 3H), 3.62 (s, 3H) MS m/e 579.2 [M+H]+.

Example 71a (3-(Benzo[b]thiophen-2-ylmethyl)-4-chloro-2-methoxyquinolin-6-yl)(1-methyl-1H-imidazol-5-yl)(6-(trifluoromethyl)pyridin-3-yl)methanamine

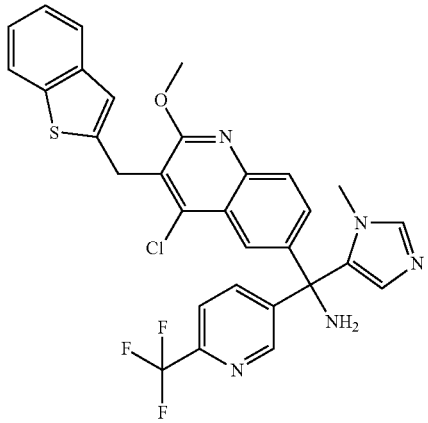 [SMILES: COc1nc2ccc(C(N)(c3ccc(C(F)(F)F)nc3)c3cncn3C)cc2c(Cl)c1Cc1cc2ccccc2s1]

A crude mixture of (3-(benzo[b]thiophen-2-ylmethyl)-4-chloro-2-methoxyquinolin-6-yl)(1-methyl-1H-imidazol-5-yl)(6-(trifluoromethyl)pyridin-3-yl)methyl acetate (0.82 g, 1.28 mmol, Intermediate 51: step d) and ammonia (7 M in MeOH, 4 mL) were combined in a sealed tube and heated in a 65° C. oil bath for 18 hours. The mixture was concentrated under reduced pressure and purified by HPLC to provide the TFA salt that was further neutralized by washing with saturated aqueous NaHCO₃ solution. The aqueous was extracted with EtOAc. The ethyl acetate extract was dried over Na₂SO₄, filtered and evaporated in vacuo to provide the title compound. ¹H NMR (400 MHz, CDCl₃) δ 8.75 (s, 1H), 8.00 (d, J=2.0 Hz, 1H), 7.83 (d, J=8.6 Hz, 1H), 7.73-7.79 (m, 1H), 7.71 (d, J=7.6 Hz, 1H), 7.64 (dd, J=8.1, 4.5 Hz, 2H), 7.43-7.50 (m, 1H), 7.19-7.31 (m, 4H), 7.10 (s, 1H), 4.53 (s, 2H), 4.15 (s, 3H), 3.44 (s, 3H); MS (ESI) 594

(3-(Benzo[b]thiophen-2-ylmethyl)-4-chloro-2-methoxyquinolin-6-yl)(1-methyl-1H-imidazol-5-yl)(6-(trifluoromethyl)pyridin-3-yl)methanamine was purified by HPLC (250 gram Chiralpak OD-H column, mobile phase: 20% ethanol and 80% heptane eluent, 80 mL/minute, 240 nm wavelength) to give 2 enantiomers. The first eluting enantiomer was Example 71b: ¹H NMR (400 MHz, CD₃OD) δ 8.91-9.02 (m, 1H), 8.77 (d, J=2.0 Hz, 1H), 8.12 (d, J=2.0 Hz, 1H), 7.98-8.04 (m, 1H), 7.94 (d, J=8.6 Hz, 1H), 7.87 (d, J=8.1 Hz, 1H), 7.70 (d, J=8.1 Hz, 1H), 7.60-7.68 (m, 2H), 7.24 (dd, J=10.9, 7.8 Hz, 2H), 7.11 (s, 1H), 6.87-6.95 (m, 1H), 5.49 (s, 2H), 4.55 (s, 2H), 4.15 (s, 3H), 3.73 (s, 3H); MS (ESI) 594 and the second eluting enantiomer was Example 71b: ¹H NMR (400 MHz, CDCl₃) δ 8.76 (s, 1H), 8.00 (d, J=2.0 Hz, 1H), 7.84 (d, J=8.6 Hz, 2H), 7.76 (d, J=2.0 Hz, 1H), 7.71 (d, J=8.1 Hz, 1H), 7.60-7.68 (m, 2H), 7.47 (dd, J=8.8, 2.3 Hz, 1H), 7.19-7.33 (m, 3H), 7.10 (s, 1H), 6.48 (broad s, 1H), 4.53 (s, 2H), 4.15 (s, 3H), 3.50 (s, 3H); MS (ESI) 594

Example 72

1-(4-((2,4-bis(Difluoromethoxy)-3-(pyrimidin-5-ylmethyl)quinolin-6-yl)(4-fluorophenyl)(hydroxy)methyl)piperidin-1-yl)ethanone

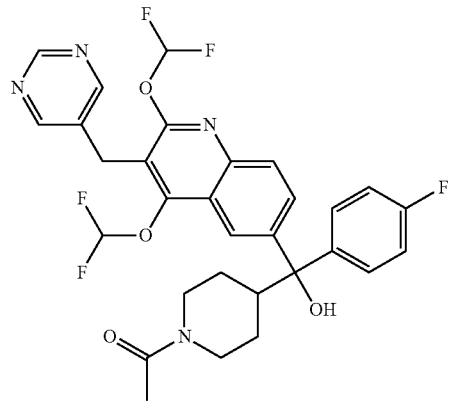 [SMILES: CC(=O)N1CCC(C(O)(c2ccc(F)cc2)c2ccc3nc(OC(F)F)c(Cc4cncnc4)c(OC(F)F)c3c2)CC1]

n-BuLi (1.6 M in THF, 0.26 mL, 0.41 mmol) was added dropwise over a 1 minute period to a mixture of 6-bromo-2,4-bis(difluoromethoxy)-3-(pyrimidin-5-ylmethyl)quinoline (0.16 g, 0.37 mmol, Intermediate 50) and 1-(4-(4-fluorobenzoyl)piperidin-1-yl)ethanone (0.10 g, 0.41 mmol, Intermediate 44) in dry THF (3.8 mL) at −78° C. Stirring was continued at −78° C. for 10 minutes. The reaction mixture was then placed in an ice bath and stirred at 0° C. for 1 hour. The reaction was then quenched with aqueous NH₄Cl, diluted with water and extracted with EtOAc (2×). The EtOAc extracts were dried over Na₂SO₄, filtered, evaporated in vacuo and purified by FCC (0-10% MeOH in DCM, gradient) to provide the title compound. ¹H NMR (400 MHz, CDCl₃) δ 9.00-9.19 (m, 1H), 8.61-8.79 (m, 2H), 8.05-8.22 (m, 1H), 7.69-7.93 (m, 3H), 7.37-7.56 (m, 2H), 6.93-7.13 (m, 2H), 6.36-6.89 (m, 1H), 4.59-4.83 (m, 1H), 4.20 (s, 2H), 3.67-3.97 (m, 1H), 2.95-3.23 (m, 1H), 2.43-2.83 (m, 2H), 2.04 (s, 3H), 1.61-1.79 (m, 1H), 1.30-1.51 (m, 3H); MS (ESI) 603 [M+H]+.

Example 73a 1-(4-((2-Chloro-4-(difluoromethoxy)-3-(pyrimidin-5-ylmethyl)quinolin-6-yl)(hydroxy)(phenyl)methyl)piperidin-1-yl)ethanone

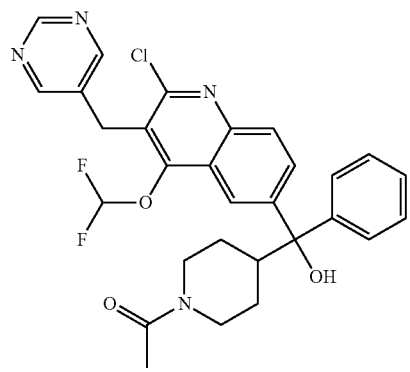 [SMILES: CC(=O)N1CCC(C(O)(c2ccccc2)c2ccc3nc(Cl)c(Cc4cncnc4)c(OC(F)F)c3c2)CC1]

n-BuLi (1.6 M in THF, 0.26 mL, 0.41 mmol) was added dropwise over a 1 minute period to a mixture of 6-bromo-2-chloro-4-(difluoromethoxy)-3-(pyrimidin-5-ylmethyl)quinoline (0.20 g, 0.50 mmol, Intermediate 49: step c) and 1-(4-benzoylpiperidin-1-yl)ethanone (0.13 g, 0.55 mmol, Intermediate 18) in dry THF (5 mL) at −78° C. Stirring was continued at −78° C. for 10 minutes. The reaction mixture was then placed in an ice bath and stirred at 0° C. for 1 hour. The reaction was then quenched with aqueous NH$_4$Cl, diluted with water and extracted with EtOAc (2×). The EtOAc extracts were dried over Na$_2$SO$_4$, filtered, evaporated in vacuo and purified by FCC (0-10% MeOH in DCM, gradient) to provide the title compound.

1-(4-((2-Chloro-4-(difluoromethoxy)-3-(pyrimidin-5-ylmethyl)quinolin-6-yl)(hydroxy)(phenyl)methyl)piperidin-1-yl)ethanone was purified by HPLC (200 gram Chiralpak AS, 1000 angstrom Daicel column, mobile phase: 5% ethanol and 95% ACN eluent, 80 mL/minute, 242 nm wavelength) to give 2 enantiomers. The first eluting enantiomer was Example 73b: $^1$H NMR (400 MHz, CDCl$_3$) δ 9.03-9.25 (m, 1H), 8.53-8.87 (m, 1H), 8.14-8.27 (m, 1H), 7.92-8.02 (m, 1H), 7.76-7.89 (m, 1H), 7.48-7.58 (m, 2H), 7.32-7.42 (m, 2H), 7.18-7.26 (m, 2H), 6.32-6.90 (m, 1H), 4.53-4.86 (m, 1H), 4.37 (s, 2H), 3.71-3.97 (m, 1H), 2.97-3.22 (m, 1H), 2.70-2.84 (m, 1H), 2.48-2.70 (m, 1H), 2.01 (s, 3H), 1.62-1.81 (m, 1H), 1.29-1.49 (m, 3H); MS (ESI) 553 and the second eluting enantiomer was Example 73c: $^1$H NMR (400 MHz, CDCl$_3$) δ 9.06-9.25 (m, 1H), 8.61-8.85 (m, 1H), 8.13-8.30 (m, 1H), 7.92-8.08 (m, 1H), 7.75-7.91 (m, 1H), 7.47-7.64 (m, 3H), 7.31-7.44 (m, 3H), 6.38-6.90 (m, 1H), 4.62-4.92 (m, 1H), 4.39 (s, 2H), 3.67-3.98 (m, 1H), 2.44-3.08 (m, 3H), 1.94-2.17 (m, 3H), 1.66-1.86 (m, 1H), 1.32-1.52 (m, 3H); MS (ESI) 553.

Example 74a 1-(4-((4-Chloro-2-methoxy-3-(4-(trifluoromethyl)benzyl)quinolin-6-yl)(hydroxy)(1-methyl-1H-1,2,3-triazol-5-yl)methyl)piperidin-1-yl)ethanone

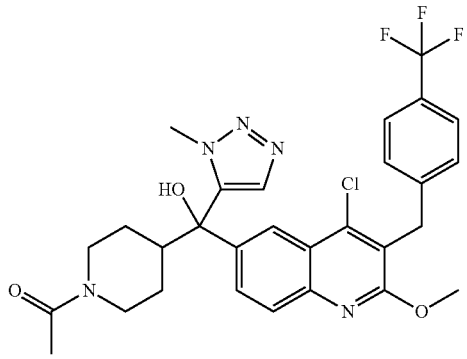 [SMILES: COc1nc2ccc(C(O)(c3cnnn3C)C3CCN(C(C)=O)CC3)cc2c(Cl)c1Cc1ccc(C(F)(F)F)cc1]

n-BuLi (2.5 M in THF, 0.60 mL, 1.5 mmol) was added dropwise over a 3 minute period to a mixture of 6-bromo-4-chloro-2-methoxy-3-(4-(trifluoromethyl)benzyl)quinoline (0.5 g, 1.16 mmol, Intermediate 12: step d) and 1-(4-(1-methyl-1H-1,2,3-triazole-5-carbonyl)piperidin-1-yl)ethanone (0.27 g, 1.16 mmol, Intermediate 52: step b) in dry THF (8 mL) at −78° C. Stirring was continued at −78° C. for 10 minutes. The reaction mixture was then immersed in an ice bath and stirred at 0° C. for 1 hour. The reaction was then quenched with saturated aqueous NaHCO$_3$, diluted with water and extracted with EtOAc (2×). The EtOAc extracts were dried over Na$_2$SO$_4$, filtered, evaporated in vacuo and purified by FCC (0-10% MeOH in DCM, gradient) to provide the title compound. $^1$H NMR (400 MHz, DMSO-d$_6$) δ 8.10 (s, 2H), 7.80 (d, J=8.6 Hz, 1H), 7.64 (d, J=8.1 Hz, 2H), 7.45 (d, J=8.1 Hz, 2H), 6.25 (s, 1H), 4.41-4.57 (m, 0.5H), 4.34 (s, 2.5H), 4.01 (s, 3H), 3.67-3.94 (m, 0.5H), 3.63 (d, J=3.5 Hz, 3H), 3.08-3.23 (m, 0.5H), 2.82-2.96 (m, 0.5H), 2.56-2.74 (m, 1.5H), 2.27-2.44 (m, 0.5H), 1.84-2.05 (m, 4H), 1.65-1.84 (m, 0.5H), 0.76-1.38 (m, 3H); MS (ESI) 588.

1-(4-((4-Chloro-2-methoxy-3-(4-(trifluoromethyl)benzyl)quinolin-6-yl)(hydroxy)(1-methyl-1H-1,2,3-triazol-5-yl)methyl)piperidin-1-yl)ethanone was purified by HPLC (Chiral OD column, 100% ethanol, 80 mL/minute) to give 2 enantiomers. The first eluting enantiomer was Example 74b: (two conformers) $^1$H NMR (400 MHz, DMSO-d$_6$) δ 8.11 (br. s., 2H), 7.81 (d, J=8.6 Hz, 1H), 7.64 (d, J=7.6 Hz, 2H), 7.45 (d, J=7.6 Hz, 2H), 6.27 (br. s., 1H), 4.41-4.57 (m, 0.5H), 4.34 (br. s., 2.5H), 4.01 (s, 3H), 3.82-3.94 (m, 0.5H), 3.66-3.79 (m, 0.5H), 3.55-3.66 (m, 3H), 3.08-3.27 (m, 0.5H), 2.85-3.00 (m, 0.5H), 2.57-2.75 (m, 1.5H), 2.30-2.47 (m, 0.5H), 1.82-2.05 (m, 4H), 0.72-1.47 (m, 3H); MS (ESI) 588, and the second eluting enantiomer was Example 74c: $^1$H NMR (DMSO-d$_6$) (two conformers) δ 8.11 (s, 2H), 7.81 (d, J=8.6 Hz, 1H), 7.64 (d, J=8.1 Hz, 2H), 7.45 (d, J=8.1 Hz, 2H), 6.27 (s, 1H), 4.41-4.59 (m, 0.5H), 4.34 (s, 2.5H), 4.01 (s, 3H), 3.80-3.93 (m, 0.5H), 3.66-3.75 (m, 0.5H), 3.34 (s, 3H), 3.03-3.22 (m, 0.5H), 2.82-2.97 (m, 0.5H), 2.55-2.72 (m, 1.5H), 2.30-2.44 (m, 0.5H), 1.77-2.03 (m, 4H), 1.11 (m, 3H); MS (ESI) 588.

Example 75a (4-Chloro-2-methoxy-3-(4-(trifluoromethyl)benzyl)quinolin-6-yl)(1-methyl-1H-1,2,3-triazol-5-yl)(6-(trifluoromethyl)pyridin-3-yl)methanol

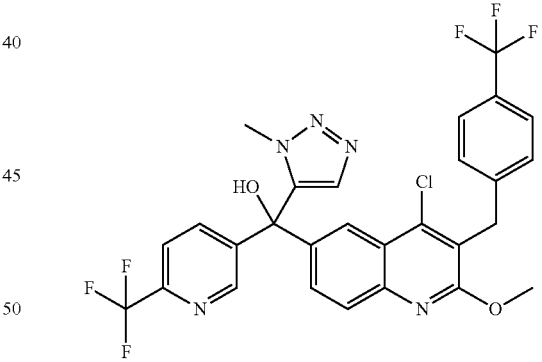

A solution of n-BuLi (2.5 M in hexanes, 1.85 mL, 4.62 mmol) was added dropwise by syringe to a mixture of 6-bromo-4-chloro-2-methoxy-3-(4-(trifluoromethyl)benzyl)quinoline (0.31 g, 0.72 mmol, Intermediate 12: step d) and (1-methyl-1H-1,2,3-triazol-5-yl)(6-(trifluoromethyl)pyridin-3-yl)methanone (0.29 g, 1.16 mmol, Intermediate 53: step b) in dry THF (8 mL) at −78° C. over a three minute period. The mixture was stirred at −78° C. for 10 minutes then was immersed in an ice H$_2$O bath and stirred at 0° C. for 1 hour. The solution was quenched with saturated aqueous NaHCO$_3$, warmed to room temperature, and the layers were separated. The aqueous layer was further extracted with EtOAc and the organic extracts were washed with brine, dried over Na$_2$SO$_4$, filtered and evaporated in vacuo. The residue was purified by FCC [(30% EtOH in EtOAc)/heptane, gradient] to provide the title compound. MS (ESI) 608 [M+H]+.

(4-Chloro-2-methoxy-3-(4-(trifluoromethyl)benzyl)quinolin-6-yl)(1-methyl-1H-1,2,3-triazol-5-yl)(6-(trifluoromethyl)pyridin-3-yl)methanol was purified by chiral HPLC (Diacel OD column, 100% MeOH, 80 mL/minute, 240 nm wavelength) to give two enantiomers. The first eluting enantiomer was Example 75b: $^1$H NMR (400 MHz, CDCl$_3$) δ 8.75-8.81 (m, 1H), 8.06 (d, J=2.0 Hz, 1H), 7.87 (d, J=9.1 Hz, 2H), 7.68-7.74 (m, 1H), 7.45-7.54 (m, 3H), 7.39 (s, 2H), 7.08-7.13 (m, 1H), 4.34 (s, 2H), 4.09 (s, 3H), 3.87 (s, 3H); MS (ESI) 608 [M+H]+; and the second eluting enantiomer was Example 75c: $^1$H NMR (400 MHz, CDCl$_3$) δ 8.77 (d, J=2.0 Hz, 1H), 8.06 (d, J=2.5 Hz, 1H), 7.87 (d, J=8.6 Hz, 2H), 7.72 (s, 1H), 7.44-7.55 (m, 3H), 7.38 (d, J=8.1 Hz, 2H), 7.00-7.18 (m, 1H), 4.33 (s, 2H), 4.09 (s, 3H), 3.86 (s, 3H); MS (ESI) 608 [M+H]+.

Example 76

(4-chloro-2-methoxy-3-(4-(trifluoromethoxy)benzyl)quinolin-6-yl)bis(1,2-dimethyl-1H-imidazol-5-yl)methanol

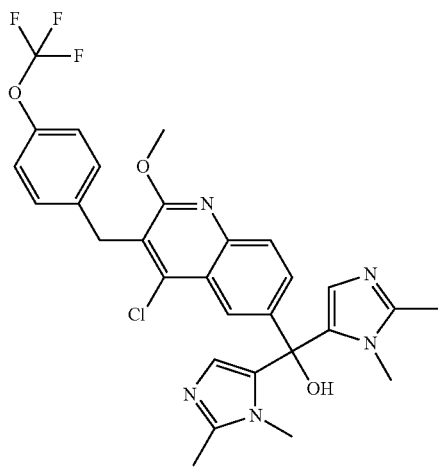 [SMILES: COc1nc2ccc(C(O)(c3cnc(C)n3C)c3cnc(C)n3C)cc2c(Cl)c1Cc1ccc(OC(F)(F)F)cc1]

To a 25 mL round bottom flask was added 5-bromo-1,2-dimethyl-1H-imidazole (0.22 g, 1.11 mmol) and dry THF (2 mL). The mixture was cooled to −78° C. and n-BuLi (2.5 M in THF, 0.4 mL, 0.97 mmol) was added dropwise over one minute. Stirring was continued for 10 minutes at −78° C. and a solution of methyl 4-chloro-2-methoxy-3-(4-(trifluoromethoxy)benzyl)quinoline-6-carboxylate (0.12 g, 0.28 mmol, Intermediate 54: step d) in dry THF (4 mL) was added slowly. Stirring was continued at −78° C. for 10 minutes then the mixture was cooled to 0° C. in an ice bath. The mixture was stirred for 30 minutes then quenched with saturated aqueous NH$_4$Cl solution. Water was added and the mixture was extracted with EtOAc (2×). The EtOAc extracts were combined, washed with brine, dried over Na$_2$SO$_4$, filtered and evaporated in vacuo. The residue was purified by FCC (0-10% MeOH/DCM, gradient) to provide the title compound as a tan solid. $^1$H NMR (400 MHz, CD$_3$OD) δ 8.24 (s, 1H), 7.84 (s, 1H), 7.59 (s, 1H), 7.34 (s, 2H), 7.17 (s, 2H), 6.15 (s, 2H), 4.35 (s, 2H), 4.09 (s, 3H), 3.50 (s, 6H), 2.36 (s, 6H); MS (ESI) 586

Example 77a 3-(4-(1H-Pyrazol-1-yl)benzyl)-6-((4-chlorophenyl)(hydroxy)(1-methyl-1H-imidazol-5-yl)methyl)-8-methylquinoline-2,4-dicarbonitrile

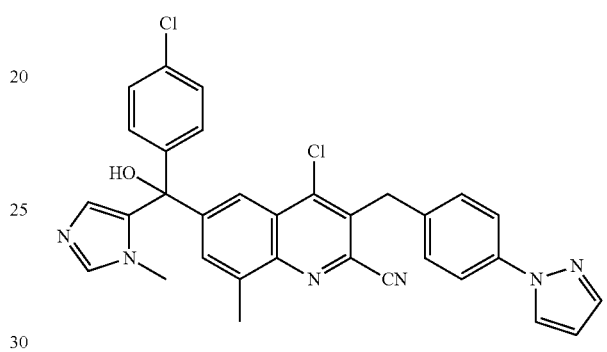

A solution of LaCl$_3$·2LiCl in THF (0.36 mL, 0.22 mmol, 0.6 M in THF) was added to a solution of 3-(4-(1H-pyrazol-1-yl)benzyl)-6-(1-methyl-1H-imidazole-5-carbonyl)quinoline-2,4-dicarbonitrile (50 mg, 0.08 mmol, Intermediate 14: step e) in THF (1.8 mL) at room temperature. After 15 minutes of stirring, a solution of 4-chlorophenyl magnesium bromide (0.32 mL, 0.32 mmol) in diethylether was added dropwise at 0° C. After stirring for 30 minutes, the reaction mixture was quenched with a saturated aqueous solution of NH$_4$Cl and the mixture was partitioned between water and DCM. The layers were separated and the aqueous phase was further extracted with DCM. The organic layers were combined, washed with saturated aqueous NaCl solution, dried (MgSO$_4$), filtered, and concentrated to dryness. The crude product was purified by flash column chromatography (silica gel, 0-7% MeOH-DCM) to provide the title compound. MS m/e 570.3 (M+H)+.

3-(4-(1H-Pyrazol-1-yl)benzyl)-6-((4-chlorophenyl)(hydroxy)(1-methyl-1H-imidazol-5-yl)methyl)-8-methylquinoline-2,4-dicarbonitrile was purified by chiral HPLC (Chiralcel OD, 100% methanol) to give 2 enantiomers. The first eluting enantiomer was Example 77b: $^1$H NMR (400 MHz, CDCl$_3$) δ ppm 8.21 (d, J=1.4 Hz, 1H), 7.88 (dd, J=2.5, 0.5 Hz, 1H), 7.71-7.61 (m, 4H), 7.49 (d, J=8.7 Hz, 2H), 7.40-7.29 (m, 5H), 6.51-6.37 (m, 2H), 4.63 (s, 2H), 4.31 (s, 1H), 3.39 (s, 3H), 2.74 (s, 3H); MS m/e 570.3 (M+H)+ and the second eluting enantiomer was Example 77c: $^1$H NMR (400 MHz, CDCl$_3$) δ ppm 8.21 (d, J=1.6 Hz, 1H), 7.88 (d, J=2.2 Hz, 1H), 7.73-7.60 (m, 4H), 7.49 (d, J=8.6 Hz, 2H), 7.40 (s, 1H), 7.36-7.31 (m, 4H), 6.49-6.39 (m, 2H), 4.63 (s, 2H), 3.40 (s, 3H), 2.74 (s, 3H); MS m/e 570.3 (M+H)+.

Example 78

1-(4-((3-(4-(1H-Pyrazol-1-yl)benzyl)-2,4-dichloro-8-methylquinolin-6-yl)(hydroxy)(6-(trifluoromethyl)pyridin-3-yl)methyl)piperidin-1-yl)ethanone

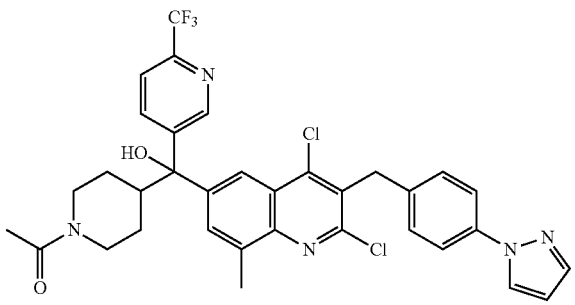 [SMILES: CC(=O)N1CCC(C(O)(c2ccc(C(F)(F)F)nc2)c2cc(C)c3nc(Cl)c(Cc4ccc(-n5cccn5)cc4)c(Cl)c3c2)CC1]

A solution of n-butyllithium (1.6 M in hexanes, 1 mL, 1.6 mmol) was added dropwise by syringe to a solution of 3-(4-(1H-pyrazol-1-yl)benzyl)-6-bromo-2,4-dichloro-8-methylquinoline (0.79 g, 1.76 mmol, Intermediate 57) in dry deoxygenated THF (24 mL) at −78° C. After 2 minutes, a solution of 1-(4-(6-(trifluoromethyl)nicotinoyl)piperidin-1-yl)ethanone (0.528 g, 1.76 mmol, Intermediate 56: step d) in dry THF (6 mL) was added dropwise by syringe. An additional 2 mL of THF was used to complete the quantitative addition. After 10 minutes, the flask was removed from the dry-ice bath and placed into an ice-water bath. After 1 hour, the reaction was quenched with saturated aqueous ammonium chloride solution and the mixture was partitioned between water and EtOAc. The layers were separated and the aqueous phase was further extracted with EtOAc. The organic layers were combined, washed with saturated aqueous NaCl solution, dried (MgSO4), filtered, and concentrated to dryness. The crude product was purified by flash column chromatography (silica gel, 50-100% EtOAc-DCM) to provide the title compound. MS m/e 668.2 (M+H)+.

Example 79a 3-(4-(1H-Pyrazol-1-yl)benzyl)-6-((1-acetylpiperidin-4-yl)(hydroxy)(6(trifluoromethyl)pyridin-3-yl)methyl)-8-methyl-8-methylquinoline-2,4-dicarbonitrile

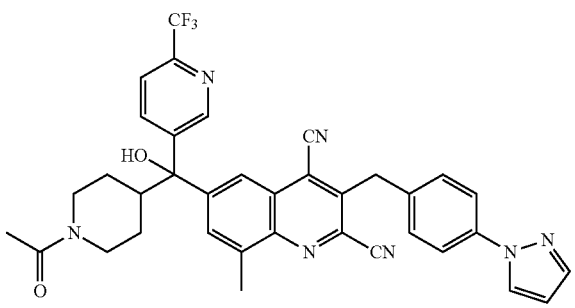 [SMILES: CC(=O)N1CCC(C(O)(c2ccc(C(F)(F)F)nc2)c2cc(C)c3nc(C#N)c(Cc4ccc(-n5cccn5)cc4)c(C#N)c3c2)CC1]

A microwave vial was charged with 1-(4-((3-(4-(1H-pyrazol-1-yl)benzyl)-2,4-dichloro-8-methylquinolin-6-yl)(hydroxy)(6-(trifluoromethyl)pyridin-3-yl)methyl)piperidin-1-yl)ethanone (560 mg, 0.84 mmol, Example 78), Zn(CN)2 (319.6 mg, 2.722 mmol), Pd2dba3 (115 mg, 0.126 mmol), zinc dust (27.4 mg, 0.419 mmol) and dicyclohexyl(2',4',6'-triisopropyl-[1,1'-biphenyl]-2-yl)phosphine (X-Phos, 82.3 mg, 0.168 mmol). Dimethylacetamide (14 mL) was then added and the mixture was sparged with nitrogen for 10 minutes and placed in a pre-heated aluminum block at 120° C. for 4 hours. The mixture was cooled to room temperature and was filtered through Celite®, rinsing with EtOAc, DCM and MeOH. The residue was purified by reverse-phase HPLC (5-85% CH3CN—H2O, 0.05% TFA). The product was converted to the free base (neutralized with saturated aqueous NaHCO3 and extracted with DCM) and the organic fractions were concentrated to afford the title compound. MS m/e 650.3 (M+H)+.

3-(4-(1H-Pyrazol-1-yl)benzyl)-6-((1-acetylpiperidin-4-yl)(hydroxy)(6(trifluoromethyl)pyridin-3-yl)methyl)-8-methylquinoline-2,4-dicarbonitrile was purified by chiral SFC (Chiralpak AD-H, 5 μm, 250×20 mm, mobile phase: 65% CO2, 35% mixture of methanol-isopropanol 50/50 v/v) to give two enantiomers. The first eluting enantiomer was Example 79b: 1H NMR (600 MHz, CDCl3, mixture of rotamers) δ ppm 8.97-8.90 (m, 1H), 8.32-8.24 (m, 1H), 8.12 (dt, J=8.4, 2.3 Hz, 1H), 7.88 (t, J=2.2 Hz, 1H), 7.80 (s, 0.5H), 7.73 (s, 0.5H), 7.71-7.62 (m, 4H), 7.50-7.47 (m, 2H), 6.46-6.45 (m, 1H), 4.74-4.68 (m, 1H), 4.63 (d, J=2.2 Hz, 2H), 3.89 (d, J=13.7 Hz, 0.5H), 3.83 (d, J=13.7 Hz, 0.5H), 3.46 (s, 0.5H), 3.38 (s, 0.5H), 3.19-3.06 (m, 1H), 2.88-2.85 (m, 1H), 2.78 (s, 1.5H), 2.77 (s, 1.5H), 2.64-2.58 (m, 1H), 2.04 (s, 1.5H), 2.03 (s, 1.5H), 1.55-1.34 (m, 4H); MS m/e 650.3 (M+H)+ and the second eluting enantiomer was Example 79c: 1H NMR (600 MHz, CDCl3, mixture of rotamers) δ ppm 8.96-8.92 (m, 1H), 8.32-8.29 (m, 1H), 8.13 (dt, J=8.3, 2.9 Hz, 1H), 7.88 (t, J=2.4 Hz, 1H), 7.80 (s, 0.5H), 7.73 (s, 0.5H), 7.71-7.61 (m, 4H), 7.52-7.45 (m, 2H), 6.46-6.44 (m, 1H), 4.72-4.65 (m, 1H), 4.63 (d, J=3.1 Hz, 2H), 3.98-3.77 (m, 1H), 3.20-3.07 (m, 1H), 2.88-2.84 (m, 1H), 2.78 (s, 1.5H), 2.77 (s, 1.5H), 2.65-2.55 (m, 1H), 2.02 (s, 3H), 1.57-1.31 (m, 4H); MS m/e 650.3 (M+H)+.

Example 80

1-(4-((3-(4-(1H-Pyrazol-1-yl)benzyl)-2,4-dichloro-8-methylquinolin-6-yl)(hydroxy)(1-methyl-1H-imidazol-5-yl)methyl)piperidin-1-yl)ethanone

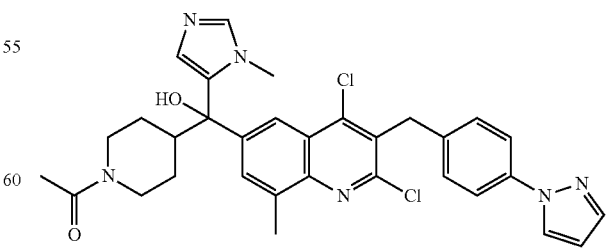

The title compound was prepared analogously to the method described in Example 78 using 1-(4-(1-methyl-1H-imidazole-5-carbonyl)piperidin-1-yl)ethanone (Intermediate 58: step c) in place of 1-(4-(6-(trifluoromethyl)nicotinoyl)piperidin-1-yl)ethanone (Intermediate 56: step d). MS m/e 603.3 (M+H)⁺.

Example 81a 3-(4-(1H-Pyrazol-1-yl)benzyl)-6-((1-acetylpiperidin-4-yl)(hydroxy)(1-methyl-1H-imidazol-5-yl)methyl)-8-methylquinoline-2,4-dicarbonitrile

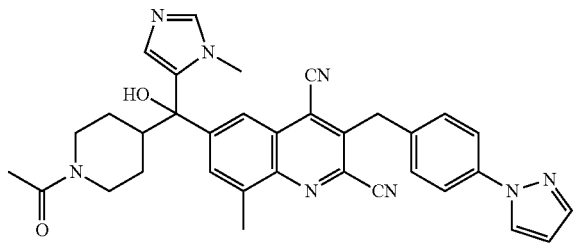 [SMILES: CC(=O)N1CCC(C(O)(c2cc(C)c3nc(C#N)c(Cc4ccc(-n5cccn5)cc4)c(C#N)c3c2)c2cncn2C)CC1]

The title compound was prepared analogously to the method described in Example 79a using 1-(4-((3-(4-(1H-pyrazol-1-yl)benzyl)-2,4-dichloro-8-methylquinolin-6-yl)(hydroxy)(1-methyl-1H-imidazol-5-yl)methyl)piperidin-1-yl)ethanone (Example 80) in place of 1-(4-((3-(4-(1H-pyrazol-1-yl)benzyl)-2,4-dichloro-8-methylquinolin-6-yl)(hydroxy)(6-(trifluoromethyl)pyridin-3-yl)methyl)piperidin-1-yl)ethanone (Example 78). MS m/e 585.3 (M+H)⁺.

3-(4-(1H-Pyrazol-1-yl)benzyl)-6-((1-acetylpiperidin-4-yl)(hydroxy)(1-methyl-1H-imidazol-5-yl)methyl)-8-methylquinoline-2,4-dicarbonitrile was purified by chiral SFC (Chiralpak AD-H, 5 μm, 250×20 mm, mobile phase: 65% CO₂, 35% ethanol) to give two enantiomers. The first eluting enantiomer was Example 81b: ¹H NMR (500 MHz, CDCl₃, mixture of rotamers) δ ppm 8.24 (d, J=15.4 Hz, 1H), 7.88 (d, J=2.5 Hz, 1H), 7.72-7.63 (m, 3H), 7.53 (dd, J=8.6, 3.8 Hz, 2H), 7.44 (s, 1H), 7.33-7.29 (m, 1H), 7.22 (d, J=2.0 Hz, 1H), 6.46-6.44 (m, 1H), 4.75 (d, J=13.5 Hz, 0.5H), 4.64 (s, 2H), 4.58 (d, J=13.5 Hz, 0.5H), 3.94 (d, J=13.6 Hz, 0.5H), 3.73 (d, J=13.5 Hz, 0.5H), 3.40 (s, 0.5H), 3.3 (s, 1.5H), 3.28 (s, 1.5H), 3.21-3.16 (m, 0.5H), 2.97 (t, J=13.0 Hz, 0.5H), 2.74 (s, 3H), 2.64 (t, J=13.0 Hz, 0.5H), 2.52-2.41 (m, 1H), 2.34 (d, J=13.1 Hz, 0.5H), 2.26 (d, J=13.1 Hz, 0.5H), 2.02 (s, 3H), 1.48-1.01 (m, 4H); MS m/e 585.3 (M+H)⁺ and the second eluting enantiomer was Example 81c: ¹H NMR (500 MHz, CDCl₃, mixture of rotamers) δ ppm 8.24 (d, J=15.7 Hz, 1H), 7.88 (d, J=2.5 Hz, 1H), 7.72-7.64 (m, 3H), 7.53 (dd, J=8.6, 3.8 Hz, 2H), 7.44 (s, 1H), 7.31 (d, J=3.7 Hz, 1H), 7.22 (t, J=1.5 Hz, 1H), 6.46-6.45 (m, 1H), 4.75 (d, J=13.6 Hz, 0.5H), 4.64 (s, 2H), 4.58 (d, J=13.5 Hz, 0.5H), 3.94 (d, J=13.6 Hz, 0.5H), 3.73 (d, J=13.7 Hz, 0.5H), 3.43 (s, 1H), 3.29 (s, 1.5H), 3.28 (s, 1.5H), 3.25-3.13 (m, 0.5H), 2.97 (t, J=13.0 Hz, 0.5H), 2.74 (s, 3H), 2.64 (t, J=12.9 Hz, 0.5H), 2.55-2.41 (m, 1H), 2.34 (d, J=13.2 Hz, 0.5H), 2.26 (d, J=13.2 Hz, 0.5H), 2.02 (s, 3H), 1.47-0.96 (m, 4H); MS m/e 585.3 (M+H)⁺.

Example 82

(3-(4-(1H-Pyrazol-1-yl)benzyl)-2,4-dichloro-8-methylquinolin-6-yl)(1-methyl-1H-imidazol-5-yl)(2-(trifluoromethyl)pyridin-4-yl)methanol

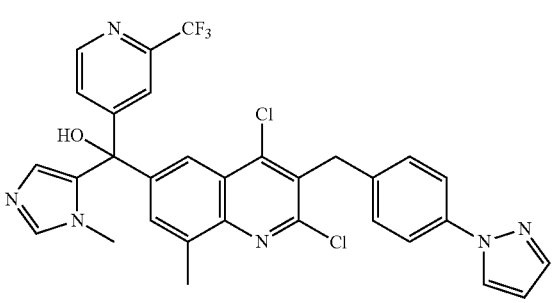 [SMILES: Cc1cc(C(O)(c2ccnc(C(F)(F)F)c2)c2cncn2C)cc2c(Cl)c(Cc3ccc(-n4cccn4)cc3)c(Cl)nc12]

The title compound was prepared analogously to the method described in Example 78, using (1-methyl-1H-imidazol-5-yl)(2-(trifluoromethyl)pyridin-4-yl)methanone (Intermediate 27: step b) in place of 1-(4-(6-(trifluoromethyl)nicotinoyl)piperidin-1-yl)ethanone (Intermediate 56: step d). MS m/e 623.2 (M+H)⁺.

Example 83a 3-(4-(1H-Pyrazol-1-yl)benzyl)-6-(hydroxy(1-methyl-1H-imidazol-5-yl)(2-(trifluoromethyl)pyridin-4-yl)methyl)-8-methylquinoline-2,4-dicarbonitrile

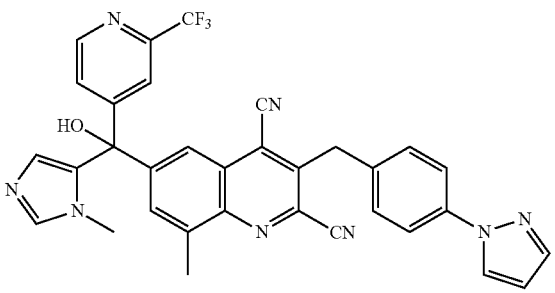 [SMILES: Cc1cc(C(O)(c2ccnc(C(F)(F)F)c2)c2cncn2C)cc2c(C#N)c(Cc3ccc(-n4cccn4)cc3)c(C#N)nc12]

The title compound was prepared analogously to the method described in Example 79a, using (3-(4-(1H-pyrazol-1-yl)benzyl)-2,4-dichloro-8-methylquinolin-6-yl)(1-methyl-1H-imidazol-5-yl)(2-(trifluoromethyl)pyridin-4-yl)methanol (Example 82) in place of 1-(4-(3-(4-(1H-pyrazol-1-yl)benzyl)-2,4-dichloro-8-methylquinolin-6-yl)(hydroxy)(6-(trifluoromethyl)pyridin-3-yl)methyl)piperidin-1-yl)ethanone (Example 78). MS m/e 605.3 (M+H)⁺.

3-(4-(1H-Pyrazol-1-yl)benzyl)-6-(hydroxy(1-methyl-1H-imidazol-5-yl)(2-(trifluoromethyl)pyridin-4-yl)methyl)-8-methylquinoline-2,4-dicarbonitrile was purified by chiral SFC (Chiralpak OD-H, 5 μm, 250×20 mm, mobile phase: 0.3% isopropyl amine, 60% CO₂, 40% isopropanol) to give two enantiomers. The first eluting enantiomer was Example 83b: ¹H NMR (500 MHz, CDCl₃) δ ppm 8.73 (d, J=5.1 Hz, 1H), 8.23 (d, J=1.9 Hz, 1H), 7.90-7.82 (m, 2H), 7.71-7.62 (m, 3H), 7.61 (s, 1H), 7.52-7.45 (m, 3H), 7.38 (s, 1H), 6.44 (dd, J=2.5, 1.8 Hz, 1H), 6.42 (s, 1H), 5.22 (s, 1H), 4.63 (s, 2H), 3.36 (s, 3H), 2.77 (s, 3H); MS m/e 605.3 (M+H)⁺ and the second eluting enantiomer was Example 83c: ¹H NMR (500 MHz, CDCl₃) δ ppm 8.73 (d, J=5.1 Hz, 1H), 8.23 (dd, J=2.1, 0.8 Hz, 1H), 7.87 (ddd, J=5.5, 2.2, 0.8 Hz, 2H), 7.70-7.63 (m, 3H), 7.61 (dd, J=1.9, 1.1 Hz, 1H), 7.53-7.44 (m, 3H), 7.38 (d, J=1.2 Hz, 1H), 6.44 (dd, J=2.5, 1.8 Hz, 1H), 6.42 (d, J=1.1 Hz, 1H), 5.20 (s, 1H), 4.63 (s, 2H), 3.36 (s, 3H), 2.77 (s, 3H); MS m/e 605.3 (M+H)⁺.

Example 84a (4-Chloro-2-methoxy-3-(4-(trifluoromethyl)benzyl)quinolin-6-yl)(2,6-dimethylpyridin-4-yl)(1-methyl-1H-1,2,3-triazol-5-yl)methanol

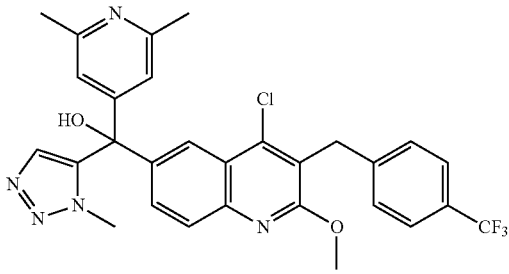 [SMILES: COc1nc2ccc(C(O)(c3cc(C)nc(C)c3)c3cnnn3C)cc2c(Cl)c1Cc1ccc(C(F)(F)F)cc1]

The title compound was prepared analogously to the method described in Example 78 using 6-bromo-4-chloro-2-methoxy-3-(4-(trifluoromethyl)benzyl)quinoline (Intermediate 12: step d) in place of 3-(4-(1H-pyrazol-1-yl)benzyl)-6-bromo-2,4-dichloro-8-methylquinoline (Intermediate 57) and (1-methyl-1H-1,2,3-triazol-5-yl)(2-(trifluoromethyl)pyridin-4-yl)methanone (Intermediate 29: step b) in place of 1-(4-(6-(trifluoromethyl)nicotinoyl)piperidin-1-yl)ethanone (Intermediate 56: step d). MS m/e 568.2 (M+H)⁺.

(4-Chloro-2-methoxy-3-(4-(trifluoromethyl)benzyl)quinolin-6-yl)(2,6-dimethylpyridin-4-yl)(1-methyl-1H-1,2,3-triazol-5-yl)methanol was purified by chiral SFC (Chiralcel OD-H, 5 μm, 250×20 mm, mobile phase: 0.3% isopropyl amine, 70% CO₂, 30% mixture of ethanol-isopropanol 50/50 v/v) to give two enantiomers. The first eluting enantiomer was Example 84b: ¹H NMR (600 MHz, CDCl₃) δ ppm 8.06 (d, J=2.2 Hz, 1H), 7.85 (d, J=8.7 Hz, 1H), 7.50 (d, J=8.0 Hz, 2H), 7.47 (dd, J=8.7, 2.2 Hz, 1H), 7.39 (d, J=8.0 Hz, 2H), 7.13 (s, 1H), 6.89 (s, 2H), 4.34 (s, 2H), 4.09 (s, 3H), 3.86 (s, 3H), 3.28 (s, 1H), 2.52 (s, 6H); MS m/e 568.2 (M+H)⁺ and the second eluting enantiomer was Example 84c: ¹H NMR (600 MHz, CDCl₃) δ ppm 8.05 (d, J=2.2 Hz, 1H), 7.85 (d, J=8.8 Hz, 1H), 7.50 (d, J=8.0 Hz, 2H), 7.47 (dd, J=8.8, 2.2 Hz, 1H), 7.39 (d, J=8.0 Hz, 2H), 7.13 (s, 1H), 6.89 (s, 2H), 4.34 (s, 2H), 4.09 (s, 3H), 3.86 (s, 3H), 3.22 (s, 1H), 2.52 (s, 6H); MS m/e 568.2 (M+H)⁺.

Example 85a (4-Chloro-2-methoxy-3-(4-(trifluoromethyl)benzyl)quinolin-6-yl)(1-methyl-1H-1,2,3-triazol-5-yl)(tetrahydro-2H-pyran-4-yl)methanol

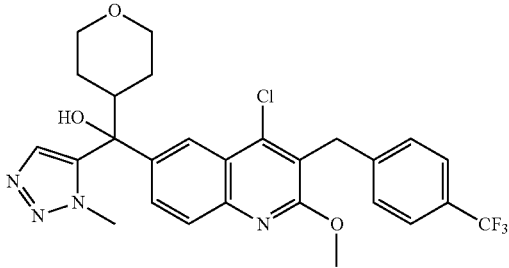 [SMILES: COc1nc2ccc(C(O)(c3cnnn3C)C3CCOCC3)cc2c(Cl)c1Cc1ccc(C(F)(F)F)cc1]

The title compound was prepared analogously to the method described in Example 78 using 6-bromo-4-chloro-2-methoxy-3-(4-(trifluoromethyl)benzyl)quinoline (Intermediate 12: step d) in place of 3-(4-(1H-pyrazol-1-yl)benzyl)-6-bromo-2,4-dichloro-8-methylquinoline (Intermediate 57) and (1-methyl-1H-1,2,3-triazol-5-yl)(tetrahydro-2H-pyran-4-yl)methanone (Intermediate 30) in place of 1-(4-(6-(trifluoromethyl)nicotinoyl)piperidin-1-yl)ethanone (Intermediate 56: step d). MS m/e 547.2 (M+H)⁺.

(4-Chloro-2-methoxy-3-(4-(trifluoromethyl)benzyl)quinolin-6-yl)(1-methyl-1H-1,2,3-triazol-5-yl)(tetrahydro-2H-pyran-4-yl)methanol was purified by chiral SFC (Chiralpak AD-H, 5 μm, 250×20 mm, mobile phase: 0.3% isopropyl amine, 75% CO₂, 25% mixture of methanol-isopropanol 50/50 v/v) to give two enantiomers. The first eluting enantiomer was Example 85b: ¹H NMR (600 MHz, CDCl₃) δ ppm 8.11 (d, J=2.1 Hz, 1H), 7.82-7.76 (m, 2H), 7.51 (d, J=8.1 Hz, 2H), 7.40 (d, J=8.0 Hz, 2H), 7.37 (dd, J=8.8, 2.1 Hz, 1H), 4.35 (s, 2H), 4.13-4.08 (m, 1H), 4.07 (s, 3H), 3.92 (dd, J=11.5, 4.3 Hz, 1H), 3.74 (s, 3H), 3.52 (td, J=11.8, 2.0 Hz, 1H), 3.34 (td, J=12.0, 2.2 Hz, 1H), 2.53-2.48 (m, 1H), 2.42 (s, 1H), 2.03-1.93 (m, 1H), 1.65-1.56 (m, 1H), 1.49-1.42 (m, 1H), 1.05-1.03 (m, 1H); MS m/e 547.2 (M+H)⁺ and the second eluting enantiomer was Example 85c: ¹H NMR (600 MHz, CDCl₃) δ ppm 8.11 (d, J=2.1 Hz, 1H), 7.81-7.75 (m, 2H), 7.51 (d, J=8.1 Hz, 2H), 7.40 (d, J=8.0 Hz, 2H), 7.37 (dd, J=8.7, 2.1 Hz, 1H), 4.35 (s, 2H), 4.10 (dd, J=11.7, 3.5 Hz, 1H), 4.07 (s, 3H), 3.92 (dd, J=11.7, 3.9 Hz, 1H), 3.74 (s, 3H), 3.52 (td, J=11.7, 2.0 Hz, 1H), 3.34 (td, J=12.0, 2.2 Hz, 1H), 2.53-2.48 (m, 1H), 2.44 (s, 1H), 2.02-1.93 (m, 1H), 1.64-1.57 (m, 1H), 1.49-1.39 (m, 1H), 1.05-1.03 (m, 1H); MS m/e 547.2 (M+H)⁺.

Example 86a (4-Chloro-2-methoxy-3-(4-(trifluoromethyl)benzyl)quinolin-6-yl)(1,2-dimethyl-1H-imidazol-5-yl)(tetrahydro-2H-pyran-4-yl)methanol

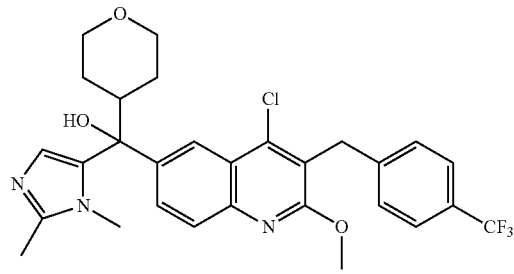 [SMILES: COc1nc2ccc(C(O)(c3cnc(C)n3C)C3CCOCC3)cc2c(Cl)c1Cc1ccc(C(F)(F)F)cc1]

The title compound was prepared analogously to the method described in Example 78, using 6-bromo-4-chloro-2-methoxy-3-(4-(trifluoromethyl)benzyl)quinoline (Intermediate 12: step d) in place of 3-(4-(1H-pyrazol-1-yl)benzyl)-6-bromo-2,4-dichloro-8-methylquinoline (Intermediate 57) and (1,2-dimethyl-1H-imidazol-5-yl)(tetrahydro-2H-pyran-4-yl)methanone (Intermediate 31) in place of 1-(4-(6-(trifluoromethyl)nicotinoyl)piperidin-1-yl)ethanone (Intermediate 56: step d). MS m/e 560.2 (M+H)⁺.

(4-Chloro-2-methoxy-3-(4-(trifluoromethyl)benzyl)quinolin-6-yl)(1,2-dimethyl-1H-imidazol-5-yl)(tetrahydro-2H-pyran-4-yl)methanol was purified by chiral SFC (Chiralcel OD-H, 5 μm, 250×20 mm, mobile phase: 0.3% isopropyl amine, 70% CO₂, 30% methanol) to give two enantiomers. The first eluting enantiomer was Example 86b: ¹H NMR (400 MHz, CDCl₃) δ ppm 8.14 (s, 1H), 7.75 (dd, J=8.8, 0.6 Hz, 1H), 7.51 (d, J=8.0 Hz, 2H), 7.42-7.40 (m, 3H), 7.08 (s, 1H), 4.35 (s, 2H), 4.08-4.06 (m, 4H), 3.88 (dd, J=11.7, 4.1 Hz, 1H), 3.55-3.48 (m, 1H), 3.39-3.26 (m, 1H), 3.13 (s, 3H), 2.52-2.39 (m, 1H), 2.28 (s, 3H), 2.21-2.08 (m, 2H), 1.57-1.55 (m, 1H), 1.42-1.37 (m, 1H), 1.04-1.0 (m, 1H); MS m/e 560.2 (M+H)$^+$ and the second eluting enantiomer was Example 86c: $^1$H NMR (400 MHz, CDCl$_3$) δ ppm 8.14 (s, 1H), 7.76 (d, J=8.8 Hz, 1H), 7.51 (d, J=8.0 Hz, 2H), 7.42-7.40 (m, 3H), 7.08 (s, 1H), 4.35 (s, 2H), 4.08-4.06 (m, 4H), 3.88 (dd, J=11.9, 4.1 Hz, 1H), 3.55-3.49 (m, 1H), 3.37-3.26 (m, 1H), 3.14 (s, 3H), 2.48-2.42 (m, 1H), 2.28 (s, 3H), 2.24-2.06 (m, 2H), 1.61-1.57 (m, 1H), 1.45-1.36 (m, 1H), 1.04-1.01 (m, 1H); MS m/e 560.2 (M+H)$^+$.

Example 87a 1-(3-((4-Chloro-2-methoxy-3-(4-(trifluoromethyl)benzyl)quinolin-6-yl)(2,6-dimethylpyridin-3-yl)(hydroxy)methyl)azetidin-1-yl)ethanone

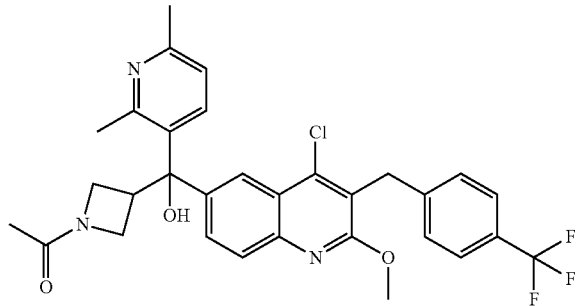 [SMILES: COc1nc2ccc(C(O)(c3ccc(C)nc3C)C3CN(C(C)=O)C3)cc2c(Cl)c1Cc1ccc(C(F)(F)F)cc1]

To a flask containing crude azetidin-3-yl(4-chloro-2-methoxy-3-(4-(trifluoromethyl)-benzyl)quinolin-6-yl)(2,6-dimethylpyridin-3-yl)methanol and 6-(azetidin-3-yl(2,6-dimethylpyridin-3-yl)(hydroxy)methyl)-4-chloro-3-(4-(trifluoromethyl)benzyl)-quinolin-2-ol (630 mg, 1.16 mmol, Example 126) was added DCM (20 mL) which gave a suspension at room temperature. Triethylamine (1 mL, 6.9 mmol) was added, followed by acetic anhydride (0.30 mL, 3 mmol) and the initial suspension became homogeneous after about 2 minutes. The mixture was heated to 40° C. for 4 hours then quenched with brine and extracted with DCM (3×25 mL). The combined organics were dried over MgSO$_4$, filtered and concentrated to dryness. The residue was purified by FCC (5% MeOH-EtOAc increasing to 10% MeOH) to provide the title compound as a white solid. $^1$H NMR (400 MHz, CD$_3$OD) δ 8.26 (dd, J=4.1, 2.0 Hz, 2H), 7.81-7.71 (m, 4H), 7.53 (d, J=8.2 Hz, 4H), 7.46-7.37 (m, 6H), 7.25-7.17 (m, 2H), 4.45-4.33 (m, 5H), 4.30-4.07 (m, 4H), 4.04 (d, J=1.3 Hz, 5H), 4.01-3.97 (m, 1H), 3.85 (t, J=8.6 Hz, 1H), 3.77-3.59 (m, 3H), 2.49 (d, J=1.6 Hz, 6H), 2.18 (s, 6H), 1.83 (d, J=13.7 Hz, 6H); MS (ESI): mass calcd. Chemical Formula: C$_{31}$H$_{29}$ClF$_3$N$_3$O$_3$, Exact Mass: 583.2. m/z found 583.9 [M+H]$^+$. 1-(3-((4-Chloro-2-methoxy-3-(4-(trifluoromethyl)benzyl)quinolin-6-yl)(2,6-dimethylpyridin-3-yl)(hydroxy)methyl)azetidin-1-yl)ethanone was purified by chiral SFC (Stationary phase: CHIRALPAK AD-H 5 μm 250×20 mm, Mobile phase: 75% CO$_2$, 25% i-PrOH (0.3% iPrNH$_2$)) to give two enantiomers. The first eluting enantiomer was Example 87b and the second eluting enantiomer was Example 87c.

Example 88a (4-Chloro-2-methoxy-3-(4-(trifluoromethyl)benzyl)quinolin-6-yl)(2,6-dimethylpyridin-3-yl)(1-methyl-1H-imidazol-5-yl)methanol

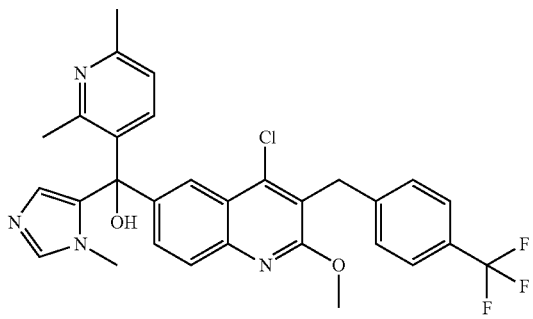 [SMILES: COc1nc2ccc(C(O)(c3ccc(C)nc3C)c3cncn3C)cc2c(Cl)c1Cc1ccc(C(F)(F)F)cc1]

To a flask containing 5-bromo-1-methyl-1H-imidazole (650 mg, 4.04 mmol) was added THF (10 mL) and the clear homogeneous solution was stirred at room temperature as iPrMgCl (2 M in diethylether, 2 mL, 4 mmol) was added. A whitish suspension resulted. The suspension was stirred at room temperature for 30 minutes, then a solution of 4-chloro-2-methoxy-3-(4-(trifluoromethyl)benzyl)quinolin-6-yl)(2,6-dimethylpyridin-3-yl)methanone (660 mg, 1.36 mmol, Intermediate 81: step b) in THF (5 mL) containing LaCl$_3$—LiCl complex (0.5 M solution THF, 5 mL, 2.5 mmol) was added to the reaction mixture. The reaction mixture was stirred overnight at 35° C. After 14 hours, the reaction mixture was quenched with saturated aqueous NH$_4$Cl solution. The aqueous portion was extracted with EtOAc (3×40 mL) and the combined organics were washed with brine and dried over MgSO$_4$. The brine portion was back-extracted with DCM (3×40 mL) and dried over MgSO$_4$. The organics were filtered and concentrated to dryness to afford a tan oil. The residue was purified by FCC (2% MeOH-DCM increasing to 10% MeOH) to provide the title compound as an off white solid. $^1$H NMR (500 MHz, CDCl$_3$) δ 8.13 (d, J=2.0 Hz, 1H), 7.76 (d, J=8.7 Hz, 1H), 7.50 (d, J=8.2 Hz, 2H), 7.44-7.35 (m, 4H), 7.31 (d, J=11.4 Hz, 1H), 7.05 (d, J=8.0 Hz, 1H), 6.90 (d, J=8.0 Hz, 1H), 6.19 (s, 1H), 4.67 (s, 1H), 4.32 (s, 2H), 4.07 (s, 3H), 3.46 (s, 3H), 2.52 (s, 3H), 2.45-2.33 (m, 3H); MS (ESI): mass calcd. Chemical Formula: C$_{30}$H$_{26}$ClF$_3$N$_4$O$_2$, Exact Mass: 566.2. m/z found 567.1 [M+H]$^+$.

(4-Chloro-2-methoxy-3-(4-(trifluoromethyl)benzyl)quinolin-6-yl)(2,6-dimethylpyridin-3-yl)(1-methyl-1H-imidazol-5-yl)methanol was purified by chiral SFC (Stationary phase: CHIRALPAK AD-H 5 μm 250×20 mm, Mobile phase: 75% CO$_2$, 25% EtOH), to give two enantiomers. The first eluting enantiomer was Example 88b and the second eluting enantiomer was Example 88c.

Example 89

(4-Chloro-2-methoxy-3-(4-(trifluoromethyl)benzyl)quinolin-6-yl)(1-methyl-1H-1,2,3-triazol-5-yl)(1-methyl-1H-imidazol-5-yl)methanol

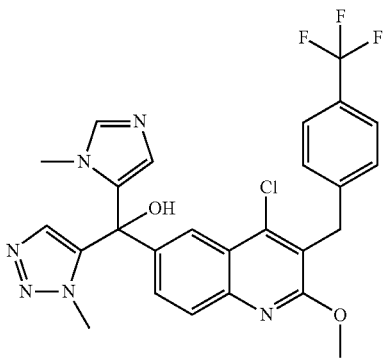 [SMILES: COc1nc2ccc(C(O)(c3cncn3C)c3cnnn3C)cc2c(Cl)c1Cc1ccc(C(F)(F)F)cc1]

To a flask containing 1-methyl-1H-1,2,3-triazole (100 mg, 1.2 mmol) was added THF (10 mL) and the colorless solution was cooled to −43° C. using a CH$_3$CN—CO$_2$ bath. Then, n-BuLi (2.5 M in hexanes, 490 μL, 1.23 mmol) was added dropwise which afforded an opaque mixture. The mixture was stirred at −40° C. for 30 minutes, then a homogeneous solution of (4-chloro-2-methoxy-3-(4-(trifluoromethyl)benzyl)quinolin-6-yl)(1-methyl-1H-imidazol-5-yl)methanone (255 mg, 0.54 mmol, Intermediate 80: step b) in 2 mL THF was introduced. After 5 minutes, the reaction mixture was then placed in an ice-water bath. The reaction was quenched after 20 minutes with aqueous NH$_4$Cl solution and the aqueous portion was extracted with EtOAc (3×30 mL) and EtOAc:THF (1:1, 30 mL). The combined organics were washed with brine, dried over MgSO$_4$, filtered and concentrated. The solid was triturated with MeOH and filtered to give a yellow filtrate which was concentrated and chromatographed on silica gel (3% MeOH-DCM increasing to 10% MeOH) to afford the title compound. $^1$H NMR (500 MHz, CDCl$_3$) δ 8.22 (d, J=2.1 Hz, 1H), 7.76 (d, J=8.7 Hz, 2H), 7.49 (d, J=8.1 Hz, 2H), 7.41-7.35 (m, 3H), 7.10 (s, 1H), 6.99 (s, 1H), 6.22 (s, 1H), 4.29 (s, 2H), 4.07 (s, 3H), 3.89 (s, 3H), 3.41 (s, 3H). MS (ESI): mass calcd. for Chemical Formula: C$_{26}$H$_{22}$ClF$_3$N$_6$O$_2$; Exact Mass: 542.14. m/z found 542.9 [M+H]$^+$.

(4-Chloro-2-methoxy-3-(4-(trifluoromethyl)benzyl)quinolin-6-yl)(1-methyl-1H-1,2,3-triazol-5-yl)(1-methyl-1H-imidazol-5-yl)methanol was purified by chiral SFC (Stationary phase: CHIRALPAK AD-H 5 μm, 250×20 mm, Mobile phase: 80% CO$_2$, 20% mixture of MeOH/iPrOH, 50/50 v/v (+0.3% iPrNH$_2$)), to give Example 89b as the first compound eluted from the chiral column and Example 89c as the second compound eluted from the chiral column.

Example 90a (4-Chloro-2-methoxy-3-(4-(trifluoromethyl)benzyl)quinolin-6-yl)(1-methyl-1H-1,2,3-triazol-5-yl)(1-methylazetidin-3-yl)methanol

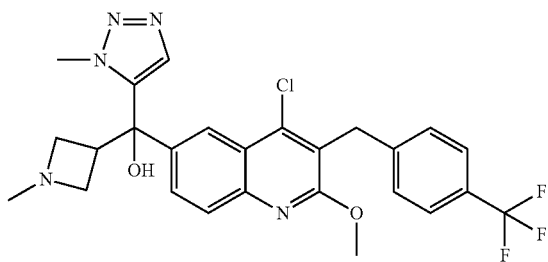 [SMILES: COc1nc2ccc(C(O)(c3cnnn3C)C3CN(C)C3)cc2c(Cl)c1Cc1ccc(C(F)(F)F)cc1]

To a flask containing azetidin-3-yl(4-chloro-2-methoxy-3-(4-(trifluoromethyl)benzyl)quinolin-6-yl)(1-methyl-1H-1,2,3-triazol-5-yl)methanol (252 mg, 0.49 mmol, Example 124) was added MeOH (5 mL), formaldehyde (0.5 mL, 6.72 mmol), acetic acid (0.15 mL, 2.62 mmol) and sodium cyanoborohydride (1 M solution in THF, 1 mL, 1 mmol) at room temperature. The reaction mixture was stirred at room temperature for 24 hours and then the contents were concentrated to dryness and the residue was dissolved in DCM. 1 N Aqueous NaOH was then added to adjust the pH of the solution to pH 10. The aqueous portion was extracted with DCM (3×25 mL) and CHCl$_3$ (2×25 mL). The organics were combined, washed with brine, dried over MgSO$_4$, filtered and concentrated to dryness. The residue was purified by FCC (2% 2 M NH$_3$-MeOH increasing to 10% 2 M NH$_3$-MeOH) to provide the title compound as an off white solid. $^1$H NMR (500 MHz, CDCl$_3$) δ 8.34 (d, J=2.0 Hz, 1H), 7.75 (d, J=8.7 Hz, 1H), 7.48-7.52 7.50 (m, 3H), 7.44-7.32 (m, 3H), 4.35 (s, 2H), 4.06 (s, 3H), 3.75 (s, 3H), 3.56-3.47 (m, 1H), 3.46-3.36 (m, 1H), 3.31-3.17 (m, 1H), 3.12-3.01 (m, 1H), 3.00-2.90 (m, 1H), 2.31 (s, 3H); MS (ESI): mass calcd: Chemical Formula: C$_{26}$H$_{25}$ClF$_3$N$_5$O$_2$, Exact Mass: 531.2. m/z found 532.1 [M+H]$^+$.

(4-Chloro-2-methoxy-3-(4-(trifluoromethyl)benzyl)quinolin-6-yl)(1-methyl-1H-1,2,3-triazol-5-yl)(1-methylazetidin-3-yl)methanol was purified by chiral SFC (Stationary phase: CHIRALCEL OJ-H 5 μm 250×20 mm, Mobile phase: 75% CO$_2$, 25% EtOH (0.3% iPrNH$_2$)) to give two enantiomers. The first eluting enantiomer was Example 90b and the second eluting enantiomer was Example 90c.

Example 91

3-((4-Chloro-2-methoxy-3-(4-(trifluoromethyl)benzyl)quinolin-6-yl)(hydroxy)(1-methyl-1H-1,2,3-triazol-5-yl)methyl)azetidine-1-carboxamide

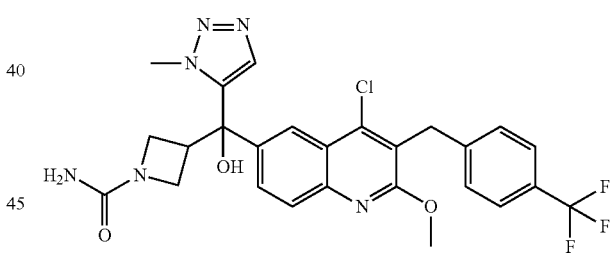

To a flask containing azetidin-3-yl(4-chloro-2-methoxy-3-(4-(trifluoromethyl)benzyl)quinolin-6-yl)(2,6-dimethylpyridin-3-yl)methanol (500 mg, 0.97 mmol, Example 124) was added DCM (10 mL) and triethylamine (0.5 mL, 3.61 mmol) followed by isocyanatotrimethylsilane (0.5 mL, 3.69 mmol) at room temperature. After 8 hours, additional isocyanatotrimethylsilane (0.5 mL, 3.69 mmol) was introduced and the mixture was stirred for an additional 24 hours at which time a precipitate had formed. The precipitate was collected by filtration and washed with Et$_2$O to afford the title compound as a white solid. The mother liquors were treated with MeOH and chromatographed on silica gel (3% MeOH-DCM increasing to 10% MeOH) to provide additional title compound. $^1$H NMR (500 MHz, CD$_3$OD) δ 8.37 (d, J=1.9 Hz, 1H), 7.86-7.77 (m, 2H), 7.54 (d, J=8.2 Hz, 2H), 7.50-7.35 (m, 3H), 4.39 (s, 2H), 4.22 (t, J=8.5 Hz, 1H), 4.14-4.02 (m, 4H), 4.01-3.88 (m, 1H), 3.65-3.72 (m, 4H), 3.63-3.52 (m, 1H); MS (ESI): mass calc. Chemical Formula: C$_{26}$H$_{24}$ClF$_3$N$_6$O$_3$, Exact Mass: 560.2. m/z found 561.1 [M+H]$^+$.

Example 92a 2,4-Dimethylthiazol-5-yl)(2-methoxy-3-(4-(trifluoromethyl)benzyl)quinolin-6-yl)(1-methyl-1H-1,2,3-triazol-5-yl)methanol

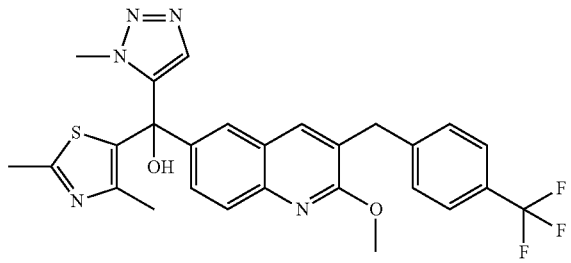 [SMILES: COc1nc2ccc(C(O)(c3sc(C)nc3C)c3cnnn3C)cc2cc1Cc1ccc(C(F)(F)F)cc1]

To a 50 mL Parr flask containing (4-chloro-2-methoxy-3-(4-(trifluoromethyl)benzyl)quinolin-6-yl)(2,4-dimethylthiazol-5-yl)(1-methyl-1H-1,2,3-triazol-5-yl)methanol (265 mg, 0.46 mmol, Intermediate 59) was added EtOH (30 mL) and Et$_3$N (2 mL) followed by 5% palladium on carbon (70 mg). The reaction mixture was shaken at 50 psi H$_2$ for 7 hours. The contents were filtered through a Celite® pad, rinsed with EtOH, and concentrated to dryness. The residue was purified by FCC (1% MeOH-DCM increasing to 5% MeOH) to provide the title compound as a white amorphous solid. $^1$H NMR (500 MHz, CDCl$_3$) δ 7.86 (d, J=8.7 Hz, 1H), 7.60-7.55 (m, 3H), 7.54 (t, J=3.7 Hz, 1H), 7.48 (t, J=4.1 Hz, 1H), 7.36 (d, J=8.0 Hz, 2H), 7.20 (s, 1H), 4.09 (s, 3H) 4.09 (s, 2H), 3.89 (s, 3H), 2.57 (s, 3H), 2.12 (s, 3H), 1.60 (s, 3H); MS (ESI): mass calc. for Chemical Formula: C$_{27}$H$_{24}$F$_3$N$_5$O$_2$S, Exact Mass: 539.2. m/z found 540.1 [M+H]$^+$.

(2,4-Dimethylthiazol-5-yl)(2-methoxy-3-(4-(trifluoromethyl)benzyl)quinolin-6-yl)(1-methyl-1H-1,2,3-triazol-5-yl)methanol was purified by chiral HPLC under SFC condition (Kromasil 5-cellucoat column using 10% EtOH/CO2 with 0.2% TEA) to give two enantiomers. The first eluting enantiomer was Example 92b and the second eluting enantiomer was Example 92c.

Example 93

(4-Chloro-2-methoxy-3-(4-(trifluoromethyl)benzyl)quinolin-6-yl)(3,5-dimethylisoxazol-4-yl)(1-methyl-1H-1,2,3-triazol-5-yl)methanol

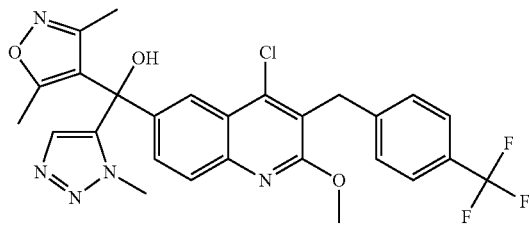 [SMILES: COc1nc2ccc(C(O)(c3c(C)noc3C)c3cnnn3C)cc2c(Cl)c1Cc1ccc(C(F)(F)F)cc1]

To a flask containing 1-methyl-1H-1,2,3-triazole (200 mg, 2.41 mmol) was added THF (17 mL) and the solution was cooled to −43° C. using a CH$_3$CN—CO$_2$ bath. n-BuLi, (2.5 M in hexanes, 0.88 mL, 2.19 mmol) was then added dropwise to provide a white suspension. The suspension was stirred at −40° C. for 20 minutes, then a homogeneous solution of (4-chloro-2-methoxy-3-(4-(trifluoromethyl)benzyl)quinolin-6-yl)(3,5-dimethylisoxazol-4-yl)methanone (500 mg, 1.05 mmol, Intermediate 63: step b) in 2 mL THF was introduced. A dark brownish solution immediately resulted. The reaction mixture was allowed to warm gradually to 0° C. over 25 minutes, then was quenched with aqueous NH$_4$Cl solution. The aqueous portion was extracted with EtOAc (3×35 mL) and the combined organics were washed with brine, dried over MgSO$_4$, filtered and concentrated to dryness. The residue was purified by FCC (20% EtOAc-hexanes increasing to 50% EtOAc) to provide the title compound as a white solid. $^1$H NMR (500 MHz, CDCl$_3$) δ 8.08 (d, J=2.1 Hz, 1H), 7.85 (d, J=8.7 Hz, 1H), 7.61-7.46 (m, 3H), 7.39 (d, J=8.1 Hz, 2H), 6.94 (s, 1H), 4.81 (s, 1H), 4.32 (s, 2H), 4.09 (s, 3H), 3.98 (s, 3H), 1.95 (s, 3H), 1.82 (s, 3H); MS (ESI): mass calc. for Chemical Formula: C$_{27}$H$_{23}$ClF$_3$N$_5$O$_3$; Exact Mass: 557.1. m/z found, 557.9 (M+H).

Example 94

6-((3,5-Dimethylisoxazol-4-yl)(hydroxy)(1-methyl-1H-1,2,3-triazol-5-yl)methyl)-2-methoxy-3-(4-(trifluoromethyl)benzyl)quinoline-4-carbonitrile

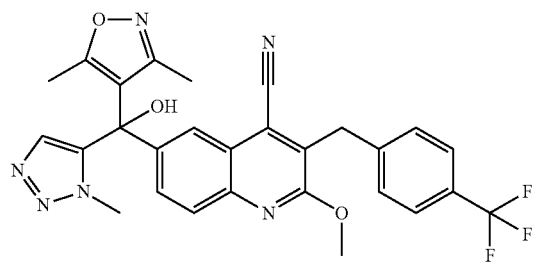 [SMILES: COc1nc2ccc(C(O)(c3c(C)noc3C)c3cnnn3C)cc2c(C#N)c1Cc1ccc(C(F)(F)F)cc1]

(4-Chloro-2-methoxy-3-(4-(trifluoromethyl)benzyl)quinolin-6-yl)(3,5-dimethylisoxazol-4-yl)(1-methyl-1H-1,2,3-triazol-5-yl)methanol (180 mg, 0.32 mmol, Example 93), zinc cyanide (77 mg, 0.66 mol), X-phos (45 mg, 0.94 mmol), Pd$_2$(dba)$_3$ (50 mg, 0.055 mmol) and zinc metal (3 mg, 0.19 mmol) were added to a large microwave vial. DMA (4 mL, sparged with argon for 35 minutes) was added and the vial was sealed and evacuated. The mixture was heated to 125° C. in a preheated aluminum heating mantle. After 1 hour, the mixture was allowed to cool to room temperature and then was filtered through a Celite® pad and rinsed with EtOAc-MeOH (10:1). The effluent was concentrated under reduced pressure and the crude material was chromatographed directly on silica gel (20% EtOAc-hexanes increasing to 50% EtOAc) to provide the title compound as an off white solid. $^1$H NMR (500 MHz, CDCl$_3$) δ 8.17 (d, J=2.1 Hz, 1H), 7.87 (d, J=8.8 Hz, 1H), 7.53 (d, J=8.2 Hz, 2H), 7.46 (d, J=8.2 Hz, 2H), 7.40 (dd, J=8.8, 2.2 Hz, 1H), 6.92 (s, 1H), 5.38 (s, 1H), 4.43-4.29 (m, 2H), 4.12 (s, 3H), 4.01 (s, 3H), 1.95 (s, 3H), 1.82 (s, 3H); MS (ESI): mass calc. for Chemical Formula: $C_{28}H_{23}F_3N_6O_3$; Exact Mass: 548.2. m/z found 549.0 (M+H).

Example 95

(2,4-Dichloro-3-(4-(methylthio)benzyl)quinolin-6-yl)(2,6-dimethylpyridin-3-yl)(1-methyl-1H-1,2,3-triazol-5-yl)methanol

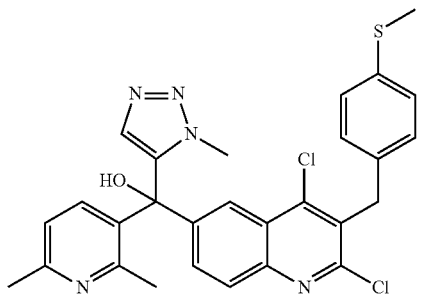

The title compound was prepared using 6-bromo-2,4-dichloro-3-(4-(methylthio)benzyl)quinoline (Intermediate 74: step b) in place of 6-bromo-2,4-dichloro-3-(4-(trifluoromethyl)benzyl)quinoline (Intermediate 12: step c) using the procedure described for Example 139. $^1$H NMR (400 MHz, DMSO-$d_6$) δ 8.22 (s, 1H), 8.05 (d, J=8.59 Hz, 1H), 7.62 (d, J=9.09 Hz, 1H), 7.55 (s, 1H), 7.19 (d, J=8.59 Hz, 2H), 7.15 (d, J=8.59 Hz, 2H), 7.07 (d, J=8.08 Hz, 1H), 6.93-6.98 (m, 2H), 4.43 (s, 2H), 3.86 (s, 3H), 2.434 (s, 3H), 2.426 (s, 3H), 2.23 (s, 3H); MS m/e 550.2 [M+H]$^+$.

Example 96

(3-Benzyl-4-chloro-2-(1H-pyrazol-1-yl)quinolin-6-yl)(1-methyl-1H-imidazol-5-yl)(6-(trifluoromethyl)pyridin-3-yl)methanol.TFA

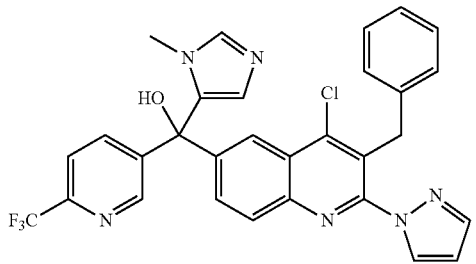 [SMILES: Cn1cncc1C(O)(c1ccc(C(F)(F)F)nc1)c1ccc2nc(-n3cccn3)c(Cc3ccccc3)c(Cl)c2c1]

A mixture of 3-benzyl-6-bromo-4-chloro-2-(1H-pyrazol-1-yl)quinoline (700 mg, 1.76 mmol, Intermediate 73: step d), (1-methyl-1H-imidazol-5-yl)(6-(trifluoromethyl)pyridin-3-yl)methanone (448 mg, 1.76 mmol, Intermediate 2: step c), and 18 mL of THF was sparged with $N_2$ and then cooled to −78° C. To the mixture was added n-BuLi (1.6 M in hexanes, 1.5 mL, 2.4 mmol) dropwise. The reaction mixture was stirred at −78° C. for 10 minutes, then the acetone-dry ice bath was replaced with a water-ice bath. Stirring was continued for 1 hour at 4° C. Saturated $NH_4Cl$ (aqueous) was added and the organic layer was separated. The aqueous layer was extracted with dichloromethane. The combined organic phases were dried ($Na_2SO_4$), filtered, and concentrated to dryness. The crude was purified by flash column chromatography (silica gel, 5-10% MeOH in DCM) followed by reverse phase HPLC (water/acetonitrile/0.1% TFA) to provide the title compound. $^1$H NMR (400 MHz, MeOH-d4) δ 9.06 (s, 1H), 8.86 (s, 1H), 8.44 (s, 1H), 8.07-8.17 (m, 3H), 7.90 (d, J=8.08 Hz, 1H), 7.79-7.87 (m, 2H), 7.04-7.17 (m, 4H), 6.88 (d, J=7.58 Hz, 2H), 6.50 (s, 1H), 4.78 (s, 2H), 3.72 (s, 3H); MS m/e 575.2 [M+H]$^+$.

Example 97

(3-Benzyl-4-chloro-2-(trifluoromethyl)quinolin-6-yl)(1-methyl-1H-imidazol-5-yl)(pyridin-2-yl)methanol•TFA

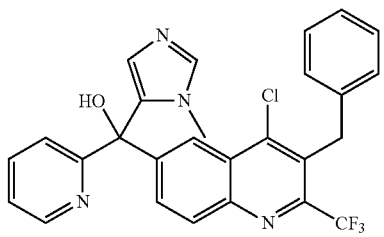

To a solution of 3-benzyl-4-chloro-6-iodo-2-(trifluoromethyl)quinoline (containing about 33% molar of 3-benzyl-4-chloro-2-(trifluoromethyl)quinoline as an impurity, 539 mg, Intermediate 71: step b) in THF (4 mL) at −78° C. was added iPrMgCl (2.0 M in THF, 0.6 mL, 1.2 mmol). After stirring for about 8 minutes, the cooling bath was removed, and stirring was continued for 15 minutes. Then, (1-methyl-1H-imidazol-5-yl)(pyridin-2-yl)methanone (215 mg, 1.15 mmol, Intermediate 33: step b) was added in neat. After stirring at room temperature overnight, the mixture became clear brown and was heated at 55° C. for 45 minutes. The mixture was quenched with saturated $NH_4Cl$ aqueous solution, and extracted with EtOAc. The organic phase was separated, dried over $Na_2SO_4$, filtered, and concentrated. The crude mixture was purified by flash column chromatography (silica gel, 20-50% EtOAc in heptanes, 5-10% MeOH in DCM) followed by reverse phase HPLC (water/acetonitrile/0.1% TFA) to provide the title compound. $^1$H NMR (400 MHz, $CD_3OD$) δ 8.97 (s, 1H), 8.61 (d, J=4.04 Hz, 1H), 8.57 (d, J=2.02 Hz, 1H), 8.24 (d, J=9.09 Hz, 1H), 8.08 (dd, J=2.02, 9.09 Hz, 1H), 7.92 (dt, J=2.02, 8.08 Hz, 1H), 7.80 (d, J=8.08 Hz, 1H), 7.42 (dd, J=5.05, 7.07 Hz, 1H), 7.20-7.27 (m, 2H), 7.18 (d, J=7.58 Hz, 1H), 7.11 (d, J=1.52, 1H), 6.99 (d, J=7.07 Hz, 2H), 4.56 (s, 2H), 3.63 (s, 3H); MS m/e 509.0 [M+H]$^+$.

Example 98a (3-Benzyl-4-methoxy-2-(trifluoromethyl)quinolin-6-yl)(1-methyl-1H-imidazol-5-yl)(pyridin-2-yl)methanol•TFA

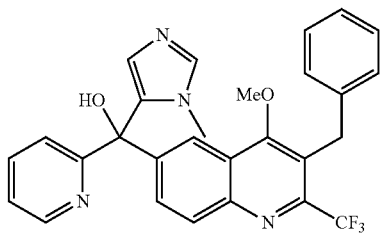 [SMILES: COc1c(Cc2ccccc2)c(C(F)(F)F)nc2ccc(C(O)(c3ccccn3)c3cncn3C)cc12]

A mixture of (3-benzyl-4-chloro-2-(trifluoromethyl)quinolin-6-yl)(1-methyl-1H-imidazol-5-yl)(pyridin-2-yl)methanol•TFA (84 mg, 0.11 mmol, Example 97) and 0.5 M NaOMe in MeOH (0.80 mL, 0.40 mmol) in a sealed tube was heated at 82° C. for 24 hours. The solvent was evaporated, and the residue was partitioned between EtOAc and water. The organic layer was dried over $Na_2SO_4$, filtered, and concentrated. The crude was purified by reverse phase HPLC (water/acetonitrile/0.1% TFA) to provide the title compound as a white solid. $^1$H NMR (400 MHz, $CD_3OD$) δ 8.96 (s, 1H), 8.61 (d, J=4.04 Hz, 1H), 8.28 (d, J=2.02 Hz, 1H), 8.20 (d, J=9.09 Hz, 1H), 8.00 (dd, J=2.02, 9.09 Hz, 1H), 7.96 (dd, J=2.02, 8.08 Hz, 1H), 7.80 (d, J=8.08 Hz, 1H), 7.39-7.45 (m, 1H), 7.19-7.26 (m, 2H), 7.12-7.18 (m, 1H), 7.09 (d, J=2.02 Hz, 1H), 7.06 (d, J=7.07 Hz, 2H), 4.36 (s, 2H), 3.78 (s, 3H), 3.63 (s, 3H); MS m/e 505.0 $[M+H]^+$.

Example 98a was neutralized by partitioning between saturated $NaHCO_3$ aqueous solution and DCM. The organic layer was dried ($Na_2SO_4$), filtered, concentrated, and purified by chiral HPLC (AD-H column, 90% $CO_2$/10% MeOH/0.2% isopropylamine) to give two pure enantiomers. The first eluting enantiomer was Example 98b: $^1$H NMR (400 MHz, $CDCl_3$) δ 8.64 (d, J=4.55 Hz, 1H), 8.19 (d, J=9.09 Hz, 1H), 8.04 (d, J=2.02 Hz, 1H), 7.85 (dd, J=2.02, 9.09 Hz, 1H), 7.71 (dt, J=1.52, 7.83 Hz, 1H), 7.49 (s, 1H), 7.33 (dd, J=5.31, 7.33 Hz, 1H), 7.14-7.29 (m, 4H), 7.11 (d, J=7.07 Hz, 2H), 6.71 (br. s., 1H), 6.36 (s, 1H), 4.34 (s, 2H), 3.66 (s, 3H), 3.43 (s, 3H); MS m/e 505.2 $[M+H]^+$ and the second eluting enantiomer was Example 98c: $^1$H NMR (400 MHz, $CDCl_3$) δ 8.64 (d, J=4.55 Hz, 1H), 8.19 (d, J=9.09 Hz, 1H), 8.04 (s, J=1.52 Hz, 1H), 7.85 (dd, J=1.77, 8.84 Hz, 1H), 7.71 (dt, J=1.67, 7.58 Hz, 1H), 7.49 (s, 1H), 7.33 (dd, J=5.05, 6.57 Hz, 1H), 7.14-7.28 (m, 4H), 7.11 (d, J=7.58 Hz, 2H), 6.71 (br. s., 1H), 6.36 (s, 1H), 4.34 (s, 2H), 3.68 (s, 3H), 3.43 (s, 3H); MS m/e 505.2 $[M+H]^+$.

Example 99a

3-Benzyl-6-(hydroxy(1-methyl-1H-imidazol-5-yl)(pyridin-2-yl)methyl)-2-(trifluoromethyl)quinoline-4-carbonitrile•TFA

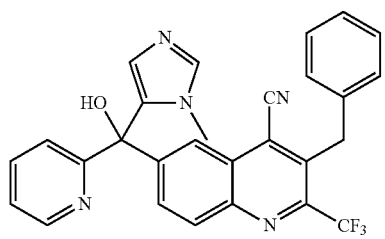 [SMILES: Cn1cncc1C(O)(c1ccc2nc(C(F)(F)F)c(Cc3ccccc3)c(C#N)c2c1)c1ccccn1]

A pressure tube containing (3-benzyl-4-chloro-2-(trifluoromethyl)quinolin-6-yl)(1-methyl-1H-imidazol-5-yl)(pyridin-2-yl)methanol•TFA (86 mg, 0.12 mmol, Example 97), $Pd_2(dba)_3$ (10 mg, 0.011 mmol), dicyclohexyl(2',4',6'-triisopropyl-[1,1'-biphenyl]-2-yl)phosphine (X-Phos, 10 mg, 0.021 mmol), zinc cyanide (12 mg, 0.10 mmol) and zinc nanopowder (2.3 mg, 0.035 mmol) in N,N-dimethylacetamide (1 mL) was sparged with nitrogen for 8 minutes, and then heated at 120° C. for 2 hours. The mixture was allowed to cool to room temperature, EtOAc and saturated $NH_4Cl$ aqueous solution were added. The organic layer was separated, and the aqueous layer was extracted with EtOAc. The combined organic layers were dried ($Na_2SO_4$), filtered, and concentrated. The residue was purified by reverse phase HPLC (water/acetonitrile/0.1% TFA) to provide the title compound. $^1$H NMR (400 MHz, $CD_3OD$) δ 8.98 (s, 1H), 8.62 (d, J=4.04 Hz, 1H), 8.47 (d, J=2.02 Hz, 1H), 8.32 (d, J=9.09 Hz, 1H), 8.17 (dd, J=2.02, 9.09 Hz, 1H), 7.93 (dt, J=2.02, 7.58 Hz, 1H), 7.83 (d, J=8.08 Hz, 1H), 7.40-7.45 (m, 1H), 7.24-7.31 (m, 2H), 7.18-7.24 (m, 1H), 7.15 (d, J=1.52 Hz, 1H), 7.05 (d, J=7.58 Hz, 2H), 4.64 (s, 2H), 3.63 (s, 3H); MS m/e 500.3 $[M+H]^+$.

Example 99a was neutralized by partitioning between saturated $NaHCO_3$ aqueous solution and DCM. The organic layer was dried ($Na_2SO_4$), filtered, concentrated, and purified by chiral HPLC (Chiralpak AD, 50% MeOH/50% EtOH) to give two pure enantiomers. The first eluting enantiomer was Example 99b: $^1$H NMR (400 MHz, $CDCl_3$) δ 8.65 (d, J=4.55 Hz, 1H), 8.30 (d, J=1.52 Hz, 1H), 8.28 (d, J=8.59 Hz, 1H), 8.01 (dd, J=2.02, 9.09 Hz, 1H), 7.76 (dt, J=1.52, 7.83 Hz, 1H), 7.50 (s, 1H), 7.36 (dd, J=5.05, 7.58 Hz, 1H), 7.21-7.31 (m, 4H), 7.08 (d, J=7.07 Hz, 2H), 6.76 (br. s., 1H), 6.39 (s, 1H), 4.60 (s, 2H), 3.41 (s, 3H); MS m/e 500.3 $[M+H]^+$ and the second eluting enantiomer was Example 99c: $^1$H NMR (400 MHz, $CDCl_3$) δ 8.65 (d, J=4.55 Hz, 1H), 8.31 (d, J=1.01 Hz, 1H), 8.28 (d, J=9.09 Hz, 1H), 8.01 (dd, J=1.52, 8.59 Hz, 1H), 7.76 (dt, J=1.52, 7.58 Hz, 1H), 7.52 (s, 1H), 7.35 (dd, J=5.05, 7.07 Hz, 1H), 7.17-7.30 (m, 4H), 7.08 (d, J=7.07 Hz, 2H), 6.39 (s, 1H), 4.60 (s, 2H), 3.41 (s, 3H); MS m/e 500.3 $[M+H]^+$.

Example 100

(3-Benzyl-4-chloro-2-(trifluoromethyl)quinolin-6-yl)(4-chlorophenyl)(1-methyl-1H-imidazol-5-yl)methanol•TFA

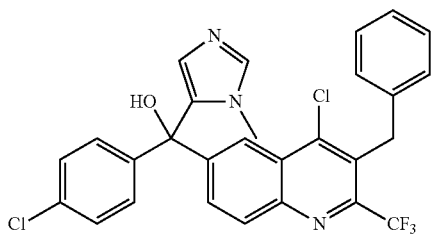 [SMILES: Cn1cncc1C(O)(c1ccc(Cl)cc1)c1ccc2nc(C(F)(F)F)c(Cc3ccccc3)c(Cl)c2c1]

The title compound was prepared using (4-chlorophenyl)(1-methyl-1H-imidazol-5-yl)methanone (Intermediate 43: step b) in place of (1-methyl-1H-imidazol-5-yl)(pyridin-2-yl)methanone (Intermediate 33: step b) using the procedure described for Example 97. $^1$H NMR (400 MHz, $CD_3OD$) δ 9.01 (s, 1H), 8.40 (d, J=2.02 Hz, 1H), 8.28 (d, J=9.09 Hz, 1H), 7.94 (dd, J=2.02, 9.09 Hz, 1H), 7.40-7.49 (m, 4H), 7.20-7.27 (m, 2H), 7.14-7.20 (m, 1H), 6.96-7.02 (m, 3H), 4.56 (s, 2H), 3.70 (s, 3H); MS m/e 542.1 $[M+H]^+$.

Example 101a (3-Benzyl-4-methoxy-2-(trifluoromethyl)quinolin-6-yl)(4-chlorophenyl)(1-methyl-1H-imidazol-5-yl)methanol•TFA

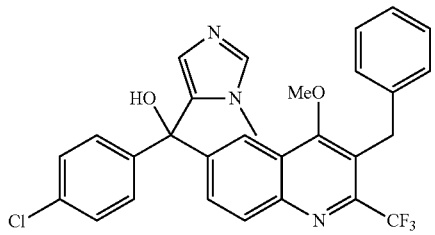 [SMILES: COc1c(Cc2ccccc2)c(C(F)(F)F)nc2ccc(C(O)(c3ccc(Cl)cc3)c3cncn3C)cc12]

The title compound was prepared using (3-benzyl-4-chloro-2-(trifluoromethyl)quinolin-6-yl)(4-chlorophenyl)(1-methyl-1H-imidazol-5-yl)methanol•TFA (Example 100) in place of (3-benzyl-4-chloro-2-(trifluoromethyl)quinolin-6-yl)(1-methyl-1H-imidazol-5-yl)(pyridin-2-yl)methanol•TFA (Example 97) using the procedure described for Example 98a. $^1$H NMR (400 MHz, CD$_3$OD) δ 9.01 (s, 1H), 8.22 (d, J=8.59 Hz, 1H), 8.12 (s, 1H), 7.83-7.92 (m, 1H), 7.39-7.52 (m, 4H), 7.17-7.27 (m, 2H), 7.11-7.18 (m, 1H), 7.06 (d, J=7.58 Hz, 2H), 6.97 (s, 1H), 4.36 (s, 2H), 3.75 (s, 3H), 3.71 (s, 3H); MS m/e 538.0 [M+H]$^+$.

Example 101a was neutralized by partitioning between saturated NaHCO$_3$ aqueous solution and DCM. The organic layer was dried (Na$_2$SO$_4$), filtered, concentrated, and purified by chiral HPLC (Chiralpack OJ, 100% MeOH) to give two pure enantiomers. The first eluting enantiomer was Example 101b: $^1$H NMR (400 MHz, CDCl$_3$) δ 8.15 (d, J=8.59 Hz, 1H), 7.98 (d, J=2.02 Hz, 1H), 7.75 (dd, J=2.02, 9.09 Hz, 1H), 7.32 (s, 4H), 7.21-7.25 (m, 3H), 7.14-7.20 (m, 1H), 7.11 (d, J=7.58 Hz, 2H), 6.30-6.35 (m, 1H), 4.97 (br. s., 1H), 4.33 (s, 2H), 3.64 (s, 3H), 3.33 (s, 3H); MS m/e 538.2 [M+H]$^+$ and the second eluting enantiomer was Example 101c: $^1$H NMR (400 MHz, CDCl$_3$) δ 8.16 (dd, J=2.53, 9.09 Hz, 1H), 7.99 (d, J=2.02 Hz, 1H), 7.76 (dd, J=2.02, 9.09 Hz, 1H), 7.32 (s, 4H), 7.21-7.28 (m, 3H), 7.14-7.19 (m, 1H), 7.11 (d, J=7.58 Hz, 2H), 6.32-6.38 (m, 1H), 4.33 (s, 2H), 3.64 (s, 3H), 3.35 (s, 3H); MS m/e 538.2 [M+H]$^+$.

Example 102

3-Benzyl-6-((4-chlorophenyl)(hydroxy)(1-methyl-1H-imidazol-5-yl)methyl)-2-(trifluoromethyl)quinolin-4-ol•TFA

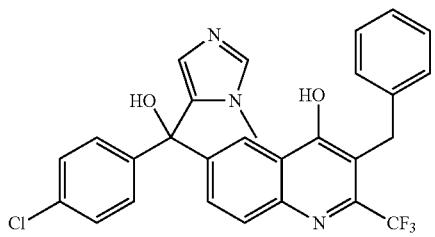 [SMILES: Cn1cncc1C(O)(c1ccc(Cl)cc1)c1ccc2nc(C(F)(F)F)c(Cc3ccccc3)c(O)c2c1]

The title compound was isolated from the reaction that formed Example 101a. $^1$H NMR (400 MHz, CD$_3$OD) δ 8.97 (s, 1H), 8.08 (d, J=1.52 Hz, 1H), 7.82-7.93 (m, 2H), 7.43 (d, J=8.59 Hz, 2H), 7.37 (d, J=8.59 Hz, 2H), 7.16-7.23 (m, 2H), 7.08-7.16 (m, 3H), 6.89 (s, 1H), 4.12 (s, 2H), 3.68 (s, 3H); MS m/e 524.1 [M+H]$^+$.

Example 103

3-Benzyl-6-((4-chlorophenyl)(hydroxy)(1-methyl-1H-imidazol-5-yl)methyl)-2-(trifluoromethyl)quinoline-4-carbonitrile•TFA

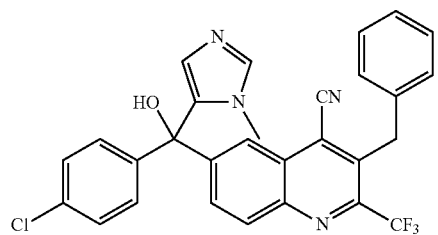 [SMILES: Cn1cncc1C(O)(c1ccc(Cl)cc1)c1ccc2nc(C(F)(F)F)c(Cc3ccccc3)c(C#N)c2c1]

A pressure tube containing (3-benzyl-4-chloro-2-(trifluoromethyl)quinolin-6-yl)(4-chlorophenyl)(1-methyl-1H-imidazol-5-yl)methanol•TFA (167 mg, 0.220 mmol, Example 100), Pd$_2$(dba)$_3$ (30 mg, 0.033 mmol), dicyclohexyl(2',4',6'-triisopropyl-[1,1'-biphenyl]-2-yl)phosphine (X-Phos, 16 mg, 0.034 mmol), zinc cyanide (15 mg, 0.13 mmol) and zinc nanopowder (3.5 mg, 0.054 mmol) in N,N-dimethylacetamide (1 mL) was sparged with nitrogen for 8 minutes, and then heated at 120° C. for 4 hours. The mixture was allowed to cool to room temperature and filtered through a syringe filter. The filtrate was concentrated in vacuo, EtOAc and saturated NH$_4$Cl aqueous solution were added. The organic layer was separated, and the aqueous layer was extracted with EtOAc. The combined organic layers were dried (Na$_2$SO$_4$), filtered, and concentrated. The residue was purified by reverse phase HPLC (water/acetonitrile/0.1% TFA) to provide the title compound. $^1$H NMR (400 MHz, CD$_3$OD) δ 9.02 (s, 1H), 8.34 (d, J=9.09 Hz, 1H), 8.31 (d, J=1.52 Hz, 1H), 8.01 (dd, J=2.02, 9.09 Hz, 1H), 7.44-7.49 (m, 4H), 7.24-7.30 (m, 2H), 7.18-7.24 (m, 1H), 7.06 (d, J=7.58 Hz, 2H), 7.03 (d, J=2.02 Hz, 1H), 4.64 (s, 2H), 3.71 (s, 3H); MS m/e 533.3 [M+H]$^+$.

Example 104

3-Benzyl-6-((4-cyanophenyl)(hydroxy)(1-methyl-1H-imidazol-5-yl)methyl)-2-(trifluoromethyl)quinoline-4-carbonitrile•TFA

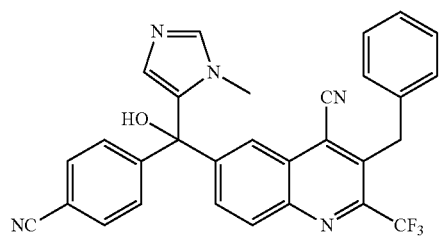 [SMILES: Cn1cncc1C(O)(c1ccc(C#N)cc1)c1ccc2nc(C(F)(F)F)c(Cc3ccccc3)c(C#N)c2c1]

The title compound was isolated from the reaction that formed Example 103. $^1$H NMR (400 MHz, CD$_3$OD) δ 9.05 (s, 1H), 8.36 (d, J=9.09 Hz, 1H), 8.31 (d, J=2.02 Hz, 1H), 8.02

(dd, J=2.02, 8.59 Hz, 1H), 7.83 (d, J=8.59 Hz, 2H), 7.69 (d, J=8.59 Hz, 2H), 7.25-7.31 (m, 2H), 7.19-7.24 (m, 1H), 7.10 (d, J=1.52 Hz, 1H), 7.06 (d, J=7.07 Hz, 2H), 4.64 (s, 2H), 3.70 (s, 3H); MS m/e 524.3 [M+H]⁺.

Example 105

(3-Benzyl-4-chloro-2-(trifluoromethyl)quinolin-6-yl)(1-methyl-1H-imidazol-5-yl)(6-(trifluoromethyl)pyridin-3-yl)methanol•TFA

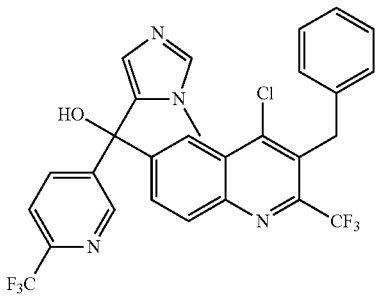 [SMILES: Cn1cncc1C(O)(c1ccc(C(F)(F)F)nc1)c1ccc2nc(C(F)(F)F)c(Cc3ccccc3)c(Cl)c2c1]

The title compound was prepared using (1-methyl-1H-imidazol-5-yl)(6-(trifluoromethyl)pyridin-3-yl)methanone (Intermediate 2: step c) in place of (1-methyl-1H-imidazol-5-yl)(pyridin-2-yl)methanone (Intermediate 33: step b) using the procedure described for Example 97. ¹H NMR (400 MHz, CD₃OD) δ 9.07 (s, 1H), 8.87 (d, J=2.53 Hz, 1H), 8.48 (d, J=2.02 Hz, 1H), 8.32 (d, J=9.09 Hz, 1H), 8.12 (dd, J=2.27, 8.34 Hz, 1H), 7.94 (dd, J=2.02, 8.59 Hz, 1H), 7.90 (d, J=8.08 Hz, 1H), 7.20-7.27 (m, 2H), 7.14-7.20 (m, 2H), 7.00 (d, J=7.07 Hz, 2H), 4.57 (s, 2H), 3.72 (s, 3H); MS m/e 577.0 [M+H]⁺.

Example 106a (3-Benzyl-4-methoxy-2-(trifluoromethyl)quinolin-6-yl)(1-methyl-1H-imidazol-5-yl)(6-(trifluoromethyl)pyridin-3-yl)methanol•TFA

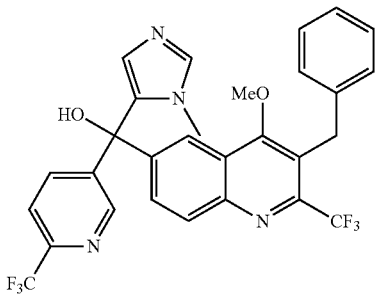 [SMILES: COc1c(Cc2ccccc2)c(C(F)(F)F)nc2ccc(C(O)(c3ccc(C(F)(F)F)nc3)c3cncn3C)cc12]

The title compound was prepared using (3-benzyl-4-chloro-2-(trifluoromethyl)quinolin-6-yl)(1-methyl-1H-imidazol-5-yl)(6-(trifluoromethyl)pyridin-3-yl)methanol•TFA (Example 105) in place of (3-benzyl-4-chloro-2-(trifluoromethyl)quinolin-6-yl)(1-methyl-1H-imidazol-5-yl)(pyridin-2-yl)methanol•TFA (Example 97) using the procedure described for Example 98a with the exception that the reaction was carried out at 70° C. for 16 hours. ¹H NMR (400 MHz, CD₃OD) δ 9.06 (s, 1H), 8.87 (d, J=2.02 Hz, 1H), 8.27 (d, J=8.59 Hz, 1H), 8.21 (d, J=2.53 Hz, 1H), 8.12 (dd, J=2.02, 8.59 Hz, 1H), 7.90 (d, J=8.08 Hz, 1H), 7.87 (dd, J=2.27, 8.84 Hz, 1H), 7.19-7.26 (m, 2H), 7.12-7.18 (m, 2H), 7.07 (d, J=7.07 Hz, 2H), 4.37 (s, 2H), 3.78 (s, 3H), 3.72 (s, 3H); MS m/e 573.2 [M+H]⁺.

Example 106a was neutralized by partitioning between saturated NaHCO₃ aqueous solution and DCM. The organic layer was dried (Na₂SO₄), filtered, concentrated, and purified by chiral HPLC (AD-H column, 80% CO₂/20% 2-propanol/0.2% isopropylamine) to give two pure enantiomers. The first eluting enantiomer was Example 106b: ¹H NMR (400 MHz, CDCl₃) δ 8.82 (s, 1H), 8.18 (d, J=9.09 Hz, 1H), 8.07 (s, 1H), 7.90 (d, J=8.08 Hz, 1H), 7.75 (d, J=8.59 Hz, 1H), 7.64 (d, J=8.08 Hz, 1H), 7.20-7.30 (m, 2H), 7.13-7.21 (m, 2H), 7.10 (d, J=7.58 Hz, 2H), 6.23 (br. s, 1H), 4.33 (s, 2H), 3.67 (s, 3H), 3.31 (s, 3H); MS m/e 573.2 [M+H]⁺ and the second eluting enantiomer was Example 106c: ¹H NMR (400 MHz, CDCl₃) δ 8.82 (s, 1H), 8.19 (d, J=9.09 Hz, 1H), 8.07 (d, J=2.02 Hz, 1H), 7.89 (d, J=8.08 Hz, 1H), 7.75 (dd, J=2.02, 9.09 Hz, 1H), 7.64 (d, J=8.08 Hz, 1H), 7.21-7.27 (m, 2H), 7.14-7.21 (m, 2H), 7.10 (d, J=7.07 Hz, 2H), 6.23 (br. s., 1H), 4.34 (s, 2H), 3.67 (s, 3H), 3.31 (s, 3H); MS m/e 573.2 [M+H]⁺.

Example 107

3-Benzyl-6-(hydroxy(1-methyl-1H-imidazol-5-yl)(6-(trifluoromethyl)pyridin-3-yl)methyl)-2-(trifluoromethyl)quinolin-4-ol•TFA

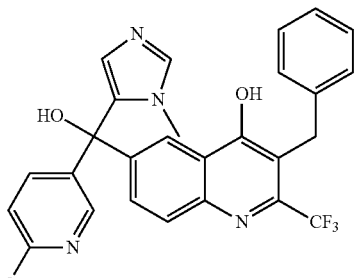

The title compound was isolated from the reaction that formed Example 106a. ¹H NMR (400 MHz, CD₃OD) δ 9.03 (s, 1H), 8.80 (d, J=2.02 Hz, 1H), 8.09 (d, J=2.02 Hz, 1H), 8.02 (dd, J=2.02, 8.59 Hz, 1H), 7.94 (d, J=9.09 Hz, 1H), 7.84-7.91 (m, 2H), 7.16-7.23 (m, 2H), 7.09-7.16 (m, 3H), 7.06 (d, J=1.52 Hz, 1H), 4.13 (s, 2H), 3.69 (s, 3H); MS m/e 558.9 [M+H]⁺.

Example 108a

3-Benzyl-6-(hydroxy(1-methyl-1H-imidazol-5-yl)(6-(trifluoromethyl)pyridin-3-yl)methyl)-2-(trifluoromethyl)quinoline-4-carbonitrile•TFA

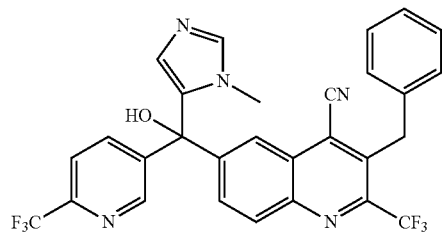 [SMILES: Cn1cncc1C(O)(c1ccc(C(F)(F)F)nc1)c1ccc2nc(C(F)(F)F)c(Cc3ccccc3)c(C#N)c2c1]

The title compound was prepared using (3-benzyl-4-chloro-2-(trifluoromethyl)quinolin-6-yl)(1-methyl-1H-imidazol-5-yl)(6-(trifluoromethyl)pyridin-3-yl)methanol•TFA (Example 105) in place of (3-benzyl-4-chloro-2-(trifluoromethyl)quinolin-6-yl)(4-chlorophenyl)(1-methyl-1H-imidazol-5-yl)methanol•TFA (Example 100) using the procedure described for Example 103. ¹H NMR (400 MHz, CD₃OD) δ 9.06 (s, 1H), 8.87 (d, J=2.02 Hz, 1H), 8.39 (d, J=8.59 Hz, 1H), 8.36 (d, J=2.02 Hz, 1H), 8.12 (dd, J=2.02, 8.08 Hz, 1H), 8.01 (dd, J=2.02, 9.09 Hz, 1H), 7.90 (d, J=8.59 Hz, 1H), 7.25-7.32 (m, 2H), 7.23 (d, J=7.07 Hz, 1H), 7.19 (d, J=1.52 Hz, 1H), 7.07 (d, J=7.07 Hz, 2H), 4.65 (s, 2H), 3.72 (s, 3H); MS m/e 568.2 [M+H]⁺.

Example 108a was neutralized by partitioning between saturated NaHCO₃ aqueous solution and DCM. The organic layer was dried (Na₂SO₄), filtered, concentrated, and purified by chiral HPLC (Chiralcel OJ, 100% MeOH) to give two pure enantiomers. The first eluting enantiomer was Example 108b: ¹H NMR (400 MHz, CDCl₃) δ 8.76 (d, J=2.02 Hz, 1H), 8.43 (d, J=2.02 Hz, 1H), 8.23 (d, J=8.59 Hz, 1H), 7.92 (dd, J=2.02, 8.08 Hz, 1H), 7.73 (dd, J=2.02, 8.59 Hz, 1H), 7.65 (d, J=8.08 Hz, 1H), 7.24-7.31 (m, 2H), 7.18-7.24 (m, 2H), 7.08 (d, J=7.07 Hz, 2H), 6.22 (s, 1H), 4.60 (s, 2H), 3.33 (s, 3H); MS m/e 568.2 [M+H]⁺ and the second eluting enantiomer was Example 108c: ¹H NMR (400 MHz, CDCl₃) δ 8.77 (s, 1H), 8.44 (d, J=2.02 Hz, 1H), 8.23 (d, J=9.09 Hz, 1H), 7.93 (dd, J=2.02, 8.59 Hz, 1H), 7.74 (dd, J=2.02, 9.09 Hz, 1H), 7.66 (d, J=8.59 Hz, 1H), 7.20-7.33 (m, 4H), 7.09 (d, J=7.07 Hz, 2H), 6.26 (s, 1H), 4.61 (s, 2H), 3.34 (s, 3H); MS m/e 568.2 [M+H]⁺.

Example 109

(3-Benzyl-2,4-dichloroquinolin-6-yl)(1-methyl-1H-imidazol-5-yl)(6-(trifluoromethyl)pyridin-3-yl)methanol•TFA

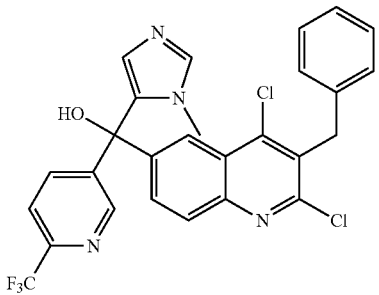

A solution of 3-benzyl-6-bromo-2,4-dichloroquinoline (3.13 g, 8.53 mmol, Intermediate 73: step c) in THF (50 mL) was sparged with N₂ for 10 minutes and cooled to −78° C. To the solution was added n-BuLi (1.6 M in hexanes, 6.90 mL, 11.0 mmol) dropwise and the color changed to dark red. After stirring for 5 minutes at −78° C., (1-methyl-1H-imidazol-5-yl)(6-(trifluoromethyl)pyridin-3-yl)methanone (2.18 g, 8.53 mmol, Intermediate 2: step c) was added followed by 15 mL of THF. The reaction mixture was stirred at −78 to −55° C. for about 13 minutes, then the acetone-dry ice bath was replaced with a water-ice bath. Stirring was continued for 1 hour at 4° C. Saturated NH₄Cl (aq) was added and the organic layer was separated. The aqueous layer was extracted with dichloromethane. The combined organic phases were dried (Na₂SO₄), filtered, and concentrated to dryness. The crude material was purified by flash column chromatography (silica gel, 100% EtOAc, 5-10% MeOH in DCM) followed by reverse phase HPLC (water/acetonitrile/0.1% TFA) to provide the title compound as a white solid. ¹H NMR (400 MHz, CD₃OD) δ 9.04 (s, 1H), 8.84 (d, J=2.53 Hz, 1H), 8.38 (d, J=2.02 Hz, 1H), 8.04-8.11 (m, 2H), 7.89 (d, J=8.08 Hz, 1H), 7.83 (dd, J=2.27, 8.84 Hz, 1H), 7.23-7.29 (m, 2H), 7.15-7.23 (m, 3H), 7.12 (s, 1H), 4.56 (s, 2H), 3.71 (s, 3H).

Example 110

(3-Benzyl-4-chloro-2-methoxyquinolin-6-yl)(1-methyl-1H-imidazol-5-yl)(6-(trifluoromethyl)pyridin-3-yl)methanol•TFA

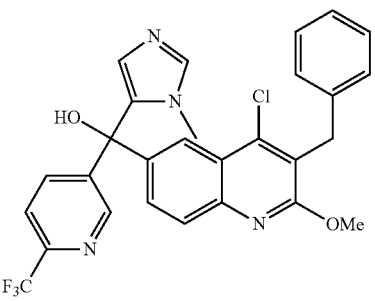

A mixture of (3-benzyl-2,4-dichloroquinolin-6-yl)(1-methyl-1H-imidazol-5-yl)(6-(trifluoromethyl)pyridin-3-yl)methanol (1.10 g, 2.02 mmol, Example 109) and 0.5 M NaOMe in MeOH (13 mL, 6.5 mmol) in a sealed tube was heated at 53° C. for 1 hour. More 0.5 M NaOMe in MeOH (6.5 mL, 3.3 mmol) was added, and the mixture was stirred at the same temperature for another 5 hours. The solvent was evaporated in vacuo, and the residue was diluted with DMF and filtered through a syringe filter. The filtrate was purified by reverse phase HPLC (water/acetonitrile/0.1% TFA) to provide the title compound. ¹H NMR (400 MHz, CD₃OD) δ 9.03 (s, 1H), 8.83 (d, J=2.02 Hz, 1H), 8.22 (d, J=2.02 Hz, 1H), 8.08 (dd, J=2.02, 8.08 Hz, 1H), 7.92 (d, J=8.59 Hz, 1H), 7.88 (d, J=8.08 Hz, 1H), 7.66 (dd, J=2.27, 8.84 Hz, 1H), 7.22 (d, J=4.04 Hz, 4H), 7.10-7.18 (m, 1H), 7.06 (d, J=1.52 Hz, 1H), 4.28 (s, 2H), 4.07 (s, 3H), 3.71 (s, 3H); MS m/e 539.1 [M+H]⁺.

Example 111a (3-Benzyl-4-chloro-2-(1-methyl-1H-pyrazol-4-yl)quinolin-6-yl)(1-methyl-1H-imidazol-5-yl)(6-(trifluoromethyl)pyridin-3-yl)methanol

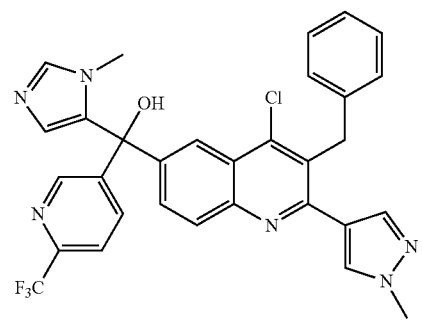 [SMILES: Cn1cc(-c2nc3ccc(C(O)(c4ccc(C(F)(F)F)nc4)c4cncn4C)cc3c(Cl)c2Cc2ccccc2)cn1]

A mixture of (3-benzyl-2,4-dichloroquinolin-6-yl)(1-methyl-1H-imidazol-5-yl)(6-(trifluoromethyl)pyridin-3-yl)methanol (523 mg, 0.960 mmol, Example 109), 1-methyl-4-(4,4,5,5-tetramethyl-1,3,2-dioxaborolan-2-yl)-1H-pyrazole (262 mg, 1.26 mmol), PdCl$_2$(dppf) (71 mg, 0.097 mmol), K$_2$CO$_3$ (266 mg, 1.92 mmol), 1,4-dioxane (20 mL), and water (5 mL) was sparged with N$_2$ for about 12 minutes, and then heated at 70° C. for 18 hours. After cooling to room temperature, the mixture was filtered through a syringe filter. The filtrate was concentrated, and the residue was partitioned between DCM and water. The organic layer was dried (Na$_2$SO$_4$), filtered, concentrated, and purified by reverse phase HPLC (water/acetonitrile/0.1% TFA) to provide the title compound as a TFA salt. $^1$H NMR (400 MHz, MeOH-d4) δ 9.05 (s, 1H), 8.85 (s, 1H), 8.38 (d, J=2.02 Hz, 1H), 8.16 (d, J=8.59 Hz, 1H), 8.11 (d, J=8.08 Hz, 1H), 7.86-7.94 (m, 2H), 7.76-7.86 (m, 1H), 7.71 (s, 1H), 7.24-7.32 (m, 2H), 7.18-7.23 (m, 1H), 7.14 (s, 1H), 7.03 (d, J=7.07 Hz, 2H), 4.58 (s, 2H), 3.90 (s, 3H), 3.73 (s, 3H). This TFA salt was neutralized by partitioning between saturated NaHCO$_3$ aqueous solution and DCM. The organic layer was dried (Na$_2$SO$_4$), filtered, concentrated, and purified by chiral HPLC (Chiralcel OD, 85% heptanes/15% ethanol) to give two enantiomers which were further purified on a silica gel column (0-8% MeOH in DCM) to give the two compounds as white solids. The first eluting enantiomer, Example 111b, $^1$H NMR (400 MHz, CDCl$_3$) δ 8.82-8.86 (m, 1H), 8.27 (d, J=2.02 Hz, 1H), 8.04 (d, J=9.09 Hz, 1H), 7.94 (d, J=8.59 Hz, 1H), 7.70 (s, 1H), 7.63-7.69 (m, 3H), 7.27-7.32 (m, 3H), 7.19-7.24 (m, 1H), 7.05 (d, J=7.07 Hz, 2H), 6.36 (s, 1H), 4.51 (s, 2H), 3.89 (s, 3H), 3.37 (s, 3H); MS m/e 589.2 [M+H]$^+$. The second enantiomer to elute off chiral column, Example 111c, $^1$H NMR (400 MHz, CHLOROFORM-d) δ 8.84 (d, J=2.02 Hz, 1H), 8.28 (d, J=2.02 Hz, 1H), 8.04 (d, J=8.59 Hz, 1H), 7.94 (dd, J=2.02, 8.08 Hz, 1H), 7.70 (s, 1H), 7.63-7.69 (m, 3H), 7.27-7.32 (m, 3H), 7.19-7.24 (m, 1H), 7.05 (d, J=7.07 Hz, 2H), 6.36 (br. s., 1H), 4.51 (s, 2H), 3.89 (s, 3H), 3.38 (s, 3H); MS m/e 589.2 [M+H]$^+$.

Example 112a

3-Benzyl-6-(hydroxy(1-methyl-1H-imidazol-5-yl)(6-(trifluoromethyl)pyridin-3-yl)methyl)-2-(1-methyl-1H-pyrazol-4-yl)quinoline-4-carbonitrile•TFA

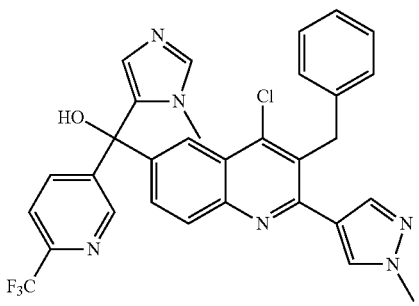 [SMILES: Cn1cc(-c2nc3ccc(C(O)(c4ccc(C(F)(F)F)nc4)c4cncn4C)cc3c(Cl)c2Cc2ccccc2)cn1]

The title compound was prepared using (3-benzyl-4-chloro-2-(1-methyl-1H-pyrazol-4-yl)quinolin-6-yl)(1-methyl-1H-imidazol-5-yl)(6-(trifluoromethyl)pyridin-3-yl)methanol•TFA (Example 111) in place of (3-benzyl-4-chloro-2-(trifluoromethyl)quinolin-6-yl)(4-chlorophenyl)(1-methyl-1H-imidazol-5-yl)methanol•TFA (Example 100) using the procedure described for Example 103, with the exception that the reaction was carried out at 115-123° C. for 3 hours. $^1$H NMR (400 MHz, CD$_3$OD) δ 9.06 (s, 1H), 8.85-8.89 (m, 1H), 8.24 (d, J=2.02 Hz, 1H), 8.21 (d, J=9.09 Hz, 1H), 8.12 (dd, J=2.02, 8.08 Hz, 1H), 7.97 (s, 1H), 7.91 (d, J=8.08 Hz, 1H), 7.86 (dd, J=2.02, 9.09 Hz, 1H), 7.81 (s, 1H), 7.25-7.31 (m, 2H), 7.19-7.24 (m, 1H), 7.16 (d, J=1.52 Hz, 1H), 7.02 (d, J=7.58 Hz, 2H), 4.67 (s, 2H), 3.90 (s, 3H), 3.74 (s, 3H). Example 112a was neutralized by partitioning between saturated NaHCO$_3$ aqueous solution and DCM. The organic layer was dried (Na$_2$SO$_4$), filtered, concentrated, and purified by chiral HPLC (Chiralpack OD, 80% heptanes/20% ethanol) to give two pure enantiomers. The first eluting enantiomer was Example 112b: $^1$H NMR (400 MHz, CDCl$_3$) δ 8.79-8.82 (m, 1H), 8.31 (d, J=2.02 Hz, 1H), 8.06 (d, J=9.09 Hz, 1H), 7.96 (dd, J=2.02, 8.08 Hz, 1H), 7.76 (s, 1H), 7.65-7.70 (m, 2H), 7.59 (dd, J=2.02, 9.09 Hz, 1H), 7.25-7.31 (m, 2H), 7.19-7.25 (m, 2H), 7.02 (d, J=7.07 Hz, 2H), 6.94 (br. s., 1H), 6.32 (s, 1H), 4.59 (s, 2H), 3.90 (s, 3H), 3.36 (s, 3H); MS m/e 580.2 [M+H]$^+$. The second enantiomer to elute off chiral column, Example 112c, was further purified by flash column chromatography (0-8% MeOH in DCM). $^1$H NMR (400 MHz, CHLOROFORM-d) δ 8.80 (s, 1H), 8.31 (d, J=1.52 Hz, 1H), 8.06 (d, J=9.09 Hz, 1H), 7.96 (d, J=8.59 Hz, 1H), 7.76 (s, 1H), 7.63-7.71 (m, 2H), 7.59 (dd, J=2.02, 9.09 Hz, 1H), 7.25-7.31 (m, 2H), 7.19-7.25 (m, 2H), 7.03 (d, J=7.07 Hz, 2H), 6.87 (br. s., 1H), 6.33 (s, 1H), 4.60 (s, 2H), 3.90 (s, 3H), 3.36 (s, 3H); MS m/e 580.2 [M+H]$^+$.

Example 113a (3-Benzyl-4-chloro-2-(1-methyl-1H-imidazol-2-yl)quinolin-6-yl)(1-methyl-1H-imidazol-5-yl)(6-(trifluoromethyl)pyridin-3-yl)methanol•TFA

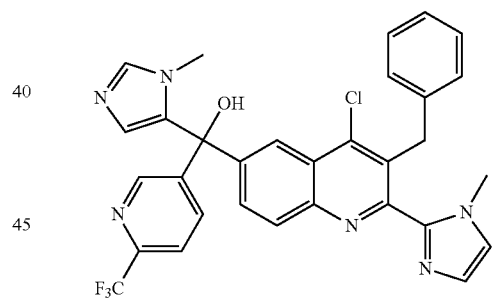

A mixture of (3-benzyl-2,4-dichloroquinolin-6-yl)(1-methyl-1H-imidazol-5-yl)(6-(trifluoromethyl)pyridin-3-yl)methanol (1.01 g, 1.86 mmol, Example 109), 1-methyl-2-(tributylstannyl)-1H-imidazole (1.42 g, 3.68 mmol), Pd(PPh$_3$)$_4$ (206 mg, 0.180 mmol), and toluene (10 mL) was sparged with N$_2$ for about 10 minutes, then heated at 83° C. for 16 hours and 110° C. for 3 hours. After cooling down to room temperature, the mixture was concentrated in vacuo and DCM was added. The precipitated solid was filtered and dissolved in DMSO and MeOH. A few drops of TFA were added to improve solubility. The mixture was purified by reverse phase HPLC (water/acetonitrile/0.1% TFA) to provide the title compound as a TFA salt. $^1$H NMR (400 MHz, MeOH-d4) δ 9.06 (s, 1H), 8.94 (s, 1H), 8.86 (d, J=2.02 Hz, 1H), 8.54 (d, J=2.02 Hz, 1H), 8.22 (d, J=9.09 Hz, 1H), 8.16 (dd, J=2.02, 8.08 Hz, 1H), 7.90-7.94 (m, 2H), 7.64 (d, J=1.52 Hz, 1H), 7.19-7.26 (m, 3H), 7.18 (d, J=1.52 Hz, 1H), 6.86-6.90 (m, 2H), 4.54 (s, 2H), 3.74 (s, 3H), 3.47 (s, 3H).

This TFA salt was neutralized by partitioning between saturated NaHCO₃ aqueous solution and DCM. The organic layer was dried (Na₂SO₄), filtered, concentrated, and purified by chiral HPLC (Chiralpak AD, 85% CO₂/15% ethanol/0.2% isopropylamine) to give two enantiomers. The first eluting enantiomer, example 113b ¹H NMR (400 MHz, MeOH-d4) δ 9.09 (s, 1H), 8.97 (s, 1H), 8.87 (d, J=2.02 Hz, 1H), 8.55 (d, J=2.02 Hz, 1H), 8.22 (d, J=9.09 Hz, 1H), 8.16 (dd, J=2.27, 8.34 Hz, 1H), 7.89-7.96 (m, 2H), 7.66 (d, J=1.52 Hz, 1H), 7.19-7.27 (m, 3H), 7.18 (d, J=1.52 Hz, 1H), 6.88 (d, J=6.57 Hz, 2H), 4.54 (s, 2H), 3.75 (s, 3H), 3.47 (s, 3H); MS m/e 588.7 [M+H]⁺. Example 113c, the second enantiomer to elute was further purified by reverse phase HPLC (water/acetonitrile/ 0.1% TFA) to give the title compound. ¹H NMR (400 MHz, CD₃OD) δ 9.08 (s, 1H), 8.97 (s, 1H), 8.87 (d, J=2.02 Hz, 1H), 8.55 (d, J=2.02 Hz, 1H), 8.22 (d, J=9.09 Hz, 1H), 8.16 (dd, J=2.27, 8.34 Hz, 1H), 7.89-7.95 (m, 2H), 7.66 (d, J=1.52 Hz, 1H), 7.19-7.27 (m, 3H), 7.18 (d, J=1.52 Hz, 1H), 6.88 (d, J=6.57 Hz, 2H), 4.54 (s, 2H), 3.75 (s, 3H), 3.47 (s, 3H); MS m/e 588.7 [M+H]⁺.

Example 114a

3-Benzyl-6-(hydroxy(1-methyl-1H-imidazol-5-yl)(6-(trifluoromethyl)pyridin-3-yl)methyl)-2-(1H-pyrazol-1-yl)quinoline-4-carbonitrile•TFA

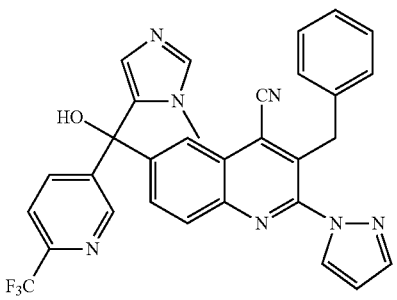 [SMILES: Cn1cncc1C(O)(c1ccc(C(F)(F)F)nc1)c1ccc2nc(-n3cccn3)c(Cc3ccccc3)c(C#N)c2c1]

The title compound was prepared using (3-benzyl-4-chloro-2-(1H-pyrazol-1-yl)quinolin-6-yl)(1-methyl-1H-imidazol-5-yl)(6-(trifluoromethyl)pyridin-3-yl)methanol (Example 96) in place of (3-benzyl-4-chloro-2-(trifluoromethyl)quinolin-6-yl)(4-chlorophenyl)(1-methyl-1H-imidazol-5-yl)methanol•TFA (Example 100) using the procedure described for Example 103, with the exception that the reaction was carried out at 110° C. for 3 hours. ¹H NMR (400 MHz, MeOH-d4) δ 9.07 (s, 1H), 8.87 (s, 1H), 8.31 (d, J=2.02 Hz, 1H), 8.25 (d, J=2.53 Hz, 1H), 8.18 (d, J=8.59 Hz, 1H), 8.12 (dd, J=2.02, 8.08 Hz, 1H), 7.87-7.94 (m, 2H), 7.85 (d, J=1.52 Hz, 1H), 7.17 (d, J=1.52 Hz, 1H), 7.06-7.15 (m, 3H), 6.87-6.93 (m, 2H), 6.51-6.53 (m, 1H), 4.97 (s, 2H), 3.73 (s, 3H); MS m/e 565.8 [M+H]⁺.

The obtained TFA salt was neutralized by partitioning between saturated NaHCO₃ aqueous solution and DCM. The organic layer was dried (Na₂SO₄), filtered, concentrated, and purified by chiral HPLC (Chiralcel OD, 80% heptanes/20% ethanol) to give two enantiomers. The two enantiomers were further purified by dissolving in a mixture of Et₂O and DCM and filtering through filter paper. The purified solid was then dissolved in 10% MeOH/DCM, 2 drops of TFA were added, then the solutions were concentrated in vacuo, and dried. The first eluting enantiomer was Example 114b: ¹H NMR (400 MHz, CD₃OD) δ 9.06 (s, 1H), 8.87 (d, J=2.02 Hz, 1H), 8.31 (d, J=2.02 Hz, 1H), 8.25 (d, J=2.53 Hz, 1H), 8.18 (d, J=8.59 Hz, 1H), 8.12 (dd, J=2.27, 8.34 Hz, 1H), 7.87-7.93 (m, 2H), 7.85 (d, J=1.52 Hz, 1H), 7.17 (d, J=1.52 Hz, 1H), 7.08-7.12 (m, 3H), 6.87-6.92 (m, 2H), 6.50-6.54 (m, 1H), 4.97 (s, 2H), 3.73 (s, 3H); MS m/e 566.1 [M+H]⁺; the second eluting enantiomer was Example 114c: ¹H NMR (400 MHz, CD₃OD) δ 9.07 (s, 1H), 8.87 (d, J=2.02 Hz, 1H), 8.32 (d, J=2.02 Hz, 1H), 8.24 (d, J=2.53 Hz, 1H), 8.18 (d, J=8.59 Hz, 1H), 8.13 (dd, J=2.27, 8.34 Hz, 1H), 7.86-7.94 (m, 2H), 7.85 (d, J=1.52 Hz, 1H), 7.17 (d, J=1.52 Hz, 1H), 7.07-7.14 (m, 3H), 6.86-6.92 (m, 2H), 6.50-6.54 (m, 1H), 4.96 (s, 2H), 3.73 (s, 3H); MS m/e 566.1 [M+H]⁺.

Example 115a 1-(4-((3-Benzyl-4-chloro-2-(trifluoromethyl)quinolin-6-yl)(hydroxy)(1-methyl-1H-imidazol-5-yl)methyl)piperidin-1-yl)ethanone•TFA

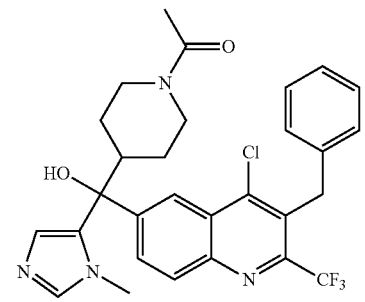 [SMILES: CC(=O)N1CCC(C(O)(c2ccc3nc(C(F)(F)F)c(Cc4ccccc4)c(Cl)c3c2)c2cncn2C)CC1]

A mixture of 3-benzyl-6-bromo-4-chloro-2-(trifluoromethyl)quinoline (632 mg, 1.58 mmol, Intermediate 72: step b), 1-(4-(1-methyl-1H-imidazole-5-carbonyl)piperidin-1-yl)ethanone (371 mg, 1.58 mmol, Intermediate 58: step c), and 15 mL of THF was sparged with N₂ and cooled to −78° C. To the mixture was added n-BuLi (1.6 M in hexanes, 2.6 mL, 4.2 mmol) dropwise. The reaction mixture was stirred at −78° C. for 10 minutes, then the acetone-dry ice bath was replaced with a water-ice bath. Stirring was continued for 20 minutes at 4° C. Saturated NH₄Cl (aq) was added and the organic layer was separated. The aqueous layer was extracted with dichloromethane. The combined organic phases were dried (Na₂SO₄), filtered, and concentrated to dryness. The crude material was purified by flash column chromatography (silica gel, 0-10% MeOH in DCM) followed by reverse phase HPLC (water/acetonitrile/0.1% TFA) to afford the title compound as a TFA salt. ¹H NMR (400 MHz, MeOH-d4, ~1:1 mixture of rotamers) δ 8.84 (s, 1H), 8.51 (d, J=9.09 Hz, 1H), 8.24 (d, J=9.09 Hz, 1H), 8.07 (s, 1H), 7.78 (d, J=9.09 Hz, 1H), 7.21-7.29 (m, 2H), 7.15-7.21 (m, 1H), 7.01 (d, J=7.07 Hz, 2H), 4.65 (d, J=13.14 Hz, 0.5H), 4.57 (s, 2H), 4.45 (d, J=13.14 Hz, 0.5H), 4.03 (d, J=13.64 Hz, 0.5H), 3.84 (d, J=14.15 Hz, 0.5H), 3.59 (s, 1.5H), 3.57 (s, 1.5H), 3.23-3.32 (m, overlapping with solvent), 3.03 (td, J=2.02, 13.14 Hz, 0.5H), 2.66-2.82 (m, 1H), 2.53 (td, J=2.53, 13.64 Hz, 0.5H), 2.09-2.24 (m, 1H), 2.07 (s, 1.5H), 2.02 (s, 1.5H), 1.41-1.60 (m, 1H), 1.26-1.39 (m, 1H), 1.11-1.26 (m, 1H), 1.05 (d, J=13.14 Hz, 0.5H); MS m/e 557.1 [M+H]⁺.

The TFA salt was neutralized by partitioning between saturated NaHCO₃ aqueous solution and DCM. The organic layer was dried (Na₂SO₄), filtered, concentrated, and purified by chiral HPLC (Chiralcel OD, 100% ethanol) to give two enantiomers. For each enantiomer, the purified solid was then dissolved in DCM, one drop of TFA was added, then the solutions were concentrated in vacuo, and dried. The first eluting enantiomer was Example 115b: $^1$H NMR (400 MHz, CDCl$_3$, ~1:1 mixture of rotamers) δ 8.38 (d, J=14.15 Hz, 1H), 8.16 (dd, J=4.29, 8.84 Hz, 1H), 7.64 (t, J=8.84 Hz, 1H), 7.23-7.34 (m, 3H), 7.15-7.23 (m, 2H), 7.07 (d, J=7.07 Hz, 2H), 4.64 (d, J=12.63 Hz, 0.5H), 4.54 (s, 2H), 3.90 (d, J=13.64 Hz, 0.5H), 3.71 (d, J=13.64 Hz, 0.5H), 3.31 (s, 1.5H), 3.27 (s, 1.5H), 3.16 (t, J=13.14 Hz, 0.5H), 2.96 (t, J=12.38 Hz, 0.5H), 2.61 (t, J=12.63 Hz, 0.5H), 2.15-2.55 (m, 3H), 2.01 (s, 1.5H), 1.96 (s, 1.5H), 1.11-1.52 (m, 2H), 1.05 (d, J=12.63, 1H); MS m/e 557.1 [M+H]$^+$ and the second eluting enantiomer was Example 115c: $^1$H NMR (400 MHz, CDCl$_3$, ~1:1 mixture of rotamers) δ 8.37 (d, J=14.15 Hz, 1H), 8.16 (dd, J=4.29, 8.84 Hz, 1H), 7.64 (t, J=8.59 Hz, 1H), 7.23-7.36 (m, 3H), 7.15-7.23 (m, 2H), 7.07 (d, J=7.07 Hz, 2H), 4.56-4.71 (m, 1H), 4.54 (s, 2H), 3.91 (d, J=13.14 Hz, 0.5H), 3.72 (d, J=12.63 Hz, 0.5H), 3.30 (s, 1.5H), 3.27 (s, 1.5H), 3.11-3.22 (m, 0.5H), 2.96 (t, J=12.38 Hz, 0.5H), 2.61 (t, J=12.63 Hz, 0.5H), 2.37-2.56 (m, 1.5H), 2.33 (d, J=12.63 Hz, 0.5H), 2.16-2.26 (m, 1H), 2.01 (s, 1.5H), 1.97 (s, 1.5H), 1.15-1.48 (m, 2H), 1.06 (d, 0.5H); MS m/e 557.1 [M+H]$^+$.

Example 116

(2,4-Dichloro-3-(4-(methylsulfonyl)benzyl)quinolin-6-yl)(2,6-dimethylpyridin-3-yl)(1-methyl-1H-1,2,3-triazol-5-yl)methanol

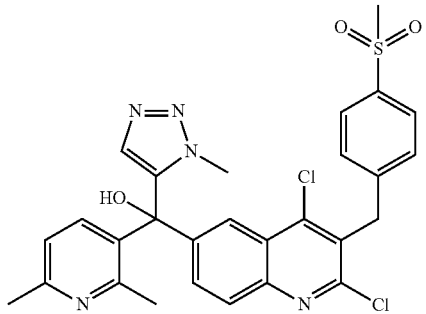 [SMILES: Cc1ccc(C(O)(c2ccc3nc(Cl)c(Cc4ccc(S(C)(=O)=O)cc4)c(Cl)c3c2)c2cnnn2C)c(C)n1]

A suspension of (2,4-dichloro-3-(4-(methylthio)benzyl)quinolin-6-yl)(2,6-dimethylpyridin-3-yl)(1-methyl-1H-1,2,3-triazol-5-yl)methanol (1.10 g, 2.00 mmol, Example 95), 3-chloroperbenzoic acid (~77%, 1.62 g, 7.23 mmol) and DCM (100 mL) was stirred at room temperature for 2.5 hours, during which it became a clear solution. LCMS showed mainly methylsulfonate product and methylsulfonyl pyridine-oxide by-product. To the mixture was added tribromophosphine (1.0 M in DCM, 3.2 mL, 3.2 mmol) dropwise (a white suspension formed at the end of the addition). DMF (10 mL) was then added and the suspension dissolved. After stirring for ~30 minutes, additional tribromophosphine (1.0 M in DCM, 3.2 mL, 3.2 mmol) was added. After stirring for 1 hour, 1 M K$_2$CO$_3$ (aqueous) was added, the organic layer was separated. The aqueous layer was further extracted with DCM. The combined organic phases were washed with 1 M K$_2$CO$_3$ (aqueous), and the aqueous layer was back extracted with DCM. The organic phase was dried (Na$_2$SO$_4$), filtered, and concentrated. The residue was purified by flash column chromatography (silica gel, 30-100% EtOAc in heptanes, 10% MeOH in DCM) to provide the title compound. $^1$H NMR (400 MHz, CHLOROFORM-d) δ 8.25 (d, J=2.02 Hz, 1H), 8.02 (d, J=9.09 Hz, 1H), 7.93 (br. s., 1H), 7.86 (d, J=8.59 Hz, 2H), 7.58 (dd, J=2.27, 8.84 Hz, 1H), 7.44 (d, J=8.59 Hz, 2H), 6.91-6.98 (m, 2H), 6.87 (s, 1H), 4.61 (s, 2H), 3.94 (s, 3H), 3.03 (s, 3H), 2.54 (s, 3H), 2.36 (s, 3H); MS m/e 582.2 [M+H]$^+$.

Example 117a (4-Chloro-2-methoxy-3-(4-(methylsulfonyl)benzyl)quinolin-6-yl)(2,6-dimethylpyridin-3-yl)(1-methyl-1H-1,2,3-triazol-5-yl)methanol

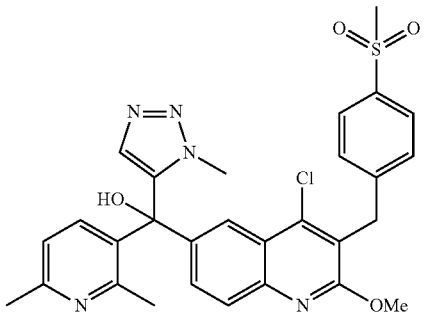

A mixture of (2,4-dichloro-3-(4-(methylsulfonyl)benzyl)quinolin-6-yl)(2,6-dimethylpyridin-3-yl)(1-methyl-1H-1,2,3-triazol-5-yl)methanol (300 mg, 0.520 mmol, Example 116) and 0.5 M NaOMe in MeOH (1.3 mL, 0.65 mmol) in a sealed tube was heated at 53° C. for 1 hour, then filtered through a syringe filter. The filtrate was purified by reverse phase HPLC (water/acetonitrile/0.1% TFA) to provide the title compound as a TFA salt. $^1$H NMR (400 MHz, MeOH-d4) δ 8.23 (d, J=2.02 Hz, 1H), 7.93 (d, J=9.09 Hz, 1H), 7.84 (dd, J=1.52, 8.59 Hz, 3H), 7.68 (d, J=8.08 Hz, 1H), 7.49-7.53 (m, 3H), 7.17 (s, 1H), 4.44 (s, 2H), 4.09 (s, 3H), 3.98 (s, 3H), 3.07 (s, 3H), 2.76 (s, 3H), 2.65 (s, 3H); MS m/e 578.3 [M+H]$^+$.

This TFA salt was neutralized by partitioning between saturated NaHCO$_3$ aqueous solution and DCM. The organic layer was dried (Na$_2$SO$_4$), filtered, concentrated, and purified by chiral HPLC (Chiralpak OD-H, 80% heptanes/20% EtOH) to give two enantiomers. The first eluting enantiomer was Example 117b: $^1$H NMR (400 MHz, CDCl$_3$) δ 8.08 (d, J=2.02 Hz, 1H), 7.80-7.85 (m, 3H), 7.48 (d, J=8.59 Hz, 2H), 7.40 (dd, J=2.27, 8.84 Hz, 1H), 6.95 (s, 2H), 6.93 (s, 1H), 4.37 (s, 2H), 4.09 (s, 3H), 3.94 (s, 3H), 3.01 (s, 3H), 2.55 (s, 3H), 2.38 (s, 3H); MS m/e 578.1 [M+H]$^+$ and the second eluting enantiomer was Example 117c: $^1$H NMR (400 MHz, CDCl$_3$) δ 8.08 (d, J=2.02 Hz, 1H), 7.81-7.86 (m, 3H), 7.48 (d, J=8.08 Hz, 2H), 7.40 (dd, J=2.02, 8.59 Hz, 1H), 6.95 (s, 2H), 6.93 (s, 1H), 5.30 (s, 1H), 4.37 (s, 2H), 4.09 (s, 3H), 3.94 (s, 3H), 3.01 (s, 3H), 2.55 (s, 3H), 2.38 (s, 3H); MS m/e 578.1 [M+H]⁺.

Example 118a (3-(4-(1H-Pyrazol-1-yl)benzyl)-4-chloro-2-methoxyquinolin-6-yl)(4-chlorophenyl)(1-methyl-1H-imidazol-5-yl)methanamine•TFA

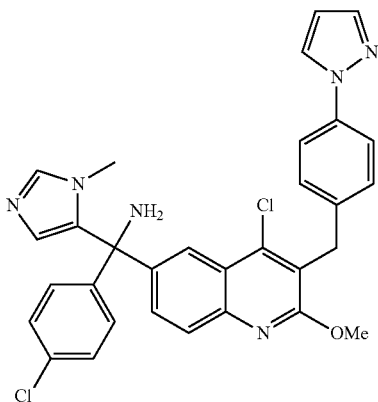 [SMILES: COc1nc2ccc(C(N)(c3ccc(Cl)cc3)c3cncn3C)cc2c(Cl)c1Cc1ccc(-n2cccn2)cc1]

To a solution of (3-(4-(1H-pyrazol-1-yl)benzyl)-4-chloro-2-methoxyquinolin-6-yl)(4-chlorophenyl)(1-methyl-1H-imidazol-5-yl)methanol (132 mg, 0.230 mmol, Intermediate 83) and DMF (1.6 mL) was added NaH (60% in mineral oil, 20 mg, 0.50 mmol) at room temperature. After stirring for 10 minutes, acetic anhydride (0.062 mL, 0.66 mmol) was added followed by 1.5 mL of DMF. After stirring for 1 hour, NH₃ (7.0 M in MeOH, 0.30 mL, 2.1 mmol) was added. The mixture was stirred for 22 hours, filtered through a syringe filter, and purified by reverse phase HPLC (water/acetonitrile/0.1% TFA) to give the title compound as a TFA salt. ¹H NMR (400 MHz, MeOH-d4) δ 8.90 (s, 1H), 8.15 (d, J=2.53 Hz, 1H), 8.05 (d, J=2.02 Hz, 1H), 7.99 (d, J=8.59 Hz, 1H), 7.69 (d, J=1.52 Hz, 1H), 7.53-7.63 (m, 5H), 7.38 (d, J=8.59 Hz, 2H), 7.32 (d, J=8.59 Hz, 2H), 6.98 (s, 1H), 6.47-6.51 (m, 1H), 4.36 (s, 2H), 4.12 (s, 3H), 3.58 (s, 3H); MS m/e 569.1 [M+H]⁺

This TFA salt was neutralized by partitioning between saturated NaHCO₃ aqueous solution and DCM. The organic layer was dried (Na₂SO₄), filtered, concentrated, and purified by chiral HPLC (Chiralcel OD, 100% MeOH) to give two enantiomers. The purified solids were then dissolved in DCM, one drop of TFA was added, then the solutions were concentrated in vacuo, and dried. The first eluting enantiomer was Example 118b: ¹H NMR (400 MHz, CDCl₃) δ 7.98-8.01 (m, 1H), 7.85 (d, J=2.53 Hz, 1H), 7.79 (d, J=8.59 Hz, 1H), 7.69 (s, 1H), 7.56 (d, J=8.59 Hz, 2H), 7.44-7.52 (m, 2H), 7.36 (d, J=8.59 Hz, 2H), 7.31 (d, J=8.59 Hz, 2H), 7.21 (d, J=8.59 Hz, 2H), 6.41 (d, J=8.08 Hz, 2H), 4.31 (s, 2H), 4.10 (s, 3H), 3.42 (s, 3H); MS m/e 569.1 [M+H]⁺ and the second eluting enantiomer was Example 118c: ¹H NMR (400 MHz, CDCl₃) δ 7.97-8.02 (m, 1H), 7.83-7.88 (m, 1H), 7.79 (d, J=8.59 Hz, 1H), 7.69 (s, 1H), 7.56 (d, J=8.59 Hz, 2H), 7.44-7.52 (m, 2H), 7.36 (d, J=8.59 Hz, 2H), 7.31 (d, J=8.08 Hz, 2H), 7.17-7.25 (m, 2H), 6.41 (d, J=8.08 Hz, 2H), 4.31 (s, 2H), 4.08 (s, 3H), 3.42 (s, 3H); MS m/e 569.2 [M+H]⁺.

Example 119a 1-(3-(4-(1H-Pyrazol-1-yl)benzyl)-4-chloro-2-methoxyquinolin-6-yl)-1-(4-chlorophenyl)-N-methyl-1-(1-methyl-1H-imidazol-5-yl)methanamine•TFA

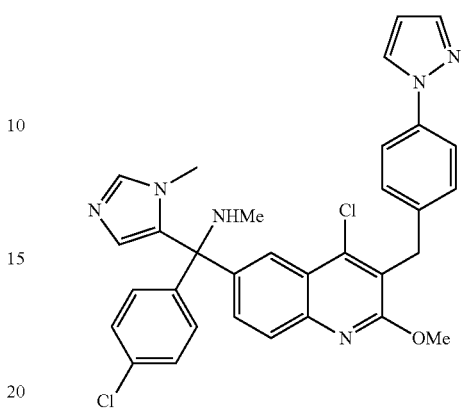

The title compound was prepared using NH₂Me in place of NH₃ using the procedure described for Example 118a. ¹H NMR (400 MHz, MeOH-d4) δ 8.93 (br. s., 1H), 8.31 (d, J=2.02 Hz, 1H), 8.13 (d, J=2.53 Hz, 1H), 7.88 (d, J=8.59 Hz, 1H), 7.72 (dd, J=2.27, 8.84 Hz, 1H), 7.68 (d, J=1.52 Hz, 1H), 7.59 (d, J=8.59 Hz, 2H), 7.52 (d, J=8.59 Hz, 2H), 7.41-7.49 (m, 3H), 7.36 (d, J=8.59 Hz, 2H), 6.49 (t, J=2.02 Hz, 1H), 4.34 (s, 2H), 4.08 (s, 3H), 3.60 (s, 3H), 2.29 (s, 3H); MS m/e 583.2 [M+H]⁺.

Example 119a was purified Chiralpak OD-H column (80% heptanes/20% EtOH) was used in the chiral HPLC purification to give two enantiomers. The two enantiomers were further purified by flash column chromatography (silica gel, 0-8% MeOH in DCM) and converted to TFA salts. The first eluting enantiomer was Example 119b: ¹H NMR (400 MHz, CD₃OD) δ 8.95 (br. s., 1H), 8.31 (d, J=2.53 Hz, 1H), 8.13 (d, J=2.53 Hz, 1H), 7.89 (d, J=9.09 Hz, 1H), 7.72 (dd, J=2.27, 8.84 Hz, 1H), 7.68 (s, 1H), 7.59 (d, J=8.59 Hz, 2H), 7.49-7.56 (m, 3H), 7.43-7.49 (m, 2H), 7.36 (d, J=8.59 Hz, 2H), 6.48-6.50 (m, 1H), 4.34 (s, 2H), 4.08 (s, 3H), 3.62 (s, 1H), 3.58 (s, 3H), 2.32 (s, 3H); MS m/e 583.2 [M+H]⁺ and the second eluting enantiomer was Example 119c: ¹H NMR (400 MHz, CD₃OD) δ 8.92 ((br. s., 1H), 8.31 (d, J=2.02 Hz, 1H), 8.13 (d, J=2.53 Hz, 1H), 7.88 (d, J=9.09 Hz, 1H), 7.72 (dd, J=2.29, 8.84 Hz, 1H), 7.68 (d, J=2.02 Hz, 1H), 7.60 (d, J=8.59 Hz, 2H), 7.52 (d, J=8.59 Hz, 2H), 7.43-7.47 (m, 3H), 7.37 (d, J=8.59 Hz, 2H), 6.48-6.50 (m, 1H), 4.35 (s, 2H), 4.08 (s, 3H), 3.60 (s, 3H), 2.28 (s, 3H); MS m/e 583.2 [M+H]⁺.

Example 120a (3-Benzyl-4-chloro-2-methoxyquinolin-6-yl)(1-methyl-1H-imidazol-5-yl)(6-(trifluoromethyl)pyridin-3-yl)methanamine•TFA

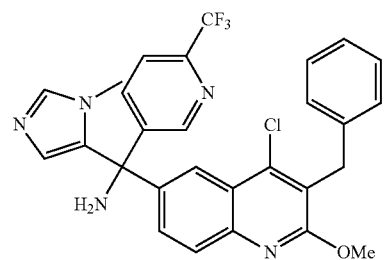 [SMILES: COc1nc2ccc(C(N)(c3ccc(C(F)(F)F)nc3)c3cncn3C)cc2c(Cl)c1Cc1ccccc1]

To a solution of (3-benzyl-4-chloro-2-methoxyquinolin-6-yl)(1-methyl-1H-imidazol-5-yl)(6-(trifluoromethyl)pyridin-3-yl)methanol (446 mg, 0.830 mmol, Example 110) and DMF (15 mL) was added NaH (60% in mineral oil, 90 mg, 2.3 mmol) at room temperature. After stirring for 15 minutes, acetic anhydride (0.16 mL, 1.7 mmol) was added. After stirring for 1 hour, NH$_3$ (7.0 M in MeOH, 1.0 mL, 7.0 mmol) was added. The mixture was stirred overnight and concentrated in vacuo. The residue was partitioned between EtOAc and water. The organic layers were washed with water, and the aqueous layer was back extracted with EtOAc. The extracts were dried (Na$_2$SO$_4$), filtered, and concentrated. The residue was purified by reverse phase HPLC (water/acetonitrile/0.1% TFA) to afford the title compound as a TFA salt. $^1$H NMR (400 MHz, MeOH-d4) δ 8.97 (s, 1H), 8.77 (d, J=2.02 Hz, 1H), 8.11 (d, J=2.02 Hz, 1H), 8.00 (dd, J=2.27, 8.34 Hz, 1H), 7.94 (d, J=9.09 Hz, 1H), 7.88 (d, J=8.08 Hz, 1H), 7.62 (dd, J=2.27, 8.84 Hz, 1H), 7.20-7.24 (m, 4H), 7.12-7.18 (m, 1H), 6.94 (d, J=1.52 Hz, 1H), 4.30 (s, 2H), 4.08 (s, 3H), 3.72 (s, 3H); MS m/e 538.2 [M+H]$^+$.

This TFA salt was neutralized by partitioning between saturated NaHCO$_3$ aqueous solution and DCM. The organic layer was dried (Na$_2$SO$_4$), filtered, concentrated, and purified by chiral HPLC (Chiralpak IC, 70% heptanes/30% EtOH) to give two enantiomers. The purified solids were then dissolved in DCM, one drop of TFA was added, then the solutions were concentrated in vacuo and dried. The first eluting enantiomer was Example 120b: $^1$H NMR (400 MHz, CDCl$_3$) δ 8.75 (d, J=2.02 Hz, 1H), 8.00 (d, J=2.02 Hz, 1H), 7.82 (d, J=9.09 Hz, 1H), 7.77 (dd, J=2.27, 8.34 Hz, 1H), 7.65 (d, J=8.59 Hz, 1H), 7.49 (s, 1H), 7.45 (dd, J=2.27, 8.84 Hz, 1H), 7.22-7.31 (m, 4H), 7.17-7.21 (m, 1H), 6.42 (s, 1H), 4.30 (s, 2H), 4.09 (s, 3H), 3.44 (s, 3H); MS m/e 538.2 [M+H]$^+$ and the second eluting enantiomer was Example 120c: $^1$H NMR (400 MHz, CDCl$_3$) δ 8.75 (d, J=2.02 Hz, 1H), 8.00 (d, J=2.02 Hz, 1H), 7.82 (d, J=8.59 Hz, 1H), 7.77 (dd, J=2.27, 8.34 Hz, 1H), 7.65 (d, J=8.08 Hz, 1H), 7.49 (s, 1H), 7.45 (dd, J=2.27, 8.84 Hz, 1H), 7.22-7.32 (m, 4H), 7.17-7.21 (m, 1H), 6.42 (s, 1H), 4.30 (s, 2H), 4.09 (s, 3H), 3.44 (s, 3H); MS m/e 538.2 [M+H]$^+$.

Example 121a 1-(4-Chloro-2-methoxy-3-(4-(trifluoromethyl)benzyl)quinolin-6-yl)-1-(2,6-dimethylpyridin-3-yl)-N-methyl-1-(1-methyl-1H-1,2,3-triazol-5-yl)methanamine•TFA

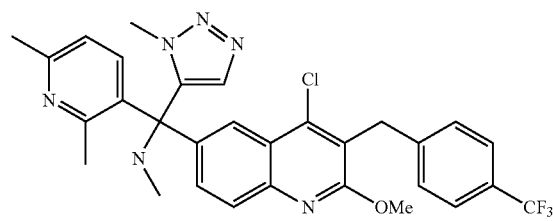 [SMILES: CNC(c1ccc2nc(OC)c(Cc3ccc(C(F)(F)F)cc3)c(Cl)c2c1)(c1ccc(C)nc1C)c1cnnn1C]

A mixture of (S)-(4-chloro-2-methoxy-3-(4-(trifluoromethyl)benzyl)quinolin-6-yl)(2,6-dimethylpyridin-3-yl)(1-methyl-1H-1,2,3-triazol-5-yl)methyl acetate (170 mg, 0.280 mmol, Intermediate 62) and NH$_2$Me in MeOH (2.0 M, 2.0 mL, 4.0 mmol) in a sealed pressure tube was heated at 60° C. for 6 hours, then concentrated in vacuo. The residue was purified by flash column chromatography (silica gel, 30-100% EtOAc in heptanes) to give the title compound. $^1$H NMR (400 MHz, CHLOROFORM-d) δ 8.16 (d, J=2.02 Hz, 1H), 7.80 (d, J=9.09 Hz, 1H), 7.75 (d, J=8.59 Hz, 1H), 7.65 (s, 1H), 7.51 (d, J=8.08 Hz, 2H), 7.47 (dd, J=2.27, 8.84 Hz, 1H), 7.40 (d, J=8.08 Hz, 2H), 7.08 (d, J=8.08 Hz, 1H), 4.35 (s, 2H), 4.08 (s, 3H), 3.83 (s, 3H), 2.56 (s, 3H), 2.18 (s, 3H), 2.16 (s, 3H); MS m/e 581.3 [M+H]$^+$. Example 121a was purified by chiral HPLC (Chiralpak OD-H, 80% heptanes/20% EtOH) to give two enantiomers. The purified solids were then dissolved in DCM, one drop of TFA was added, then the solutions were concentrated in vacuo and dried. The first eluting enantiomer was Example 121b: $^1$H NMR (400 MHz, CDCl$_3$) δ 8.17 (d, J=2.02 Hz, 1H), 7.80 (d, J=8.59 Hz, 1H), 7.75 (d, J=8.08 Hz, 1H), 7.66 (s, 1H), 7.51 (d, J=8.08 Hz, 2H), 7.47 (dd, J=2.27, 8.84 Hz, 1H), 7.40 (d, J=8.08 Hz, 2H), 7.08 (d, J=8.08 Hz, 1H), 4.35 (s, 2H), 4.08 (s, 3H), 3.83 (s, 3H), 2.56 (s, 3H), 2.19 (s, 3H), 2.16 (s, 3H); MS m/e 581.1 [M+H]$^+$ and the second eluting enantiomer was Example 121c: $^1$H NMR (400 MHz, CDCl$_3$) δ 8.17 (d, J=2.02 Hz, 1H), 7.80 (d, J=8.59 Hz, 1H), 7.75 (d, J=8.08 Hz, 1H), 7.66 (s, 1H), 7.51 (d, J=8.08 Hz, 2H), 7.47 (dd, J=2.27, 8.84 Hz, 1H), 7.40 (d, J=8.59 Hz, 2H), 7.08 (d, J=8.08 Hz, 1H), 4.35 (s, 2H), 4.08 (s, 3H), 3.83 (s, 3H), 2.56 (s, 3H), 2.19 (s, 3H), 2.16 (s, 3H); MS m/e 581.1 [M+H]$^+$.

Example 122a 1-(4-Chloro-2-methoxy-3-(4-(trifluoromethyl)benzyl)quinolin-6-yl)-1-(2,6-dimethylpyridin-3-yl)-N,N-dimethyl-1-(1-methyl-1H-1,2,3-triazol-5-yl)methanamine•TFA

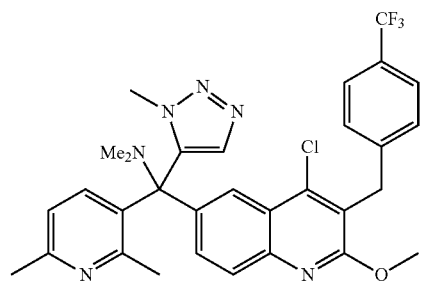 [SMILES: COc1nc2ccc(C(c3ccc(C)nc3C)(c3cnnn3C)N(C)C)cc2c(Cl)c1Cc1ccc(C(F)(F)F)cc1]

A mixture of (S)-(4-chloro-2-methoxy-3-(4-(trifluoromethyl)benzyl)quinolin-6-yl)(2,6-dimethylpyridin-3-yl)(1-methyl-1H-1,2,3-triazol-5-yl)methyl acetate (110 mg, 0.180 mmol, Intermediate 62) and NHMe$_2$ in MeOH (2.0 M, 1.5 mL, 3.0 mmol) in a sealed pressure tube was heated at 65° C. for 16 hours, then concentrated in vacuo. The residue was purified by reverse phase HPLC (water/acetonitrile/0.1% TFA). The collected TFA salt was neutralized by partitioning between saturated NaHCO$_3$ aqueous solution and DCM. The organic layer was dried (Na$_2$SO$_4$), filtered, and concentrated to give the title compound. $^1$H NMR (400 MHz, CHLOROFORM-d) δ 8.33 (br. s., 1H), 7.78-7.85 (m, 2H), 7.48-7.55 (m, 3H), 7.36-7.45 (m, 3H), 7.16 (d, J=7.58 Hz, 1H), 4.37 (s, 2H), 4.10 (s, 3H), 3.93 (br. s., 3H), 2.55 (s, 3H), 2.01 (br. s., 6H), 1.96 (br. s, 3H); MS m/e 595.2 [M+H]$^+$.

Example 122a was purified by chiral HPLC (Chiralpak OD-H, 80% heptanes/20% EtOH) to give two enantiomers, which were purified again by flash column chromatography (silica gel, 0-8% MeOH in DCM). The first enantiomer to elute off chiral column was Example 122b: $^1$H NMR (400 MHz, CHLOROFORM-d) δ 8.33 (br. s., 2H), 7.76-7.89 (m, 3H), 7.52 (d, J=8.59 Hz, 2H), 7.43 (d, J=8.08 Hz, 2H), 7.16 (d, J=7.58 Hz, 1H), 4.37 (s, 2H), 4.10 (s, 3H), 3.93 (br. s., 3H), 2.55 (s, 3H), 1.82-2.17 (m, 9H); MS m/e 595.2 [M+H]$^+$. The second enantiomer to elute off chiral column was Example 122c: $^1$H NMR (400 MHz, CDCl$_3$) δ 8.14-8.44 (m, 2H), 7.76-7.91 (m, 3H), 7.52 (d, J=8.08 Hz, 2H), 7.43 (d, J=8.08 Hz, 2H), 7.16 (d, J=7.58 Hz, 1H), 4.37 (s, 2H), 4.10 (s, 3H), 3.97 (s, 3H), 2.55 (s, 3H), 1.82-2.18 (m, 9H); MS m/e 595.2 [M+H]$^+$. The two purified enantiomers were then each dissolved in DCM, one drop of TFA was added, and the solution was concentrated in vacuo, and dried to provide the title compounds.

Example 123 tert-Butyl-3-((4-chloro-2-methoxy-3-(4-(trifluoromethyl)benzyl)quinolin-6-yl)(hydroxy)(1-methyl-1H-1,2,3-triazol-5-yl)methyl)azetidine-1-carboxylate

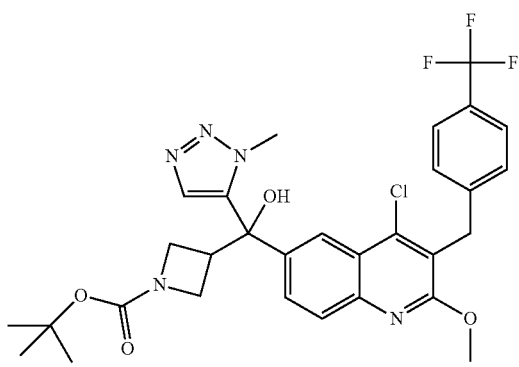 [SMILES: COc1nc2ccc(C(O)(c3cnnn3C)C3CN(C(=O)OC(C)(C)C)C3)cc2c(Cl)c1Cc1ccc(C(F)(F)F)cc1]

To a flask containing 1-methyl-1H-1,2,3-triazole (430 mg, 0.8 mmol) was added THF (15 mL) and the solution was cooled to −43° C. using a CH$_3$CN—CO$_2$ bath. Then, n-BuLi, (2.5 M in hexanes, 0.7 mL, 1.75 mmol) was added dropwise. The reaction mixture was stirred at −40° C. for 30 minutes, then tert-butyl-3-(4-chloro-2-methoxy-3-(4-(trifluoromethyl)benzyl)quinoline-6-carbonyl)-azetidine-1-carboxylate (430 mg, 0.8 mmol, Intermediate 61: step b) in 2 mL THF was introduced. The reaction mixture was allowed to warm to room temperature over 30 minutes, and was quenched after 45 minutes with aqueous NH$_4$Cl solution. The aqueous portion was extracted with EtOAc (3×30 mL). The combined organics were washed with brine, dried over MgSO$_4$, filtered and concentrated. Chromatography on Silica gel (10% acetone-hexane increasing to 30% acetone) afforded the title compound as a white amorphous solid. $^1$H NMR (500 MHz, CDCl$_3$) δ 8.24 (d, J=2.1 Hz, 1H), 7.78 (d, J=8.8 Hz, 1H), 7.56-7.47 (m, 3H), 7.40 (d, J=8.1 Hz, 2H), 7.35 (dd, J=8.7, 2.1 Hz, 1H), 4.35 (s, 2H), 4.20 (t, J=8.8 Hz, 1H), 4.07 (s, 3H), 4.00 (dd, J=9.3, 5.6 Hz, 1H), 3.92 (dd, J=8.9, 5.7 Hz, 1H), 3.67 (s, 3H), 3.62 (t, J=8.8 Hz, 1H), 3.52-3.38 (m, 1H), 1.38 (s, 9H); MS (ESI): mass calcd: Chemical Formula: C$_{30}$H$_{31}$ClF$_3$N$_5$O$_4$; Exact Mass: 617.2. m/z found 617.8 [M+H]$^+$.

Example 124

Azetidin-3-yl(4-chloro-2-methoxy-3-(4-(trifluoromethyl)benzyl)quinolin-6-yl)(1-methyl-1H-1,2,3-triazol-5-yl)methanol

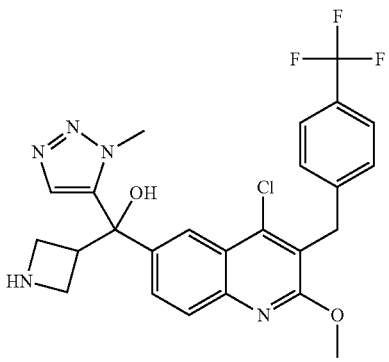 [SMILES: COc1nc2ccc(C(O)(c3cnnn3C)C3CNC3)cc2c(Cl)c1Cc1ccc(C(F)(F)F)cc1]

To a flask containing tert-butyl 3-((4-chloro-2-methoxy-3-(4-(trifluoromethyl)benzyl)quinolin-6-yl)(hydroxy)(1-methyl-1H-1,2,3-triazol-5-yl)methyl)azetidine-1-carboxylate (165 mg, 0.27 mmol, Example 123) was added formic acid (5 mL) at room temperature followed by 6 N aqueous HCl (0.21 mL). The mixture was stirred at room temperature for 40 minutes and then MeOH (5 mL) was added and the mixture was stirred for 20 minutes before concentrating. The resulting oil was chromatographed directly on silica gel (10% 2 M NH$_3$-MeOH-DCM increasing to 12% 2 M NH$_3$-MeOH) to provide the title compound as an off white powder. $^1$H NMR (500 MHz, CDCl$_3$) δ 8.30 (d, J=2.1 Hz, 1H), 8.20 (s, 1H), 7.92 (s, 1H), 7.76 (d, J=8.8 Hz, 1H), 7.47 (d, J=8.1 Hz, 2H), 7.42-7.32 (m, 3H), 4.52-4.34 (m, 2H), 4.33-4.16 (m, 3H), 4.05 (s, 3H), 3.96-3.80 (m, 1H), 3.71 (s, 4H); MS (ESI): mass calcd. Chemical Formula: C$_{25}$H$_{23}$ClF$_3$N$_5$O$_2$; Exact Mass: 517.2. m/z found 517.9 [M+H]$^+$.

Example 125 tert-Butyl-3-((4-chloro-2-methoxy-3-(4-(trifluoromethyl)benzyl)quinolin-6-yl)(2,6-dimethylpyridin-3-yl)(hydroxy)methyl)azetidine-1-carboxylate

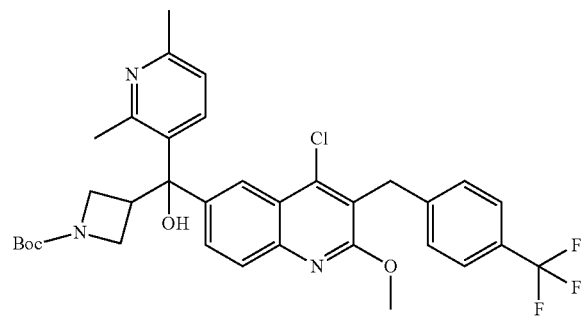 [SMILES: COc1nc2ccc(C(O)(c3ccc(C)nc3C)C3CN(C(=O)OC(C)(C)C)C3)cc2c(Cl)c1Cc1ccc(C(F)(F)F)cc1]

A flask containing 2,6-dimethylpyridine (277 mg, 1.49 mmol) and THF (5 mL) was cooled to −78° C. and then n-BuLi (2.5 M in hexanes, 0.610 mL, 1.52 mmol) was added dropwise producing a homogeneous orange solution. After 3 minutes, tert-butyl 3-(4-chloro-2-methoxy-3-(4-(trifluoromethyl)benzyl)quinoline-6-carbonyl)azetidine-1-carboxylate (505 mg, 0.94 mmol, Intermediate 61: step b) in 3 mL THF was introduced. After 5 minutes, the −78° C. bath was replaced with an ice-water bath. After 30 minutes, the reaction mixture was quenched with aqueous NH$_4$Cl solution and extracted with EtOAc (3×30 mL). The combined organics were washed with brine, dried over MgSO$_4$, filtered and concentrated. This material was combined with a batch from a duplicate experiment for chromatography on silica gel (5% acetone-DCM increasing to 30% acetone with 1% MeOH) which provided the title compound as an off white amorphous solid. $^1$H NMR (500 MHz, CDCl$_3$) δ 8.10 (d, J=1.8 Hz, 1H), 7.73 (dd, J=8.7, 1.5 Hz, 1H), 7.60 (d, J=8.1 Hz, 1H), 7.51 (d, J=7.9 Hz, 2H), 7.37 (dd, J=25.7, 8.4 Hz, 4H), 7.05 (d, J=8.0 Hz, 1H), 4.34 (s, 2H), 4.12-4.02 (m, 5H), 3.93-3.84 (m, 1H), 3.78-3.71 (m, 1H), 3.59-3.49 (m, 1H), 2.70 (s, 1H), 2.51 (s, 3H), 2.14 (s, 3H), 1.41 (s, 9H); MS (ESI): mass calcd. Chemical Formula: C$_{34}$H$_{35}$ClF$_3$N$_3$O$_4$, Exact Mass: 641.2. m/z found 641.9 [M+H]$^+$.

Example 126

Azetidin-3-yl(4-chloro-2-methoxy-3-(4-(trifluoromethyl)benzyl)quinolin-6-yl)(2,6-dimethylpyridin-3-yl)methanol

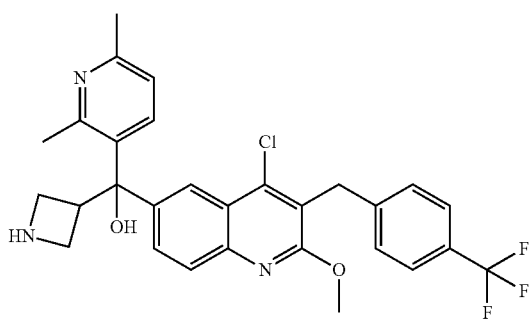 [SMILES: COc1nc2ccc(C(O)(c3ccc(C)nc3C)C3CNC3)cc2c(Cl)c1Cc1ccc(C(F)(F)F)cc1]

To a flask containing tert-butyl 3-((4-chloro-2-methoxy-3-(4-(trifluoromethyl)benzyl)quinolin-6-yl)(2,6-dimethylpyridin-3-yl)(hydroxy)methyl)azetidine-1-carboxylate (700 mg, 1.09 mmol, Example 125) was added formic acid (10 mL, 265 mmol) at room temperature followed by 6 N aqueous HCl (500 µL). After 45 minutes, MeOH was added (10 mL) and the mixture was stirred for 15 minutes and then concentrated to provide the title compound as a crude product. MS (ESI): mass calcd. Chemical Formula: C$_{29}$H$_{27}$ClF$_3$N$_3$O$_2$; Exact Mass: 541.2. m/z found 541.9 [M+H]$^+$.

Example 127

{4-Chloro-2-[(2-methoxyethyl)(methyl)amino]-3-[4-(1H-pyrazol-1-yl)benzyl]quinolin-6-yl}(4-chlorophenyl)(1-methyl-1H-imidazol-5-yl)methanol

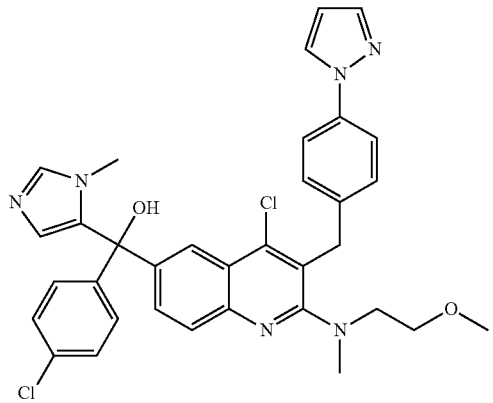 [SMILES: COCCN(C)c1nc2ccc(C(O)(c3ccc(Cl)cc3)c3cncn3C)cc2c(Cl)c1Cc1ccc(-n2cccn2)cc1]

(3-(4-(1H-Pyrazol-1-yl)benzyl)-2,4-dichloroquinolin-6-yl)(4-chlorophenyl)(1-methyl-1H-imidazol-5-yl)methanol (100 mg, 0.174 mmol, Intermediate 64), N-(2-methoxyethyl)methylamine (775 µL, 8.70 mmol), and methanol (2 mL) were combined in a reaction tube, which was then sealed and heated to 100° C. for 48 hours. The contents were then cooled to room temperature, transferred to a round bottom flask and the solvent was removed via reduced pressure distillation. The residue was then taken up into EtOAc, transferred to a separatory funnel and extracted twice with a saturated, aqueous NH$_4$Cl solution. The organic phase was separated and dried over MgSO$_4$, filtered and concentrated under reduced pressure. The crude product was purified by flash column chromatography (silica gel, 0-10% DCM/(10% of a 2 M NH$_3$ MeOH in DCM)) then further purified via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to afford the title compound. MS (ESI): mass calcd. for C$_{34}$H$_{32}$Cl$_2$N$_6$O$_2$, 626.2. m/z found, 627.4 [M+H]$^+$. $^1$H NMR (600 MHz, CD$_3$OD) δ ppm 8.10 (d, J=2.3 Hz, 1H), 8.07 (d, J=2.0 Hz, 1H), 7.97 (s, 1H), 7.82 (d, J=8.8 Hz, 1H), 7.66 (d, J=1.4 Hz, 1H), 7.63 (dd, J=8.8, 2.0 Hz, 1H), 7.57 (d, J=8.5 Hz, 2H), 7.38-7.31 (m, 4H), 7.24 (d, J=8.4 Hz, 2H), 6.48-6.45 (m, 1H), 6.42 (s, 1H), 4.43 (s, 2H), 3.54-3.49 (m, 5H), 3.42 (t, J=5.6 Hz, 2H), 3.23 (s, 3H), 2.93 (s, 3H).

Example 128

{4-Chloro-2-[(2-methoxyethyl)(methyl)amino]-3-[4-(1H-pyrazol-1-yl)benzyl]quinolin-6-yl}(1-methyl-1H-imidazol-5-yl)[6-(trifluoromethyl)pyridin-3-yl]methanol

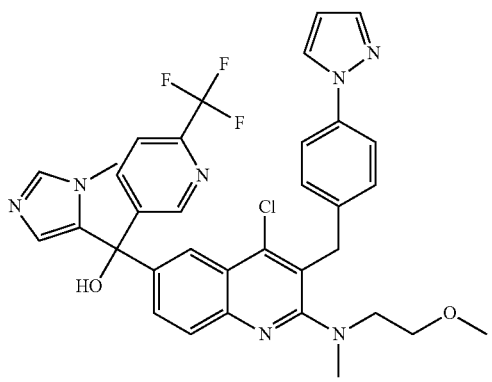 [SMILES: COCCN(C)c1nc2ccc(C(O)(c3ccc(C(F)(F)F)nc3)c3cncn3C)cc2c(Cl)c1Cc1ccc(-n2cccn2)cc1]

{2,4-Dichloro-3-[4-(1H-pyrazol-1-yl)benzyl]quinolin-6-yl}(1-methyl-1H-imidazol-5-yl) [6-(trifluoromethyl)pyridin-3-yl]methanol (200 mg, 0.33 mmol, Intermediate 65), N-(2-methoxymethyl)methylamine (735 µL, 8.20 mmol), and methanol (2 mL) were combined in a reaction tube, which was then sealed and heated to 100° C. for 48 hours. The contents were then cooled to room temperature, transferred to a round bottom flask and the solvent was removed via reduced pressure distillation. The residue was then taken up into EtOAc, transferred to a separatory funnel and extracted twice with saturated, aqueous NH$_4$Cl solution. The organic phase was separated and dried over MgSO$_4$, filtered and concentrated under reduced pressure. The crude product was purified via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to afford the title compound. MS (ESI): mass calcd. for C$_{34}$H$_{31}$ClF$_3$N$_7$O$_2$, 661.2. m/z found, 662.2 [M+H]$^+$. $^1$H NMR (600 MHz, CD$_3$OD) δ ppm 8.78 (d, J=1.8 Hz, 1H), 8.14-8.09 (m, 2H), 8.00 (d, J=8.3 Hz, 1H), 7.85 (d, J=8.8 Hz, 1H), 7.81 (d, J=8.3 Hz, 1H), 7.73 (s, 1H), 7.67 (s, 1H), 7.66-7.61 (m, 1H), 7.62-7.56 (m, 2H), 7.26 (d, J=8.2 Hz, 2H), 6.50-6.45 (m, 1H), 6.35 (s, 1H), 4.45 (s, 2H), 3.53 (t, J=5.5 Hz, 2H), 3.47 (s, 3H), 3.43 (t, J=5.5 Hz, 2H), 3.24 (s, 3H), 2.94 (s, 3H).

Example 129

{2,4-Bis[methoxy(methyl)amino]-3-[4-(1H-pyrazol-1-yl)benzyl]quinolin-6-yl}(1-methyl-1H-imidazol-5-yl)[6-(trifluoromethyl)pyridin-3-yl]methanol

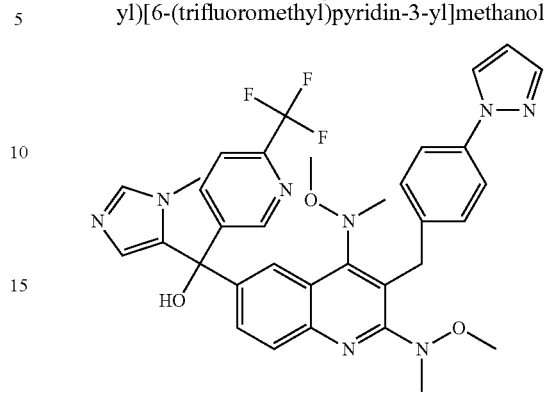

(3-(4-(1H-Pyrazol-1-yl)benzyl)-2,4-dichloroquinolin-6-yl)(1-methyl-1H-imidazol-5-yl)(6-(trifluoromethyl)pyridin-3-yl)methanol (100 mg, 0.164 mmol, Intermediate 65), N,O-dimethylhydroxylamine hydrochloride (327 mg, 2.82 mmol), and dimethylformamide (2 mL) were combined in a reaction tube, which was then sealed and heated to 100° C. for 48 hours. The contents were then cooled, transferred to a separatory funnel, diluted with EtOAc, extracted with a saturated, aqueous NH$_4$Cl solution, then four times with deionized water. The organic phase was separated and dried over MgSO$_4$, filtered and concentrated under reduced pressure. The crude material was purified via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to afford the title compound. MS (ESI): mass calcd. for C$_{34}$H$_{33}$F$_3$N$_8$O$_3$, 658.3. m/z found, 659.3 [M+H]$^+$. $^1$H NMR (600 MHz, CD$_3$OD) δ 8.75 (d, J=2.1 Hz, 1H), 8.34 (d, J=2.0 Hz, 1H), 8.13 (dd, J=2.5, 0.5 Hz, 1H), 8.01 (dd, J=8.6, 2.7 Hz, 2H), 7.84 (d, J=8.2 Hz, 1H), 7.82 (s, 1H), 7.75 (dd, J=8.9, 2.2 Hz, 1H), 7.69-7.65 (m, 1H), 7.60-7.55 (m, 2H), 7.21 (d, J=8.7 Hz, 2H), 6.48 (dd, J=2.4, 1.9 Hz, 1H), 6.38 (s, 1H), 4.43 (s, 2H), 3.51 (s, 3H), 3.46 (s, 3H), 3.13 (s, 3H), 3.30 (s, 3H), 2.89 (s, 3H).

Example 130

{2,4-Dichloro-3-[4-(1H-pyrazol-1-yl)benzyl]quinolin-6-yl}(1-methyl-1H-imidazol-5-yl)pyrimidin-2-ylmethanol.TFA 3-(4-(1H-Pyrazol-1-yl)benzyl)-6-bromo-2,4-dichloroquinoline (1.10 g, 2.54 mmol, Intermediate 3: step c) and (1-methyl-1H-imidazol-5-yl)(pyrimidin-2-yl)methanone (500 mg, 2.66 mmol, Intermediate 66: step b) were dissolved in THF (250 mL) in a dry round bottom flask, then cooled to −78° C. in a dry ice acetone bath under an $N_2$ atmosphere. n-BuLi (1.6 M in hexanes, 1.51 mL, 2.42 mmol) was then added dropwise via syringe over approximately 2 minutes. The contents were stirred at −78° C. for approximately 2 hours, then the dry ice bath was removed and the contents were allowed to warm to room temperature and stir for approximately 1 hour. The reaction was then re-cooled to 0° C. and quenched with saturated, aqueous $NH_4Cl$, then transferred to a separatory funnel with EtOAc. The organic phase was separated, then the aqueous layer was back extracted with EtOAc. The combined organic phases were dried over $MgSO_4$, filtered and concentrated under reduced pressure. The crude product was purified by flash column chromatography (silica gel, 0-10% DCM/(10% of a 2 M $NH_3$ MeOH in DCM)) then further purified via reverse phase chromatography using acetonitrile with 0.05% trifluoroacetic acid in water as eluent to afford the title compound. MS (ESI): mass calcd. for $C_{28}H_{21}Cl_2N_7O$, 541.1. m/z found, 542.2 [M+H]$^+$. $^1$H NMR (400 MHz, CD$_3$OD) δ ppm 8.86 (d, J=4.9 Hz, 2H), 8.57 (d, J=1.6 Hz, 1H), 8.15 (dd, J=2.5, 0.4 Hz, 1H), 8.05 (dd, J=8.9, 2.0 Hz, 1H), 7.94 (d, J=8.9 Hz, 1H), 7.71-7.66 (m, 2H), 7.66-7.60 (m, 2H), 7.45 (t, J=4.9 Hz, 1H), 7.35-7.28 (m, 2H), 6.52-6.47 (m, 1H), 6.42 (s, 1H), 4.58 (s, 2H), 3.40 (s, 3H).

Example 131a

{4-Chloro-2-methoxy-3-[4-(1H-pyrazol-1-yl)benzyl]quinolin-6-yl}(1-methyl-1H-imidazol-5-yl)pyrimidin-2-ylmethanol

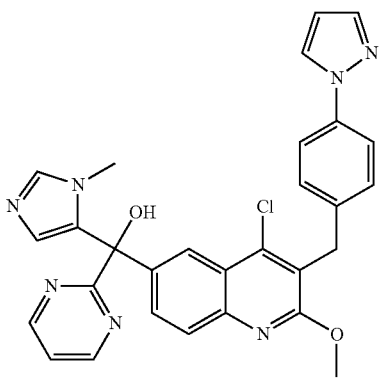 [SMILES: COc1nc2ccc(C(O)(c3ncccn3)c3cncn3C)cc2c(Cl)c1Cc1ccc(-n2cccn2)cc1]

{2,4-Dichloro-3-[4-(1H-pyrazol-1-yl)benzyl]quinolin-6-yl}(1-methyl-1H-imidazol-5-yl)pyrimidin-2-ylmethanol (58 mg, 0.107 mmol, Example 130), toluene (2 mL), and sodium methoxide (116 mg, 2.14 mmol) were combined in a round bottom flask equipped with a stirbar and condenser under an $N_2$ atmosphere. The reaction contents were heated to reflux and refluxed overnight. The reaction was cooled to room temperature and the contents were transferred to a separatory funnel with EtOAc dilution, and extracted with saturated, aqueous $NH_4Cl$ then saturated, aqueous $NaHCO_3$ solutions. The organic phase was separated, dried over $MgSO_4$, filtered and concentrated under reduced pressure. The crude material was purified via reverse phase chromatography using acetonitrile with 0.05% trifluoroacetic acid in water as eluent. The fractions from the purification containing the desired product were transferred to a separatory funnel with EtOAc and extracted with a saturated, aqueous $NaHCO_3$ solution. The aqueous layer was separated, extracted with EtOAc, then the combined organic phases were dried over $MgSO_4$, filtered and concentrated under reduced pressure to afford the title compound. MS (ESI): mass calcd. for $C_{29}H_{24}ClN_7O_2$, 537.2. m/z found, 538.3 [M+H]$^+$. $^1$H NMR (400 MHz, CD$_3$OD) δ ppm 8.84 (d, J=4.9 Hz, 2H), 8.39 (d, J=1.8 Hz, 1H), 8.13-8.07 (m, 1H), 7.86 (dd, J=8.8, 2.0 Hz, 1H), 7.78 (d, J=8.7 Hz, 1H), 7.66 (d, J=1.3 Hz, 2H), 7.56 (d, J=8.6 Hz, 2H), 7.42 (t, J=4.9 Hz, 1H), 7.32 (d, J=8.6 Hz, 2H), 6.50-6.45 (m, 1H), 6.42 (s, 1H), 4.27 (s, 2H), 4.04 (s, 3H), 3.39 (s, 3H).

{4-Chloro-2-methoxy-3-[4-(1H-pyrazol-1-yl)benzyl]quinolin-6-yl}(1-methyl-1H-imidazol-5-yl)pyrimidin-2-ylmethanol was purified on a chiralcel OD column (20 μm, Diacel) with methanol to provide two enantiomers. The first eluting enantiomer was Example 131b: MS (ESI): mass calcd. for $C_{29}H_{24}ClN_7O_2$, 537.2. m/z found, 538.3 [M+H]$^+$; $^1$H NMR (600 MHz, CD$_3$OD) δ ppm 8.85 (d, J=4.9 Hz, 2H), 8.39 (d, J=1.9 Hz, 1H), 8.11 (d, J=1.9 Hz, 1H), 7.86 (dd, J=8.8, 2.0 Hz, 1H), 7.78 (d, J=8.8 Hz, 1H), 7.67 (d, J=1.4 Hz, 1H), 7.62 (s, 1H), 7.57 (d, J=8.5 Hz, 2H), 7.42 (t, J=4.9 Hz, 1H), 7.34 (d, J=8.4 Hz, 2H), 6.49-6.45 (m, 1H), 6.40 (s, 1H), 4.30 (s, 2H), 4.05 (s, 3H), 3.38 (s, 3H) and the second eluting enantiomer was Example 131c: MS (ESI): mass calcd. for $C_{29}H_{24}ClN_7O_2$, 537.2. m/z found, 538.3 [M+H]$^+$; $^1$H NMR (600 MHz, CD$_3$OD) δ ppm 8.85 (d, J=4.9 Hz, 2H), 8.39 (d, J=1.9 Hz, 1H), 8.12 (s, 1H), 7.86 (dd, J=8.8, 1.9 Hz, 1H), 7.79 (d, J=8.6 Hz, 1H), 7.67 (s, 1H), 7.62 (s, 1H), 7.58 (d, J=8.4 Hz, 2H), 7.43 (t, J=4.9 Hz, 1H), 7.35 (d, J=7.4 Hz, 2H), 6.48 (d, J=1.8 Hz, 1H), 6.39 (s, 1H), 4.32 (s, 2H), 4.06 (s, 3H), 3.39 (s, 3H).

Example 132

{4-Chloro-2-(dimethylamino)-3-[4-(1H-pyrazol-1-yl)benzyl]quinolin-6-yl}(1-methyl-1H-imidazol-5-yl)[6-(trifluoromethyl)pyridin-3-yl]methanol

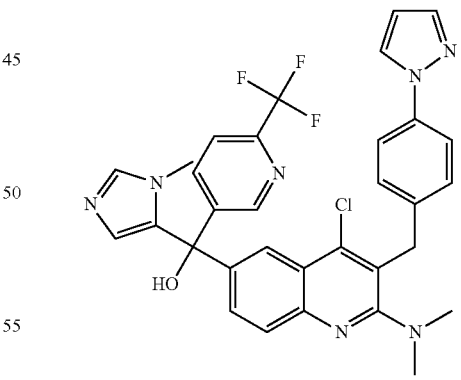

Purification of the crude reaction mixture from the synthesis of 1-(4-chloro-6-{hydroxy(1-methyl-1H-imidazol-5-yl)[6-(trifluoromethyl)pyridin-3-yl]methyl}-3-[4-(1H-pyrazol-1-yl)benzyl]quinolin-2-yl)azetidin-3-ol (Example 134a) also afforded the title compound as a byproduct of dimethylamine addition. MS (ESI): mass calcd. for $C_{32}H_{27}ClF_3N_7O$, 617.2. m/z found, 618.2 [M+H]$^+$. $^1$H NMR (600 MHz, CD$_3$OD) δ ppm 8.77 (d, J=2.0 Hz, 1H), 8.13 (d, J=2.3 Hz, 1H), 8.10 (d, J=2.0 Hz, 1H), 8.00 (dd, J=8.3, 2.1 Hz, 1H), 7.87 (d, J=8.8 Hz, 1H), 7.82 (d, J=8.2 Hz, 1H), 7.73 (s, 1H), 7.68 (d, J=1.6 Hz, 1H), 7.63 (dd, J=8.8, 2.1 Hz, 1H), 7.62-7.59 (m, 2H), 7.26 (d, J=8.6 Hz, 2H), 6.50-6.47 (m, 1H), 6.34 (d, J=1.0 Hz, 1H), 4.45 (s, 2H), 3.48 (s, 3H), 2.92 (s, 6H).

Example 133a

{4-Chloro-2-(3-methoxyazetidin-1-yl)-3-[4-(1H-pyrazol-1-yl)benzyl]quinolin-6-yl}(1-methyl-1H-imidazol-5-yl)[6-(trifluoromethyl)pyridin-3-yl]methanol

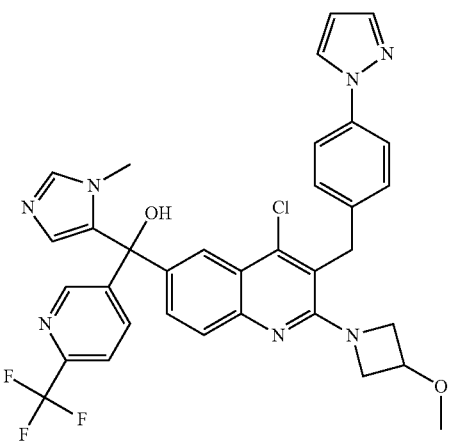 [SMILES: COC1CN(c2nc3ccc(C(O)(c4ccc(C(F)(F)F)nc4)c4cncn4C)cc3c(Cl)c2Cc2ccc(-n3cccn3)cc2)C1]

{2,4-Dichloro-3-[4-(1H-pyrazol-1-yl)benzyl]quinolin-6-yl}(1-methyl-1H-imidazol-5-yl)pyrimidin-2-ylmethanol (200 mg, 0.328 mmol, Intermediate 65), 3-methoxyazetidine hydrochloride (427 mg, 3.28 mmol), and DMF (2 mL) were combined in a reaction tube, then sealed and heated to 100° C. and maintained at that temperature overnight. The reaction vessel was then cooled to room temperature and the contents were transferred to a separatory funnel with EtOAc dilution, and extracted once with saturated, aqueous NH$_4$Cl solution, then extracted three times with deionized water. The organic phase was separated, dried over MgSO$_4$, filtered and concentrated under reduced pressure. The crude material was purified via reverse phase chromatography using acetonitrile with ammonium hydroxide in water as eluent to provide the title compound. MS (ESI): mass calcd. for $C_{34}H_{29}ClF_3N_7O_2$, 659.2. m/z found, 660.3 [M+H]$^+$. $^1$H NMR (600 MHz, CD$_3$OD) δ ppm 8.78 (d, J=2.1 Hz, 1H), 8.11 (dd, J=2.5, 0.4 Hz, 1H), 8.07 (d, J=2.1 Hz, 1H), 8.01 (dd, J=8.2, 2.1 Hz, 1H), 7.80 (d, J=8.2 Hz, 1H), 7.77-7.73 (m, 2H), 7.67 (d, J=1.4 Hz, 1H), 7.62-7.59 (m, 2H), 7.59-7.56 (m, 1H), 7.17 (d, J=8.7 Hz, 2H), 6.49-6.46 (m, 1H), 6.37 (s, 1H), 4.34-4.29 (m, 4H), 4.19-4.13 (m, 1H), 4.02-3.97 (m, 2H), 3.48 (s, 3H), 3.22 (s, 3H).

{4-Chloro-2-(3-methoxyazetidin-1-yl)-3-[4-(1H-pyrazol-1-yl)benzyl]quinolin-6-yl}(1-methyl-1H-imidazol-5-yl)[6-(trifluoromethyl)pyridin-3-yl]methanol was purified on a chiralcel OD-H column with 80% pentane, 20% ethanol to provide two enantiomers. The first eluting enantiomer was Example 133b: MS (ESI): mass calcd. for $C_{34}H_{29}ClF_3N_7O_2$, 659.2. m/z found, 660.3 [M+H]$^+$; $^1$H NMR (400 MHz, CDCl$_3$) δ ppm 8.81 (d, J=1.4 Hz, 1H), 8.08 (d, J=1.9 Hz, 1H), 7.91-7.83 (m, 2H), 7.71 (d, J=8.8 Hz, 1H), 7.66 (d, J=1.3 Hz, 1H), 7.62 (d, J=8.2 Hz, 1H), 7.57 (d, J=8.6 Hz, 2H), 7.46 (dd, J=8.8, 2.1 Hz, 1H), 7.19-7.12 (m, 3H), 6.45-6.41 (m, 1H), 6.25 (s, 1H), 4.32-4.23 (m, 4H), 4.19-4.11 (m, 1H), 4.06-3.99 (m, 2H), 3.32 (s, 3H), 3.25 (s, 3H) and the second eluting enantiomer was Example 133c: MS (ESI): mass calcd. for $C_{34}H_{29}ClF_3N_7O_2$, 659.2. m/z found, 660.3 [M+H]$^+$; $^1$H NMR (400 MHz, CDCl$_3$) δ ppm 8.81 (d, J=1.5 Hz, 1H), 8.08 (d, J=2.0 Hz, 1H), 7.91-7.82 (m, 2H), 7.71 (d, J=8.8 Hz, 1H), 7.66 (d, J=1.6 Hz, 1H), 7.62 (d, J=8.2 Hz, 1H), 7.58 (d, J=8.6 Hz, 2H), 7.46 (dd, J=8.8, 2.1 Hz, 1H), 7.21-7.12 (m, 3H), 6.46-6.41 (m, 1H), 6.26 (s, 1H), 4.32-4.23 (m, 4H), 4.20-4.11 (m, 1H), 4.06-3.98 (m, 2H), 3.32 (s, 3H), 3.25 (s, 3H).

Example 134a 1-(4-Chloro-6-{hydroxy(1-methyl-1H-imidazol-5-yl)[6-(trifluoromethyl)pyridin-3-yl]methyl}-3-[4-(1H-pyrazol-1-yl)benzyl]quinolin-2-yl)azetidin-3-ol

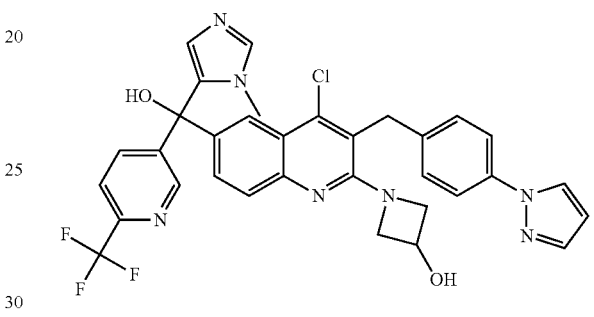

{2,4-Dichloro-3-[4-(1H-pyrazol-1-yl)benzyl]quinolin-6-yl}(1-methyl-1H-imidazol-5-yl)pyrimidin-2-ylmethanol (100 mg, 0.164 mmol, Intermediate 65), 3-hydroxyazetidine hydrochloride (189 mg, 1.64 mmol), and DMF (2 mL) were combined in a reaction tube, then sealed and heated to 100° C. and maintained at that temperature for 24 hours. The reaction solution was taken up into EtOAc, transferred to a reparatory funnel and extracted twice with a saturated, aqueous NH$_4$Cl solution. The organic phase was separated, dried over MgSO$_4$, filtered and concentrated under reduced pressure. The crude material was purified via reverse phase chromatography using acetonitrile with ammonium hydroxide in water as eluent to afford the title compound. MS (ESI): mass calcd. for $C_{33}H_{27}ClF_3N_7O_2$, 645.2. m/z found, 646.3 [M+H]$^+$. $^1$H NMR (600 MHz, CD$_3$OD) δ ppm 8.78 (d, J=2.0 Hz, 1H), 8.13 (dd, J=2.5, 0.4 Hz, 1H), 8.06 (d, J=2.0 Hz, 1H), 8.01 (dd, J=8.2, 2.0 Hz, 1H), 7.81 (d, J=8.1 Hz, 1H), 7.76 (d, J=8.8 Hz, 1H), 7.72 (s, 1H), 7.68 (d, J=1.4 Hz, 1H), 7.64-7.59 (m, 2H), 7.57 (dd, J=8.8, 2.2 Hz, 1H), 7.19 (d, J=8.7 Hz, 2H), 6.50-6.46 (m, 1H), 6.35 (s, 1H), 4.55-4.49 (m, 1H), 4.39-4.34 (m, 2H), 4.34 (s, 2H), 3.99-3.93 (m, 2H), 3.48 (s, 3H).

1-(4-Chloro-6-{hydroxy(1-methyl-1H-imidazol-5-yl) [6-(trifluoromethyl)pyridin-3-yl]methyl}-3-[4-(1H-pyrazol-1-yl)benzyl]quinolin-2-yl)azetidin-3-ol was purified on a chiralcel OD-H column with 80% pentane, 20% ethanol to provide two enantiomers. The first eluting enantiomer was Example 134b: MS (ESI): mass calcd. for $C_{33}H_{27}ClF_3N_7O_2$, 645.2. m/z found, 646.3 [M+H]$^+$; $^1$H NMR (400 MHz, CDCl$_3$) δ ppm 8.77 (s, 1H), 8.06 (d, J=1.9 Hz, 1H), 7.90-7.83 (m, 1H), 7.82 (d, J=2.3 Hz, 1H), 7.69-7.63 (m, 2H), 7.61 (d, J=8.3 Hz, 1H), 7.50 (d, J=8.5 Hz, 2H), 7.41 (dd, J=8.8, 2.0 Hz, 1H), 7.22 (s, 1H), 7.10 (d, J=8.5 Hz, 2H), 6.43-6.39 (m, 1H), 6.28 (s, 1H), 4.60-4.51 (m, 1H), 4.35-4.26 (m, 2H), 4.24 (s, 2H), 4.01-3.93 (m, 2H), 3.32 (s, 3H) and the second enantiomer was Example 134c: MS (ESI): mass calcd. for $C_{33}H_{27}ClF_3N_7O_2$, 645.2. m/z found, 646.3 [M+H]$^+$; $^1$H NMR (400 MHz, CDCl$_3$) δ ppm 8.77 (s, 1H), 8.07 (d, J=1.9 Hz, 1H), 7.87 (d, J=8.1 Hz, 1H), 7.82 (d, J=2.4 Hz, 1H), 7.70-7.64 (m, 2H), 7.61 (d, J=8.3 Hz, 1H), 7.51 (d, J=8.5 Hz, 2H), 7.41 (dd, J=8.8, 1.9 Hz, 1H), 7.24 (s, 1H), 7.11 (d, J=8.5 Hz, 2H), 6.45-6.40 (m, 1H), 6.29 (s, 1H), 4.60-4.51 (m, 1H), 4.35-4.26 (m, 2H), 4.24 (s, 2H), 4.02-3.93 (m, 2H), 3.32 (s, 3H).

Example 135a

{4-Chloro-2-(3,3-difluoroazetidin-1-yl)-3-[4-(1H-pyrazol-1-yl)benzyl]quinolin-6-yl}(1-methyl-1H-imidazol-5-yl)[6-(trifluoromethyl)pyridin-3-yl]methanol.TFA

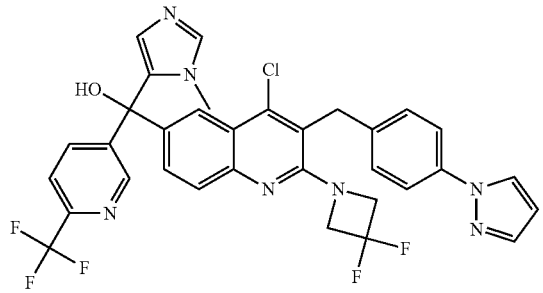 [SMILES: Cn1cncc1C(O)(c1ccc(C(F)(F)F)nc1)c1ccc2nc(N3CC(F)(F)C3)c(Cc3ccc(-n4cccn4)cc3)c(Cl)c2c1]

{2,4-Dichloro-3-[4-(1H-pyrazol-1-yl)benzyl]quinolin-6-yl}(1-methyl-1H-imidazol-5-yl) [6-(trifluoromethyl)pyridin-3-yl]methanol (200 mg, 0.33 mmol, Intermediate 65), 3,3-difluoroazetidine hydrochloride (895 mg, 6.56 mmol), and DMF (2 mL) were combined in a reaction tube, then sealed and heated to 100° C. and maintained at that temperature for 3 days. The reaction vessel was then cooled to room temperature and the contents were transferred to a separatory funnel with EtOAc dilution, then extracted three times with deionized water. The organic phase was separated, dried over MgSO$_4$, filtered and concentrated under reduced pressure. The crude material was purified via reverse phase chromatography using acetonitrile with ammonium hydroxide in water as eluent then further purified via reverse phase chromatography using acetonitrile with 0.05% trifluoroacetic acid in water as eluent to provide the title compound. MS (ESI): mass calcd. for C$_{33}$H$_{25}$ClF$_5$N$_7$O, 665.2. m/z found, 666.3 [M+H]$^+$. $^1$H NMR (600 MHz, CDCl$_3$) δ ppm 8.77 (s, 1H), 8.19-8.12 (m, 1H), 7.93-7.88 (m, 1H), 7.86 (d, J=2.5 Hz, 1H), 7.76 (d, J=8.7 Hz, 1H), 7.66 (d, J=1.8 Hz, 1H), 7.62 (d, J=8.3 Hz, 1H), 7.59 (d, J=8.2 Hz, 2H), 7.51 (d, J=9.0 Hz, 1H), 7.25-7.18 (m, 1H), 7.15 (d, J=8.2 Hz, 2H), 6.46-6.41 (m, 1H), 6.27 (s, 1H), 4.44-4.35 (m, 4H), 4.28 (s, 2H), 3.33 (s, 3H).

{4-Chloro-2-(3,3-difluoroazetidin-1-yl)-3-[4-(1H-pyrazol-1-yl)benzyl]quinolin-6-yl}(1-methyl-1H-imidazol-5-yl)[6-(trifluoromethyl)pyridin-3-yl]methanol was purified via chiral SFC (Stationary phase: CHIRALPAK 1A 5 µm 250×20 mm, Mobile phase: 60% CO$_2$, 40% mixture of MeOH/iPrOH 50/50 v/v) to provide two enantiomers. The first eluting enantiomer was Example 135b: MS (ESI): mass calcd. for C$_{33}$H$_{25}$ClF$_5$N$_7$O, 665.2. m/z found, 666.5 [M+H]$^+$; $^1$H NMR (600 MHz, CDCl$_3$) δ ppm 8.83-8.79 (m, 1H), 8.15 (d, J=2.1 Hz, 1H), 7.93-7.88 (m, 1H), 7.87 (d, J=2.5 Hz, 1H), 7.78 (d, J=8.7 Hz, 1H), 7.69-7.66 (m, 1H), 7.65 (d, J=8.3 Hz, 1H), 7.63-7.58 (m, 2H), 7.54 (dd, J=8.8, 2.1 Hz, 1H), 7.26-7.23 (m, 1H), 7.16 (d, J=8.2 Hz, 2H), 6.45 (t, J=2.1 Hz, 1H), 6.33-6.28 (m, 1H), 4.44-4.36 (m, 4H), 4.29 (s, 2H), 3.36 (s, 3H) and the second eluting enantiomer was Example 135c: MS (ESI): mass calcd. for C$_{33}$H$_{25}$ClF$_5$N$_7$O, 665.2. m/z found, 666.5 [M+H]$^+$; $^1$H NMR (600 MHz, CDCl$_3$) δ ppm 8.84-8.79 (m, 1H), 8.15 (d, J=2.1 Hz, 1H), 7.91 (dd, J=8.2, 2.2 Hz, 1H), 7.89-7.86 (m, 1H), 7.78 (d, J=8.8 Hz, 1H), 7.68 (d, J=1.7 Hz, 1H), 7.65 (d, J=8.3 Hz, 1H), 7.63-7.59 (m, 2H), 7.54 (dd, J=8.8, 2.2 Hz, 1H), 7.25-7.23 (m, 1H), 7.18-7.14 (m, 2H), 6.45 (dd, J=2.5, 1.7 Hz, 1H), 6.30 (s, 1H), 4.44-4.36 (m, 4H), 4.30 (s, 2H), 3.36 (s, 3H).

Example 136a

{2-Azetidin-1-yl-4-chloro-8-methyl-3-[4-(1H-pyrazol-1-yl)benzyl]quinolin-6-yl}(4-chlorophenyl)(1-methyl-1H-imidazol-5-yl)methanol

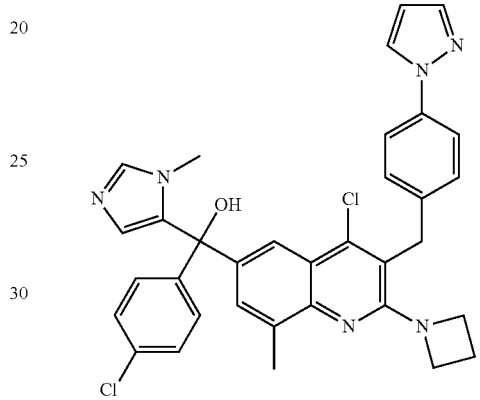

(3-(4-(1H-Pyrazol-1-yl)benzyl)-2,4-dichloro-8-methylquinolin-6-yl)(4-chlorophenyl)(1-methyl-1H-imidazol-5-yl)methanol (200 mg, 0.34 mmol, Intermediate 67), azetidine (194 mg, 3.40 mmol), and DMF (2 mL) were combined in a reaction tube, then sealed and heated to 100° C. and maintained at that temperature overnight. The reaction vessel was then cooled to room temperature and the solvent and excess azetidine were removed by reduced pressure distillation. The crude residue was taken up into EtOAc, then extracted twice with a saturated, aqueous NH$_4$Cl solution. The organic phase was separated, dried over MgSO$_4$, filtered and concentrated under reduced pressure. The crude material was purified via reverse phase chromatography using acetonitrile with ammonium hydroxide in water as eluent to afford the title compound. MS (ESI): mass calcd. for C$_{34}$H$_{30}$Cl$_2$N$_6$O, 608.2. m/z found, 609.2 [M+H]$^+$. $^1$H NMR (600 MHz, CDCl$_3$) δ ppm 7.86 (d, J=2.1 Hz, 1H), 7.84 (d, J=2.4 Hz, 1H), 7.66 (d, J=1.7 Hz, 1H), 7.57-7.54 (m, 2H), 7.37 (dd, J=2.3, 1.1 Hz, 1H), 7.32-7.29 (m, 2H), 7.25 (d, J=8.5 Hz, 2H), 7.19-7.15 (m, 2H), 7.13 (s, 1H), 6.43-6.40 (m, 1H), 6.29 (d, J=1.2 Hz, 1H), 5.80-5.74 (m, 1H), 4.27 (s, 2H), 4.11 (t, J=7.5 Hz, 4H), 3.32 (s, 3H), 2.58 (s, 3H), 2.26-2.17 (m, 2H).

{2-Azetidin-1-yl-4-chloro-8-methyl-3-[4-(1H-pyrazol-1-yl)benzyl]quinolin-6-yl}(4-chlorophenyl)(1-methyl-1H-imidazol-5-yl)methanol was purified via SFC with a Chiralpak AD-H column (5 µm 250×20 mm) using a mobile phase of 50% CO$_2$ and 50% methanol to provide two enantiomers. The first eluting enantiomer was Example 136b: MS (ESI): mass calcd. for C$_{34}$H$_{30}$Cl$_2$N$_6$O, 608.2. m/z found, 609.5 [M+H]$^+$; $^1$H NMR (600 MHz, CDCl$_3$) δ ppm 7.86-7.83 (m, 2H), 7.66 (d, J=1.7 Hz, 1H), 7.58-7.53 (m, 2H), 7.36 (dd, J=2.0, 1.1 Hz, 1H), 7.34-7.29 (m, 2H), 7.30-7.25 (m, 2H), 7.21-7.14 (m, 3H), 6.44-6.41 (m, 1H), 6.31 (s, 1H), 4.27 (s, 2H), 4.11 (t, J=7.5 Hz, 4H), 3.34 (s, 3H), 2.58 (s, 3H), 2.22 (p, J=7.5 Hz, 2H) and the second eluting enantiomer was Example 136c: MS (ESI): mass calcd. for $C_{34}H_{30}Cl_2N_6O$, 608.2. m/z found, 609.5 [M+H]+; 1H NMR (600 MHz, CDCl3) δ ppm 7.84 (dd, J=4.1, 2.3 Hz, 2H), 7.66 (s, 1H), 7.56 (d, J=8.1 Hz, 2H), 7.36 (s, 1H), 7.34-7.24 (m, 4H), 7.20-7.13 (m, 3H), 6.45-6.40 (m, 1H), 6.30 (s, 1H), 4.27 (s, 2H), 4.11 (t, J=7.5 Hz, 4H), 3.33 (s, 3H), 2.58 (s, 3H), 2.21 (p, J=7.5 Hz, 2H).

Example 137a

{2-Azetidin-1-yl-4-chloro-8-methyl-3-[4-(1H-pyrazol-1-yl)benzyl]quinolin-6-yl}(1-methyl-1H-imidazol-5-yl)[6-(trifluoromethyl)pyridin-3-yl]methanol

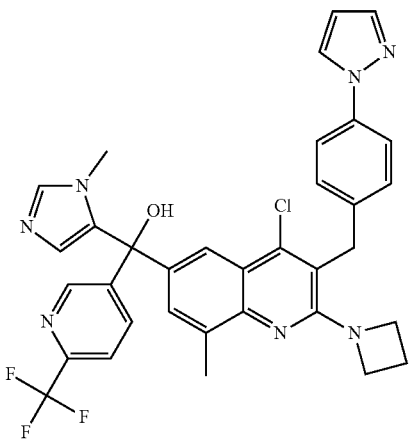 [SMILES: Cc1cc(C(O)(c2ccc(C(F)(F)F)nc2)c2cncn2C)cc2c(Cl)c(Cc3ccc(-n4cccn4)cc3)c(N3CCC3)nc12]

(3-(4-(1H-Pyrazol-1-yl)benzyl)-2,4-dichloro-8-methylquinolin-6-yl)(1-methyl-1H-imidazol-5-yl)(6-(trifluoromethyl)pyridin-3-yl)methanol (200 mg, 0.321 mmol, Intermediate 68), azetidine (183 mg, 3.21 mmol), and DMF (2 mL) were combined in a reaction tube, then sealed and heated to 100° C. and maintained at that temperature overnight. The reaction vessel was then cooled to room temperature and the solvent and excess azetidine were removed by reduced pressure distillation. The crude residue was taken up into EtOAc, then extracted twice with a saturated, aqueous NH4Cl solution. The organic phase was separated, dried over MgSO4, filtered and concentrated under reduced pressure. The crude material was purified via reverse phase chromatography using acetonitrile with ammonium hydroxide in water as eluent to provide the title compound. MS (ESI): mass calcd. for $C_{34}H_{29}ClF_3N_7O$, 643.2. m/z found, 644.3 [M+H]+. 1H NMR (600 MHz, CDCl3) δ ppm 8.82 (d, J=2.2 Hz, 1H), 7.90-7.86 (m, 2H), 7.85 (d, J=2.5 Hz, 1H), 7.66 (d, J=1.7 Hz, 1H), 7.61-7.58 (m, 1H), 7.58-7.54 (m, 2H), 7.36 (dd, J=2.3, 1.1 Hz, 1H), 7.19-7.15 (m, 2H), 7.14 (d, J=1.1 Hz, 1H), 6.73 (s, 1H), 6.45-6.40 (m, 1H), 6.24 (d, J=1.1 Hz, 1H), 4.29 (s, 2H), 4.13 (t, J=7.5 Hz, 4H), 3.33 (s, 3H), 2.58 (s, 3H), 2.28-2.19 (m, 2H).

{2-Azetidin-1-yl-4-chloro-8-methyl-3-[4-(1H-pyrazol-1-yl)benzyl]quinolin-6-yl}(1-methyl-1H-imidazol-5-yl)[6-(trifluoromethyl)pyridin-3-yl]methanol was purified via SFC with a Chiralpak 1A column (5 μm 250×20 mm) using a mobile phase of 60% CO2 and 40% ethanol to provide two enantiomers. The first eluting enantiomer was Example 137b: MS (ESI): mass calcd. for $C_{34}H_{29}ClF_3N_7O$, 643.2. m/z found, 644.6 [M+H]+; 1H NMR (600 MHz, CDCl3) δ ppm 8.81 (d, J=2.2 Hz, 1H), 7.91-7.86 (m, 2H), 7.84 (d, J=2.4 Hz, 1H), 7.66 (d, J=1.7 Hz, 1H), 7.61 (d, J=8.3 Hz, 1H), 7.56 (d, J=8.5 Hz, 2H), 7.37-7.35 (m, 1H), 7.18-7.15 (m, 3H), 6.42 (t, J=2.1 Hz, 1H), 6.25 (s, 1H), 4.28 (s, 2H), 4.13 (t, J=7.5 Hz, 4H), 3.33 (s, 3H), 2.58 (s, 3H), 2.23 (p, J=7.5 Hz, 2H) and the second eluting enantiomer was Example 137c: MS (ESI): mass calcd. for $C_{34}H_{29}ClF_3N_7O$, 643.2. m/z found, 644.5 [M+H]+.
1H NMR (600 MHz, CDCl3) δ 8.81 (d, J=2.2 Hz, 1H), 7.90-7.86 (m, 2H), 7.84 (d, J=2.5 Hz, 1H), 7.66 (d, J=1.8 Hz, 1H), 7.61 (dd, J=8.2, 0.8 Hz, 1H), 7.59-7.54 (m, 2H), 7.38-7.34 (m, 1H), 7.19-7.14 (m, 3H), 6.44-6.41 (m, 1H), 6.26 (s, 1H), 4.28 (s, 2H), 4.13 (t, J=7.5 Hz, 4H), 3.33 (s, 3H), 2.58 (s, 3H), 2.27-2.19 (m, 2H).

Example 138a

{2-Azetidin-1-yl-4-chloro-3-[4-(1H-pyrazol-1-yl)benzyl]quinolin-6-yl}(4-chlorophenyl)(1-methyl-1H-imidazol-5-yl)methanol

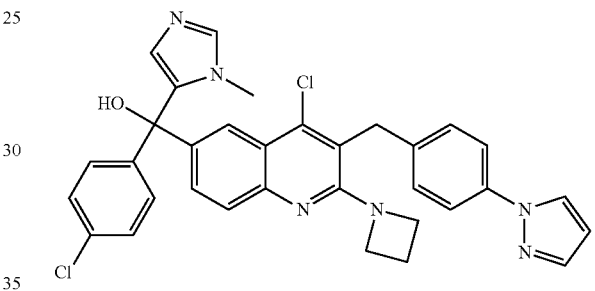

(3-(4-(1H-Pyrazol-1-yl)benzyl)-2,4-dichloroquinolin-6-yl)(4-chlorophenyl)(1-methyl-1H-imidazol-5-yl)methanol (200 mg, 0.348 mmol, Intermediate 64), azetidine (199 mg, 3.48 mmol), and DMF (2 mL) were combined in a reaction tube, then sealed and heated to 100° C. and maintained at that temperature for 24 hours. The vessel was then cooled to room temperature and the solvent was removed by reduced pressure distillation. The residue was taken up into EtOAc, transferred to a separatory funnel and extracted twice with a saturated, aqueous NH4Cl solution. The organic phase was separated, dried over MgSO4, filtered and concentrated under reduced pressure. The crude material was purified via reverse phase chromatography using acetonitrile with ammonium hydroxide in water as eluent to provide the title compound. MS (ESI): mass calcd. for $C_{33}H_{28}Cl_2N_6O$, 594.2. m/z found, 595.3 [M+H]+. 1H NMR (600 MHz, CDCl3) δ ppm 8.03 (d, J=2.1 Hz, 1H), 7.86 (d, J=2.4 Hz, 1H), 7.70-7.67 (m, 2H), 7.61-7.56 (m, 2H), 7.45 (dd, J=8.8, 2.2 Hz, 1H), 7.32-7.27 (m, 4H), 7.24 (d, J=1.1 Hz, 1H), 7.20-7.14 (m, 2H), 6.43 (t, J=2.1 Hz, 1H), 6.33 (d, J=1.2 Hz, 1H), 4.30 (s, 2H), 4.14 (t, J=7.6 Hz, 4H), 3.35 (s, 3H), 2.27-2.17 (m, 2H).

{2-Azetidin-1-yl-4-chloro-3-[4-(1H-pyrazol-1-yl)benzyl]quinolin-6-yl}(4-chlorophenyl)(1-methyl-1H-imidazol-5-yl)methanol was purified by chiral SFC on a Chiralpak IA column (5 μm, 250×20 mm) with a mobile phase of 50% CO2, 50% iPrOH) to provide two enantiomers. The first eluting enantiomer was Example 138b: MS (ESI): mass calcd. for $C_{33}H_{28}Cl_2N_6O$, 594.2. m/z found, 595.5 [M+H]+; 1H NMR (400 MHz, CDCl3) δ ppm 8.02 (d, J=2.1 Hz, 1H), 7.85 (d, J=2.4 Hz, 1H), 7.70-7.65 (m, 2H), 7.57 (d, J=8.1 Hz, 2H), 7.48-7.41 (m, 1H), 7.33-7.24 (m, 4H), 7.24-7.13 (m, 3H), 6.43 (q, J=1.6 Hz, 1H), 6.31 (t, J=3.3 Hz, 1H), 4.29 (s, 2H), 4.14 (t, J=7.5 Hz, 4H), 3.34 (s, 3H), 2.21 (p, J=7.5 Hz, 2H) and the second eluting enantiomer was Example 138c: MS (ESI): mass calcd. for C₃₃H₂₈Cl₂N₆O, 594.2. m/z found, 595.5 [M+H]⁺; ¹H NMR (400 MHz, CDCl₃) δ ppm 8.02 (d, J=2.1 Hz, 1H), 7.85 (dd, J=2.5, 0.7 Hz, 1H), 7.70-7.64 (m, 2H), 7.60-7.54 (m, 2H), 7.44 (dd, J=8.8, 2.2 Hz, 1H), 7.33-7.24 (m, 4H), 7.20-7.13 (m, 3H), 6.42 (dd, J=2.5, 1.8 Hz, 1H), 6.30 (d, J=1.2 Hz, 1H), 4.28 (s, 2H), 4.13 (t, J=7.5 Hz, 4H), 3.33 (s, 3H), 2.27-2.15 (m, 2H).

Example 139

(2,4-dichloro-3-(4-(trifluoromethyl)benzyl)quinolin-6-yl)(2,6-dimethylpyridin-3-yl)(1-methyl-1H-1,2,3-triazol-5-yl)methanol

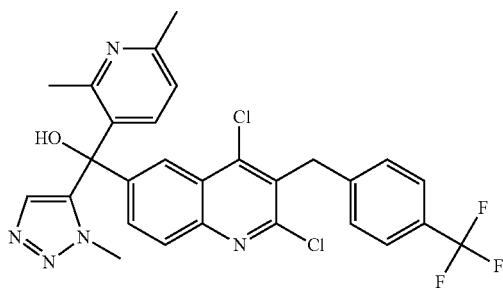 [SMILES: Cc1ccc(C(O)(c2ccc3nc(Cl)c(Cc4ccc(C(F)(F)F)cc4)c(Cl)c3c2)c2cnnn2C)c(C)n1]

6-Bromo-2,4-dichloro-3-[4-(trifluoromethyl)benzyl]quinoline (2.00 g, 4.62 mmol, Intermediate 12: step c) was dissolved in THF (250 mL) in a dry round bottom flask under an N₂ atmosphere, then cooled to −78° C. in dry ice acetone bath. n-BuLi (1.6 M in hexanes, 3.16 mL, 5.06 mmol) was then added dropwise via syringe over approximately 5 minutes and allowed to stir at that temperature for an additional 5 minutes. (2,6-Dimethylpyridin-3-yl)(1-methyl-1H-1,2,3-triazol-5-yl)methanone (1.09 g, 5.06 mmol, Intermediate 19: step b) in THF (50 mL) was then added to the reaction vessel via cannula over approximately 5 minutes. The reaction solution was stirred at −78° C. for approximately 10 minutes, then the dry ice bath was removed and replaced with an ice water bath and stirred at 0° C. for approximately 1 hour. The reaction was then quenched with a saturated, aqueous NH₄Cl solution, then transferred to a reparatory funnel with EtOAc. The organic phase was separated, dried over MgSO₄, filtered and concentrated under reduced pressure. The crude product was purified by flash column chromatography (silica gel, 0-10% DCM/(10% of a 2 M NH₃ MeOH in DCM)) to provide the title compound. MS (ESI): mass calcd. for C₃₀H₂₅Cl₂N₇O, 571.1. m/z found, 572.3 [M+H]⁺. ¹H NMR (400 MHz, CDCl₃) δ 8.23 (dd, J=2.1, 0.6 Hz, 1H), 8.02 (d, J=8.8 Hz, 1H), 7.59-7.52 (m, 3H), 7.35 (d, J=8.0 Hz, 2H), 6.98-6.91 (m, 2H), 6.86 (d, J=1.7 Hz, 1H), 4.57 (s, 2H), 3.94 (s, 3H), 2.54 (s, 3H), 2.36 (s, 3H).

Example 140a

{2-Azetidin-1-yl-4-chloro-3-[4-(trifluoromethyl)benzyl]quinolin-6-yl}(2,6-dimethylpyridin-3-yl)(1-methyl-1H-1,2,3-triazol-5-yl)methanol

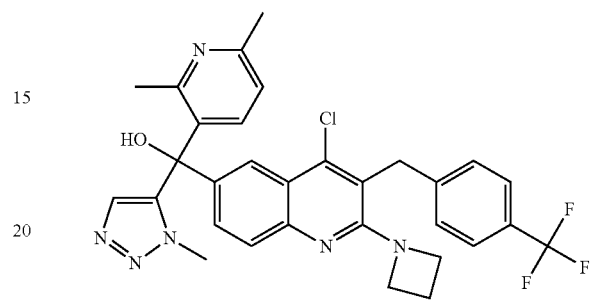

{2,4-Dichloro-3-[4-(1H-pyrazol-1-yl)benzyl]quinolin-6-yl}(2,6-dimethylpyridin-3-yl)(1-methyl-1H-1,2,3-triazol-5-yl)methanol (200 mg, 0.35 mmol, Example 139), azetidine (71 µL, 1.05 mmol) and DMF (10 mL) were combined in a reaction tube, then sealed and heated to 100° C. and maintained at that temperature for 24 hours. The contents were cooled to room temperature, transferred to a separatory funnel with EtOAc dilution, and extracted once with a saturated, aqueous NH₄Cl solution, then three times with deionized water. The organic phase was separated, dried over MgSO₄, filtered and concentrated under reduced pressure. The crude was purified via reverse phase chromatography using acetonitrile with ammonium hydroxide in water as eluent. The fractions from the purification containing the desired product were transferred to a separatory funnel with EtOAc and extracted with a saturated, aqueous NaHCO₃ solution. The aqueous layer was separated, extracted with EtOAc, then the combined organic phases were dried over MgSO₄, filtered and concentrated under reduced pressure to afford the title compound. MS (ESI): mass calcd. for C₃₁H₂₈ClF₃N₆O, 592.2. m/z found, 593.5 [M+H]⁺. ¹H NMR (400 MHz, CDCl₃) δ ppm 7.96 (dd, J=2.2, 0.6 Hz, 1H), 7.74 (d, J=8.8 Hz, 1H), 7.57-7.52 (m, 2H), 7.33 (dd, J=8.8, 2.2 Hz, 1H), 7.25-7.20 (m, 2H), 7.02-6.93 (m, 3H), 4.34 (d, J=1.6 Hz, 2H), 4.16 (t, J=7.6 Hz, 4H), 3.94 (s, 3H), 2.56 (s, 3H), 2.40 (s, 3H), 2.32-2.20 (m, 2H).

{2-Azetidin-1-yl-4-chloro-3-[4-(trifluoromethyl)benzyl]quinolin-6-yl}(2,6-dimethylpyridin-3-yl)(1-methyl-1H-1,2,3-triazol-5-yl)methanol was purified via SFC with a Chiralpak AD-H column (5 µm 250×20 mm) using a mobile phase of 70% CO₂ and a 30% mixture of (MeOH/iPrOH 50/50 v/v (+0.3% iPrNH₂)) to provide two enantiomers. The first eluting enantiomer was Example 140b: MS (ESI): mass calcd. for C₃₁H₂₈ClF₃N₆O, 592.2. m/z found, 593.5 [M+H]⁺; ¹H NMR (400 MHz, CDCl₃) δ ppm 7.98 (d, J=2.2 Hz, 1H), 7.70 (d, J=8.8 Hz, 1H), 7.54 (d, J=8.0 Hz, 2H), 7.30 (dd, J=8.8, 2.2 Hz, 1H), 7.23 (d, J=8.0 Hz, 2H), 6.98 (d, J=8.0 Hz, 1H), 6.92 (d, J=8.7 Hz, 2H), 4.32 (s, 2H), 4.15 (t, J=7.6 Hz, 4H), 3.91 (s, 3H), 2.52 (s, 3H), 2.36 (s, 3H), 2.31-2.19 (m, 2H) and the second eluting enantiomer was Example 140c: MS (ESI): mass calcd. for C₃₁H₂₈ClF₃N₆O, 592.2. m/z found, 593.5 [M+H]⁺; ¹H NMR (400 MHz, CDCl₃) δ ppm 8.00 (d, J=2.2 Hz, 1H), 7.68 (d, J=8.8 Hz, 1H), 7.54 (d, J=8.0 Hz, 2H), 7.30

(dd, J=8.8, 2.2 Hz, 1H), 7.22 (d, J=8.0 Hz, 2H), 6.97 (d, J=8.0 Hz, 1H), 6.91 (d, J=8.1 Hz, 1H), 6.86 (s, 1H), 4.30 (s, 2H), 4.14 (t, J=7.6 Hz, 4H), 3.90 (s, 3H), 2.50 (s, 3H), 2.33 (s, 3H), 2.31-2.20 (m, 2H).

Example 141a

{2-Azetidin-1-yl-4-chloro-3-[4-(1H-pyrazol-1-yl)benzyl]quinolin-6-yl}(2,6-dimethylpyridin-3-yl)(1-methyl-1H-1,2,3-triazol-5-yl)methanol

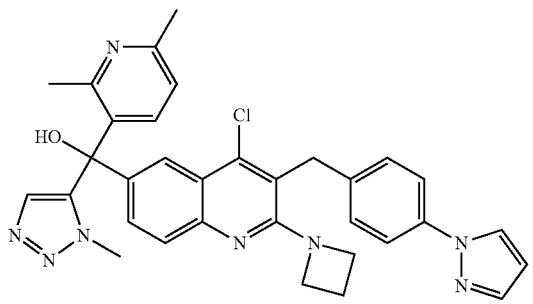 [SMILES: Cc1ccc(C(O)(c2ccc3nc(N4CCC4)c(Cc4ccc(-n5cccn5)cc4)c(Cl)c3c2)c2cnnn2C)c(C)n1]

{2,4-Dichloro-3-[4-(1H-pyrazol-1-yl)benzyl]quinolin-6-yl}(2,6-dimethylpyridin-3-yl)(1-methyl-1H-1,2,3-triazol-5-yl)methanol (198 mg, 0.347 mmol, Example 151), azetidine (70 μL, 1.04 mmol), and DMF (2 mL) were combined in a reaction tube, then sealed and heated to 100° C. and maintained at that temperature for 24 hours. The residue was taken up into EtOAc, transferred to a reparatory funnel and extracted twice with a saturated, aqueous NH$_4$Cl solution. The organic phase was separated then dried over MgSO$_4$, filtered and concentrated under reduced pressure. The crude material was purified via reverse phase chromatography using acetonitrile with ammonium hydroxide in water as eluent to provide the title compound. MS (ESI): mass calcd. for C$_{33}$H$_{31}$ClN$_8$O, 590.2. m/z found, 591.5 [M+H]$^+$. $^1$H NMR (400 MHz, CDCl$_3$) δ ppm 8.07-8.02 (m, 1H), 7.78 (d, J=8.4 Hz, 1H), 7.64-7.56 (m, 2H), 7.38-7.31 (m, 1H), 7.08-6.99 (m, 4H), 6.98 (s, 1H), 6.88-6.77 (m, 2H), 5.89 (d, J=1.9 Hz, 1H), 4.29 (s, 2H), 4.12 (t, J=7.5 Hz, 4H), 3.93 (s, 3H), 2.47 (s, 3H), 2.34 (s, 3H), 2.31-2.18 (m, 2H).

{2-Azetidin-1-yl-4-chloro-3-[4-(1H-pyrazol-1-yl)benzyl]quinolin-6-yl}(2,6-dimethylpyridin-3-yl)(1-methyl-1H-1,2,3-triazol-5-yl)methanol was purified via SFC with a Chiralpack AD-H column (5 μm 250×20 mm) using a mobile phase of 65% CO$_2$, 35% iPrOH (0.3% iPrNH$_2$) to provide two enantiomers. The first eluting enantiomer was Example 141b: MS (ESI): mass calcd. for C$_{33}$H$_{31}$ClN$_8$O, 590.2. m/z found, 591.5 [M+H]$^+$; $^1$H NMR (600 MHz, CDCl$_3$) δ ppm 8.06-8.01 (m, 1H), 7.76 (d, J=8.3 Hz, 1H), 7.62-7.56 (m, 1H), 7.54 (d, J=1.9 Hz, 1H), 7.37-7.30 (m, 1H), 6.96 (s, 4H), 6.90-6.84 (m, 2H), 6.68 (d, J=8.1 Hz, 1H), 5.99 (d, J=1.9 Hz, 1H), 4.24 (d, J=1.6 Hz, 2H), 4.10 (t, J=7.5 Hz, 4H), 3.91 (s, 3H), 2.38 (s, 3H), 2.27-2.19 (m, 5H) and the second eluting enantiomer was Example 141c: MS (ESI): mass calcd. for C$_{33}$H$_{31}$ClN$_8$O, 590.2. m/z found, 591.5 [M+H]$^+$; $^1$H NMR (600 MHz, CDCl$_3$) δ 7.95 (d, J=8.3 Hz, 1H), 7.68 (d, J=8.4 Hz, 1H), 7.51 (t, J=8.5, 7.0, 1.9 Hz, 1H), 7.48-7.42 (m, 1H), 7.26 (t, J=7.7, 2.0 Hz, 1H), 6.91-6.84 (m, 4H), 6.80 (d, J=8.0 Hz, 1H), 6.78-6.74 (m, 1H), 6.61-6.54 (m, 1H), 5.97-5.90 (m, 1H), 4.15 (s, 2H), 4.06-3.99 (m, 4H), 3.83 (s, 3H), 2.29 (s, 3H), 2.19-2.10 (m, 5H).

Example 142

{4-Chloro-8-methyl-2-(methylsulfonyl)-3-[4-(1H-pyrazol-1-yl)benzyl]quinolin-6-yl}(4-chlorophenyl)(1-methyl-1H-imidazol-5-yl)methanol

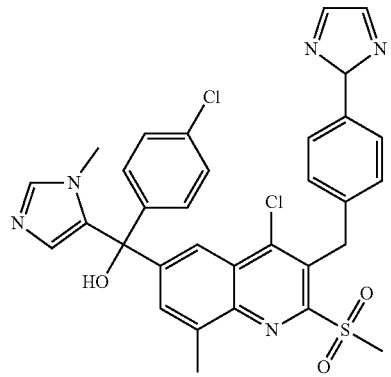 [SMILES: Cc1cc(C(O)(c2ccc(Cl)cc2)c2cncn2C)cc2c(Cl)c(Cc3ccc(C4N=CC=N4)cc3)c(S(C)(=O)=O)nc12]

(3-(4-(1H-Pyrazol-1-yl)benzyl)-2,4-dichloro-8-methylquinolin-6-yl)(4-chlorophenyl)(1-methyl-1H-imidazol-5-yl)methanol (100 mg, 0.17 mmol, Intermediate 67), methanesulfinic acid (16.3 mg, 0.20 mmol), and DMF (2 mL) were combined in a reaction tube then sealed and heated to 100° C. and allowed to react at that temperature overnight. Analysis after overnight reaction showed only partial conversion, so additional methanesulfinic acid (13.3 mg, 0.17 mmol) was added and the vessel was resealed and heated to 100° C. for an additional 24 hours. The reaction vessel was then cooled to room temperature and solvent was removed by reduced pressure distillation. The crude residue was taken up into EtOAc, then extracted twice with a saturated, aqueous NH$_4$Cl solution. The organic phase was separated, dried over MgSO$_4$, filtered and concentrated under reduced pressure. The crude material was purified via reverse phase chromatography using acetonitrile with ammonium hydroxide in water as eluent to afford the title compound. MS (ESI): mass calcd. for C$_{32}$H$_{27}$Cl$_2$N$_5$O$_3$S, 631.1. m/z found, 632.5 [M+H]$^+$. $^1$H NMR (600 MHz, CDCl$_3$) δ ppm 8.73-8.69 (m, 1H), 7.87 (dd, J=2.5, 0.6 Hz, 1H), 7.68 (d, J=1.8 Hz, 1H), 7.65 (dd, J=1.9, 1.0 Hz, 1H), 7.60-7.57 (m, 2H), 7.37 (s, 1H), 7.35-7.30 (m, 4H), 7.20-7.16 (m, 2H), 6.44 (dd, J=2.5, 1.8 Hz, 1H), 6.37 (s, 1H), 5.06 (s, 2H), 4.48 (s, 1H), 3.39 (s, 3H), 2.92 (s, 3H), 2.74 (s, 3H).

Example 143a

{4-Chloro-2-(cyclopropylamino)-3-[4-(trifluoromethyl)benzyl]quinolin-6-yl}(2,6-dimethylpyridin-3-yl)(1-methyl-1H-1,2,3-triazol-5-yl)methanol

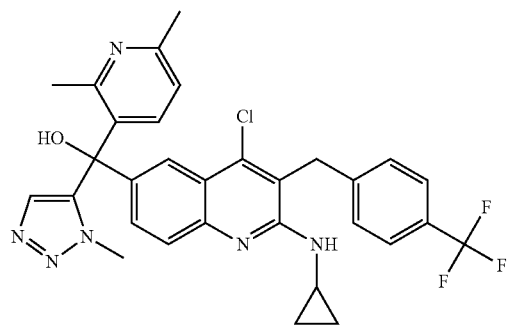 [SMILES: Cc1ccc(C(O)(c2ccc3nc(NC4CC4)c(Cc4ccc(C(F)(F)F)cc4)c(Cl)c3c2)c2cnnn2C)c(C)n1]

{2,4-Dichloro-3-[4-(1H-pyrazol-1-yl)benzyl]quinolin-6-yl}(2,6-dimethylpyridin-3-yl)(1-methyl-1H-1,2,3-triazol-5-yl)methanol (250 mg, 0.437 mmol, Example 139), cyclopropylamine (268 µL, 4.37 mmol), diisopropylethyl amine (0.75 mL, 4.4 mmol), and NMP (3 mL) were combined in a reaction tube, then sealed and heated to 140° C. and maintained at that temperature for 24 hours. The contents were cooled to room temperature, transferred to a separatory funnel with EtOAc dilution, and extracted once with a saturated, aqueous NH$_4$Cl solution, then four times with deionized water. The organic phase was separated, dried over MgSO$_4$, filtered and concentrated under reduced pressure. The crude material was purified by flash column chromatography (silica gel, 0-10% DCM/(10% of a 2 M NH$_3$ MeOH in DCM)) then via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to provide the title compound. MS (ESI): mass calcd. for C$_{31}$H$_{28}$ClF$_3$N$_6$O, 592.2. m/z found, 593.5 [M+H]$^+$. $^1$H NMR (600 MHz, CD$_3$OD) δ ppm 8.33 (d, J=2.2 Hz, 1H), 8.22 (d, J=8.8 Hz, 1H), 7.81 (d, J=8.3 Hz, 1H), 7.72-7.67 (m, 2H), 7.60 (d, J=8.1 Hz, 2H), 7.37 (d, J=8.0 Hz, 2H), 7.18 (s, 1H), 4.52 (s, 2H), 3.99 (s, 3H), 3.04-2.96 (m, 1H), 2.77 (s, 3H), 2.65 (s, 3H), 1.16-1.12 (m, 2H), 0.83-0.74 (m, 2H).

{2-Azetidin-1-yl-4-chloro-3-[4-(1H-pyrazol-1-yl)benzyl]quinolin-6-yl}(2,6-dimethylpyridin-3-yl)(1-methyl-1H-1,2,3-triazol-5-yl)methanol was purified via SFC with a Chiralpack AD-H column (5 µm 250×20 mm) using a mobile phase of 75% CO$_2$, 25% mixture of (MeOH/iPrOH 50/50 v/v (+0.3% iPrNH$_2$)) to provide two enantiomers. The first eluting enantiomer was Example 143b: MS (ESI): mass calcd. for C$_{31}$H$_{28}$ClF$_3$N$_6$O, 592.2. m/z found, 593.2 [M+H]$^+$; $^1$H NMR (600 MHz, CDCl$_3$) δ ppm 8.02 (d, J=2.2 Hz, 1H), 7.77 (d, J=8.8 Hz, 1H), 7.56 (d, J=8.0 Hz, 2H), 7.32 (dd, J=8.8, 2.2 Hz, 1H), 7.26 (d, J=8.0 Hz, 2H), 6.99 (d, J=8.0 Hz, 1H), 6.93 (d, J=8.3 Hz, 2H), 4.23 (s, 2H), 3.93 (s, 3H), 2.95-2.86 (m, 1H), 2.53 (s, 3H), 2.37 (s, 3H), 0.86-0.76 (m, 2H), 0.39-0.32 (m, 2H) and the second eluting enantiomer was Example 143c: MS (ESI): mass calcd. for C$_{31}$H$_{28}$ClF$_3$N$_6$O, 592.2. m/z found, 593.2 [M+H]$^+$; $^1$H NMR (600 MHz, CDCl$_3$) δ ppm 8.02 (d, J=2.2 Hz, 1H), 7.77 (d, J=8.8 Hz, 1H), 7.56 (d, J=8.0 Hz, 2H), 7.32 (dd, J=8.8, 2.2 Hz, 1H), 7.26 (d, J=8.0 Hz, 2H), 6.99 (d, J=8.0 Hz, 1H), 6.93 (d, J=8.3 Hz, 2H), 4.23 (s, 2H), 3.93 (s, 3H), 2.95-2.87 (m, 1H), 2.53 (s, 3H), 2.37 (s, 3H), 0.85-0.77 (m, 2H), 0.39-0.32 (m, 2H).

Example 144a

{2-Chloro-4-(cyclopropylamino)-3-[4-(trifluoromethyl)benzyl]quinolin-6-yl}(2,6-dimethylpyridin-3-yl)(1-methyl-1H-1,2,3-triazol-5-yl)methanol

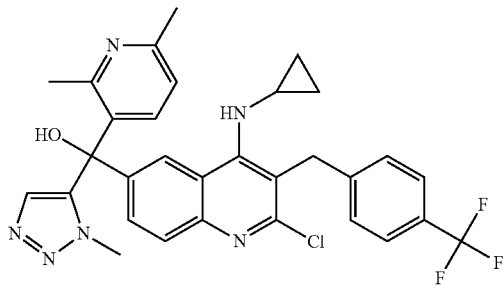 [SMILES: Cc1ccc(C(O)(c2ccc3nc(Cl)c(Cc4ccc(C(F)(F)F)cc4)c(NC4CC4)c3c2)c2cnnn2C)c(C)n1]

Purification of the crude reaction mixture from the synthesis of {4-chloro-2-(cyclopropylamino)-3-[4-(trifluoromethyl)benzyl]quinolin-6-yl}(2,6-dimethylpyridin-3-yl)(1-methyl-1H-1,2,3-triazol-5-yl)methanol (Example 143a) also afforded the title compound as a regioisomer. MS (ESI): mass calcd. for C$_{31}$H$_{28}$ClF$_3$N$_6$O, 592.2. m/z found, 593.5 [M+H]$^+$. $^1$H NMR (600 MHz, CD$_3$OD) δ ppm 8.86 (d, J=2.1 Hz, 1H), 7.91 (d, J=9.0 Hz, 1H), 7.79 (d, J=8.4 Hz, 1H), 7.74 (dd, J=9.0, 2.0 Hz, 1H), 7.67 (d, J=8.4 Hz, 1H), 7.58 (d, J=8.0 Hz, 2H), 7.33 (d, J=8.0 Hz, 2H), 7.25 (s, 1H), 4.47 (s, 2H), 4.00 (s, 3H), 3.03-2.97 (m, 1H), 2.78 (s, 3H), 2.70 (s, 3H), 0.75-0.63 (m, 2H), 0.44-0.36 (m, 2H).

{2-Chloro-4-(cyclopropylamino)-3-[4-(trifluoromethyl)benzyl]quinolin-6-yl}(2,6-dimethylpyridin-3-yl)(1-methyl-1H-1,2,3-triazol-5-yl)methanol was purified via SFC with a Chiracel OD-H column (5 µm 250×20 mm) using a mobile phase of 70% CO$_2$ and a 30% mixture of (EtOH/iPrOH 50/50 v/v (+0.3% iPrNH$_2$)) to provide two enantiomers. The first eluting enantiomer was Example 144b: MS (ESI): mass calcd. for C$_{31}$H$_{28}$ClF$_3$N$_6$O, 592.2. m/z found, 593.2 [M+H]$^+$; $^1$H NMR (600 MHz, CDCl$_3$) δ ppm 8.02 (d, J=2.2 Hz, 1H), 7.77 (d, J=8.8 Hz, 1H), 7.56 (d, J=8.0 Hz, 2H), 7.32 (dd, J=8.8, 2.2 Hz, 1H), 7.26 (d, J=8.0 Hz, 2H), 6.99 (d, J=8.0 Hz, 1H), 6.93 (d, J=8.3 Hz, 2H), 4.23 (s, 2H), 3.93 (s, 3H), 2.95-2.87 (m, 1H), 2.53 (s, 3H), 2.37 (s, 3H), 0.85-0.76 (m, 2H), 0.41-0.32 (m, 2H) and the second eluting enantiomer was Example 144c: MS (ESI): mass calcd. for C$_{31}$H$_{28}$ClF$_3$N$_6$O, 592.2. m/z found, 593.2 [M+H]$^+$; $^1$H NMR (600 MHz, CDCl$_3$) δ ppm 8.33 (d, J=2.1 Hz, 1H), 7.86 (d, J=8.9 Hz, 1H), 7.58 (dd, J=8.9, 2.1 Hz, 1H), 7.54 (d, J=8.0 Hz, 2H), 7.26 (d, J=8.0 Hz, 2H), 6.94-6.89 (m, 2H), 6.80 (s, 1H), 4.31 (s, 2H), 3.88 (s, 3H), 2.60-2.51 (m, 1H), 2.49 (s, 3H), 2.35 (s, 3H), 0.52-0.34 (m, 2H), 0.19-0.05 (m, 2H).

Example 145a

{4-Chloro-3-[4-(1H-pyrazol-1-yl)benzyl]-2-pyrrolidin-1-ylquinolin-6-yl}(1-methyl-1H-imidazol-5-yl)[6-(trifluoromethyl)pyridin-3-yl]methanol

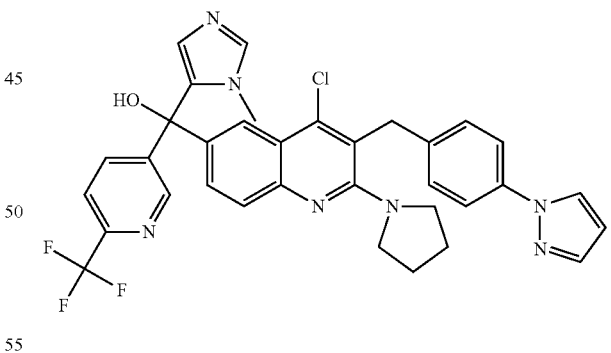

{2,4-Dichloro-3-[4-(1H-pyrazol-1-yl)benzyl]quinolin-6-yl}(1-methyl-1H-imidazol-5-yl)pyrimidin-2-ylmethanol (100 mg, 0.164 mmol, Intermediate), pyrrolidine (118 mg, 1.64 mmol) and DMF (2 mL) were combined in a reaction tube, then sealed and heated to 100° C. and maintained at that temperature for 24 hours. The vessel was then cooled to room temperature and solvent was removed by a stream of nitrogen. The crude material was purified via reverse phase chromatography using acetonitrile with ammonium hydroxide in water as eluent to provide the title compound. MS (ESI): mass calcd. for C$_{34}$H$_{29}$ClF$_3$N$_7$O, 643.2. m/z found, 644.3 [M+H]$^+$. $^1$H NMR (600 MHz, CDCl$_3$) δ ppm 8.84 (d, J=1.5 Hz, 1H), 8.03 (d, J=1.8 Hz, 1H), 7.98 (s, 1H), 7.94 (dd, J=8.2, 1.6 Hz, 1H), 7.86 (d, J=2.4 Hz, 1H), 7.71 (d, J=8.8 Hz, 1H), 7.66 (d, J=1.5 Hz, 1H), 7.60 (d, J=8.3 Hz, 1H), 7.58 (d, J=8.6 Hz, 2H), 7.50 (dd, J=8.8, 1.9 Hz, 1H), 7.19 (d, J=8.6 Hz, 2H), 6.43 (s, 1H), 6.43-6.41 (m, 1H), 4.42 (s, 2H), 3.56-3.45 (m, 7H), 1.88-1.76 (m, 4H).

{4-Chloro-3-[4-(1H-pyrazol-1-yl)benzyl]-2-pyrrolidin-1-ylquinolin-6-yl}(1-methyl-1H-imidazol-5-yl)[6-(trifluoromethyl)pyridin-3-yl]methanol was purified on a chiralcel OD column with 80-20 pentane/ethanol to provide two enantiomers. The first eluting enantiomer was Example 145b: MS (ESI): mass calcd. for $C_{34}H_{29}ClF_3N_7O$, 643.2. m/z found, 644.3 [M+H]$^+$; $^1$H NMR (400 MHz, CDCl$_3$) δ ppm 8.81 (d, J=1.8 Hz, 1H), 8.06 (d, J=2.0 Hz, 1H), 7.87 (dd, J=8.4, 2.1 Hz, 2H), 7.68 (d, J=8.8 Hz, 1H), 7.65 (d, J=1.6 Hz, 1H), 7.63-7.55 (m, 3H), 7.43 (dd, J=8.8, 2.1 Hz, 1H), 7.19 (d, J=8.5 Hz, 2H), 7.13 (s, 1H), 6.46-6.40 (m, 1H), 6.23 (d, J=0.8 Hz, 1H), 4.41 (s, 2H), 3.58-3.48 (m, 4H), 3.32 (s, 3H), 1.90-1.78 (m, 4H) and the second eluting enantiomer was Example 145c: MS (ESI): mass calcd. for $C_{34}H_{29}ClF_3N_7O$, 643.2. m/z found, 644.3 [M+H]$^+$; $^1$H NMR (400 MHz, CDCl$_3$) δ ppm 8.81 (d, J=1.8 Hz, 1H), 8.06 (d, J=2.0 Hz, 1H), 7.91-7.83 (m, 2H), 7.68 (d, J=8.8 Hz, 1H), 7.66 (d, J=1.5 Hz, 1H), 7.61 (d, J=8.3 Hz, 1H), 7.59-7.55 (m, 2H), 7.44 (dd, J=8.8, 2.1 Hz, 1H), 7.19 (d, J=8.5 Hz, 2H), 7.14 (s, 1H), 6.46-6.40 (m, 1H), 6.24 (s, 1H), 4.41 (s, 2H), 3.59-3.48 (m, 4H), 3.32 (s, 3H), 1.89-1.77 (m, 4H).

Example 146a

{4-Chloro-2-morpholin-4-yl-3-[4-(1H-pyrazol-1-yl)benzyl]quinolin-6-yl}(1-methyl-1H-imidazol-5-yl)[6-(trifluoromethyl)pyridin-3-yl]methanol

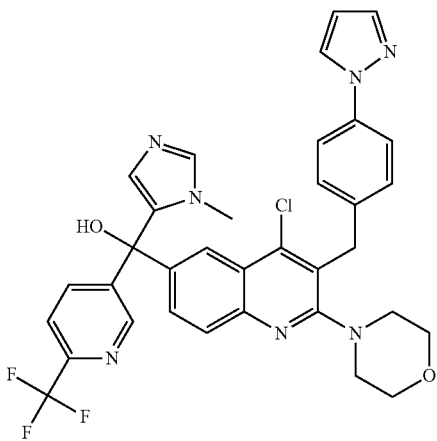 [SMILES: Cn1cncc1C(O)(c1ccc(C(F)(F)F)nc1)c1ccc2nc(N3CCOCC3)c(Cc3ccc(-n4cccn4)cc3)c(Cl)c2c1]

{2,4-Dichloro-3-[4-(1H-pyrazol-1-yl)benzyl]quinolin-6-yl}(1-methyl-1H-imidazol-5-yl)pyrimidin-2-ylmethanol (100 mg, 0.164 mmol, Intermediate 65), morpholine (144 mg, 1.64 mmol) and DMF (2 mL) were combined in a reaction tube, then sealed and heated to 100° C. and maintained at that temperature for 48 hours. The vessel was then cooled to room temperature and the solvent was removed by a stream of nitrogen. The crude material was purified via reverse phase chromatography using acetonitrile with ammonium hydroxide in water as eluent to afford the title compound. MS (ESI): mass calcd. for $C_{34}H_{29}ClF_3N_7O_2$, 659.2. m/z found, 660.3 [M+H]$^+$. $^1$H NMR (600 MHz, CDCl$_3$) δ ppm 8.80 (d, J=1.9 Hz, 1H), 8.17 (d, J=2.0 Hz, 1H), 7.88-7.83 (m, 3H), 7.63 (d, J=1.4 Hz, 1H), 7.60-7.52 (m, 3H), 7.25 (s, 1H), 7.22 (d, J=8.7 Hz, 2H), 7.10 (s, 1H), 6.42 (dd, J=2.4, 1.9 Hz, 1H), 6.21 (d, J=0.9 Hz, 1H), 4.38 (s, 2H), 3.83-3.75 (m, 4H), 3.30 (s, 3H), 3.25-3.16 (m, 4H).

{4-Chloro-2-morpholin-4-yl-3-[4-(1H-pyrazol-1-yl)benzyl]quinolin-6-yl}(1-methyl-1H-imidazol-5-yl)[6-(trifluoromethyl)pyridin-3-yl]methanol was purified on a chiralcel OD column with 80-20 pentane/ethanol to provide two enantiomers. The first eluting enantiomer was Example 146b: MS (ESI): mass calcd. for $C_{34}H_{29}ClF_3N_7O_2$, 659.2. m/z found, 660.3 [M+H]$^+$; $^1$H NMR (400 MHz, CDCl$_3$) δ ppm 8.80 (d, J=1.7 Hz, 1H), 8.17 (d, J=2.0 Hz, 1H), 7.92-7.81 (m, 3H), 7.65 (d, J=1.6 Hz, 1H), 7.62 (d, J=8.2 Hz, 1H), 7.60-7.53 (m, 3H), 7.22 (d, J=8.5 Hz, 2H), 7.15 (s, 1H), 6.81 (s, 1H), 6.46-6.39 (m, 1H), 6.25 (s, 1H), 4.38 (s, 2H), 3.83-3.75 (m, 4H), 3.32 (s, 3H), 3.25-3.17 (m, 4H) and the second eluting enantiomer was Example 146c: MS (ESI): mass calcd. for $C_{34}H_{29}ClF_3N_7O_2$, 659.2. m/z found, 660.3 [M+H]$^+$; $^1$H NMR (400 MHz, CDCl$_3$) δ ppm 8.80 (d, J=1.7 Hz, 1H), 8.17 (d, J=1.9 Hz, 1H), 7.92-7.81 (m, 3H), 7.65 (d, J=1.5 Hz, 1H), 7.62 (d, J=8.3 Hz, 1H), 7.60-7.52 (m, 3H), 7.22 (d, J=8.5 Hz, 2H), 7.16 (s, 1H), 6.65 (s, 1H), 6.46-6.40 (m, 1H), 6.26 (s, 1H), 4.38 (s, 2H), 3.84-3.76 (m, 4H), 3.32 (s, 3H), 3.26-3.17 (m, 4H).

Example 147a

{4-Chloro-2-(3-fluoroazetidin-1-yl)-3-[4-(1H-pyrazol-1-yl)benzyl]quinolin-6-yl}(1-methyl-1H-imidazol-5-yl)[6-(trifluoromethyl)pyridin-3-yl]methanol

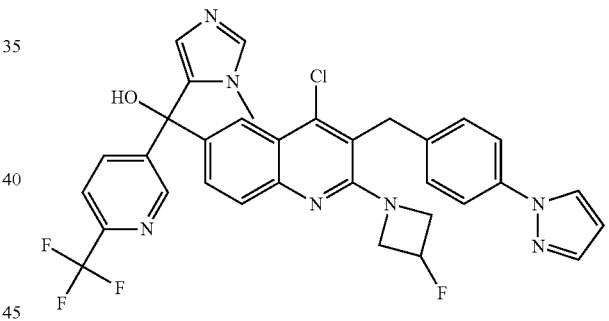

{2,4-Dichloro-3-[4-(1H-pyrazol-1-yl)benzyl]quinolin-6-yl}(1-methyl-1H-imidazol-5-yl)pyrimidin-2-ylmethanol (100 mg, 0.164 mmol, Intermediate 65), 3-fluoroazetidine hydrochloride (183 mg, 1.64 mmol) and DMF (2 mL) were combined in a reaction tube, then sealed and heated to 100° C. and maintained at that temperature for 24 hours. The residue was taken up into EtOAc, transferred to a reparatory funnel and extracted twice with a saturated, aqueous NH$_4$Cl solution. The organic phase was separated, dried over MgSO$_4$, filtered and concentrated under reduced pressure. The crude material was purified via reverse phase chromatography using acetonitrile with ammonium hydroxide in water as eluent to afford the title compound. MS (ESI): mass calcd. for $C_{33}H_{26}ClF_4N_7O$, 647.2. m/z found, 648.2 [M+H]$^+$. $^1$H NMR (600 MHz, CDCl$_3$) δ ppm 8.82 (d, J=1.7 Hz, 1H), 8.09 (d, J=2.0 Hz, 1H), 7.97-7.93 (m, 1H), 7.86 (d, J=2.3 Hz, 1H), 7.76 (d, J=8.8 Hz, 1H), 7.67 (d, J=1.5 Hz, 1H), 7.64 (d, J=8.3 Hz, 1H), 7.59 (d, J=8.6 Hz, 2H), 7.55-7.51 (m, 1H), 7.26 (s, 1H), 7.16 (d, J=8.6 Hz, 2H), 6.46-6.42 (m, 1H), 6.39 (s, 1H), 4.41-4.31 (m, 2H), 4.29 (s, 2H), 4.27-4.18 (m, 3H), 3.44 (s, 3H).

{4-Chloro-2-(3-fluoroazetidin-1-yl)-3-[4-(1H-pyrazol-1-yl)benzyl]quinolin-6-yl}(1-methyl-1H-imidazol-5-yl)[6-(trifluoromethyl)pyridin-3-yl]methanol was purified on SFC with a Chiralpak AD column using the eluent 80% $CO_2$ and 20% (2-propanol+0.2% isopropylamine) to provide two enantiomers. The first eluting enantiomer was Example 147b: MS (ESI): mass calcd. for $C_{33}H_{26}ClF_4N_7O$, 647.2. m/z found, 648.2 [M+H]$^+$; $^1$H NMR (600 MHz, CDCl$_3$) δ ppm 8.84-8.78 (m, 1H), 8.10 (d, J=2.1 Hz, 1H), 7.90 (dd, J=8.2, 2.2 Hz, 1H), 7.86 (d, J=2.5 Hz, 1H), 7.75 (d, J=8.8 Hz, 1H), 7.68 (d, J=1.8 Hz, 1H), 7.64 (d, J=8.2 Hz, 1H), 7.61-7.58 (m, 2H), 7.50 (dd, J=8.8, 2.1 Hz, 1H), 7.26-7.24 (m, 1H), 7.19-7.14 (m, 2H), 6.44 (dd, J=2.5, 1.8 Hz, 1H), 6.32 (s, 1H), 5.37-5.17 (m, 1H), 4.40-4.31 (m, 2H), 4.29 (s, 2H), 4.27-4.18 (m, 2H), 3.36 (s, 3H) and the second eluting enantiomer was Example 147c: MS (ESI): mass calcd. for $C_{33}H_{26}ClF_4N_7O$, 647.2. m/z found, 648.3 [M+H]$^+$; $^1$H NMR (600 MHz, CDCl$_3$) δ ppm 8.84-8.79 (m, 1H), 8.09 (d, J=2.1 Hz, 1H), 7.95-7.89 (m, 1H), 7.86 (dd, J=2.5, 0.6 Hz, 1H), 7.75 (d, J=8.8 Hz, 1H), 7.68 (d, J=1.8 Hz, 1H), 7.65 (d, J=8.2 Hz, 1H), 7.62-7.57 (m, 2H), 7.55-7.49 (m, 2H), 7.19-7.13 (m, 2H), 6.44 (dd, J=2.5, 1.8 Hz, 1H), 6.38 (s, 1H), 5.34-5.18 (m, 1H), 4.41-4.31 (m, 2H), 4.29 (s, 2H), 4.27-4.18 (m, 2H), 3.41 (s, 3H).

Example 148a

{4-Chloro-2-(3,3-difluoroazetidin-1-yl)-3-[4-(trifluoromethyl)benzyl]quinolin-6-yl}(2,6-dimethylpyridin-3-yl)(1-methyl-1H-1,2,3-triazol-5-yl)methanol

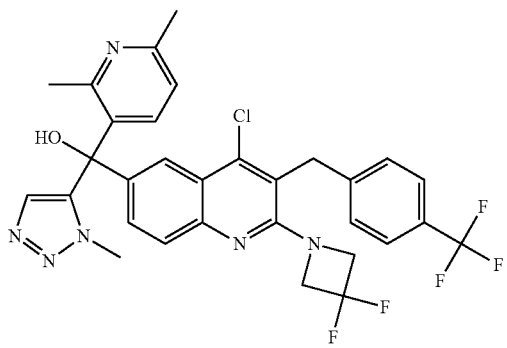 [SMILES: Cc1ccc(C(O)(c2ccc3nc(N4CC(F)(F)C4)c(Cc4ccc(C(F)(F)F)cc4)c(Cl)c3c2)c2cnnn2C)c(C)n1]

{2,4-Dichloro-3-[4-(1H-pyrazol-1-yl)benzyl]quinolin-6-yl}(2,6-dimethylpyridin-3-yl)(1-methyl-1H-1,2,3-triazol-5-yl)methanol (250 mg, 0.437 mmol, Example 139), 3,3-difluoroazetidine hydrochloride (113 μL, 0.873 mmol), diisopropylethyl amine (0.151 mL, 0.873 mmol) and NMP (1 mL) were combined in a reaction tube, then sealed and heated to 140° C. and maintained at that temperature for 24 hours. Analysis showed the reaction was incomplete therefore additional difluoroazetidine hydrochloride (113 μL, 0.873 mmol) was added and the contents refluxed for an additional 48 hours. The contents were cooled to room temperature, transferred to a separatory funnel with EtOAc dilution, and extracted once with a saturated, aqueous NH$_4$Cl solution then three times with deionized water. The organic phase was separated, dried over MgSO$_4$, filtered and concentrated under reduced pressure. The crude material was purified via reverse phase chromatography using acetonitrile with ammonium hydroxide in water as eluent to provide the title compound. MS (ESI): mass calcd. for $C_{31}H_{26}ClF_5N_6O$, 628.2. m/z found, 629.5 [M+H]$^+$. $^1$H NMR (400 MHz, CDCl$_3$) δ ppm 8.08 (d, J=2.1 Hz, 1H), 7.79 (d, J=8.8 Hz, 1H), 7.56 (d, J=8.1 Hz, 2H), 7.43 (dd, J=8.8, 2.2 Hz, 1H), 7.23 (d, J=8.0 Hz, 2H), 7.04-6.94 (m, 2H), 6.85 (s, 1H), 4.45-4.34 (m, 4H), 4.32 (s, 2H), 3.92 (s, 3H), 2.55 (s, 3H), 2.38 (s, 3H).

{2,4-Dichloro-3-[4-(1H-pyrazol-1-yl)benzyl]quinolin-6-yl}(2,6-dimethylpyridin-3-yl)(1-methyl-1H-1,2,3-triazol-5-yl)methanol was purified via SFC with a Chiralpak AD-H column (5 μm 250×20 mm) using a mobile phase of 85% $CO_2$ and a 15% mixture of (MeOH/iPrOH 50/50 v/v (+0.3% iPrNH$_2$)) to provide two enantiomers. The first eluting enantiomer was Example 148b: MS (ESI): mass calcd. for $C_{31}H_{26}ClF_5N_6O$, 628.2. m/z found, 629.7 [M+H]$^+$; $^1$H NMR (400 MHz, CDCl$_3$) δ ppm 8.07 (d, J=2.1 Hz, 1H), 7.78 (d, J=8.8 Hz, 1H), 7.56 (d, J=8.1 Hz, 2H), 7.41 (dd, J=8.8, 2.2 Hz, 1H), 7.23 (d, J=8.0 Hz, 2H), 7.01-6.91 (m, 2H), 6.87 (s, 1H), 4.45-4.34 (m, 3H), 4.31 (s, 2H), 3.93 (s, 3H), 2.54 (s, 3H), 2.37 (s, 3H) and the second eluting enantiomer was Example 148c: MS (ESI): mass calcd. for $C_{31}H_{26}ClF_5N_6O$, 628.2. m/z found, 629.7 [M+H]$^+$; $^1$H NMR (400 MHz, CDCl$_3$) δ ppm 8.07 (d, J=2.1 Hz, 1H), 7.78 (d, J=8.8 Hz, 1H), 7.57 (d, J=8.0 Hz, 2H), 7.39 (dd, J=8.8, 2.2 Hz, 1H), 7.22 (d, J=8.0 Hz, 2H), 6.98-6.91 (m, 2H), 6.90-6.86 (m, 1H), 4.46-4.35 (m, 4H), 4.31 (s, 2H), 3.93 (s, 3H), 2.53 (s, 3H), 2.36 (s, 3H).

Example 149

(4-Chloro-2-methoxy-3-(4-(trifluoromethyl)benzyl)quinolin-6-yl)bis(1-methyl-1H-imidazol-5-yl)methanol

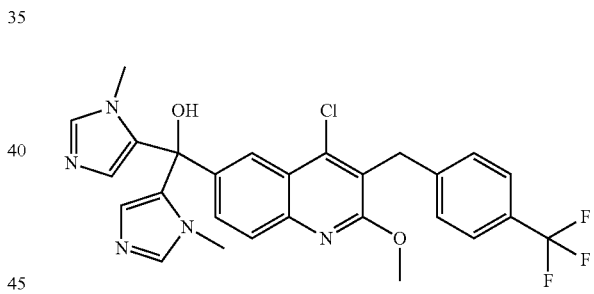

n-BuLi (1.6 M in hexanes, 0.34 mL, 0.56 mmol) was added dropwise to a mixture of 6-bromo-2,4-dichloro-3-(4-(trifluoromethyl)benzyl)quinoline (0.20 g, 0.467 mmol, Intermediate 12: step d) and bis(1-methyl-1H-imidazol-5-yl)methanone (0.097 g, 0.513 mmol, Intermediate 55: step b) in dry THF at −78° C. over a 30 minute period. Stirring was continued at −78° C. for 10 minutes. The reaction mixture was warmed up to 0° C., stirred for 35 minutes and then saturated aqueous NH$_4$Cl was added. The mixture was warmed to room temperature, H$_2$O was added and the layers were separated. The aqueous layer was extracted with EtOAc and the combined organic extracts washed with brine, dried over Na$_2$SO$_4$, evaporated in vacuo and chromatographed (10% MeOH in CH$_2$Cl$_2$) to provide the title compound. $^1$H NMR (400 MHz, CDCl$_3$) δ 8.21 (br. s., 1H), 7.75 (d, J=8.6 Hz, 1H), 7.50 (d, J=8.1 Hz, 2H), 7.36-7.46 (m, 3H), 7.27-7.32 (m, 2H), 6.33 (br. s., 2H), 4.31 (br. s., 2H), 4.07 (s, 3H), 3.44-3.56 (m, 6H); MS (ESI) [M+H]$^+$

Example 150

(2,4-Dichloro-3-(4-fluorobenzyl)quinolin-6-yl)(1-methyl-1H-imidazol-5-yl)(6-(trifluoromethyl)pyridin-3-yl)methanol

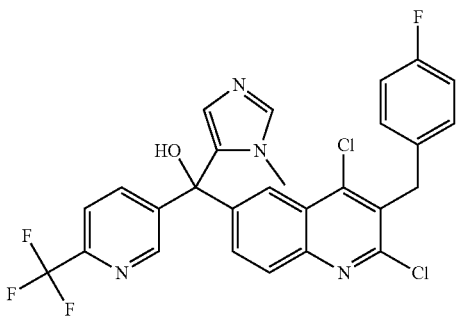 [SMILES: Cn1cncc1C(O)(c1ccc(C(F)(F)F)nc1)c1ccc2nc(Cl)c(Cc3ccc(F)cc3)c(Cl)c2c1]

A solution of n-BuLi (2.5 M in hexanes, 2.04 mL, 5.1 mmol) was added dropwise by syringe to a solution of 6-bromo-2,4-dichloro-3-(4-fluorobenzyl)quinoline (2.003 g, 5.202 mmol, Intermediate 42: step c) in dry THF (52 mL) in a dry ice-acetone bath. After 1-2 minutes, a solution of (1-methyl-1H-imidazol-5-yl)(6-(trifluoromethyl)pyridin-3-yl)methanone (1.328 g, 5.203 mmol, Intermediate 2: step c) in dry THF (5 mL) was added dropwise. The reaction was stirred for 5 minutes, then switched to an ice bath for 2.5 hours. The reaction was then removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated to dryness. The crude product was purified by flash column chromatography (silica gel, 0-2.5% MeOH-DCM) to provide the title compound. $^1$H NMR (400 MHz, DMSO-$d_6$) δ 8.79 (d, J=2.1 Hz, 1H), 8.26 (d, J=2.0 Hz, 1H), 8.05 (d, J=8.8 Hz, 1H), 8.01-7.97 (m, 1H), 7.95-7.91 (m, 1H), 7.81-7.75 (m, 2H), 7.60 (s, 1H), 7.27-7.20 (m, 2H), 7.16-7.08 (m, 2H), 6.28 (d, J=1.2 Hz, 1H), 4.45 (s, 2H), 3.35 (s, 3H); MS m/e 561.2 [M+H]$^+$.

Example 151

(3-(4-(1H-Pyrazol-1-yl)benzyl)-2,4-dichloroquinolin-6-yl)(2,6-dimethylpyridin-3-yl)(1-methyl-1H-1,2,3-triazol-5-yl)methanol

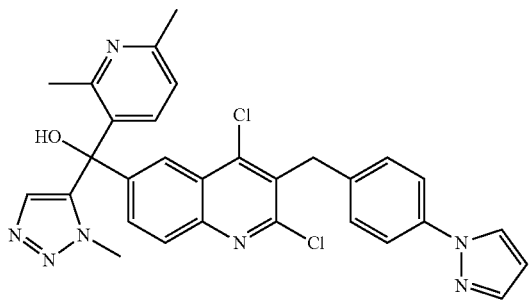 [SMILES: Cc1ccc(C(O)(c2ccc3nc(Cl)c(Cc4ccc(-n5cccn5)cc4)c(Cl)c3c2)c2cnnn2C)c(C)n1]

6-Bromo-2,4-dichloro-3-phenylquinoline (2.00 g, 4.62 mmol, Intermediate 3: step c) was dissolved in THF (250 mL) in a dry round bottom flask under an $N_2$ atmosphere, then cooled to −45° C. in a dry ice acetone bath. n-BuLi (1.6 M in hexanes, 3.18 mL, 5.08 mmol) was then added dropwise via syringe over approximately 2 minutes and the resulting mixture was allowed to stir at that temperature for an additional 2 minutes. (2,6-Dimethylpyridin-3-yl)(1-methyl-1H-1,2,3-triazol-5-yl)methanone (1.10 g, 5.08 mmol, Intermediate 19: step b) in THF (15 mL) was then added to the reaction vessel via cannula over approximately 5 minutes. The reaction solution was stirred at −78° C. for approximately 5 minutes, then the dry ice bath was removed and replaced with an ice water bath and stirred at 0° C. for approximately 1 hour. The reaction was then quenched with a saturated, aqueous $NH_4Cl$ solution, then transferred to a separatory funnel with EtOAc. The organic phase was separated, then the aqueous layer was back extracted with EtOAc and the combined organic phases were dried over $MgSO_4$, filtered and concentrated under reduced pressure. The crude product was purified by flash column chromatography (silica gel, 0-10% DCM/(10% of a 2 M $NH_3$ MeOH in DCM)) then further purified via reverse phase chromatography using acetonitrile with ammonium hydroxide in water as eluent to afford the title compound. MS (ESI): mass calcd. For $C_{30}H_{25}Cl_2N_7O$, 570.5. m/z found, 570.5 [M+H]$^+$. $^1$H NMR (400 MHz, CDCl$_3$) δ 8.27-8.22 (m, 1H), 8.07-8.02 (m, 1H), 7.84-7.77 (m, 1H), 7.73-7.67 (m, 1H), 7.61 (d, J=1.9 Hz, 1H), 7.18-7.13 (m, 2H), 7.04-6.98 (m, 3H), 6.86 (d, J=8.2 Hz, 1H), 6.76 (d, J=8.1 Hz, 1H), 5.91 (d, J=1.9 Hz, 1H), 4.51 (s, 2H), 3.94 (s, 3H), 2.40 (s, 3H), 2.32 (s, 3H).

Example 152

3-Benzyl-6-(hydroxy(1-methyl-1H-imidazol-5-yl)(pyridin-2-yl)methyl)-2-(trifluoromethyl)quinolin-4-ol•TFA

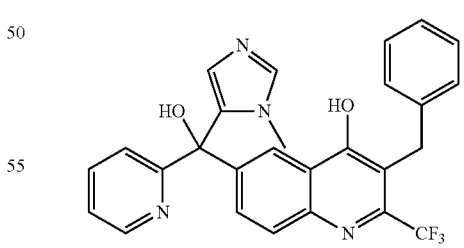

The title compound was isolated from the reaction that formed example 98a. $^1$H NMR (400 MHz, MeOH-d4) δ 8.94 (s, 1H), 8.60 (d, J=4.55 Hz, 1H), 8.29 (d, J=2.02 Hz, 1H), 7.88-7.95 (m, 2H), 7.85 (d, J=8.59 Hz, 1H), 7.70 (d, J=8.08 Hz, 1H), 7.42 (dd, J=5.05, 7.07 Hz, 1H), 7.16-7.22 (m, 2H), 7.06-7.16 (m, 3H), 7.02 (s, 1H), 4.12 (s, 2H), 3.62 (s, 3H); MS m/e 491.0 [M+H]$^+$.

Example 153

3-Benzyl-6-(hydroxy(1-methyl-1H-imidazol-5-yl)(6-(trifluoromethyl)pyridin-3-yl)methyl)-2-(1-methyl-1H-imidazol-2-yl)quinoline-4-carbonitrile•TFA

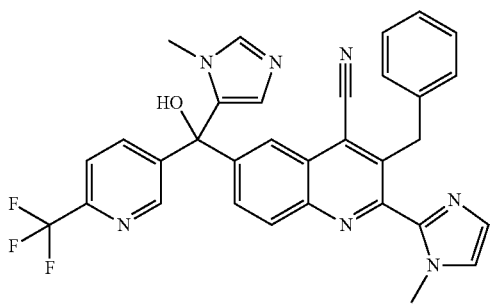 [SMILES: Cn1cncc1C(O)(c1ccc(C(F)(F)F)nc1)c1ccc2nc(-c3nccn3C)c(Cc3ccccc3)c(C#N)c2c1]

The title compound was prepared using (3-benzyl-4-chloro-2-(1-methyl-1H-imidazol-2-yl)quinolin-6-yl)(1-methyl-1H-imidazol-5-yl)(6-(trifluoromethyl)pyridin-3-yl)methanol•TFA (Example 113a) in place of (3-benzyl-4-chloro-2-(trifluoromethyl)quinolin-6-yl)(4-chlorophenyl)(1-methyl-1H-imidazol-5-yl)methanol•TFA (Example 100) using the procedure described for Example 103, with the exception that the reaction was carried out at 110° C. for 3 hours. $^1$H NMR (400 MHz, MeOH-d4) δ 9.10 (s, 1H), 8.95 (s, 1H), 8.88 (d, J=2.53 Hz, 1H), 8.44 (d, J=2.02 Hz, 1H), 8.30 (d, J=9.09 Hz, 1H), 8.18 (dd, J=2.27, 8.34 Hz, 1H), 7.99 (dd, J=2.02, 8.59 Hz, 1H), 7.92 (d, J=8.08 Hz, 1H), 7.79 (d, J=1.52 Hz, 1H), 7.21-7.26 (m, 4H), 6.88 (d, J=6.06 Hz, 2H), 4.59 (s, 2H), 3.76 (s, 3H), 3.40 (s, 3H); MS m/e 579.9 [M+H]$^+$.

Example 154a 3-(4-(1H-pyrazol-1-yl)benzyl)-6-((4-chlorophenyl)(hydroxy)(1-methyl-1H-imidazol-5-yl)methyl)-2-(diethylamino)quinoline-4-carbonitrile

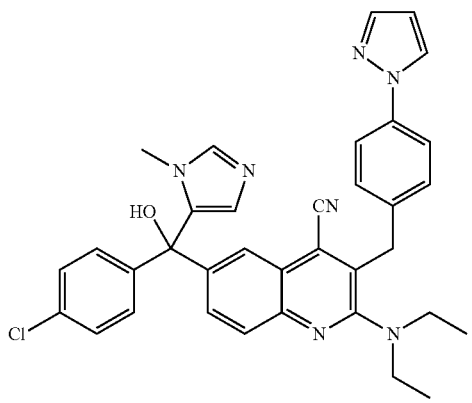 [SMILES: CCN(CC)c1nc2ccc(C(O)(c3ccc(Cl)cc3)c3cncn3C)cc2c(C#N)c1Cc1ccc(-n2cccn2)cc1]

A tube was charged with (3-(4-(1H-pyrazol-1-yl)benzyl)-4-chloro-2-(diethylamino)quinolin-6-yl)(4-chlorophenyl)(1-methyl-1H-imidazol-5-yl)methanol (216 mg, 0.353 mmol, Intermediate 86: step b), Pd$_2$(dba)$_3$ (32.3 mg, 0.0353 mmol), dicyclohexyl(2',4',6'-triisopropyl-[1,1'-biphenyl]-2-yl)phosphine (X-Phos, 19.6 mg, 0.0353 mmol), Zn(CN)$_2$ (21.5 mg, 0.183 mmol), and zinc nanopowder (4.6 mg, 0.0706 mmol). The tube was evacuated and re-filled with argon (three cycles). Dimethylacetamide (1.4 mL) was then added, argon was bubbled through the mixture for 10 min, and the mixture was heated at 120° C. for 1.5 hours. The mixture was filtered through Celite®, washing with EtOAc. The filtrate was washed sequentially with 2 M aqueous NH$_4$OH, water, and half-saturated aqueous NaCl. The organic phase was dried (Na$_2$SO$_4$), filtered, and concentrated. The residue was purified by RP-HPLC (30-70% CH$_3$CN—H$_2$O, 0.1% TFA). HPLC fractions were basified (saturated aqueous NaHCO$_3$), partially concentrated, and extracted with DCM (3×). The organic extract was dried over Na$_2$SO$_4$, filtered, and concentrated to afford the title compound. MS m/e 602.2 [M+H]$^+$.

Example 154a was purified by chiral HPLC (Chiralpak OD, 20% EtOH-heptane) to give 2 enantiomers. Both enantiomers were then further purified on silica gel columns (0-5% MeOH-DCM). Example 154b: (first enantiomer to elute off chiral column) $^1$H NMR (400 MHz, DMSO-d6) δ 8.38-8.47 (m, 1H), 7.92 (d, J=1.96 Hz, 1H), 7.83 (d, J=9.05 Hz, 1H), 7.74 (d, J=8.56 Hz, 2H), 7.71 (d, J=1.96 Hz, 2H), 7.59 (dd, J=2.08, 8.93 Hz, 1H), 7.39-7.47 (m, 2H), 7.31-7.37 (m, 2H), 7.29 (d, J=8.56 Hz, 2H), 7.09 (s, 1H), 6.46-6.55 (m, 1H), 6.20 (s, 1H), 4.39 (s, 2H), 3.35 (s, 3H), 3.23-3.32 (m, 4H), 1.03 (t, J=6.97 Hz, 6H); MS m/e 602.2 [M+H]$^+$ and Example 154c: (second enantiomer to elute off chiral column) $^1$H NMR (400 MHz, DMSO-d6) δ 8.43 (d, J=2.45 Hz, 1H), 7.92 (d, J=1.96 Hz, 1H), 7.83 (d, J=9.05 Hz, 1H), 7.74 (d, J=8.56 Hz, 2H), 7.67-7.72 (m, 2H), 7.59 (dd, J=2.08, 8.93 Hz, 1H), 7.39-7.46 (m, 2H), 7.24-7.36 (m, 4H), 7.09 (s, 1H), 6.47-6.55 (m, 1H), 6.19 (d, J=0.98 Hz, 1H), 4.39 (s, 2H), 3.33-3.38 (m, 3H), 3.22-3.33 (m, 4H), 1.03 (t, J=6.97 Hz, 6H); MS m/e 602.2 [M+H]$^+$.

Example 155

(4-chlorophenyl)(2,4-dichloro-3-(4-(trifluoromethyl)benzyl)quinolin-6-yl)(1-methyl-1H-imidazol-5-yl)methanol•TFA

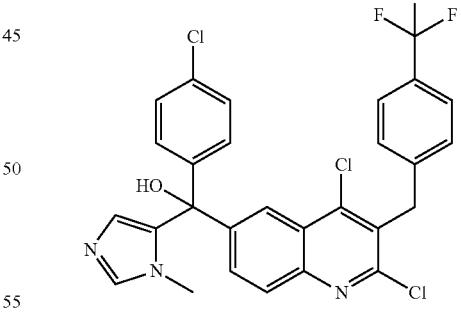

A solution of n-BuLi (1.6 Min hexanes, 0.14 mL, 0.23 mmol) was added dropwise by syringe over a 10 minute period to a mixture of 6-bromo-2,4-dichloro-3-(4-(trifluoromethyl)benzyl)quinoline (83.0 mg, 0.191 mmol, Intermediate 12: step c) and (4-chlorophenyl)(1-methyl-1H-imidazol-5-yl)methanone (46.8 mg, 0.191 mmol, Intermediate 43: step b) in dry THF (5 mL) and a dry ice-acetone bath. The reaction was stirred for 30 minutes, then removed from the cold bath and allowed to warm to room temperature and stir overnight. The reaction was quenched with saturated aqueous ammonium chloride. The mixture was partitioned between water and ethyl acetate. The separated aqueous phase was further extracted with ethyl acetate. The organic phase was dried (MgSO$_4$), filtered, and concentrated. The crude material was purified via reverse phase chromatography using acetonitrile with 0.05% trifluoroacetic acid in water as eluent. $^1$H NMR (500 MHz, CDCl$_3$) δ 8.40 (s, 1H), 8.18 (d, J=1.8 Hz, 1H), 8.02 (d, J=8.8 Hz, 1H), 7.74 (dd, J=8.9, 1.8 Hz, 1H), 7.53 (d, J=8.2 Hz, 2H), 7.38-7.30 (m, 6H), 6.57 (s, 1H), 4.57 (s, 2H), 3.61 (s, 3H); MS m/e 578.1 [M+H]$^+$.

Example 156a (4-chloro-2-methoxy-3-(4-(trifluoromethyl)benzyl) quinolin-6-yl)(2,4-dimethyloxazol-5-yl)(1-methyl-1H-1,2,3-triazol-5-yl)methanol

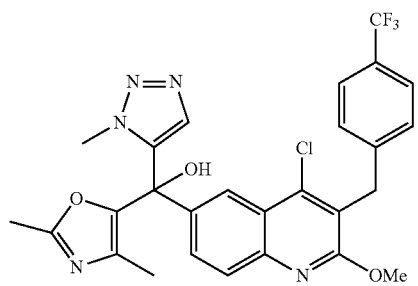 [SMILES: COc1nc2ccc(C(O)(c3oc(C)nc3C)c3cnnn3C)cc2c(Cl)c1Cc1ccc(C(F)(F)F)cc1]

To a flask containing 1-methyl-1H-1,2,3-triazole (200 mg, 2.41 mmol, prepared according to PCT Int. Appl., 2008098104) was added THF (20 mL) and the colorless solution was cooled to −40° C. Then, n-BuLi (2.5 M in hexanes, 1.0 mL, 2.5 mmol) was added drop wise which afforded a dark reddish-brown viscous solution. The mixture was stirred at −30° C. for 35 minutes, then a homogeneous THF solution of (4-chloro-2-methoxy-3-(4-(trifluoromethyl)benzyl)quinolin-6-yl)(2,4-dimethyloxazol-5-yl)methanone (500 mg, 1.05 mmol, in 4 mL THF, Intermediate 87: step b) was introduced at −20° C. The reaction mixture became a dark brown color and was then placed in an ice-water bath and allowed to warm gradually to room temperature. After 45 minutes, the mixture was quenched with aqueous NH$_4$Cl solution and extracted with EtOAc:THF (10:2), 4×50 mL. The combined organics were washed with brine, dried over Na$_2$SO$_4$, filtered and concentrated to provide a brown oil. Chromatography on silica gel (3% MeOH-DCM increasing to 5% MeOH-DCM) to provide the title compound as a faint amber solid. MS m/e 558.2 [M+H]$^+$. $^1$H NMR (400 MHz, CDCl$_3$) δ ppm 8.15 (d, J=2.0 Hz, 1H), 7.86 (d, J=8.8 Hz, 1H), 7.54-7.47 (m, 3H), 7.40 (d, J=8.1 Hz, 2H), 7.14 (s, 1H), 4.35 (s, 2H), 4.10 (s, 3H), 4.03 (s, 1H), 3.92 (s, 3H), 2.40 (s, 3H), 1.54 (s, 3H).

Example 156a was separated by Chiral HPLC (Chiralpak AD column, 5 uM, using EtOH to provide the first eluting enantiomer as Example 156b $^1$H NMR (400 MHz, CDCl$_3$) δ ppm 8.15 (d, J=2.1 Hz, 1H), 7.86 (d, J=8.7 Hz, 1H), 7.56-7.46 (m, 3H), 7.40 (d, J=8.0 Hz, 2H), 7.14 (s, 1H), 4.34 (s, 2H), 4.09 (s, 3H), 3.91 (s, 3H), 2.40 (s, 3H), 1.54 (s, 3H); and the second eluting enantiomer as Example 156c $^1$H NMR (400 MHz, CDCl$_3$) δ 8.15 (d, J=2.1 Hz, 1H), 7.86 (d, J=8.7 Hz, 1H), 7.55-7.48 (m, 3H), 7.40 (d, J=8.1 Hz, 2H), 7.14 (s, 1H), 4.35 (s, 2H), 4.10 (s, 3H), 3.92 (s, 3H), 2.41 (s, 3H), 1.54 (s, 3H).

Example 157a 1-(4-((3-(4-(1H-Pyrazol-1-yl)benzyl)-4-chloro-2-methoxyquinolin-6-yl)(4-fluorophenyl)(hydroxy)methyl)piperidin-1-yl)ethanone

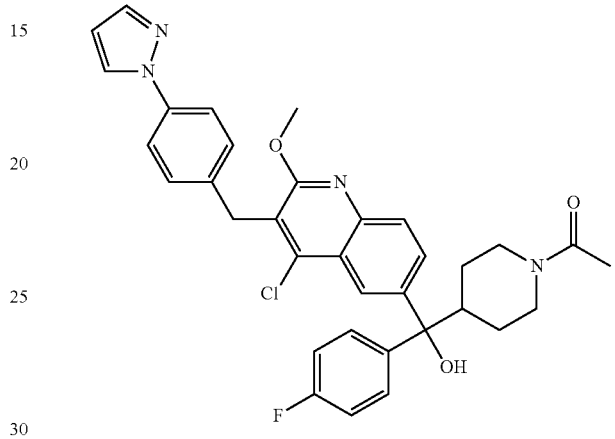

The title compound was prepared by substituting (2,6-dimethylpyridin-3-yl)(1-methyl-1H-1,2,3-triazol-5-yl)methanone (Intermediate 19: step b) with 1-(4-(4-fluorobenzoyl)piperidin-1-yl)ethanone (Intermediate 44) then following the procedure described for the preparation of Example 17. $^1$H NMR (400 MHz, CHLOROFORM-d) δ: 8.26 (s, 1H), 7.79-7.89 (m, 2H), 7.69 (s, 1H), 7.65 (br. s, 2H), 7.56 (d, J=8.59 Hz, 2H), 7.49 (dd, J=8.34, 5.31 Hz, 2H), 7.36 (d, J=8.6 Hz, 2H), 7.01 (t, J=8.59 Hz, 2H), 6.44 (s, 1H), 4.60-4.79 (m., 1H), 4.32 (s, 2H), 4.09 (s, 3H), 3.73-3.92 (m, 1H), 3.00-3.19 (m, 1H), 2.72 (br. s, 1H), 2.51-2.61 (m, 1H), 2.05 (s, 3H), 1.58-1.71 (m, 2H), 1.28-1.44 (m, 2H); MS (ESI) 599.

Example 157a was separated by Chiral HPLC (Chiralpak OD column (20 microhm; Daicel), using 100% MeOH as eluent at wavelength 242 nM to provide Example 157b (the first eluting enantiomer) $^1$H NMR (400 MHz., CHLOROFORM-d) δ: 8.26 (br. s., 1H), 7.85 (s, 1H), 7.73-7.81 (m, 1H), 7.59-7.71 (m, 2H), 7.56 (d, J=8.6 Hz, 2H), 7.44-7.53 (m, 2H), 7.35 (d, J=8.6 Hz, 2H), 6.95-7.11 (m, 2H), 6.43 (s, 1H), 4.69 (t, J=13.4 Hz, 1H), 4.31 (s, 2H), 4.06 (s, 3H), 3.82 (t, J=15.7 Hz, 1H), 3.00-3.18 (m, 1H), 2.65-2.79 (m, 1H), 2.48-2.65 (m, 1H), 2.03 (d, J=4.5 Hz, 3H), 1.25-1.68 (m, 4H); MS (ESI) 599 and Example 157c (the second eluting enantiomer) $^1$H NMR (400 MHz., CHLOROFORM-d) δ: 8.20-8.30 (m, 1H), 7.85 (d, J=2.5 Hz, 1H), 7.73-7.81 (m, 1H), 7.59-7.71 (m, 2H), 7.56 (d, J=8.6 Hz, 2H), 7.44-7.53 (m, 2H), 7.36 (d, J=8.1 Hz, 2H), 6.94-7.07 (m, 2H), 6.43 (s, 1H), 4.63-4.76 (m, 1H), 4.31 (s, 2H), 4.06 (s, 3H), 3.75-3.91 (m, 1H), 2.99-3.18 (m, 1H), 2.66-2.80 (m, 1H), 2.50-2.63 (m, 1H), 2.04 (d, J=4.5 Hz, 3H), 1.53-1.70 (m, 4H), 1.23-1.53 (m, 3H); MS (ESI) 599

Example 158a (3-(4-(1H-Pyrazol-1-yl)benzyl)-4-chloro-2-methoxyquinolin-6-yl)(4-fluorophenyl)(pyridin-3-yl)methanol

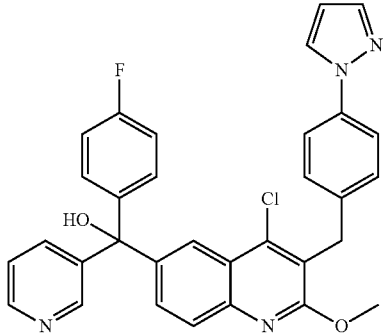 [SMILES: COc1nc2ccc(C(O)(c3ccc(F)cc3)c3cccnc3)cc2c(Cl)c1Cc1ccc(-n2cccn2)cc1]

A solution of n-BuLi (2.5 M in hexanes, 0.095 mL, 0.238 mmol) was added dropwise by syringe to a solution of 3-(4-(1H-pyrazol-1-yl)benzyl)-6-bromo-4-chloro-2-methoxyquinoline (105.5 mg, 0.246 mmol, Intermediate 10) in dry THF (2.5 mL) in a dry ice-acetone bath. After 1.5 minutes, a solution of commercially available (4-fluorophenyl)(pyridin-3-yl)methanone (58.7 mg, 0.292 mmol) in dry THF (0.2 mL) was added dropwise. The reaction mixture was stirred for 5 minutes in a dry ice-acetone bath, then the reaction flask was placed into an ice-water bath. After 10 minutes, the mixture was warmed to room temperature and the reaction was quenched with methanol and water. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 10-50% EtOAc-Hexanes followed by 0-10% MeOH-DCM) to provide the title compound as a white solid. $^1$H NMR (400 MHz, CDCl$_3$) δ ppm 8.50-8.48 (m, 1H), 8.43 (dd, J=4.8, 1.6 Hz, 1H), 8.02 (d, J=2.1 Hz, 1H), 7.83 (d, J=2.4 Hz, 1H), 7.77 (d, J=8.8 Hz, 1H), 7.67-7.64 (m, 2H), 7.55-7.52 (m, 2H), 7.50 (dd, J=8.8, 2.2 Hz, 1H), 7.33 (d, J=8.6 Hz, 2H), 7.26-7.20 (m, 3H), 7.03-6.96 (m, 2H), 6.42-6.40 (m, 1H), 4.28 (s, 2H), 4.07 (s, 3H); MS m/e 551.2 [M+H]$^+$.

Example 158a was purified by chiral HPLC (ChiralPak AD, 100% methanol) to provide two pure enantiomers. The first eluting enantiomer was Example 158b: $^1$H NMR (500 MHz, CDCl$_3$) δ ppm 8.51 (d, J=1.5 Hz, 1H), 8.46 (d, J=3.7 Hz, 1H), 8.02 (d, J=2.1 Hz, 1H), 7.83 (d, J=2.4 Hz, 1H), 7.78 (d, J=8.8 Hz, 1H), 7.68-7.65 (m, 2H), 7.56-7.52 (m, 2H), 7.50 (dd, J=8.8, 2.2 Hz, 1H), 7.34 (d, J=8.6 Hz, 2H), 7.27-7.22 (m, 3H), 7.04-6.97 (m, 2H), 6.48-6.38 (m, 1H), 4.29 (s, 2H), 4.08 (s, 3H); MS m/e 551.3 [M+H]$^+$. The second eluting enantiomer was Example 158c: $^1$H NMR (500 MHz, CDCl$_3$) δ ppm 8.50 (d, J=1.8 Hz, 1H), 8.45 (d, J=3.5 Hz, 1H), 8.02 (d, J=2.1 Hz, 1H), 7.83 (d, J=2.4 Hz, 1H), 7.78 (d, J=8.8 Hz, 1H), 7.68-7.64 (m, 2H), 7.56-7.52 (m, 2H), 7.50 (dd, J=8.8, 2.2 Hz, 1H), 7.33 (d, J=8.6 Hz, 2H), 7.27-7.21 (m, 3H), 7.04-6.97 (m, 2H), 6.44-6.39 (m, 1H), 4.29 (s, 2H), 4.07 (s, 3H); MS m/e 551.3 [M+H]$^+$.

Example 159a (3-(4-(1H-Pyrazol-1-yl)benzyl)-4-chloro-2-methoxyquinolin-6-yl)(3,4-dimethoxyphenyl)(pyridin-3-yl)methanol

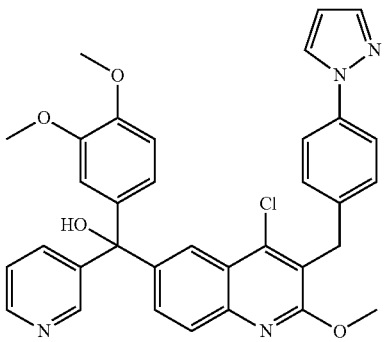 [SMILES: COc1ccc(C(O)(c2cccnc2)c2ccc3nc(OC)c(Cc4ccc(-n5cccn5)cc4)c(Cl)c3c2)cc1OC]

A solution of n-BuLi (2.5 M in hexanes, 0.05 mL, 0.125 mmol) was added dropwise by syringe to a solution of 3-(4-(1H-pyrazol-1-yl)benzyl)-6-bromo-4-chloro-2-methoxyquinoline (32.9 mg, 0.135 mmol, Intermediate 10) in dry THF (2 mL) in a dry ice-acetone bath. After 5 minutes, a solution of (3,4-dimethoxyphenyl)(pyridin-3-yl)methanone (32.9 mg, 0.135 mmol, Intermediate 88: step b) in dry THF (0.2 mL) was added dropwise. The reaction mixture was stirred for 5 minutes in a dry ice-acetone bath, then the reaction flask was placed into an ice-water bath. After 10 minutes, the mixture was warmed to room temperature and the reaction was quenched with saturated ammonium chloride. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 20-100% EtOAc-Hexanes) to provide the title compound as a white solid. $^1$H NMR (400 MHz, CDCl$_3$) δ ppm 8.61 (d, J=1.8 Hz, 1H), 8.53 (dd, J=4.8, 1.6 Hz, 1H), 8.10 (d, J=2.0 Hz, 1H), 7.85 (d, J=2.4 Hz, 1H), 7.79 (d, J=8.8 Hz, 1H), 7.69 (dt, J=8.0, 2.0 Hz, 2H), 7.57-7.52 (m, 3H), 7.35 (d, J=8.6 Hz, 2H), 7.29-7.25 (m, 1H), 6.91 (d, J=2.2 Hz, 1H), 6.79 (d, J=8.5 Hz, 1H), 6.66 (dd, J=8.4, 2.2 Hz, 1H), 6.44-6.42 (m, 1H), 4.31 (s, 2H), 4.08 (s, 3H), 3.88 (s, 3H), 3.76 (s, 3H); MS m/e 593.2 [M+H]$^+$.

Example 159a was purified by chiral HPLC (ChiralPak AD, 50:50 ethanol/methanol) to provide two pure enantiomers. The first eluting enantiomer was Example 159b: $^1$H NMR (500 MHz, CDCl$_3$) δ ppm 8.59 (d, J=1.7 Hz, 1H), 8.50 (d, J=3.7 Hz, 1H), 8.09 (d, J=2.1 Hz, 1H), 7.84 (d, J=2.4 Hz, 1H), 7.78 (d, J=8.8 Hz, 1H), 7.72-7.68 (m, 1H), 7.67 (d, J=1.6 Hz, 1H), 7.57-7.52 (m, 3H), 7.35 (d, J=8.5 Hz, 2H), 7.28-7.24 (m, 1H), 6.91 (d, J=2.1 Hz, 1H), 6.78 (d, J=8.5 Hz, 1H), 6.65 (dd, J=8.4, 2.1 Hz, 1H), 6.46-6.40 (m, 1H), 4.30 (s, 2H), 4.08 (s, 3H), 3.87 (s, 3H), 3.74 (s, 3H); MS m/e 593.3 [M+H]$^+$. The second eluting enantiomer was Example 159c: $^1$H NMR (500 MHz, CDCl$_3$) δ ppm 8.59 (s, 1H), 8.49 (d, J=3.7 Hz, 1H), 8.09 (d, J=2.1 Hz, 1H), 7.84 (d, J=2.4 Hz, 1H), 7.78 (d, J=8.8 Hz, 1H), 7.72-7.68 (m, 1H), 7.67 (d, J=1.6 Hz, 1H), 7.56-7.51 (m, 3H), 7.34 (d, J=8.6 Hz, 2H), 7.29-7.24 (m, 1H), 6.91 (d, J=2.1 Hz, 1H), 6.77 (d, J=8.5 Hz, 1H), 6.64 (dd, J=8.4, 2.1 Hz, 1H), 6.47-6.36 (m, 1H), 4.29 (s, 2H), 4.07 (s, 3H), 3.87 (s, 3H), 3.74 (s, 3H); MS m/e 593.3 [M+H]+.

Example 160a (3-(4-(1H-Pyrazol-1-yl)benzyl)-4-chloro-2-methoxyquinolin-6-yl)(4-fluorophenyl)(1-methyl-1H-imidazol-5-yl)methanol

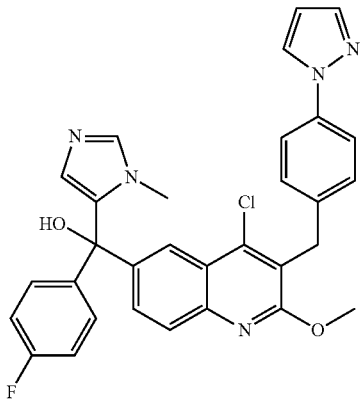 [SMILES: COc1nc2ccc(C(O)(c3ccc(F)cc3)c3cncn3C)cc2c(Cl)c1Cc1ccc(-n2cccn2)cc1]

A solution of n-BuLi (2.5 M in hexanes, 0.07 mL, 0.175 mmol) was added dropwise by syringe to a solution of 3-(4-(1H-pyrazol-1-yl)benzyl)-6-bromo-4-chloro-2-methoxyquinoline (75.8 mg, 0.177 mmol, Intermediate 10) in dry THF (3 mL) in a dry ice-acetone bath. After 1 minute, a solution of (4-fluorophenyl)(1-methyl-1H-imidazol-5-yl)methanone (37.8 mg, 0.185 mmol, Intermediate 89: step b) in dry THF (0.6 mL) was added dropwise. The reaction mixture was stirred for 5 minutes in a dry ice-acetone bath, then warmed to room temperature and the reaction was quenched with methanol and water. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 0-50% EtOAc-Hexanes) to provide the title compound as a clear foam. $^1$H NMR (400 MHz, CDCl$_3$) δ ppm 8.12 (d, J=2.1 Hz, 1H), 7.84 (d, J=2.4 Hz, 1H), 7.77 (d, J=8.7 Hz, 1H), 7.66 (d, J=1.6 Hz, 1H), 7.57-7.50 (m, 3H), 7.35 (d, J=8.6 Hz, 2H), 7.34-7.29 (m, 2H), 7.25 (s, 1H), 7.04-6.96 (m, 2H), 6.45-6.40 (m, 1H), 6.30 (s, 1H), 4.30 (s, 2H), 4.08 (s, 3H), 3.34 (s, 3H); MS m/e 554.1 [M+H]+.

Example 160a was purified by chiral HPLC (ChiralPak AD, 50:50 ethanol/methanol) to provide two pure enantiomers. The first eluting enantiomer was Example 160b: $^1$H NMR (500 MHz, CDCl$_3$) δ ppm 8.10 (d, J=2.2 Hz, 1H), 7.83 (d, J=2.5 Hz, 1H), 7.77 (d, J=8.7 Hz, 1H), 7.66 (d, J=1.7 Hz, 1H), 7.56-7.53 (m, 2H), 7.52 (dd, J=8.6, 2.0 Hz, 1H), 7.39 (s, 1H), 7.37-7.29 (m, 4H), 7.00 (t, J=8.7 Hz, 2H), 6.43-6.40 (m, 1H), 6.35-6.32 (m, 1H), 4.29 (s, 2H), 4.07 (s, 3H), 3.37 (s, 3H); MS m/e 554.3 [M+H]+. The second eluting enantiomer was Example 160c: $^1$H NMR (500 MHz, CDCl$_3$) δ ppm 8.08 (d, J=2.2 Hz, 1H), 7.82 (d, J=2.5 Hz, 1H), 7.76 (d, J=8.7 Hz, 1H), 7.66 (d, J=1.7 Hz, 1H), 7.56-7.49 (m, 4H), 7.36-7.29 (m, 4H), 6.99 (t, J=8.4 Hz, 2H), 6.42-6.39 (m, 1H), 6.35 (s, 1H), 4.28 (s, 2H), 4.06 (s, 3H), 3.38 (s, 3H); MS m/e 554.2 [M+H]+.

Example 161a (3-(4-(1H-Pyrazol-1-yl)benzyl)-4-chloro-2-methoxyquinolin-6-yl)(3,4-dichlorophenyl)(pyridin-3-yl)methanol

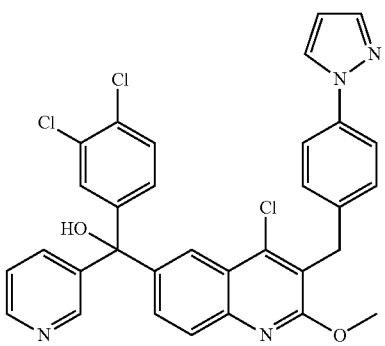 [SMILES: COc1nc2ccc(C(O)(c3cccnc3)c3ccc(Cl)c(Cl)c3)cc2c(Cl)c1Cc1ccc(-n2cccn2)cc1]

A solution of n-BuLi (2.5 M in hexanes, 0.07 mL, 0.175 mmol) was added dropwise by syringe to a solution of 3-(4-(1H-pyrazol-1-yl)benzyl)-6-bromo-4-chloro-2-methoxyquinoline (78.6 mg, 0.183 mmol, Intermediate 10) in dry THF (3 mL) in a dry ice-acetone bath. After 1 minute, a solution of (3,4-dichlorophenyl)(pyridin-3-yl)methanone (50.2 mg, 0.199 mmol, Intermediate 90: step b) in dry THF (0.2 mL) was added dropwise. The reaction mixture was stirred for 10 minutes in a dry ice-acetone bath, then the reaction flask was placed into an ice-water bath. After 20 minutes, the mixture was warmed to room temperature and the reaction was quenched with methanol. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 0-50% EtOAc-Hexanes) to provide the title compound as a clear oil. $^1$H NMR (400 MHz, CDCl$_3$) δ ppm 8.37 (d, J=2.0 Hz, 1H), 8.32 (dd, J=4.8, 1.4 Hz, 1H), 8.01 (d, J=2.1 Hz, 1H), 7.81 (dd, J=2.5, 0.4 Hz, 1H), 7.75 (d, J=8.8 Hz, 1H), 7.64-7.58 (m, 2H), 7.53-7.48 (m, 2H), 7.46 (d, J=2.2 Hz, 1H), 7.44 (dd, J=8.8, 2.2 Hz, 1H), 7.34-7.30 (m, 3H), 7.17 (dd, J=7.8, 4.7 Hz, 1H), 7.06 (dd, J=8.4, 2.2 Hz, 1H), 6.39 (dd, J=2.4, 1.9 Hz, 1H), 4.26 (s, 2H), 4.07 (s, 3H); MS m/e 601.1 [M+H]+.

Example 161a was purified by chiral HPLC (ChiralPak AD, 50:50 ethanol/methanol) to provide two pure enantiomers. The first eluting enantiomer was Example 161b: $^1$H NMR (500 MHz, CDCl$_3$) δ ppm 8.52-8.48 (m, 2H), 8.01 (d, J=2.2 Hz, 1H), 7.84 (d, J=2.3 Hz, 1H), 7.80 (d, J=8.7 Hz, 1H), 7.67 (d, J=1.7 Hz, 1H), 7.66-7.62 (m, 1H), 7.56-7.52 (m, 2H), 7.49-7.46 (m, 2H), 7.39 (d, J=8.4 Hz, 1H), 7.36-7.32 (m, 2H), 7.28-7.24 (m, 1H), 7.11 (dd, J=8.4, 2.2 Hz, 1H), 6.43-6.41 (m, 1H), 4.29 (s, 2H), 4.08 (s, 3H); MS m/e 601.2 [M+H]+. The second eluting enantiomer was Example 161c: $^1$H NMR (500 MHz, CDCl$_3$) δ ppm 8.55-8.47 (m, 2H), 8.01 (d, J=2.2 Hz, 1H), 7.83 (d, J=2.4 Hz, 1H), 7.79 (d, J=8.8 Hz, 1H), 7.67-7.63 (m, 2H), 7.56-7.51 (m, 2H), 7.49-7.45 (m, 2H), 7.39 (d, J=8.4 Hz, 1H), 7.36-7.32 (m, 2H), 7.29-7.26 (m, 1H), 7.11 (dd, J=8.4, 2.2 Hz, 1H), 6.43-6.40 (m, 1H), 4.29 (s, 2H), 4.08 (s, 3H); MS m/e 601.2 [M+H]+.

Example 162a ((3-(4-(1H-Pyrazol-1-yl)benzyl)-4-chloro-2-methoxyquinolin-6-yl)(pyridin-3-yl)(4-(trifluoromethyl)phenyl)methanol

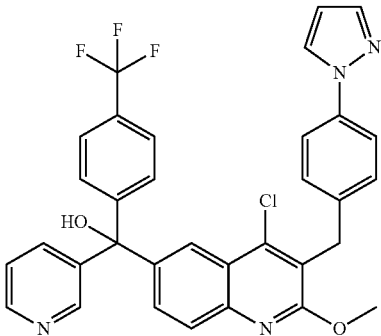 [SMILES: COc1nc2ccc(C(O)(c3ccc(C(F)(F)F)cc3)c3cccnc3)cc2c(Cl)c1Cc1ccc(-n2cccn2)cc1]

A solution of n-BuLi (2.5 M in hexanes, 0.07 mL, 0.175 mmol) was added dropwise by syringe to a solution of 3-(4-(1H-pyrazol-1-yl)benzyl)-6-bromo-4-chloro-2-methoxyquinoline (75.9 mg, 0.177 mmol, Intermediate 10) in dry THF (3 mL) in a dry ice-acetone bath. After 1.5 minutes, a solution of pyridin-3-yl(4-(trifluoromethyl)phenyl)methanone (48.0 mg, 0.191 mmol, Intermediate 91: step b) in dry THF (0.2 mL) was added dropwise. The reaction mixture was stirred for 5 minutes in a dry ice-acetone bath, then the reaction flask was placed into an ice-water bath. After 10 minutes, the mixture was warmed to room temperature and the reaction was quenched with methanol and water. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 10-50% EtOAc-Hexanes) to provide the title compound as a white solid. $^1$H NMR (500 MHz, CDCl$_3$) δ ppm 8.51 (d, J=2.2 Hz, 1H), 8.48 (dd, J=4.8, 1.4 Hz, 1H), 8.02 (d, J=2.1 Hz, 1H), 7.83 (d, J=2.4 Hz, 1H), 7.79 (d, J=8.8 Hz, 1H), 7.66 (d, J=1.6 Hz, 1H), 7.66-7.63 (m, 1H), 7.59 (d, J=8.4 Hz, 2H), 7.54 (d, J=8.5 Hz, 2H), 7.49 (dd, J=8.8, 2.2 Hz, 1H), 7.46 (d, J=8.3 Hz, 2H), 7.34 (d, J=8.5 Hz, 2H), 7.26-7.23 (m, 1H), 6.42 (t, J=2.1 Hz, 1H), 4.29 (s, 2H), 4.08 (s, 3H); MS m/e 602.1 [M+H]$^+$.

Example 162a was purified by chiral HPLC (ChiralPak AD, 100% ethanol) to provide two pure enantiomers. The first eluting enantiomer was Example 162b: MS m/e 601.3 [M+H]$^+$. The second eluting enantiomer was Example 162c: MS m/e 601.3 [M+H]$^+$.

Example 163

Di-tert-butyl 3,3'-((4-chloro-2-methoxy-3-(4-(trifluoromethyl)benzyl)quinolin-6-yl)(hydroxy)methylene)bis(azetidine-1-carboxylate)

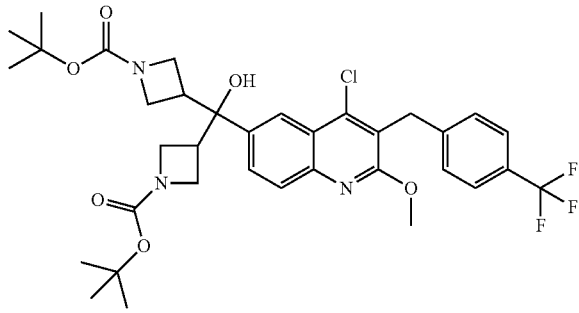 [SMILES: COc1nc2ccc(C(O)(C3CN(C(=O)OC(C)(C)C)C3)C3CN(C(=O)OC(C)(C)C)C3)cc2c(Cl)c1Cc1ccc(C(F)(F)F)cc1]

n-BuLi (1.60 M in hexane, 0.752 mL, 0.12 mmol) was added dropwise under argon to a slurry of 6-bromo-4-chloro-2-methoxy-3-(4-(trifluoromethyl)benzyl)quinoline (51.8 mg, 0.12 mmol, Intermediate 12: step d) in diethyl ether (0.8 mL) at ~−70° C. with stirring. The grey slurry was immediately transferred to an ice bath for ~30 seconds at which point a homogeneous dark amber solution formed. The reaction was then immediately transferred back to the dry ice/acetone bath and after stirring for 2 minutes was treated with a solution of di-tert-butyl 3,3'-carbonylbis(azetidine-1-carboxylate) (42.7 mg, 0.125 mmol, Intermediate 85: step b) in toluene (0.4 mL) over 50 seconds. After 5 minutes stirring at ~−70° C., the reaction was removed from the cold bath and stirred under ambient conditions for 1 minute and then transferred to an ice bath and stirred for 30 minutes. The homogeneous yellow reaction was then quenched with 5 M aqueous NH$_4$Cl (0.035 mL), diluted with EtOAc (3 mL), dried (Na$_2$SO$_4$), filtered, and concentrated. The residue was flash chromatographed (0-100% EtOAc in heptane over 16 column volumes) to provide a 65/35 mol fraction ratio of the title compound/di-tert-butyl 3,3'-carbonylbis(azetidine-1-carboxylate) as a thick yellow oil. This mixture was used in the next step without further purification. $^1$H NMR (400 MHz, CDCl$_3$) δ 8.14 (d, J=2.02 Hz, 1H), 7.83 (d, J=8.59 Hz, 1H), 7.58 (dd, J=2.02, 9.09 Hz, 1H), 7.51 (d, J=8.59 Hz, 2H), 7.40 (d, J=8.08 Hz, 2H), 4.36 (s, 2H), 4.03-4.16 (m, 5H), 3.92 (t, J=8.59 Hz, 2H), 3.54-3.67 (m, 4H), 3.11-3.21 (m, 2H), 1.39 (s, 18H); MS m/e 692.2 [M+H]$^+$.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants (K$_D$).

In a ThermoFluor® experiment where protein stability is monitored as the temperature is steadily increased, an equilibrium binding ligand causes the midpoint of an unfolding transition (T$_m$) to occur at a higher temperature. The shift in the melting point described as a ΔT$_m$ is proportional to the concentration and affinity of the ligand. The compound potency may be compared as a rank order of either ΔT$_m$ values at a single compound concentration or in terms of K$_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 mL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:
Reference RORγt $T_m$: 47.8° C.
$\Delta H_{(Tm)}$=115 kcal/mol
$\Delta C_{p(Tm)}$=3 kcal/mol Cell Based Biological Data Compounds were assessed for RORgt functional modulation using either the RORgt ligand binding domain (LBD) reporter assay, or the RORgt full-length (FL) reporter assay. Data from either assay can be used to demonstrate functional modulation of RORgt activity by compounds RORγt (LBD) Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. C935A), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the *renilla* luciferase gene under control of the SV40 promoter. *Renilla* luciferase expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 µg of pBIND-RORγt LBD or pBIND-RORγt LBD-AF2 and 5 µg pGL4.31 (Promega Cat no. C935A) using Fugene 6 (Invitrogen Cat no. E2691) at a 1:6 ratio of DNA:Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 µL 1× Glo Lysis Buffer (Promega). Dual Glo Luciferase Reagent (50 µL/well) was then added and firefly luciferase luminescence was read on an Envision after a ten minute incubation. Finally, Stop and Glo reagent (50 µL/well) was added and *renilla* luciferase luminescence was read on an Envision after a ten minute incubation. To calculate the effect of compounds on RORγt activity, the ratio of firefly to *renilla* luciferase was determined and plotted against compound concentration. Agonist compounds increase RORγt-driven luciferase expression, and antagonist or inverse agonist compounds decrease luciferase expression.

RORγt (Full-Length Human) Reporter Assay

A reporter assay was used to test functional activity of RORγt modulatory compounds on transcriptional activation driven by full-length human RORγt. Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and *Renilla* luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM_001001523.1 (SEQ ID NO:1). HEK293T cells were plated at 35000 per well in 96-well plate in medium of MEM with 8.6% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.1% and DMSO 0.1%. After overnight (16 to 20 hours) incubation, media were removed and cells were lysed with 20 μL 1× Passive Lysis Buffer (Promega) for 10-15 minutes. Luminescence was measured using a BMG LUMIstar OPTIMA plate reader, after addition of 75 μL/well firefly luciferase buffer, followed by 75 μL/well *Renilla* luciferase buffer. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total CD4+ T cells were isolated from the peripheral blood mononuclear cells (PBMC) of healthy donors using a CD4+ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, $IC_{50}$ (μM) |
| --- | --- | --- | --- | --- | --- | --- |
| 1a | ND | ND | ND | ND | ND | ND |
| 1b | 0.043 | 0.1 | 99 | ND | ND | 0.14 |
| 1c | 0.0015 | 0.022 | 98 | 0.015 | 101** | 0.03 |
| 2a | ND | ND | ND | ND | ND | ND |
| 2b | 0.11 | 0.13 | 101 | ND | ND | 0.3 |
| 2c | ND | ND | ND | ND | ND | ND |
| 3 | 0.046 | ND | ND | 0.078 | 95 | 0.11 |
| 4 | 0.000006 | ND | ND | 0.05 | 101 | ND |
| 5 | 0.000041 | ND | ND | 0.11 | 66**** | ND |
| 6 | 0.000046 | ND | ND | 0.061 | 55 | ND |
| 7 | 0.000032 | ND | ND | 0.078 | 90 | ND |
| 8 | 0.000009 | ND | ND | 0.024 | 101 | ND |
| 9 | 0.000055 | ND | ND | 0.068 | 75**** | ND |
| 10 | 0.00017 | ND | ND | 0.13 | 67 | ND |
| 11 | 0.000013 | ND | ND | 0.033 | 102 | ND |
| 12 | 0.0007 | 0.0031 | 99 | ND | ND | 0.0024 |
| 13 | 0.00027 | 0.2 | 96 | ND | ND | 0.1 |
| 14a | 0.017 | 0.042 | 105 | ND | ND | ND |
| 14b | 0.14 | 0.12 | 105 | ND | ND | 0.56 |
| 14c | 0.0055 | 0.024 | 106 | ND | ND | 0.03 |
| 15a | ND | ND | ND | ND | ND | ND |
| 15b | 0.14 | 0.41 | 99 | ND | ND | 0.95 |
| 15c | 0.017 | 0.028 | 97 | ND | ND | 0.02 |
| 16a | 0.0084 | 0.0098 | 101 | ND | ND | ND |
| 16b | 0.033 | 0.091 | 96 | ND | ND | 0.091 |
| 16c | 0.0046 | 0.02 | 100 | ND | ND | 0.01 |
| 17a | 0.00091 | 0.01 | 99 | ND | ND | ND |
| 17b | 0.2 | 0.66 | 97 | ND | ND | ND |
| 17c | 0.00029 | 0.009 | 101 | ND | ND | 0.00098 |
| 18a | 0.014 | 0.046 | 99 | ND | ND | ND |
| 18b | 0.008 | 0.083 | 99 | ND | ND | 0.014 |
| 18c | 0.05 | 0.088 | 91 | ND | ND | ND |
| 19a | 0.00036 | 0.021 | 100 | ND | ND | ND |
| 19b | 0.00038 | 0.0053 | 100 | ND | ND | ND |
| 19c | 0.0012 | 0.013 | 100 | ND | ND | ND |
| 20a | 0.0011 | 0.04 | 91 | ND | ND | ND |
| 20b | 0.39 | 1.4 | 84 | ND | ND | ND |
| 20c | 0.00062 | 0.057, ~0.03 | 93 | ND | ND | ND |
| 21a | 0.00031 | 0.006 | 101 | ND | ND | ND |
| 21b | 0.022 | 0.13 | 99 | ND | ND | ND |
| 21c | 0.00008 | 0.0087 | 98 | ND | ND | 0.0032 |
| 22a | ND | ND | ND | ND | ND | ND |
| 22b | 0.48 | 0.79 | 97 | ND | ND | ND |
| 22c | 0.002 | 0.011 | 98 | ND | ND | ND |
| 23a | 0.00014 | 0.018 | 99 | ND | ND | ND |
| 23b | 0.082 | 0.2 | 94 | ND | ND | ND |
| 23c | 0.00003 | 0.046 | 97 | 0.0029 | 101*** | 0.002 |
| 24a | 0.0015 | 0.0046 | 100 | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, IC$_{50}$ (μM) |
|---|---|---|---|---|---|---|
| 24b | 0.13 | ~0.22 | 92 | ND | ND | ND |
| 24c | 0.00032 | 0.025 | 97 | ND | ND | 0.0047 |
| 25a | ND | ND | ND | ND | ND | ND |
| 25b | 0.00001 | 0.0019, <0.003 | 100 | ND | ND | 0.0021 |
| 25c | 0.00002 | 0.0021 | 99 | ND | ND | 0.0018 |
| 26a | 0.0031 | 0.033 | 101 | 0.039 | 90 | ND |
| 26b | 0.015 | ND | ND | 0.055 | 95 | 0.045 |
| 26c | 0.00077 | ND | ND | 0.024 | 89 | ND |
| 27a | 0.0014 | 0.0044 | 101 | 0.009 | 95*** | ND |
| 27b | 0.00063 | ND | ND | 0.009 | 100 | ND |
| 27c | 0.014 | ND | ND | 0.017 | 88** | ND |
| 28a | 0.00025 | 0.011 | 99 | 0.006 | 99*** | ND |
| 28b | 0.16 | ND | ND | 0.22 | 93 | ND |
| 28c | 0.00012 | ND | ND | 0.0033 | 99 | ND |
| 29a | 0.00006 | ND | ND | 0.0039 | 101*** | ND |
| 29b | 0.00004 | ND | ND | 0.0033 | 101 | ND |
| 29c | 0.00015 | ND | ND | 0.0034 | 101 | ND |
| 30a | 0.00028 | ND | ND | ND | ND | ND |
| 30b | 0.3 | ND | ND | 0.24 | 52** | ND |
| 30c | 0.000092 | ND | ND | 0.011 | 100 | ND |
| 31 | 0.00079 | ND | ND | 0.021 | 99 | ND |
| 32a | 0.0011 | ND | ND | 0.008 | 95 | ND |
| 32b | 0.00086 | ND | ND | ND | ND | ND |
| 32c | 0.0013 | ND | ND | ND | ND | ND |
| 33a | 0.00005 | ND | ND | ND | ND | ND |
| 33b | 0.00008 | ND | ND | 0.0029 | 98** | ND |
| 33c | 0.00084 | ND | ND | 0.006 | 100 | ND |
| 34a | 0.00003 | ND | ND | ND | ND | ND |
| 34b | 0.00003 | ND | ND | 0.013 | 94 | ND |
| 34c | 0.0068 | ND | ND | 0.047 | 95 | ND |
| 35 | 0.003 | ND | ND | 0.012 | 100 | ND |
| 36 | 0.00073 | ND | ND | 0.007 | 93 | ND |
| 37 | 0.0019 | ND | ND | 0.01 | 93 | ND |
| 38a | 0.055 | 0.0019 | 100 | ND | ND | ND |
| 38b | 0.15 | 0.25 | 94 | ND | ND | ND |
| 38c | 0.0052 | 0.014 | 98 | ND | ND | 0.021 |
| 39a | 0.066 | 0.072 | 92 | ND | ND | 0.11 |
| 39b | 1.1 | 1.2 | 86 | ND | ND | ND |
| 39c | 0.019 | 0.081 | 98 | ND | ND | 0.037 |
| 40a | 0.0041 | 0.0082 | 98 | ND | ND | ND |
| 40b | 0.56 | 0.87 | 88 | ND | ND | ND |
| 40c | 0.00071 | 0.0023, ~0.3 | 94 | 0.0044 | 103 | 0.02 |
| 41a | 0.0028 | 0.024 | 99 | ND | ND | ND |
| 41b | 1.2 | 1.6 | 92 | ND | ND | ND |
| 41c | 0.0064 | 0.0059 | 99 | ND | ND | ND |
| 42a | 0.00038 | ND | ND | 0.014 | 101 | ND |
| 42b | 0.97 | ND | ND | ND | ND | ND |
| 42c | 0.00018 | ND | ND | 0.006 | 100 | ND |
| 43a | 0.001 | 0.0079 | 98 | ND | ND | ND |
| 43b | 0.00049 | 0.01 | 98 | ND | ND | ND |
| 43c | 0.00096 | 0.0053 | 99 | ND | ND | 0.014 |
| 44a | 0.0027 | 0.0076 | 97 | ND | ND | ND |
| 44b | 0.0052 | 0.024 | 99 | ND | ND | 0.017 |
| 44c | 0.009 | 0.019 | 99 | ND | ND | 0.0025 |
| 45 | 0.00021 | ND | ND | 0.047 | 106**** | ND |
| 46a | 0.069 | 2 | 72 | ND | ND | ND |
| 46b | 0.64 | ~6 | 59 | ND | ND | ND |
| 46c | 0.012 | ~6 | 62 | ND | ND | 0.27 |
| 47a | 0.012 | ~6 | 18 | ND | ND | ND |
| 47b | 0.11 | ~2 | 54 | ND | ND | ND |
| 47c | 0.0066 | ~6 | 42 | ND | ND | 3 |
| 48a | 0.00085 | 0.45 | 61 | ND | ND | ND |
| 48b | 0.25 | ~6 | 53 | ND | ND | ND |
| 48c | 0.0003 | ~0.08 | 63 | 0.01 | 65 | 0.0023 |
| 49a | 0.0017 | 0.052 | 84 | ND | ND | ND |
| 49b | 0.41 | ~3 | 62 | ND | ND | ND |
| 49c | 0.0027 | 0.038, ~0.02 | 83 | ND | ND | ND |
| 50 | 0.01 | ~4 | 82 | ND | ND | ND |
| 51a | ND | ND | ND | ND | ND | ND |
| 51b | 0.0039 | 0.17 | 46 | ND | ND | ~6 |
| 51c | 0.2 | >6 | 4 | ND | ND | ND |
| 52a | 0.00033 | ND | ND | ND | ND | ND |
| 52b | 0.55 | ND | ND | ND | ND | ND |
| 52c | 0.00008 | ND | ND | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, IC$_{50}$ (μM) |
|---|---|---|---|---|---|---|
| 53a | ND | ND | ND | ND | ND | ND |
| 53b | 0.0012 | >6 | 32 | ND | ND | 0.64 |
| 53c | 0.048 | 0.68 | 74 | ND | ND | 0.42 |
| 54a | 0.018 | 0.16 | 99 | 0.1 | 96**** | ND |
| 54b | 0.39 | 0.66 | 95 | ND | ND | ND |
| 54c | 0.0077 | 0.041 | 103 | ND | ND | 0.04 |
| 55a | 0.011 | 0.032 | 104 | ND | ND | ND |
| 55b | 0.53 | 0.5 | 96 | ND | ND | ND |
| 55c | 0.0045 | 0.093 | 100 | ND | ND | 0.056 |
| 56 | 0.2 | 0.45 | 101 | ND | ND | ND |
| 57a | 0.00003 | 0.022 | 100 | ND | ND | ND |
| 57b | 0.18 | ND | ND | ND | ND | 0.32 |
| 57c | 0.00002 | ND | ND | ND | ND | ND |
| 58a | ND | ND | ND | ND | ND | ND |
| 58b | 3.6 | ND | ND | ND | ND | ND |
| 58c | 0.37 | ND | ND | ND | ND | 0.65 |
| 59a | ND | ND | ND | ND | ND | ND |
| 59b | 0.034 | ND | ND | ND | ND | 0.07 |
| 59c | 0.8 | ND | ND | ND | ND | 1.1 |
| 60 | 3.1 | 0.62, ~2 | 83 | ND | ND | ND |
| 61 | 0.012 | 0.083 | 99 | ND | ND | ND |
| 62 | 0.041 | 0.12 | 107 | ND | ND | ND |
| 63 | 0.068 | 0.14 | 99 | ND | ND | ND |
| 64a | ND | ND | ND | ND | ND | ND |
| 64b | 0.54 | 0.73 | 103 | ND | ND | ND |
| 64c | 0.039 | 0.079 | 107 | ND | ND | 0.049 |
| 65a | 0.00019 | 0.0099 | 74 | ND | ND | ND |
| 65b | 0.000095 | 0.022 | 74 | ND | ND | ND |
| 65c | 0.00048 | 0.0072 | 81 | ND | ND | 0.007 |
| 66a | 0.00059 | 0.0082 | 90 | ND | ND | ND |
| 66b | 0.0011 | 0.0031 | 82 | ND | ND | ND |
| 66c | 0.0022 | 0.0026 | 90 | ND | ND | ND |
| 67 | 0.0001 | ND | ND | ND | ND | ND |
| 68 | 0.053 | 0.065 | 101 | ND | ND | ND |
| 69a | ND | ND | ND | ND | ND | ND |
| 69b | 0.0018 | 0.036 | 100 | ND | ND | 0.006 |
| 69c | 0.035 | 0.069 | 99 | ND | ND | 0.084 |
| 70 | 0.12 | 0.43 | 94 | ND | ND | ND |
| 71a | 0.061 | 0.21 | 98 | ND | ND | ND |
| 71b | 0.032 | 0.23 | 96 | ND | ND | 0.19 |
| 71c | 0.27 | 0.83 | 94 | ND | ND | ND |
| 72 | 1.1 | 1.2 | 53 | ND | ND | ND |
| 73a | 0.59 | >6 | 45 | ND | ND | ND |
| 73b | 0.044 | 0.7 | 35 | ND | ND | ND |
| 73c | 0.48 | >6 | 21 | ND | ND | ND |
| 74a | 0.0031 | ~0.01 | 98 | ND | ND | ND |
| 74b | 0.005 | 0.015 | 102 | 0.019 | 99 | 0.025 |
| 74c | 0.0077 | 0.02 | 101 | 0.022 | 96 | 0.036 |
| 75a | 0.0033 | ND | ND | 0.026 | 96 | ND |
| 75b | 0.0068 | ND | ND | 0.037 | 97 | ND |
| 75c | 0.0025 | ND | ND | 0.049 | 96 | ND |
| 76 | 0.00003 | ND | ND | ND | ND | ND |
| 77a | ND | ND | ND | ND | ND | ND |
| 77b | ND | ND | ND | ND | ND | ND |
| 77c | ND | ND | ND | ND | ND | ND |
| 78 | ND | ND | ND | ND | ND | ND |
| 79a | ND | ND | ND | ND | ND | ND |
| 79b | 0.58 | 0.76 | 92 | ND | ND | ND |
| 79c | 0.045 | 0.23 | 103 | ND | ND | 0.42 |
| 80 | ND | ND | ND | ND | ND | ND |
| 81a | ND | ND | ND | ND | ND | ND |
| 81b | 0.036 | 0.31 | 97 | ND | ND | 2.6 |
| 81c | 0.049 | 0.56 | 97 | ND | ND | ND |
| 82 | ND | ND | ND | ND | ND | ND |
| 83a | ND | ND | ND | ND | ND | ND |
| 83b | 0.00067 | 0.013 | 104 | ND | ND | 0.003 |
| 83c | 0.45 | 1.5 | 100 | ND | ND | ND |
| 84a | ND | ND | ND | ND | ND | ND |
| 84b | 0.18 | 0.21 | 103 | 0.089 | 92 | 0.22 |
| 84c | 0.000003 | 0.006 | 100 | 0.0045 | 100* | 0.0017 |
| 85a | ND | ND | ND | ND | ND | ND |
| 85b | 0.00031 | 0.0013 | 99 | 0.0059 | 100 | 0.003 |
| 85c | 0.0028 | 0.017 | 100 | 0.015 | 100 | 0.015 |
| 86a | ND | ND | ND | ND | ND | ND |
| 86b | 0.027 | ND | ND | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, IC$_{50}$ (μM) |
|---|---|---|---|---|---|---|
| 86c | 0.00006 | ND | ND | ND | ND | 0.044 |
| 87a | 0.0018 | 0.0068 | 100 | ND | ND | ND |
| 87b | 0.00073 | 0.013 | 100 | ND | ND | ND |
| 87c | 0.003 | 0.015 | 97 | ND | ND | ND |
| 88a | 0.0003 | 0.0042, ~0.02 | 98 | ND | ND | ND |
| 88b | 0.48 | 0.74 | 95 | ND | ND | ND |
| 88c | 0.00008 | 0.01 | 98 | 0.0026 | 107 | 0.0071 |
| 89a | 0.00029 | 0.0048 | 98 | ND | ND | ND |
| 89b | 0.0012 | <0.002 | 97 | ND | ND | 0.00013 |
| 89c | 0.00026 | <0.002 | 97 | ND | ND | <0.0001 |
| 90a | 0.005 | ND | ND | ND | ND | ND |
| 90b | 0.58 | ND | ND | 1.2 | 30 | ND |
| 90c | 0.0034 | ND | ND | 0.21 | 94 | 0.068 |
| 91 | 0.0002 | ND | ND | ND | ND | ND |
| 92a | 0.092 | 0.079 | 101 | ND | ND | ND |
| 92b | 2 | 2.8 | 79 | ND | ND | ND |
| 92c | 0.019 | 0.03 | 96 | ND | ND | 0.03 |
| 93 | 0.0006 | ND | ND | 0.009 | 102** | ND |
| 94 | 0.00048 | ND | ND | 0.0043 | 103** | ND |
| 95 | ND | ND | ND | ND | ND | ND |
| 96 | ND | ND | ND | ND | ND | ND |
| 97 | 0.067 | 0.2 | 96 | ND | ND | ND |
| 98a | 0.59 | 0.83 | 101 | ND | ND | ND |
| 98b | 2.2 | ~5 | 74 | ND | ND | ND |
| 98c | 0.38 | 0.42 | 96 | ND | ND | 0.69 |
| 99a | 0.02 | 0.097 | 93 | ND | ND | ND |
| 99b | 0.81 | ~2 | 86 | ND | ND | ND |
| 99c | 0.012 | 0.02 | 97 | ND | ND | 0.018 |
| 100 | 0.025 | 0.22 | 78 | ND | ND | ND |
| 101a | 0.071 | 0.54 | 96 | ND | ND | ND |
| 101b | 0.038 | 0.37 | 62 | ND | ND | 0.03 |
| 101c | 0.85 | 1.4 | 89 | ND | ND | ND |
| 102 | 1.3 | 1.9 | 94 | ND | ND | ND |
| 103 | 0.0094 | 0.033 | 81 | ND | ND | ND |
| 104 | 0.0063 | 0.019 | 82 | ND | ND | ND |
| 105 | 0.0056 | >6 | 38 | ND | ND | ND |
| 106a | 0.048 | ~4 | 84 | ND | ND | ND |
| 106b | 0.11 | 0.67 | 94 | ND | ND | ND |
| 106c | 0.018 | ~5 | 65 | ND | ND | ND |
| 107 | 3.4 | 5.6 | 57 | ND | ND | ND |
| 108a | 0.0044 | 0.03 | 90 | ND | ND | ND |
| 108b | 0.0012 | 1.1 | 55 | ND | ND | ND |
| 108c | 0.046 | 0.96, ~1 | 83 | ND | ND | ND |
| 109 | 0.014 | ~4 | 80 | ND | ND | ND |
| 110 | 0.02 | >6 | 20 | ND | ND | ND |
| 111a | ND | ND | ND | ND | ND | ND |
| 111b | 1.4 | ~0.9 | 99 | ND | ND | ND |
| 111c | 22 | ~5 | 92 | ND | ND | ND |
| 112a | 6.6 | 1 | 91 | ND | ND | ND |
| 112b | 2.2 | 0.45 | 92 | ND | ND | 2.8 |
| 112c | 13 | ~5 | 71 | ND | ND | ND |
| 113a | ND | ND | ND | ND | ND | ND |
| 113b | 23 | ~6 | 58 | ND | ND | ND |
| 113c | 1.2 | ~2 | 90 | ND | ND | ND |
| 114a | ND | ND | ND | ND | ND | ND |
| 114b | 0.12 | 1.4 | 86 | ND | ND | ND |
| 114c | 0.71 | 1.9 | 71 | ND | ND | ND |
| 115a | ND | ND | ND | ND | ND | ND |
| 115b | 0.058 | 0.48 | 67 | ND | ND | 2.6 |
| 115c | 0.017 | 0.11 | 70 | ND | ND | ~0.2 |
| 116 | ND | ND | ND | ND | ND | ND |
| 117a | ND | ND | ND | ND | ND | ND |
| 117b | 1.3 | ~4 | 88 | ND | ND | ND |
| 117c | 0.0055 | 0.052 | 101 | ND | ND | 0.029 |
| 118a | ND | ND | ND | ND | ND | ND |
| 118b | 2.5 | 0.7 | 94 | ND | ND | ND |
| 118c | 0.11 | 0.21 | 97 | ND | ND | 0.05 |
| 119a | ND | ND | ND | ND | ND | ND |
| 119b | 0.49 | 0.47 | 97 | ND | ND | ND |
| 119c | 0.28 | 0.63 | 90 | ND | ND | ND |
| 120a | ND | ND | ND | ND | ND | ND |
| 120b | 0.13 | >6 | 27 | ND | ND | ND |
| 120c | 1.1 | ~6 | 66 | ND | ND | ND |
| 121a | ND | ND | ND | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, IC$_{50}$ (μM) |
|---|---|---|---|---|---|---|
| 121b | 0.37 | 0.41 | 98 | ND | ND | 0.17 |
| 121c | 0.13 | 0.22 | 101 | ND | ND | 0.18 |
| 122a | ND | ND | ND | ND | ND | ND |
| 122b | >83 | 1.4 | 98 | ND | ND | ND |
| 122c | 0.0022 | 0.087 | 99 | ND | ND | ND |
| 123 | 0.0052 | 0.071 | 101 | ND | ND | ND |
| 124 | 0.24 | 0.67 | 93 | ND | ND | ND |
| 125 | 0.0094 | 0.29 | 100 | ND | ND | ND |
| 126 | ND | ND | ND | ND | ND | ND |
| 127 | 0.35 | 0.24 | 101 | ND | ND | ND |
| 128 | 0.097 | ND | ND | ND | ND | ND |
| 129 | 1.7 | 1.5 | 110 | ND | ND | ND |
| 130 | 0.64 | 0.51 | 94 | ND | ND | ND |
| 131a | ND | ND | ND | ND | ND | ND |
| 131b | 9 | ~6 | 59 | ND | ND | ND |
| 131c | 0.22 | 1.6 | 100 | ND | ND | ND |
| 132 | 0.036 | 0.045 | 108 | ND | ND | ND |
| 133a | ND | ND | ND | ND | ND | ND |
| 133b | 0.33 | 0.84 | 99 | ND | ND | ND |
| 133c | 12 | 1.2 | 82 | ND | ND | ND |
| 134a | ND | ND | ND | ND | ND | ND |
| 134b | 0.22 | 0.42 | 101 | ND | ND | ~2 |
| 134c | 1.2 | 1.1 | 96 | ND | ND | ND |
| 135a | 0.036 | 0.27 | 97 | ND | ND | ND |
| 135b | 0.16 | 0.26 | 99 | ND | ND | 0.31 |
| 135c | 0.023 | 0.077 | 95 | ND | ND | 0.045 |
| 136a | 0.15 | 0.14 | 94 | ND | ND | ND |
| 136b | 2.3 | 1 | 83 | ND | ND | ND |
| 136c | 0.019 | 0.14 | 97 | ND | ND | 0.074 |
| 137a | 0.009 | 0.17 | 97 | ND | ND | ND |
| 137b | 0.041 | 0.16 | 93 | ND | ND | 0.22 |
| 137c | 0.0045 | 0.14 | 94 | ND | ND | 0.037 |
| 138a | 0.13 | 0.13 | 98 | ND | ND | ND |
| 138b | 1.3 | 0.56 | 101 | ND | ND | ND |
| 138c | 0.032 | 0.075 | 96 | ND | ND | 0.72 |
| 139 | 0.00014 | 0.02 | 98 | ND | ND | ND |
| 140a | 0.00019 | 0.022 | 99 | ND | ND | ND |
| 140b | 0.13 | ~0.1 | 101 | ND | ND | 0.028 |
| 140c | 0.00015 | 0.00066, ~0.001 | 99 | ND | ND | ND |
| 141a | 11 | >6 | 42 | ND | ND | ND |
| 141b | 17 | >6 | 20 | ND | ND | ND |
| 141c | 7.1 | >6 | 5 | ND | ND | ND |
| 142 | 1.5 | 1.6 | 87 | ND | ND | ND |
| 143a | 0.0072 | 0.038 | 101 | ND | ND | ND |
| 143b | 1.7 | 1.6 | 93 | ND | ND | ND |
| 143c | 0.0022 | ~0.01 | 102 | ND | ND | 0.015 |
| 144a | 0.012 | 0.074 | 99 | ND | ND | ND |
| 144b | 2.3 | ~3.7 | 69 | ND | ND | ND |
| 144c | 0.0025 | 0.034 | 99 | ND | ND | ND |
| 145a | ND | ND | ND | ND | ND | ND |
| 145b | 0.08 | 0.23 | 102 | ND | ND | 0.32 |
| 145c | 0.81 | 0.78 | 95 | ND | ND | ND |
| 146a | ND | ND | ND | ND | ND | ND |
| 146b | 0.084 | 0.21 | 103 | ND | ND | 0.53 |
| 146c | 0.6 | ~2 | 92 | ND | ND | ND |
| 147a | ND | ND | ND | ND | ND | ND |
| 147b | 0.06 | 0.21 | 99 | ND | ND | 0.21 |
| 147c | 0.0052 | 0.052 | 96 | ND | ND | 0.036 |
| 148a | ND | ND | ND | ND | ND | ND |
| 148b | 0.056 | 0.46 | 97 | ND | ND | ND |
| 148c | 0.00039 | ~0.006 | 98 | ND | ND | 0.0062 |
| 149 | 0.00034 | 0.0024 | 96 | ND | ND | 0.003 |
| 150 | ND | ND | ND | ND | ND | ND |
| 151 | ND | ND | ND | ND | ND | ND |
| 152 | 38 | 4.8 | 70 | ND | ND | ND |
| 153 | 15 | >6 | 44 | ND | ND | ND |
| 154a | ND | ND | ND | ND | ND | ND |
| 154b | ND | 0.14 | 101 | ND | ND | 0.067 |
| 154c | >56 | 1 | 73 | ND | ND | ND |
| 155 | ND | 0.16 | 88 | ND | ND | ND |
| 156a | 0.00063 | 0.0066 | 94 | ND | ND | ND |
| 156b | 0.075 | 0.087 | 98 | ND | ND | 0.082 |
| 156c | 0.00059 | 0.0019 | 99 | ND | ND | 0.0033 |
| 157a | 0.0039 | ~0.007 | 93 | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, $IC_{50}$ (μM) |
|---|---|---|---|---|---|---|
| 157b | 0.0017 | 0.034 | 102 | 0.019 | 90** | 0.025 |
| 157c | 0.11 | 0.16 | 99 | ND | ND | 0.37 |
| 158a | 0.021 | 0.057 | 97 | ND | ND | ND |
| 158b | 0.14 | 0.17 | 107 | ND | ND | 0.57 |
| 158c | 0.0077 | 0.13 | 100 | ND | ND | 0.022 |
| 159a | 0.029 | 0.12 | 107 | ND | ND | 0.2 |
| 159b | 0.51 | 0.37 | 107 | ND | ND | 1.8 |
| 159c | 0.014 | 0.051 | 105 | ND | ND | 0.053 |
| 160a | 0.049 | 0.059 | 112 | ND | ND | 0.089 |
| 160b | 0.46 | 0.68 | 105 | ND | ND | ND |
| 160c | 0.012 | 0.047 | 98 | ND | ND | 0.028 |
| 161a | 0.015 | 0.057 | 96 | ND | ND | 0.082 |
| 161b | 0.28 | 0.16 | 108 | ND | ND | 1 |
| 161c | 0.011 | 0.078 | 102 | ND | ND | 0.06 |
| 162a | 0.02 | 0.31 | 90 | ND | ND | 0.25 |
| 162b | 16 | 1.1 | 81 | ND | ND | ND |
| 162c | 0.0041 | 0.098 | 98 | ND | ND | 0.049 |
| 163 | ND | ND | ND | ND | ND | ND |

All data shown in Table 1 is either the value of one data point or the average of more than one data point. In cases where more than one value is shown in a table cell, values with qualifiers such as ~, > or < shown on the right side of the table cell could not be included in the averaging calculation for the value shown on the left side of the table cell. *% inhibition is shown at 0.33 μM compound concentration. % inhibition is shown at 0.67 μM compound concentration, *% inhibition is shown at 1.0 μM compound concentration, ****% inhibition at 6 μM compound concentration. ND—no data While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. A compound of Formula I wherein:

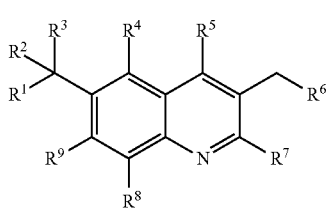

Formula I

R[1] is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;

R[2] is 1-methyl-1,2,3-triazolyl, pyridyl, pyridyl-N-oxide, 1-methyl pyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, 1-H-azetidin-3-yl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methyl pyrazol-4-yl is optionally substituted with up to two additional $CH_3$ groups;

$R^3$ is H, OH, $OCH_3$, $NHCH_3$, $N(CH_3)_2$, or $NH_2$;
$R^4$ is H, or F;
$R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, NH-cyclopropyl, $OCHF_2$, 4-hydroxy-piperidinyl, azetidin-1-yl, or fur-2-yl;
$R^6$ is pyridyl, pyrimidinyl, phenyl, benzothiophenyl, or thiophenyl; wherein said pyridyl or phenyl is optionally substituted with $N(CH_3)_2$, $SCH_3$, $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN; and said thiophenyl is optionally substituted with $CF_3$;
$R^7$ is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OC_{(1-3)}$alkyl, $OCH_2$-(1-methyl)-imidazol-2-yl, imidazol-2-yl, fur-2-yl, pyrazol-1-yl, pyrazol-4-yl, pyrid-3-yl, or pyrimidin-5-yl; thiophen-3-yl, 1-methyl-indazol-5-yl, 1-methyl-indazol-6-yl, phenyl, or

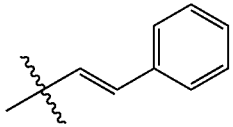 [SMILES: */C=C/c1ccccc1]

wherein said imidazolyl or pyrazolyl can be optionally substituted with a $CH_3$ group;
$A^1$ is H or $C_{(1-4)}$alkyl;
$A^2$ is H, $C_{(1-4)}$alkyl, cyclopropyl, $C_{(1-4)}$alkyl$OC_{(1-4)}$alkyl, $C_{(1-4)}$alkylOH, $C(O)C_{(1-2)}$alkyl, or $OCH_3$; or $A^1$ and $A^2$ may be taken together with their attached nitrogen to form a ring selected from the group consisting of:

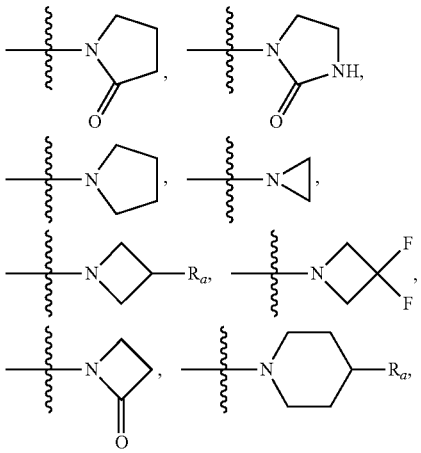

-continued

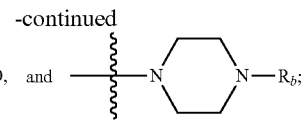

$R_a$ is H, F, $OCH_3$, or OH;
$R_b$ is $CH_3$, or phenyl;
$R^8$ is H, $CH_3$, $OCH_3$, or F;
$R^9$ is H, or F;
and pharmaceutically acceptable salts thereof;
provided that (4-chloro-2-methoxy-3-(4-(trifluoromethyl)benzyl)quinolin-6-yl)bis(1,2,5-trimethyl-1H-imidazol-4-yl)methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide, and (3-(4-(1H-pyrazol-1-yl)benzyl)-4-chloro-2-(4-methylpiperazin-1-yl)quinolin-6-yl)(1-methyl-1H-imidazol-5-yl)(6-(trifluoromethyl)pyridin-3-yl)methanol are excluded from the claim.

2. A compound of claim 1 wherein:
$R^1$ is oxazolyl, azetidinyl, imidazolyl, pyrimidinyl, triazolyl, tetrahydropyranyl, thiazolyl, pyridyl, phenyl, or isoxazolyl; wherein said pyridyl, imidazolyl, and phenyl are optionally substituted with $CH_3$, $CF_3$, Cl, F, —CN, or $OCH_3$; and optionally substituted with up to one additional group independently selected from the group consisting of Cl, $OCH_3$, and $CH_3$; and wherein said oxazolyl, triazolyl, isoxazolyl, and thiazolyl are optionally substituted with one or two $CH_3$ groups; and wherein said azetidinyl is optionally substituted with $CO_2C(CH_3)_3$, or $C(O)CH_3$;
$R^2$ is 1-methyl-1,2,3-triazol-5-yl, pyrid-3-yl, N-acetyl-piperidin-4-yl, N-Boc-azetidin-3-yl, N-acetyl-azetidin-3-yl, N-methyl-azetidin-3-yl, N-acetamidyl-azetidin-3-yl, 1-H-azetidin-3-yl, 1,2-dimethyl imidazol-5-yl, or 1-methyl imidazol-5-yl;
$R^3$ is OH, $NHCH_3$, $N(CH_3)_2$, or $NH_2$;
$R^4$ is H;
$R^5$ is H, Cl, OH, —CN, $N(CH_3)OCH_3$, NH-cyclopropyl, $OCHF_2$, or $OCH_3$;
$R^6$ is phenyl, pyrimidin-5-yl, 2-trifluoromethyl-pyrid-5-yl, 2-trifluoromethyl-thiophen-5-yl, or benzothiophenyl; wherein said phenyl is optionally substituted with pyrazol-1-yl, 1,2,4-triazol-1-yl, imidazol-1-yl, $SO_2CH_3$, $CH_3$, F, $CF_3$, $OCF_3$, $N(CH_3)_2$, —CN, or $SCH_3$;
$R^7$ is Cl, —CN, $CF_3$, $C_{(1-4)}$alkyl, $SO_2CH_3$, $OCHF_2$, $NA^1A^2$, $OCH_2CH_2OCH_3$, 1-methyl imidazol-2-yl, pyrazol-1-yl, 1-methyl pyrazol-4-yl, or $OCH_3$;
$A^1$ is H, or $C_{(1-2)}$alkyl;
$A^2$ is $C_{(1-2)}$alkyl, cyclopropyl, $CH_2CH_2OCH_3$, or $OCH_3$; or $A^1$ and $A^2$ may be taken together with their attached nitrogen to form a ring which is:

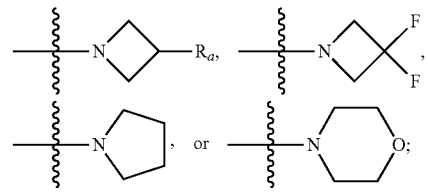

$R_a$ is H, OH, $OCH_3$, or F;
$R^8$ is H, or $CH_3$;
$R^9$ is H;
and pharmaceutically acceptable salts thereof.

3. A compound of claim selected from the group consisting of:
Another embodiment of the invention is a compound selected from the group consisting of:
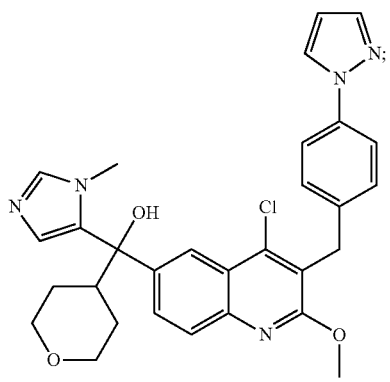
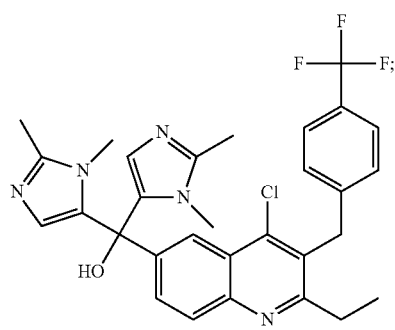
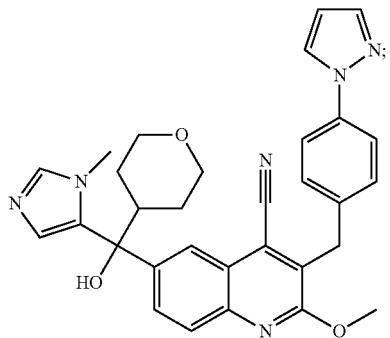
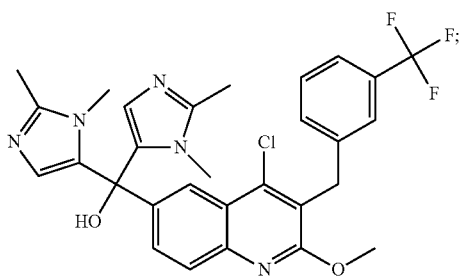
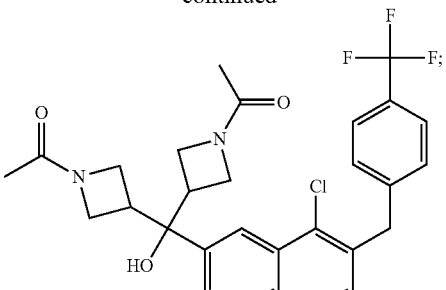
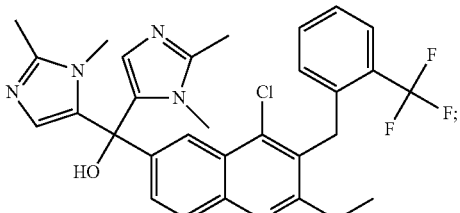
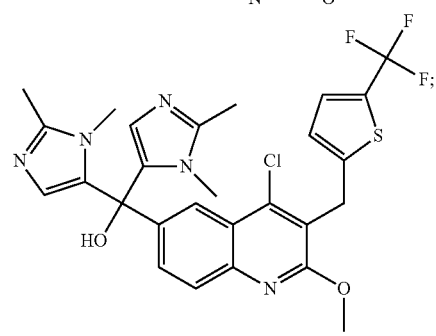
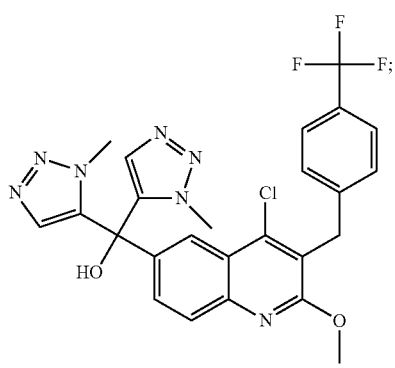
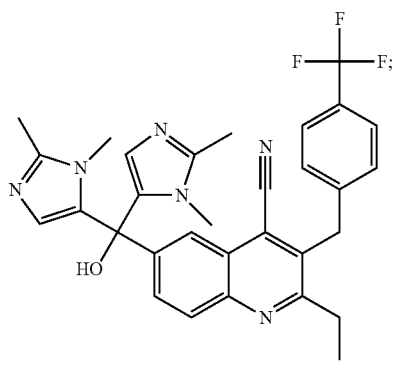

337
-continued
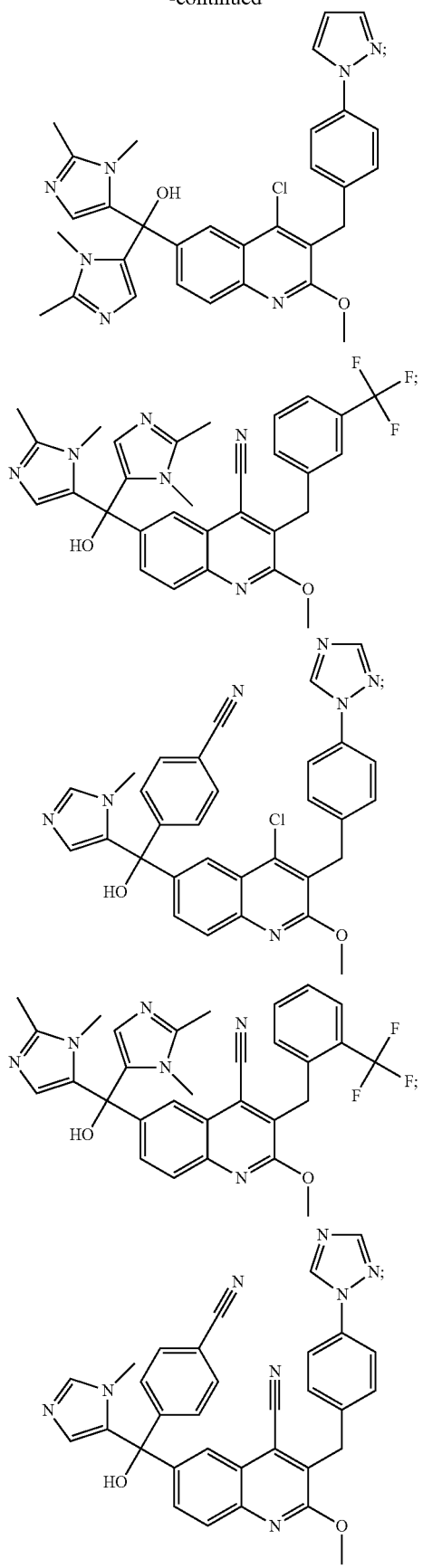
338
-continued
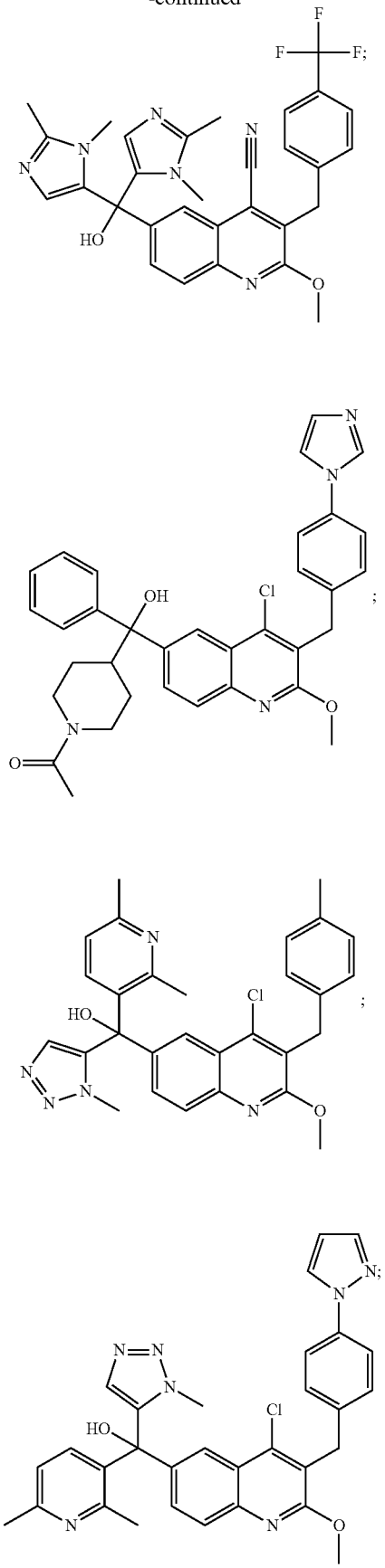

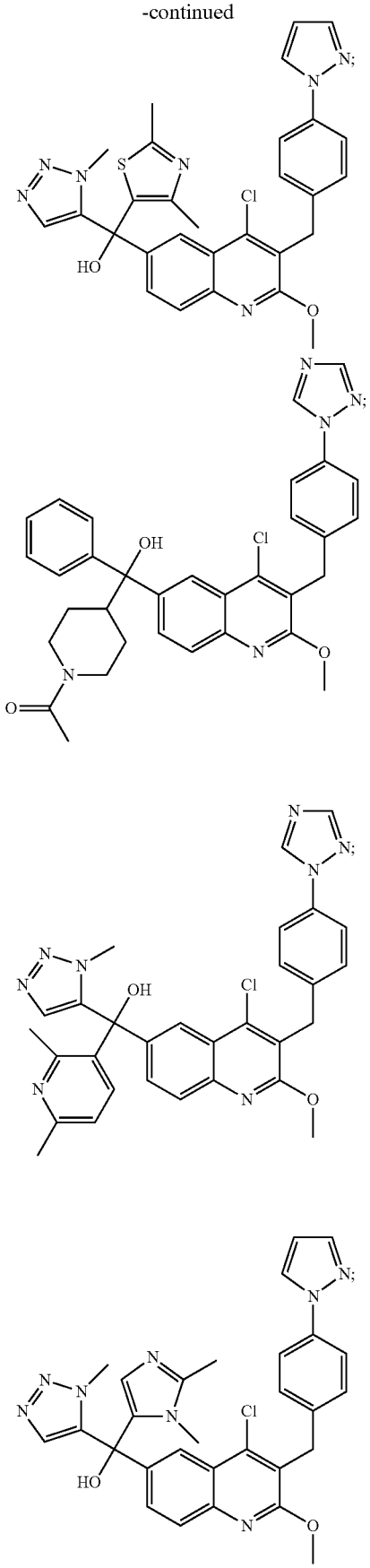
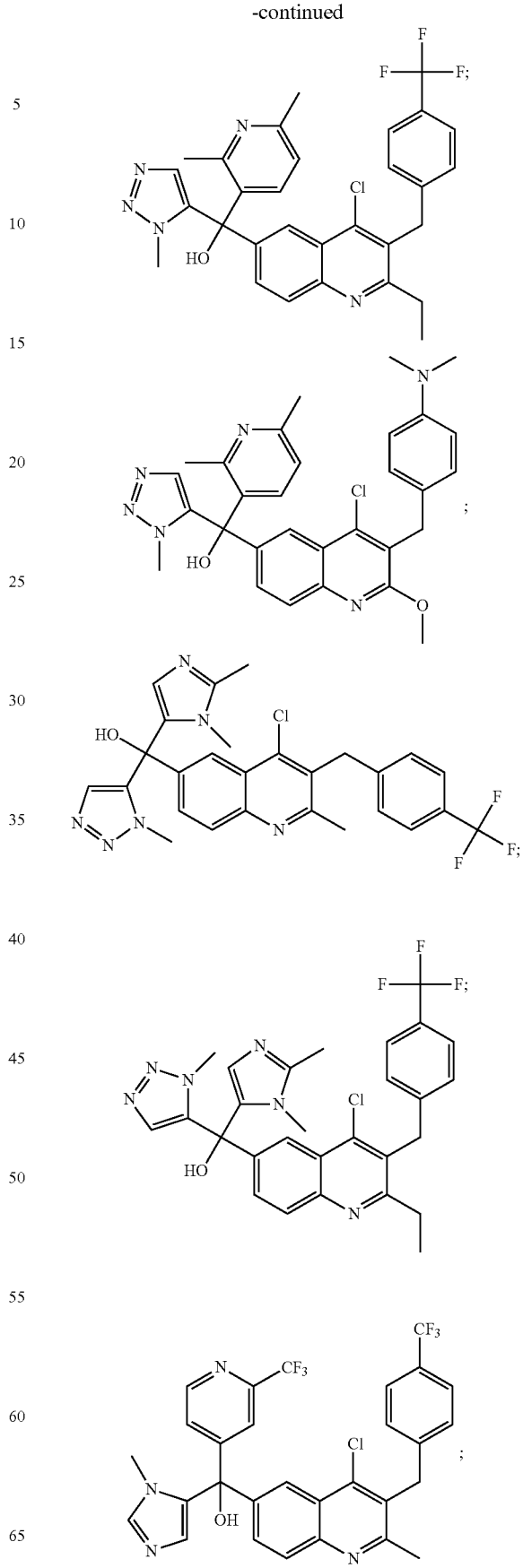

341
-continued
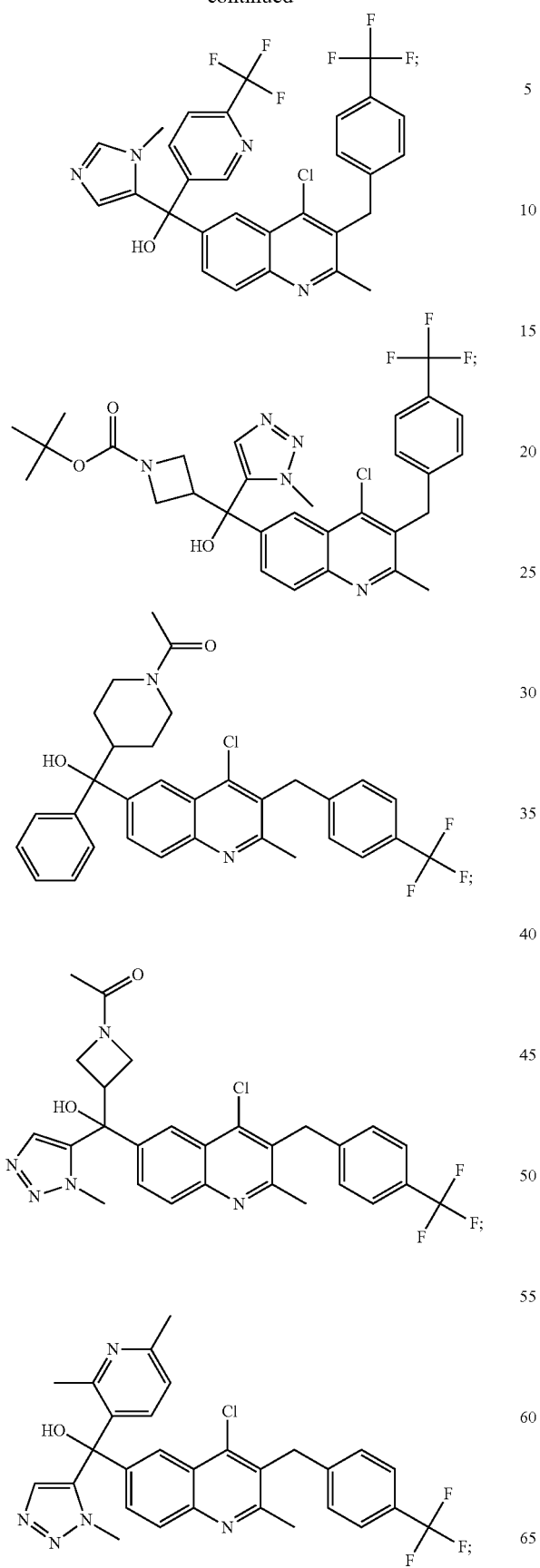
342
-continued
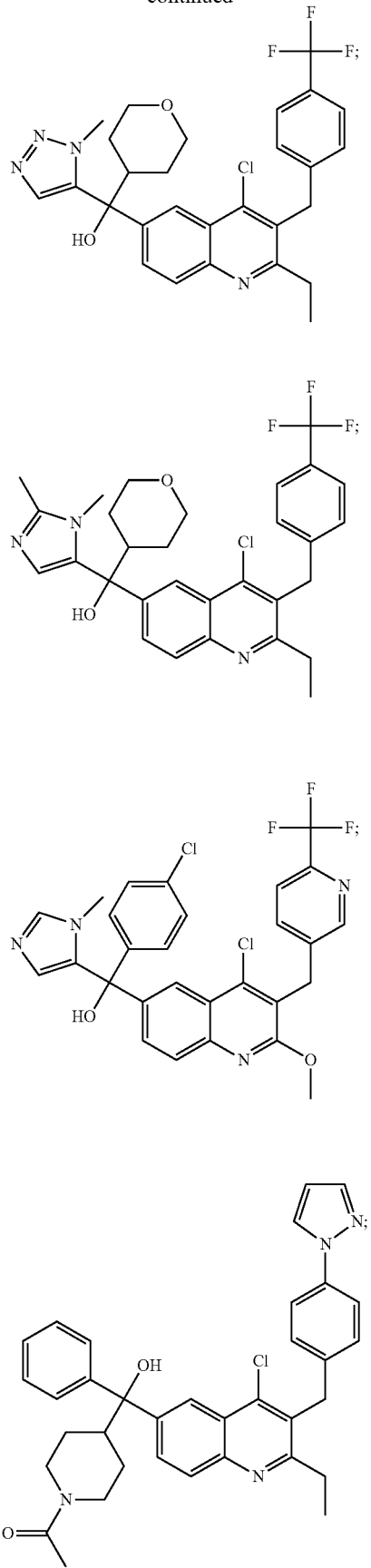

343
-continued
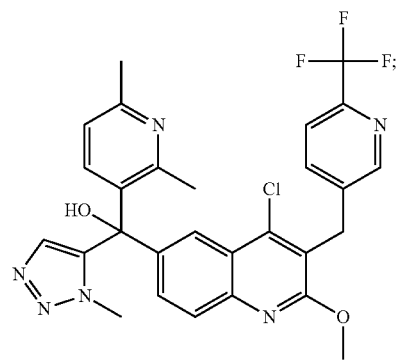
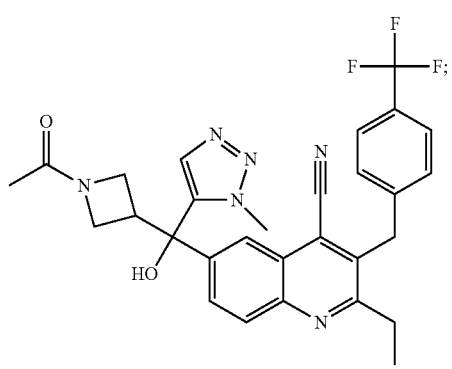
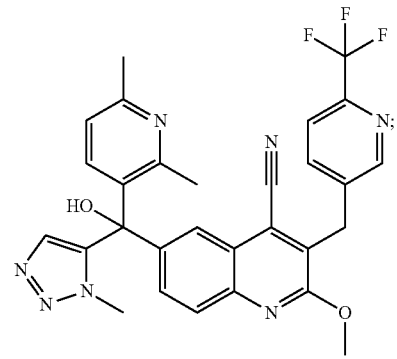
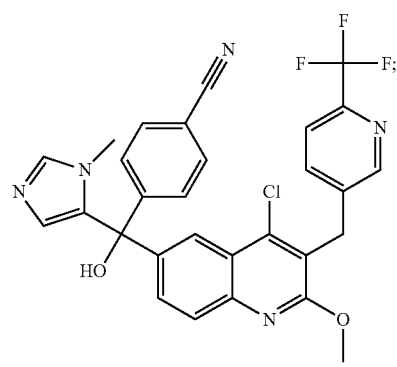
344
-continued
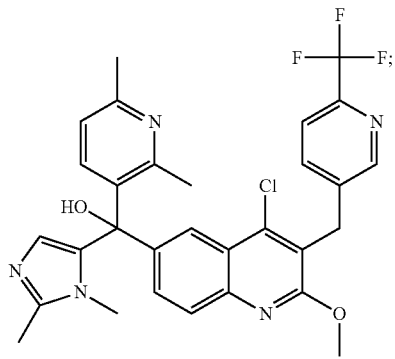
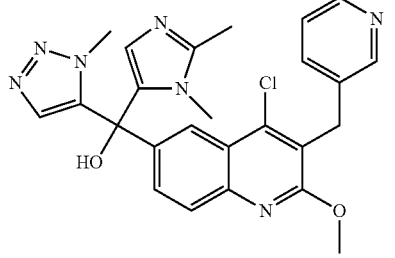
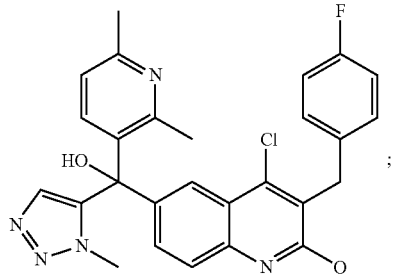
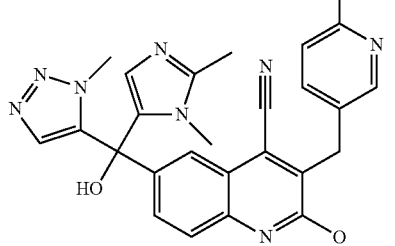
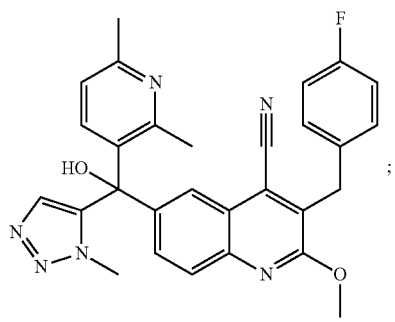

345
-continued
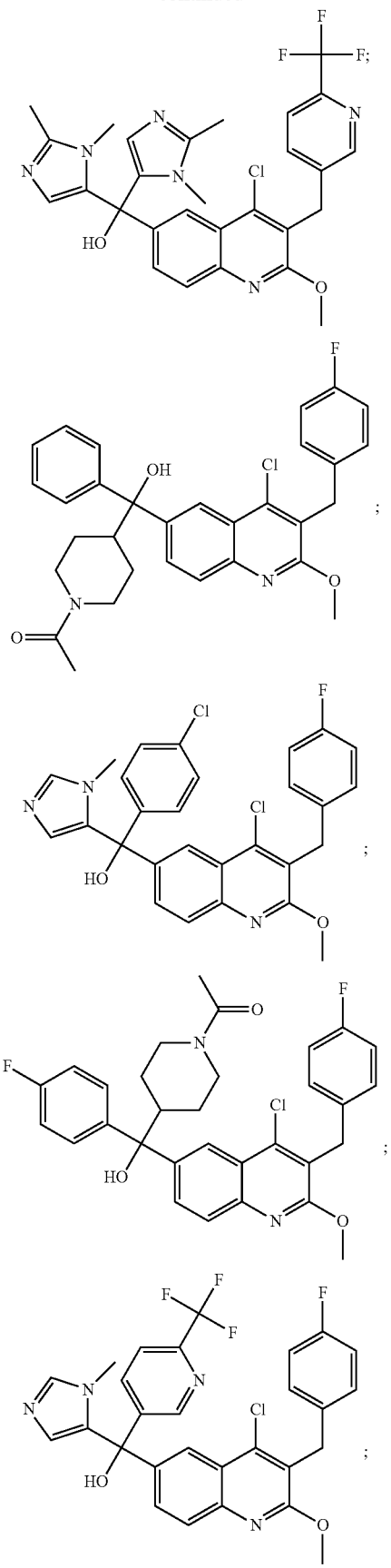
346
-continued
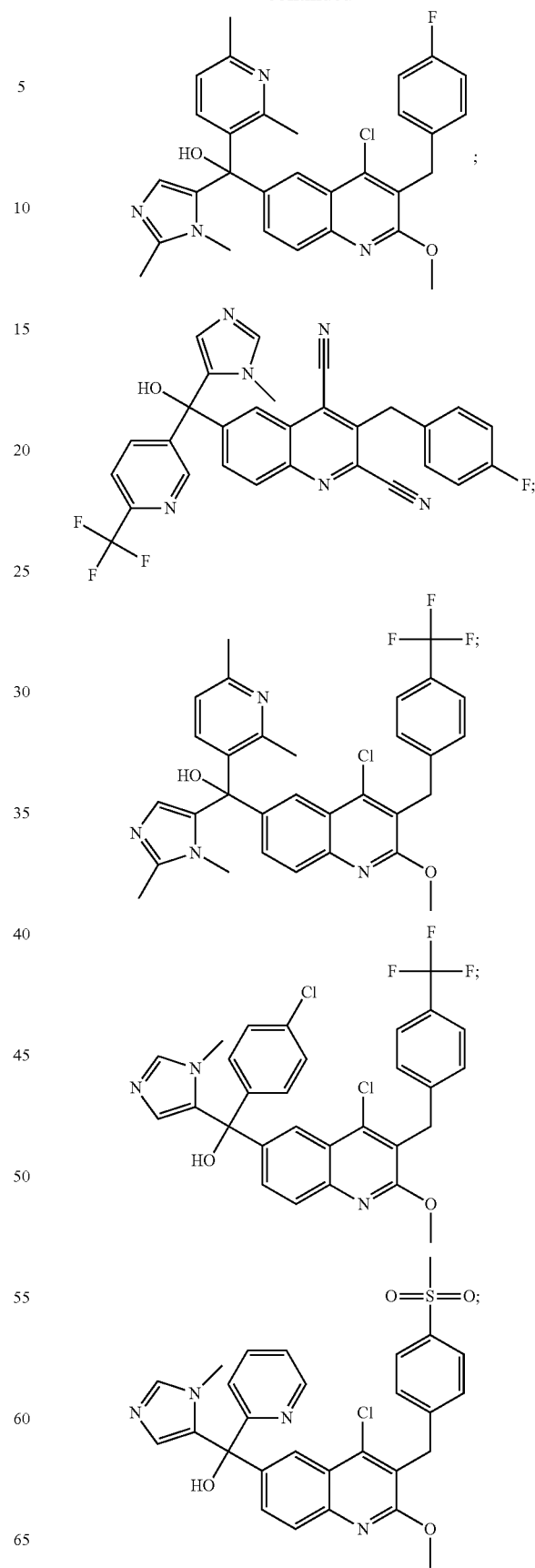

347
-continued
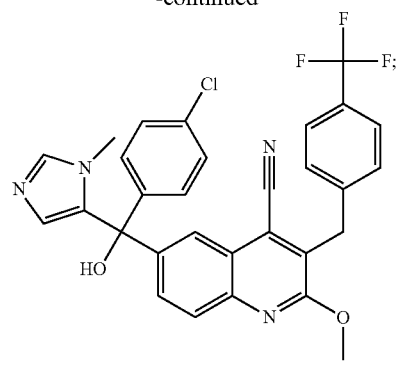
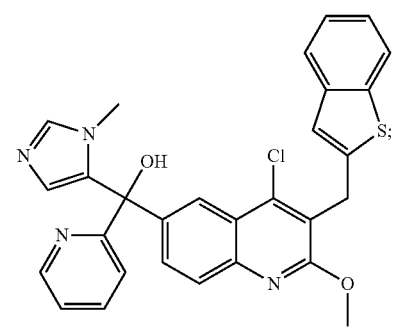
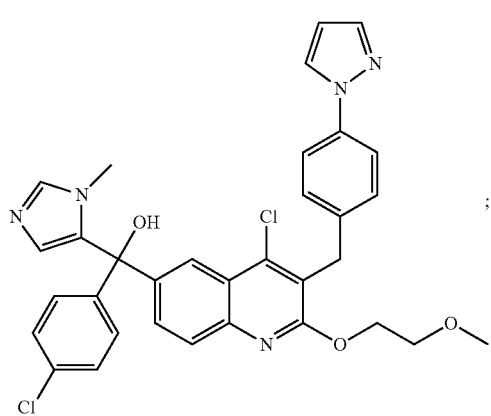
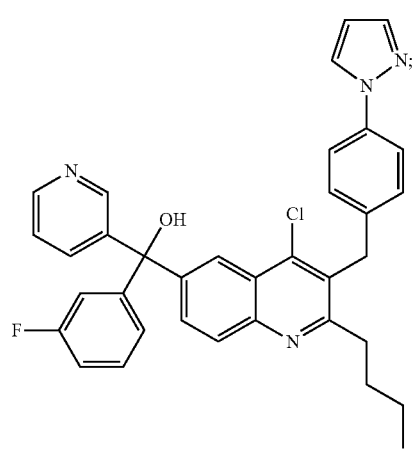
348
-continued
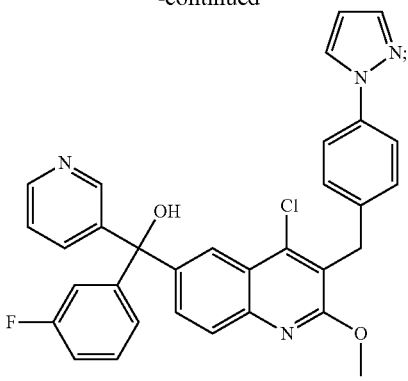
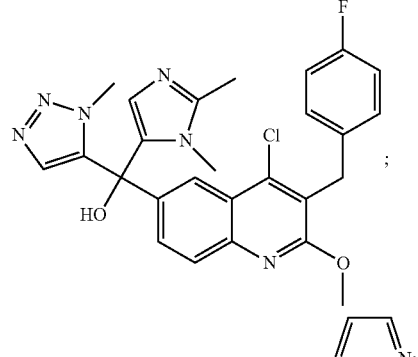
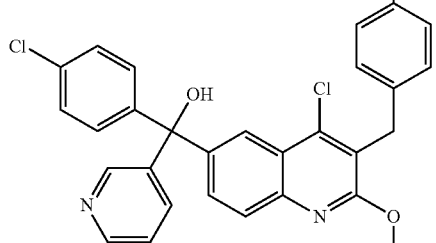
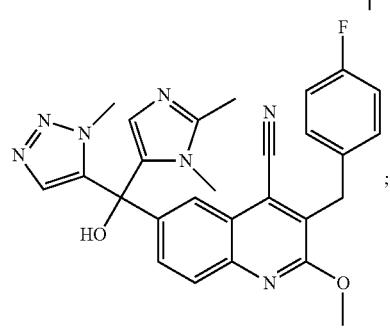
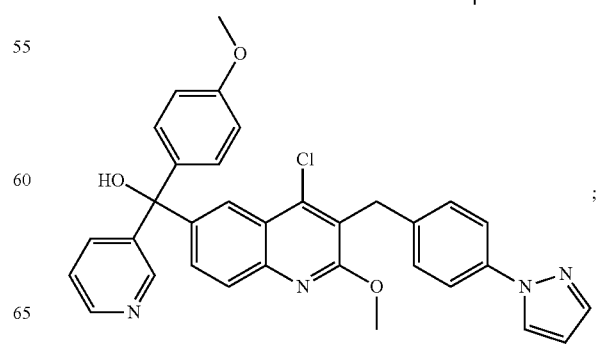

349
-continued
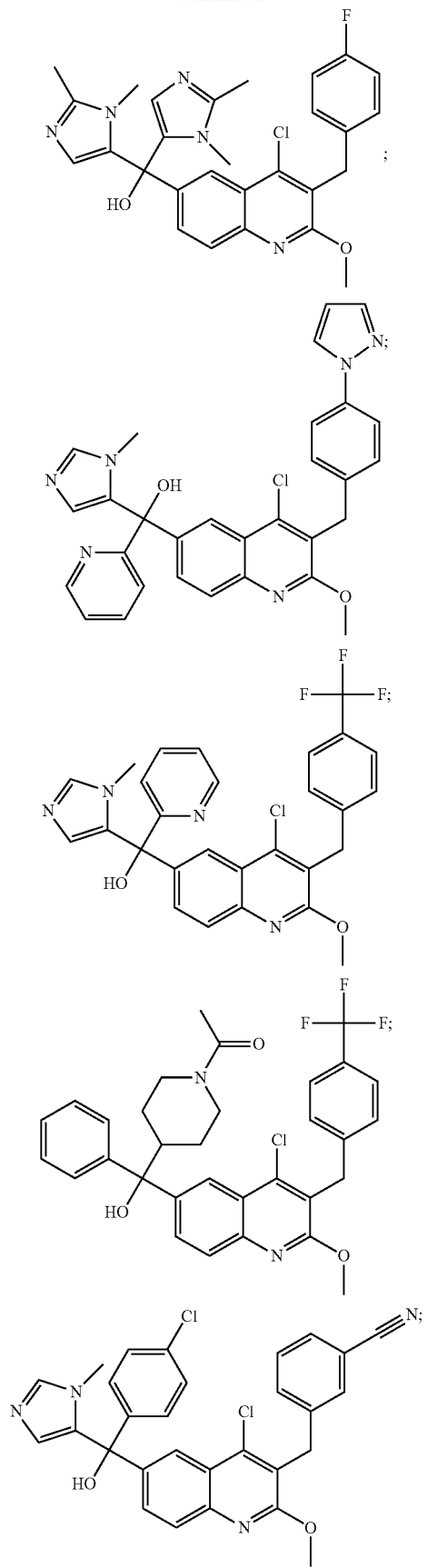
350
-continued
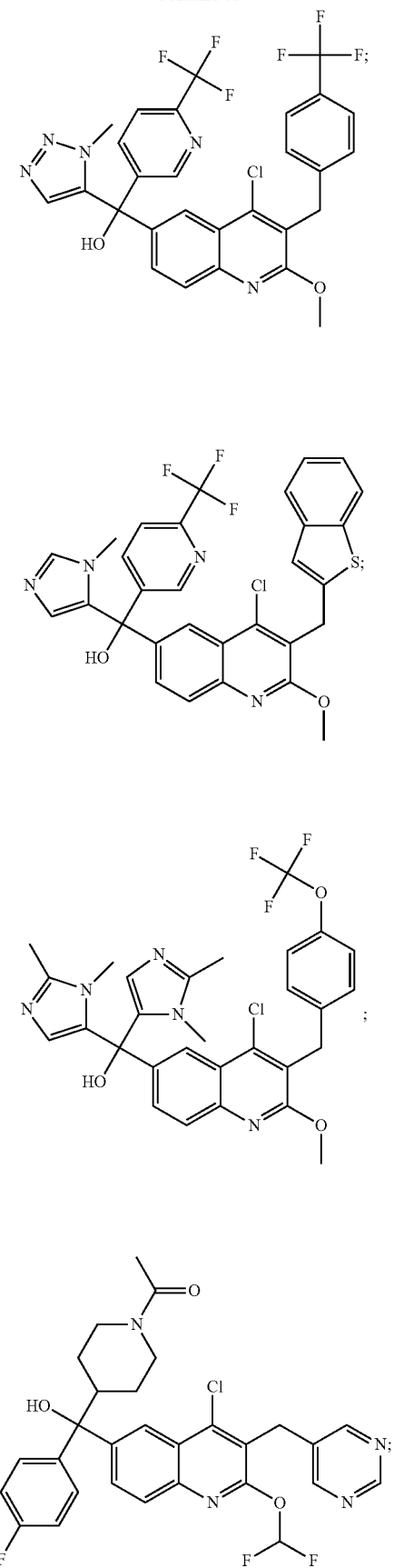

351
-continued
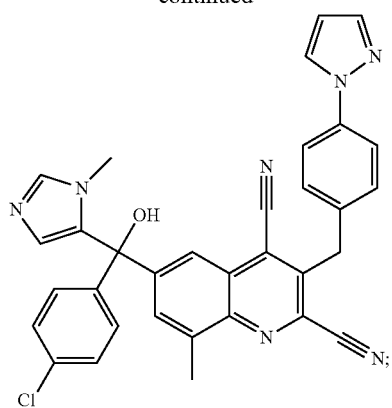
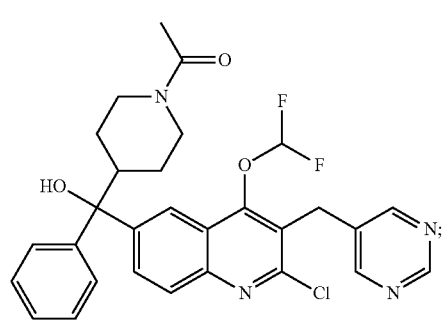
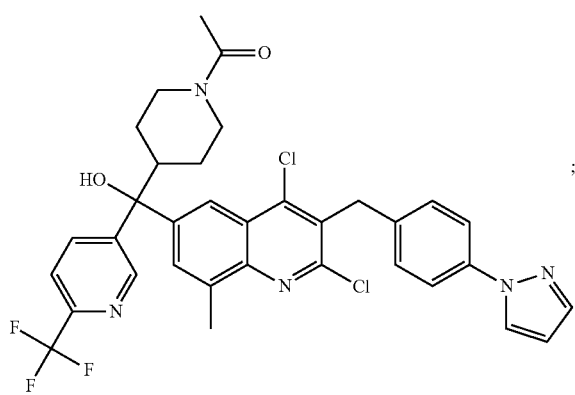
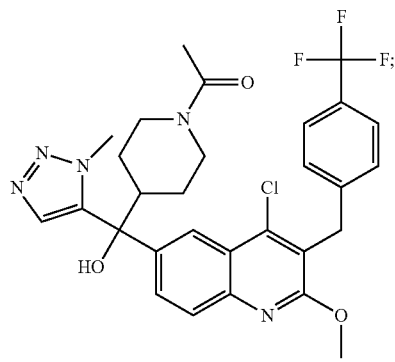
352
-continued
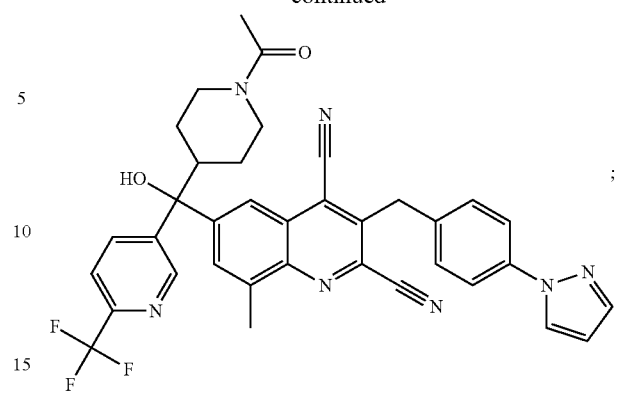
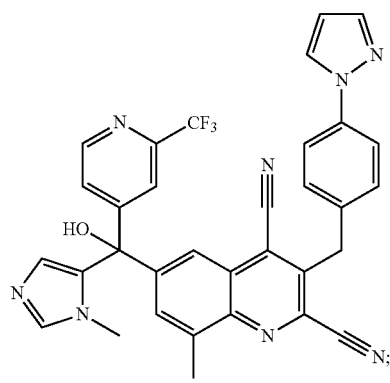
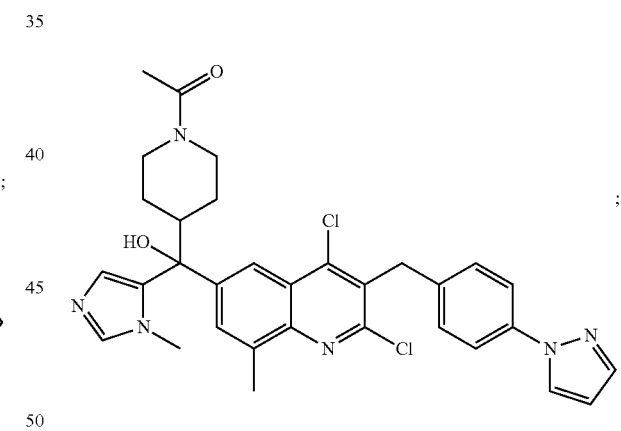
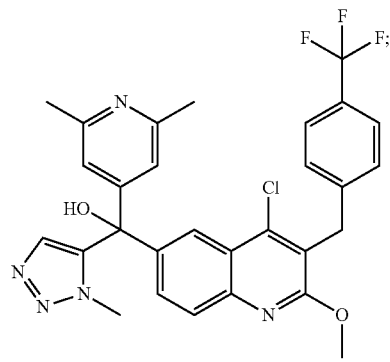

353 -continued
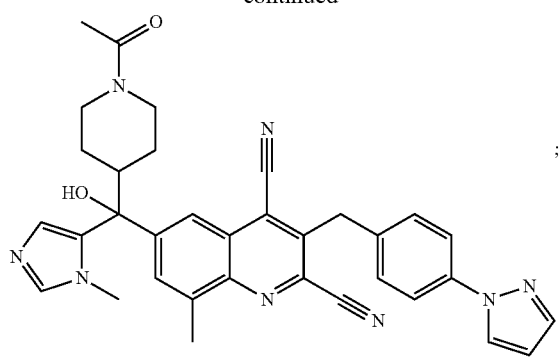
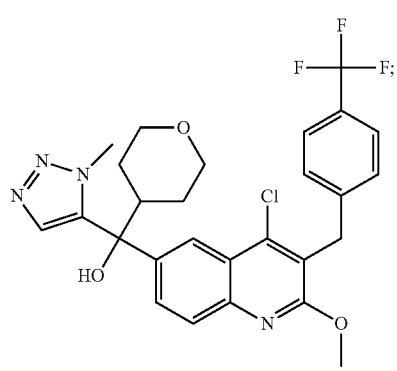
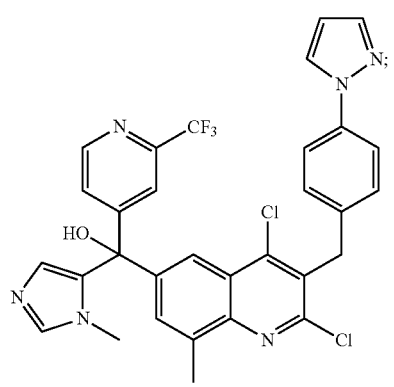
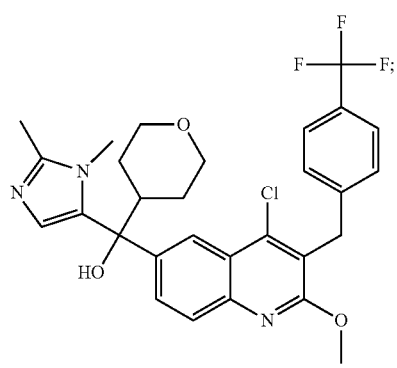
354 -continued
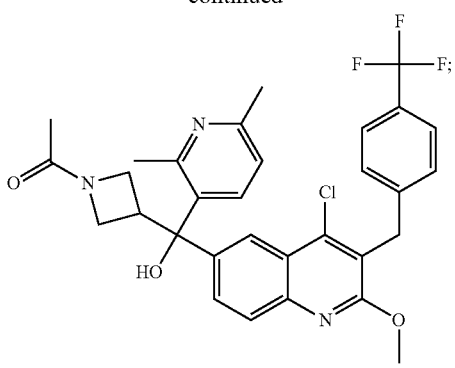
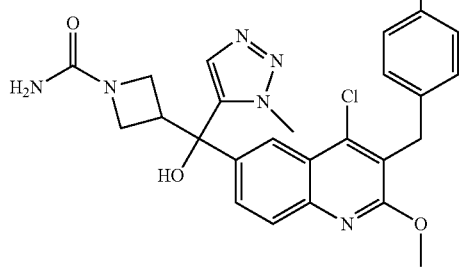
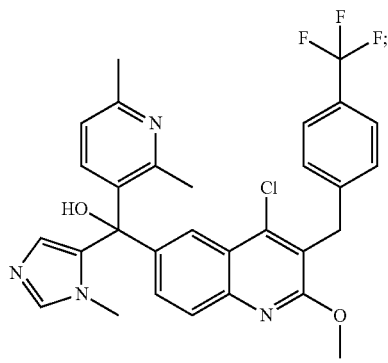
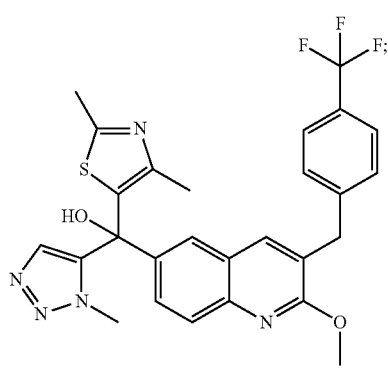

-continued
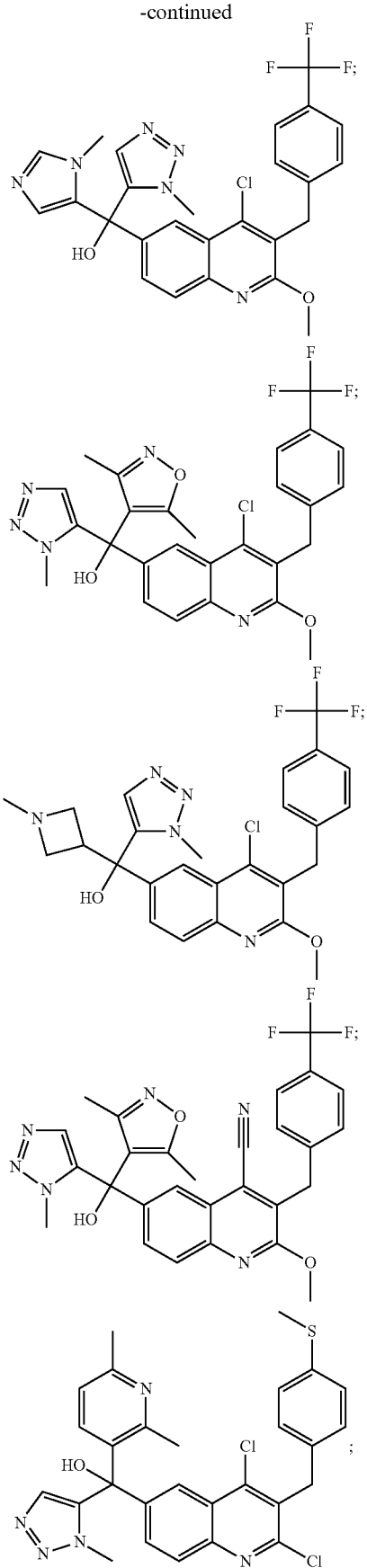
-continued
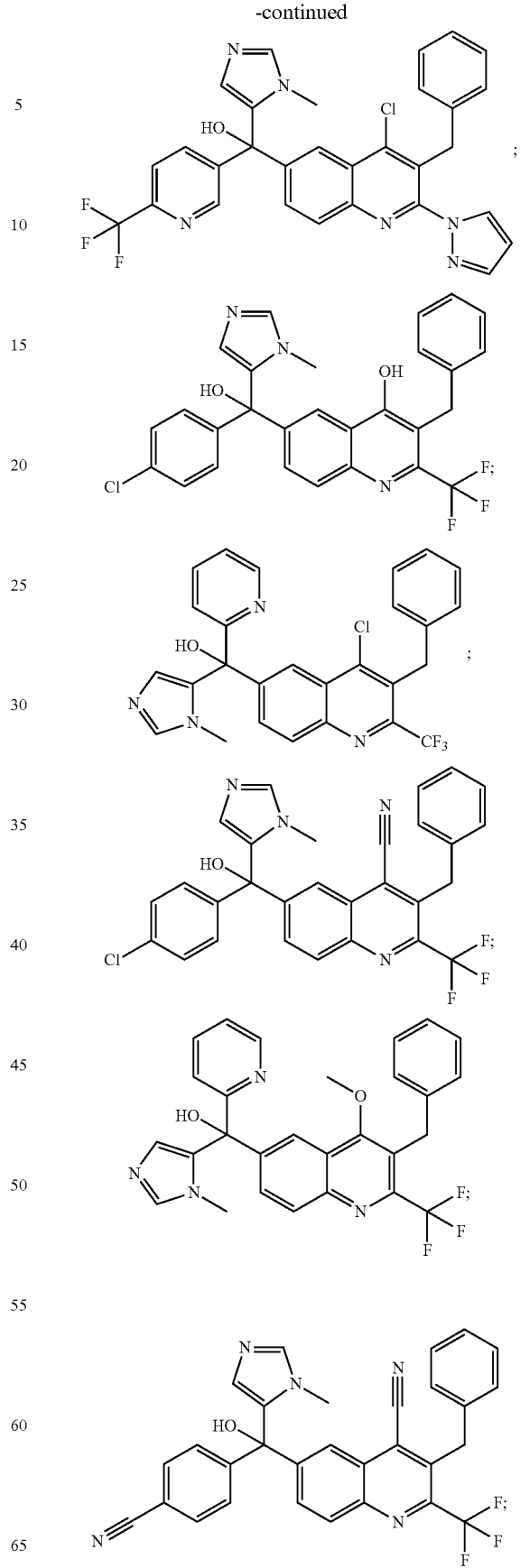

357
-continued
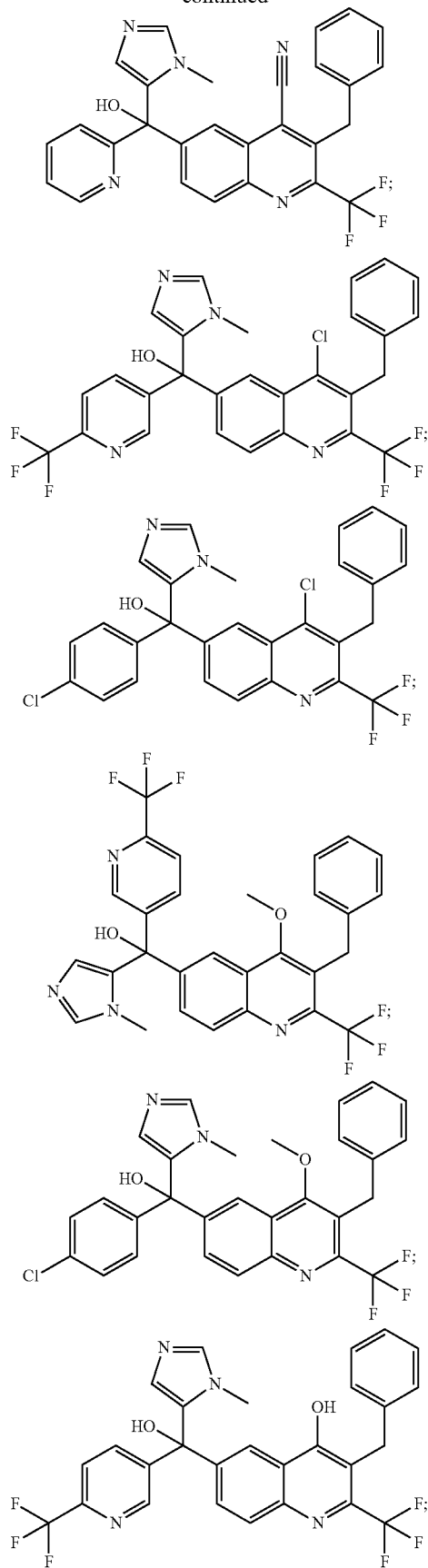
358
-continued
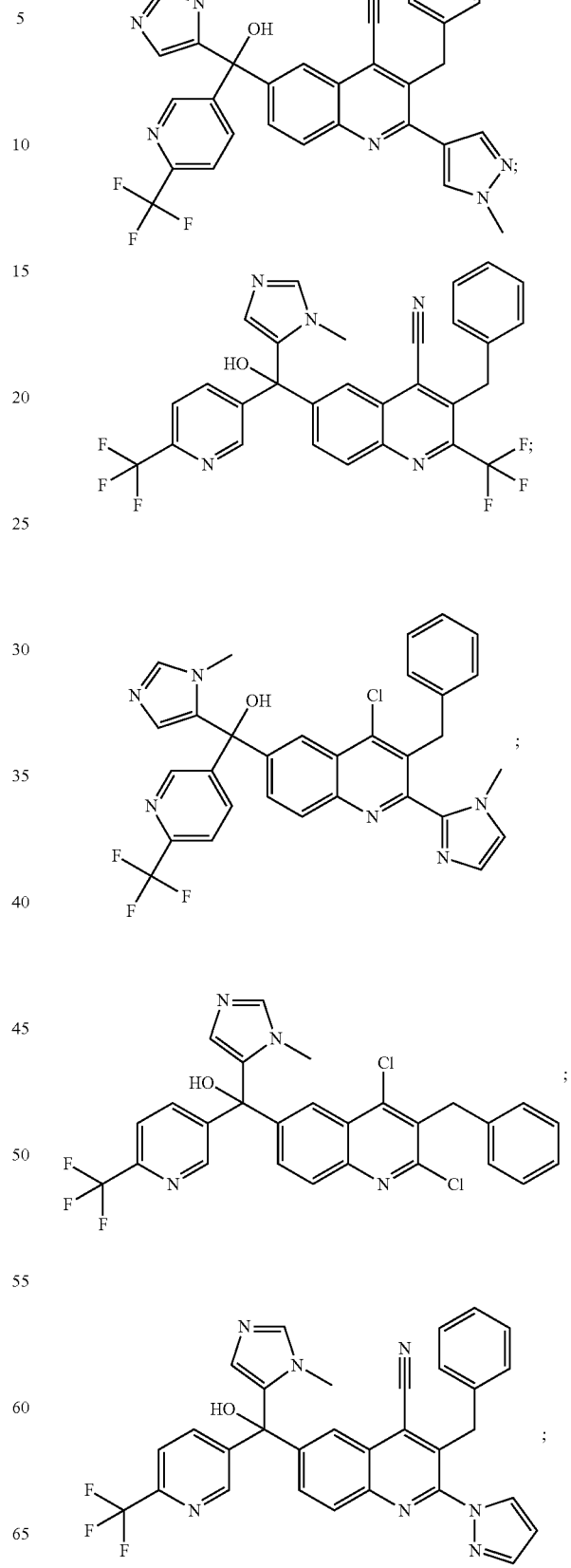

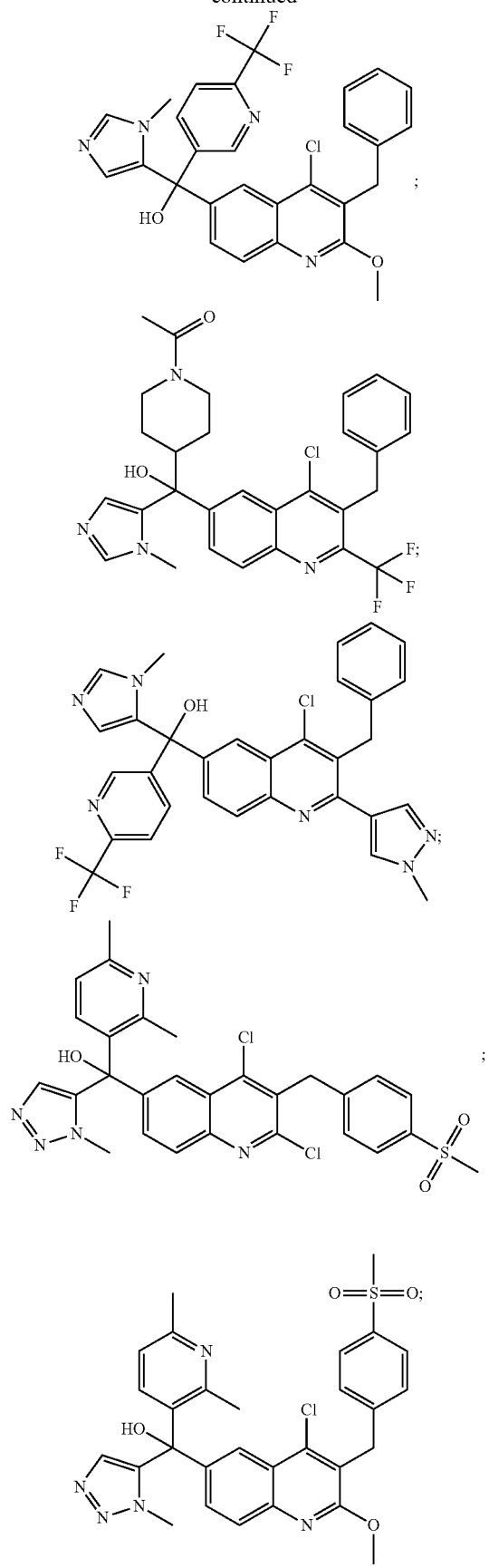
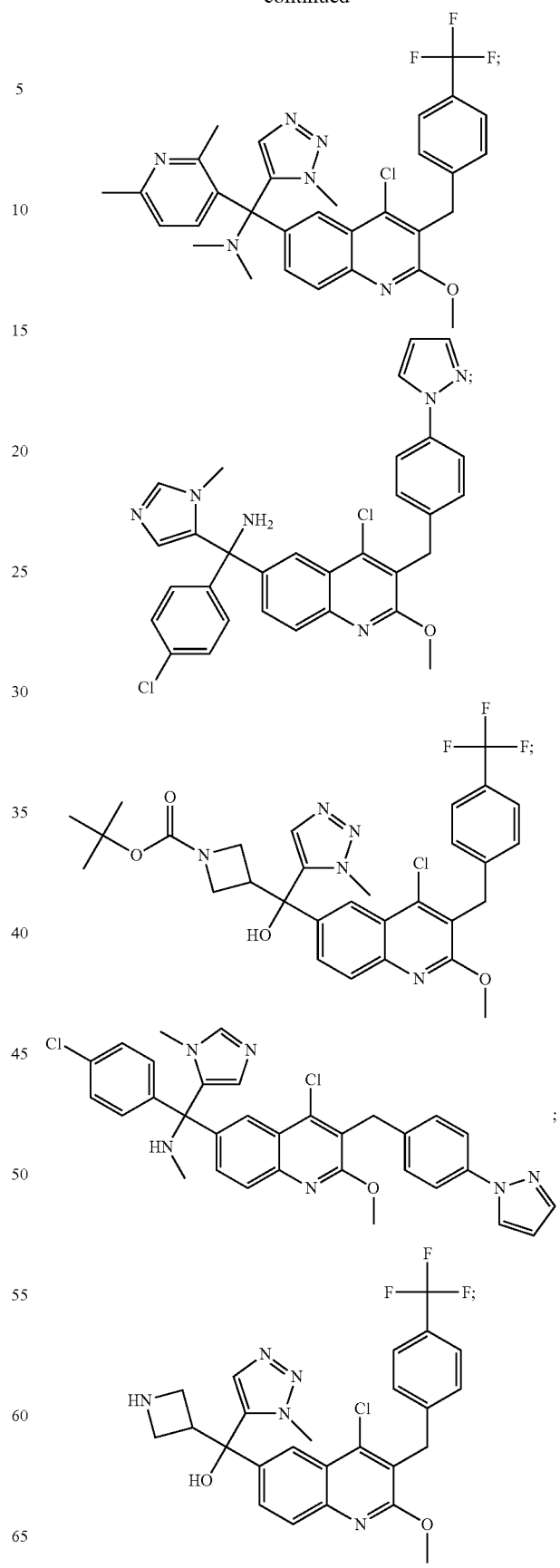

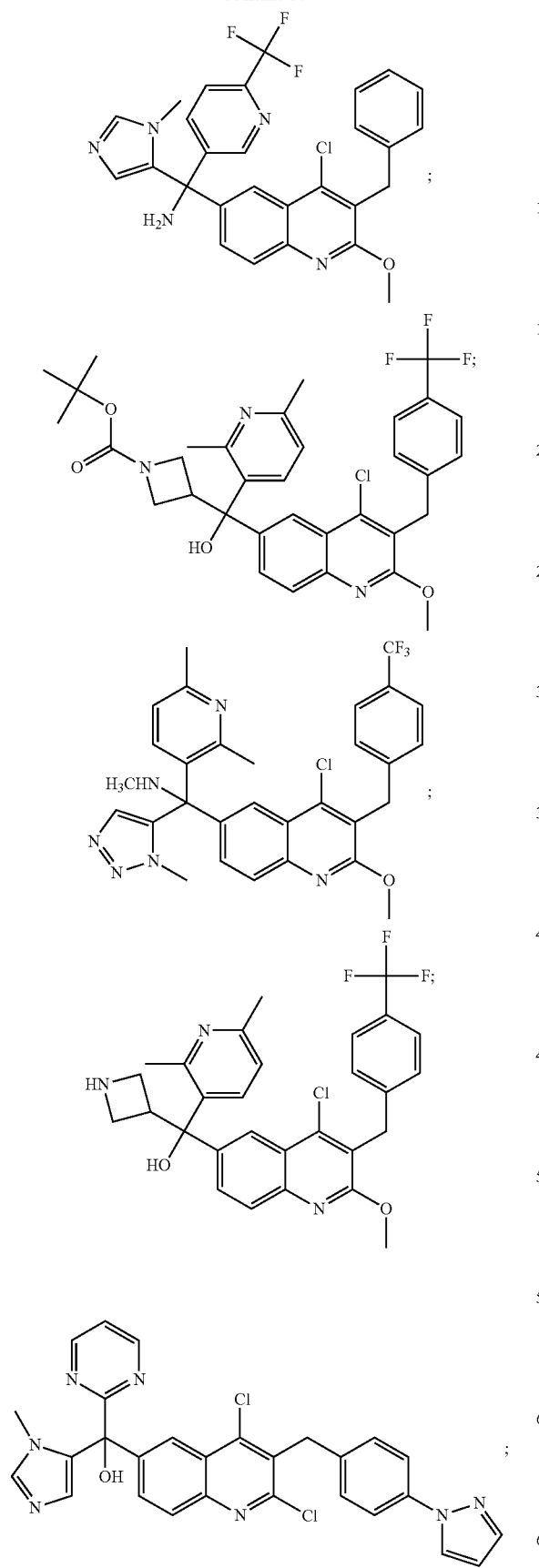

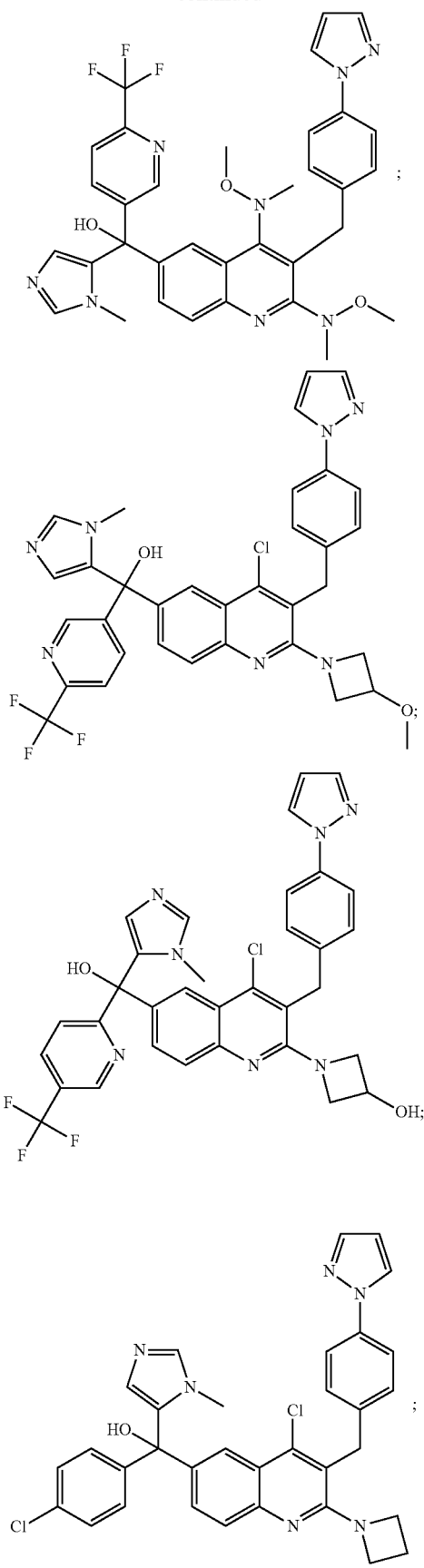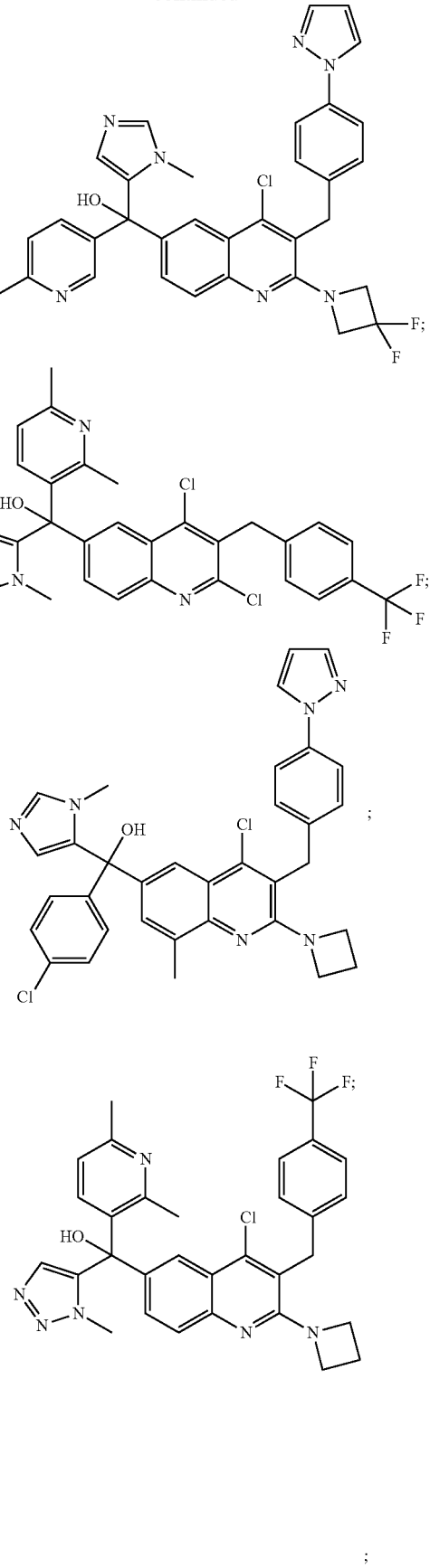

365
-continued
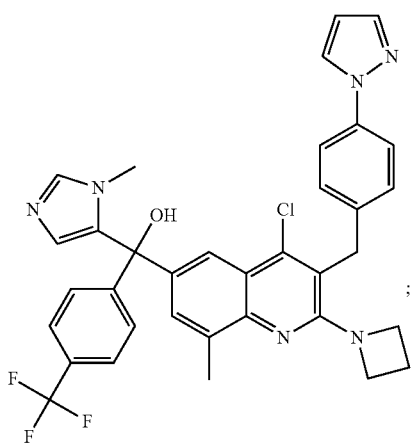
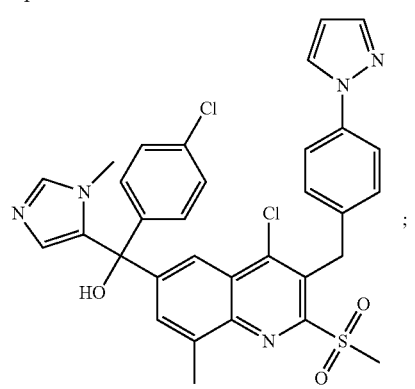
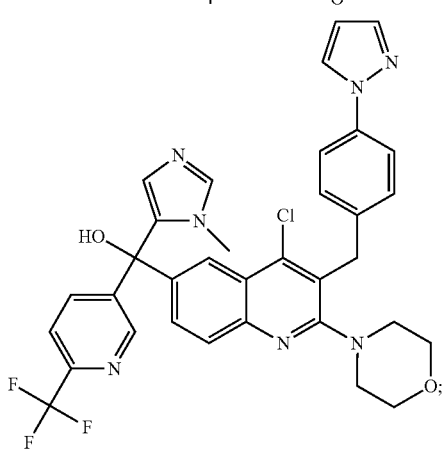
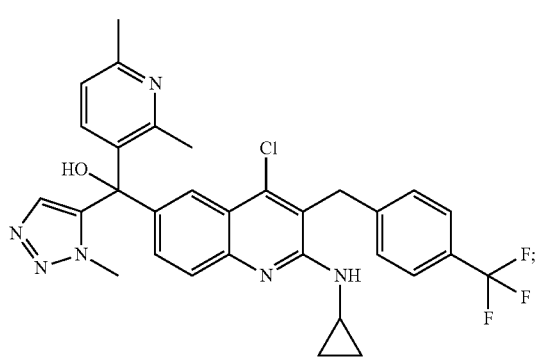
366
-continued
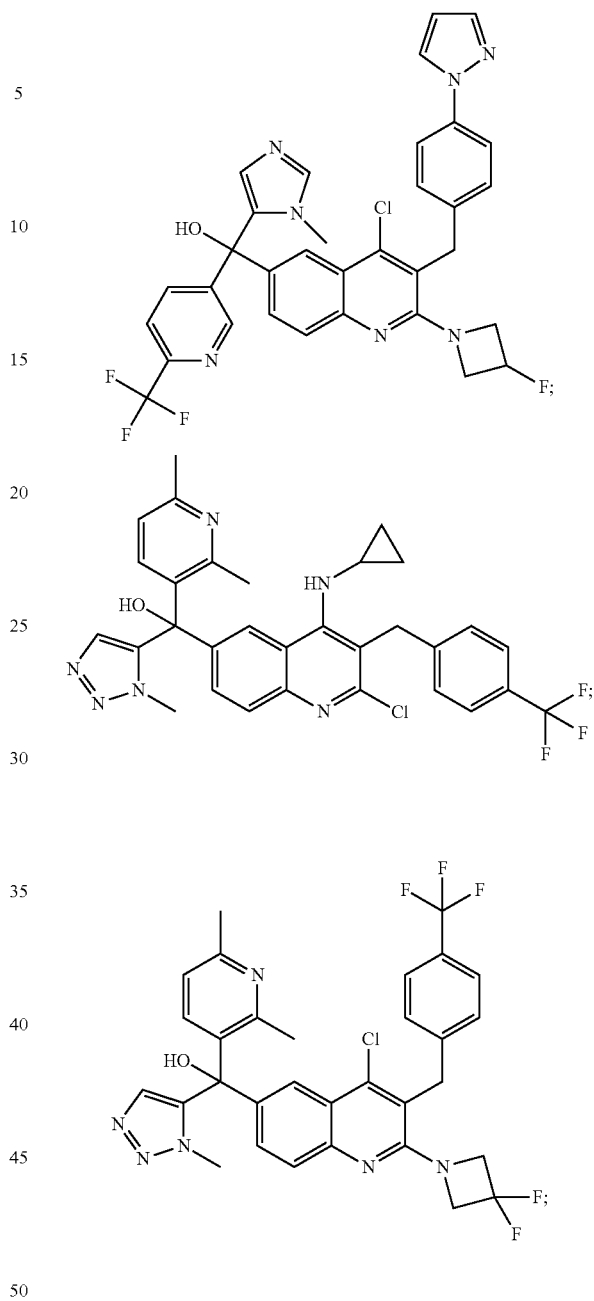
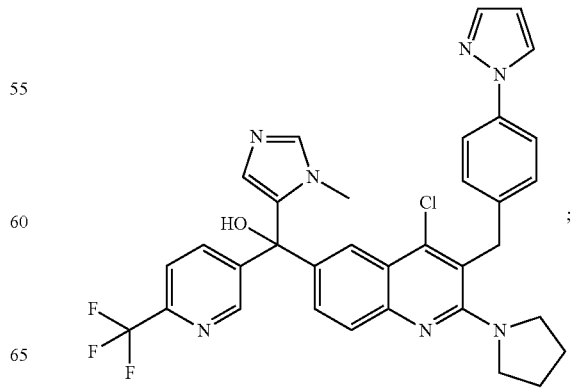

367
-continued
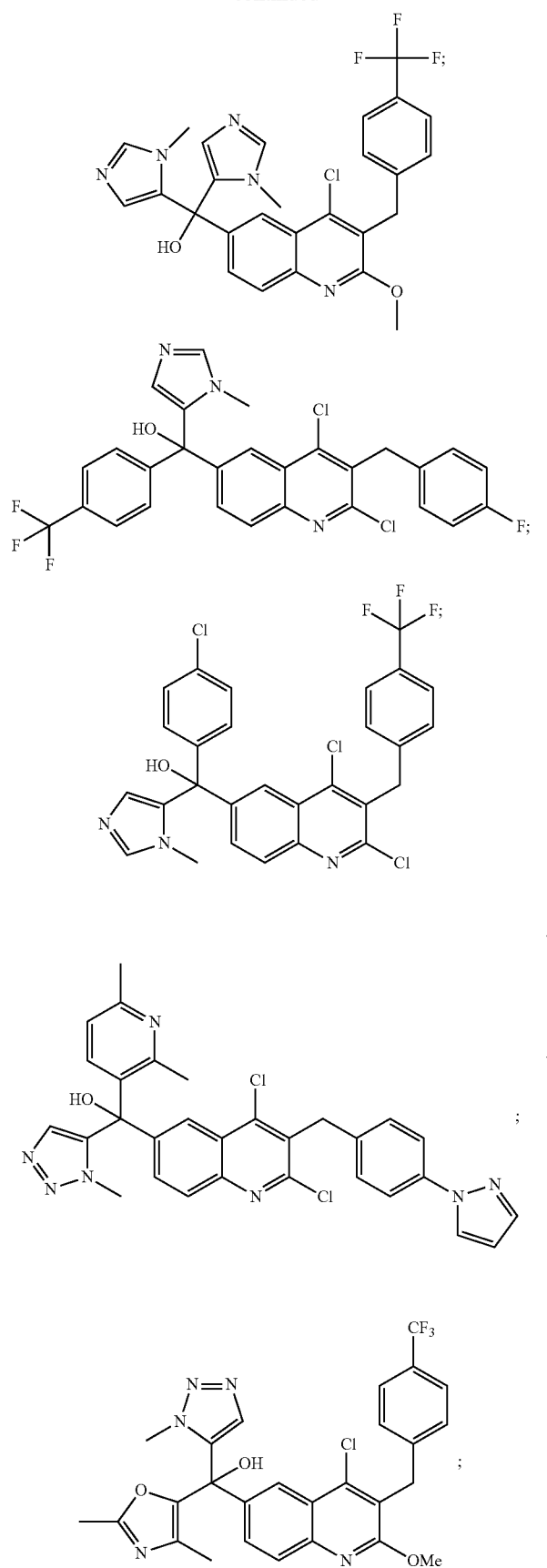
368
-continued
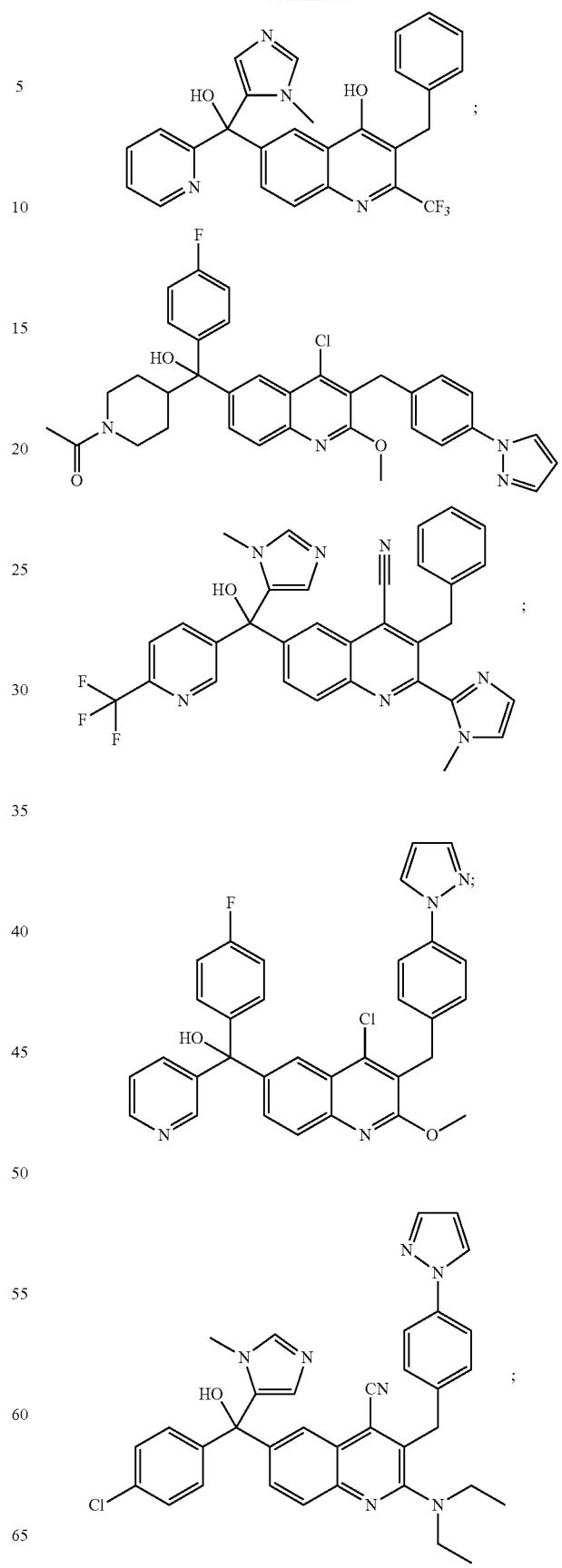

-continued

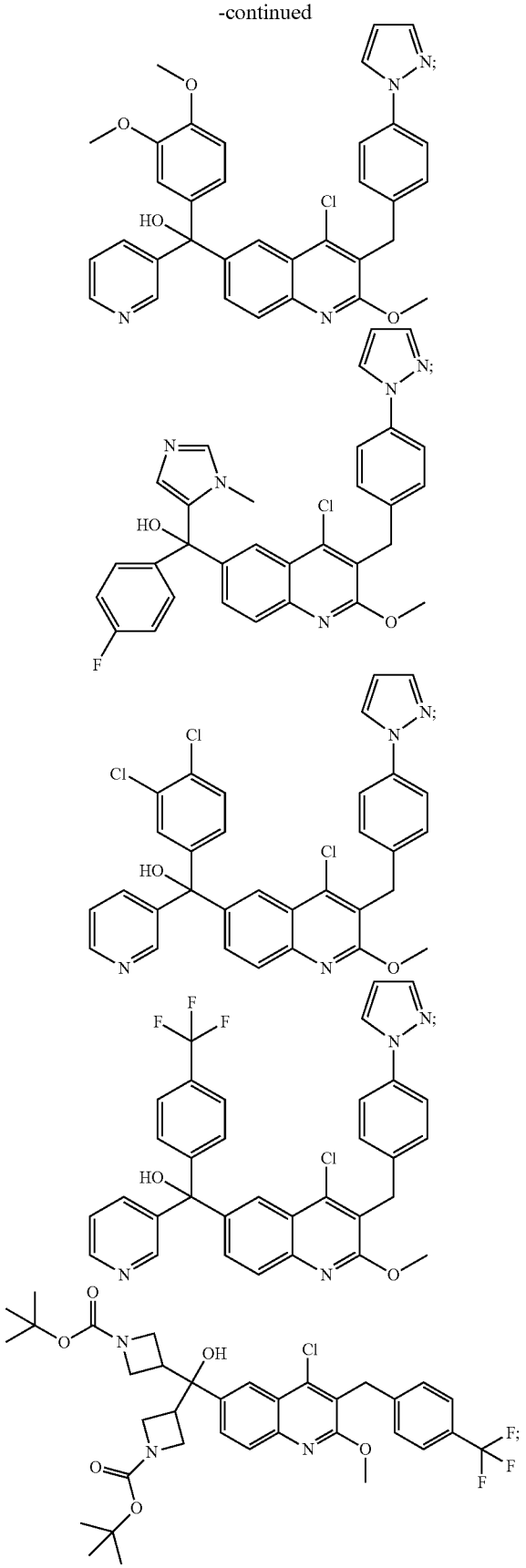

and pharmaceutically acceptable salts thereof.

4. A pharmaceutical composition, comprising a compound of claim 1 and a pharmaceutically acceptable carrier.

5. A pharmaceutical composition made by mixing a compound of claim 1 and a pharmaceutically acceptable carrier.

6. A process for making a pharmaceutical composition comprising mixing a compound of claim 1 and a pharmaceutically acceptable carrier.

7. A method for treating or ameliorating a RORγt mediated inflammatory syndrome, disorder or disease comprising administering to a subject in need thereof an effective amount of a compound of claim 1, wherein the disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus.

8. The method of claim 7, wherein the disease is psoriasis.

9. The method of claim 7, wherein the disease is rheumatoid arthritis.

10. The method of claim 7, wherein the inflammatory bowel disease is ulcerative colitis.

11. The method of claim 7, wherein the inflammatory bowel disease is Crohn's disease.

12. The method of claim 7, wherein the disease is multiple sclerosis.

13. The method of claim 7, wherein the disease is neutrophilic asthma.

14. The method of claim 7, wherein the disease is steroid resistant asthma.

15. The method of claim 7, wherein the disease is psoriatic arthritis.

16. The method of claim 7, wherein the disease is ankylosing spondylitis.

17. The method of claim 7, wherein the disease is systemic lupus erythematosus.

18. The method of claim 7, wherein the disease is chronic obstructive pulmonary disorder.

19. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: rheumatoid arthritis, and psoriasis.

20. A method for treating or ameliorating a RORγt mediated inflammatory syndrome, disorder or disease comprising administering to a subject in need thereof an effective amount of a compound of claim 1, wherein the disease is selected from the group consisting of: rheumatoid arthritis and psoriasis.

21. A method of inhibiting production of interleukin-17, comprising administering to a subject in need thereof an effective amount of a compound of claim 1.

* * * * *

SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

<400> SEQUENCE: 1

```
agagagctag gtgcagagct tcaggctgag gcgctgctga gagggcctcg ccccgcctct      60
gccgccagct gcaccccact cctggaccac cccctgctga gaaggacagg gagccaaggc     120
cggcagagcc aaggctcagt catgagaaca caaattgaag tgatcccttg caaaatctgt     180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480 aagaccccctc cagcagggggc ccaaggagca gatacccctca cctacaccctt ggggctccca     540 gacgggcagc tgccccctggg ctcctcgcct gacctgcctg aggcttctgc ctgtccccct     600
ggcctcctga aagcctcagg ctctgggccc tcatattcca acaacttggc caaggcaggg     660
ctcaatgggg cctcatgcca ccttgaatac agccctgagc ggggcaaggc tgagggcaga     720
gagagcttct atagcacagg cagccagctg accccctgacc gatgtggact tcgttttgag     780
```

```
gaacacaggc atcctgggct tggggaactg ggacagggcc cagacagcta cggcagcccc      840
agtttccgca gcacaccgga ggcaccctat gcctccctga cagagataga gcacctggtg      900
cagagcgtct gcaagtccta cagggagaca tgccagctgc ggctggagga cctgctgcgg      960
cagcgctcca acatcttctc ccgggaggaa gtgactggct accagaggaa gtccatgtgg     1020
gagatgtggg aacggtgtgc ccaccacctc accgaggcca ttcagtacgt ggtggagttc     1080
gccaagaggc tctcaggctt tatggagctc tgccagaatg accagattgt gcttctcaaa     1140
gcaggagcaa tggaagtggt gctggttagg atgtgccggg cctacaatgc tgacaaccgc     1200
acggtctttt ttgaaggcaa atacggtggc atggagctgt ccgagcctt gggctgcagc      1260 gagctcatca gctccatctt tgacttctcc cactccctaa gtgccttgca cttttccgag     1320
gatgagattg ccctctacac agcccttgtt ctcatcaatg cccatcggcc agggctccaa     1380
gagaaaagga agtagaaca gctgcagtac aatctggagc tggcctttca tcatcatctc     1440
tgcaagactc atcgccaaag catcctggca aagctgccac ccaaggggaa gcttcggagc     1500
ctgtgtagcc agcatgtgga aaggctgcag atcttccagc cctccaccc catcgtggtc      1560 caagccgctt tccctccact ctacaaggag ctcttcagca ctgaaaccga gtcacctgtg     1620
gggctgtcca agtgacctgg aagagggact ccttgcctct ccctatggcc tgctggccca     1680
cctccctgga ccccgttcca ccctcaccct tttccttcc catgaaccct ggagggtggt      1740
ccccaccagc tctttggaag tgagcagatg ctgcggctgg cttctgtca gcaggccggc      1800 ctggcagtgg gacaatcgcc agagggtggg gctggcagaa caccatctcc agcctcagct     1860
ttgacctgtc tcatttccca tattccttca cacccagctt ctggaaggca tggggtggct     1920
gggatttaag gacttctggg ggaccaagac atcctcaaga aaacaggggc atccagggct     1980
ccctggatga atagaatgca attcattcag aagctcagaa gctaagaata agcctttgaa     2040
atacctcatt gcatttccct ttgggcttcg gcttgggag atggatcaag ctcagagact      2100
ggcagtgaga gcccagaagg acctgtataa aatgaatctg gagctttaca tttctgcct      2160 ctgccttcct cccagctcag caaggaagta tttgggcacc ctaccctta cctggggtct      2220 aaccaaaaat ggatgggatg aggatgagag gctgagata attgttttat gggatttggg      2280
tgtgggacta gggtacaatg aaggccaaga gcatctcaga catagagtta aaactcaaac     2340
ctcttatgtg cactttaaag atagacttta ggggctggca caaatctgat cagagacaca     2400
tatccataca caggtgaaac acatacagac tcaacagcaa tcatgcagtt ccagagacac     2460
atgaacctga cacaatctct cttatccttg aggccacagc ttggaggagc ctagaggcct     2520
caggggaaag tcccaatcct gagggaccct cccaaacatt tccatggtgc tccagtccac     2580
tgatcttggg tctggggtga tccaaatacc acccccagctc cagctgtctt ctaccactag     2640
aagacccaag agaagcagaa gtcgctcgca ctggtcagtc ggaaggcaag atcagatcct     2700
ggaggacttt cctggcctgc ccgccagccc tgctcttgtt gtggagaagg aagcagatgt     2760
gatcacatca ccccgtcatt gggcaccgct gactccagca tggaggacac cagggagcag     2820
ggcctgggcc tgtttccccca gctgtgatct tgcccagaac ctctcttggc ttcataaaca     2880
gctgtgaacc ctcccctgag ggattaacag caatgatggg cagtcgtgga gttgggggg     2940 ttgggggtgg gattgtgtcc tctaagggga cgggttcatc tgagtaaaca taaaccccaa    3000
cttgtgccat tctttataaa atgatttaa aggcaaaaaa aaaaaaaaaa aaaa           3054
```

<210> SEQ ID NO 2
<211> LENGTH: 786

```
<212> TYPE: DNA
<213> ORGANISM: Homo sapiens

<400> SEQUENCE: 2
agcacaccgg aggcacccta tgcctccctg acagagatag agcacctggt gcagagcgtc    60
tgcaagtcct acagggagac atgccagctg cggctggagg acctgctgcg gcagcgctcc   120
aacatcttct cccggggga agtgactggc taccagagga agtccatgtg ggagatgtgg   180
gaacggtgtg cccaccacct caccgaggcc attcagtacg tggtggagtt cgccaagagg   240
ctctcaggct ttatggagct ctgccagaat gaccagattg tgcttctcaa agcaggagca   300
atggaagtgg tgctggttag gatgtgccgg gcctacaatg ctgacaaccg cacggtcttt   360
tttgaaggca aatacggtgg catggagctg ttccgagcct gggctgcag cgagctcatc    420
agctccatct ttgacttctc ccactcccta agtgccttgc acttttccga ggatgagatt   480
gccctctaca cagcccttgt tctcatcaat gcccatcggc cagggctcca agagaaaagg   540
aaagtagaac agctgcagta caatctggag ctggcctttc atcatcatct ctgcaagact   600
catcgccaaa gcatcctggc aaagctgcca cccaagggga agcttcggag cctgtgtagc   660
cagcatgtgg aaaggctgca gatcttccag cacctccacc ccatcgtggt ccaagccgct   720
ttccctccac tctacaagga gctcttcagc actgaaaccg agtcacctgt ggggctgtcc   780
aagtga                                                              786

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
                20                  25                  30

Thr Glu Ile Glu His Leu Val Gln Ser Val Cys Lys Ser Tyr Arg Glu
            35                  40                  45

Thr Cys Gln Leu Arg Leu Glu Asp Leu Leu Arg Gln Arg Ser Asn Ile
        50                  55                  60

Phe Ser Arg Glu Glu Val Thr Gly Tyr Gln Arg Lys Ser Met Trp Glu
65                  70                  75                  80

Met Trp Glu Arg Cys Ala His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125
```

```
Arg Met Cys Arg Ala Tyr Asn Ala Asp Asn Arg Thr Val Phe Phe Glu
            130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
            180                 185                 190

Ala His Arg Pro Gly Leu Gln Glu Lys Arg Lys Val Glu Gln Leu Gln
            195                 200                 205

Tyr Asn Leu Glu Leu Ala Phe His His His Leu Cys Lys Thr His Arg
            210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
            260                 265                 270

Thr Glu Thr Glu Ser Pro Val Gly Leu Ser Lys
            275                 280

<210> SEQ ID NO 5
<211> LENGTH: 6
<212> TYPE: PRT
<213> ORGANISM: Homo sapiens

<400> SEQUENCE: 5

Leu Tyr Lys Glu Leu Phe
1               5

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain

<400> SEQUENCE: 6

Leu Phe Lys Glu Leu Phe
1               5

<210> SEQ ID NO 7
<211> LENGTH: 786
<212> TYPE: DNA
<213> ORGANISM: Artificial Sequence
<220> FEATURE:
<223> OTHER INFORMATION: LBD with mutated AF2 domain

<400> SEQUENCE: 7
agcacaccgg aggcacccta tgcctccctg acagagatag agcacctggt gcagagcgtc      60
tgcaagtcct acaggagac atgccagctg cggctggagg acctgctgcg gcagcgctcc     120
aacatcttct cccgggagga agtgactggc taccagagga agtccatgtg ggagatgtgg    180
gaacggtgtg cccaccacct caccgaggcc attcagtacg tggtggagtt cgccaagagg    240
ctctcaggct ttatggagct gcagaat gaccagattg tgcttctcaa agcaggagca       300
atggaagtgg tgctggttag gatgtgccgg gcctacaatg ctgacaaccg cacggtcttt    360
tttgaaggca aatacggtgg catggagctg ttccgagcct gggctgcag cgagctcatc     420
```

-continued

```
agctccatct ttgacttctc ccactcccta agtgccttgc acttttccga ggatgagatt    480
gccctctaca cagccttgt tctcatcaat gccatcggc cagggctcca agagaaaagg     540
aaagtagaac agctgcagta caatctggag ctggcctttc atcatcatct ctgcaagact   600
catcgccaaa gcatcctggc aaagctgcca cccaagggga agcttcggag cctgtgtagc   660
cagcatgtgg aaaggctgca gatcttccag cacctccacc ccatcgtggt ccaagccgct   720
ttccctccac tcttcaagga gctcttcagc actgaaaccg agtcacctgt ggggctgtcc   780
aagtga                                                              786
```

<210> SEQ ID NO 8
<211> LENGTH: 261
<212> TYPE: PRT
<213> ORGANISM: Homo sapiens

<400> SEQUENCE: 8

```
Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
                245                 250                 255

Val Gly Leu Ser Lys
            260
```

<210> SEQ ID NO 9
<211> LENGTH: 261
<212> TYPE: PRT
<213> ORGANISM: Artificial Sequence
<220> FEATURE:

<223> OTHER INFORMATION: LBD with mutated AF2 domain

<400> SEQUENCE: 9

```
Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
                100                 105                 110

Asn Ala Asp Asn Arg Thr Val Phe Phe Glu Gly Lys Tyr Gly Gly Met
            115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Phe Lys Glu Leu Phe Ser Thr Glu Thr Glu Ser Pro
                245                 250                 255

Val Gly Leu Ser Lys
            260
```